US012209180B2

(12) United States Patent
Gromada et al.

(10) Patent No.: US 12,209,180 B2
(45) Date of Patent: *Jan. 28, 2025

(54) BIS-OCTAHYDROPHENANTHRENE CARBOXAMIDE DERIVATIVES AND PROTEIN CONJUGATES THEREOF FOR USE AS LXR AGONISTS

(71) Applicant: REGENERON PHARMACEUTICALS, INC., Tarrytown, NY (US)

(72) Inventors: Jesper A. Gromada, Concord, MA (US); Viktoria Gusarova, Pleasantville, NY (US); Amy Han, Hockessin, DE (US); Sokol Haxhinasto, Brookfield, CT (US); Andrew J. Murphy, Croton-on-Hudson, NY (US); William Olson, Yorktown Heights, NY (US); Matthew Sleeman, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 827 days.

This patent is subject to a terminal disclaimer.

(21) Appl. No.: 17/295,420

(22) PCT Filed: Nov. 19, 2019

(86) PCT No.: PCT/US2019/062302
§ 371 (c)(1),
(2) Date: May 19, 2021

(87) PCT Pub. No.: WO2020/106780
PCT Pub. Date: May 28, 2020

(65) Prior Publication Data
US 2022/0080052 A1    Mar. 17, 2022

Related U.S. Application Data

(60) Provisional application No. 62/769,946, filed on Nov. 20, 2018.

(51) Int. Cl.
A61K 47/68    (2017.01)
C07D 249/16   (2006.01)
C08L 5/16     (2006.01)

(52) U.S. Cl.
CPC ............ *C08L 5/16* (2013.01); *A61K 47/6803* (2017.08); *A61K 47/6849* (2017.08); *A61K 47/6883* (2017.08); *A61K 47/6889* (2017.08); *C07D 249/16* (2013.01)

(58) Field of Classification Search
None
See application file for complete search history.

(56) References Cited

U.S. PATENT DOCUMENTS 6,908,934 B2    6/2005  Adams et al.
2003/0125357 A1  7/2003  Adams et al.
(Continued)

FOREIGN PATENT DOCUMENTS

CN    101679297 A   3/2010
EP    1398032 A1    3/2004
(Continued)

OTHER PUBLICATIONS

Zeiss et al., "Synthesis and Stereochemistry of the 3-Keto-A⁴-steroidal System from Diterpenic Acids, Journal of the American Chemical Society", vol. 75, Dec. 5, 1953, pp. 5935-5940.
(Continued)

*Primary Examiner* — Karl J Puttlitz
(74) *Attorney, Agent, or Firm* — Squire Patton Boggs (US) LLP

(57) ABSTRACT

Provided herein are compounds or payloads, linker-payloads, antibody-drug conjugates, and compositions, and
(Continued)

methods for the treatment of diseases and disorders associated with the liver X receptor, including bis-octahydrophenanthrene carboxamides and protein (e.g., antibody) drug conjugates thereof.

45 Claims, 15 Drawing Sheets

Specification includes a Sequence Listing.

(56) References Cited

U.S. PATENT DOCUMENTS

| | | |
|---|---|---|
| 2009/0030082 A1 | 1/2009 | Forman |
| 2016/0324981 A1 | 11/2016 | Pinkerton et al. |
| 2018/0334426 A1 | 11/2018 | Han et al. |
| 2019/0367631 A1 | 12/2019 | Gromada et al. |

FOREIGN PATENT DOCUMENTS

| | | | |
|---|---|---|---|
| WO | WO 01/41704 A1 | 6/2001 | |
| WO | WO 2006/000577 A1 | 1/2006 | |
| WO | WO 2018/213082 A1 | 11/2018 | |
| WO | 2019217591 | * 11/2019 | |
| WO | WO 2019/217591 A1 | 11/2019 | |

OTHER PUBLICATIONS

Zhou et al., "Tyrosine kinase inhibitory activity of dehydroabietylamine derivatives tested by homogeneous time-resolved fluorescence based high throughput screening model", Chinese Journal of Natural Medicines 2013, 11(5), pp. 506-513.

Chin et al., "Miniaturization of Cell-Based β-Lactamase-Dependent FRET Assays to Ultra-High Throughput Formats to Identify Agonists of Human Liver X Receptors", Assay and Drug Development Technologies, vol. 1, No. 6, 2003, pp. 777-787.

Bardyshev, "Diterpenoid Carboxylic Acid Anhydrides of the Abietane, Pimarane, and Isopimarane Series", Russian Journal of Organic Chemistry (Translation of Zhurnal Organicheskoi Khimii), 1999, 35(1), pp. 41-55.

Database Registry [online] Chemical Abstract Service, US; Retrieved from STN, Nov. 16, 1984, RN 53404-26-5, 1,2,3,4,4a,9,10,10a-Octahydro-1,4a-dimethyl-7-(1-methylethyl) -N-[[1,2,3,4,4a, 9,10,10a-octahydro-1,4a-dimethyl-7-(1-methylethyl) -1-phenanthrenyl]methyl]-1-phenanthrene methaneamine; 1 page.

Bischoff et al., "Non-redundant roles for LXRα and LXRβ in atherosclerosis susceptibility in low density lipoprotein receptor knockout mice", Journal of Lipid Research, 2010, vol. 51, pp. 900-906.

Bogan et al., "Liver X Receptor Modulation of Gene Expression Leading to Pro-luteolytic Effects in Primate Luteal Cells", Biology of Reproduction, 2012, 86(3):89, pp. 1-9.

Calkinn and Tontonoz, "Transcriptional integration of metabolism by the nuclear sterol-activated receptors LXR and FXR", Molecular Cell Biology, Apr. 2012, vol. 13, No. 4, pp. 213-224.

CAS No. 1221277-90-2, "2,4,6-Trimethyl-N-[[3'-(methylsulfonyl)[1,1'-biphenyl]-4-yl]methyl]-N-[[5-(trifluoromethyl)-2-furanyl]methyl] benzenesulfonamide", printed Mar. 2, 2016; 2 pages.

Castrillo et al., "Crosstalk between LXR and Toll-like Receptor Signaling Mediates Bacterial and Viral Antagonism of Cholesterol Metabolism", Molecular Cell, Oct. 2003, vol. 12, pp. 805-816.

Fukuchi et al., "Antiproliferative Effect of Liver X Receptor Agonists on LNCaP Human Prostate Cancer Cells", Cancer Research 64, Nov. 1, 2004, pp. 7686-7689.

Groot et al., "Synthetic LXR agonists increase LDL in CETP species", Journal of Lipid Research, 2005, vol. 46, pp. 2182-2191.

Honzumi et al., "LXRα regulates human CETP expression in vitro and in transgenic mice", Atherosclerosis 212, 2010, pp. 139-145.

Honzumi et al., "Synthetic LXR agonist inhibits the development of atherosclerosis in New Zealand White rabbits", Biochimica et Biophysica Acta 1811, 2011, pp. 1136-1145.

Joseph et al., "Synthetic LXR ligand inhibits the development of atherosclerosis in mice", PNAS, May 28, 2002, vol. 99, No. 11, pp. 7604-7609.

Koldamova et al., "The Liver X Receptor Ligand T0901317 Decreases Amyloid β Production in Vitro and in a Mouse Model of Alzheimer's Disease ", Journal of Biological Chemistry, Feb. 11, 2005, vol. 280, No. 6, pp. 4079-4088.

Laffitte et al. "Activation of liver X receptor improves glucose tolerance through coordinate regulation of glucose metabolism in liver and adipose tissue", PNAS, Apr. 29, 2003, vol. 100, No. 9, pp. 5419-5424.

Lakomy et al., "Liver X Receptor-Mediated Induction of Cholesteryl Ester Transfer Protein Expression Is Selectively Impaired in Inflammatory Macrophages", Arterioscler Thromb Vasc Biol., Nov. 2009, vol. 29, pp. 1923-1929, DOI: 10.1161/ATVBAHA.109.193201.

Leik et al., "GW3965, a synthetic liver X receptor (LXR) agonist, reduces angiotensin II-mediated pressor responses in Sprague—Dawley rats", British Journal of Pharmacology, 2007, vol. 151, pp. 450-456.

Levin et al., "Macrophage Liver X Receptor Is Required for Antiatherogenic Activity of LXR Agonists", Arterioscler Thromb Vasc Biol., Jan. 2005, pp. 135-142, DOI: 10.1161/01.ATV.0000150044. 84012.68.

Lim et al., "Targeted Delivery of LXR Agonist Using a Site-Specific Antibody-Drug Conjugate", *Bioconjugate Chemistry*, May 6, 2015, DOI: 10.1021/acs.bioconjchem.5b00203, 9 pages.

Lim et al., "Targeted Delivery of LXR Agonist Using a Site-Specific Antibody-Drug Conjugate", Bioconjugare Chem., 2015, vol. 26, pp. 2216-2222.

Lima et al., "Bioisosterism: A Useful Strategy for Molecular Modification and Drug Design", Current Medicinal Chemistry, 2005, vol. 12, pp. 23-49.

Liu et al., "Design, synthesis, and structure-activity relationship of podocarpic acid amides as liver X receptor agonists for potential treatment of atherosclerosis", Bioorganic & Medicinal Chemistry Letters 15, 2005, pp. 4574-4578.

Patani et al., "Bioisosterism: A Rational Approach in Drug Design", Chemical Reviews, 1996, vol. 96, No. 8, pp. 3147-3176.

R.H. Bible, "The Conversion of Podocarpic Acid to Nimbiol", Tetrahedron, vol. 11, No. 1-2, Jan. 1, 1960, pp. 22-29, XP055494835.

Samal et al., "The First Synthesis of Water-Soluble Cyclodextrinazafullerenes", Synthetic Communications, 2002, vol. 32, No. 21, pp. 3367-3372.

Severson et al., "Hot-Tube Reactions of Dehydroabietic Acid with Ketene-Producing Reagents. Pyrolysis of the Acid Chloride and Symmetrical and Mixed Anhydride Derivatives of Dehydroabietic Acid", Canadian Journal of Chemistry, 1973, vol. 51 (19), pp. 3236-3241, corresponds to Severson et al., "ChemInform Abstract: Hot-Tube Reactions of Dehydroabietic Acid with Ketene-Producing Reagents. Pyrolysis of the Acid Chloride and Symmetrical and Mixed Anhydride Derivatives of Dehydroabietic Acid", Chemischer Informationsdienst, Jan. 22, 1974, pages no-no, XP055494848. Weinheim DOI: 10.1002/chin.197403396 Retrieved from the Internet: URL:http://www.nrcresearchpress.com/doi/pdf/10.1139/v73-484 [retrieved on Jul. 26, 2018].

Sherwood and Short, "Podocarpic Acid. Part I", J. Chemical Society, 1938, pp. 1006-1013.

Singh et al., "Discovery and development of dimeric podocarpic acid leads as potent agonists of liver X receptor with HDL cholesterol raising activity in mice and hamsters", Bioorganic & Medicinal Chemistry Letters, 2005, vol. 15, pp. 2824-2828.

Solt et al., "LXR-Mediated Inhibition of CD4$^+$ T Helper Cells", PLoS One, Sep. 2012, vol. 7, issue 9, e46615; 11 pages.

Staveness et al., "Providing a New Aniline Bioisostere through the Photochemical Production of 1-Aminonorbornanes", Chem, vol. 5, Jan. 10, 2019, pp. 215-226.

Su et al., "Liver X receptor a induces 17ß-hydroxysteroid dehydrogenase-13 expression through SREBP-1c", *Am J Physiol Endocrinol Metab*, Mar. 7, 2017, doi: 10.1152/ajpendo.00310.2016, 33 pages.

(56) References Cited

OTHER PUBLICATIONS

Su et al., "Liver X receptor α induces 17β-hydroxysteroid dehydrogenase-13 expression through SREBP-1c", Am J Physiol Endocrinol Metab., Apr. 1, 2017:312(4), pp. E357-E367.
Tangirala et al., "Identification of macrophage liver X receptors as inhibitors of atherosclerosis", PNAS, Sep. 3, 2002, vo. 99, No. 18, p. 11896-11901.
Terasaka et al., "T-0901317, a synthetic liver X receptor ligand, inhibits development of atherosclerosis in LDL receptor-deficient mice", FEBS Letters, 2003, vol. 536, pp. 6-11.
Tice et al., "The Medicinal Chemistry of Liver X Receptor (LXR) Modulators", Journal of Medicinal Chemistry, vol. 57, No. 17, Sep. 11, 2014, pp. 7182-7205, XP055494920.
Van Der Hoorn et al., "Low dose of the liver X receptor agonist, AZ876, reduces atherosclerosis in APOE*3Leiden mice without affecting liver or plasma triglyceride levels", British Journal of Pharmacology, 2011, vol. 162, pp. 1553-1563.
Verschuren et el., "LXR agonist suppresses atherosclerotic lesion growth and promotes lesion regression in apoE*3Leiden mice: time course and mechanisms", Journal of Lipid Research, 2009, vol. 50, pp. 301-311.
Zuercher et al., "Discovery of Tertiary Sulfonamides as Potent Liver X Receptor Antagonists", Medical Chemistry, 2010, vol. 53, pp. 3412-3416.
Wen et al., "Drug Delivery Approaches in Addressing Clinical Pharmacology-Related Issues: Opportunities and Challenges", The AAPS Journal, vol. 17, No. 6, Nov. 2015, DOI: 10.1208/s12248-015-9814-9.

\* cited by examiner

FIG. 1. Synthesis of P1 and P2
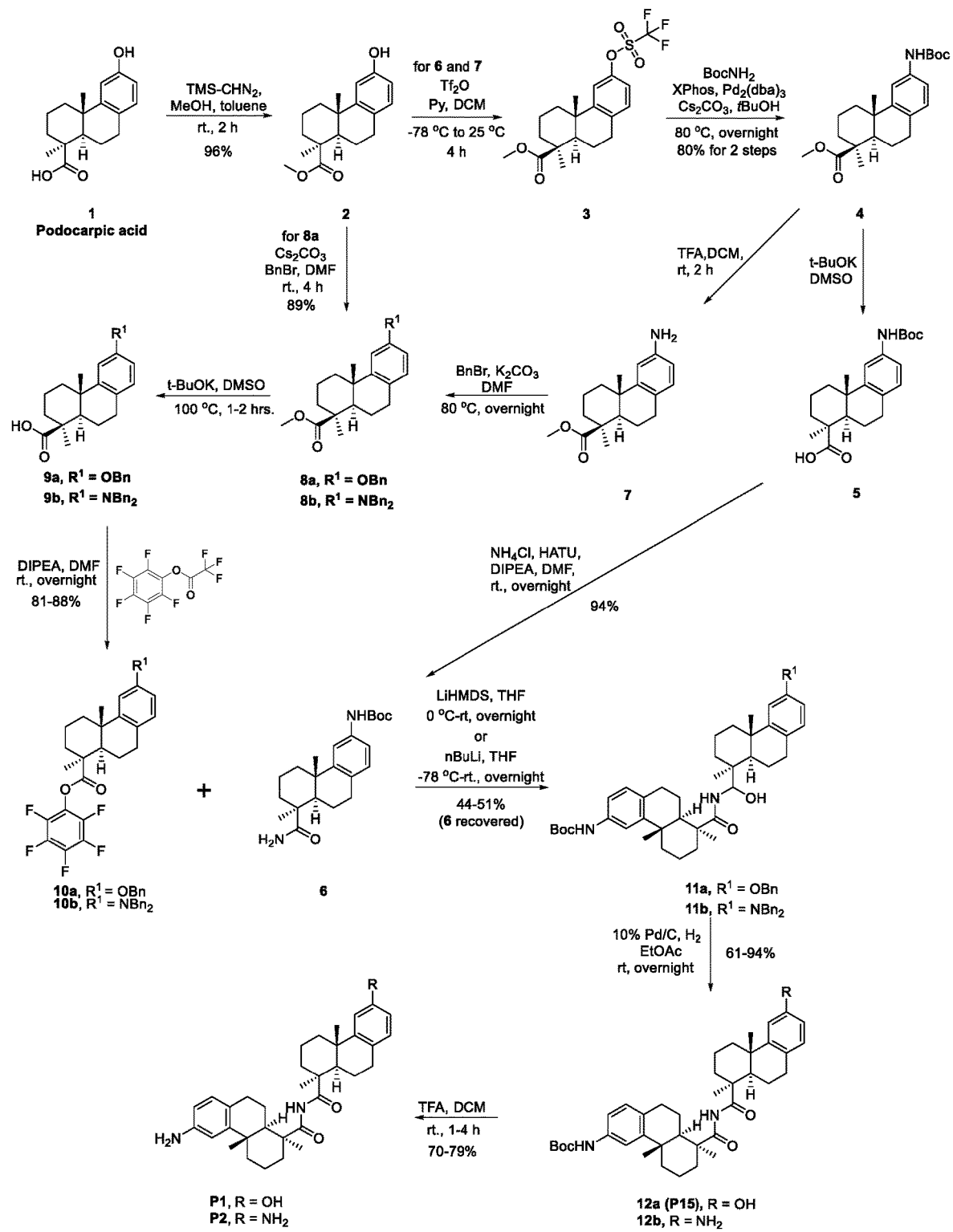

FIG. 2A. Synthesis of Payloads P3-P9, P13, P14, and P17
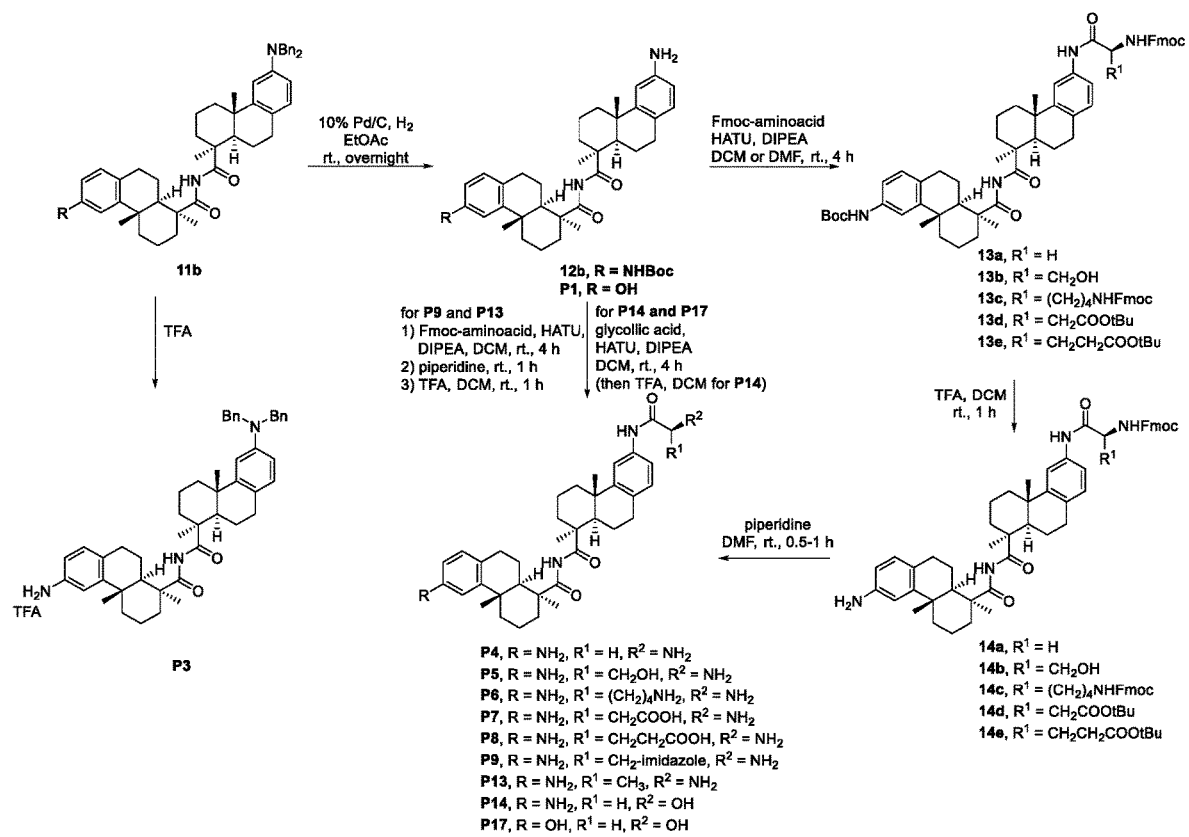

FIG. 2B. Synthesis of Payloads P10 and P11
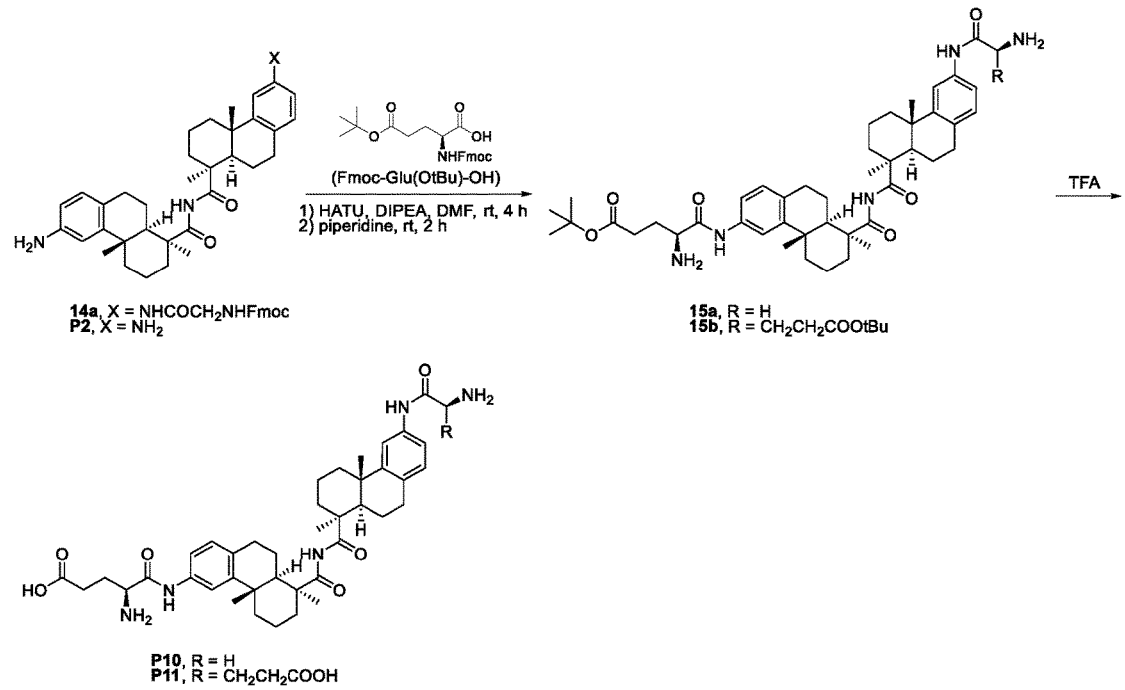
FIG. 2C. Synthesis of Payload P19
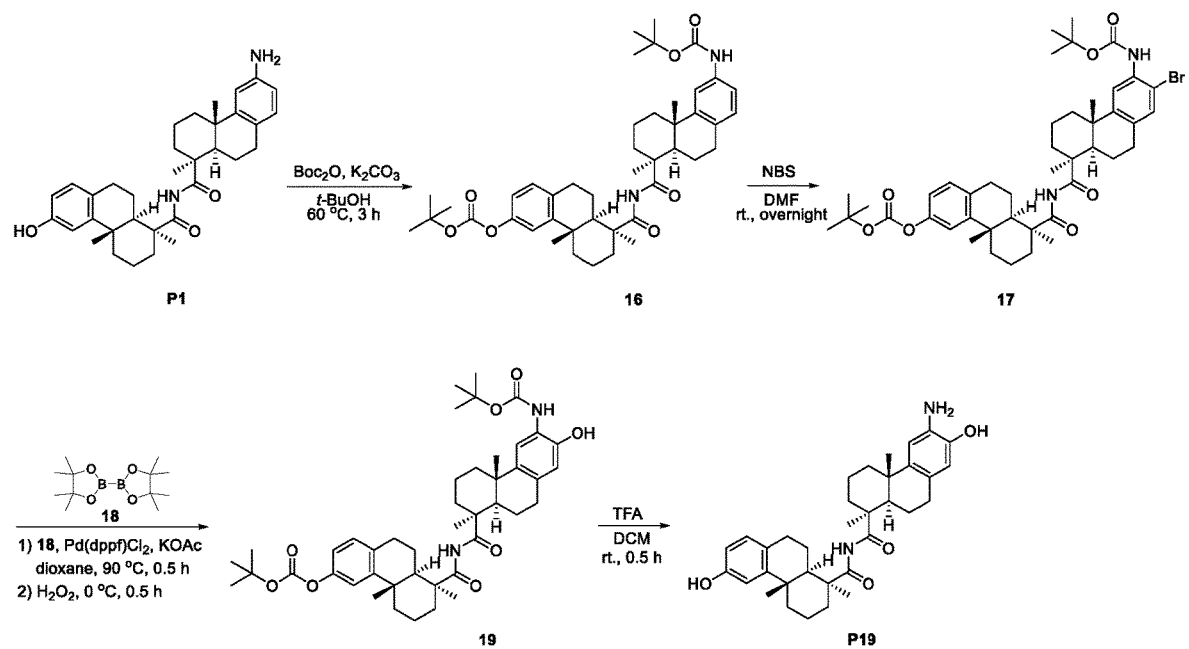

FIG. 3. General Synthesis of Linker and LP1-5 and LP20
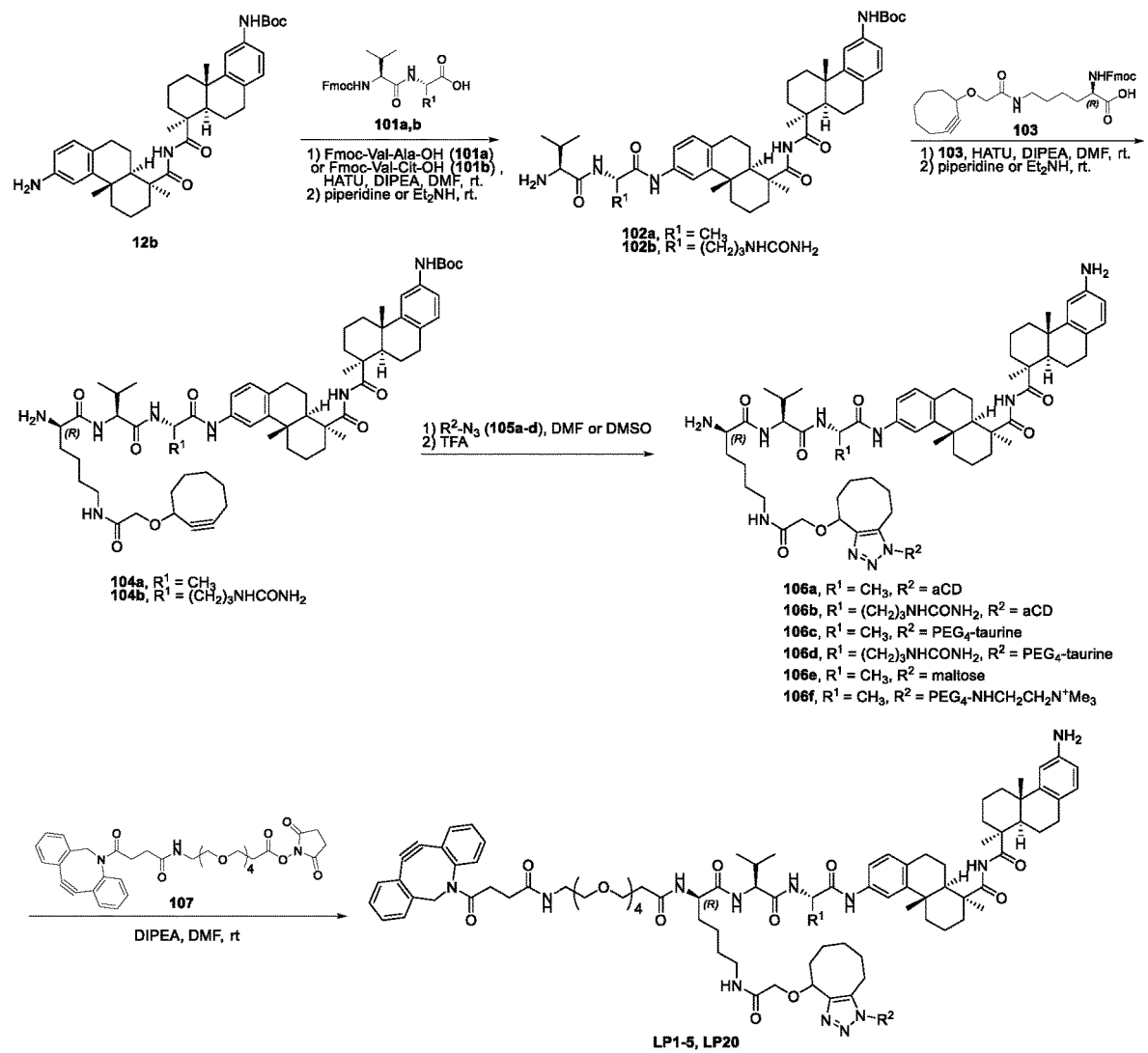
| LP | R¹ | R² |
|---|---|---|
| LP1 | $CH_3$ | αCD |
| LP2 | $(CH_2)_3NHCONH_2$ | αCD |
| LP3 | $CH_3$ | $PEG_4$-taurine |
| LP4 | $(CH_2)_3NHCONH_2$ | $PEG_4$-taurine |
| LP5 | $CH_3$ | Maltose |
| LP20 | $CH_3$ | $PEG_4$-$NHCH_2CH_2N^+Me_3$ |

FIG. 4. Synthesis of LP6
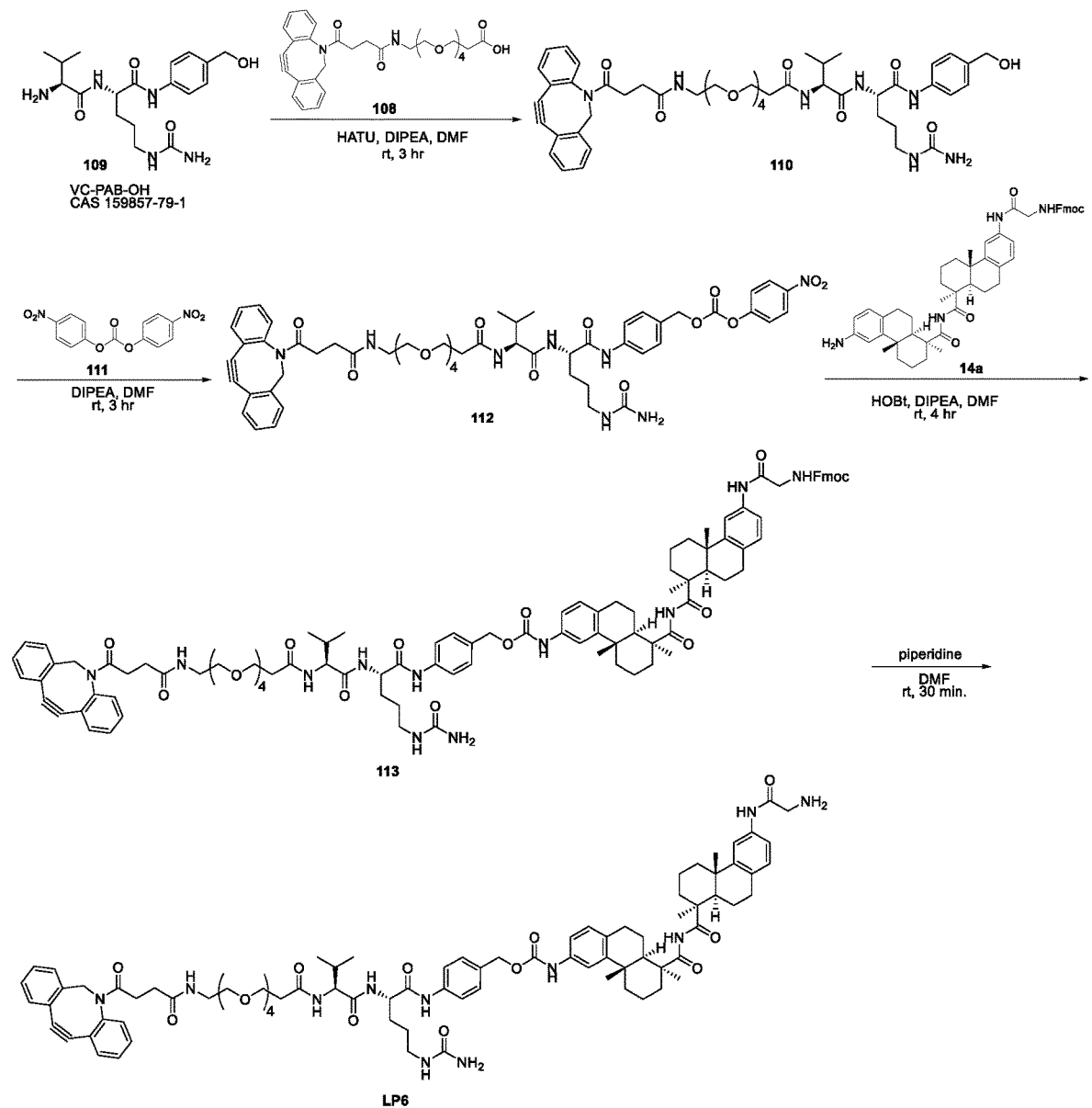

FIG. 5. Synthesis of LP7
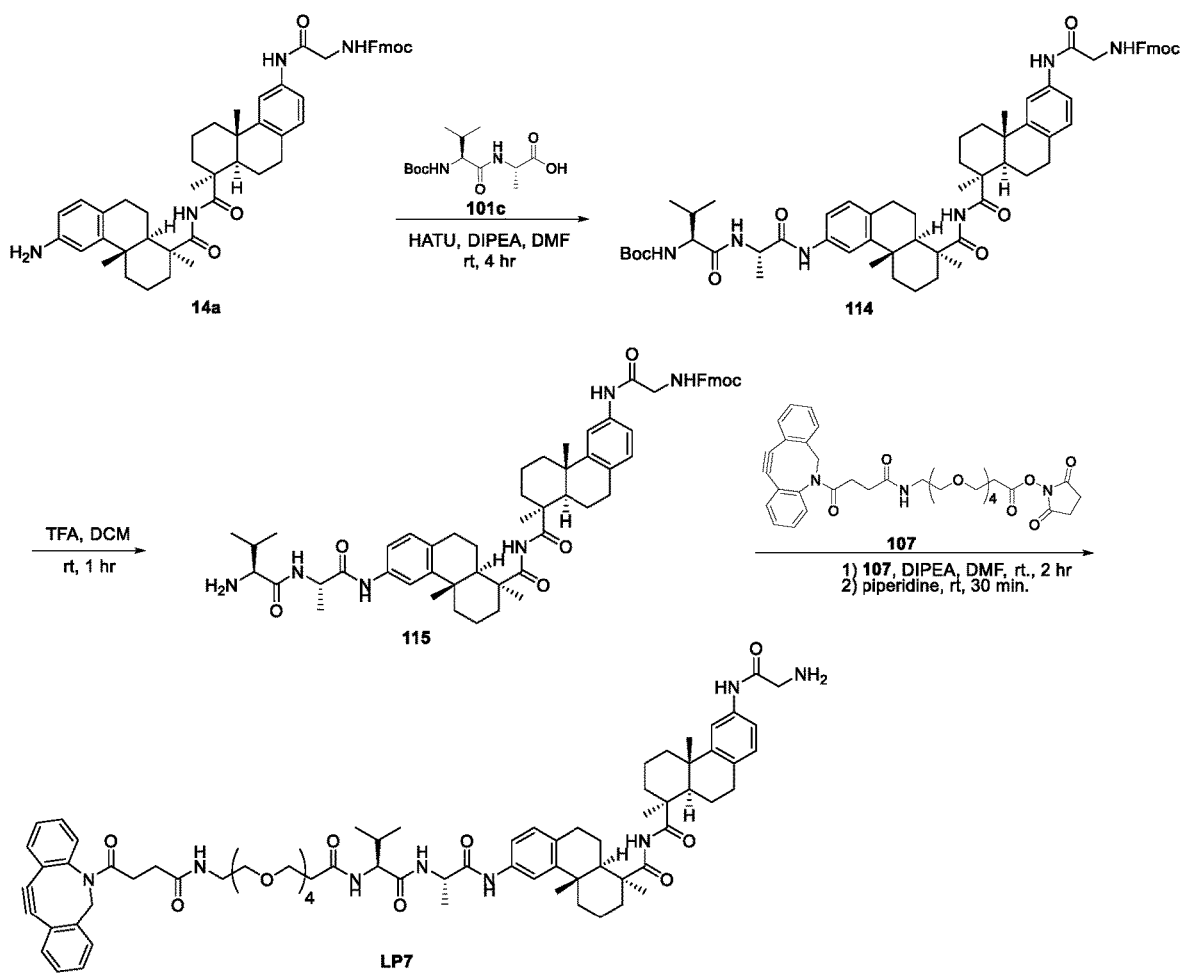

FIG. 6. Synthesis of LP8
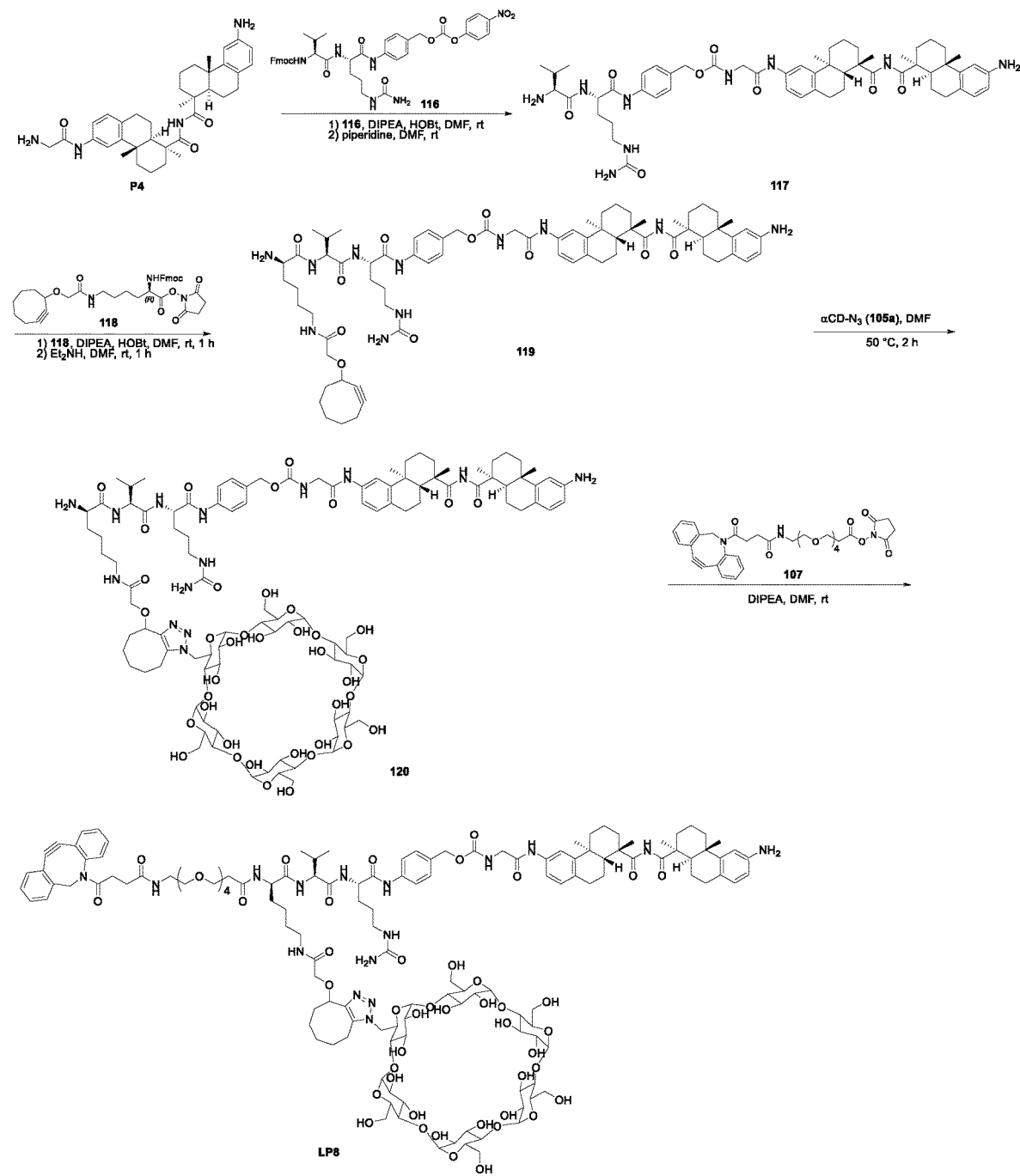

FIG. 7. Synthesis of LP9
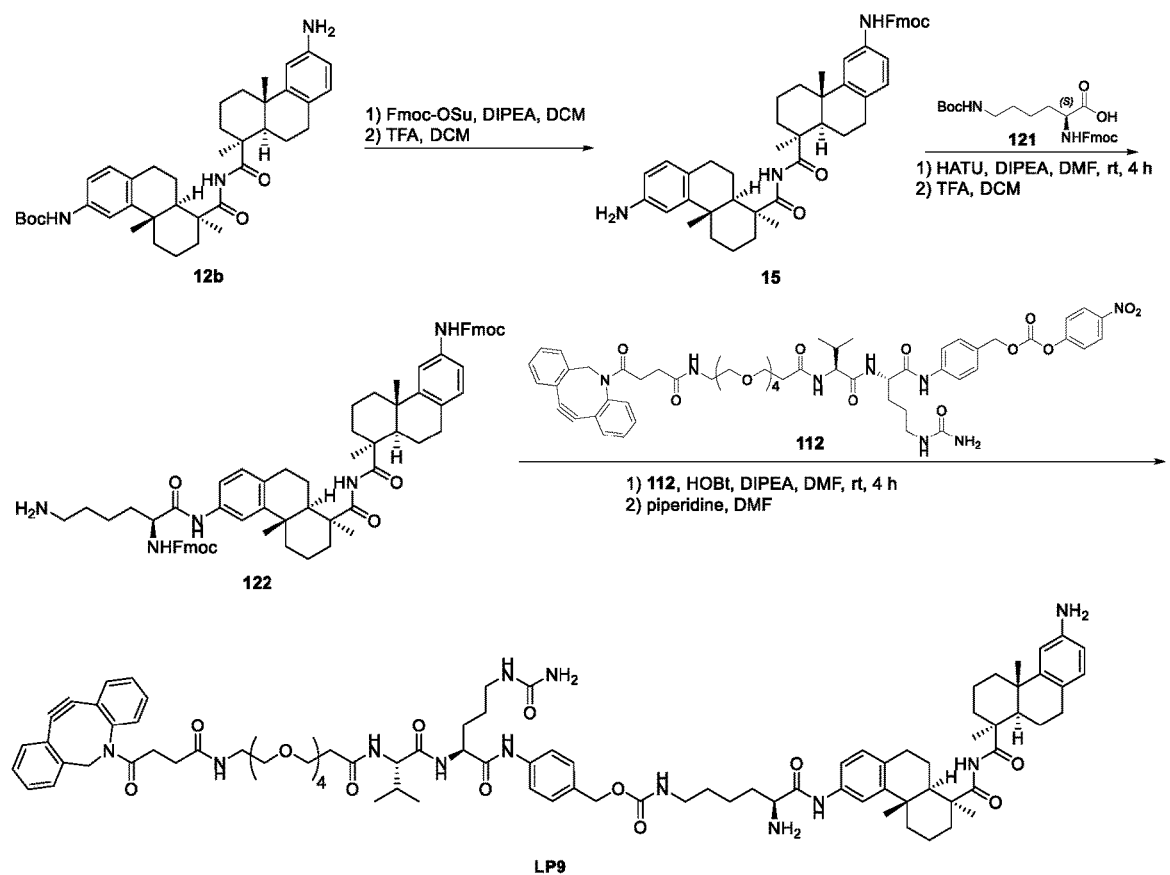

FIG. 8. Synthesis of LP10 and LP11
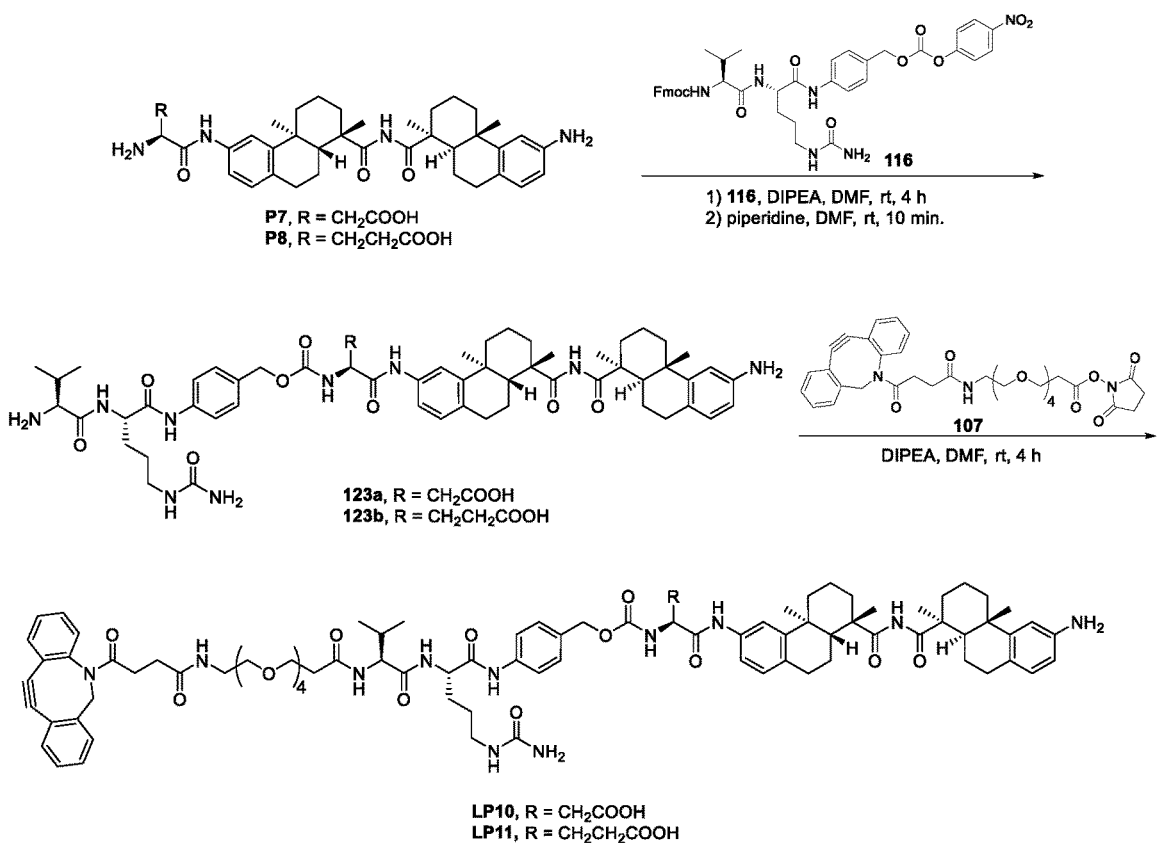

FIG. 9. Synthesis of P12 and LP12; and P16 and LP16
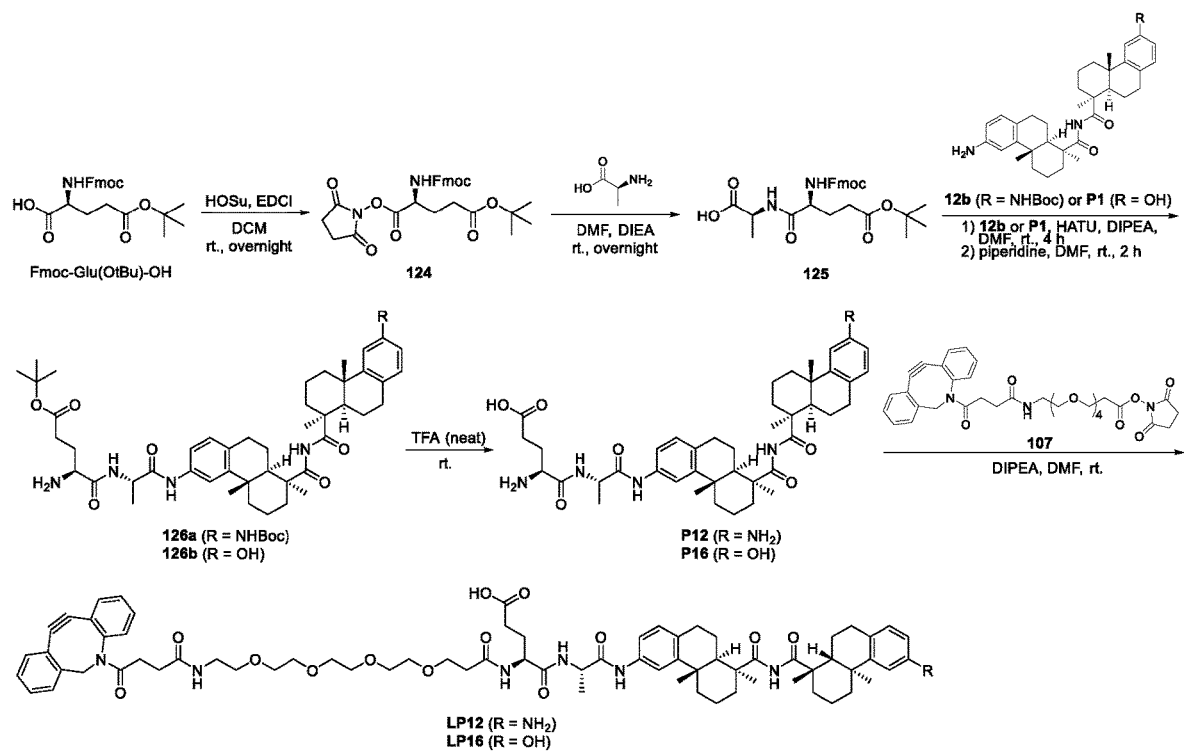

FIG. 9A. Synthesis of LP13 and LP14
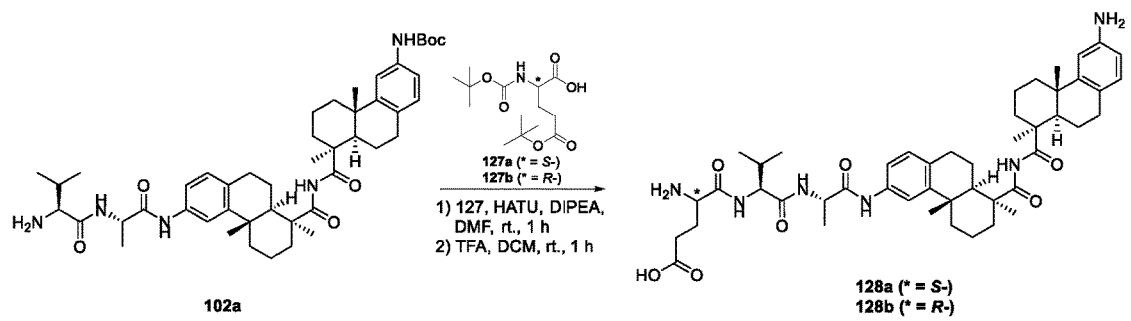
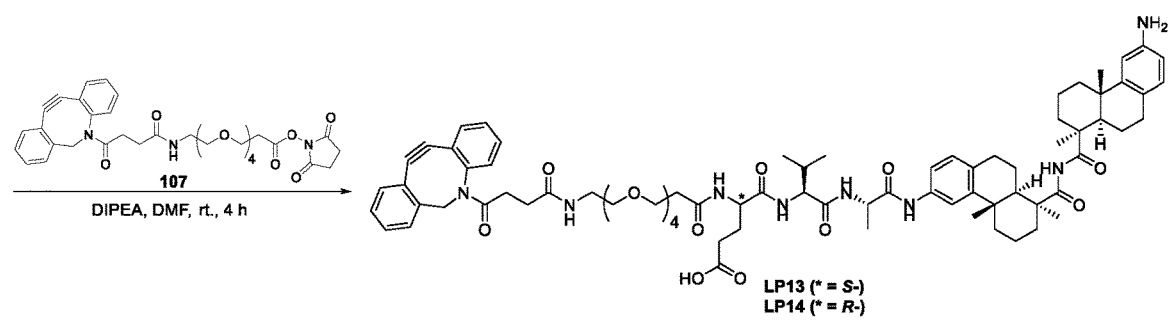
FIG. 9B. Synthesis of LP15
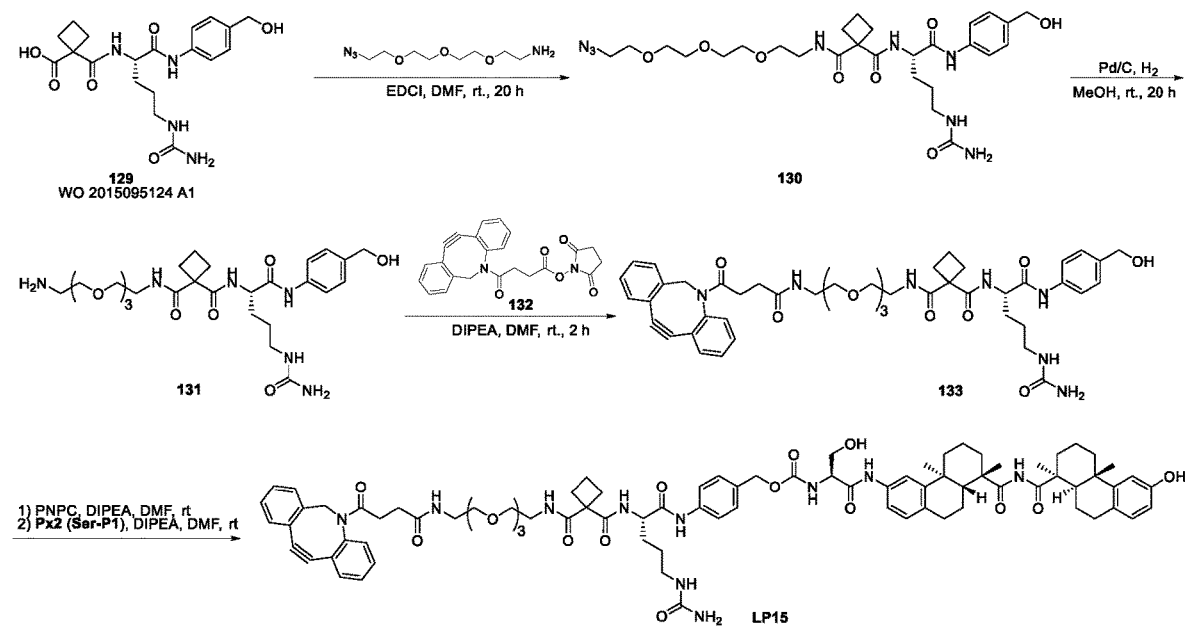

FIG. 9C. Synthesis of P18 and LP17 and LP18
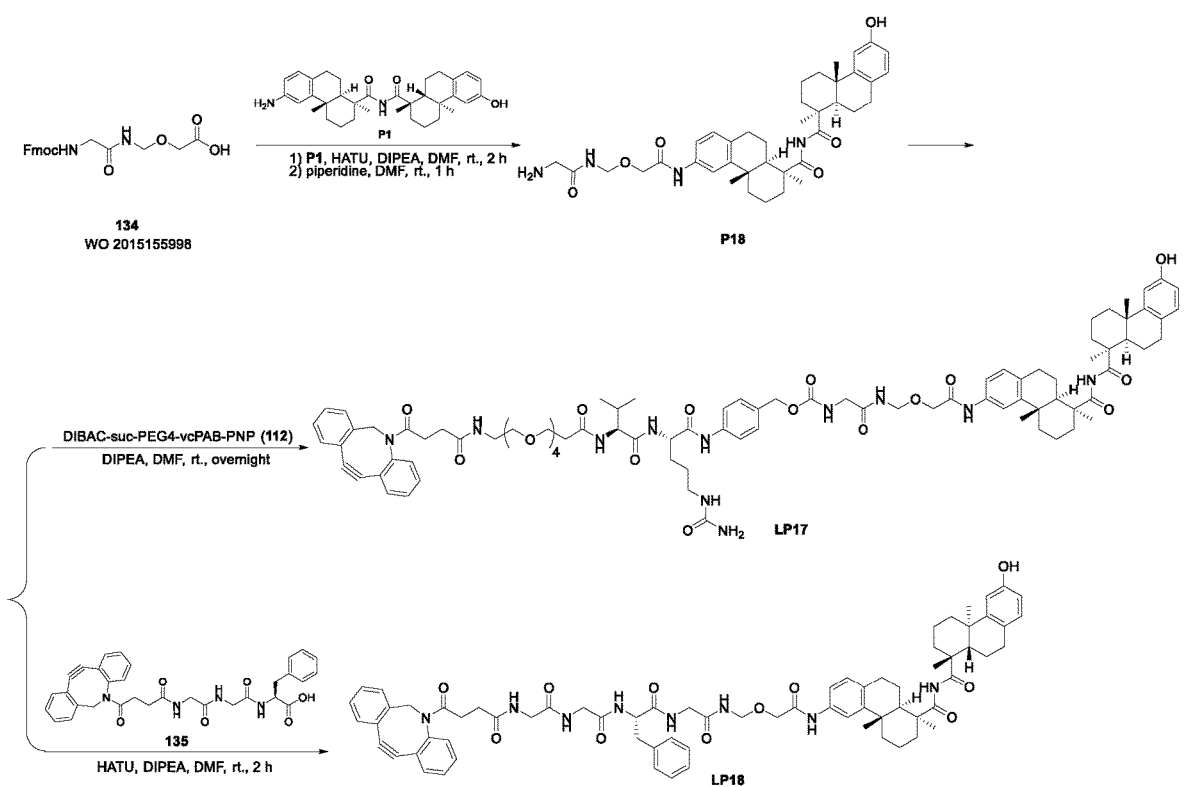

FIG. 9D. Synthesis of LP19
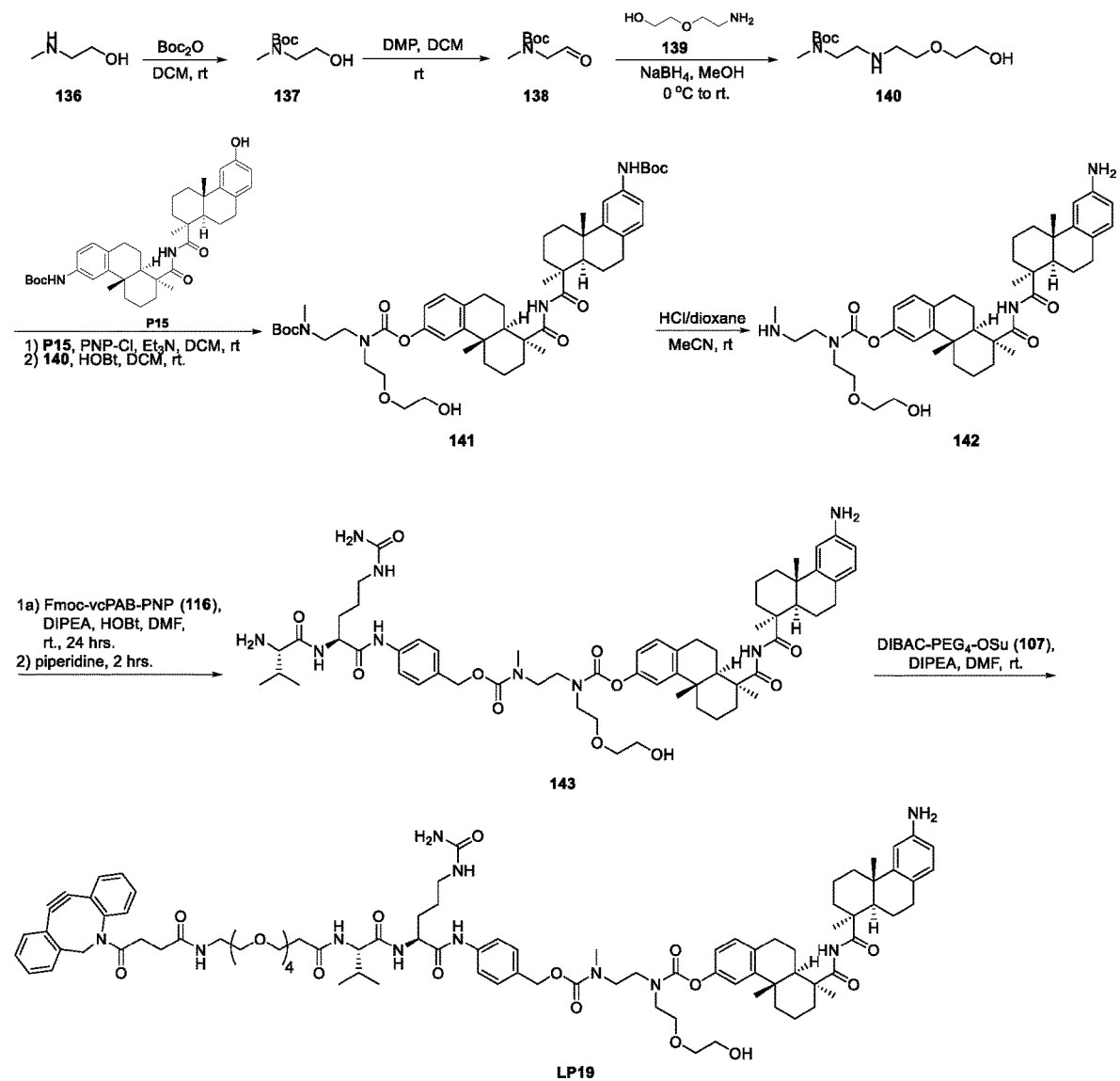

FIG. 10. Synthesis of Azide 105a
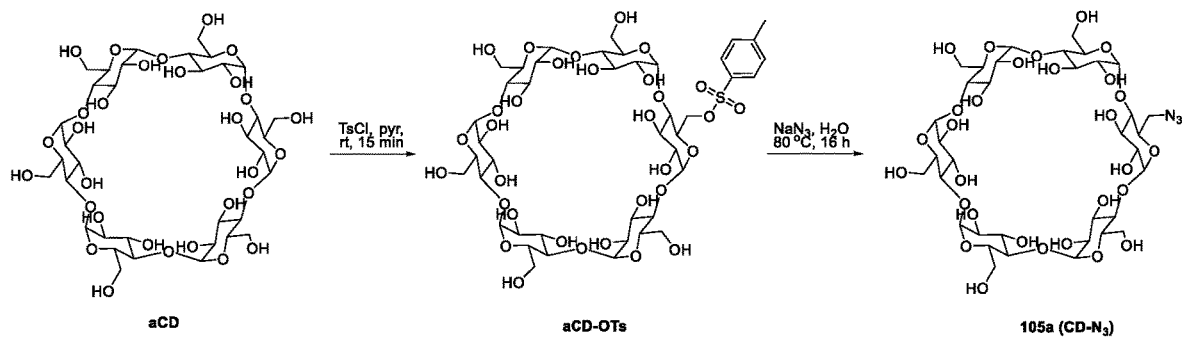
FIG. 11. Synthesis of Azide 105b
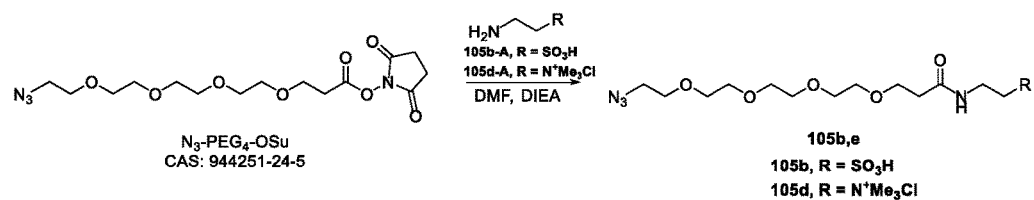
FIG. 12. Synthesis of intermediate 105c
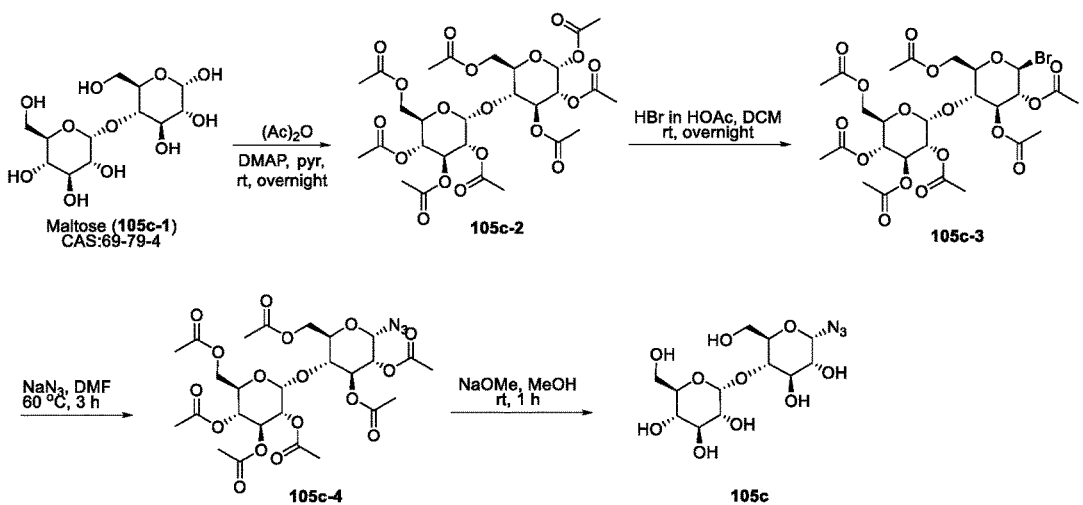

FIG. 13. Activation of Cholesterol Efflux by an anti-MSR1 ADC Having a P2 Payload
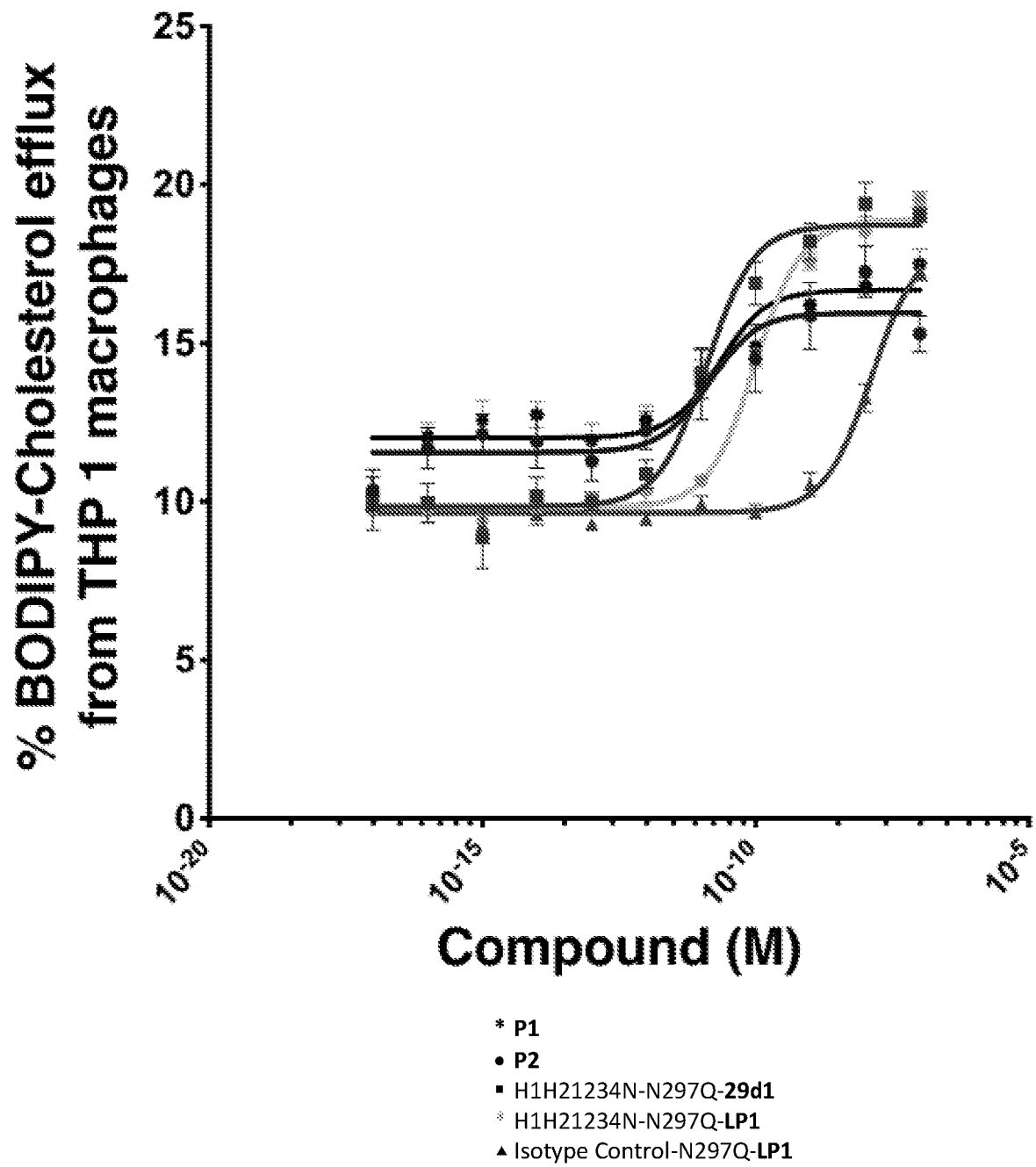

BIS-OCTAHYDROPHENANTHRENE CARBOXAMIDE DERIVATIVES AND PROTEIN CONJUGATES THEREOF FOR USE AS LXR AGONISTS

CROSS-REFERENCE

This application is the National Stage of International Application No. PCT/US2019/062302, filed Nov. 19, 2019, which claims the benefit U.S. Provisional Application No. 62/769,946, filed Nov. 18, 2018, the contents of which are hereby incorporated by reference in their entireties.

FIELD

Provided herein are novel, bis-octahydrophenanthrene carboxamides and protein conjugates thereof, and methods for treating a variety of diseases, disorders, and conditions including administering the bis-octahydrophenanthrene carboxamides, and protein conjugates thereof.

BACKGROUND

Antibody-drug conjugates (ADCs) are antibodies that are attached to biologically active small molecule drugs, thus combining the targeting specificity of antibodies with the mode-of-action and potency of small molecule drugs. The therapeutic utility of ADCs has been validated in cancer treatment and is a major ongoing focus of study. ADCETRIS® (brentuximab vedotin) and KADCYLA® (ado-trastuzumab emtansine) are two ADCs approved for the treatment of certain cancer types, and at least forty ADCs are currently in clinical development.

Liver X Receptor (LXR) includes LXRα and LXRβ which are ligand-dependent transcription factors that control the expression of genes involved in cholesterol, lipid and glucose homeostasis, inflammation, and innate immunity. LXRα is highly expressed in liver, intestine, adipose tissue, and differentiated macrophages; and LXRβ is ubiquitously expressed. LXRs have various biological functions including (i) stimulating the expression of cholesterol transporters, for example, ABCA1 and ABCG1, both of which mediate cellular cholesterol efflux; and (ii) negatively regulating macrophage inflammatory gene expression via repression of NF-kB activation. LXRs have also been implicated in atherosclerosis, proliferative disorders, neurodegenerative disorders, and inflammation. Proliferative disorders include melanomas, lung cancer, oral squamous carcinoma, and prostate cancer. (Pencheva et al. 2004; Wu et al. 2015; Kaneko et al. 2015; Chuu et al. 2006) Neurodegenerative disorders include Alzheimer's disease and myelin gene expression. (Terwel et al. 2011; Sandoval-Hernandez et al. 2016; Meffre et al. 2014) Inflammation includes inflammatory bowel disease, ulcerative colitis, Crohn's disease, and arthritis. (Anderson et al. 2011; Huang et al. 2015; Cui et al. 2012). Macrophage LXRs are known to include anti-atherogenic activity. LXR agonists are believed to be capable of (i) inhibiting the initiation and delay the progression of atherosclerosis; (ii) mitigating atherosclerosis and stabilizing established atherosclerotic lesions; and (iii) reducing lesion macrophage content by apoptosis.

The therapeutic potential of small molecule LXR modulators is limited by, for example, undesired modulation of LXR at non-target cells and/or low bioavailability. Modulation of LXR at non-target cells can lead to undesirable side effects, and low bioavailability may manifest for myriad reasons including, without limitation, low solubility that further exacerbates poor therapeutic windows for treatment. The development of ADCs comprising LXR modulators would allow for target-specific modulation of LXR, thereby avoiding side-effects caused by off-target modulation of LXR. Furthermore, such ADCs would provide improved modulation of biological targets, improved bioavailability, and improved therapeutic window. Therefore, there is a continuing need for effective treatments of, for example, metabolic diseases using small molecule ADCs of LXR modulators.

SUMMARY

Provided herein are compounds useful, for example, for the treatment of metabolic diseases including, without limitation, dyslipidemia. Also provided herein are compounds useful, for example, for the treatment of inflammation or a neurodegenerative disease.

In one embodiment, provided herein are compounds of Formula I:

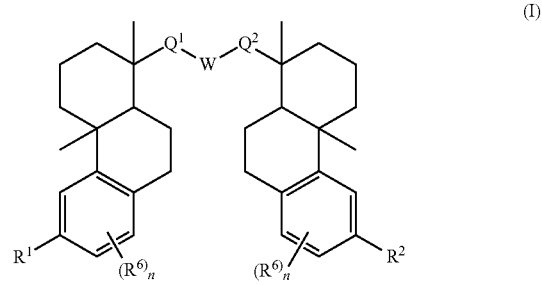

(I)

or a pharmaceutically acceptable salt, solvate, or stereoisomeric form thereof, wherein each of $Q^1$ and $Q^2$ is independently —$CH_2$—, —C(O)—, —C(H)(OH)—, —C(OH)$_2$—, —$SO_2$—, —SO—, —PO(OR$^3$)—, —PO(NR$^3$NR$^4$)—, —NR$^3$—, or —N=;

W is —$CH_2$—, —N(H)—, or —O—;

$R^1$ is —N(H)R$^4$ or —N(R$^5$)$_2$;

$R^2$ is —N(H)R$^4$;

each $R^4$ is, independently in each instance, hydrogen, an amino acid residue, an N-alkyl amino acid residue, a peptide residue, a biodegradable moiety, alkyl, substituted alkyl, acyl, or substituted acyl;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —$CH_2OH$, or at least one primary or secondary nitrogen;

each $R^6$ is independently halo, $C_{1-6}$ alkyl, $C_{1-6}$ alkoxy, —CN, O-glucose, O-amino acid residue, or O-PEG$_{n1}$, wherein each n is an integer from 0-14, and each n1 is an integer from 1-12; and each $R^3$ is independently hydrogen, alkyl, or aryl.

In one embodiment, provided herein are compounds according to Formula I:

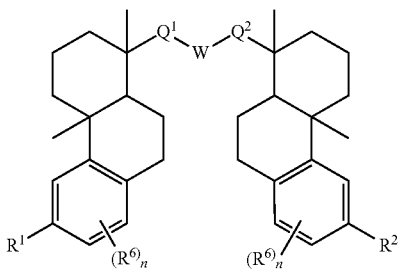

(I)

or a pharmaceutically acceptable salt, solvate, or stereoisomeric form thereof, wherein each of $Q^1$ and $Q^2$ is independently —$CH_2$—, —C(O)—, —C(H)(OH)—, —$C(OH)_2$—, —$SO_2$—, —SO—, —$PO(OR^3)$—, —$PO(NR^3NR^4)$—, —$NR^3$—, or —N=;

W is —$CH_2$—, —N(H)—, or —O—;

$R^1$ is —$N(H)R^4$ or —$N(R^5)_2$;

$R^2$ is —$N(H)R^4$;

each $R^4$ is, independently in each instance, hydrogen, an amino acid residue, an N-alkyl amino acid residue, a peptide residue, a biodegradable moiety, or alkyl;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —$CH_2OH$, or at least one primary or secondary nitrogen;

each $R^6$ is independently halo, $C_{1-6}$ alkyl, $C_{1-6}$ alkoxy, —CN, O-glucose, O-amino acid residue, or O-$PEG_{n1}$, wherein each n is an integer from 0-14, and each n1 is an integer from 1-12; and each $R^3$ is independently hydrogen, alkyl, or aryl.

In another embodiment, set forth herein is a linker-payload having a compound according to Formula I, above, bonded to a linker.

In another embodiment, set forth herein is an antibody-drug conjugate having a compound of Formula I or linker-payload, above, bonded to an antibody or an antigen binding fragment thereof.

In one embodiment, set forth herein are compounds according to Formulae A, B, C, or D:

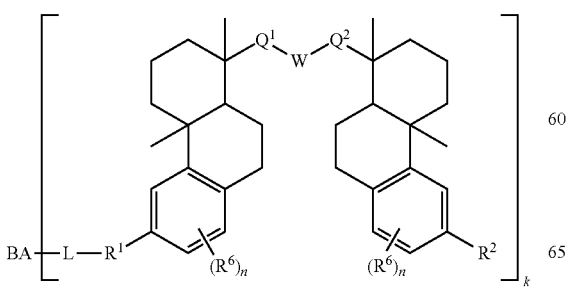

(A)

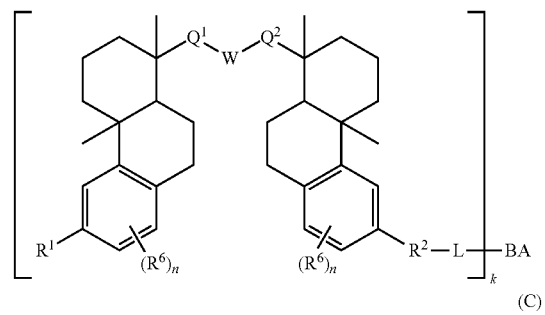

(B)

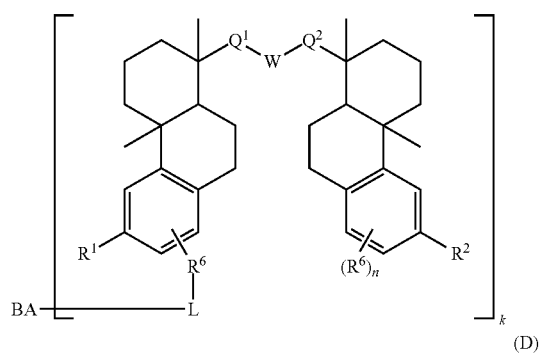

(C)

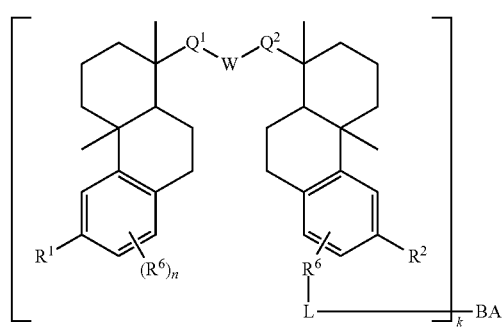

(D)

or a pharmaceutically acceptable salt, or stereoisomeric form thereof, wherein

L is a linker;

BA is a binding agent;

k is an integer from 1 to 30;

each of $Q^1$ and $Q^2$ is independently —$CH_2$—, —C(O)—, —C(H)(OH)—, —$C(OH)_2$—, —$SO_2$—, —SO—, —$PO(OR^3)$—, —$PO(NR^3NR^4)$—, —$NR^3$—, or —N=;

W is —$CH_2$—, —N(H)—, or —O—;

$R^1$ is —$N(H)R^4$, —$N(H)R^4$—, —N(H)—, —$N(R^5)_2$, or —$N(R^5)_2$—;

$R^2$ is —$N(H)R^4$, —$N(H)R^4$—, or —N(H)—;

each $R^4$ is, independently in each instance, hydrogen, an amino acid residue, an N-alkyl amino acid residue, a peptide residue, a biodegradable moiety, alkyl, substituted alkyl, acyl, substituted acyl, or -alkylene-;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —$CH_2OH$, or at least one primary or secondary nitrogen;

each $R^6$ is independently halo, $C_{1-6}$ alkyl, $C_{1-6}$ alkylene, $C_{1-6}$ alkoxy, —CN, O-glucose, O-amino acid residue, or O-PEG$_{n1}$, wherein each n is an integer from 0-14, and each n1 is an integer from 1-12; and each R$^3$ is independently hydrogen, alkyl, or aryl.

In another embodiment, set forth herein are compounds according to Formulae A, B, C, or D:

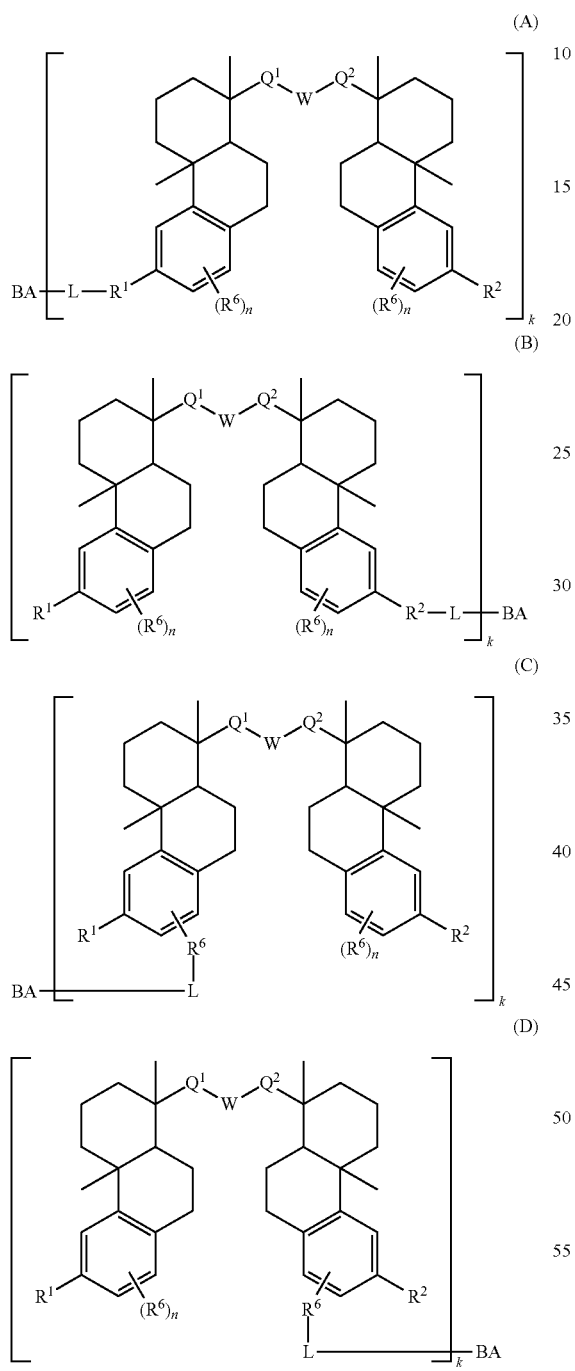

or a pharmaceutically acceptable salt, or stereoisomeric form thereof, wherein

L is a linker;

BA is a binding agent;

k is an integer from 1 to 30;

each of Q$^1$ and Q$^2$ is independently —CH$_2$—, —C(O)—, —C(H)(OH)—, —C(OH)$_2$—, —SO$_2$—, —SO—, —PO(OR$^3$)—, —PO(NR$^3$NR$^4$)—, —NR$^3$—, or —N═;

W is —CH$_2$—, —N(H)—, or —O—;

R$^1$ is —N(H)R$^4$, —N(H)R$^4$—, —N(H)—, —N(R$^5$)$_2$, or —N(R$^5$)$_2$—;

R$^2$ is —N(H)R$^4$, —N(H)R$^4$—, or —N(H)—;

each R$^4$ is, independently in each instance, hydrogen, an amino acid residue, an N-alkyl amino acid residue, a peptide residue, a biodegradable moiety, alkyl, or -alkylene-;

R$^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —CH$_2$OH, or at least one primary or secondary nitrogen;

each R$^6$ is independently halo, C$_{1-6}$ alkyl, C$_{1-6}$ alkylene, C$_{1-6}$ alkoxy, —CN, O-glucose, O-amino acid residue, or O-PEG$_{n1}$, wherein each n is an integer from 0-14, and each n1 is an integer from 1-12; and each R$^3$ is independently hydrogen, alkyl, or aryl.

In another embodiment, set forth herein is a pharmaceutical composition, including a compound, linker-payload, or antibody-drug conjugate described herein and a pharmaceutically acceptable excipient, carrier, or diluent.

In another embodiment, set forth herein is a method for the treatment of dyslipidemia, a metabolic disease, inflammation, or a neurodegenerative disease in a subject including the administration to the subject of an effective treatment amount of a compound, linker-payload, or antibody-drug conjugate, or pharmaceutical composition described herein.

In another embodiment, set forth herein are methods for making the compounds, linker-payloads, or antibody-drug conjugates, and compositions described herein.

BRIEF DESCRIPTIONS OF THE DRAWING

FIGS. 1 and 2 show synthetic chemistry schemes for payloads, compounds, and bis-octahydrophenanthrene carboxamides.

FIGS. 3-9 show synthetic chemistry schemes for linker-payloads, cyclodextrin-based linker-payloads, PEG$_4$-taurine-based linker-payloads, and maltose-based linker-payloads.

FIGS. 10-12 show synthetic chemistry schemes for cyclodextrin-azides, azido-PEG$_4$-taurines, and maltose-azides.

FIG. 13 shows EC$_{50}$ plots for the activation of cholesterol efflux by an anti-MSR1 ADC having a P2 payload.

DESCRIPTION OF EXEMPLARY EMBODIMENTS

Provided herein are compounds or payloads, linker-payloads, antibody-drug conjugates, compositions, and methods useful for treating, for example, dyslipidemia, a metabolic disease, inflammation, or a neurodegenerative disease, in a subject.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 10%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

When referring to the compounds or payloads, linker-payloads (LPs), or antibody-drug conjugates provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, and constitutional isomers thereof, cyclopropyl, cyclobutyl, cyclopentyl, and cyclohexyl.

As used herein, "constitutional isomers" refers to compounds that have the same molecular formula, but different chemical structures resulting from the way the atoms are arranged. Exemplary constitutional isomers include n-propyl and isopropyl; n-butyl, sec-butyl, and tert-butyl; and n-pentyl, isopentyl, and neopentyl, and the like.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted.

As used herein, the term "O-amino acid" or "HO-amino acid" designates an amino acid wherein the native amino group at the N-terminus of an amino acid or an amino acid sequence has been replaced with an oxygen or hydroxyl group, respectively. For example, "O-AAAA" or "HO-AAAA" is intended to designate an amino acid sequence (AAAA) wherein the native amino group at the N-terminus has been replaced with an oxygen or hydroxyl group, respectively (e.g.,

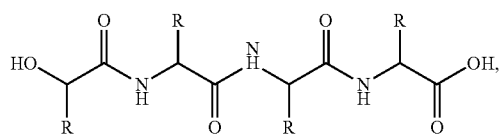

where each R is an amino acid side chain). Similarly, the terms "O-amino acid residue" or "HO-amino acid residue" refers to the chemical moiety within a compound that remains after a chemical reaction. For example, "O-amino acid residue" or "HO-amino acid residue" refers to the product of an amide coupling or peptide coupling of an O-amino acid or a HO-amino acid to a suitable coupling partner; wherein, for example, a water molecule is expelled after the amide or peptide coupling of the O-amino acid or a HO-amino acid, resulting in the product having the O-amino acid residue or a HO-amino acid residue incorporated therein.

Designation of an amino acid or amino acid residue without specifying its stereochemistry is intended to encompass the L-form of the amino acid, the D-form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, —$CF_3$, —$CH_2CF_3$, —$CCl_2F$, and —$CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O— for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, and a hexoxy moiety, cyclopropoxy, cyclobutoxy, cyclopentoxy, and cyclohexoxy (i.e.,

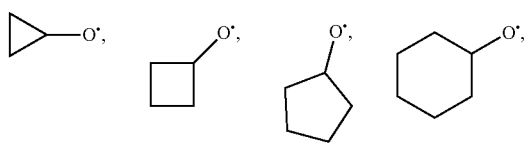

respectively).

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are not limited to phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

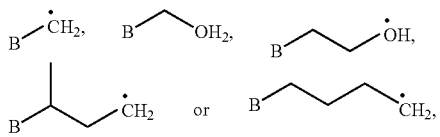

wherein B is an aromatic moiety, e.g., phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group. An alkylaryl can be represented by the structure, e.g.,

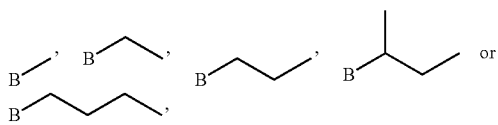

wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.,

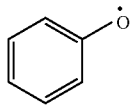

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "$R^aR^bN$-aryloxy" refers to a monovalent moiety that is a radical of an aromatic compound wherein the ring atoms are carbon atoms and wherein the ring is substituted with at least one $R^aR^bN$-substituent and at least one oxygen radical, i.e., the aromatic compound includes a single bond to an $R^aR^bN$-substituent and a single bond to an oxygen atom and wherein the radical is localized on the oxygen atom, e.g.,

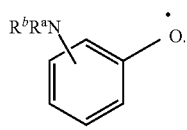

$R^aR^bN$-aryloxy substituents bond to the compound which they substitute through this oxygen atom. $R^aR^bN$-aryloxy is optionally substituted. $R^aR^bN$-aryloxy includes, but is not limited to, those having 6 to 20 ring carbon atoms, for example, $C_{6-20}$ $(R^aR^bN)_{nn}$-aryloxy, 6 to 15 ring carbon atoms, for example, $C_{6-15}$ $(R^aR^bN)_{nn}$-aryloxy, and 6 to 10 ring carbon atoms, for example, $C_{6-10}$ $(R^aR^bN)_{nn}$-aryloxy, wherein nn represents the number of $R^aR^bN$-substituents. An example of an $R^aR^bN$-aryloxy moiety includes, but is not limited to 4-(dimethylamino)-phenoxy,

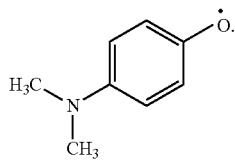

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl. As used herein, "heteroalkylene," "heteroalkenylene," and "heteroalkynylene" are divalent forms of heteroalkyl, heteroalkenyl, and heteroalkynyl, respectively.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "Lewis acid" refers to a molecule or ion that accepts an electron lone pair. The Lewis acids used in the methods described herein are those other than protons. Lewis acids include, but are not limited to, non-metal acids, metal acids, hard Lewis acids, and soft Lewis acids. Lewis acids include, but are not limited to, Lewis acids of aluminum, boron, iron, tin, titanium, magnesium, copper, antimony, phosphorus, silver, ytterbium, scandium, nickel, and zinc. Illustrative Lewis acids include, but are not limited to, $AlBr_3$, $AlCl_3$, $BCl_3$, boron trichloride methyl sulfide, $BF_3$, boron trifluoride methyl etherate, boron trifluoride methyl sulfide, boron trifluoride tetrahydrofuran, dicyclohexylboron trifluoromethanesulfonate, iron (III) bromide, iron (III) chloride, tin (IV) chloride, titanium (IV) chloride, titanium (IV) isopropoxide, $Cu(OTf)_2$, $CuCl_2$, $CuBr_2$, zinc chloride, alkylaluminum halides ($R_nAlX_{3-n}$, wherein R is hydrocarbyl), $Zn(OTf)_2$, $ZnCl_2$, $Yb(OTf)_3$, $Sc(OTf)_3$, $MgBr_2$, $NiCl_2$, $Sn(OTf)_2$, $Ni(OTf)_2$, and $Mg(OTf)_2$.

As used herein, "N-containing heterocycloalkyl," refers to a cycloalkyl in which one or more carbon atoms are replaced by heteroatoms and wherein at least one heteroatom is a nitrogen atom. Suitable heteroatoms in addition to nitrogen, include, but are not limited to oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "O-glucose" refers to a monovalent moiety attached via an exocyclic glucose oxygen atom. Suitable O-glucose moieties include, without limitation,

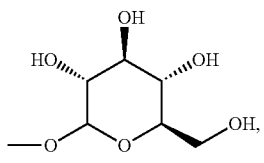

and the like.

As used herein, "O-PEG$_{n1}$" refers to a monovalent moiety attached via the terminal oxygen atom, where n1 is from 1 to 100. For example, when n1 is 1, then O-PEG$_{n1}$ is —O—CH$_2$CH$_2$OH; when n1 is two, then O-PEG$_{n1}$ is —O—CH$_2$CH$_2$O—CH$_2$CH$_2$OH; and when n1 is three, then O-PEG$_{n1}$ is —O—CH$_2$CH$_2$O—CH$_2$CH$_2$O—CH$_2$CH$_2$OH.

As used herein, "optionally substituted," when used to describe a radical moiety, for example, optionally substituted alkyl, means that such moiety is optionally bonded to one or more substituents. Examples of such substituents include, but are not limited to, halo, cyano, nitro, optionally substituted haloalkyl, azido, epoxy, optionally substituted heteroaryl, optionally substituted heterocycloalkyl,

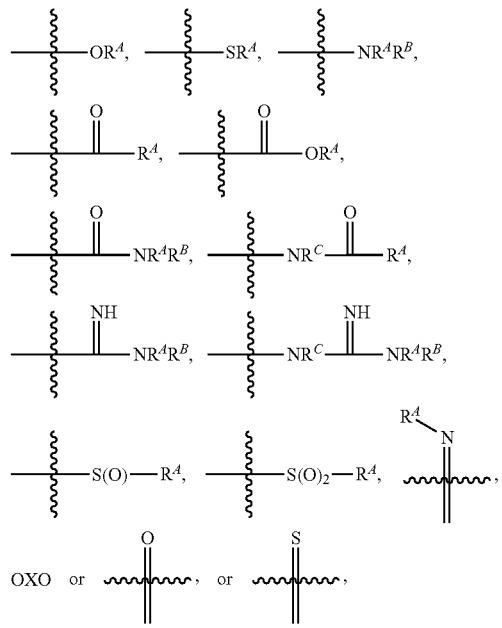

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "acyl" refers to

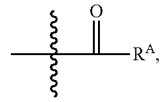

where $R^A$ is alkyl, or optionally substituted alkyl. As also used herein, "optionally substituted acyl" refers to when $R^A$ is optionally substituted.

As used herein, "binding agent" refers to any molecule, e.g., protein, capable of binding with specificity to a given binding partner, e.g., antigen.

As used herein, "linker" refers to a divalent, trivalent, or multivalent moiety that covalently links the binding agent to one or more compounds described herein, for instance payload compounds and enhancement agents.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refers to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxide hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "regioisomer," "regioisomers," or "mixture of regioisomers" refers to the product(s) of 1,3-cycloadditions or strain-promoted alkyne-azide cycloadditions (SPAACs)—otherwise known as click reactions—that derive from suitable azides (e.g., —$N_3$, or PEG-$N_3$ derivitized antibodies) treated with suitable alkynes. In certain embodiments, for example, regioisomers and mixtures of regioisomers are characterized by the click reaction products shown below:

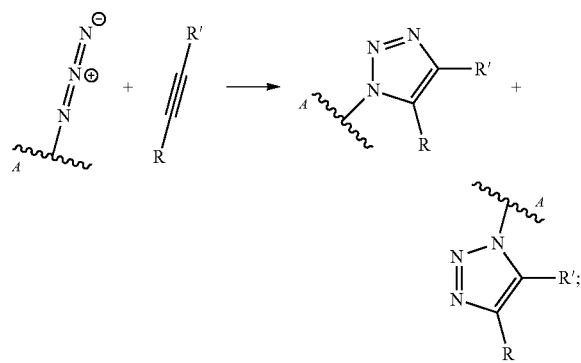

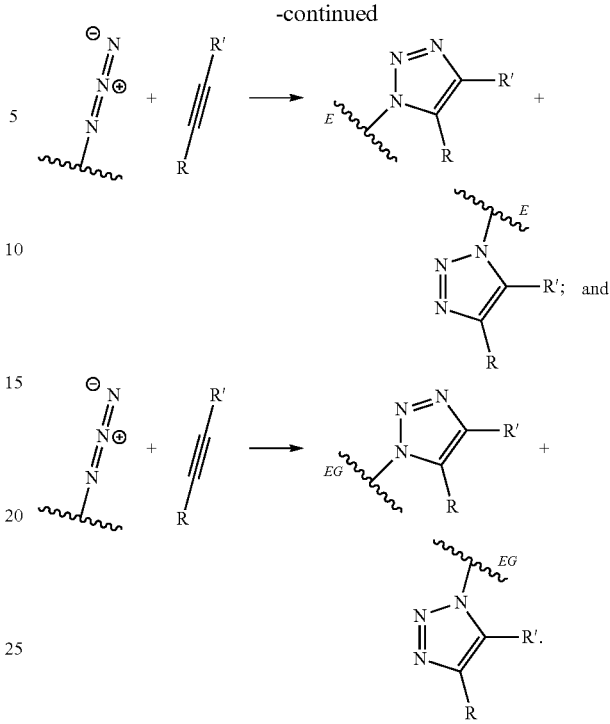

In certain embodiments, more than one suitable azide and more than one suitable alkyne can be utilized within a synthetic scheme en route to a product, where each pair of azide-alkyne can participate in one or more independent click reactions to generate a mixture of regioisomeric click reaction products. For example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers in a sample of an ADC described herein. By way of further example, a person of skill will recognize that a first suitable azide may independently react with a first suitable alkyne, and a second suitable azide may independently react with a second suitable alkyne, en route to a product, resulting in the generation of four possible click reaction regioisomers or a mixture of the four possible click reaction regioisomers in a sample of an LP described herein.

As used herein, the term "residue" refers to the chemical moiety within a compound that remains after a chemical reaction. For example, the term "amino acid residue" or "N-alkyl amino acid residue" refers to the product of an amide coupling or peptide coupling of an amino acid or a N-alkyl amino acid to a suitable coupling partner; wherein, for example, a water molecule is expelled after the amide or peptide coupling of the amino acid or the N-alkylamino acid, resulting in the product having the amino acid residue or N-alkyl amino acid residue incorporated therein.

As used herein, "therapeutically effective amount" refers to an amount (e.g., of a compound or payload) that is sufficient to provide a therapeutic benefit to a patient in the treatment or management of a disease or disorder, or to delay or minimize one or more symptoms associated with the disease or disorder.

Certain groups, moieties, substituents, and atoms are depicted with a wiggly line that intersects a bond or bonds to indicate the atom through which the groups, moieties, substituents, atoms are bonded. For example, a phenyl group that is substituted with a propyl group depicted as:

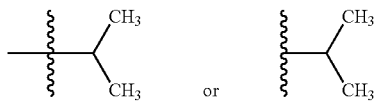

has the following structure:

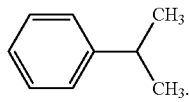

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

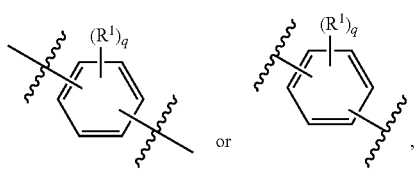

wherein subscript q is an integer from 0 to 4 and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

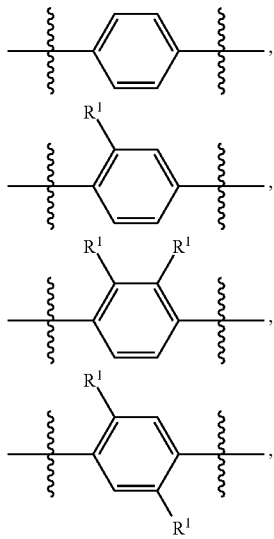

-continued

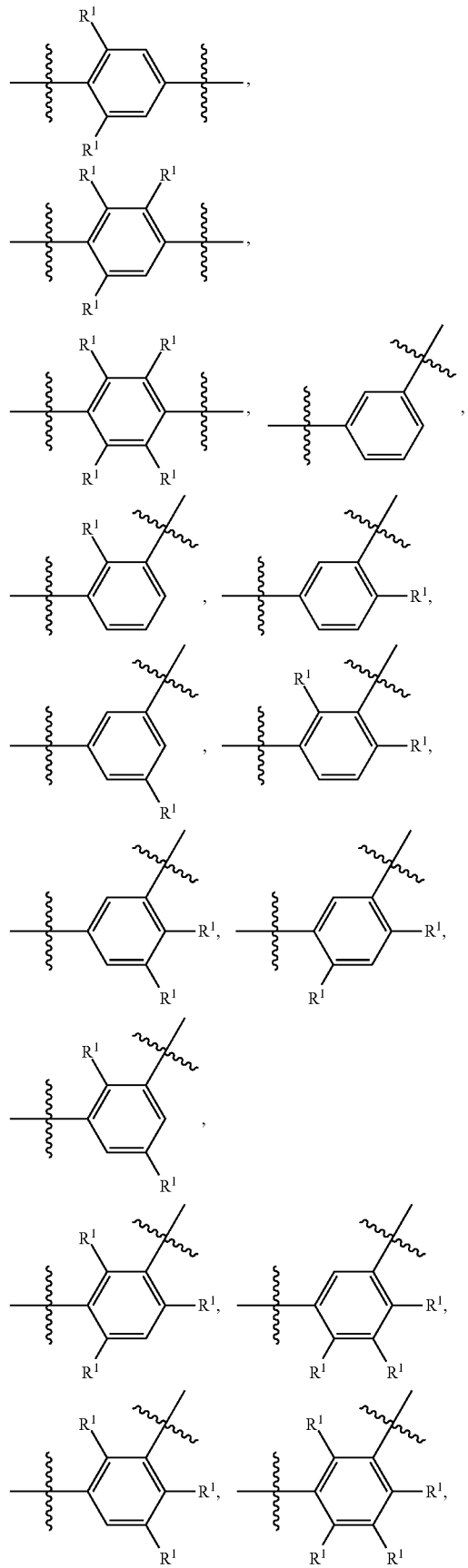

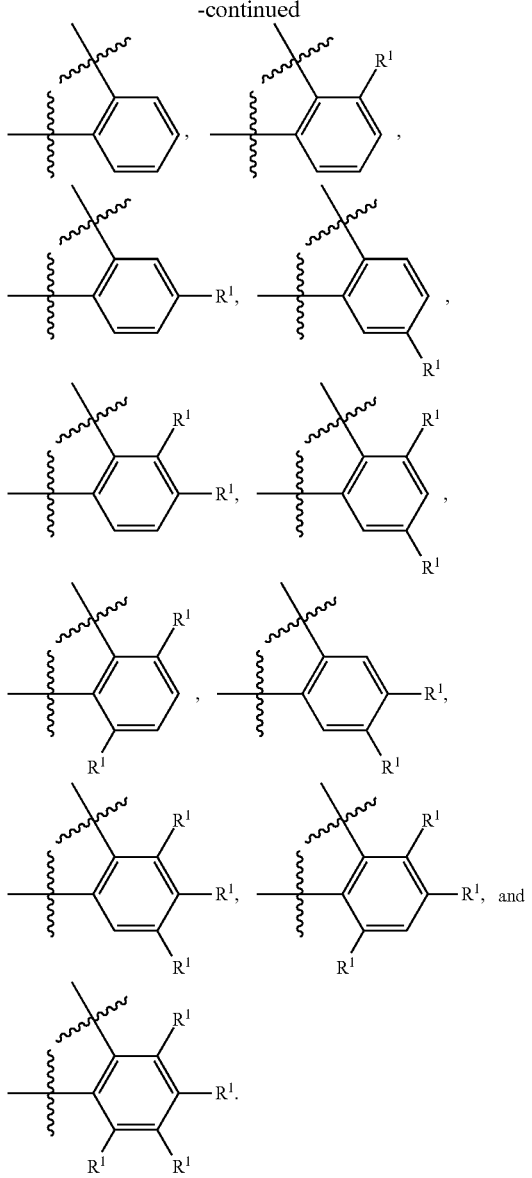

As used herein, the phrase "reactive linker," or the abbreviation "RL" refers to a monovalent group that includes a reactive group and spacer group, depicted for example, as

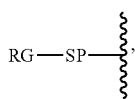

wherein RG is the reactive group and SP is the spacer group. As described herein, a reactive linker may include more than one reactive group and more than one spacer group. The spacer group is any divalent moiety that bridges the reactive group to another group, such as a payload. The reactive linkers (RL), together with the payloads to which they are bonded, provide intermediates ("linker-payloads") useful as synthetic precursors for the preparation of the antibody conjugates described herein. The reactive linker includes a reactive group ("RG"), which is a functional group or moiety that is capable of reacting with a reactive portion of another group, for instance, an antibody, modified antibody, or antigen binding fragment thereof, or an enhancement group. The moiety resulting from the reaction of the reactive group with the antibody, modified antibody, or antigen binding fragment thereof, together with the linking group, include the "binding agent linker" ("BL") portion of the conjugate, described herein. In certain embodiments, the "reactive group" is a functional group or moiety (e.g., maleimide or N-hydroxysuccinimide (NHS) ester) that reacts with a cysteine or lysine residue of an antibody or antigen-binding fragment thereof. In certain embodiments, the "reactive group" is a functional group or moiety that is capable of undergoing a click chemistry reaction (see, e.g., click chemistry, Huisgen *Proc. Chem. Soc.* 1961, Wang et al. *J. Am. Chem. Soc.* 2003, and Agard et al. *J. Am. Chem. Soc.* 2004). In some embodiments of said click chemistry reaction, the reactive group is an alkyne that is capable of undergoing a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with alkynes in the absence of copper catalysts. Suitable alkynes also include, but are not limited to, dibenzoazacyclooctyne or

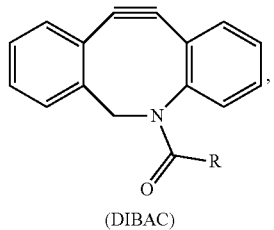
(DIBAC)

dibenzocyclooctyne or

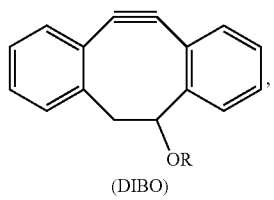
(DIBO)

biarylazacyclooctynone or

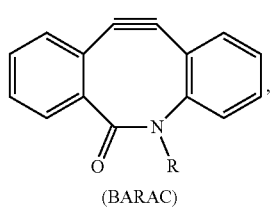
(BARAC)

difluorinated cyclooctyne or

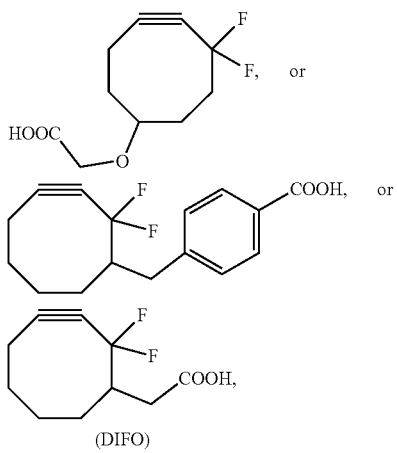

(DIFO)

substituted, e.g., fluorinated alkynes, aza-cycloalkynes, bicycle[6.1.0]nonyne or

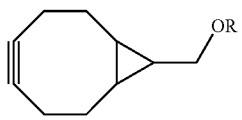

(BCN, where R is alkyl, alkoxy, or acyl), and derivatives thereof. Particularly useful alkynes include

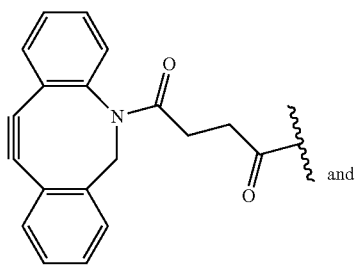

and

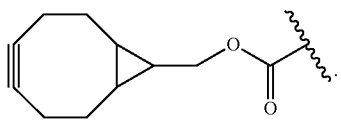

Linker-payloads including such reactive groups are useful for conjugating antibodies that have been functionalized with azido groups. Such functionalized antibodies include antibodies functionalized with azido-polyethylene glycol groups. In certain embodiments, such a functionalized antibody is derived by treating an antibody having at least one glutamine residue, e.g., heavy chain Gln295, with a compound bearing an amino group and an azide group, in the presence of the enzyme transglutaminase.

In some examples, the reactive group is an alkyne, e.g.,

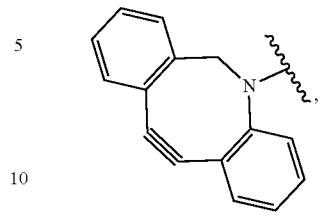

which can react via click chemistry with an azide, e.g.,

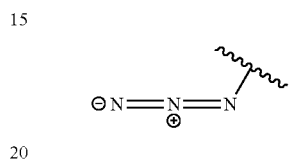

to form a click chemistry product, e.g.,

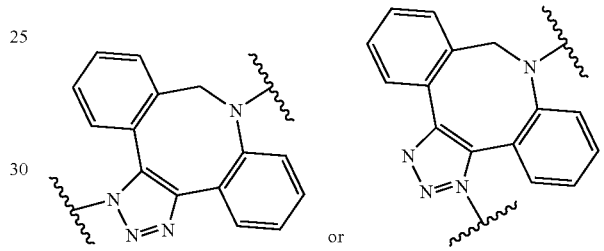

In some examples, the group reacts with an azide on a modified antibody or antigen binding fragment thereof. In some examples, the reactive group is an alkyne, e.g.,

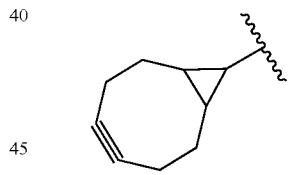

which can react via click chemistry with an azide, e.g.,

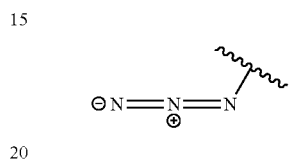

to form a click chemistry product, e.g.,

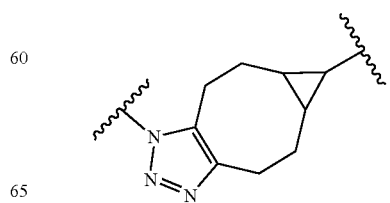

In some examples, the reactive group is an alkyne, e.g.,

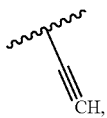 [SMILES: *C#C]

which can react via click chemistry with an azide, e.g.,

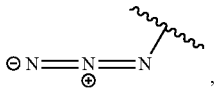

to form a click chemistry product, e.g.,

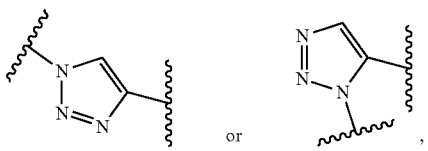 [SMILES: *c1cn(*)nn1 ; *c1cnnn1*]

In some examples, the reactive group is a functional group, e.g.,

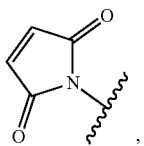

which reacts with a cysteine residue on an antibody or antigen-binding fragment thereof, to form a bond thereto, e.g.,

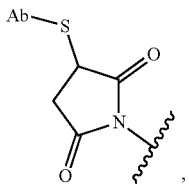

wherein Ab refers to an antibody or antigen-binding fragment thereof and S refers to the S atom on a cysteine residue through which the functional group bonds to the Ab. In some examples, the reactive group is a functional group, e.g.,

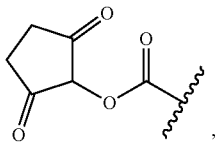 [SMILES: *C(=O)OC1C(=O)CCC1=O]

which reacts with a lysine residue on an antibody or antigen-binding fragment thereof, to form a bond thereto, e.g.,

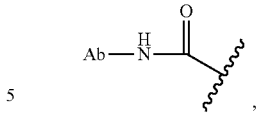

wherein Ab refers to an antibody or antigen-binding fragment thereof and NH refers to the NH atom on a lysine side chain residue through which the functional group bonds to the Ab.

As used herein, the phrase "biodegradable moiety" refers to a moiety that degrades in vivo to non-toxic, biocompatible components which can be cleared from the body by ordinary biological processes. In some embodiments, a biodegradable moiety completely or substantially degrades in vivo over the course of about 90 days or less, about 60 days or less, or about 30 days or less, where the extent of degradation is based on percent mass loss of the biodegradable moiety, and wherein complete degradation corresponds to 100% mass loss. Exemplary biodegradable moieties include, without limitation, aliphatic polyesters such as poly(s-caprolactone) (PCL), poly(3-hydroxybutyrate) (PHB), poly(glycolic acid) (PGA), poly(lactic acid) (PLA) and its copolymers with glycolic acid (i.e., poly(D,L-lactide-coglycolide) (PLGA) (Vert M, Schwach G, Engel R and Coudane J (1998) J Control Release 53(1-3):85-92; Jain R A (2000) Biomaterials 21(23):2475-2490; Uhrich K E, Cannizzaro S M, Langer R S and Shakesheff K M (1999) Chemical Reviews 99(11): 3181-3198; and Park T G (1995) Biomaterials 16(15):1123-1130, each of which are incorporated herein by reference in their entirety).

As used herein, the phrases "effective amount," "physiologically effective amount," or "prophylactically effective amount" refer to that amount of compound that is sufficient to effect treatment, when administered to a subject in need of such treatment. A "physiologically effective amount" of an active substance indicates an efficacious amount of the active substances to have a significant, externally observable effect on the patient. Thus, a physiologically effective amount affects one or more of the characteristics (e.g., phenotype) in the patient without the need for special equipment to determine the effect. For example, a physiologically effective amount of a compound disclosed herein has a significant, externally observable effect on the behavior of the patient by reducing one or more of the symptoms of the condition to be treated. Accordingly, one can determine whether an efficacious amount of the active substance has been administered by observing the patient and observing whether changes have occurred in the patient due to the active substance.

As used herein, the phrase "binding agent linker," or "BL" refers to any divalent, trivalent, or multi-valent group or moiety that links, connects, or bonds a binding agent (e.g., an antibody or an antigen-binding fragment thereof) with a payload compound set forth herein (e.g., bis-octahydrophenanthrene carboxamides) and, optionally, with one or more side chain compounds. Generally, suitable binding agent linkers for the antibody conjugates described herein are those that are sufficiently stable to exploit the circulating half-life of the antibody and, at the same time, capable of releasing the payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citrulline units, and para-aminobenzyl (PAB) units. In some embodiments, the binding agent linker (BL) includes a moiety that is formed by the reaction of the reactive group (RG) of a reactive linker (RL) and reactive portion of the binding agent, e.g., antibody, modified antibody, or antigen binding fragment thereof.

In some examples, the BL includes the following moiety:

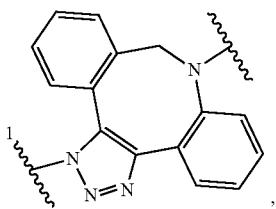

or the triazolyl regioisomer, wherein $\overset{1}{\xi}$ is the bond to the binding agent. In some examples, the BL includes the following moiety:

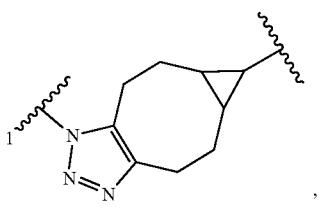

wherein $\overset{1}{\xi}$ is the bond to the binding agent. In some examples, the BL includes the following moiety:

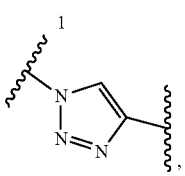 [SMILES: *c1cn(*)nn1]

or the triazolyl regioisomer, wherein $\overset{1}{\xi}$ is the bond to the binding agent. In some examples, the BL includes the following moiety:

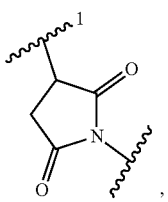

wherein $\overset{1}{\xi}$ is the bond to the cysteine of the antibody or antigen-binding fragment thereof. In some examples, the BL includes the following moiety:

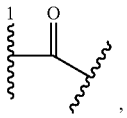

wherein $\overset{1}{\xi}$ is the bond to the lysine of the antibody or antigen-binding fragment thereof.

Compounds or Payloads

In some embodiments, set forth herein is a compound having the structure of Formula (I):

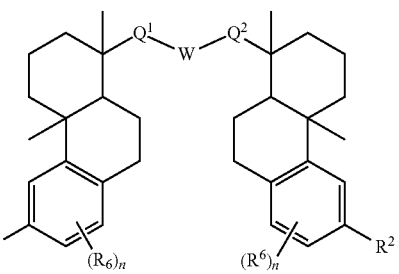

(I)

or a pharmaceutically acceptable salt, solvate, or stereoisomeric form thereof, wherein each of $Q^1$ and $Q^2$ is independently —$CH_2$—, —C(O)—, —C(H)(OH)—, or —C(OH)$_2$—;

W is —$CH_2$—, —N(H)—, or —O—;

$R^1$ is —N(H)$R^4$ or —N($R^5$)$_2$;

$R^2$ is —N(H)$R^4$;

each $R^4$ is, independently in each instance, hydrogen, an amino acid residue, an N-alkyl amino acid residue, a peptide residue, a biodegradable moiety, alkyl, substituted alkyl, acyl, or substituted acyl;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —$CH_2OH$, or at least one primary or secondary nitrogen; and each $R^6$ is independently halo, $C_{1-6}$ alkyl, $C_{1-6}$ alkoxy, —CN, O-glucose, O-amino acid residue, or O-PEG$_{n1}$, wherein each n is an integer from 0-14, and each n1 is an integer from 1-12.

In one embodiment of Formula I, $Q^1$ is —$CH_2$—, $Q^2$ is —C(O)—, and W is —$CH_2$—. In one embodiment of Formula I, $Q^1$ is —$CH_2$—, $Q^2$ is —C(O)—, and W is —O—. In one embodiment of Formula I, $Q^1$ is —$CH_2$—, $Q^2$ is —C(O)—, and W is —NH—. In any of the embodiments in this paragraph, $R^1$ is —N(H)$R^4$ or —N($R^5$)$_2$, and $R^2$ is —N(H)$R^4$. In any of the embodiments in this paragraph, $R^1$ is —N(H)$R^4$ and $R^2$ is —N(H)$R^4$. In any of the embodiments in this paragraph, $R^1$ is —N($R^5$)$_2$, and $R^2$ is —N(H)$R^4$. In any of the embodiments in this paragraph, each $R^4$ is, independently in each instance, hydrogen, an amino acid residue, an N-alkyl amino acid residue, a peptide residue, a biodegradable moiety, alkyl, substituted alkyl, acyl, or substituted acyl. In any of the embodiments in this paragraph, each $R^4$ is, independently in each instance, hydrogen, an amino acid residue, an N-alkyl amino acid residue, a peptide residue, a biodegradable moiety, or alkyl. In any of the embodiments in this paragraph, each $R^4$ is hydrogen. In any of the embodiments in this paragraph, each $R^4$ is, independently in each instance, an amino acid residue. In any of the embodiments in this paragraph, each $R^4$ is, independently in each instance, an N-alkyl amino acid residue. In any of the embodiments in this paragraph, each $R^4$ is, independently in each instance, a peptide residue. In any of the embodiments in this paragraph, each $R^4$ is, independently in each instance, a biodegradable moiety. In any of the embodiments in this paragraph, each $R^4$ is, independently in each instance, alkyl. In any of the embodiments in this paragraph, each $R^4$ is, independently in each instance, substituted alkyl. In any of the embodiments in this paragraph, each $R^4$ is, independently in each instance, acyl. In any of the embodiments in this paragraph, each $R^4$ is, independently in each instance, substituted acyl. In any embodiment in this paragraph, one $R^4$ is hydrogen, and the other $R^4$ is an amino acid residue. In any embodiment in this paragraph, one $R^4$ is hydrogen, and the other $R^4$ is a peptide residue. In any embodiment in this paragraph, one $R^4$ is hydrogen, and the other $R^4$ is substituted alkyl. In any embodiment in this paragraph, one $R^4$ is hydrogen, and the other $R^4$ is acyl. In any embodiment in this paragraph, one $R^4$ is hydrogen, and the other $R^4$ is substituted acyl. In any of the embodiments in this paragraph, $R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —CH$_2$OH, or at least one primary or secondary nitrogen. In any of the embodiments in this paragraph, $R^5$ is alkyl. In any of the embodiments in this paragraph, $R^5$ is aryl. In any of the embodiments in this paragraph, $R^5$ is arylalkyl. In any of the embodiments of this paragraph, $R^5$ is heterocycloalkyl. In any of the embodiments in this paragraph, $R^5$ is a substituted heterocycloalkyl. In any of the embodiments in this paragraph, $R^5$ is heterocycloalkyl and heterocycloalkyl includes one heteroatom selected from nitrogen and oxygen. In any of the embodiments in this paragraph, $R^5$ is heterocycloalkyl and heterocycloalkyl includes one nitrogen. In any of the embodiments in this paragraph, $R^5$ is heterocycloalkyl and heterocycloalkyl includes one oxygen. In any of the embodiments in this paragraph, $R^5$ is heterocycloalkyl and heterocycloalkyl includes two heteroatoms selected from nitrogen and oxygen. In any of the embodiments in this paragraph, $R^5$ is heterocycloalkyl and heterocycloalkyl includes two nitrogen atoms. In any of the embodiments in this paragraph, $R^5$ is heterocycloalkyl and heterocycloalkyl includes two oxygen atoms. In any of the embodiments in this paragraph, $R^5$ is heterocycloalkyl and heterocycloalkyl includes one nitrogen and one oxygen. In any of the embodiments in this paragraph, $R^5$ is heterocycloalkyl and heterocycloalkyl includes three heteroatoms selected from nitrogen and oxygen. In any of the embodiments in this paragraph, $R^5$ is heterocycloalkyl and heterocycloalkyl includes three nitrogen atoms. In any of the embodiments in this paragraph, $R^5$ is heterocycloalkyl and heterocycloalkyl includes two nitrogen atoms and one oxygen atom. In any of the embodiments of this paragraph, $R^5$ is a substituted heterocycloalkyl and includes one heteroatom selected from nitrogen and oxygen. In any of the embodiments of this paragraph, $R^5$ is a substituted heterocycloalkyl and includes one nitrogen. In any of the embodiments of this paragraph, $R^5$ is a substituted heterocycloalkyl and includes one oxygen. In any of the embodiments of this paragraph, $R^5$ is a substituted heterocycloalkyl and includes two heteroatoms selected from nitrogen and oxygen. In any of the embodiments of this paragraph, $R^5$ is a substituted heterocycloalkyl and includes two nitrogen atoms. In any of the embodiments of this paragraph, $R^5$ is a substituted heterocycloalkyl and includes two oxygen atoms. In any of the embodiments of this paragraph, $R^5$ is a substituted heterocycloalkyl and includes one nitrogen and one oxygen. In any of the embodiments of this paragraph, $R^5$ is a substituted heterocycloalkyl and includes three heteroatoms selected from nitrogen and oxygen. In any of the embodiments of this paragraph, $R^5$ is a substituted heterocycloalkyl and includes three nitrogen atoms. In any of the embodiments of this paragraph, $R^5$ is a substituted heterocycloalkyl and includes two nitrogen atoms and one oxygen atom. In any of the embodiments of this paragraph, $R^5$ is a substituted heterocycloalkyl and includes one heteroatom selected from nitrogen and oxygen, as above, and includes at least one —OH and —CH$_2$OH. In any of the embodiments of this paragraph, $R^5$ is a substituted heterocycloalkyl and includes two heteroatoms selected from nitrogen and oxygen, as above, and includes at least one —OH and —CH$_2$OH. In any of the embodiments of this paragraph, $R^5$ is a substituted heterocycloalkyl and includes three heteroatoms selected from nitrogen and oxygen, as above, and includes at least one —OH and —CH$_2$OH. In any of the embodiments of this paragraph, $R^5$ is a substituted heterocycloalkyl and includes one heteroatom selected from nitrogen and oxygen, as above, and includes at least one primary nitrogen. In any of the embodiments of this paragraph, $R^5$ is a substituted heterocycloalkyl and includes two heteroatoms selected from nitrogen and oxygen, as above, and includes at least one primary nitrogen. In any of the embodiments of this paragraph, $R^5$ is a substituted heterocycloalkyl and includes three heteroatoms selected from nitrogen and oxygen, as above, and includes at least one primary nitrogen. In any of the embodiments of this paragraph, $R^5$ is a substituted heterocycloalkyl and includes one heteroatom selected from nitrogen and oxygen, as above, and includes at least one secondary nitrogen. In any of the embodiments of this paragraph, $R^5$ is a substituted heterocycloalkyl and includes two heteroatoms selected from nitrogen and oxygen, as above, and includes at least one secondary nitrogen. In any of the embodiments of this paragraph, $R^5$ is a substituted heterocycloalkyl and includes three heteroatoms selected from nitrogen and oxygen, as above, and includes at least one secondary nitrogen. In any of the embodiments of this paragraph, each $R^6$ is independently halo, $C_{1-6}$ alkyl, $C_{1-6}$ alkoxy, —CN, O-glucose, O-amino acid residue, or O-PEG$_{n1}$, wherein each n is an integer from 0-14, and each n1 is an integer from 1-12. In any of the embodiments of this paragraph, each $R^6$ is independently halo. In any of the embodiments of this paragraph, each $R^6$ is independently $C_{1-6}$ alkyl. In any of the embodiments of this paragraph, each $R^6$ is independently $C_{1-6}$ alkoxy. In any of the embodiments in this paragraph, each $R^6$ is —CN. In any of the embodiments in this paragraph, each $R^6$ is independently an O-glucose. In any of the embodiments in this paragraph, each $R^6$ is independently an O-amino acid residue. In any embodiment in this paragraph, each $R^6$ is independently an O-PEG$_{n1}$, wherein each n1 is an integer from 1-12. In any embodiment in this paragraph, each $R^6$ is independently an O-PEG$_{n1}$, wherein each n1 is 1. In any embodiment in this paragraph, each $R^6$ is independently an O-PEG$_{n1}$, wherein each n1 is 2. In any embodiment in this paragraph, each R$^6$ is independently an O-PEG$_{n1}$, wherein each n1 is 3. In any embodiment in this paragraph, each R$^6$ is independently an O-PEG$_{n1}$, wherein each n1 is 4. In any embodiment in this paragraph, each R$^6$ is independently an O-PEG$_{n1}$, wherein each n1 is 5. In any embodiment in this paragraph, each R$^6$ is independently an O-PEG$_{n1}$, wherein each n1 is 6. In any embodiment in this paragraph, each R$^6$ is independently an O-PEG$_{n1}$, wherein each n1 is 7. In any embodiment in this paragraph, each R$^6$ is independently an O-PEG$_{n1}$, wherein each n1 is 8. In any embodiment in this paragraph, each R$^6$ is independently an O-PEG$_{n1}$, wherein each n1 is 9. In any embodiment in this paragraph, each R$^6$ is independently an O-PEG$_{n1}$, wherein each n1 is 10. In any embodiment in this paragraph, each R$^6$ is independently an O-PEG$_{n1}$, wherein each n1 is 11. In any embodiment in this paragraph, each R$^6$ is independently an O-PEG$_{n1}$, wherein each n1 is 12. In any of the embodiments of this paragraph, each R$^6$ is independently halo, C$_{1-6}$ alkyl, C$_{1-6}$ alkoxy, —CN, O-glucose, O-amino acid residue, or O-PEG$_{n1}$, wherein each n is an integer from 0-14, and each n1 is an integer from 1-12, and any combination thereof. For example, in one embodiment, one R$^6$ is halo, and the other R$^6$ is C$_{1-6}$ alkyl. Other exemplary R$^6$ combination embodiments have been contemplated, as would be appreciated by a person of skill in the art. In any of the embodiments of this paragraph, suitable amino acids as amino acid residues or to be combined as peptide residues include alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid, and any combination thereof as peptide residues, as would be appreciated by a person of skill in the art. Those of skill in the art will recognize that the amino acid residue may be achiral or chiral, for example, L-amino acid residues or D-amino acid residues. Those of skill in the art will recognize that the peptide residues may be achiral or chiral, for example, including racemic DL-amino acids or non-racemic D- or L-amino acids and diastereomeric mixtures thereof. In any of the embodiments of this paragraph, suitable arylalkyl moieties include, benzyl, phenethyl, phenylpropyl, α-methylbenzyl and each stereoisomer thereof, and 2-phenylpropyl and each stereoisomer thereof. In any of the embodiments of this paragraph, arylalkyl is benzyl. In any of the embodiments of this paragraph, arylalkyl is phenethyl. In any of the embodiments of this paragraph, arylalkyl is phenylpropyl. In any of the embodiments of this paragraph, arylalkyl is α-methylbenzyl and each stereoisomer thereof. In any of the embodiments of this paragraph, arylalkyl is (R)-α-methylbenzyl. In any of the embodiments of this paragraph, arylalkyl is (S)-α-methylbenzyl. In any of the embodiments of this paragraph, arylalkyl is 2-phenylpropyl (i.e., CH$_3$CH(Ph)CH$_2$—) and each stereoisomer thereof. In any of the embodiments of this paragraph, arylalkyl is (R)-2-phenylpropyl. In any of the embodiments of this paragraph, arylalkyl is (S)-2-phenylpropyl. In any of the embodiments in this paragraph, halo is selected from the group consisting of fluoro, chloro, bromo, and iodo. In any of the embodiments in this paragraph, halo is fluoro. In any of the embodiments in this paragraph, halo is chloro. In any of the embodiments in this paragraph, halo is bromo. In any of the embodiments in this paragraph, halo is iodo. In any of the embodiments in this paragraph, C$_{1-6}$ alkyl is selected from the group consisting of methyl, ethyl, propyl, butyl, pentyl, and hexyl, and constitutional isomers thereof. In any of the embodiments in this paragraph, C$_{1-6}$ alkyl is methyl or —CH$_3$. In any of the embodiments in this paragraph, C$_{1-6}$ alkyl is ethyl or —CH$_2$CH$_3$. In any of the embodiments in this paragraph, C$_{1-6}$ alkyl is propyl or constitutional isomers thereof. In any of the embodiments in this paragraph, C$_{1-6}$ alkyl is butyl or constitutional isomers thereof. In any of the embodiments in this paragraph, C$_{1-6}$ alkyl is pentyl or constitutional isomers thereof. In any of the embodiments in this paragraph, C$_{1-6}$ alkyl is hexyl or constitutional isomers thereof. In any of the embodiments in this paragraph, C$_{1-6}$ alkoxy is selected from the group consisting of methoxy, ethoxy, propyloxy, butyloxy, pentyloxy, and hexyloxy, and constitutional isomers thereof. In any of the embodiments in this paragraph, C$_{1-6}$ alkyl is methoxy or —OCH$_3$. In any of the embodiments in this paragraph, C$_{1-6}$ alkyl is ethoxy or —OCH$_2$CH$_3$. In any of the embodiments in this paragraph, C$_{1-6}$ alkyl is propyloxy or constitutional isomers thereof. In any of the embodiments in this paragraph, C$_{1-6}$ alkyl is butyloxy or constitutional isomers thereof. In any of the embodiments in this paragraph, C$_{1-6}$ alkyl is pentyloxy or constitutional isomers thereof. In any of the embodiments in this paragraph, C$_{1-6}$ alkyl is hexyloxy or constitutional isomers thereof.

In one embodiment of Formula I, Q$^1$ is —C(H)(OH)—, Q$^2$ is —C(O)—, and W is —CH$_2$—. In one embodiment of Formula I, Q$^1$ is —C(H)(OH)—, Q$^2$ is —C(O)—, and W is —O—. In one embodiment of Formula I, Q$^1$ is —C(H)(OH)—, Q$^2$ is —C(O)—, and W is —NH—. In any of the embodiments in this paragraph, R$^1$, R$^2$, R$^4$, R$^5$, and R$^6$ are as described above in the context of Formula I.

In one embodiment of Formula I, Q$^1$ is —C(O)—, Q$^2$ is —C(O)—, and W is —CH$_2$—. In one embodiment of Formula I, Q$^1$ is —C(O)—, Q$^2$ is —C(O)—, and W is —O—. In one embodiment of Formula I, Q$^1$ is —C(O)—, Q$^2$ is —C(O)—, and W is —NH—. In any of the embodiments in this paragraph, R$^1$, R$^2$, R$^4$, R$^5$, and R$^6$ are as described above in the context of Formula I.

In one embodiment of Formula I, Q$^1$ is —C(O)—, Q$^2$ is —CH$_2$—, and W is —CH$_2$—. In one embodiment of Formula I, Q$^1$ is —C(O)—, Q$^2$ is —CH$_2$—, and W is —O—. In one embodiment of Formula I, Q$^1$ is —C(O)—, Q$^2$ is —CH$_2$—, and W is —NH—. In any of the embodiments in this paragraph, R$^1$, R$^2$, R$^4$, R$^5$, and R$^6$ are as described above in the context of Formula I.

In one embodiment of Formula I, Q$^1$ is —C(O)—, Q$^2$ is —C(H)(OH)—, and W is —CH$_2$—. In one embodiment of Formula I, Q$^1$ is —C(O)—, Q$^2$ is —C(H)(OH)—, and W is —O—. In one embodiment of Formula I, Q$^1$ is —C(O)—, Q$^2$ is —C(H)(OH)—, and W is —NH—. In any of the embodiments in this paragraph, R$^1$, R$^2$, R$^4$, R$^5$, and R$^6$ are as described above in the context of Formula I.

In some embodiments, set forth herein is a compound or payload having the structure of Formula (II):

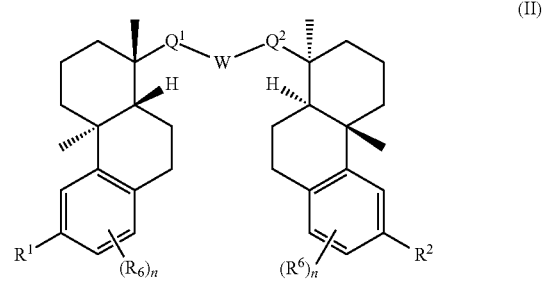

or a pharmaceutically acceptable salt, solvate, or stereoisomeric form thereof. In any of the embodiments in this paragraph, $R^1$, $R^2$, $R^4$, $R^5$, and $R^6$ are as described above in the context of Formula I.

In some embodiments, set forth herein is a compound or payload having the structure of Formula (III):

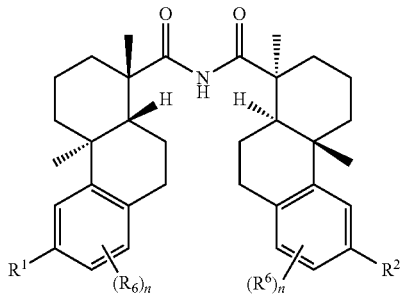

(III)

or a pharmaceutically acceptable salt, solvate, or stereoisomeric form thereof. In any of the embodiments in this paragraph, $R^1$, $R^2$, $R^4$, $R^5$, and $R^6$ are as described above in the context of Formula I.

In some embodiments, set forth herein is a compound or payload of Formulae I, II, or III wherein $R^1$ is —N(H)$R^4$. In some embodiments, set forth herein is a compound or payload of Formulae I, II, or III, wherein $R^1$ is —N($R^5$)$_2$. In any of the embodiments in this paragraph, $R^2$, $R^4$, $R^5$, and $R^6$ are as described above in the context of Formula I.

In some embodiments, set forth herein is a compound or payload of Formula I, II, or III, wherein $R^1$ is —NH$_2$; and $R^4$ is an amino acid residue, an N-alkyl amino acid residue, a peptide residue, a biodegradable moiety, alkyl, substituted alkyl, acyl, or substituted acyl. In one embodiment, set forth herein is a compound or payload of Formula I, II, or III, wherein $R^1$ is —NH$_2$; and $R^4$ is an amino acid residue. In one embodiment, set forth herein is a compound or payload of Formula I, II, or III, wherein $R^1$ is —NH$_2$; and $R^4$ is an N-alkyl amino acid residue. In one embodiment, set forth herein is a compound or payload of Formula I, II, or III, wherein $R^1$ is —NH$_2$; and $R^4$ is a peptide residue. In one embodiment, set forth herein is a compound or payload of Formula I, II, or III, wherein $R^1$ is —NH$_2$; and $R^4$ is a biodegradable moiety. In one embodiment, set forth herein is a compound or payload of Formula I, II, or III, wherein $R^1$ is —NH$_2$; and $R^4$ is alkyl. In one embodiment, set forth herein is a compound or payload of Formula I, II, or III, wherein $R^1$ is —NH$_2$; and $R^4$ is substituted alkyl. In one embodiment, set forth herein is a compound or payload of Formula I, II, or III, wherein $R^1$ is —NH$_2$; and $R^4$ is acyl. In one embodiment, set forth herein is a compound or payload of Formula I, II, or III, wherein $R^1$ is —NH$_2$; and $R^4$ is substituted acyl. In any of the embodiments in this paragraph, suitable amino acid residues are as described above in the context of Formula I. In any of the embodiments in this paragraph, suitable peptide residues are as described above in the context of Formula I. In one embodiment, set forth herein is a compound or payload wherein $R^1$ is —NH$_2$; and $R^4$ is an amino acid residue, and the amino acid residue is selected from the group consisting of alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid. In one embodiment, set forth herein is a compound or payload wherein $R^1$ is —NH$_2$; and $R^4$ is a peptide residue, wherein the peptide residue comprises amino acid residues selected from the group consisting of alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid. In any of the embodiments in this paragraph, $R^6$ is as described above in the context of Formula I.

In some embodiments, set forth herein is a compound or payload wherein $R^1$ and $R^2$ are —N(H)$R^4$. In one embodiment, set forth herein is a compound or payload wherein $R^1$ and $R^2$ are —N(H)$R^4$, and $R^4$ is, independently in each instance, an amino acid residue; and the amino acid residue is selected from the group consisting of alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid.

In certain embodiments, provided herein are compounds or payloads selected from the group consisting of:

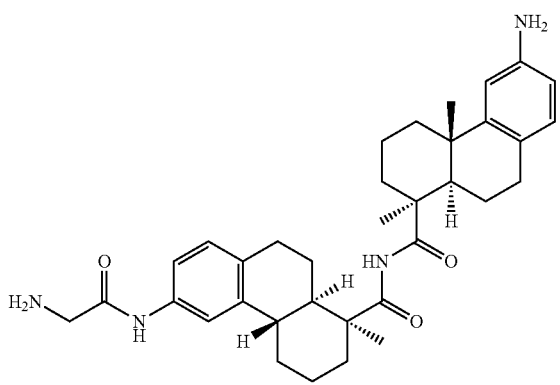

P4

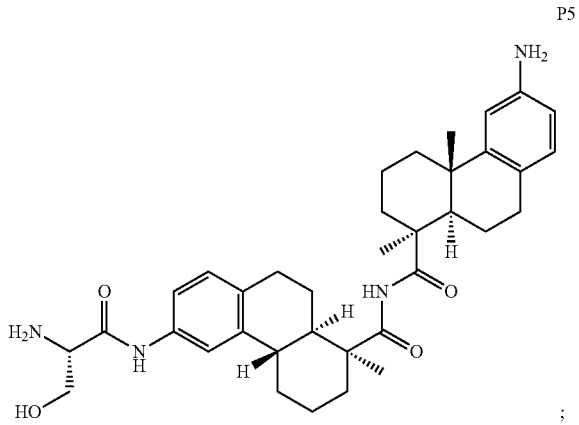

P5

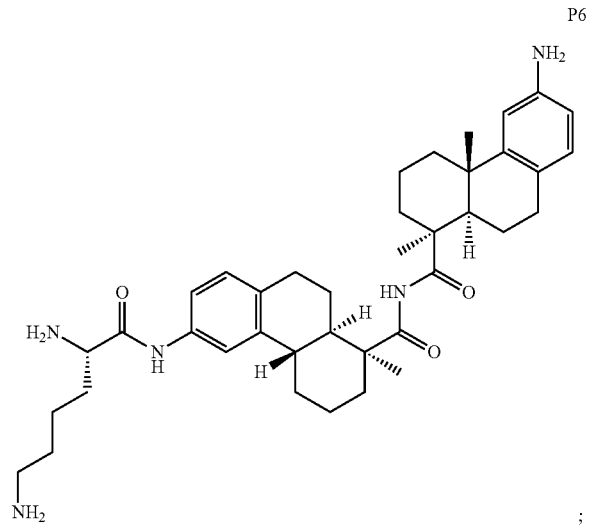
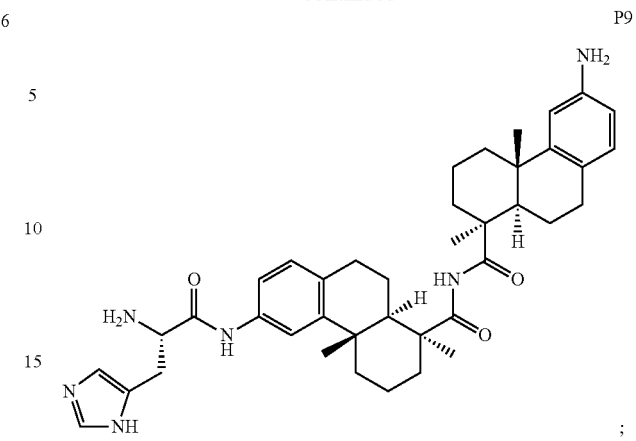
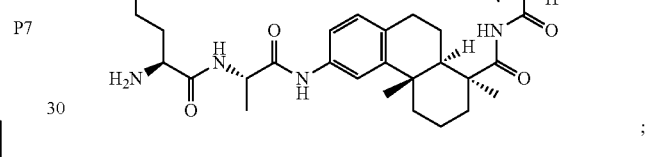
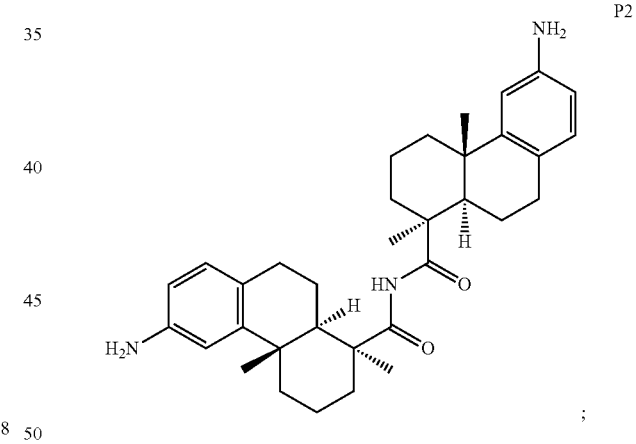
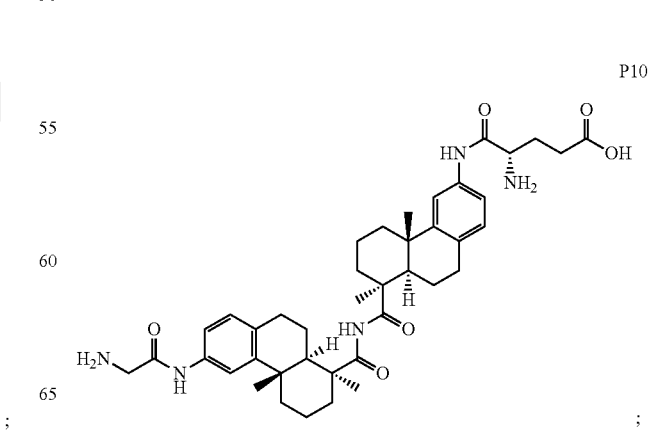

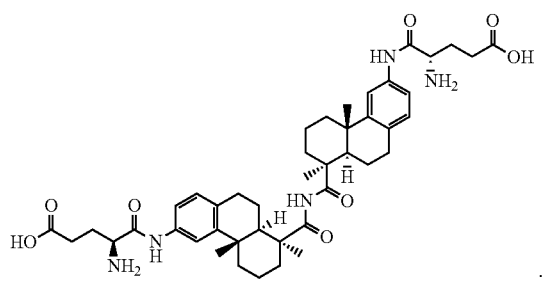
P11
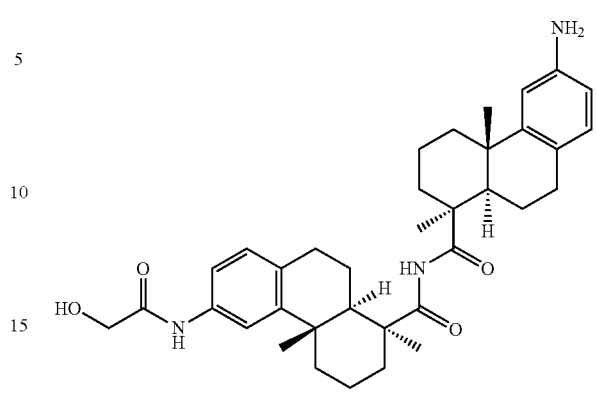
P14
; and
or a pharmaceutically acceptable salt or solvate thereof.
Further provided herein are compounds or payloads selected from the group consisting of:
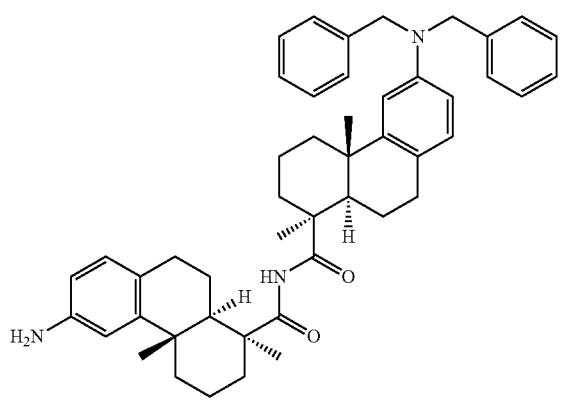
P3
;
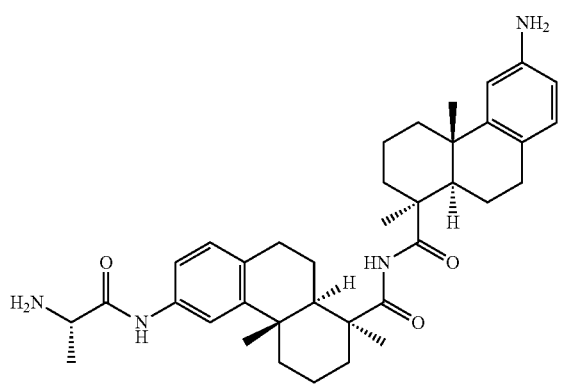
P13
;
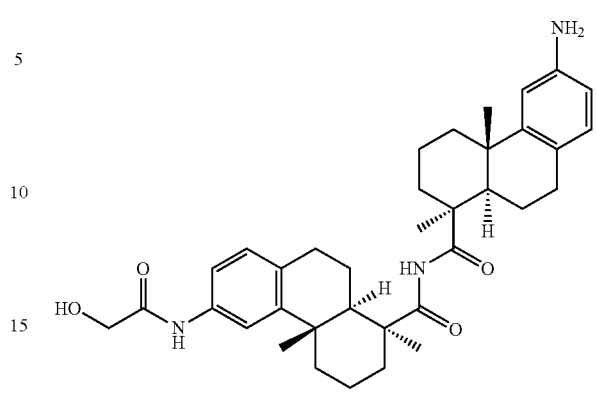
P15
;
P16
;
or a pharmaceutically acceptable salt or solvate thereof.
In one embodiment, provided herein is a compound having the following structure,

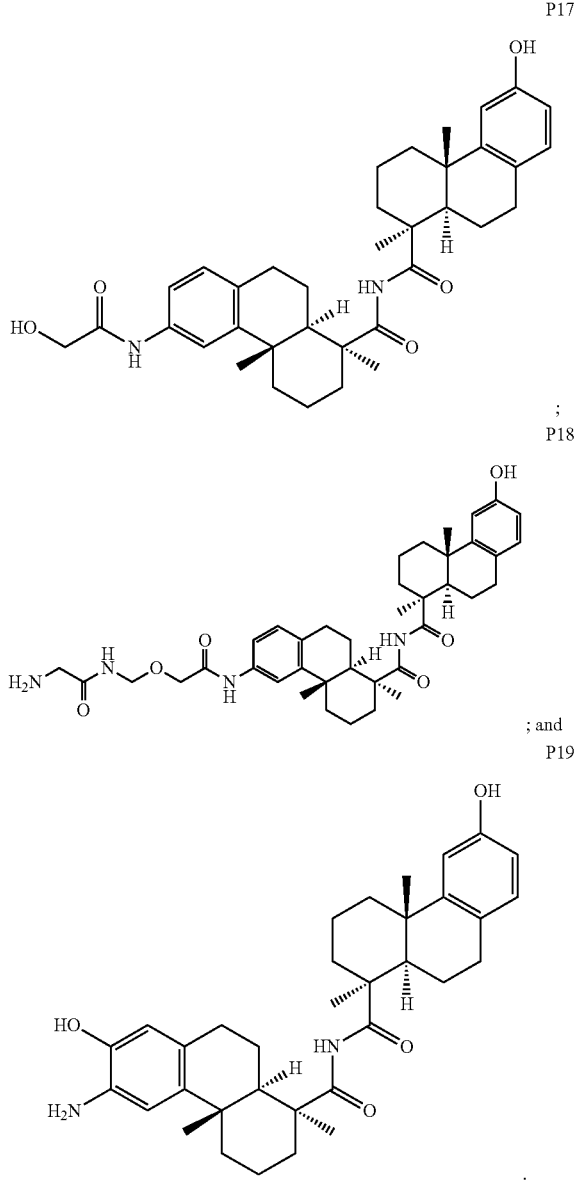

Binding Agents

Suitable binding agents for any of the conjugates provided in the instant disclosure include, but are not limited to, antibodies, lymphokines, hormones, growth factors, viral receptors, interleukins, or any other cell binding or peptide binding molecules or substances.

In some embodiments, the binding agent is an antibody or an antigen-binding fragment thereof. The antibody can be in any form known to those of skill in the art. The term "antibody," as used herein, refers to any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of this disclosure, the FRs of the antibodies (or antigen-binding portion thereof) suitable for the compounds or payloads herein may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable, standard technique(s) such as proteolytic digestion or recombinant genetic engineering technique(s) involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add, or delete amino acids, etc. Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated CDR such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein. An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain. In certain embodiments, an antigen-binding fragment of an antibody may contain at least one variable domain covalently linked to at least one constant domain.

Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60, or more) amino acids which result in a flexible or semi-flexible linkage between adjacent variable and/or constant domains in a single polypeptide molecule. As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art. In certain embodiments described herein, antibodies described herein are human antibodies. The term "human antibody," as used herein, is intended to include antibodies having variable and constant regions derived from human germline immunoglobulin sequences. The human antibodies of this disclosure may include amino acid residues not encoded by human germline immunoglobulin sequences (e.g., mutations introduced by random or site-specific mutagenesis in vitro or by somatic mutation in vivo), for example, in the CDRs and in particular CDR3. However, the term "human antibody," as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism. The antibodies of this disclosure may, in some embodiments, be recombinant human antibodies. The term "recombinant human antibody," as used herein, is intended to include all human antibodies that are prepared, expressed, created, or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge region, $C_H2$ region, or $C_H3$ region which may be desirable, for example, in production, to improve the yield of the desired antibody form. The antibodies described herein may be isolated antibodies. An "isolated antibody," as used herein, refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the instant disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals. The antibodies used herein can comprise one or more amino acid substitutions, insertions, and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2, or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be tested for one or more desired property such as, improved binding specificity, increased binding affinity, improved or enhanced antagonistic or agonistic biological properties (as the case may be), and reduced immunogenicity, etc. Antibodies and antigen-binding fragments obtained in this general manner are encompassed within the present disclosure. Antibodies useful for the compounds or payloads herein also include antibodies comprising variants of any of the HCVR, LCVR, and/or CDR amino acid sequences disclosed herein having one or more conservative substitutions. The term "epitope" refers to an antigenic determinant that interacts with a specific antigen-binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain embodiments, an epitope may include moieties of saccharides, phosphoryl groups, or sulfonyl groups on the antigen.

In certain embodiments, the antibody comprises a light chain. In certain embodiments, the light chain is a kappa light chain. In certain embodiments, the light chain is a lambda light chain. In certain embodiments, the antibody comprises a heavy chain. In some embodiments, the heavy chain is an IgA. In some embodiments, the heavy chain is an IgD. In some embodiments, the heavy chain is an IgE. In some embodiments, the heavy chain is an IgG. In some embodiments, the heavy chain is an IgM. In some embodiments, the heavy chain is an IgG1. In some embodiments, the heavy chain is an IgG2. In some embodiments, the heavy chain is an IgG3. In some embodiments, the heavy chain is an IgG4. In some embodiments, the heavy chain is an IgA1. In some embodiments, the heavy chain is an IgA2.

In some embodiments, the antibody is an antibody fragment. In some embodiments, the antibody fragment is an Fv fragment. In some embodiments, the antibody fragment is a Fab fragment. In some embodiments, the antibody fragment is a F(ab')$_2$ fragment. In some embodiments, the antibody fragment is a Fab' fragment. In some embodiments, the antibody fragment is an scFv (sFv) fragment. In some embodiments, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

The antibody can have binding specificity for any antigen deemed suitable to those of skill in the art. In certain embodiments, the antigen is a transmembrane molecule (e.g., receptor) or a growth factor. Exemplary antigens include, but are not limited to, molecules such as class A scavenger receptors including scavenger receptor A (SR-A, or MSR1), macrophage receptor with collagenous structure (MARCO), scavenger receptor with C-type lectin (SRCL), and scavenger receptor A-5 (SCARA5), COLEC12, class B macrophage scavenger receptors including CD36, LIMPII, SRBI, SRBII, class D scavenger receptor CD68, and lysosomal membrane glycoprotein (LAMP), class E scavenger receptor including lectin-like oxidized low density lipoprotein receptor 1 LOX-1 and Dectin-1, class F scavenger receptors including scavenger receptor expressed by endothelial cells-I (SREC-I) and SREC-II as well as multiple epidermal growth factor (EGF)-like domains (MEGF) 10, class G scavenger receptor CXC chemokine ligand 16 (CXCL16), class H scavenger receptors including Fasciclin, EGF-like, lamin type EGF-like and link domain-containing scavenger receptor-1 (FEEL-1) and -2 (FEEL-2), class I scavenger receptor CD163, and class J scavenger receptor receptor for advanced glycation end products (RAGE), other C-type lectin superfamily members including DEC205, CD206, Dectin-2, Mincle, DC-SIGN, and DNGR-1, and other membrane proteins such as B7 family-related member including V-set and Ig domain-containing 4 (VSIG4), Colony stimulating factor 1 receptor (CSFIR), asialoglycoprotein receptor (ASGPR), and Amyloid beta precursor-like protein 2 (APLP-2). In some embodiments, the antigen is PRLR or HER2. In some embodiments, the antibody is an anti-PRLR or anti HER2 antibody. In some embodiments, the antibody is an anti-MSR1 antibody. Exemplary anti-MSR1 antibodies are described herein.

Binding agent linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA,* 2008, 105:12451-12456), formyl glycine (see, e.g., Carrico et al., *Nat. Chem. Biol.,* 2007, 3:321-322; Agarwal et al., *Proc. Natl. Acad. Sci., USA,* 2013, 110:46-51, and Rabuka et al., Nat. Protocols, 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130).

In some examples, the binding agent is an antibody or antigen binding molecule, and the antibody is bonded to the linker through a lysine residue. In some embodiments, the antibody or antigen binding molecule is bonded to the linker through a cysteine residue.

Linkers can also be conjugated to one or more glutamine residues via transglutaminase-based chemo-enzymatic conjugation (see, e.g., Dennler et al., *Bioconjugate Chem.* 2014, 25, 569-578, and WO 2017/147542). For example, in the presence of transglutaminase, one or more glutamine residues of an antibody can be coupled to a primary amine compound. Briefly, in some embodiments, an antibody having a glutamine residue (e.g., a Gln295 residue) is treated with a primary amine compound, described in more detail below, in the presence of the enzyme transglutaminase. Primary amine compounds include, e.g., payloads, or linker-payloads, which directly provide antibody drug conjugates via transglutaminase-mediated coupling. Primary amine compounds also include linkers and spacers that are functionalized with reactive groups that can be subsequently treated with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody comprises a glutamine residue at one or more heavy chain positions numbered 295 in the EU numbering system. In the present disclosure, this position is referred to as glutamine 295, or as Gln295, or as Q295. Those of skill will recognize that this is a conserved glutamine residue in the wild type sequence of many antibodies. In other useful embodiments, the antibody can be engineered to comprise a glutamine residue. Techniques for modifying an antibody sequence to include a glutamine residue are within the skill of those in the art (see, e.g., Ausubel et al. *Current Protoc. Mol. Biol.*).

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 residue. In further embodiments, the antibody or a glutaminyl-modified antibody or antigen binding molecule comprises one or more glutamine residues at a site other than a heavy chain 295. Included herein are antibodies of this section bearing Asn297Gln (N297Q) mutation(s) described herein. Included herein are antibodies of this section bearing Gln55 (Q55) residues. As described herein, residue numbering is according to the EU numbering system.

Primary Amine Compounds

In certain embodiments, the primary amine compounds useful for the transglutaminase mediated coupling of an antibody (or antigen binding compound) comprising a glutamine can be any primary amine compound deemed useful by the practitioner of ordinary skill. Generally, the primary amine compound has the formula H$_2$N—R, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. Useful reactive groups include azides, alkynes, cycloalkynes, thiols, alcohols, ketones, aldehydes, acids, esters, hydrazides, anilines, and amines. In certain embodiments, the reactive group is selected from the group consisting of azide, alkyne, sulfhydryl, cycloalkyne, aldehyde, and carboxyl.

In certain embodiments, the primary amine compound is according to the formula H$_2$N-LL-X, where LL is a divalent spacer and X is a reactive group or protected reactive group. In particular embodiments, LL is a divalent polyethylene glycol (PEG) group. In certain embodiments, X is selected from the group consisting of —SH, —N$_3$, alkyne, aldehyde, and tetrazole. In particular embodiments, X is —N$_3$.

In certain embodiments, the primary amine compound is according to one of the following formulas:

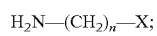

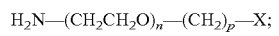

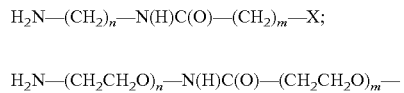

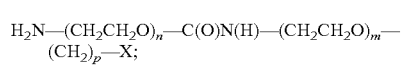

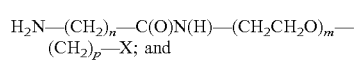

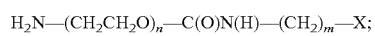

H$_2$N—(CH$_2$)$_n$—C(O)N(H)—(CH$_2$CH$_2$O)$_m$—
(CH$_2$)$_p$—X; and

H$_2$N—(CH$_2$CH$_2$O)$_n$—C(O)N(H)—(CH$_2$)$_m$—X;

where n is an integer selected from 1 to 12;
m is an integer selected from 0 to 12;
p is an integer selected from 0 to 2;
and X is selected from the group consisting of —SH, —N$_3$, —C≡CH, —C(O)H, tetrazole, and any of

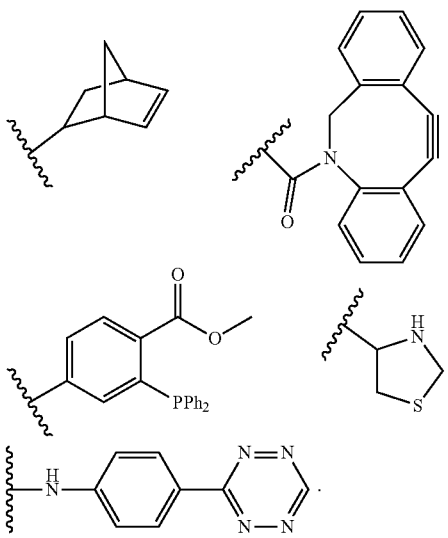

In the above, any of the alkyl (i.e., —CH$_2$—) groups can optionally be substituted, for example, with C$_{1-8}$ alkyl, methylformyl, or —SO$_3$H. In certain embodiments, the alkyl groups are unsubstituted.

In certain embodiments, the primary amine compound is selected from the group consisting of:

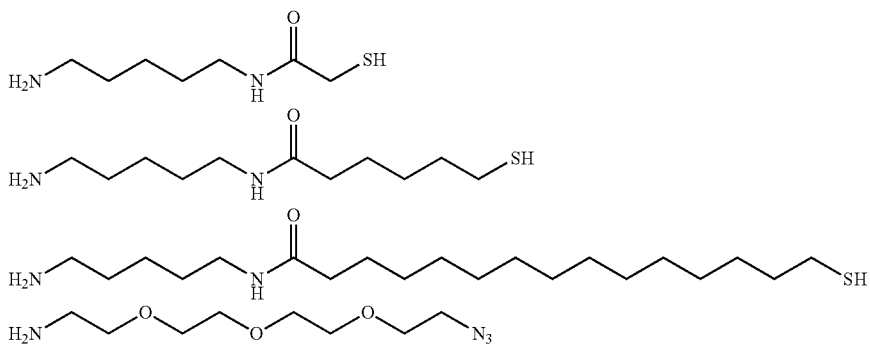

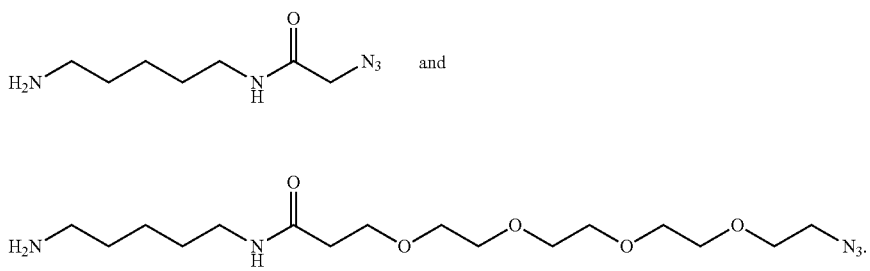

In particular embodiments, the primary amine compound is

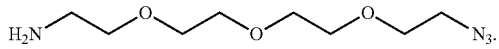 [SMILES: [N-]=[N+]=NCCOCCOCCOCCN]

Exemplary conditions for the above reactions are provided in the Examples below.

Linkers

In certain embodiments, the linker L portion of the conjugates described herein is a moiety, for instance, a divalent moiety, that covalently links a binding agent to a payload compound described herein. In other instances, the linker L is a trivalent or multivalent moiety that covalently links a binding agent to a payload compound described herein. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Payload compounds include compounds of Formulae I, II, and III above, and their residues following bonding or incorporation with linker L, wherein the combination of compounds or payloads with linker L are linker-payloads (LPs). Those of skill in the art will recognize that certain functional groups of the compound or payload moieties are convenient for linking to linkers and/or binding agents. Those groups include amines, hydroxyls, phosphates, and sugars.

In certain embodiments, the linkers are stable in physiological conditions. In certain embodiments, the linkers are cleavable, for instance, able to release at least the compound or payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety. In some embodiments, the non-cleavable linker is derived from

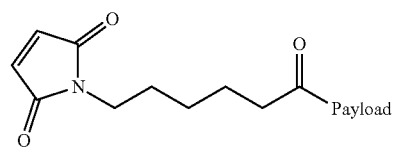

or a residue thereof. In some embodiments, the non-cleavable linker-payload is

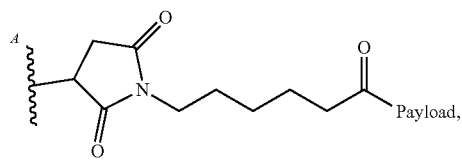

or a regioisomer thereof. In some embodiments, the non-cleavable linker is derived from

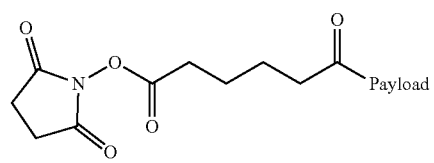

or a residue thereof. In some embodiments, the non-cleavable linker-payload is

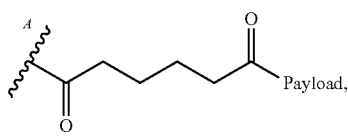

or a regioisomer thereof. In one embodiment, the linker is maleimide cyclohexane carboxylate or 4-(N-maleimidomethyl)cyclohexanecarboxylic acid (MCC). In the structures, $\overset{1}{\xi}$ indicates a bond to a binding agent. In the structures, in some examples, $-\overset{A}{\xi}-$ indicates a click chemistry residue which results from the reaction of, for example, a binding agent and a linker payload.

In some embodiments, suitable linkers include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L-, or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

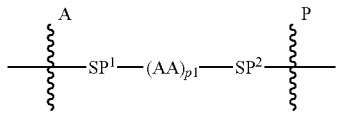

wherein:
SP$^1$ is a spacer;
SP$^2$ is a spacer;
$-\overset{A}{\xi}-$ is one or more bonds to the binding agent;
$-\overset{P}{\xi}-$ one or more bonds to the payload;
each AA is an amino acid; and
p1 is an integer from 0 to 10.

The SP$^1$ spacer is a moiety that connects the (AA)$_{p1}$ moiety to the binding agent (BA) or to a reactive group residue which is bonded to BA. Suitable SP$^1$ spacers include, but are not limited to, those comprising alkylene or polyether, or both. The ends of the spacers, e.g., the portion of the spacer bonded to the binding agent or an AA, can be moieties derived from reactive moieties that are used for purposes of coupling the antibody or an AA to the spacer during chemical synthesis of the conjugate. In certain embodiments, p1 is 0, 1, 2, 3, or 4. In particular embodiments, p1 is 0. In particular embodiments, p1 is 2. In particular embodiments, p1 is 3. In particular embodiments, p1 is 4.

In some embodiments, the SP$^1$ spacer comprises an alkylene. In some embodiments, the SP$^1$ spacer comprises a $C_{5-7}$ alkylene. In some embodiments, the SP$^1$ spacer comprises a polyether. In some embodiments, the SP$^1$ spacer comprises a polymer of ethylene oxide such as polyethylene glycol.

In some embodiments, the SP$^1$ spacer is:

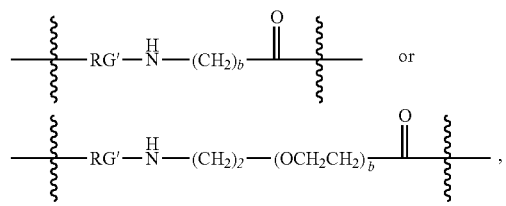

wherein:
RG' is a reactive group residue following reaction of a reactive group RG with a binding agent;
$-\overset{A}{\xi}-$ is a bond to the binding agent;
$-\overset{\xi}{\xi}-$ is a bond to (AA)$_{p1}$;
b is an integer from 2 to 8; and
p1 is an integer from 0 to 4.

The reactive group RG can be any reactive group known to those of skill in the art to be capable of forming one or more bonds to the binding agent. The reactive group RG is a moiety comprising a portion in its structure that is capable of reacting with the binding agent (e.g., reacting with an antibody at its cysteine or lysine residues, or at an azide moiety, for example, a PEG-N$_3$ functionalized antibody at one or more glutamine residues) to form a compound of Formula A, B, C, D, A', B', C', D', or A". Following conjugation to the binding agent, the reactive group becomes the reactive group residue (RG'). Illustrative reactive groups include, but are not limited to, those that comprise haloacetyl, isothiocyanate, succinimide, N-hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with azides in the absence of copper catalysts such as strained alkynes. Strained alkynes are suitable for strain-promoted alkyne-azide cycloadditions (SPAAC), cycloalkynes, e.g., cyclooctynes, ane benzannulated alkynes. Suitable alkynes include, but are not limited to, dibenzoazacyclooctyne or

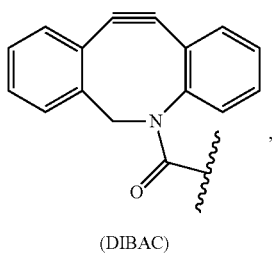 [SMILES: *C(=O)N1Cc2ccccc2C#Cc2ccccc21]

(DIBAC)

dibenzocyclooctyne or

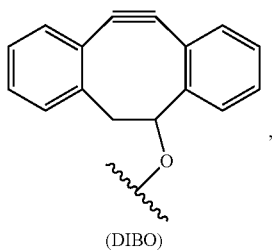

(DIBO)

biarylazacyclooctynone or

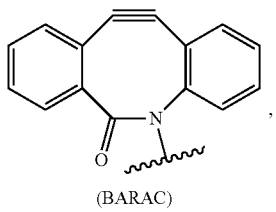

(BARAC)

difluorinated cyclooctyne or

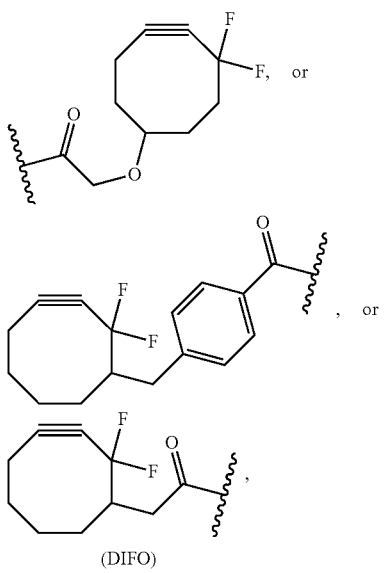

(DIFO)

substituted, e.g., fluorinated alkynes, aza-cycloalkynes, bicycle[6.1.0]nonyne or

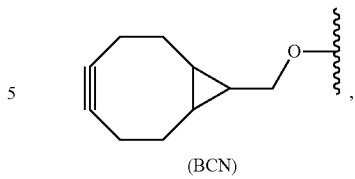

(BCN)

and derivatives thereof. Particularly useful alkynes include

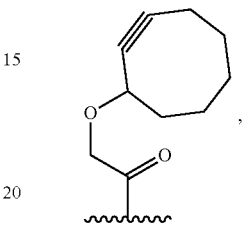

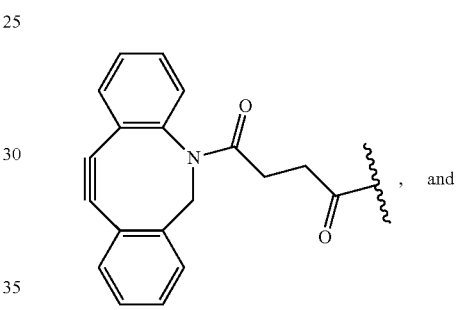

, and

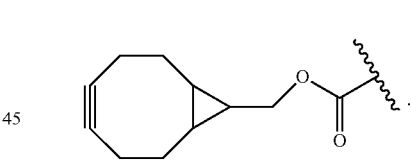

.

In certain embodiments, the binding agent is bonded directly to RG'. In certain embodiments, the binding agent is bonded to RG' via a spacer, for instance $SP^4$, below. In particular embodiments, the binding agent is bonded to RG' via a PEG spacer. As discussed in detail below, in certain embodiments, the binding agent is prepared by functionalizing with one or more azido groups. Each azido group is capable of reacting with RG to form RG'. In particular embodiments, the binding agent is derivatized with -PEG-$N_3$ linked to a glutamine residue. Exemplary —$N_3$ derivatized binding agents, methods for their preparation, and methods for their use in reacting with RG are provided herein. In certain embodiments, RG is an alkyne suitable for participation in 1,3-cycloadditions, and RG' is a 1,2,3-triazolyl moiety formed from the reaction of RG with an azido-functionalized binding agent. By way of further example, in certain embodiments, RG' is linked to the binding agent as shown in

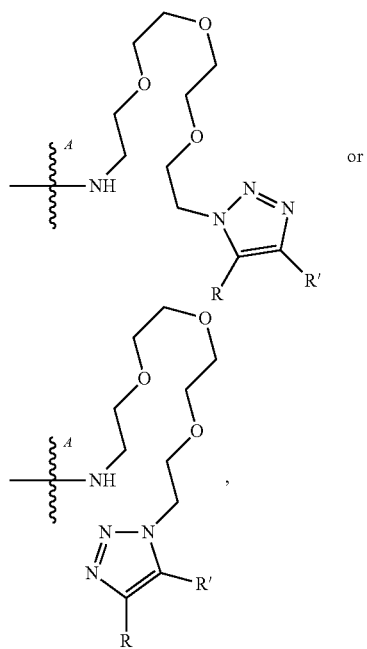

or a mixture of each regioisomer. Each R and R' is as described herein.

The SP² spacer is a moiety that connects the (AA)$_{p1}$ moiety to the payload. Suitable spacers include, but are not limited to, those described above as SP¹ spacers. Further suitable SP² spacers include, but are not limited to, those comprising alkylene or polyether, or both. The ends of the SP² spacers, e.g., the portion of the spacer directly bonded to the payload or an AA, can be moieties derived from reactive moieties that are used for purposes of coupling the payload or AA to the SP² spacer during the chemical synthesis of the conjugate. In some examples, the ends of the SP² spacers, e.g., the portion of the SP² spacer directly bonded to the payload or an AA, can be residues of reactive moieties that are used for purposes of coupling the payload or an AA to the spacer during the chemical synthesis of the conjugate.

In some embodiments, the SP² spacer is selected from the group consisting of —O—, —N(R$^{6'}$)—, —R$^{4'}$—, —R$^{5'}$—, —OR$^{5'}$—, and —OP(O)(OR$^{6'}$)O—, wherein:

R$^{4'}$ is —Z'—Y—X—;

X is selected from the group consisting of —O— and —N(H)—;

Y is selected from the group consisting of alkylene, substituted alkylene (including, without limitation, oxo substitution, i.e., =O), heteroalkylene, and substituted heteroalkylene;

Z' is selected from the group consisting of —O— and —N(H)—;

R$^{5'}$ is heterocycloalkylene or substituted heterocycloalkylene, wherein each heterocycloalkylene or substituted heterocycloalkylene includes one, two, or three heteroatoms selected from nitrogen and oxygen, including at least two moieties selected from the group consisting of —O—, —N(H)—, and

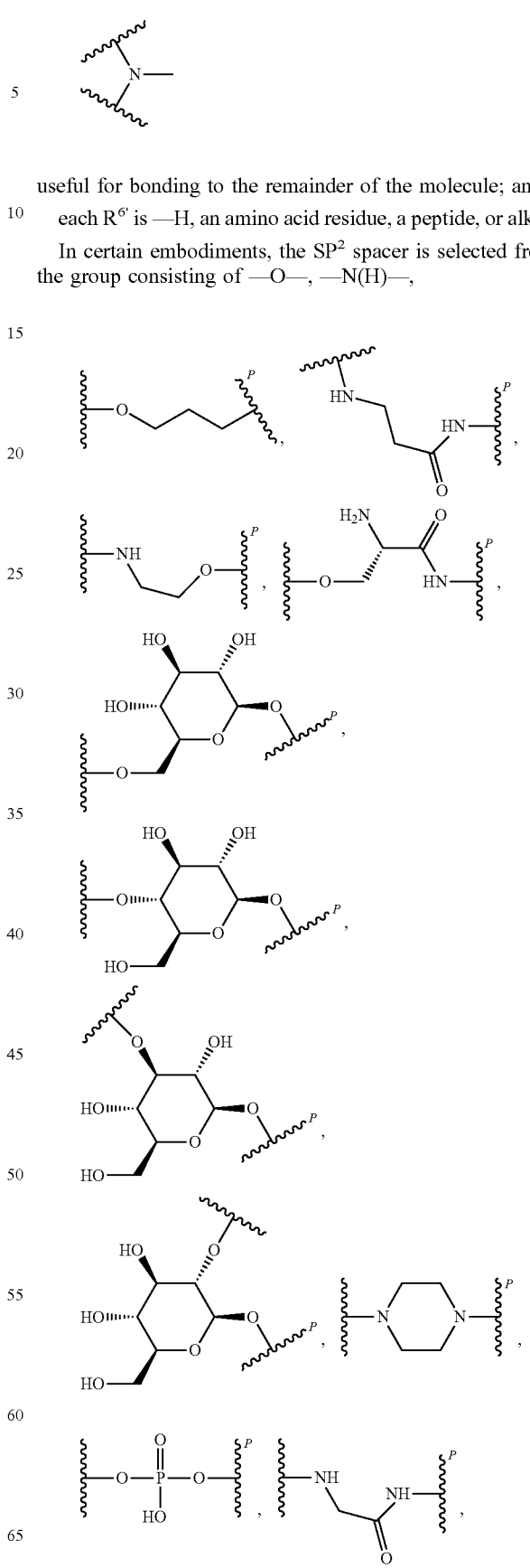

useful for bonding to the remainder of the molecule; and each R$^{6'}$ is —H, an amino acid residue, a peptide, or alkyl.

In certain embodiments, the SP² spacer is selected from the group consisting of —O—, —N(H)—,

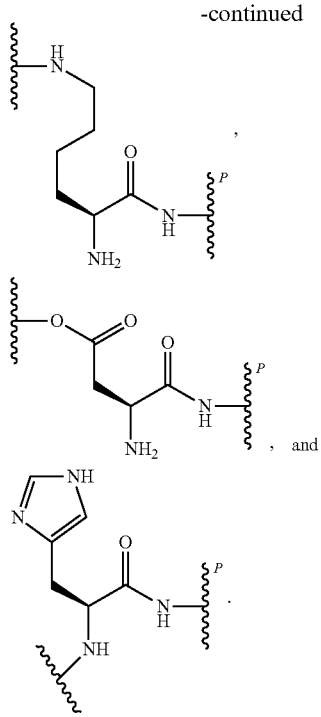

In certain embodiments, each $-\overset{P}{\underset{\xi}{\xi}}-$ is a bond to the payload, and each $-\xi-$ is a bond to $(AA)_{p1}$.

In the above formulas, each AA is an amino acid or, optionally, p-aminobenzyloxycarbonyl residue (PABC), or

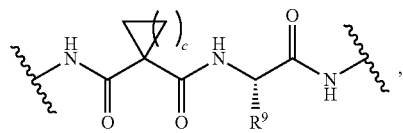

wherein c is 1, 2, 3, 4, 5, or 6. If PABC is present, preferably only one PABC is present. Preferably, the PABC residue, if present, is bonded to a terminal AA in the $(AA)_{p1}$ group, proximal to the payload. If

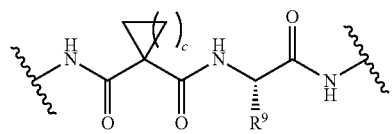

is present, then preferably c is 2. Preferably, the

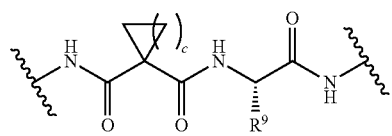

residue, if present and c is 2, is bonded to a terminal AA in the $(AA)_{p1}$ group, distal to the payload. Suitable amino acids for each AA include natural, non-natural, standard, non-standard, proteinogenic, non-proteinogenic, and L-, or D-α-amino acids. In some embodiments, the linker AA comprises alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, one or more side chains of the amino acids is linked to a side chain group, described below. In some embodiments, p1 is zero. In some embodiments, p1 is two. In some embodiments, the $(AA)_{p1}$ is valine-citrulline. In some embodiments, $(AA)_{p1}$ is citrulline-valine. In some embodiments, $(AA)_{p1}$ is valine-alanine. In some embodiments, $(AA)_{p1}$ is alanine-valine. In some embodiments, $(AA)_{p1}$ is valine-glycine. In some embodiments, $(AA)_{p1}$ is glycine-valine. In some embodiments, p1 is three. In some embodiments, the $(AA)_{p1}$ is valine-citrulline-PABC. In some embodiments, $(AA)_{p1}$ is citrulline-valine-PABC. In some embodiments, the $(AA)_{p1}$ is lysine-valine-citrulline-PABC. In some embodiments, $(AA)_{p1}$ is glutamate-valine-citrulline. In some embodiments, $(AA)_{p1}$ is glutamine-valine-citrulline. In some embodiments, $(AA)_{p1}$ is lysine-valine-alanine. In some embodiments, $(AA)_{p1}$ is lysine-valine-citrulline. In some embodiments, p1 is four. In some embodiments, $(AA)_{p1}$ is glutamate-valine-citrulline-PAB. In some embodiments, $(AA)_{p1}$ is glutamine-valine-citrulline-PABC. Those of skill will recognize PABC as a residue of p-aminobenzyloxycarbonyl with the following exemplary structures:

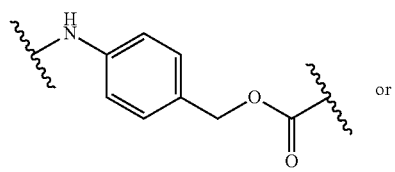 or

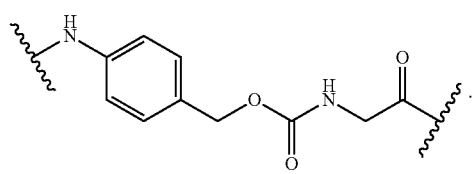

The PABC residue has been shown to facilitate cleavage of certain linkers in vitro and in vivo.

In some embodiments, the linker is:
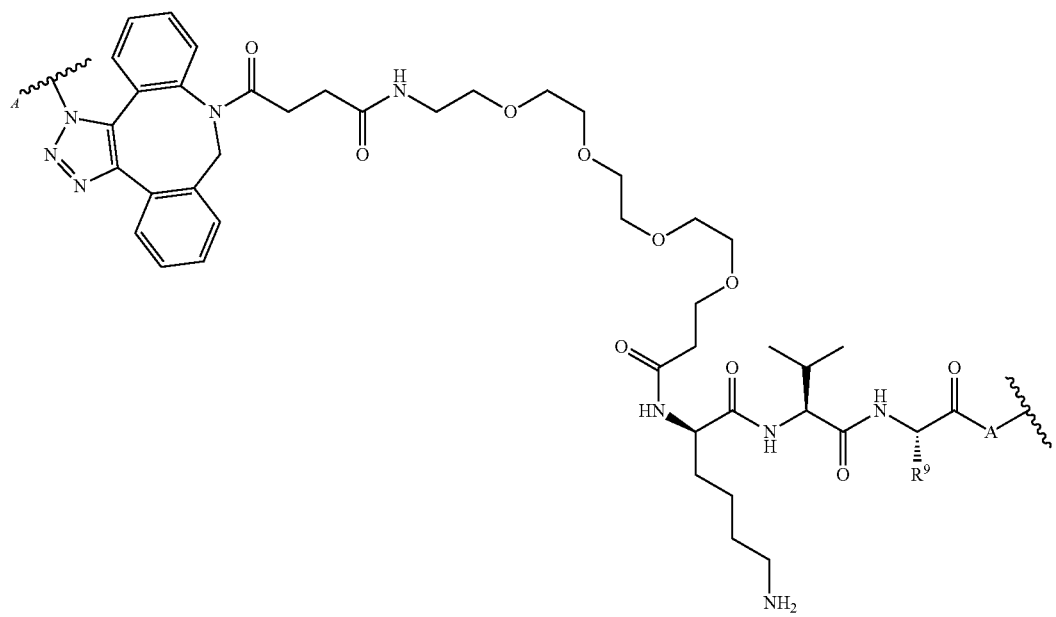
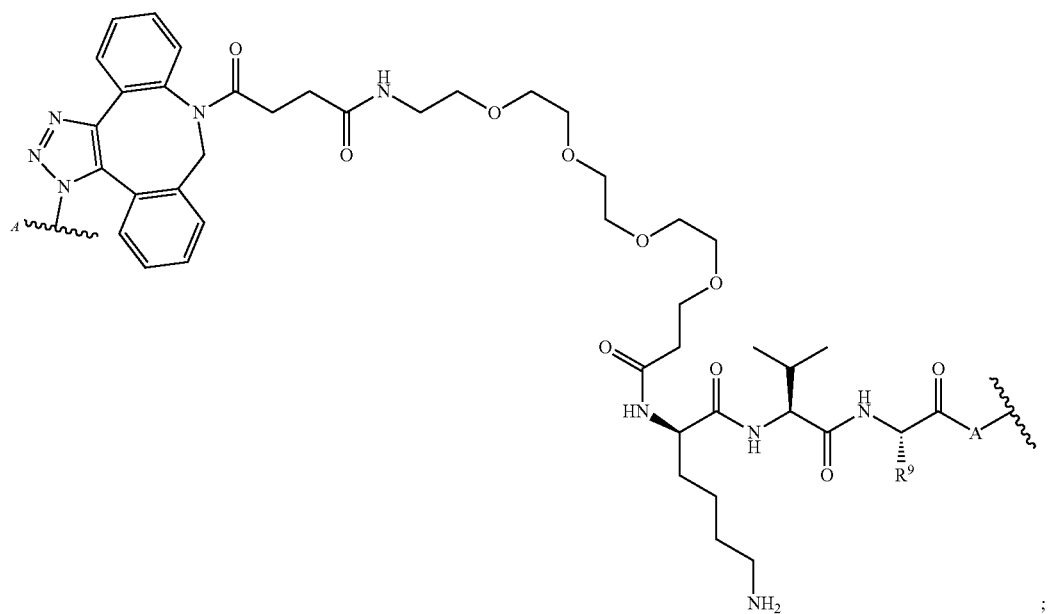
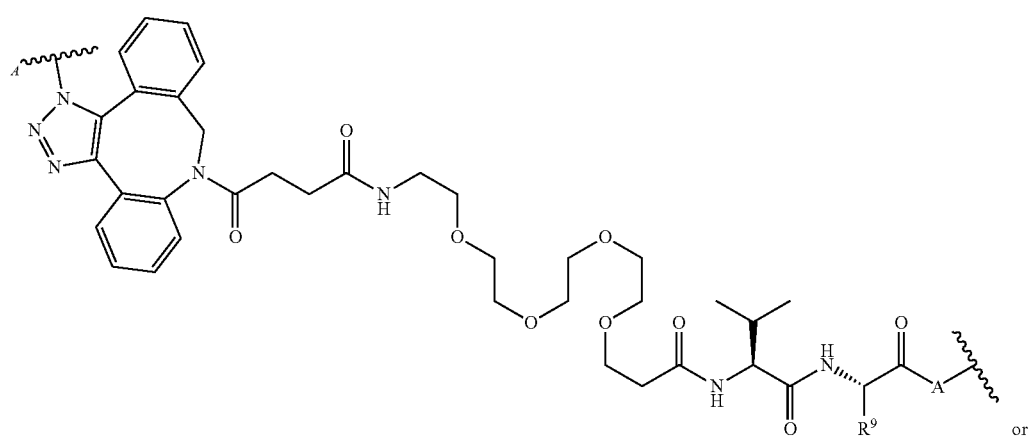
or

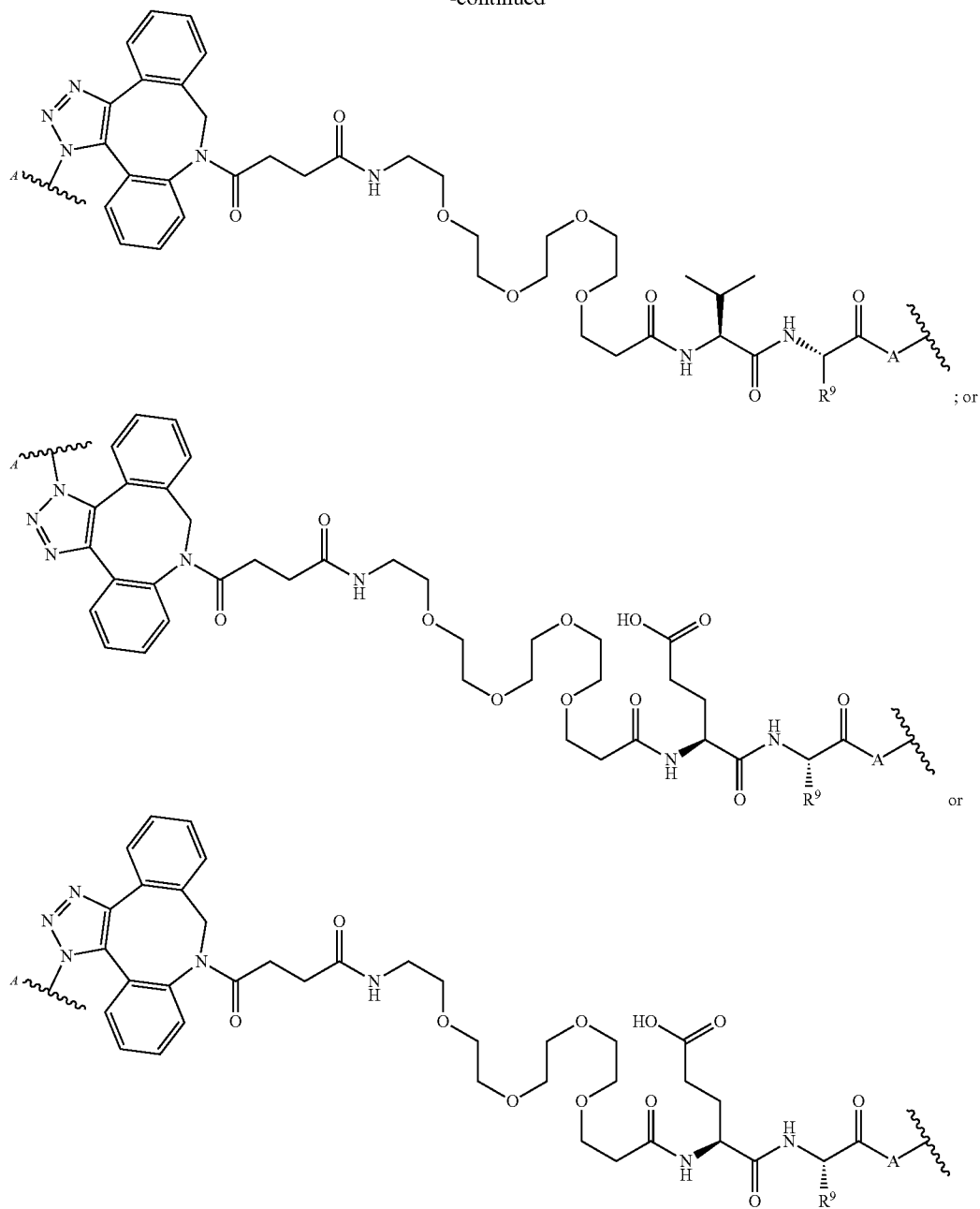
each ⸱§⸱ is a bond to the binding agent;
each ⸱§⸱ is a bond to the payload;
each $R^9$ is —CH$_3$ or —(CH$_2$)$_3$N(H)C(O)NH$_2$; and
each A is —O—, —N(H)—,
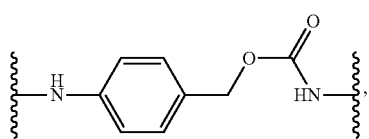
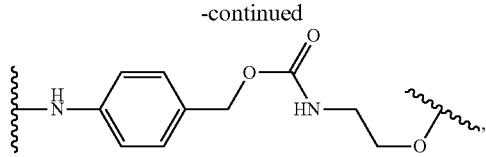
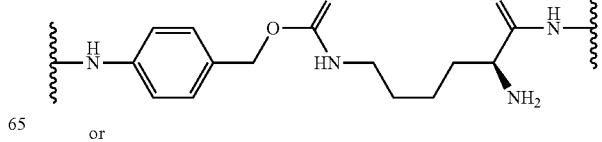
or

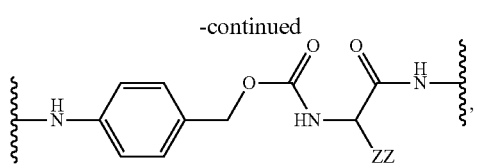

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent.

In some embodiments, the linker is:

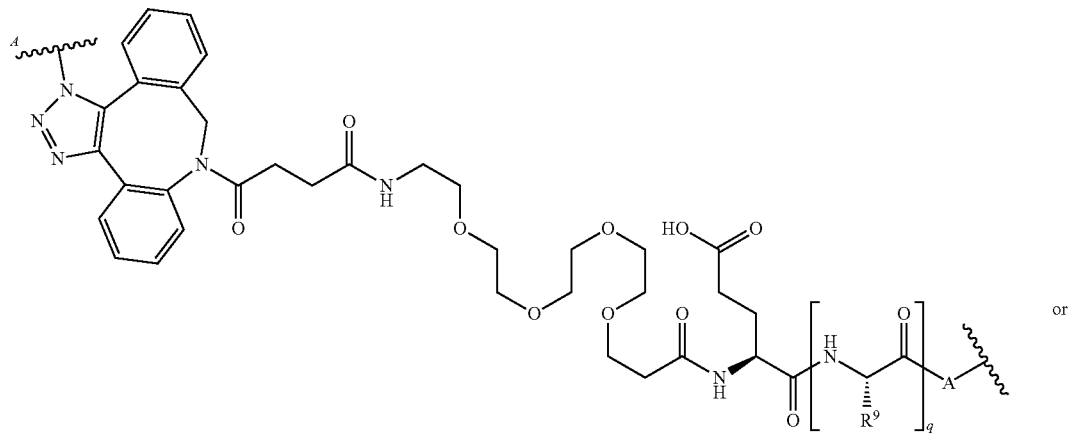

or

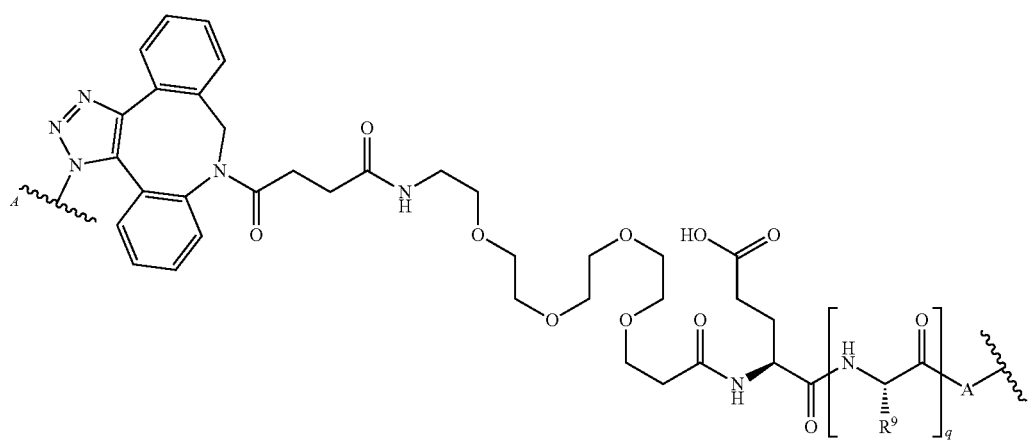

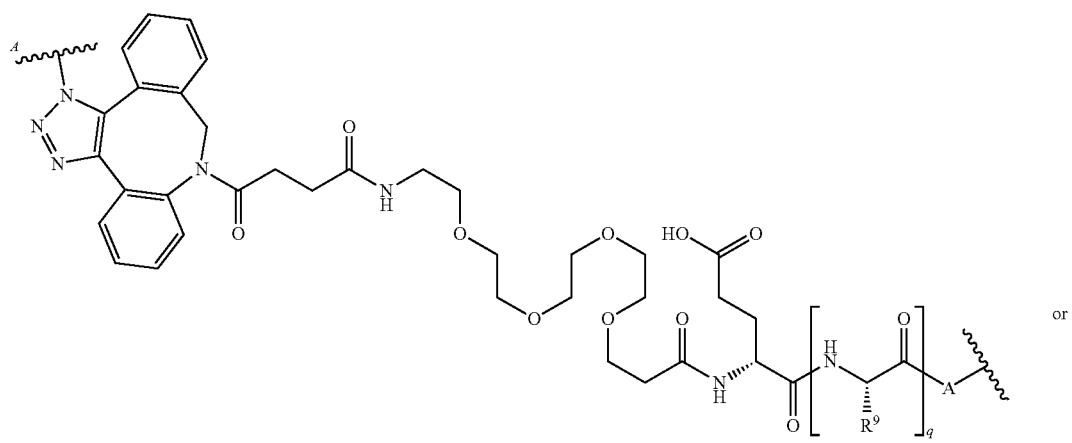

or

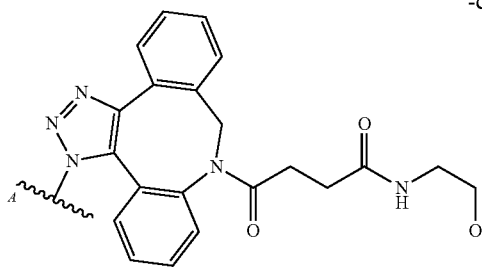

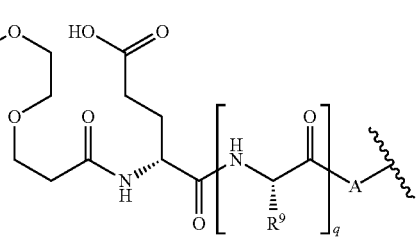

wherein:

each -§- is a bond to the binding agent;

each -¹§- is a bond the payload;

each $R^9$ is —CH$_3$, —CH(CH$_3$)$_2$, or —(CH$_2$)$_3$N(H)C(O)NH$_2$;

q is an integer from one to three; and each A is —O—, —N(H)—,

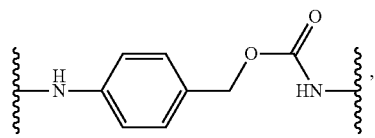

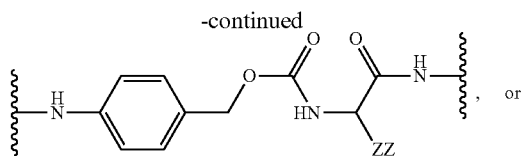

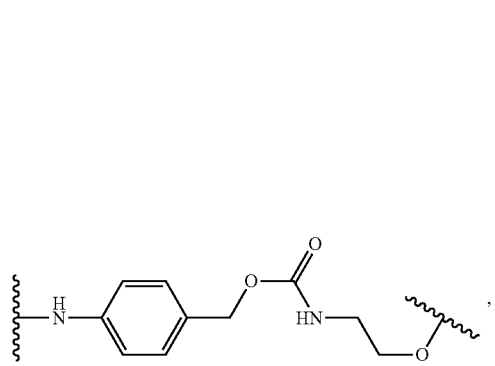

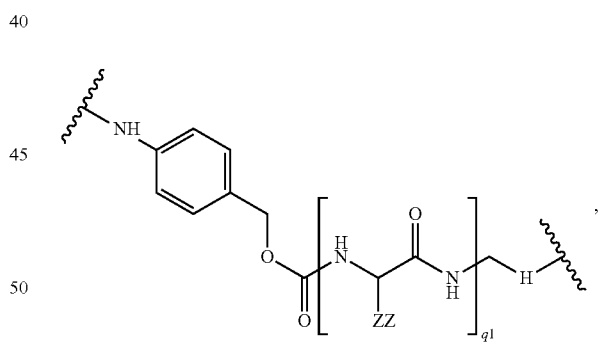

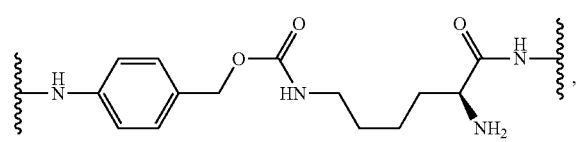

where ZZ is hydrogen, or a side chain for an amino acid as discussed elsewhere herein; q1 is an integer from one to five; and H is —O— or —NH—. For example, in one embodiment, ZZ is C$_{1-6}$ alkyl. By way of further example, in one embodiment, ZZ is C$_{1-6}$ heteroalkyl. In one embodiment, H is —O—. In one embodiment, H is —NH—. As discussed above, the bond to the binding agent can be direct, or via a spacer. In certain embodiments, the bond to the binding agent is via a PEG spacer to a glutamine residue of the binding agent.

In some embodiments, the linker is:
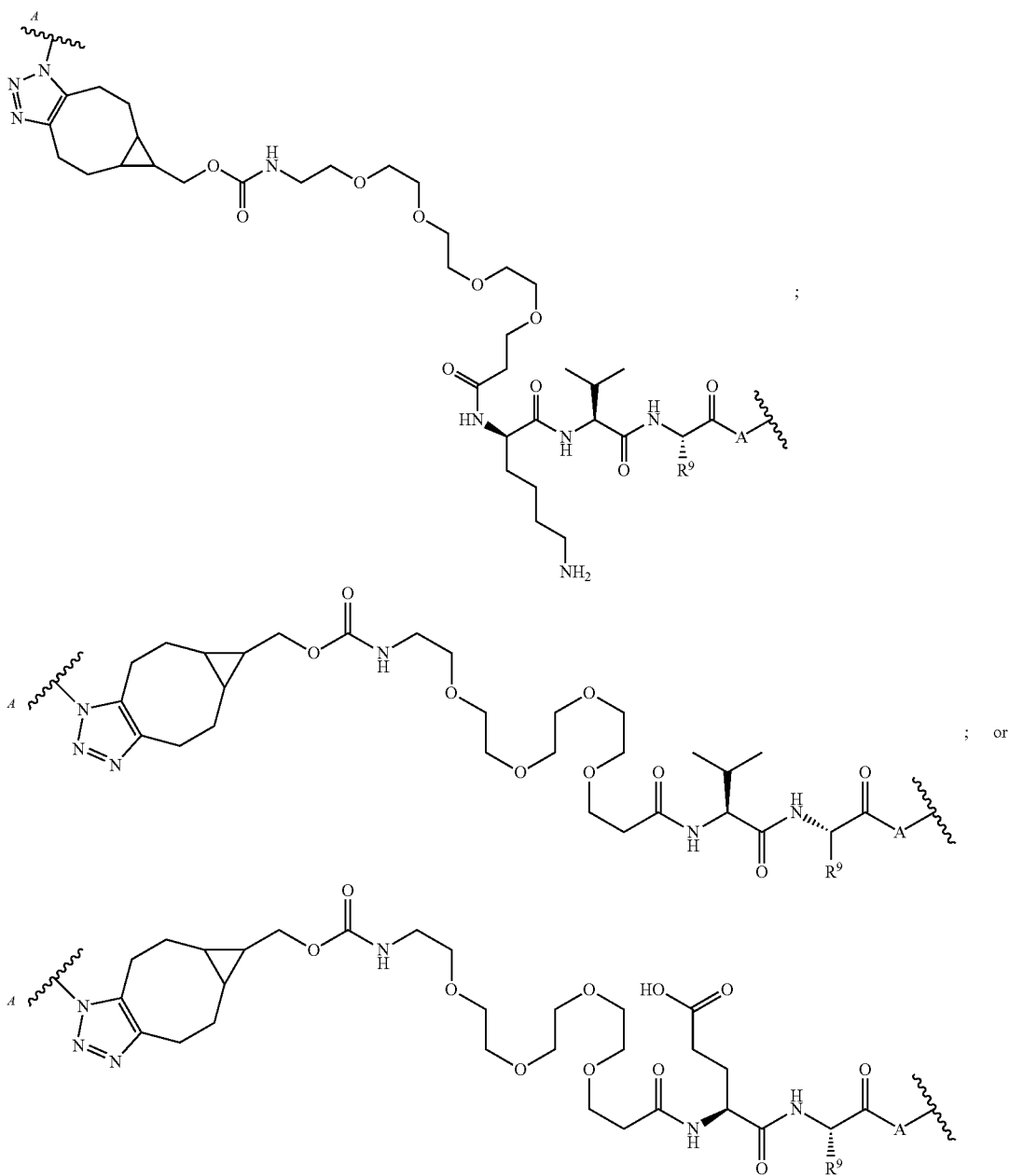
wherein:
each $\xi_1$ is a bond to the binding agent;
each $\xi$ is a bond to the payload;
each $R^9$ is —$CH_3$ or —$(CH_2)_3N(H)C(O)NH_2$; and
each A is —O—, —N(H)—,
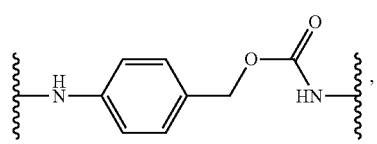
-continued
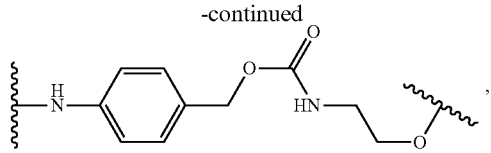
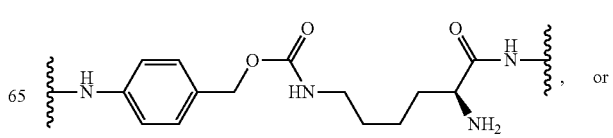

63

-continued

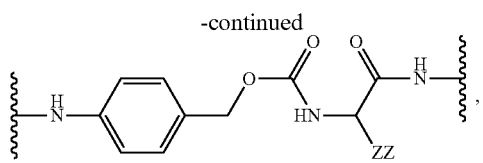

64

-continued

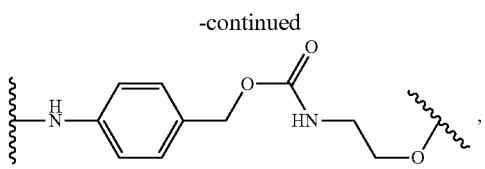

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent.

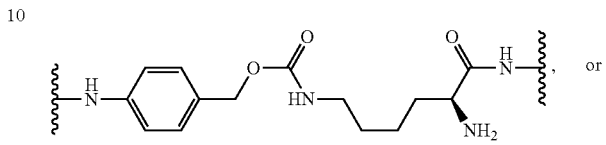

In some embodiments, the linker is:

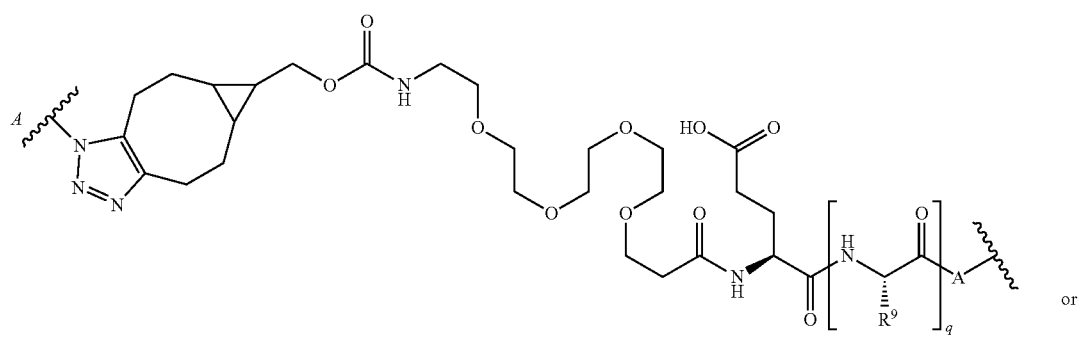

or

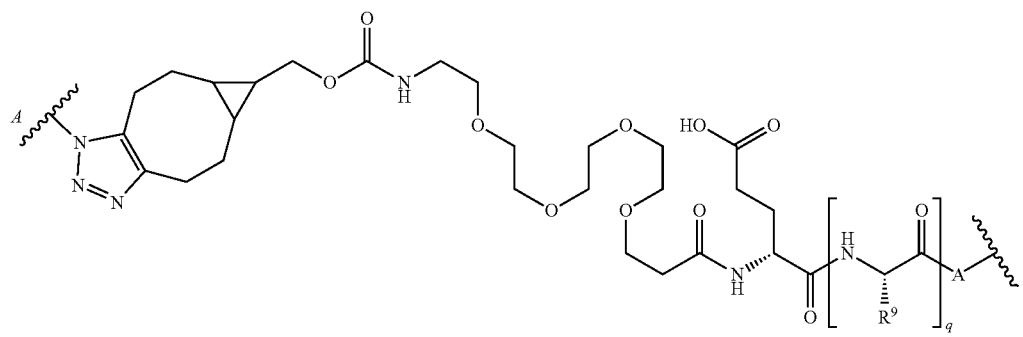

wherein:

each -§- is a bond to the binding agent;

each ⌐1⌐ is a bond to the payload;

each $R^9$ is —$CH_3$, —$CH(CH_3)_2$, or —$(CH_2)_3N(H)C(O)NH_2$;

q is an integer from one to three; and each A is —O—, —N(H)—,

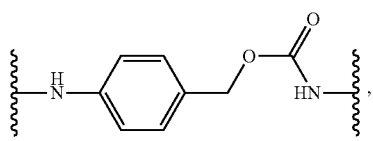

-continued

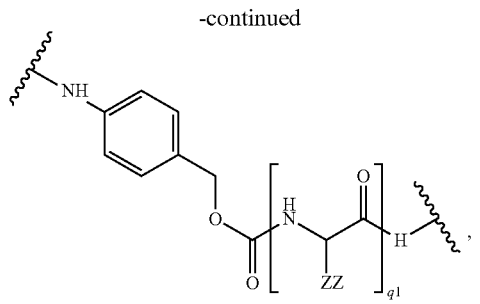

where ZZ is hydrogen, or a side chain for an amino acid as discussed elsewhere herein; q1 is an integer from one to five; and H is —O— or —NH—. For example, in one embodiment, ZZ is $C_{1-6}$ alkyl. By way of further example, in one embodiment, ZZ is $C_{1-6}$ heteroalkyl. In one embodiment, H is —O—. In one embodiment, H is —NH—. As discussed above, the bond to the binding agent can be direct, or via a spacer. In certain embodiments, the bond to the binding agent is via a PEG spacer to a glutamine residue of the binding agent.

In any of the above embodiments, the $(AA)_{p1}$ group can be modified with one or more enhancement groups. Advantageously, the enhancement group can be linked to the side chain of any amino acid in $(AA)_{p1}$. Useful amino acids for linking enhancement groups include lysine, asparagine, aspartate, glutamine, glutamate, and citrulline. The link to the enhancement group can be a direct bond to the amino acid side chain, or the link can be indirect via a spacer and/or reactive group. Useful spacers and reactive groups include any described above. The enhancement group can be any group deemed useful by those of skill in the art. For example, the enhancement group can be any group that imparts a beneficial effect to the compound, payload, linker payload, or antibody conjugate including, but not limited to, biological, biochemical, synthetic, solubilizing, imaging, detecting, and reactivity effects, and the like. In certain embodiments, the enhancement group is a hydrophilic group. In certain embodiments, the enhancement group is a cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the enhancement group is capable of improving solubility of the remainder of the conjugate. In certain embodiments, the alkyl, heteroalkyl, alkylenyl, or heteroalkylenyl sulfonic acid is substituted or non-substituted. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N($(CH_2)_{1-5}C(O)NH(CH_2)_{1-5}SO_3H)_2$, —$(CH_2)_{n2}$—C(O)N($(CH_2)_{1-5}C(O)NH(CH_2)_{1-5}SO_3H)_2$, or —$(CH_2CH_2O)_{m2}$—C(O)N($(CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N($(CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N($(CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N($(CH_2)_{1-5}C(O)NH(CH_2)_{1-5}SO_3H)_2$, wherein m2 is 1, 2, 3, 4, or 5. In some embodiments, the linker is:

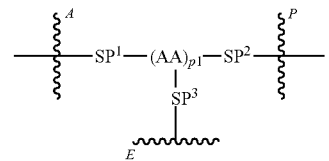

wherein:
SP$^1$ is a spacer;
SP$^2$ is a spacer;
SP$^3$ is a spacer, linked to one AA of $(AA)_{p1}$;
$-\xi-_P$ is one or more bonds to the binding agent;
$-\xi-_E$ is one or more bonds to the payload;
$-\xi-$ is one or more bonds to the enhancement group EG;
each AA is an amino acid; and
p1 is an integer from 1 to 10.

As discussed above, the bond to the binding agent can be direct, or via a spacer. In certain embodiments, the bond to the binding agent is via a PEG spacer to a glutamine residue of the binding agent.

The SP$^1$ spacer group is as described above. The SP$^2$ spacer group is as described above. Each $(AA)_{p1}$ group is as described above.

The SP$^3$ spacer is a moiety that connects the $(AA)_{p1}$ moiety to the enhancement group (EG). Suitable SP$^3$ spacers include, but are not limited to, those comprising alkylene or polyether, or both. The ends of the SP$^3$ spacers, i.e., the portion of the SP$^3$ spacer directly bonded to the enhancement group or an AA, can be moieties derived from reactive moieties that are used for purposes of coupling the enhancement group or an AA to the SP$^3$ spacer during the chemical synthesis of the conjugate. In some examples, the ends of the SP$^3$ spacers, i.e., the portion of the spacer directly bonded to the enhancement group or an AA, can be residues of reactive moieties that are used for purposes of coupling the enhancement group or an AA to the spacer during the chemical synthesis of the conjugate. In certain embodiments, SP$^3$ is a spacer, linked to one and only one AA of $(AA)_{p1}$. In certain embodiments, the SP$^3$ spacer is linked to the side chain of a lysine residue of $(AA)_{p1}$.

In some embodiments, the SP$^3$ spacer is:

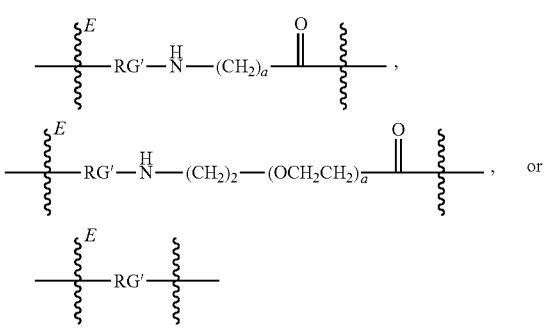

wherein:
RG' is a reactive group residue following reaction of a reactive group RG with an enhancement agent EG;
$-\xi-_P$ is a bond to the enhancement agent;
$-\xi-_1$ is a bond to $(AA)_{p1}$;
a is an integer from 2 to 8; and
p1 is an integer from 1 to 4.

The reactive group RG can be any reactive group known to those of skill in the art to be capable of forming one or more bonds to the enhancement agent. The reactive group RG is a moiety comprising a portion in its structure that is capable of reacting with the enhancement group to form a compound of Formula LPa, LPb, LPc, LPd, LPa', LPb', LPc', LPd', A, B, C, D, A', B', C', D', or A". Following conjugation to the enhancement group, the reactive group becomes the reactive group residue (RG'). The reactive group RG can be any reactive group described above. Illustrative reactive groups include, but are not limited to, those that comprise haloacetyl, isothiocyanate, succinimide, N-hydroxysuccinimide, or maleimide portions that are capable of reacting with the binding agent.

In certain embodiments, reactive groups include, but are not limited to, alkynes. In certain embodiments, the alkynes are alkynes capable of undergoing 1,3-cycloaddition reactions with azides in the absence of copper catalysts such as strained alkynes. Strained alkynes are suitable for strain-promoted alkyne-azide cycloadditions (SPAAC), cycloalkynes, e.g., cyclooctynes, ane benzannulated alkynes. Suitable alkynes include, but are not limited to, dibenzoazacyclooctyne or (DIBAC)

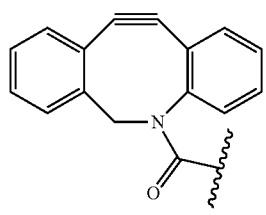

dibenzocyclooctyne or (DIBO)

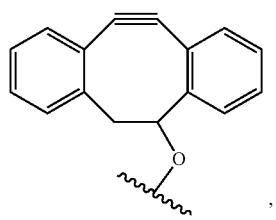

biarylazacyclooctynone or (BARAC)

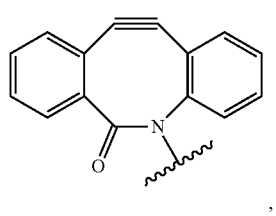

difluorinated cyclooctyne or (DIFO)

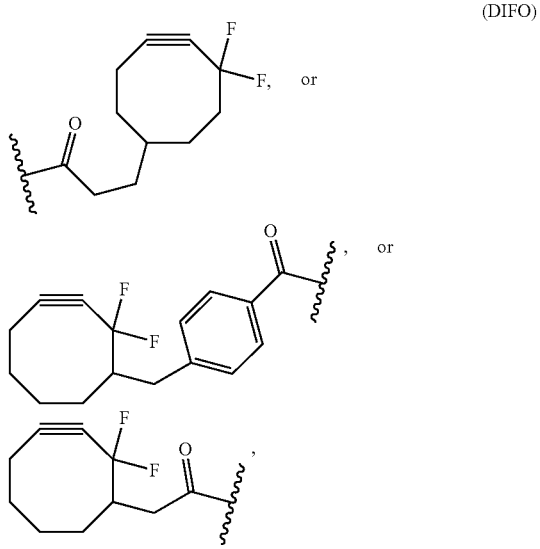

substituted, e.g., fluorinated alkynes, aza-cycloalkynes, bicycle[6.1.0]nonyne or (BCN)

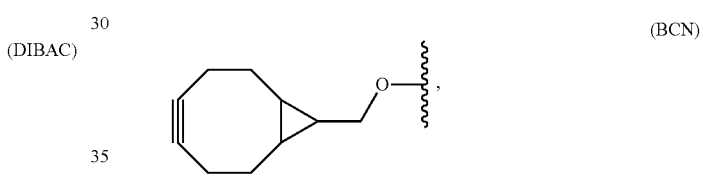

and derivatives thereof. Particularly useful alkynes include

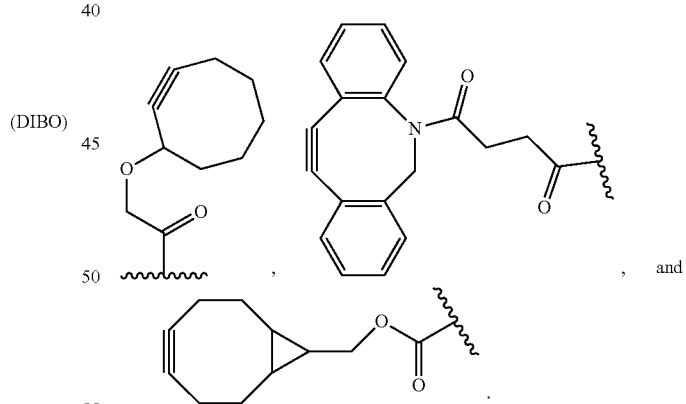

and

In some embodiments, the linker is:

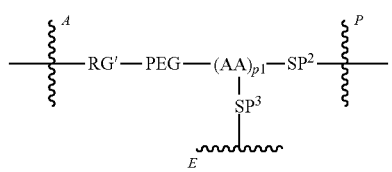

wherein:
RG' is a reactive group residue following reaction of a reactive group RG with a binding agent;
PEG is —NH-PEG4-C(O)—;
SP² is a spacer;
SP³ is a spacer, linked to one AA residue of $(AA)_{p1}$;

-⸹- is one or more bonds to the binding agent;

-⸹-P is one or more bonds to the payload;

-⸹-E is one or more bonds to the enhancement group EG;
each AA is an amino acid residue; and
p1 is an integer from 1 to 10.

As discussed above, the bond to the binding agent can be direct, or via a spacer. In certain embodiments, the bond to the binding agent is via a PEG spacer to a glutamine residue of the binding agent.

In certain embodiments, the linker is:

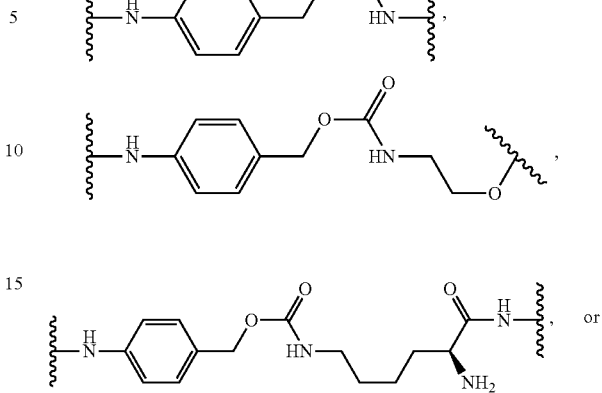

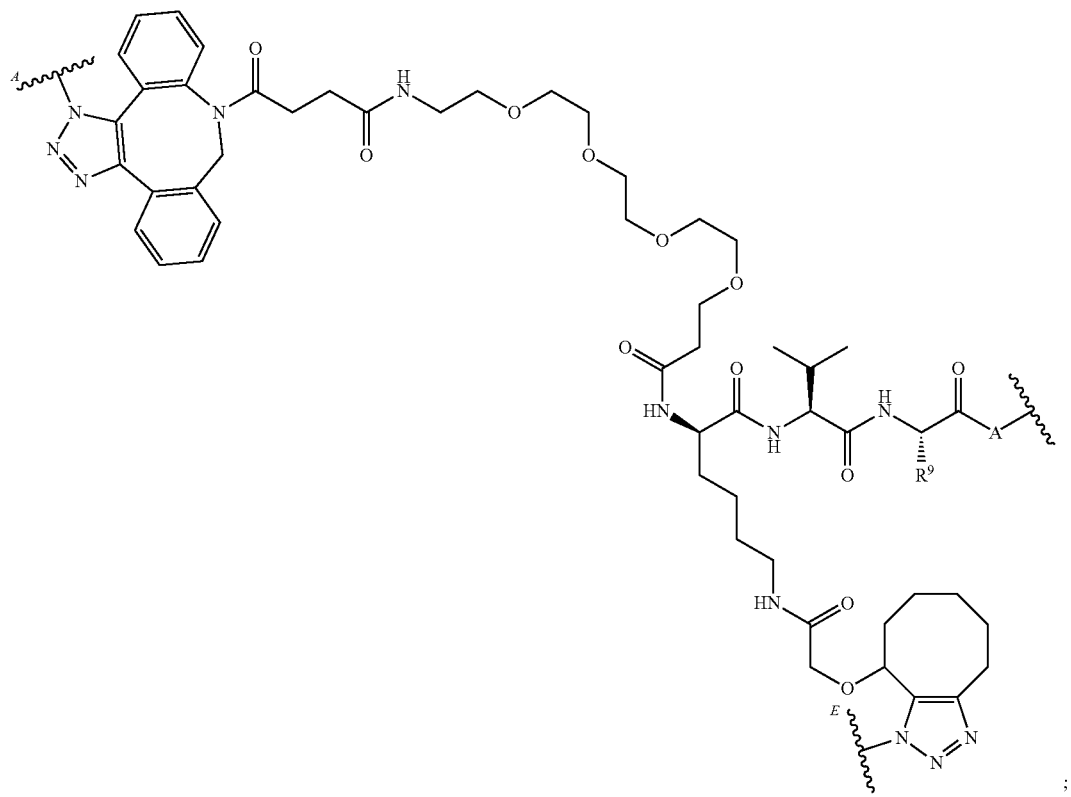

or a pharmaceutically acceptable salt, solvate, or stereoisomeric form thereof, or a regioisomer thereof, or a mixture of regioisomers thereof, wherein:

each -⸹- is a bond to the binding agent;

each -⸹-1 is a bond to the payload;

each -⸹-E is a bond to the enhancement agent;

each $R^9$ is —CH₃ or —(CH₂)₃N(H)C(O)NH₂; and each A is —O—, —N(H)—,

-continued

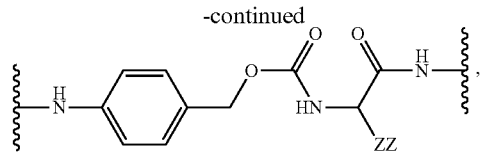

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In certain embodiments, 1,3-cycloaddition or SPAAC regioisomers, or mixture of regioisomers, are derived from PEG-N₃ derivitized antibodies treated with suitable alkynes. For example, in one embodiment, the linker is:

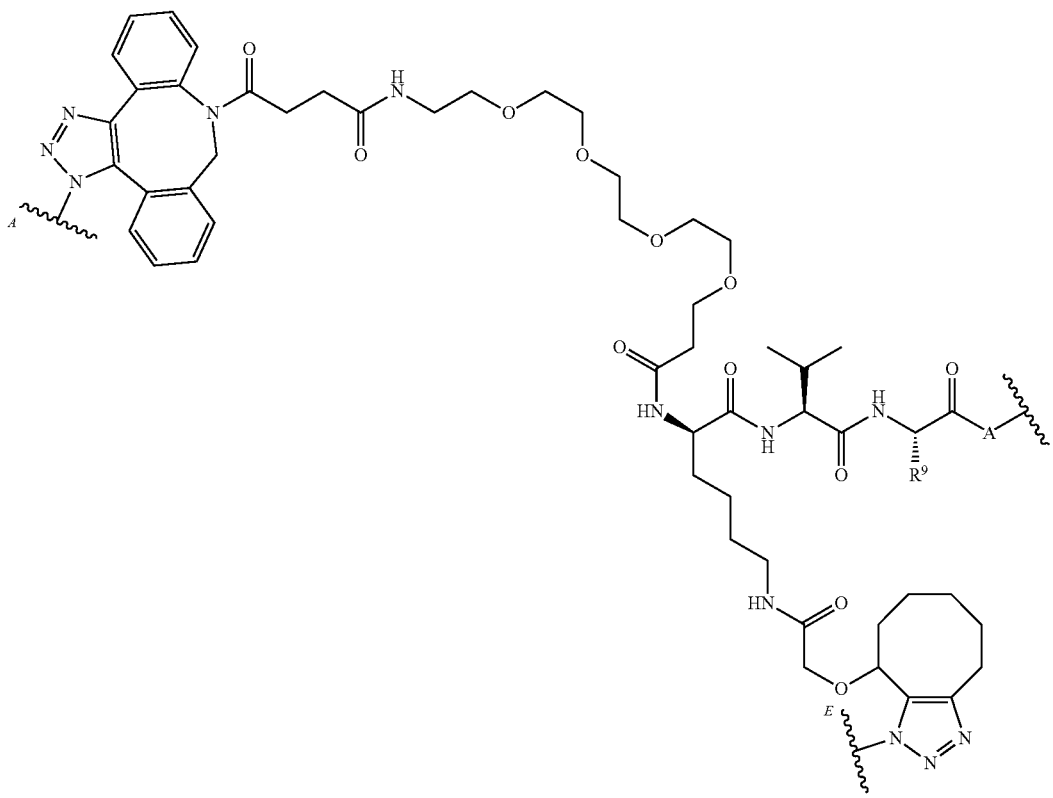
or a pharmaceutically acceptable salt, solvate, or stereoisomeric form thereof, or a regioisomer thereof, or a mixture of regioisomers thereof. By way of further example, in one embodiment, the linker is:
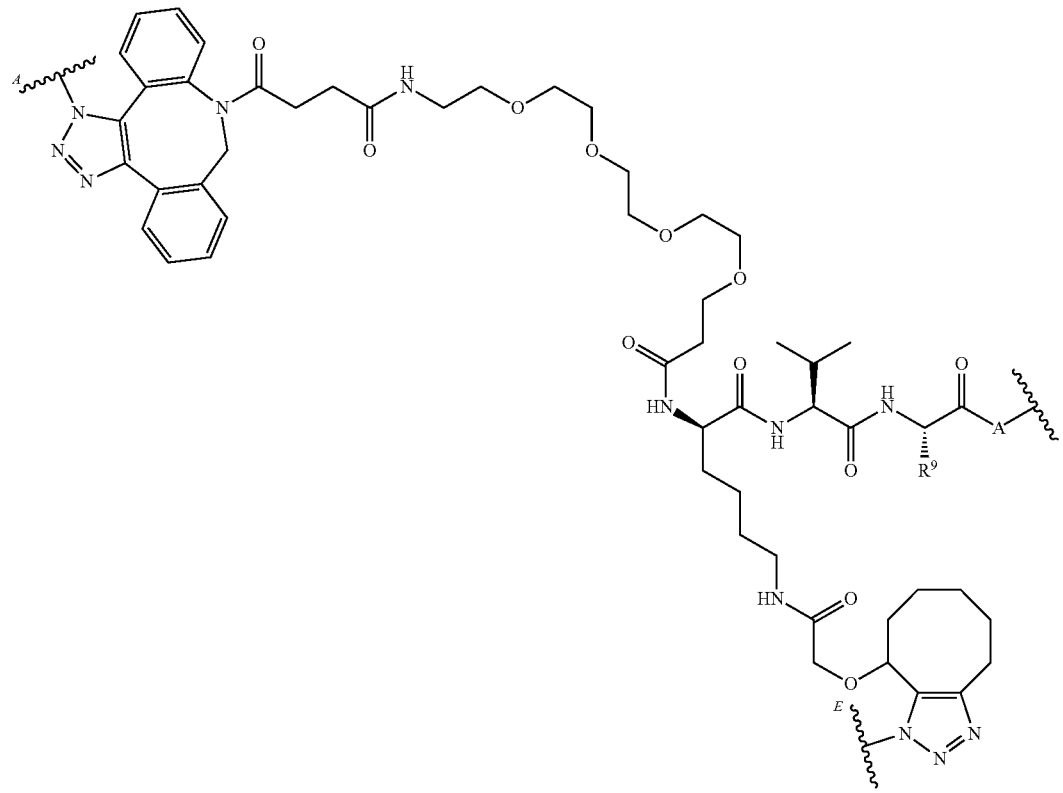

or a pharmaceutically acceptable salt, solvate, or stereoisomeric form thereof, or a regioisomer thereof, or a mixture of regioisomers thereof.

By way of further example, the linker is:

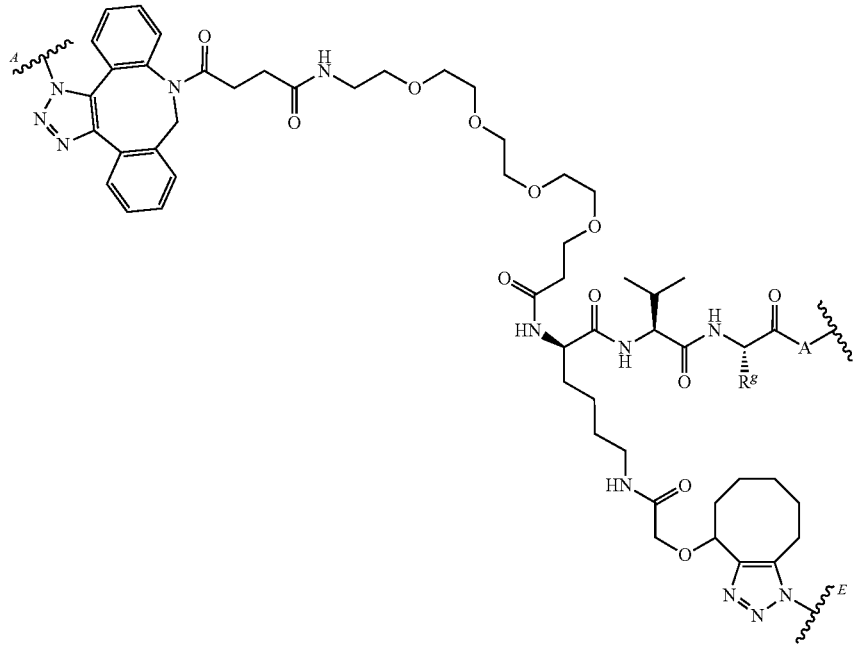

or a pharmaceutically acceptable salt, solvate, or stereoisomeric form thereof, or a regioisomer thereof, or a mixture of regioisomers thereof. By way of further example, in one embodiment, the linker is:

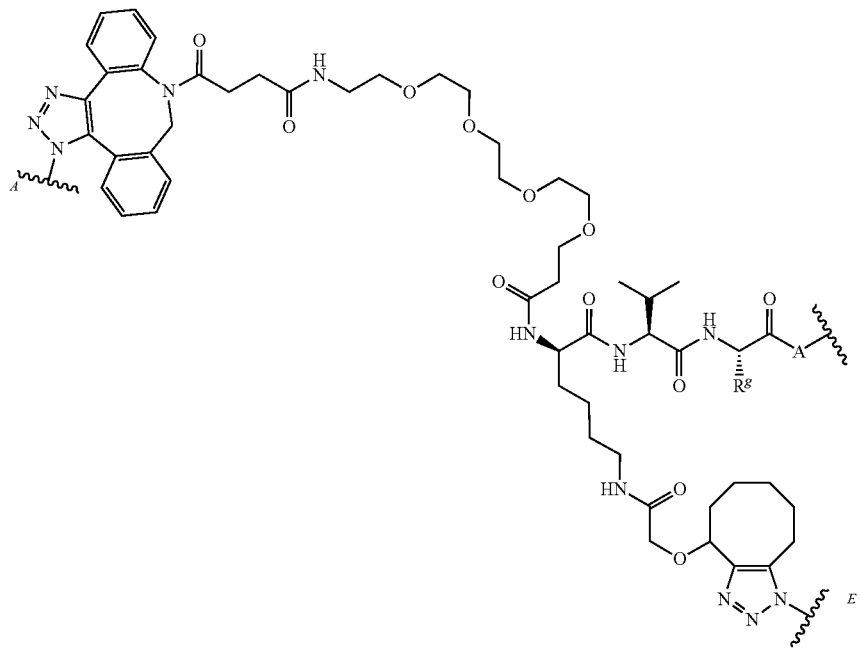

or a pharmaceutically acceptable salt, solvate, or stereoisomeric form thereof, or a regioisomer thereof, or a mixture of regioisomers thereof. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —(CH$_2$)$_{1-5}$SO$_3$H, —(CH$_2$)$_{n2}$—NH—(CH$_2$)$_{1-5}$SO$_3$H, —(CH$_2$)$_{n2}$—C(O)NH—(CH$_2$)$_{1-5}$SO$_3$H, —(CH$_2$CH$_2$O)$_{m2}$—C(O)NH—(CH$_2$)$_{1-5}$SO$_3$H, —(CH$_2$)$_{n2}$—N((CH$_2$)$_{1-5}$C(O)NH(CH$_2$)$_{1-5}$SO$_3$H)$_2$, —(CH$_2$)$_{n2}$—C(O)N((CH$_2$)$_{1-5}$C(O)NH(CH$_2$)$_{1-5}$SO$_3$H)$_2$, or —(CH$_2$CH$_2$O)$_{m2}$—C(O)N((CH$_2$)$_{1-5}$C(O)NH(CH$_2$)$_{1-5}$SO$_3$H)$_2$, wherein n2 is 1, 2, 3, 4, or 5, and m2 is 1, 2, 3, 4, or 5. In one embodiment, the alkyl or alkylenyl sulfonic acid is —(CH$_2$)$_{1-5}$SO$_3$H. In another embodiment, the heteroalkyl or heteroalkylenyl sulfonic acid is —(CH$_2$)$_{n2}$—NH—(CH$_2$)$_{1-5}$SO$_3$H, wherein n2 is 1, 2, 3, 4, or 5. In another embodiment, the alkyl, heteroalkyl, alkylenyl, or heteroalkylenyl sulfonic acid is —(CH$_2$)$_{n2}$—C(O)NH—(CH$_2$)$_{1-5}$SO$_3$H, wherein n2 is 1, 2, 3, 4, or 5. In another embodiment, the alkyl, heteroalkyl, alkylenyl, or heteroalkylenyl sulfonic acid is —(CH$_2$CH$_2$O)$_{m2}$—C(O)NH—(CH$_2$)$_{1-5}$SO$_3$H, wherein m2 is 1, 2, 3, 4, or 5. In another embodiment, the alkyl, heteroalkyl, alkylenyl, or heteroalkylenyl sulfonic acid is —(CH$_2$)$_{n2}$—N((CH$_2$)$_{1-5}$C(O)NH(CH$_2$)$_{1-5}$SO$_3$H)$_2$, wherein n2 is 1, 2, 3, 4, or 5. In another embodiment, the alkyl, heteroalkyl, alkylenyl, or heteroalkylenyl sulfonic acid is —(CH$_2$)$_{n2}$—C(O)N((CH$_2$)$_{1-5}$C(O)NH(CH$_2$)$_{1-5}$SO$_3$H)$_2$, wherein n2 is 1, 2, 3, 4, or 5. In another embodiment, the alkyl, heteroalkyl, alkylenyl, or heteroalkylenyl sulfonic acid is —(CH$_2$CH$_2$O)$_{m2}$—C(O)N((CH$_2$)$_{1-5}$C(O)NH(CH$_2$)$_{1-5}$SO$_3$H)$_2$, wherein m2 is 1, 2, 3, 4, or 5.

In some embodiments, the linker is:

each $\overset{1}{\xi}$ is a bond to the payload;

each R$^9$ is —CH$_3$ or —(CH$_2$)$_3$N(H)C(O)NH$_2$; and each A is —O—, —N(H)—,

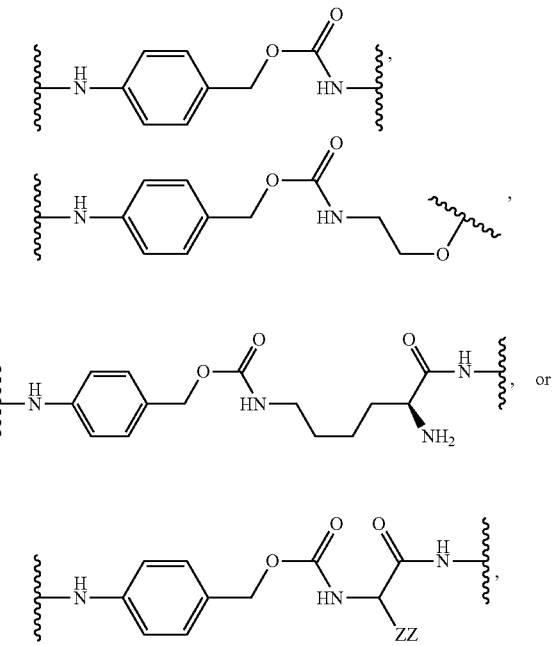

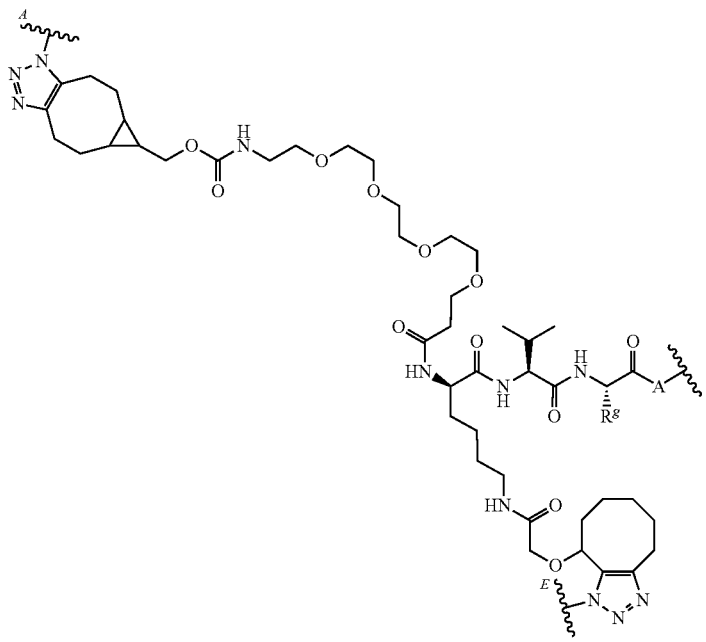

or a pharmaceutically acceptable salt, solvate, or stereoisomeric form thereof, or a regioisomer thereof, or mixture of regioisomers thereof, wherein:

each $\overset{\xi}{_E}$ is a bond to the binding agent;

each $\overset{\xi}{_E}$ is a bond to the enhancement agent;

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N($(CH_2)_{1-5}$C(O)NH$(CH_2)_{1-5}SO_3H)_2$, —$(CH_2)_{n2}$—C(O)N($(CH_2)_{1-5}$C(O)NH$(CH_2)_{1-5}SO_3H)_2$, or —$(CH_2CH_2O)_{m2}$—C(O)N($(CH_2)_{1-5}$C(O)NH$(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N($(CH_2)_{1-5}$C(O)NH$(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N($(CH_2)_{1-5}$C(O)NH$(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N($(CH_2)_{1-5}$C(O)NH$(CH_2)_{1-5}SO_3H)_2$, wherein m2 is 1, 2, 3, 4, or 5.

In some embodiments, the linker is:

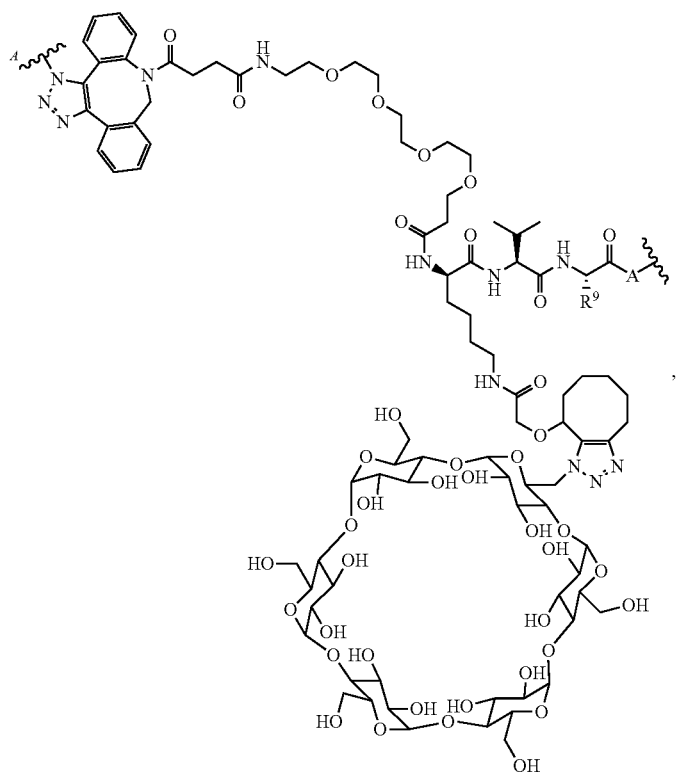

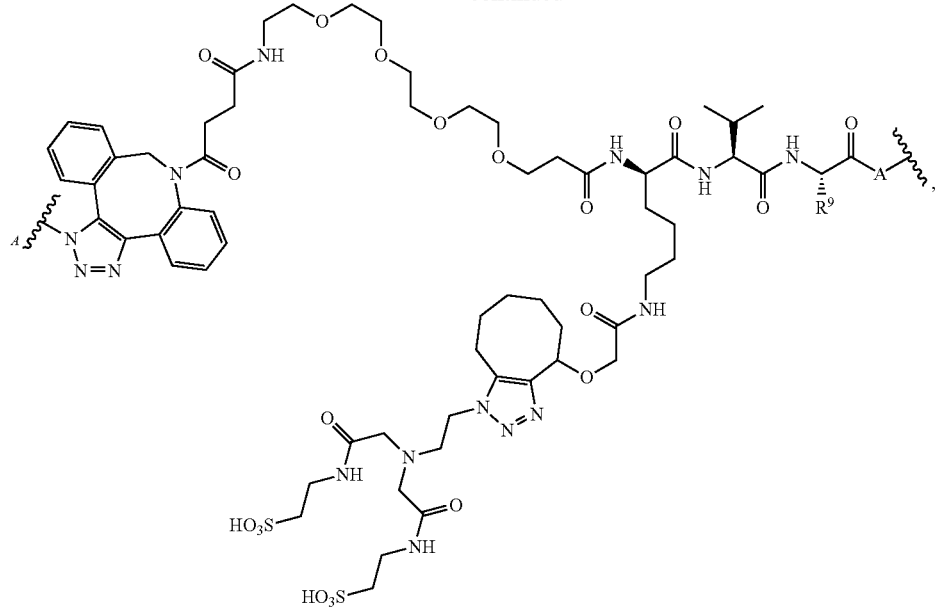
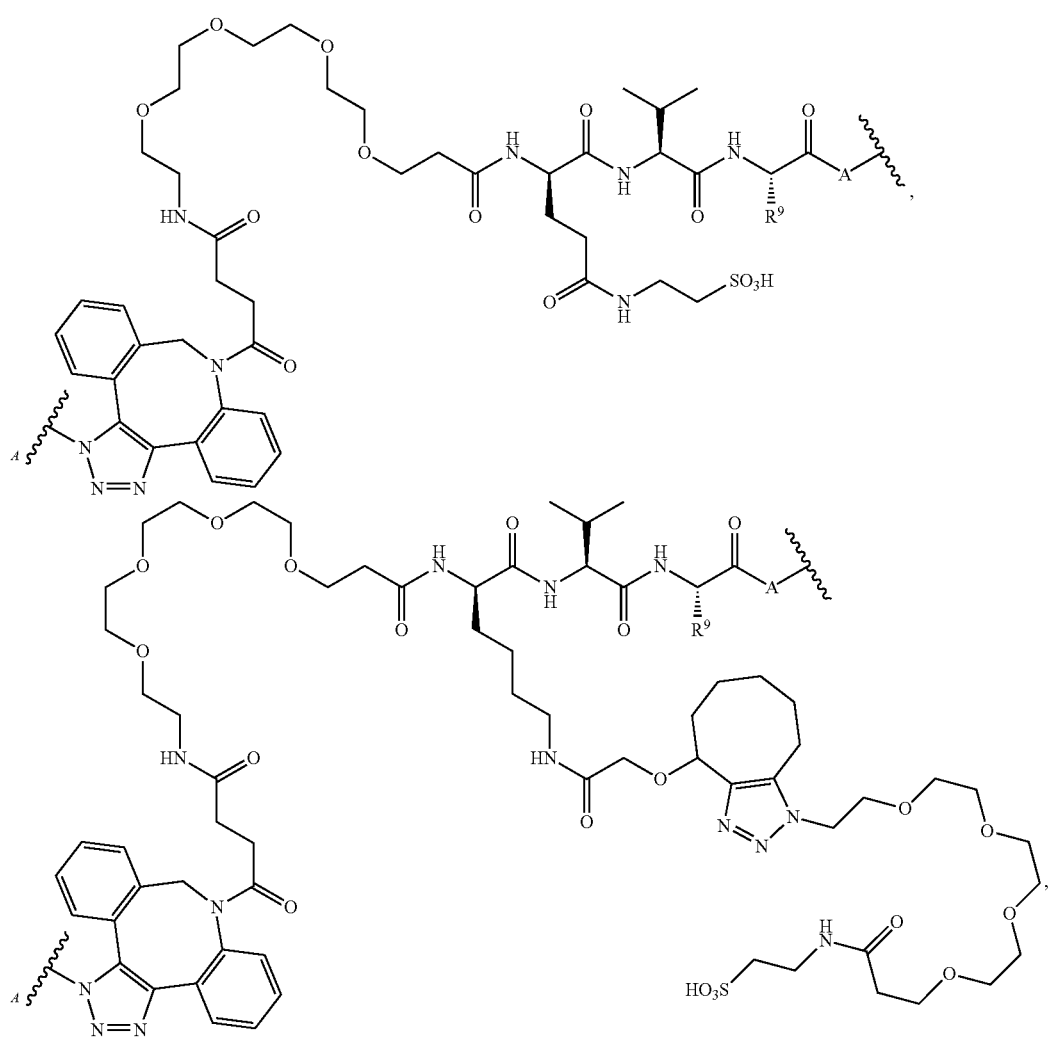

or a pharmaceutically acceptable salt, solvate, or stereoisomeric form thereof, or a regioisomer thereof, or mixture of regioisomers thereof, wherein:

each -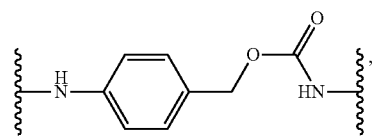 is a bond to the binding agent;

each ⌇ is a bond to the payload;
$R^9$ is —$CH_3$ or —$(CH_2)_3N(H)C(O)NH_2$; and
A is —O—, —N(H)—,

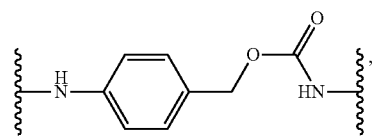

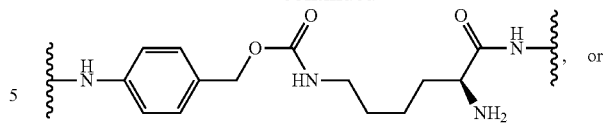

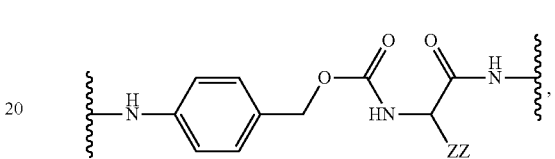

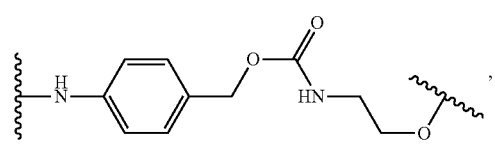

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent.

In some embodiments, the linker is:

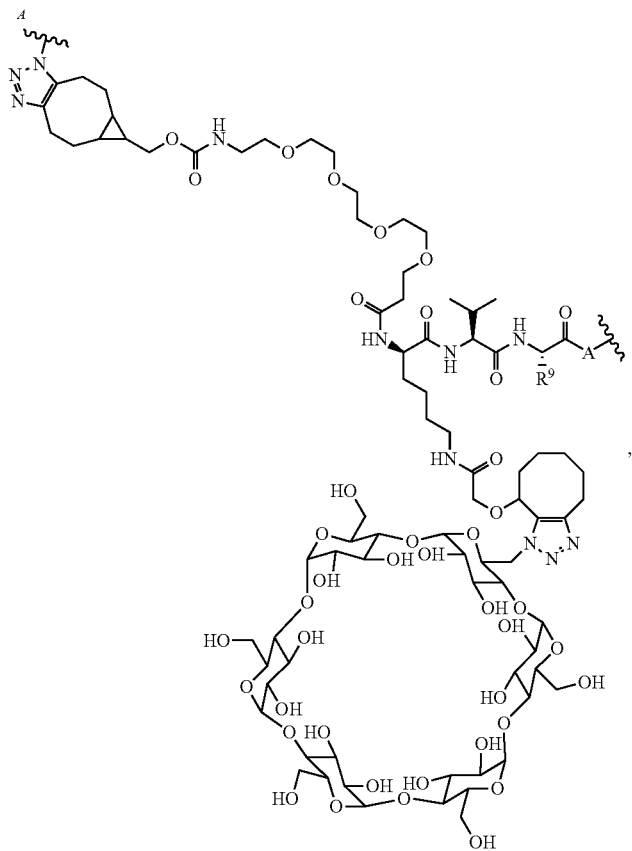

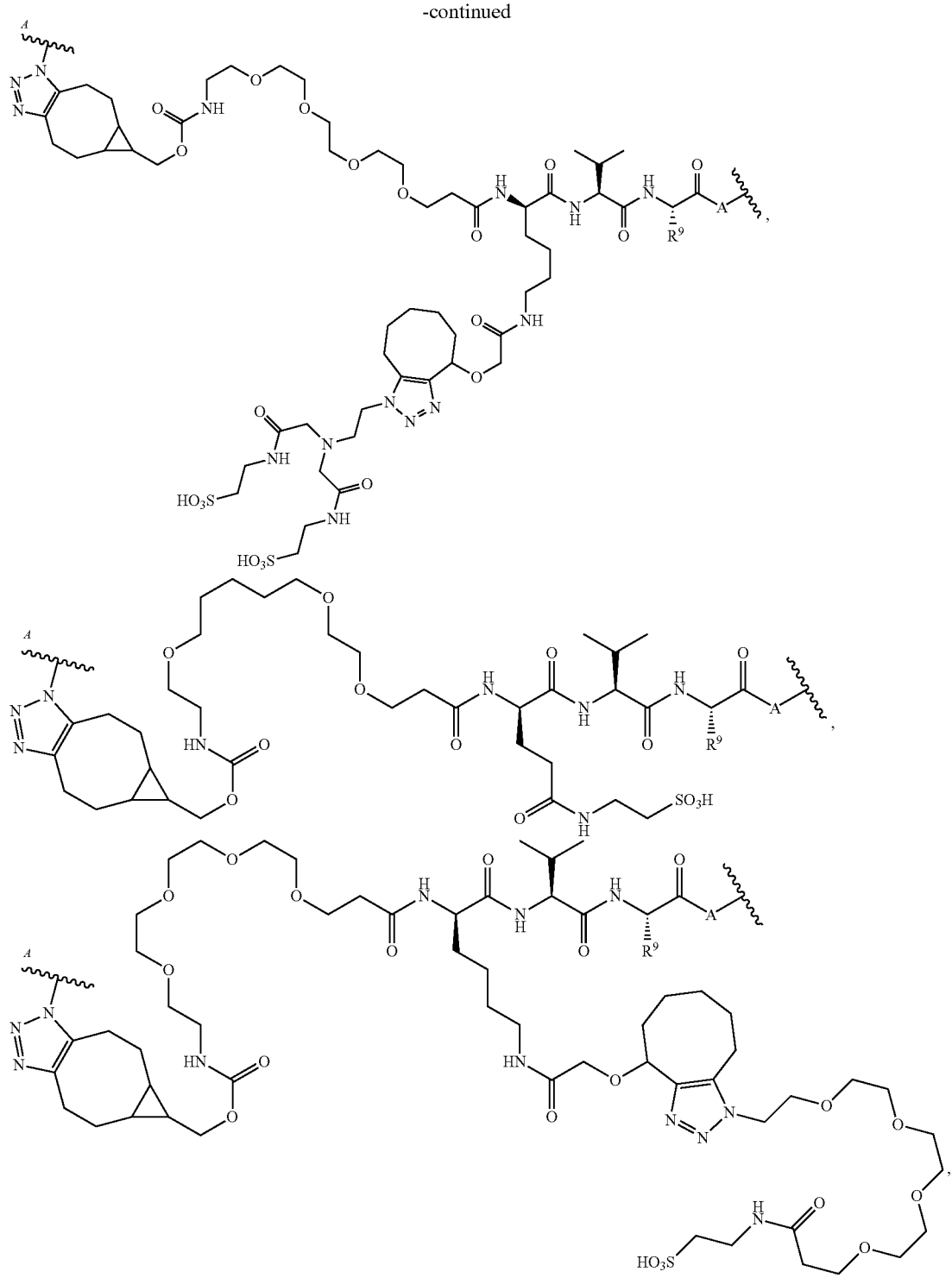
or a pharmaceutically acceptable salt, solvate, or stereoisomeric form thereof, or a regioisomer thereof, or mixture of regioisomers thereof, wherein:
each $-\xi-$ is a bond to the binding agent;
each $\xi^1$ is a bond to the payload;
$R^9$ is —CH$_3$ or —(CH$_2$)$_3$N(H)C(O)NH$_2$; and
A is —O—, —N(H)—,
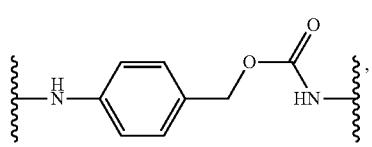

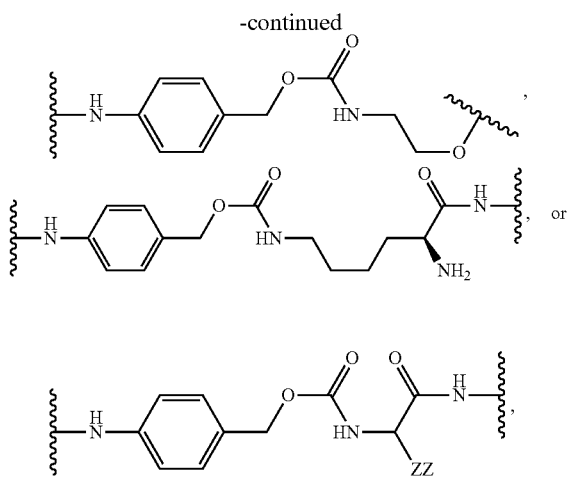

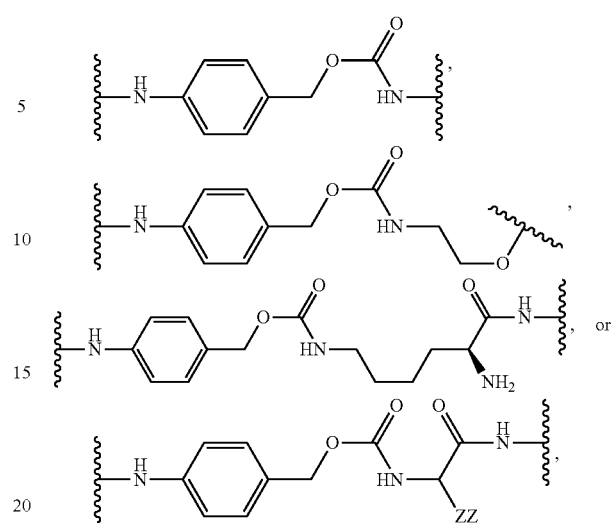

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent.

In some embodiments, the linker is:

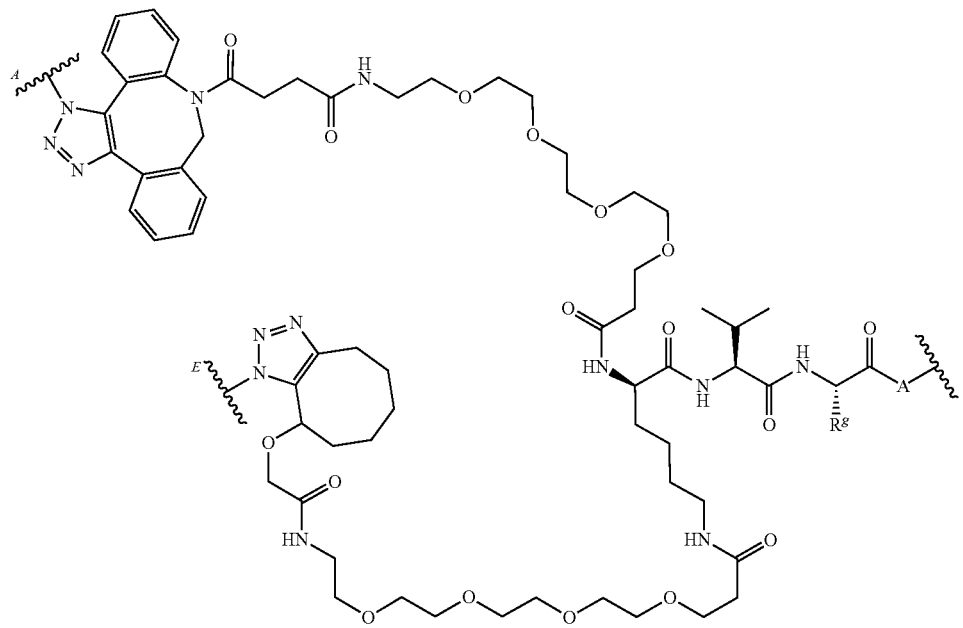

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin.

or a pharmaceutically acceptable salt, solvate, or stereoisomeric form thereof, or a regioisomer thereof, or mixture of regioisomers thereof, wherein:

each -§- is a bond to the binding agent;

each -§-¹ is a bond to the payload;

each -§-ᴱ is a bond to the enhancement group;
each $R^9$ is —$CH_3$ or —$(CH_2)_3N(H)C(O)NH_2$; and
each A is —O—, —N(H)—, In certain embodiments, the alkyl, heteroalkyl, alkylenyl, or heteroalkylenyl sulfonic acid is —(CH$_2$)$_{1-5}$SO$_3$H, —(CH$_2$)$_{n2}$—NH—(CH$_2$)$_{1-5}$SO$_3$H, —(CH$_2$)$_{n2}$—C(O)NH—(CH$_2$)$_{1-5}$SO$_3$H, —(CH$_2$CH$_2$O)$_{m2}$—C(O)NH—(CH$_2$)$_{1-5}$SO$_3$H, —(CH$_2$)$_{n2}$—N((CH$_2$)$_{1-5}$C(O)NH(CH$_2$)$_{1-5}$SO$_3$H)$_2$, —(CH$_2$)$_{n2}$—C(O)N((CH$_2$)$_{1-5}$C(O)NH(CH$_2$)$_{1-5}$SO$_3$H)$_2$, or —(CH$_2$CH$_2$O)$_{m2}$—C(O)N((CH$_2$)$_{1-5}$C(O)NH(CH$_2$)$_{1-5}$SO$_3$H)$_2$, wherein n2 is 1, 2, 3, 4, or 5, and m2 is 1, 2, 3, 4, or 5. In one embodiment, the alkyl or alkylenyl sulfonic acid is —(CH$_2$)$_{1-5}$SO$_3$H. In another embodiment, the heteroalkyl or heteroalkylenyl sulfonic acid is —(CH$_2$)$_{n2}$—NH—(CH$_2$)$_{1-5}$SO$_3$H, wherein n2 is 1, 2, 3, 4, or 5. In another embodiment, the alkyl, heteroalkyl, alkylenyl, or heteroalkylenyl sulfonic acid is —(CH$_2$)$_{n2}$—C(O)NH—(CH$_2$)$_{1-5}$SO$_3$H, wherein n2 is 1, 2, 3, 4, or 5. In another embodiment, the alkyl, heteroalkyl, alkylenyl, or heteroalkylenyl sulfonic acid is —(CH$_2$CH$_2$O)$_{m2}$—C(O)NH—(CH$_2$)$_{1-5}$SO$_3$H, wherein m2 is 1, 2, 3, 4, or 5. In another embodiment, the alkyl, heteroalkyl, alkylenyl, or heteroalkylenyl sulfonic acid is —(CH$_2$)$_{n2}$—N((CH$_2$)$_{1-5}$C(O)NH(CH$_2$)$_{1-5}$SO$_3$H)$_2$, wherein n2 is 1, 2, 3, 4, or 5. In another embodiment, the alkyl, heteroalkyl, alkylenyl, or heteroalkylenyl sulfonic acid is —(CH$_2$)$_{n2}$—C(O)N((CH$_2$)$_{1-5}$C(O)NH(CH$_2$)$_{1-5}$SO$_3$H)$_2$, wherein n2 is 1, 2, 3, 4, or 5. In another embodiment, the alkyl, heteroalkyl, alkylenyl, or heteroalkylenyl sulfonic acid is —(CH$_2$CH$_2$O)$_{m2}$—C(O)N((CH$_2$)$_{1-5}$C(O)NH(CH$_2$)$_{1-5}$SO$_3$H)$_2$, wherein m2 is 1, 2, 3, 4, or 5.

In some embodiments, the linker is:

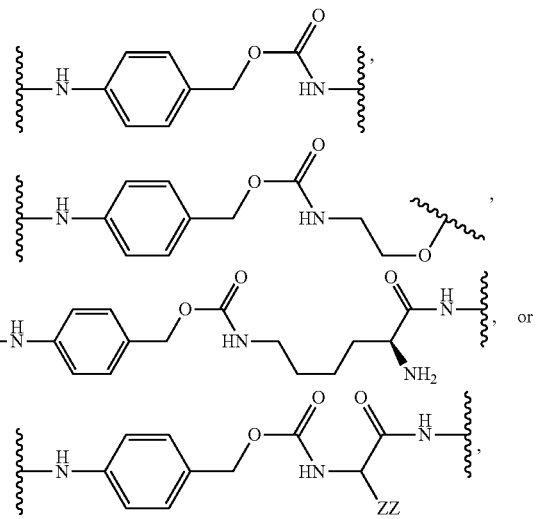

where ZZ is hydrogen, or a side chain for an amino acid as discussed elsewhere herein. For example, in one embodiment, ZZ is C$_{1-6}$ alkyl. Byway of further example, in one embodiment, ZZ is C$_{1-6}$ heteroalkyl. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin.

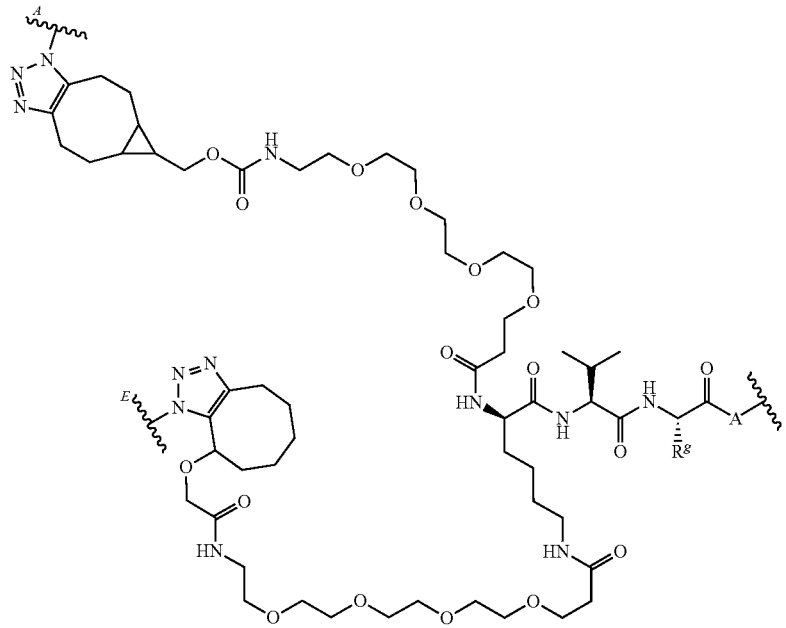

or a pharmaceutically acceptable salt, solvate, or stereoisomeric form thereof, or a regioisomer thereof, or mixture of regioisomers thereof, wherein:

each $\xi\!\!-$ is a bond the binding agent;

each $\xi\!\!1$ is a bond to the payload;

each R$^9$ is —CH$_3$ or —(CH$_2$)$_3$N(H)C(O)NH$_2$; and each A is —O—, —N(H)—, In certain embodiments, the alkyl, heteroalkyl, alkylenyl, or heteroalkylenyl sulfonic acid is —(CH$_2$)$_{1-5}$SO$_3$H, —(CH$_2$)$_{n2}$—NH—(CH$_2$)$_{1-5}$SO$_3$H, —(CH$_2$)$_{n2}$—C(O)NH—(CH$_2$)$_{1-5}$SO$_3$H, —(CH$_2$CH$_2$O)$_{m2}$—C(O)NH—(CH$_2$)$_{1-5}$SO$_3$H, —(CH$_2$)$_{n2}$—N((CH$_2$)$_{1-5}$C(O)NH(CH$_2$)$_{1-5}$SO$_3$H)$_2$, —(CH$_2$)$_{n2}$—C(O)N((CH$_2$)$_{1-5}$C(O)NH(CH$_2$)$_{1-5}$SO$_3$H)$_2$, or —(CH$_2$CH$_2$O)$_{m2}$—C(O)N((CH$_2$)$_{1-5}$C(O)NH(CH$_2$)$_{1-5}$SO$_3$H)$_2$, wherein n2 is 1, 2, 3, 4, or 5, and m2 is 1, 2, 3, 4, or 5. In one embodiment, the alkyl or alkylenyl sulfonic acid is —(CH$_2$)$_{1-5}$SO$_3$H. In another embodiment, the heteroalkyl or heteroalkylenyl sulfonic acid is —(CH$_2$)$_{n2}$—NH—(CH$_2$)$_{1-5}$SO$_3$H, wherein n2 is 1, 2, 3, 4, or 5. In another embodiment, the alkyl, heteroalkyl, alkylenyl, or heteroalkylenyl sulfonic acid is —(CH$_2$)$_{n2}$—C(O)NH—(CH$_2$)$_{1-5}$SO$_3$H, wherein n2 is 1, 2, 3, 4, or 5. In another embodiment, the alkyl, heteroalkyl, alkylenyl, or heteroalkylenyl sulfonic acid is —(CH$_2$CH$_2$O)$_{m2}$—C(O)NH—(CH$_2$)$_{1-5}$SO$_3$H, wherein m2 is 1, 2, 3, 4, or 5. In another embodiment, the alkyl, heteroalkyl, alkylenyl, or heteroalkylenyl sulfonic acid is —(CH$_2$)$_{n2}$—N((CH$_2$)$_{1-5}$C(O)NH(CH$_2$)$_{1-5}$SO$_3$H)$_2$, wherein n2 is 1, 2, 3, 4, or 5. In another embodiment, the alkyl, heteroalkyl, alkylenyl, or heteroalkylenyl sulfonic acid is —(CH$_2$)$_{n2}$—C(O)N((CH$_2$)$_{1-5}$C(O)NH(CH$_2$)$_{1-5}$SO$_3$H)$_2$, wherein n2 is 1, 2, 3, 4, or 5. In another embodiment, the alkyl, heteroalkyl, alkylenyl, or heteroalkylenyl sulfonic acid is —(CH$_2$CH$_2$O)$_{m2}$—C(O)N((CH$_2$)$_{1-5}$C(O)NH(CH$_2$)$_{1-5}$SO$_3$H)$_2$, wherein m2 is 1, 2, 3, 4, or 5.

In some embodiments, the linker is:

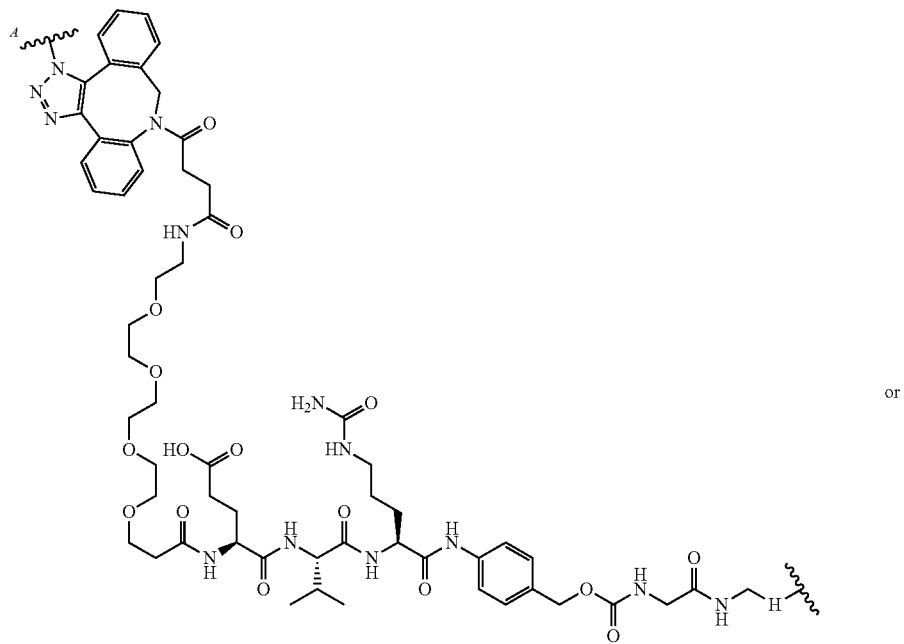

or

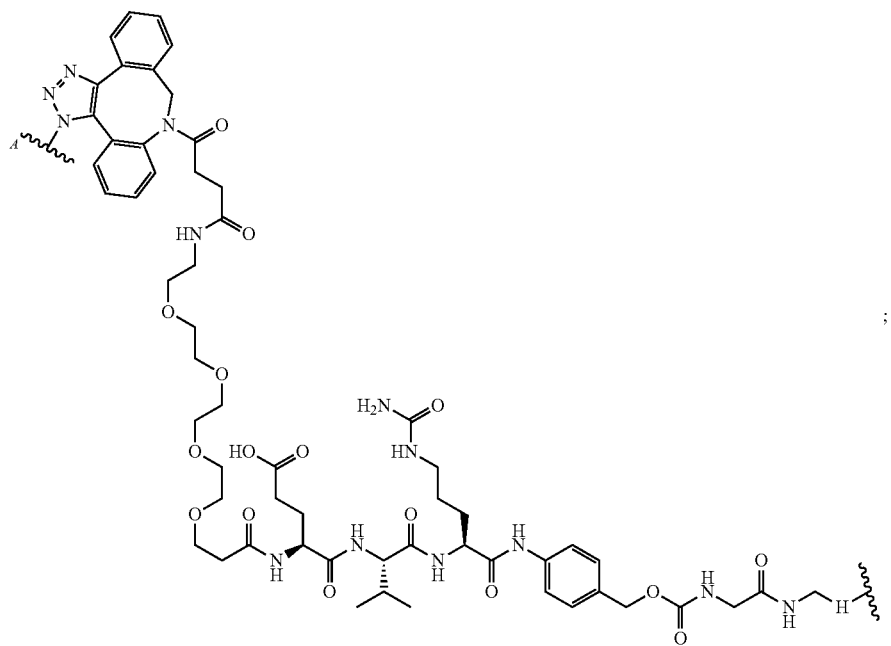

;

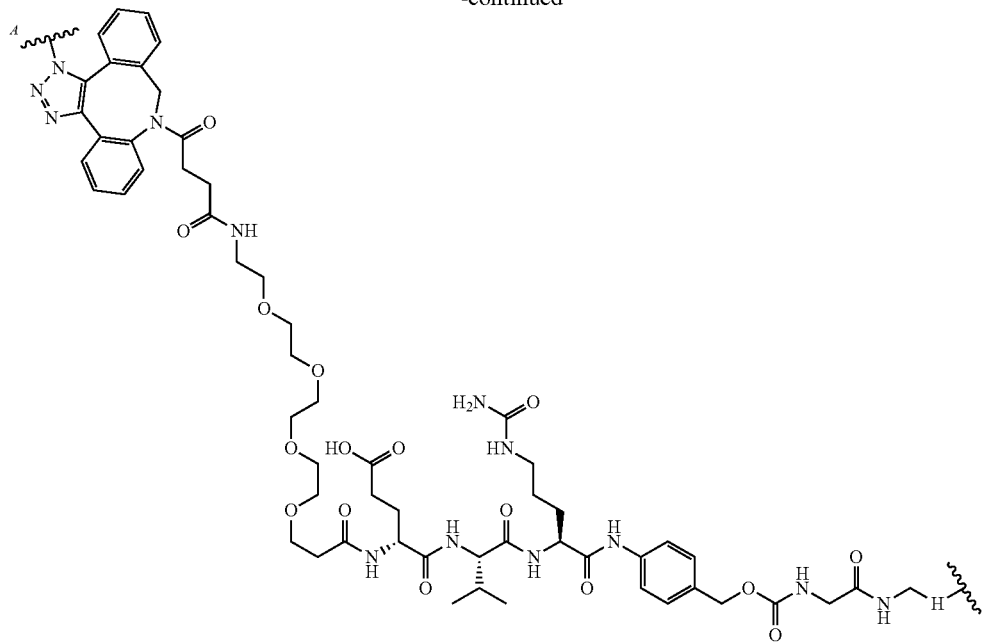
or
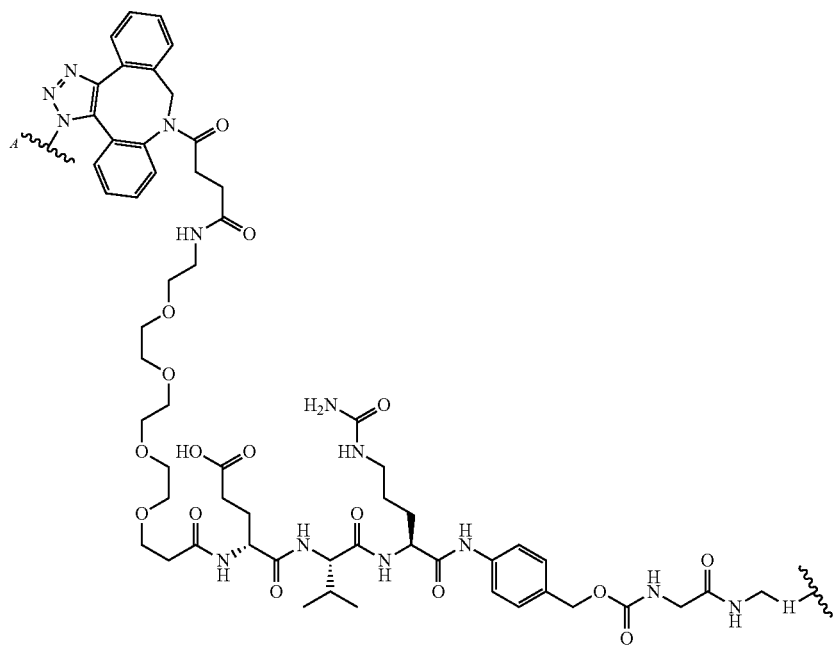
;
or a pharmaceutically acceptable salt, solvate, or stereoisomeric form thereof, or a regioisomer thereof, or mixture of regioisomers thereof, wherein:
each $-\xi-$ is a bond to the binding agent;
each $\overset{1}{\xi}$ is a bond to the payload; and H is —O— or —NH—.

In some embodiments, the linker is:
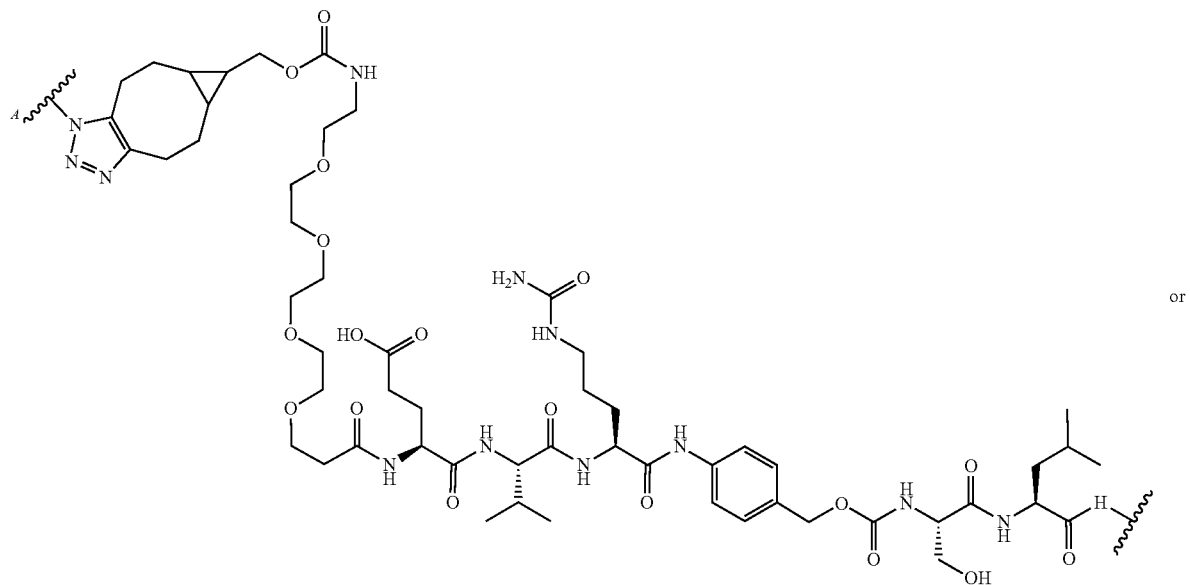
or
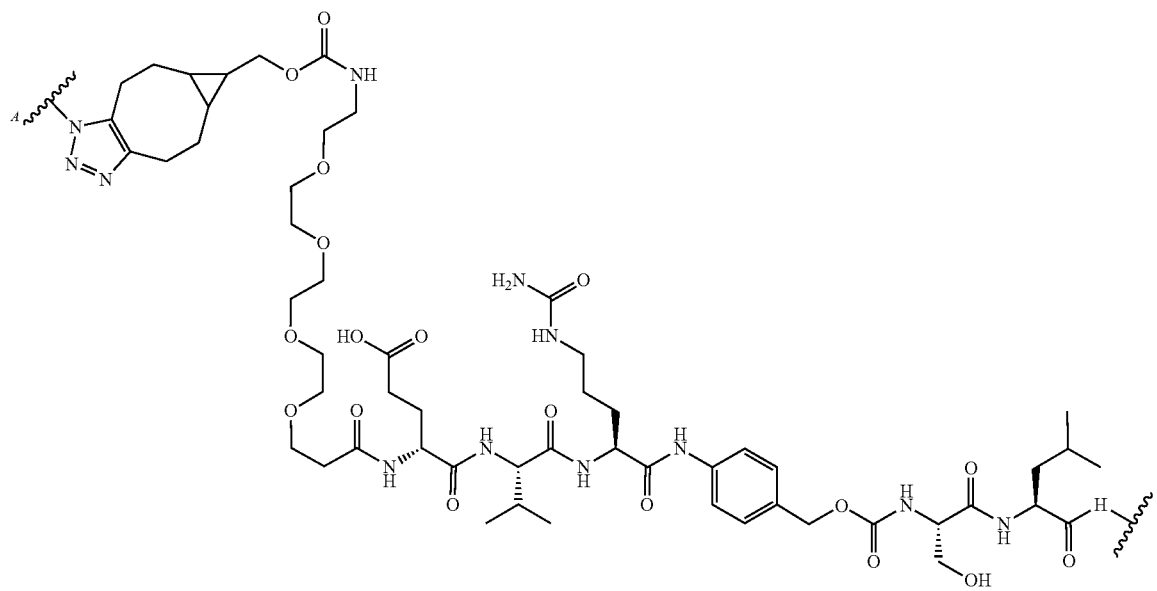
wherein:
each ⌇ξ⌇ is a bond the binding agent;
each ⌇ξ⌇ is a bond to the payload; and H is —O— or —NH—.

In some embodiments, the linker is:
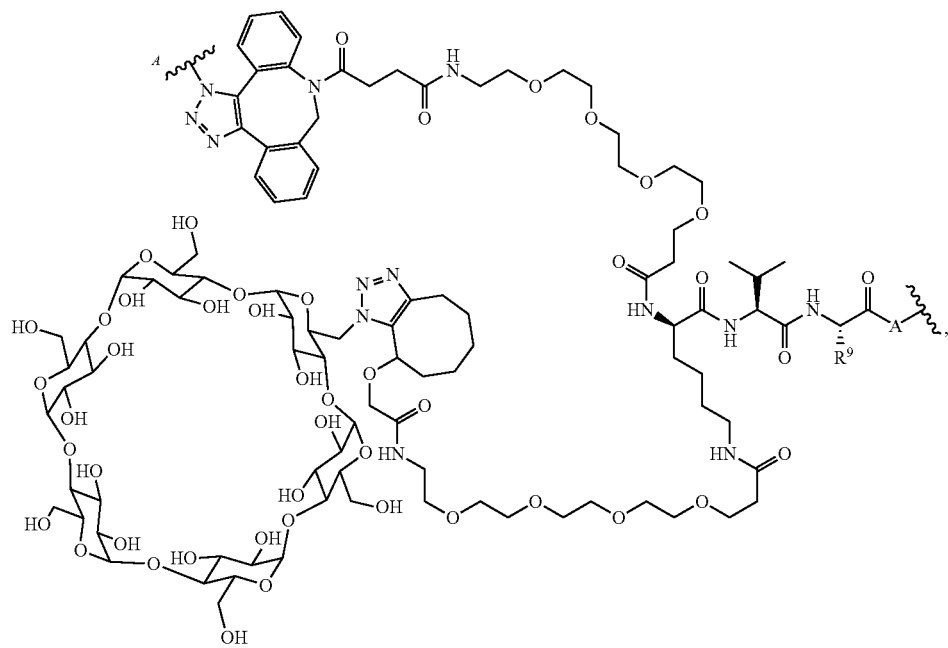
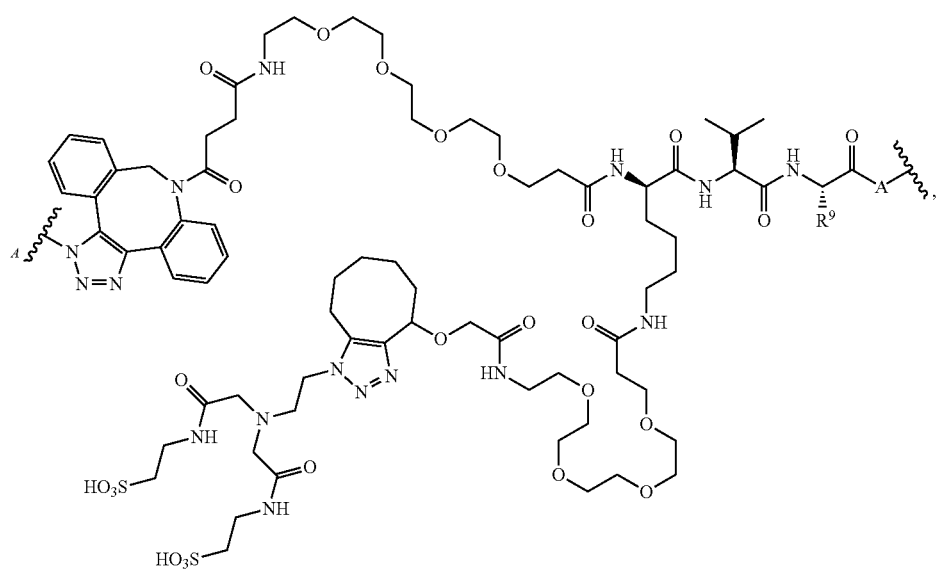

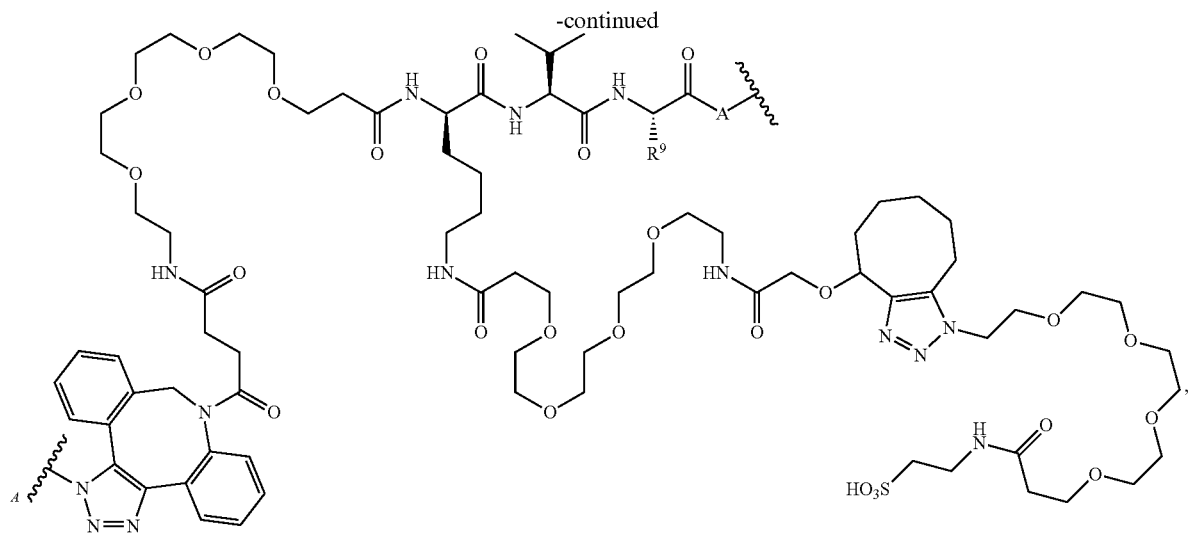

-continued or a pharmaceutically acceptable salt, solvate, or stereoisomeric form thereof, or a regioisomer thereof, or mixture of regioisomers thereof, wherein:

each ⁓§⁓ is a bond to the binding agent;

each ⁓₁§⁓ is a bond to the payload;

$R^9$ is —CH₃ or —(CH₂)₃N(H)C(O)NH₂; and

A is —O—, —N(H)—,

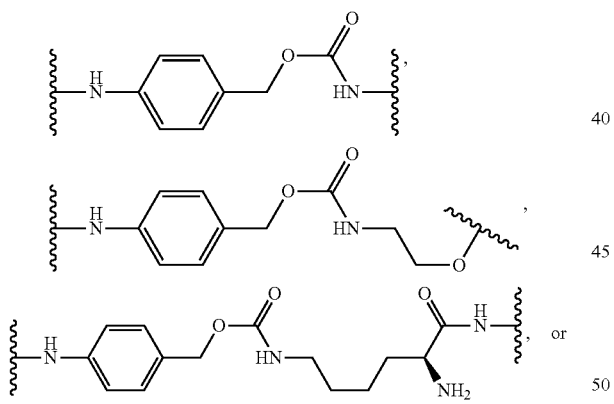

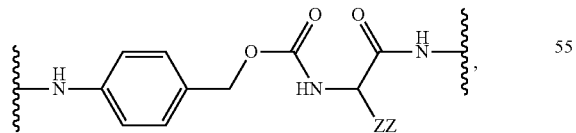

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent.

In some embodiments, the linker is:
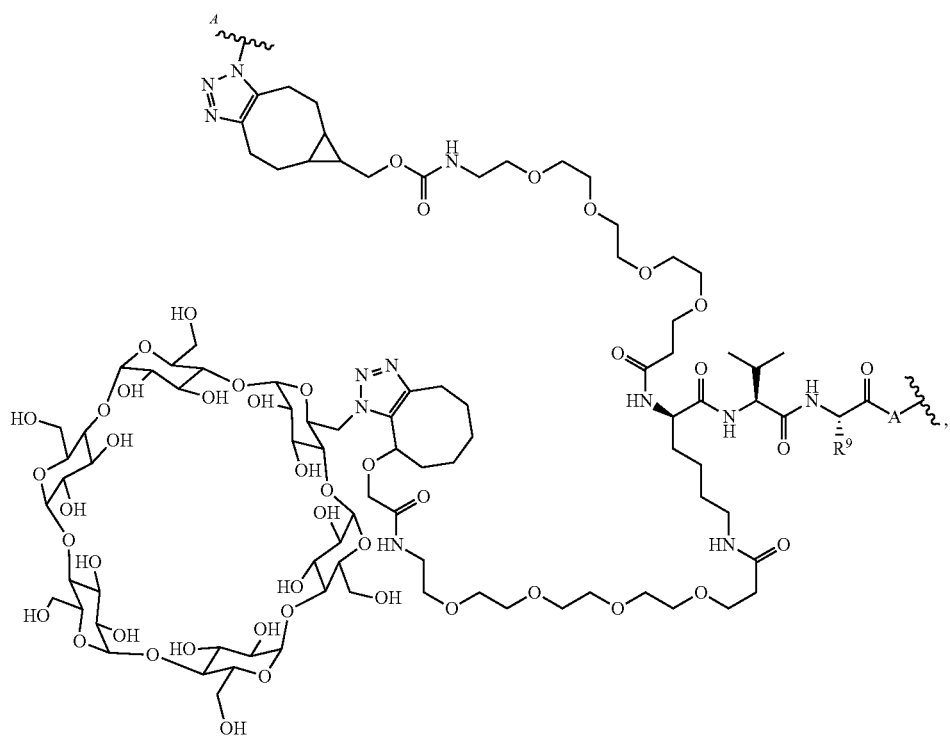
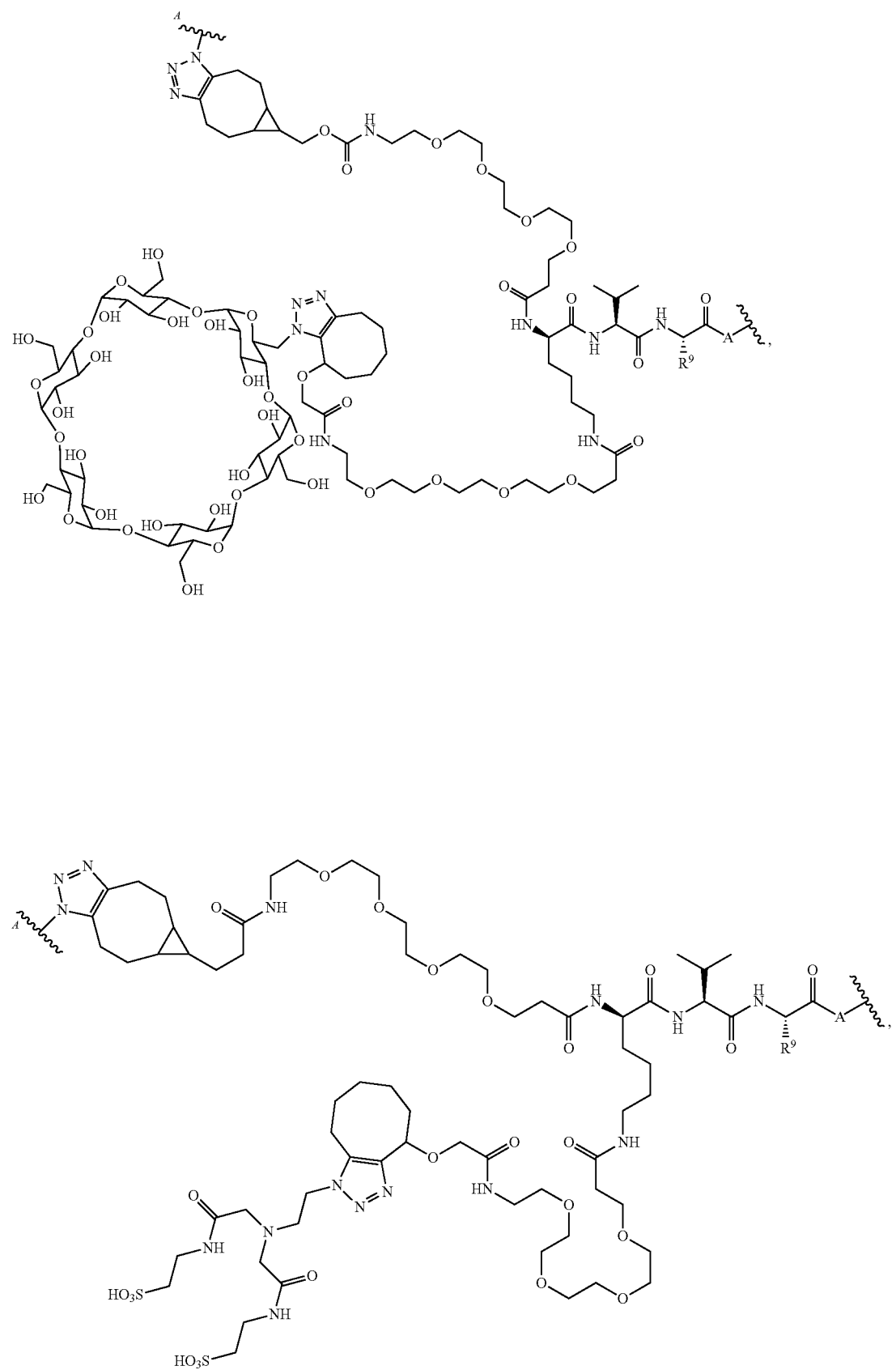

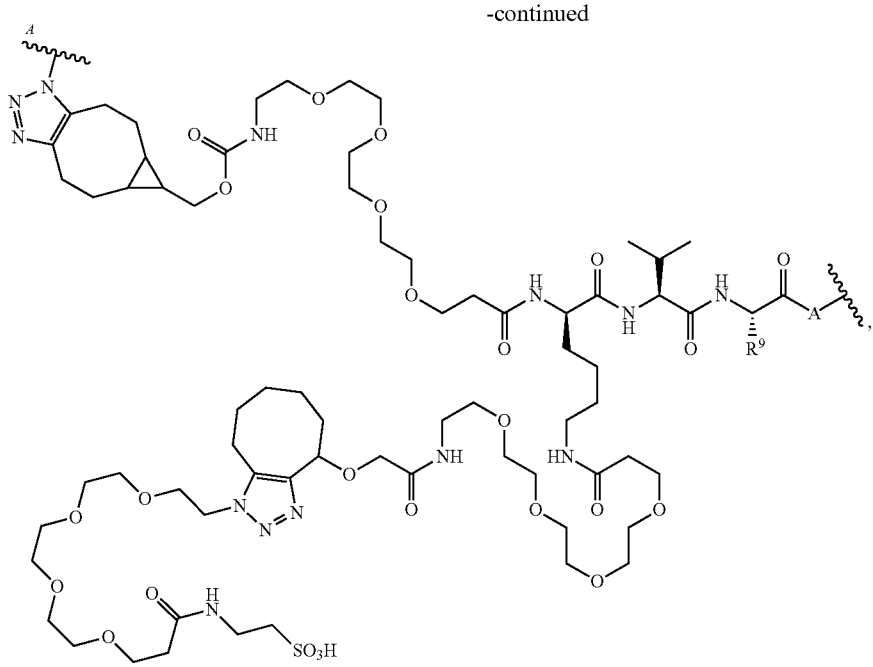

or a pharmaceutically acceptable salt, solvate, or stereoisomeric form thereof, or a regioisomer thereof, or mixture of regioisomers thereof, wherein:

each $\overset{1}{\xi}$ is a bond to the binding agent;

each $\overset{-\xi-}{}$ is a bond to the payload;

$R^9$ is —$CH_3$ or —$(CH_2)_3N(H)C(O)NH_2$; and

A is —O—, —N(H)—,

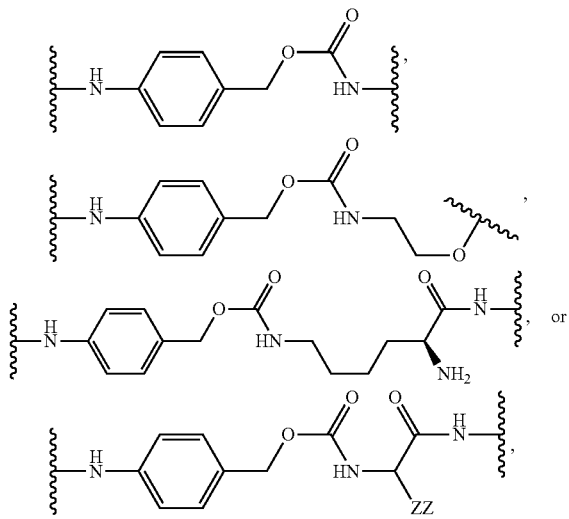

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent.

Linker-Payloads or Reactive Linker-Payloads

Provided are linker-payloads or reactive linker-payloads derived from any of the compounds or payloads (e.g., compounds or payloads of Formulae I, II, or III), and linkers described herein. In certain embodiments, described below, conjugates provided herein can be prepared from the linker-payloads or reactive linker-payloads having reactive groups RG as described above. The linker-payloads or reactive linker-payloads can be linked to enhancement groups and/or binding agents according to the methods described below.

In certain embodiments, the linker-payloads include any specific payloads embraced by any one or more of Formulae I, II, or III above, bonded to a linker(s), wherein the linker(s) described herein include a moiety that is reactive with a binding agent, antibody or antigen binding fragment thereof, and/or enhancement group described herein. In particular embodiments, the linker is bonded to $R^1$, $R^2$, or $R^6$, or divalent forms of $R^1$, $R^2$, or $R^6$, as in any one or more of payload Formulae I, II, or III above. In one embodiment, the linker-payload has a structure of Formula LPa:

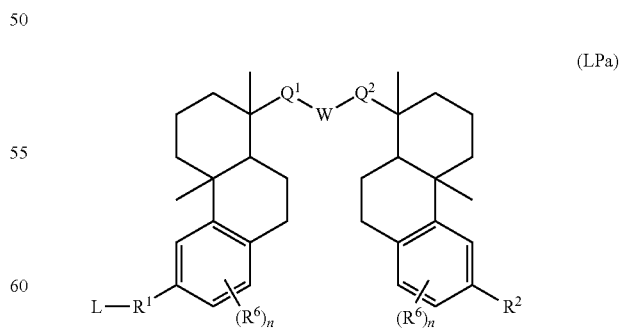

(LPa)

wherein L is a linker as described above, and $Q^1$, $Q^2$, W, —$R^1$—, $R^2$, $R^4$, $R^5$, and $R^6$ are as described in the context of Formula I above. In one embodiment, the linker-payload has a structure of Formula LPb:

(LPb)

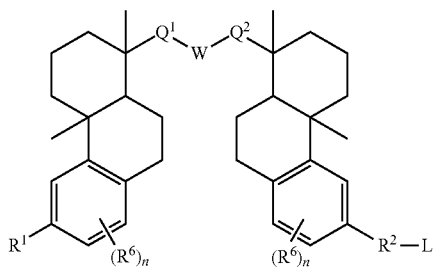

wherein L is a linker as described above, and $Q^1$, $Q^2$, W, $R^1$, —$R^2$—, $R^4$, $R^5$, and $R^6$ are as described in the context of Formula I above. In one embodiment, the linker-payload has a structure of Formula LPc:

(LPc)

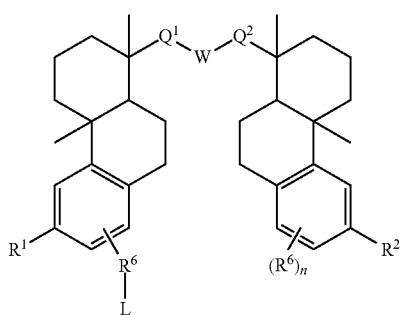

wherein L is a linker as described above, and $Q^1$, $Q^2$, W, $R^1$, $R^2$, $R^4$, $R^5$, and —$R^6$— are as described in the context of Formula I above. In one embodiment, the linker-payload has a structure of Formula LPd:

(LPd)

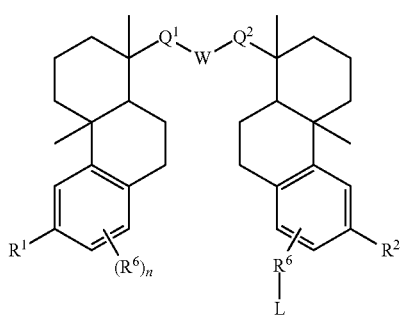

wherein L is a linker as described above, and $Q^1$, $Q^2$, W, $R^1$, $R^2$, $R^4$, $R^5$, and —$R^6$— are as described in the context of Formula I above. In one embodiment, the linker-payload has a structure of Formula LPa':

(LPa')

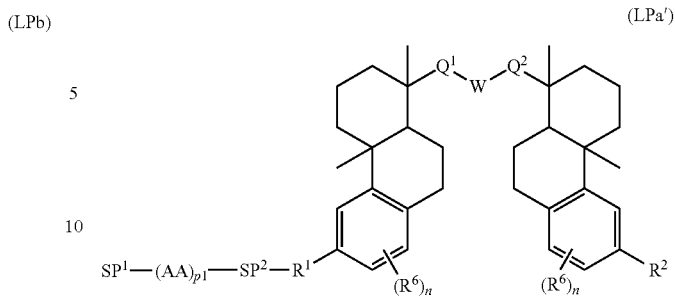

wherein $SP^1$ and $SP^2$ are spacers as described above, each AA is an amino acid residue as described above, $Q^1$, $Q^2$, W, —$R^1$—, $R^2$, $R^4$, $R^5$, and $R^6$ are as described in the context of Formula I, and p1 is an integer from 1 to 10. In one embodiment, the linker-payload has a structure of Formula LPb':

(LPb')

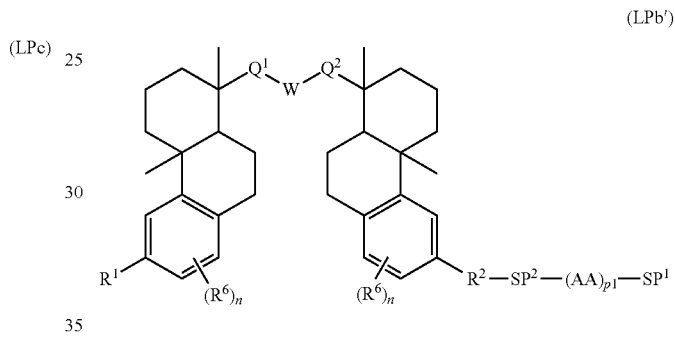

wherein $SP^1$ and $SP^2$ are spacers as described above, each AA is an amino acid residue as described above, $Q^1$, $Q^2$, W, $R^1$, —$R^2$—, $R^4$, $R^5$, and $R^6$ are as described in the context of Formula I, and p1 is an integer from 1 to 10. In one embodiment, the linker-payload has a structure of Formula LPc':

(LPc')

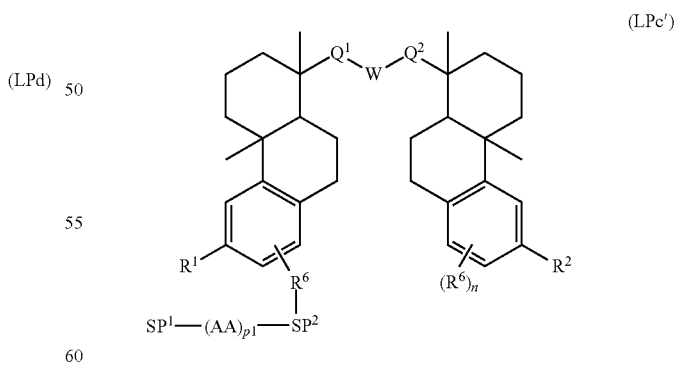

wherein $SP^1$ and $SP^2$ are spacers as described above, each AA is an amino acid residue as described above, $Q^1$, $Q^2$, W, $R^1$, $R^2$, $R^4$, $R^5$, and —$R^6$— are as described in the context of Formula I, and p1 is an integer from 1 to 10. In one embodiment, the linker-payload has a structure of Formula LPd':

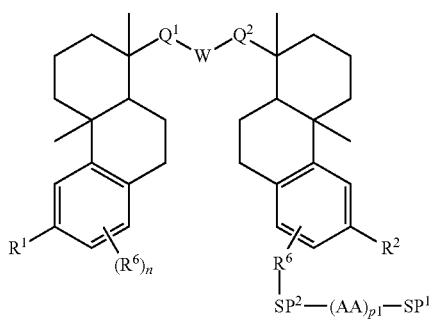

(LPd′)

wherein SP¹ and SP² are spacers as described above, each AA is an amino acid residue as described above, Q¹, Q², W, $R^1$, $R^2$, $R^4$, $R^5$, and —$R^6$— are as described in the context of Formula I, and p1 is an integer from 1 to 10. In any of the embodiments in this paragraph, p1 is 1, 2, 3, 4, 5, 6, 7, 8, 9, or 10. In any of the embodiments in this paragraph, the linker L or spacer SP² is bonded to an aryl nitrogen, or an amino acid residue alone or within a peptide. In any of the embodiments in this paragraph, each $R^4$ is, independently in each instance, hydrogen, an amino acid residue, an N-alkyl amino acid residue, a peptide residue, a biodegradable moiety, alkyl, substituted alkyl, acyl, or substituted acyl. In any of the embodiments in this paragraph, each $R^4$ is, independently in each instance, hydrogen, an amino acid residue, an N-alkyl amino acid residue, a peptide residue, a biodegradable moiety, or alkyl.

In some embodiments, the linker-payload or reactive linker-payload is:

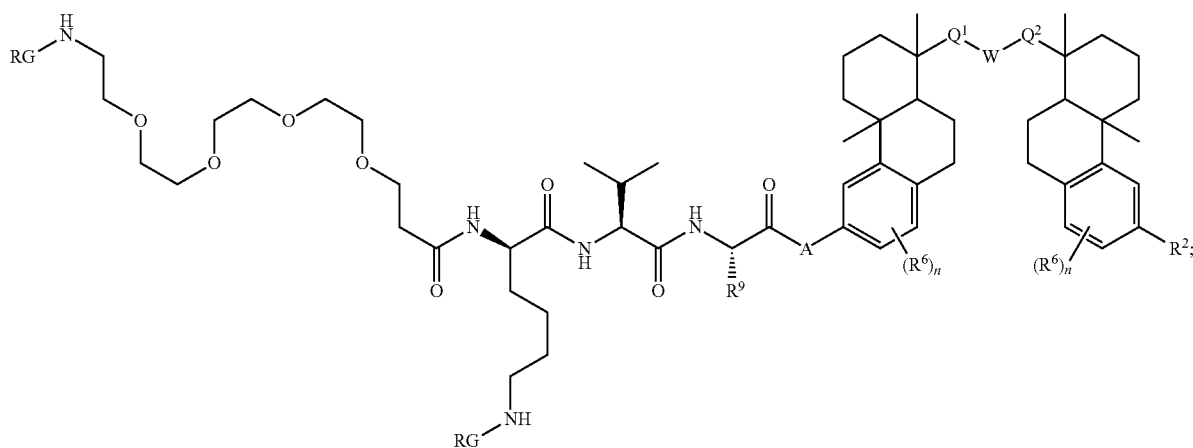

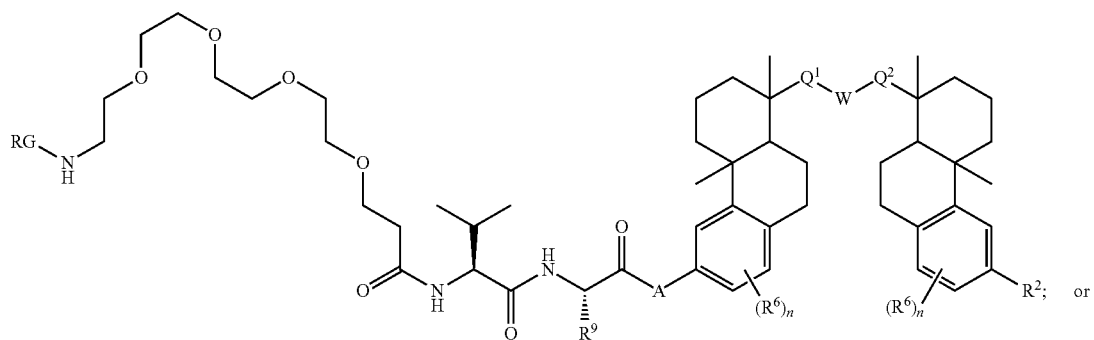

or

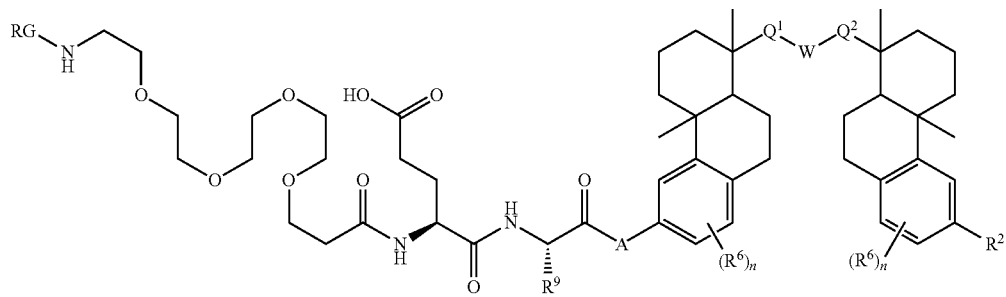

or a pharmaceutically acceptable salt, solvate, or stereoisomeric form thereof wherein:

each RG is a reactive group, as described herein;
$Q^1$, $Q^2$, W, $R^1$, $R^2$, $R^4$, $R^5$, and $R^6$ are as described in the context of Formula I;
each $R^9$ is —$CH_3$ or —$(CH_2)_3N(H)C(O)NH_2$; and
each A is —O—, —N(H)—,

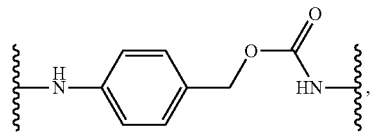

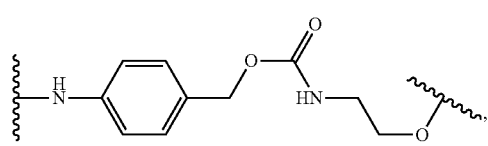

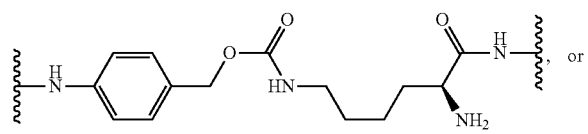, or

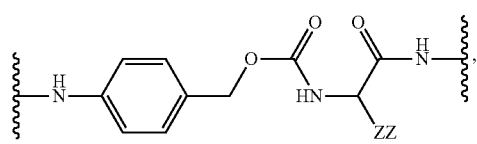

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the linker-payload or reactive linker-payload is:

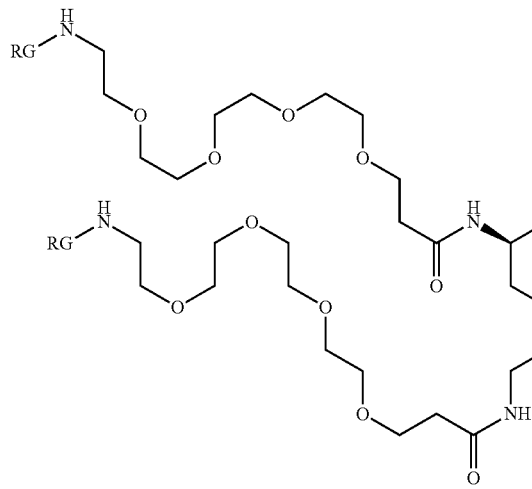

or a pharmaceutically acceptable salt, solvate, or stereoisomeric form thereof wherein:

each RG is a reactive group, as described herein;
$Q^1$, $Q^2$, W, $R^1$, $R^2$, $R^4$, $R^5$, and $R^6$ are as described in the context of Formula I;
each $R^9$ is —$CH_3$ or —$(CH_2)_3N(H)C(O)NH_2$; and
each A is —O—, —N(H)—,

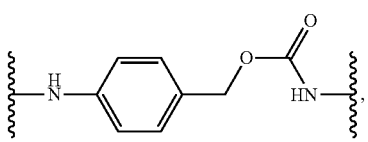

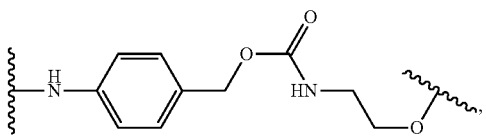

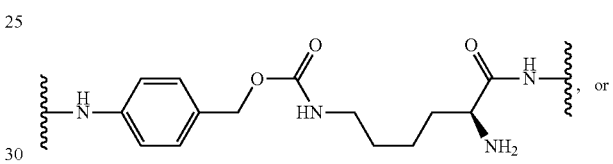, or

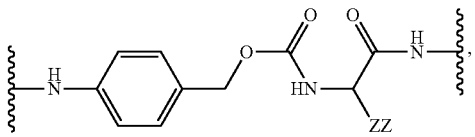

where ZZ is hydrogen, or a side chain for an amino acid as discussed elsewhere herein. For example, in one embodiment, ZZ is $C_{1-6}$ alkyl. Byway of further example, in one embodiment, ZZ is $C_{1-6}$ heteroalkyl.

In some embodiments, the linker-payload or reactive linker-payload is:

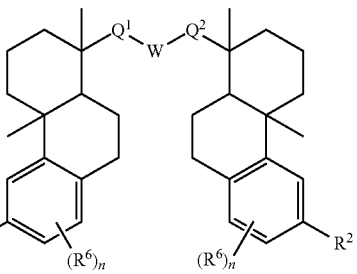

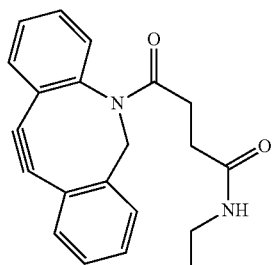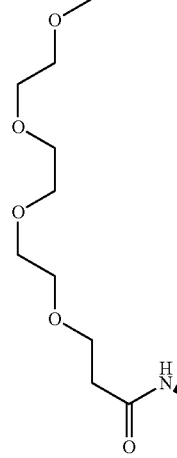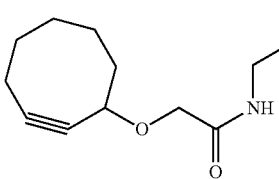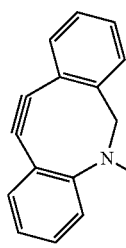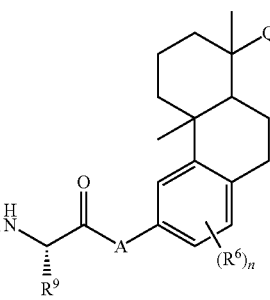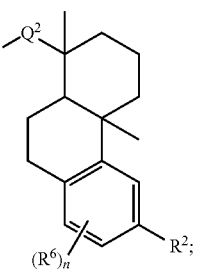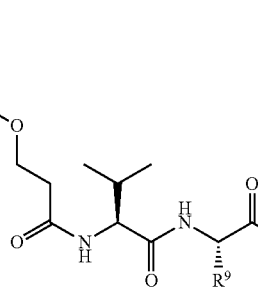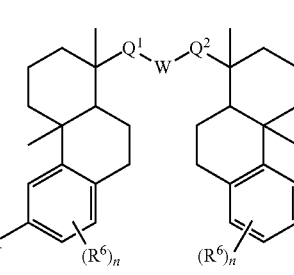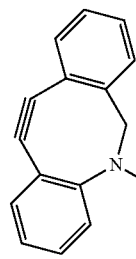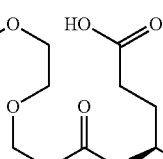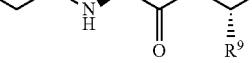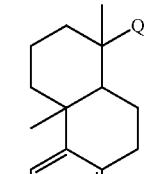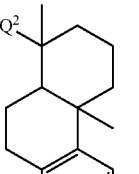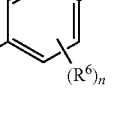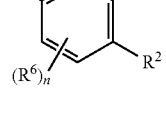

or a pharmaceutically acceptable salt, solvate, or stereoisomeric form thereof wherein:

$Q^1$, $Q^2$, W, $R^1$, $R^2$, $R^4$, $R^5$, and $R^6$ are as described in the context of Formula I;

each $R^9$ is —CH$_3$ or —(CH$_2$)$_3$N(H)C(O)NH$_2$; and each A is —O—, —N(H)—,

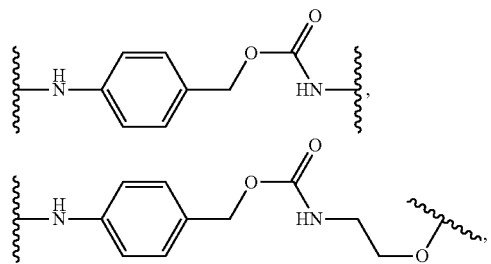

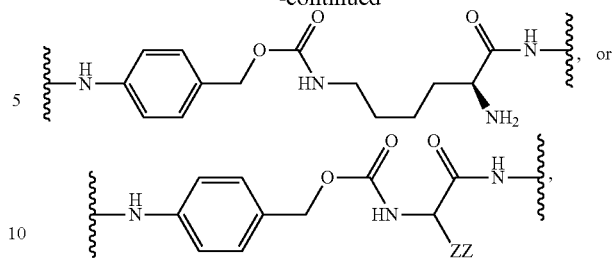

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the linker-payload or reactive linker-payload is:

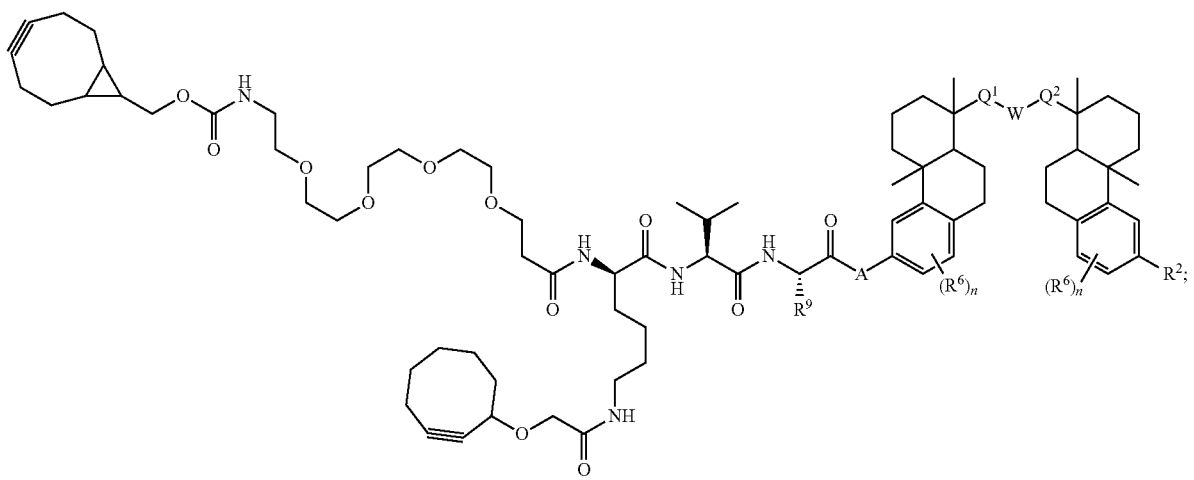

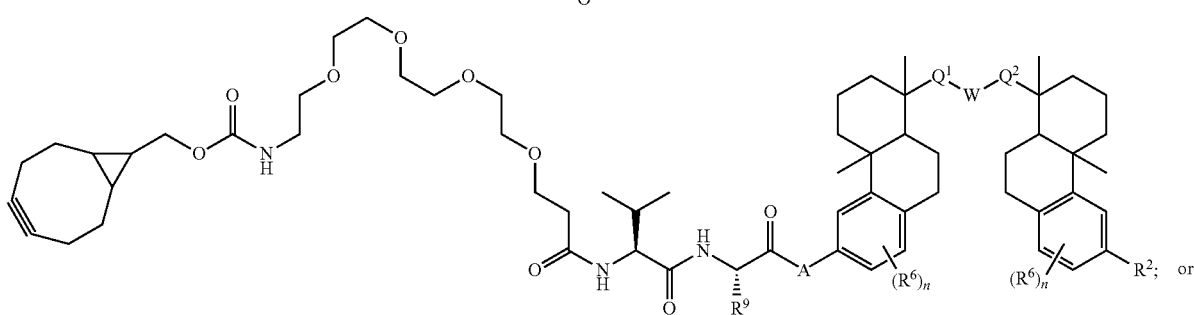

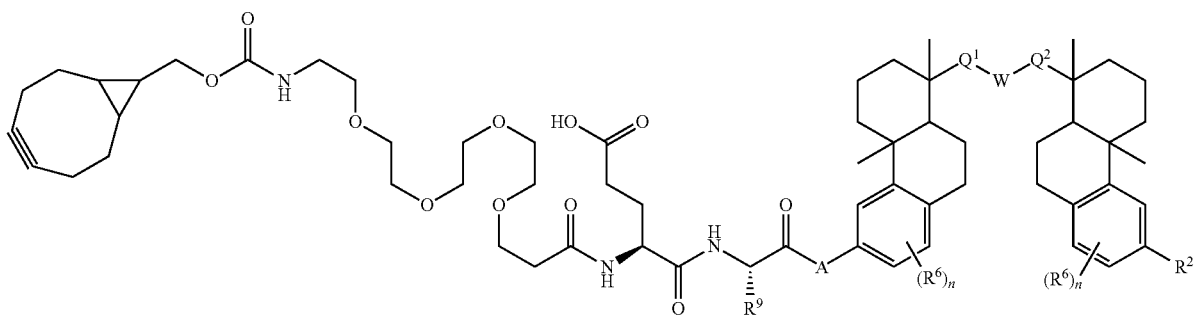

or a pharmaceutically acceptable salt, solvate, or stereoisomeric form thereof wherein:

Q$^1$, Q$^2$, W, R$^1$, R$^2$, R$^4$, R$^5$, and R$^6$ are as described in the context of Formula I;
each R$^9$ is —CH$_3$ or —(CH$_2$)$_3$N(H)C(O)NH$_2$; and
each A is —O—, —N(H)—,

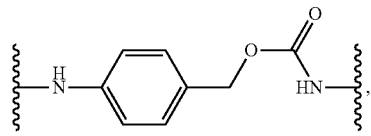

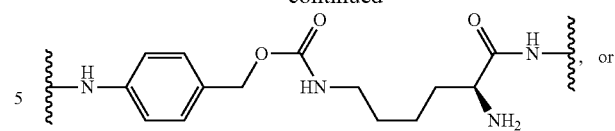

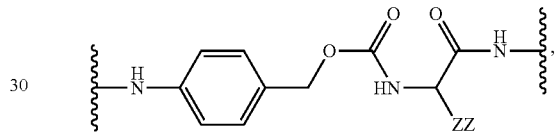

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl.

In some embodiments, the reactive linker-payload is:

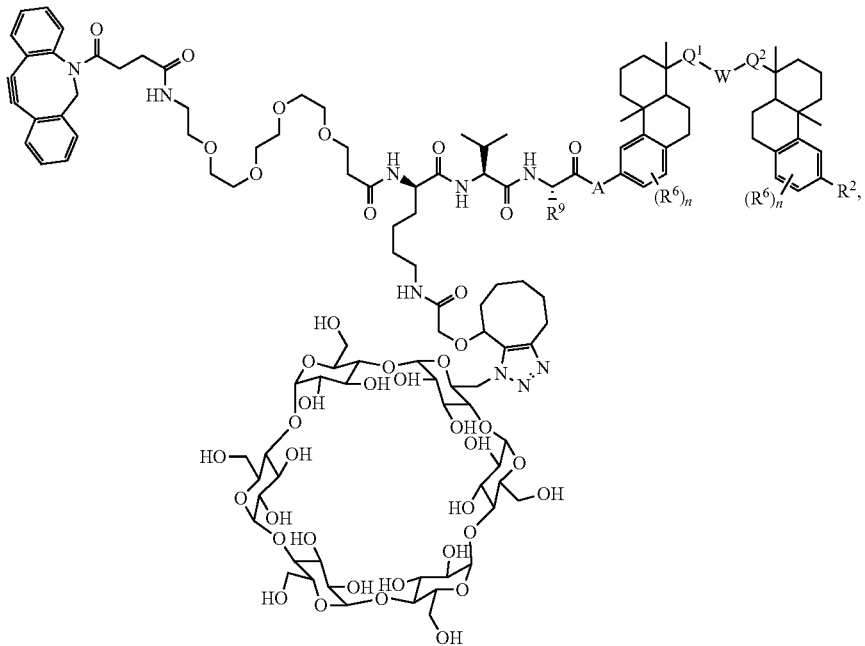

115
-continued
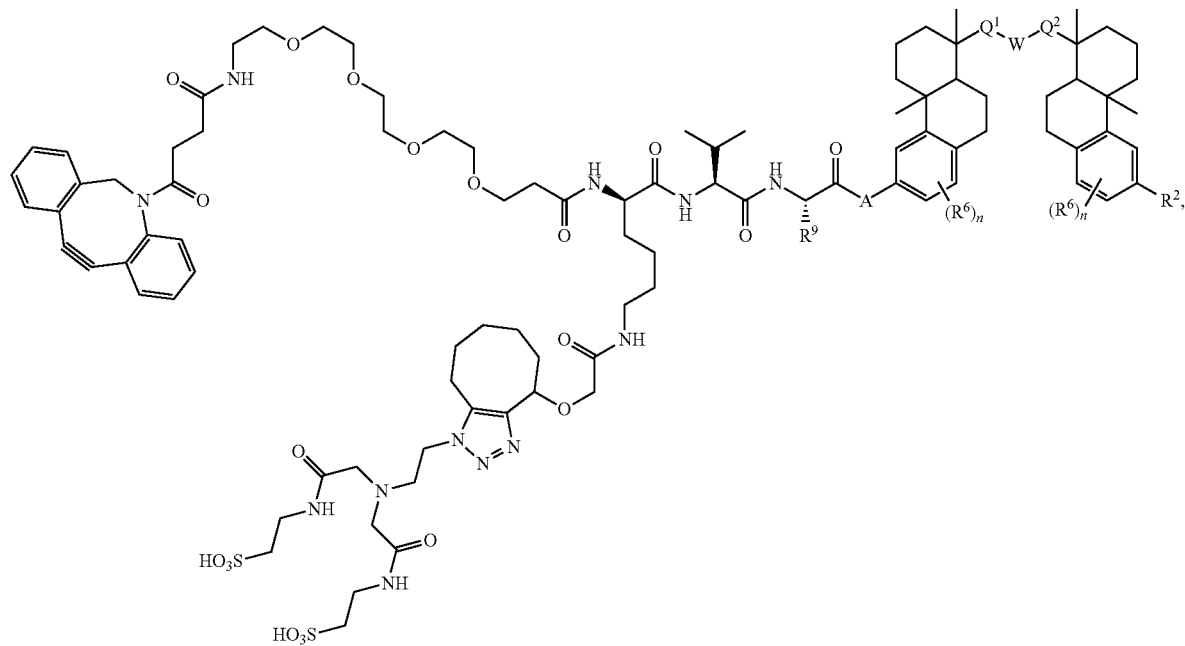
116
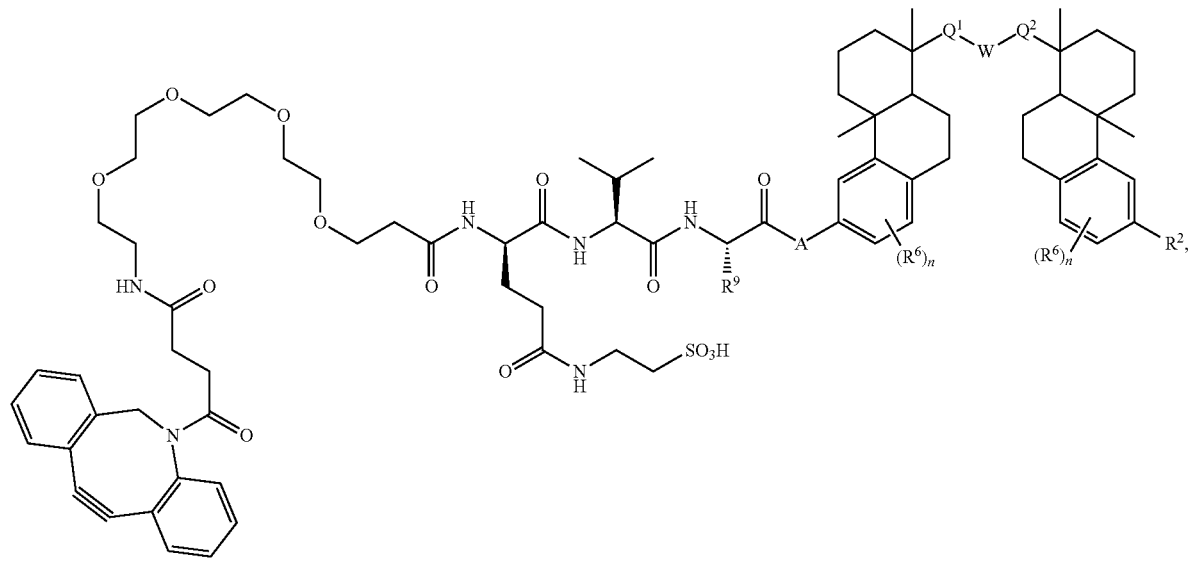

-continued

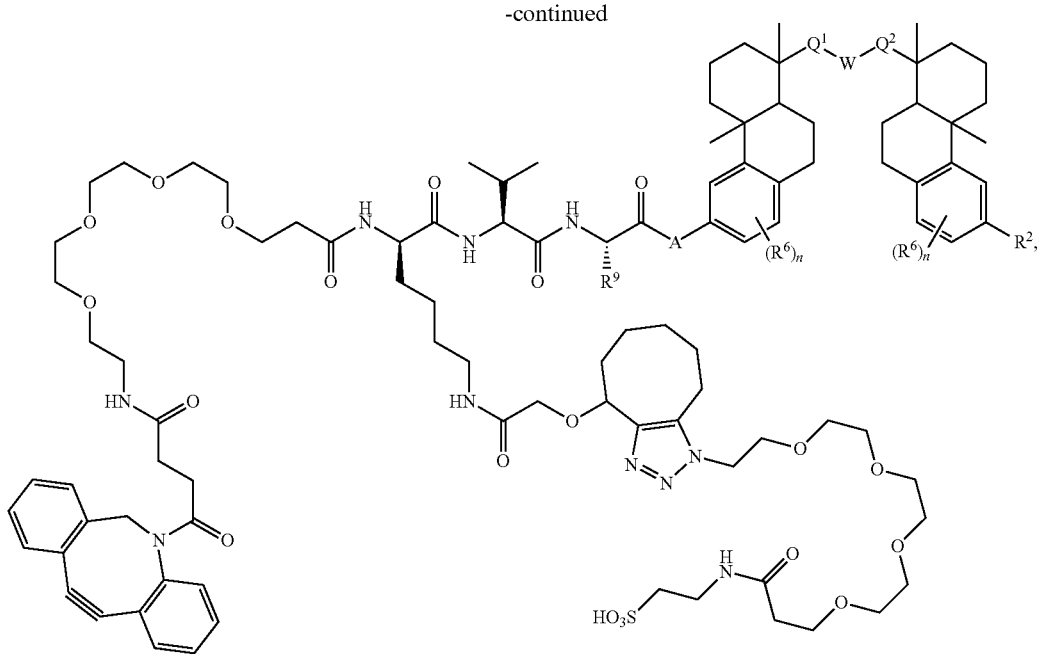

or a pharmaceutically acceptable salt, solvate, or stereoisomeric form thereof, or a regioisomer thereof, wherein:

$Q^1$, $Q^2$, W, $R^1$, $R^2$, $R^4$, $R^5$, and $R^6$ as described in the context of Formula I;

each $R^9$ is —$CH_3$ or —$(CH_2)_3N(H)C(O)NH_2$; and each A is —O—, —N(H)—,

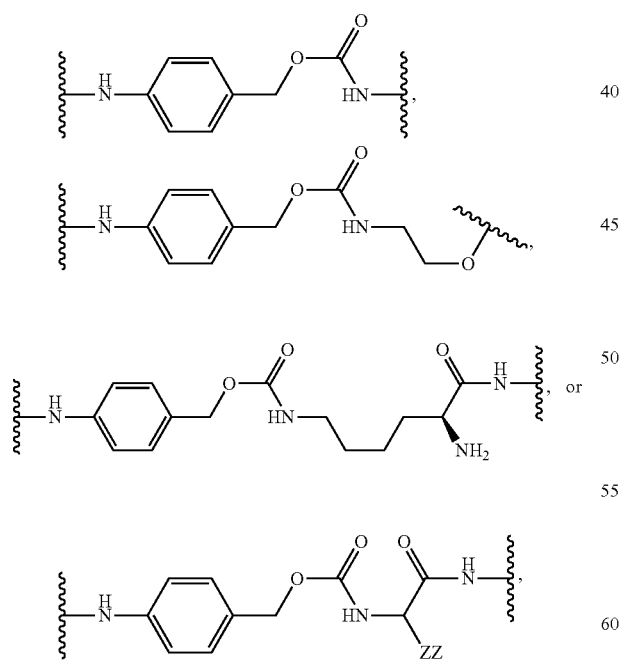

where ZZ is hydrogen, or a side chain for an amino acid as discussed elsewhere herein. For example, in one embodiment, ZZ is $C_{1-6}$ alkyl. Byway of further example, in one embodiment, ZZ is $C_{1-6}$ heteroalkyl.

In some embodiments, the reactive linker-payload is:
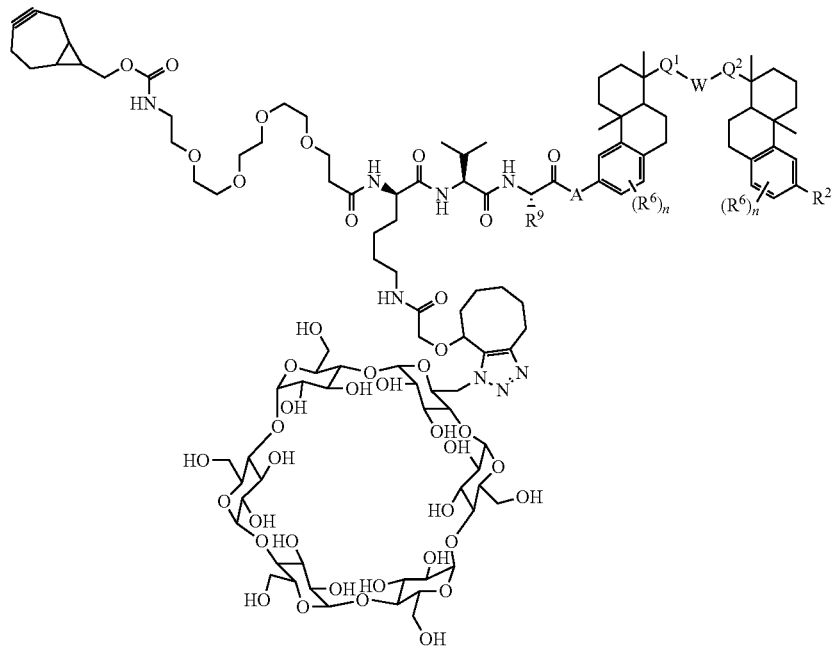
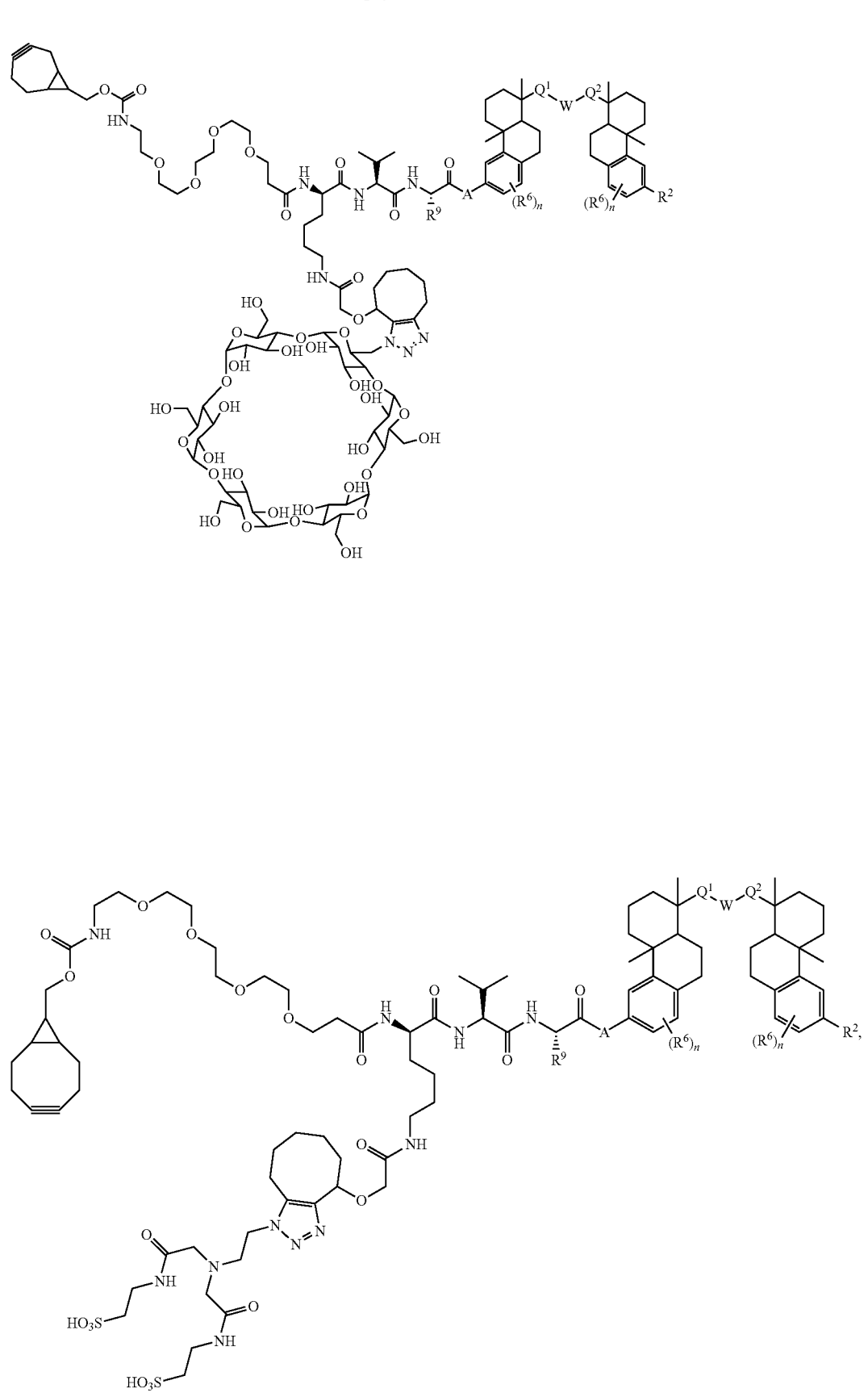

-continued

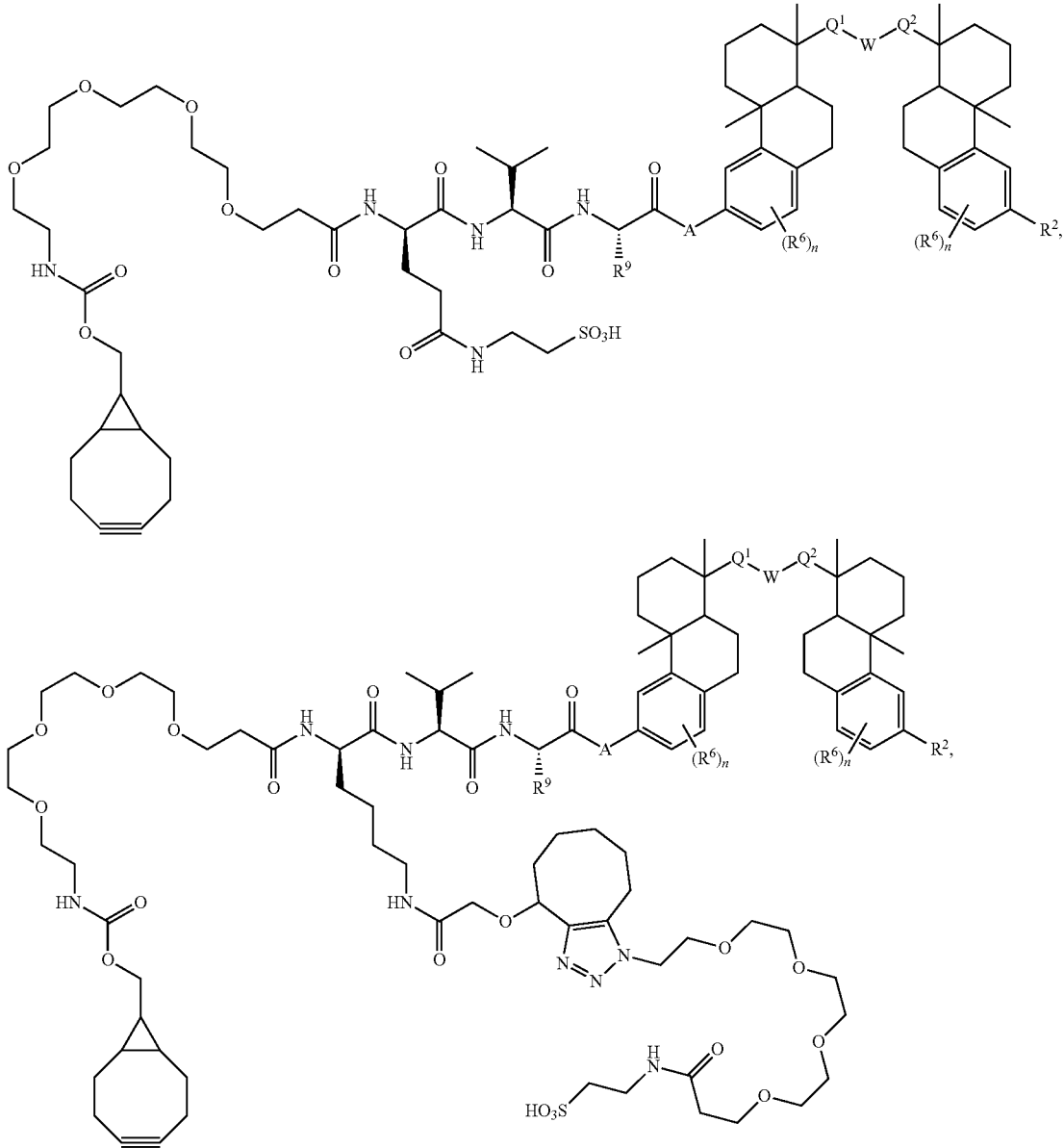

or a pharmaceutically acceptable salt, solvate, or stereoisomeric form thereof, or a regioisomer thereof, wherein:
$Q^1$, $Q^2$, W, $R^1$, $R^2$, $R^4$, $R^5$, and $R^6$ are as described in the context of Formula I;
each $R^9$ is —CH$_3$ or —(CH$_2$)$_3$N(H)C(O)NH$_2$; and
each A is —O—, —N(H)—, H

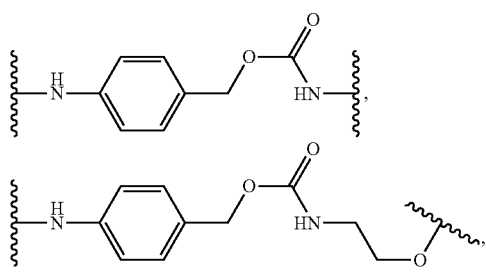

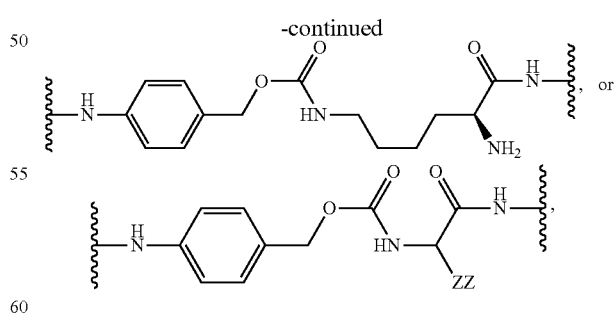

where ZZ is hydrogen, or a side chain for an amino acid as discussed elsewhere herein. For example, in one embodiment, ZZ is $C_{1-6}$ alkyl. Byway of further example, in one embodiment, ZZ is $C_{1-6}$ heteroalkyl.

In some embodiments, the linker-payload or reactive linker-payload is:

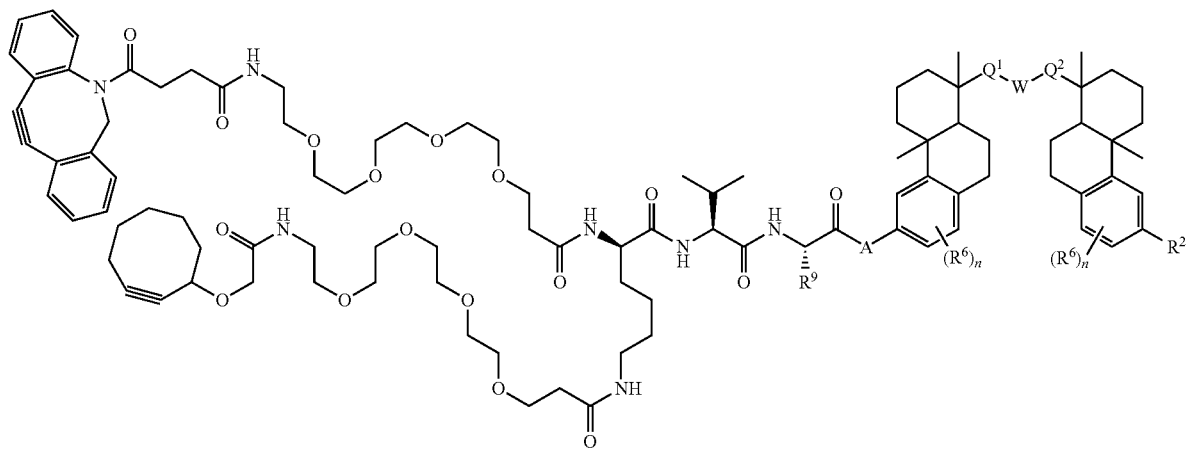

or a pharmaceutically acceptable salt, solvate, or stereoisomeric form thereof wherein:
  $Q^1$, $Q^2$, W, $R^1$, $R^2$, $R^4$, $R^5$, and $R^6$ are as described in the context of Formula I;
  each $R^9$ is —$CH_3$ or —$(CH_2)_3N(H)C(O)NH_2$; and
  each A is —O—, —N(H)—H

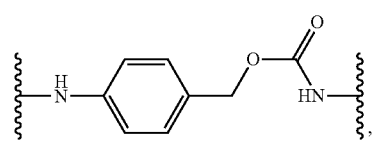

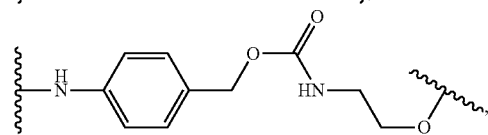

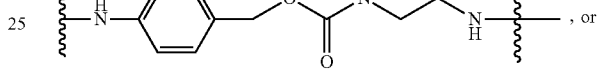

-continued

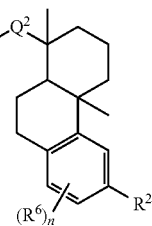

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the linker-payload or reactive linker-payload is:

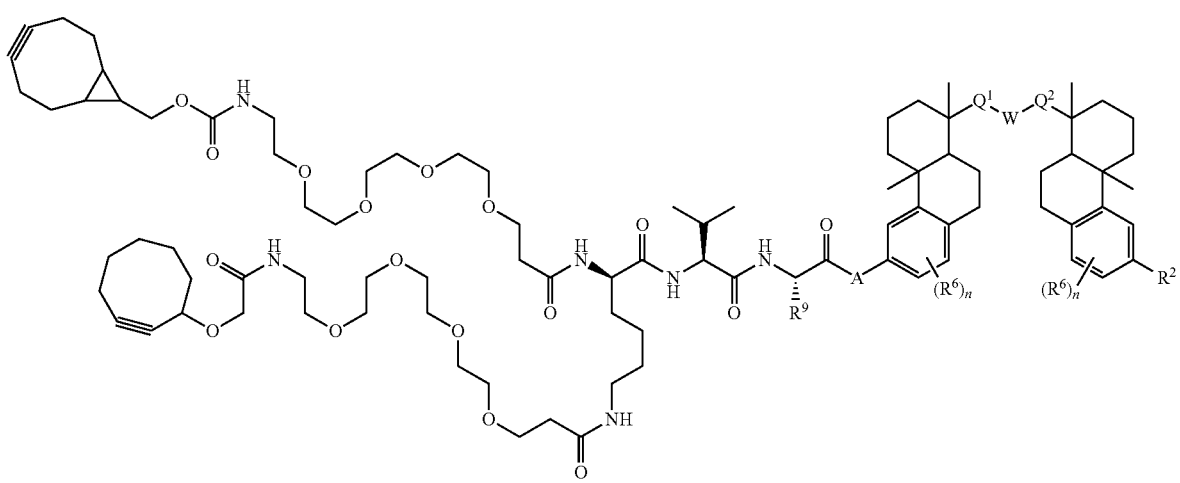

or a pharmaceutically acceptable salt, solvate, or stereoisomeric form thereof, wherein:

$Q^1$, $Q^2$, W, $R^1$, $R^2$, $R^4$, $R^5$, and $R^6$ are as described in the context of Formula I;

each $R^9$ is —CH$_3$ or —(CH$_2$)$_3$N(H)C(O)NH$_2$; and each A is —O—, —N(H)—,

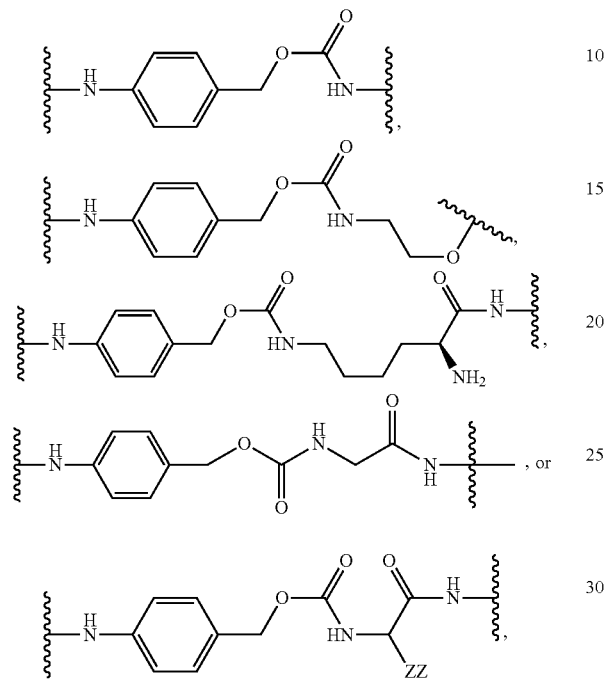

where ZZ is hydrogen, or a side chain for an amino acid as discussed elsewhere herein. For example, in one embodiment, ZZ is C$_{1-6}$ alkyl. By way of further example, in one embodiment, ZZ is C$_{1-6}$ heteroalkyl.

In some embodiments, the linker-payload or reactive linker-payload is:

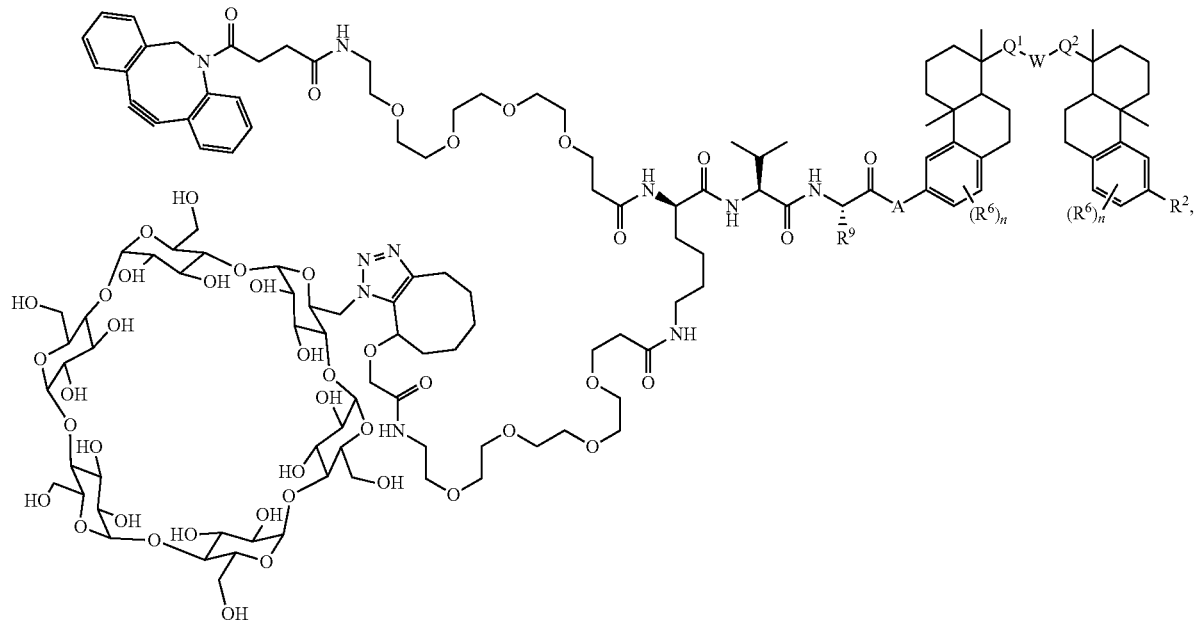

-continued
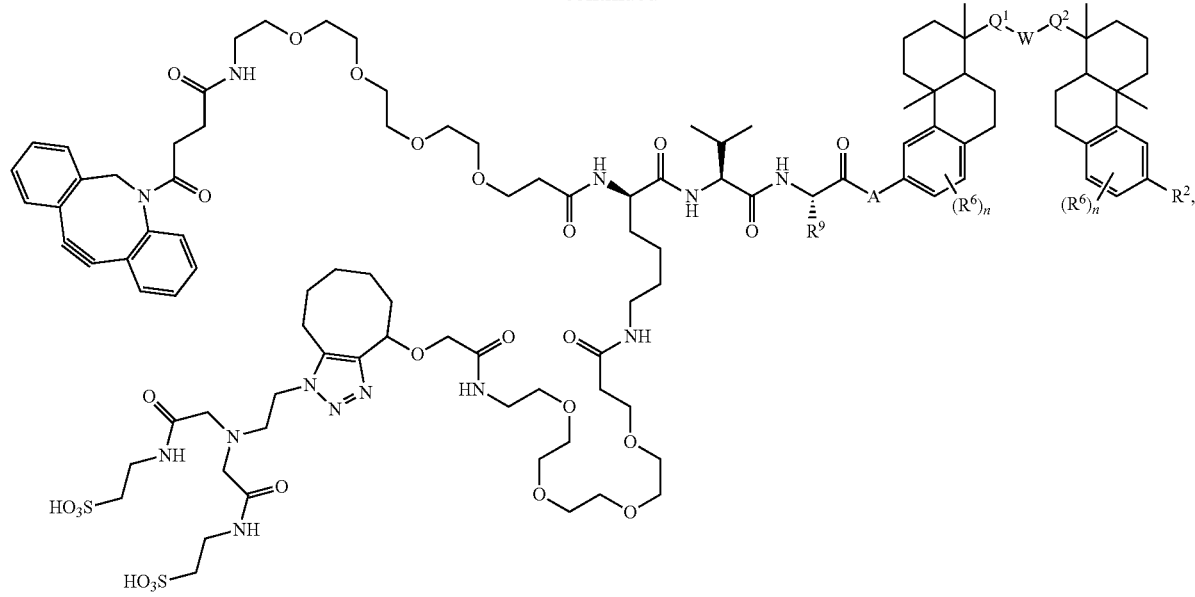
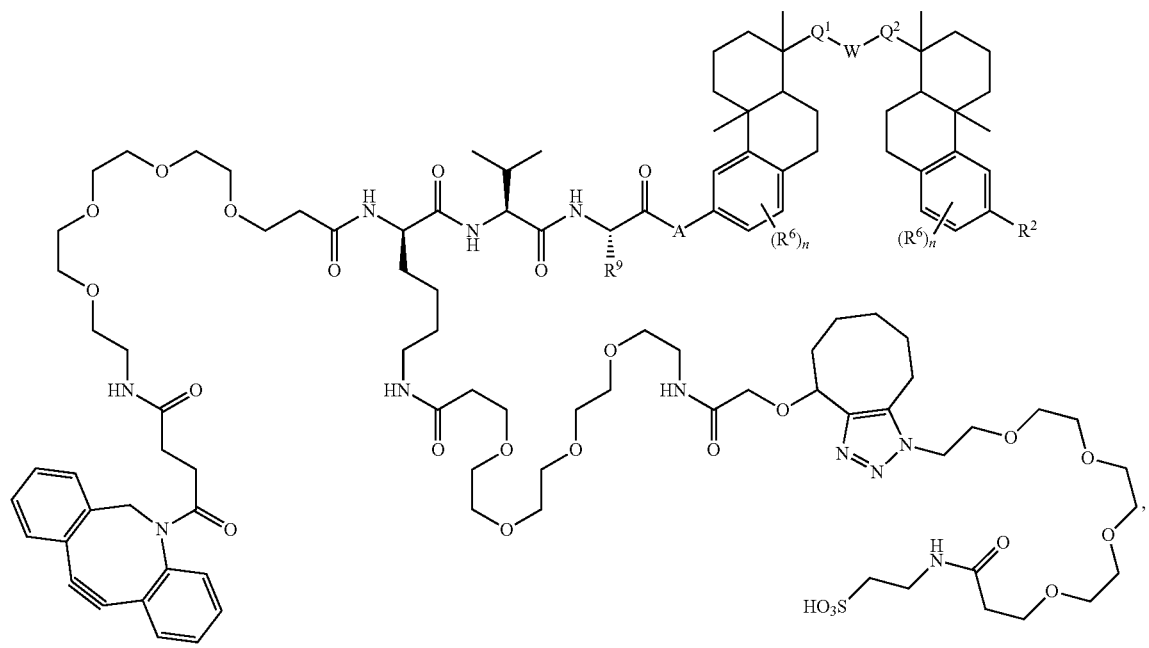
or a pharmaceutically acceptable salt, solvate, or stereoisomeric form thereof, or a regioisomer thereof, wherein:
$Q^1$, $Q^2$, W, $R^1$, $R^2$, $R^4$, $R^5$, and $R^6$ are as described in the context of Formula I;
each $R^9$ is —$CH_3$ or —$(CH_2)_3N(H)C(O)NH_2$; and
each A is —O—, —N(H)—,
-continued
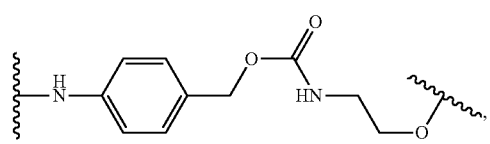
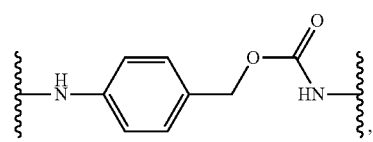
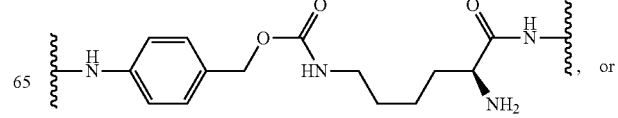, or -continued
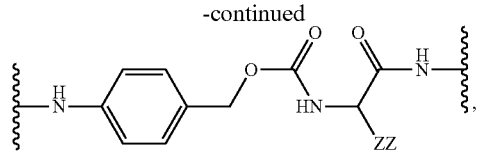
where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.
In some embodiments, the linker-payload or reactive linker-payload is:
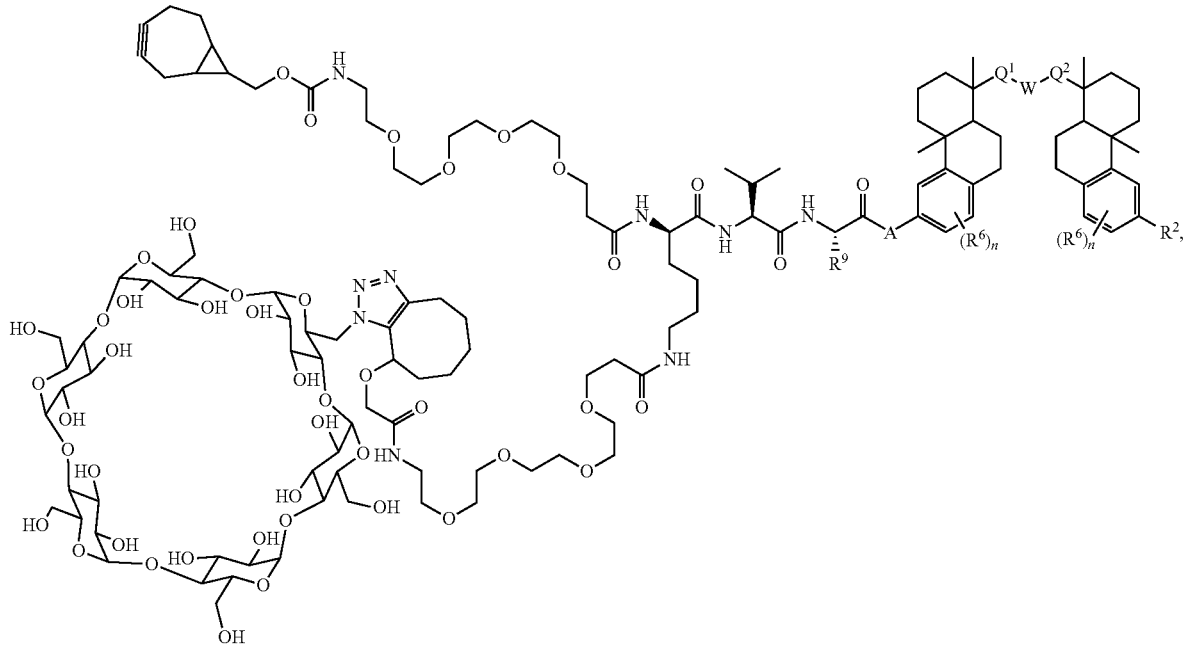
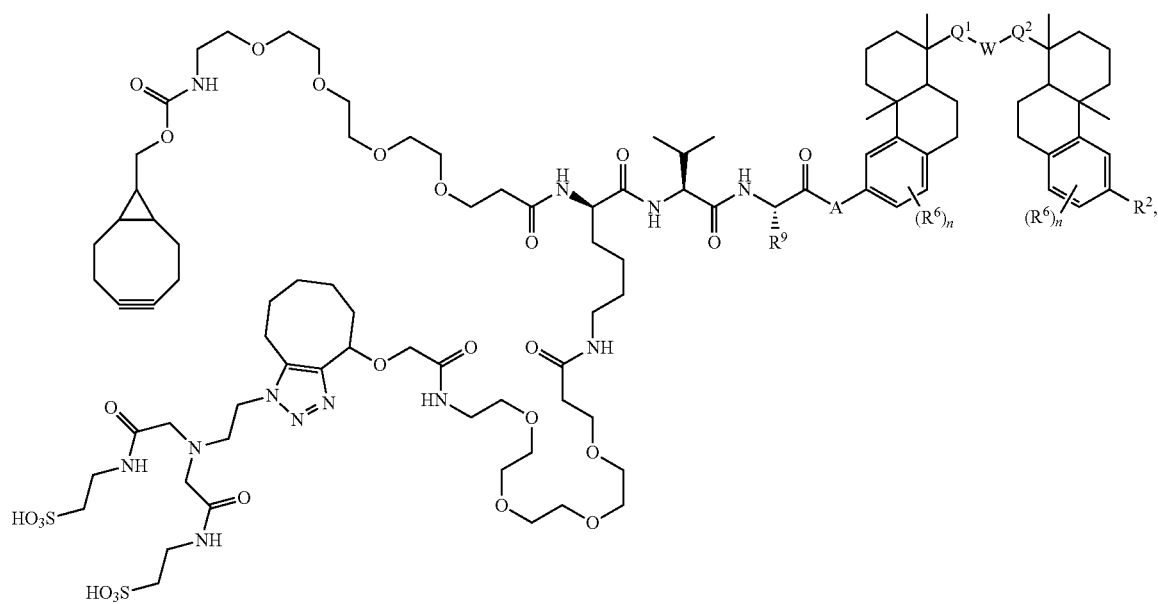

-continued

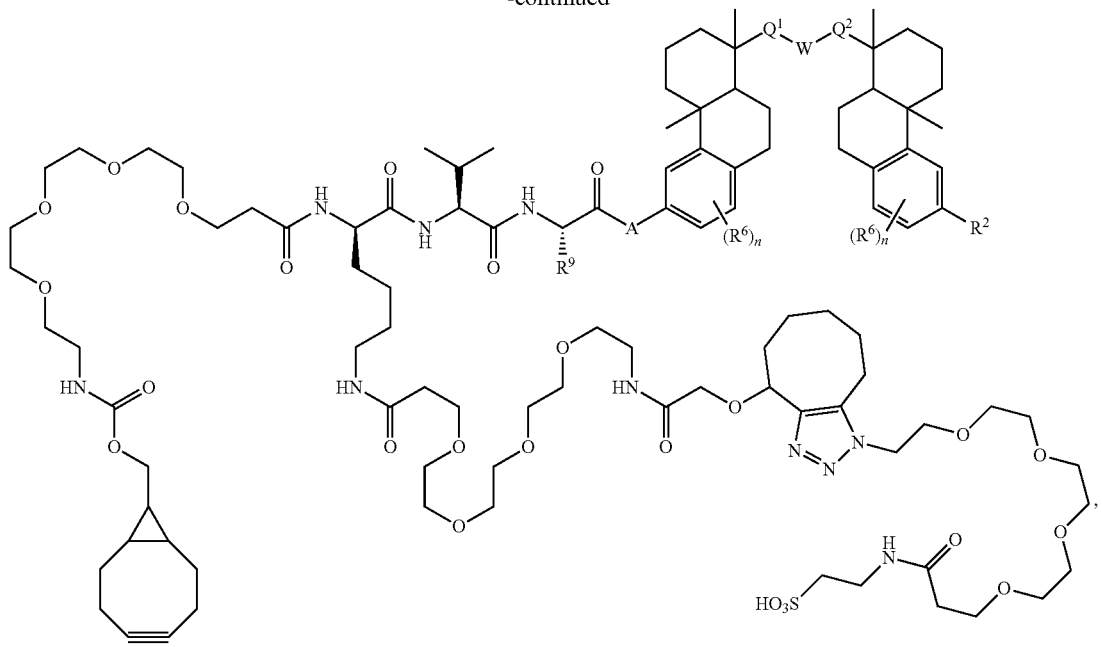

or a pharmaceutically acceptable salt, solvate, or stereoisomeric form thereof, or a regioisomer thereof, wherein:

$Q^1$, $Q^2$, W, $R^1$, $R^2$, $R^4$, $R^5$, and $R^6$ are as described in the context of Formula I;

each $R^9$ is —$CH_3$ or —$(CH_2)_3N(H)C(O)NH_2$; and each A is —O—, —N(H)—,

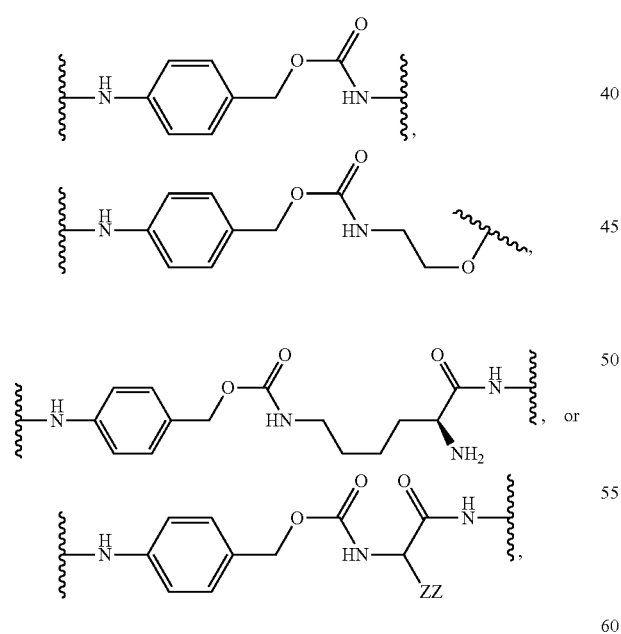

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the linker-payload or reactive linker-payload is selected from:

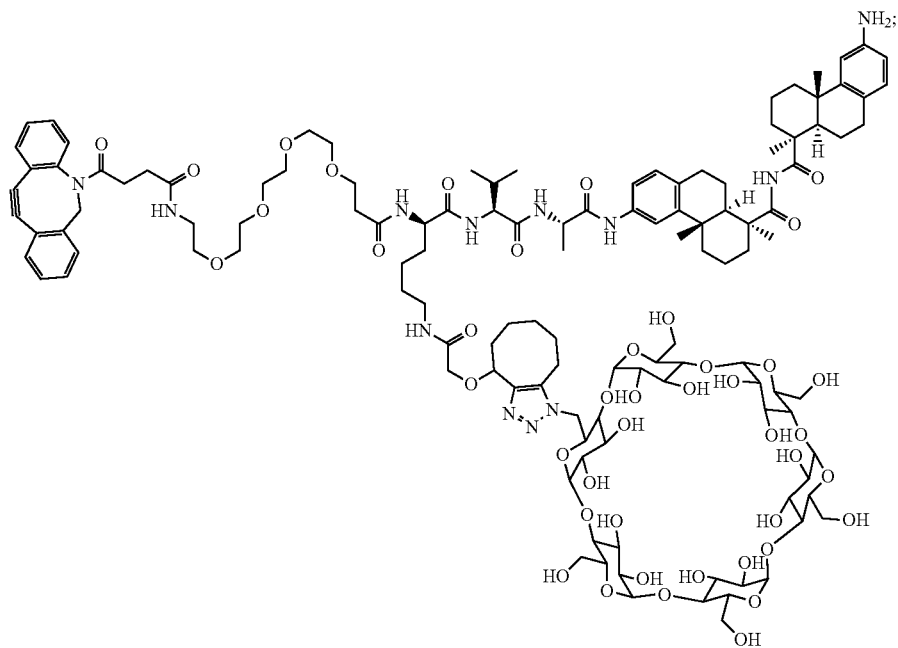
LP1
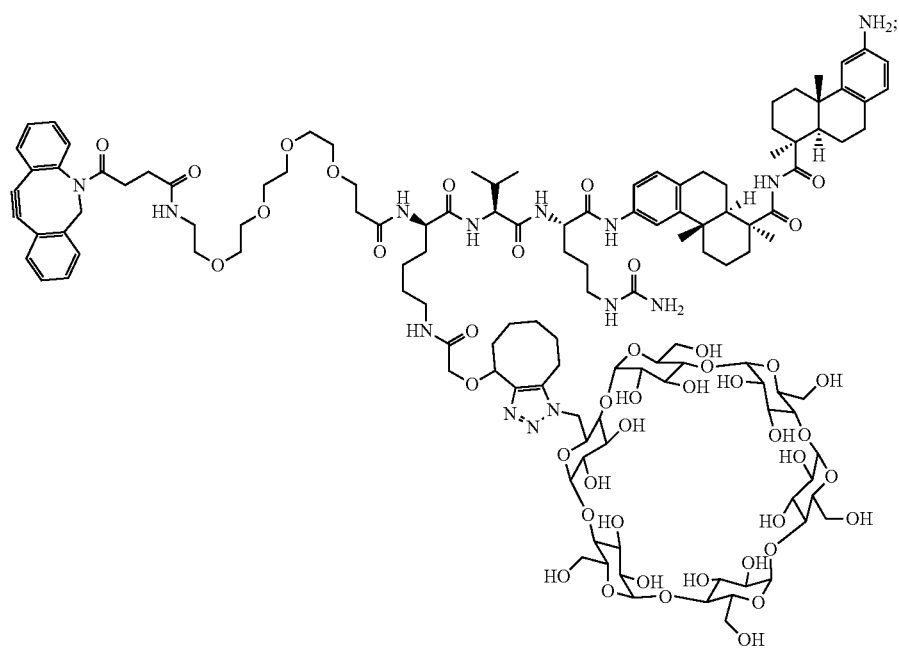
LP2

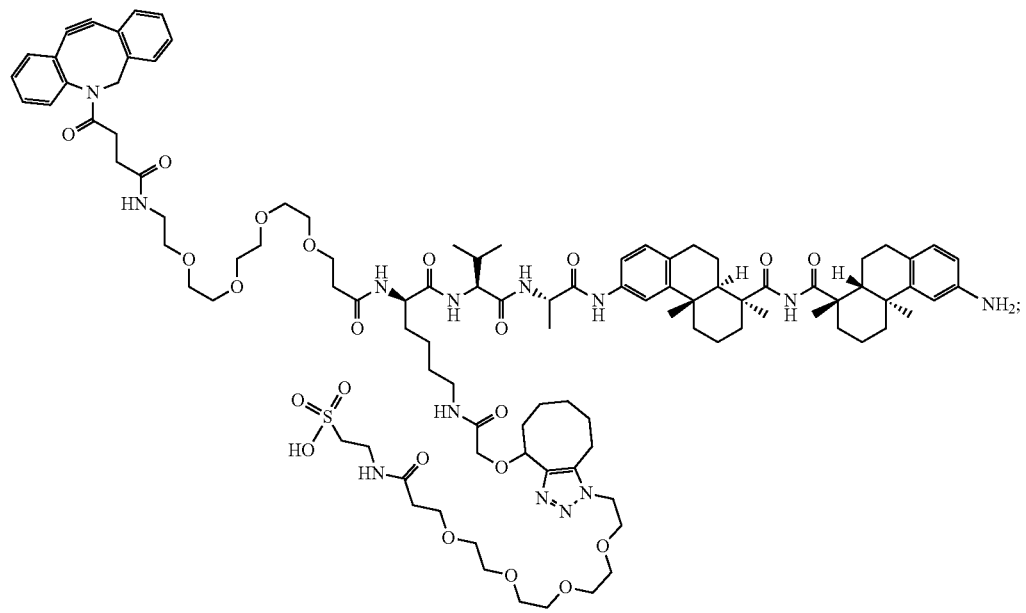
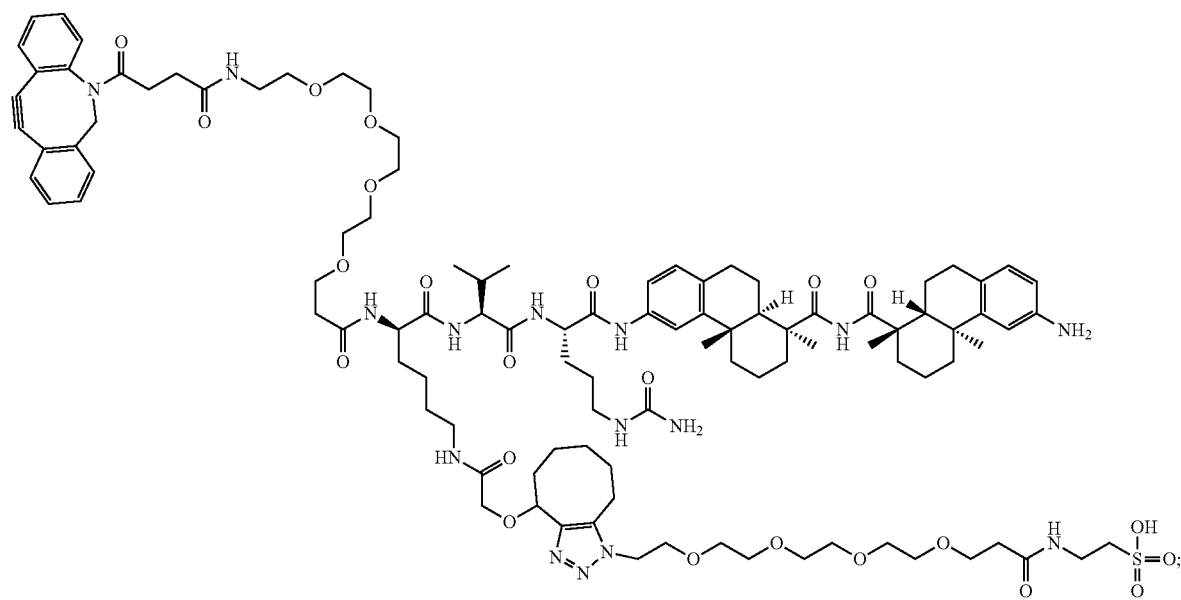

LP5
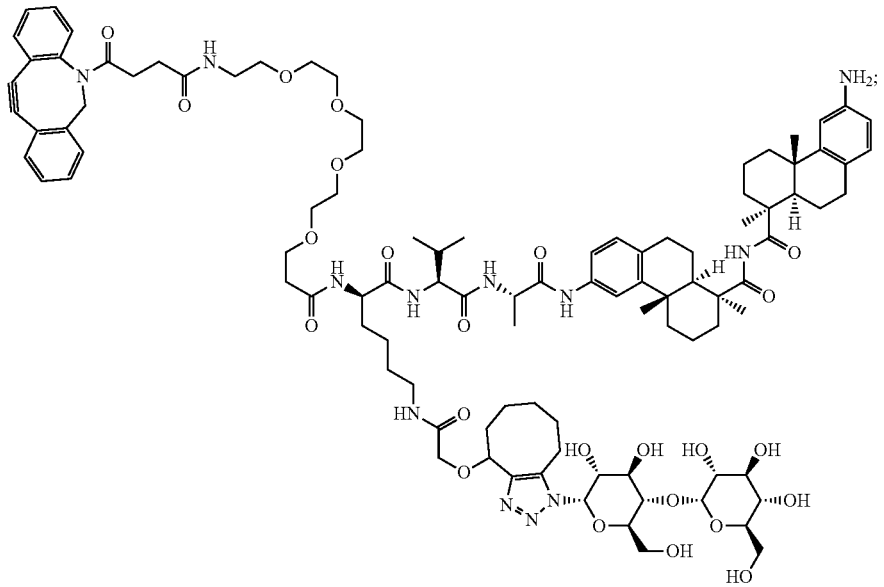
LP6
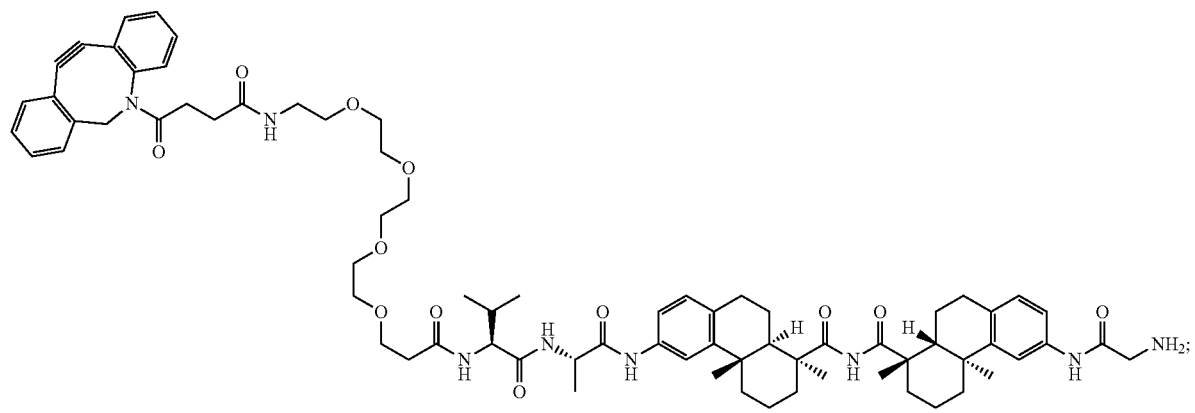
LP7
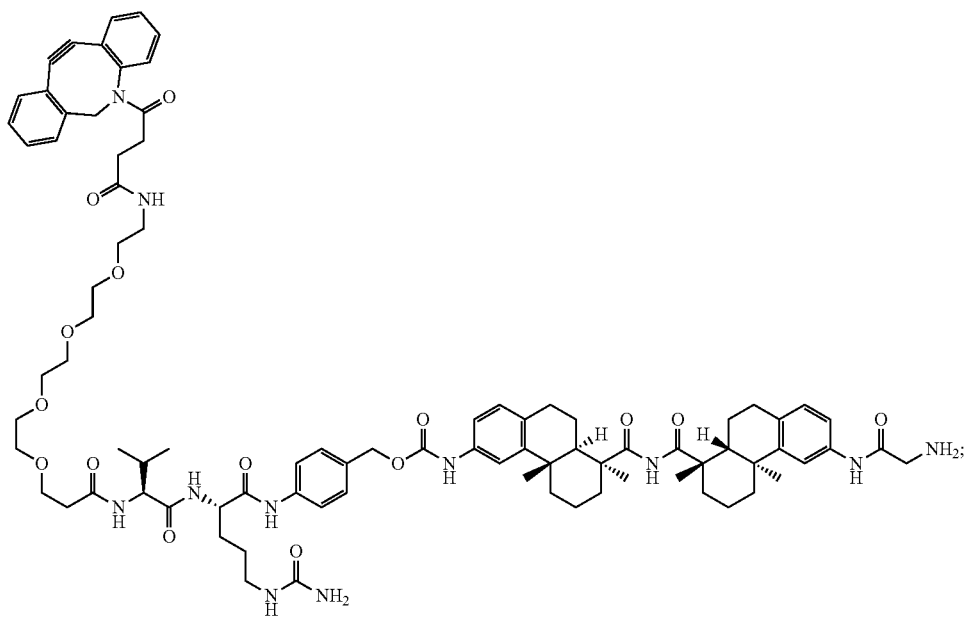

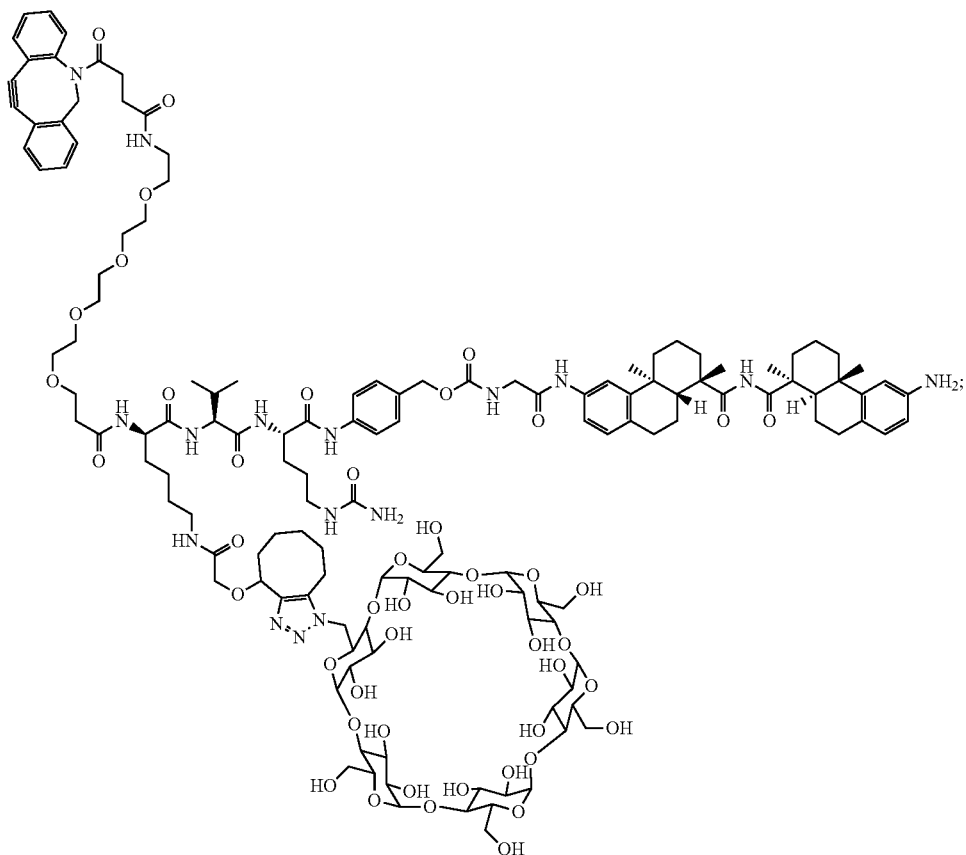
LP8
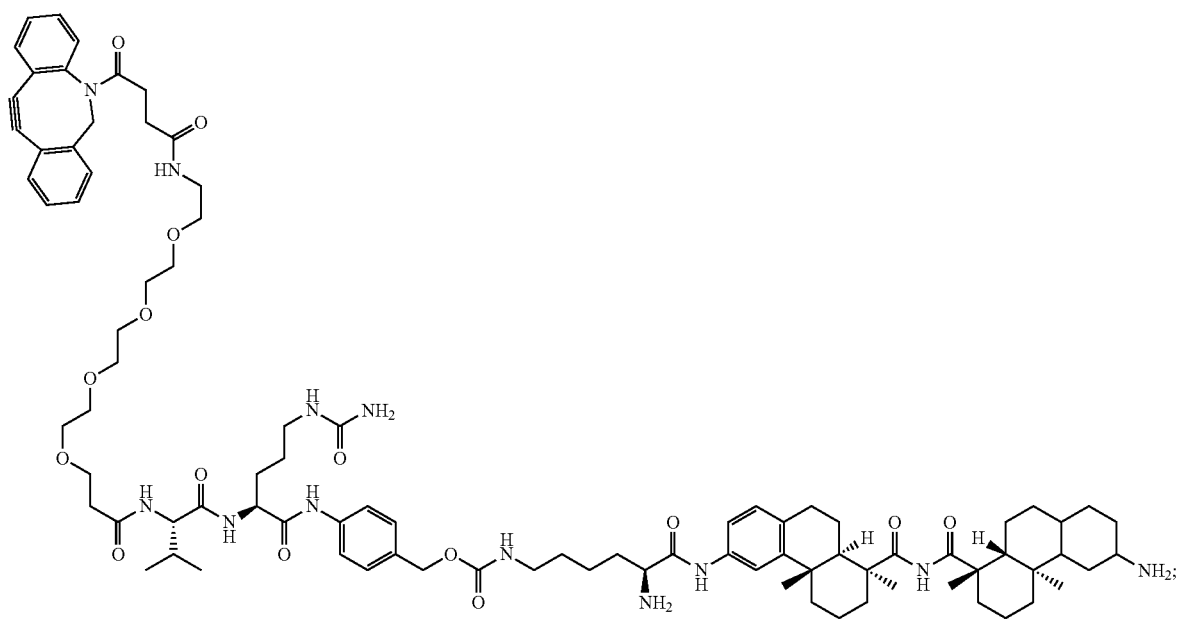
LP9

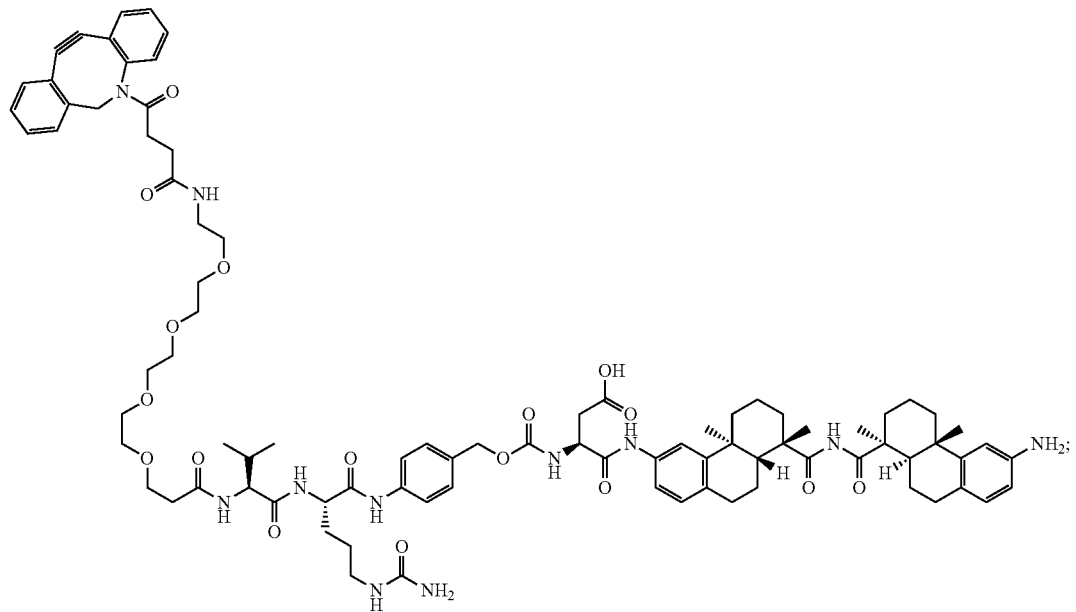
LP10
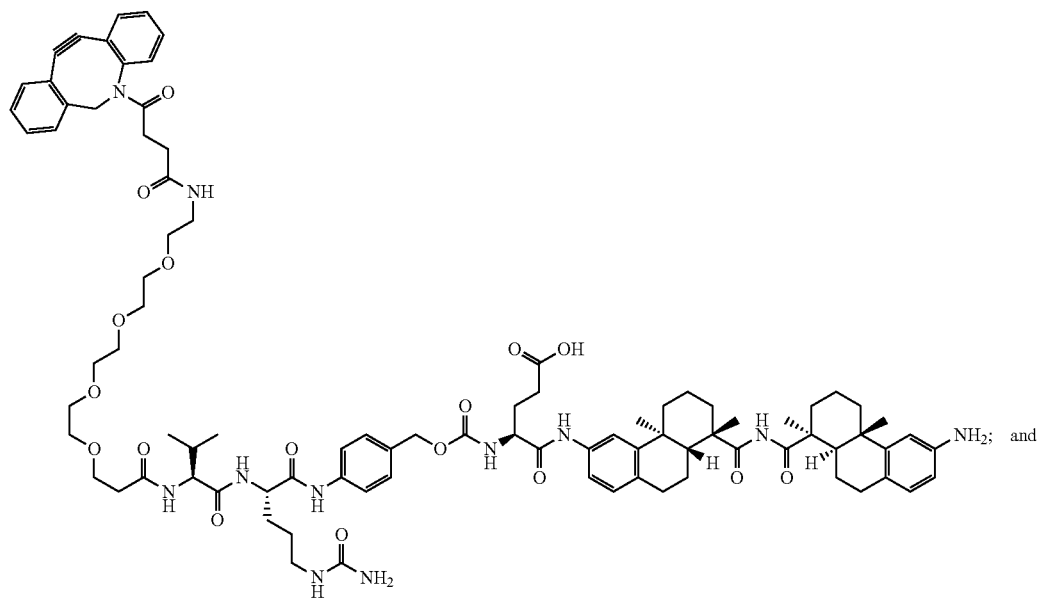
LP11

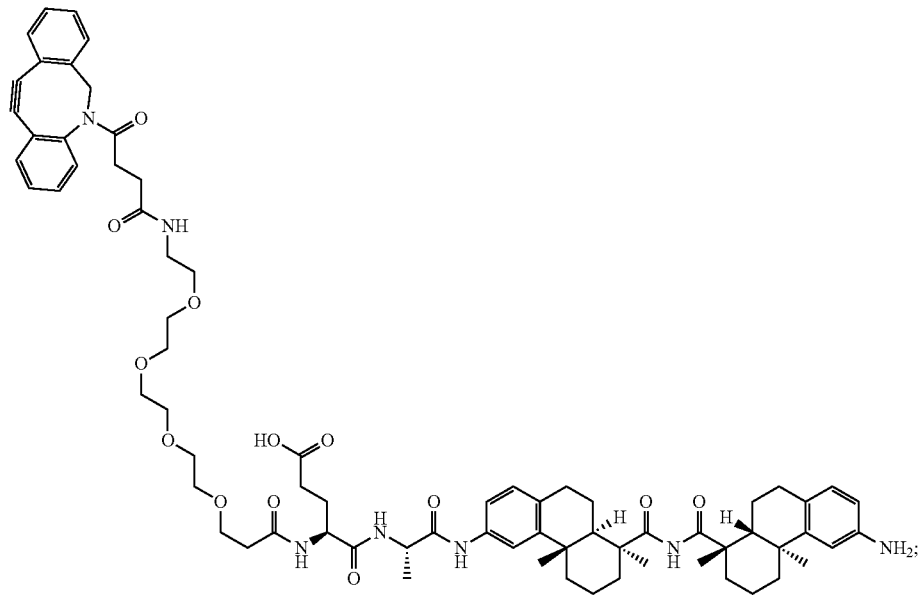
LP12
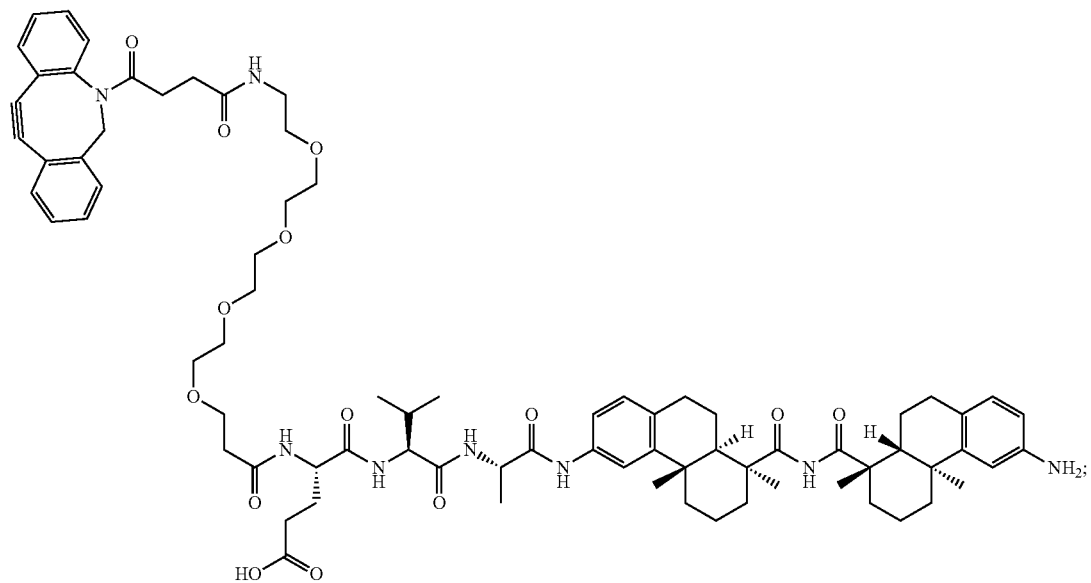
LP13

LP14
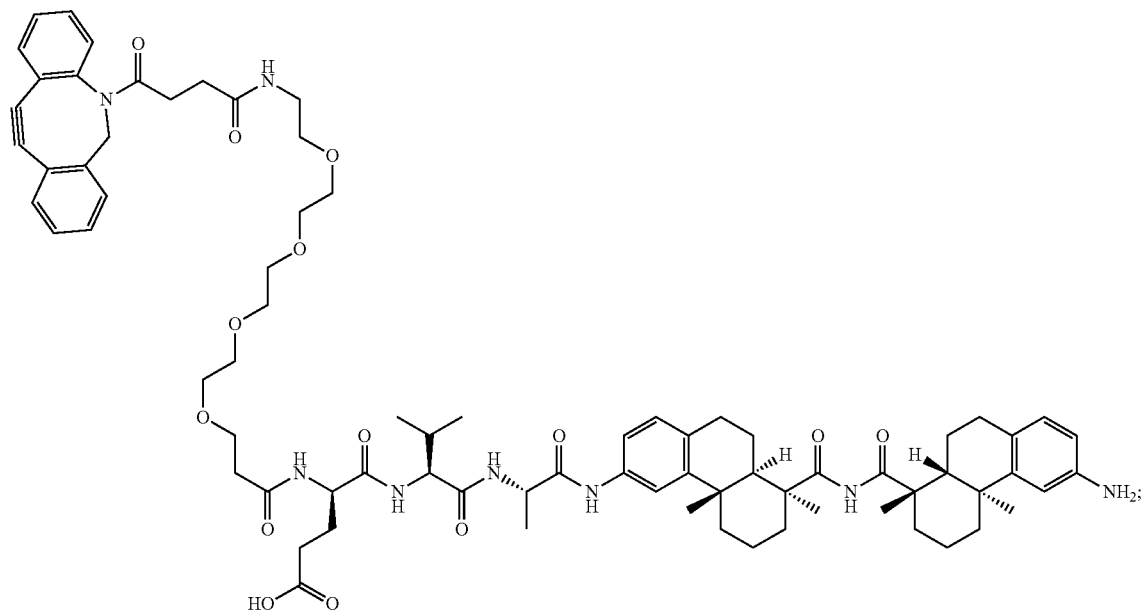
LP20
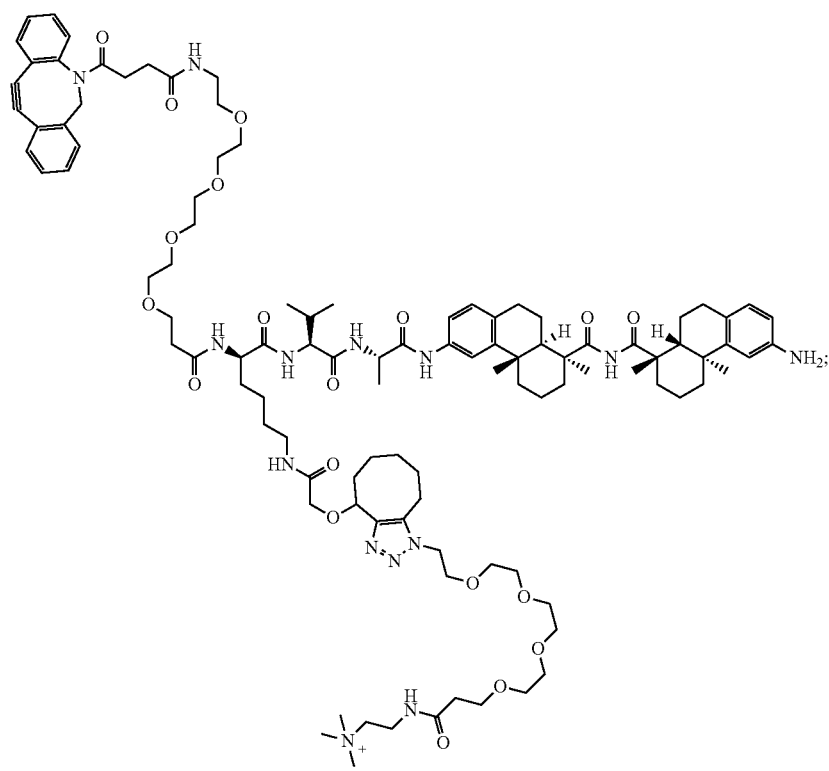
a pharmaceutically acceptable salt or solvate thereof.
Further provided herein are linker-payloads selected from the group consisting of:

LP15
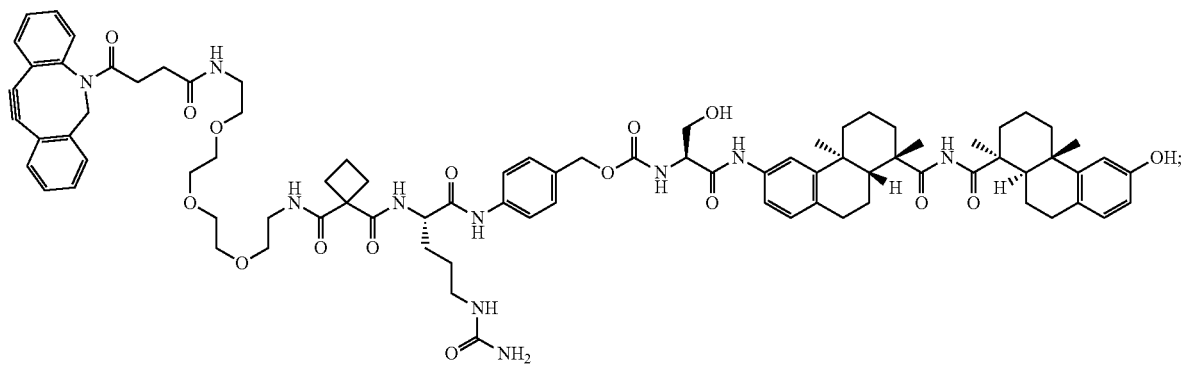
LP16
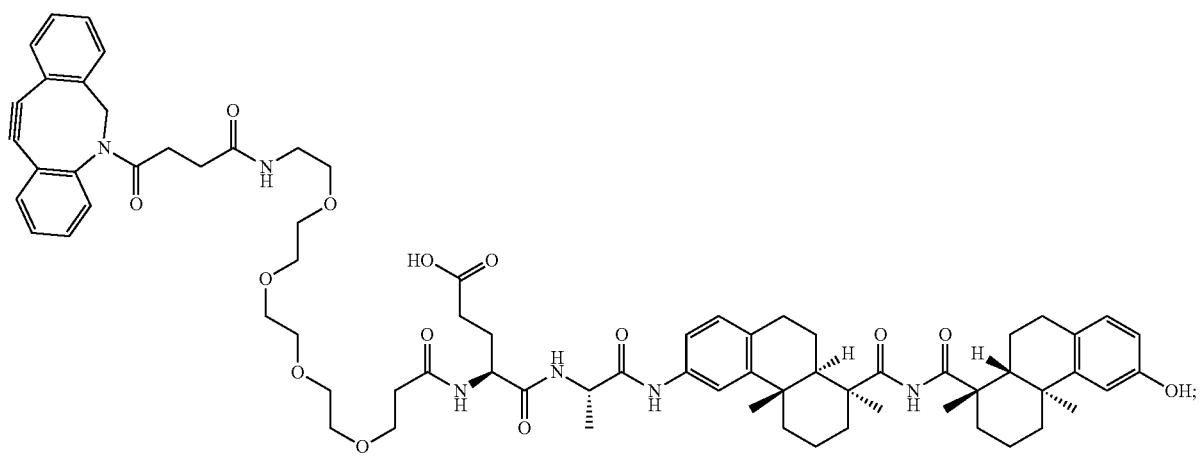
LP17
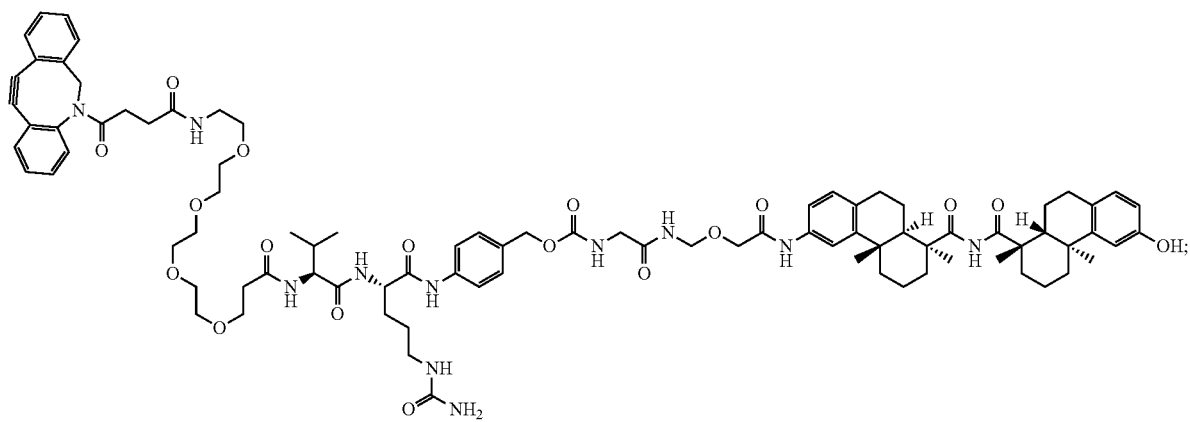

LP18

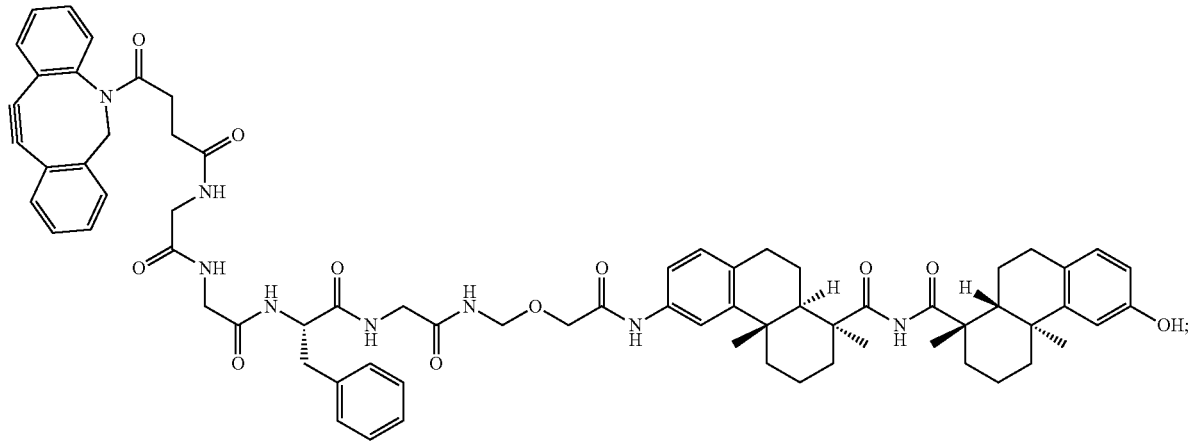

LP19

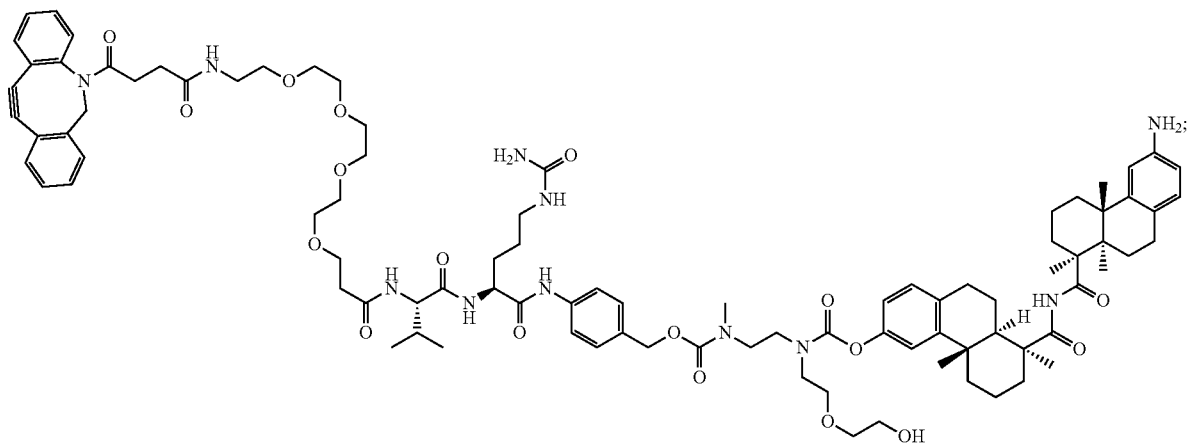

a pharmaceutically acceptable salt or solvate thereof.

The above linkers, linker-payloads, or reactive linker-payloads are useful for providing the following conjugates.

Conjugates/Antibody Drug Conjugates (ADCs)

Provided herein are antibodies, or an antigen binding fragments thereof, wherein said antibodies are conjugated to one or more compounds of Formula I, II, or III as described herein.

Provided herein are compounds or conjugates of Formula A:

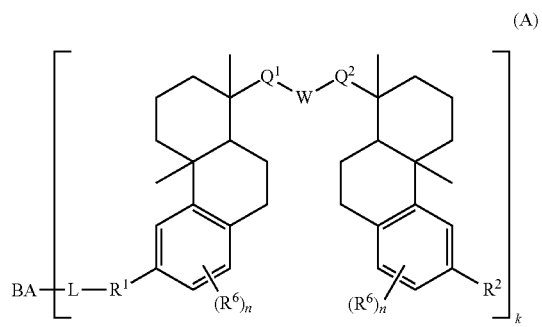

(A)

or a pharmaceutically acceptable salt, or stereoisomeric form thereof, wherein BA is a binding agent, L is a linker, $Q^1$, $Q^2$, W, —$R^1$—, $R^2$, $R^4$, $R^5$, and $R^6$ are as described above in the context of Formula I, and k is 1, 2, 3, 4, 5, 6, 7, 8, 9, or 10. In certain embodiments, compounds or payloads conjugated to -L-BA in Formula A include one or more compounds of Formulae I, II, and/or III as described above, wherein BA is a binding agent; L is a linker; and k is 1, 2, 3, 4, 5, 6, 7, 8, 9, or 10. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4. In any of the embodiments in this paragraph, each $R^4$ is, independently in each instance, hydrogen, an amino acid residue, an N-alkyl amino acid residue, a peptide residue, a biodegradable moiety, alkyl, substituted alkyl, acyl, or substituted acyl. In any of the embodiments in this paragraph, each $R^4$ is, independently in each instance, hydrogen, an amino acid residue, an N-alkyl amino acid residue, a peptide residue, a biodegradable moiety, or alkyl.

Provided herein are compounds or conjugates of Formula B:

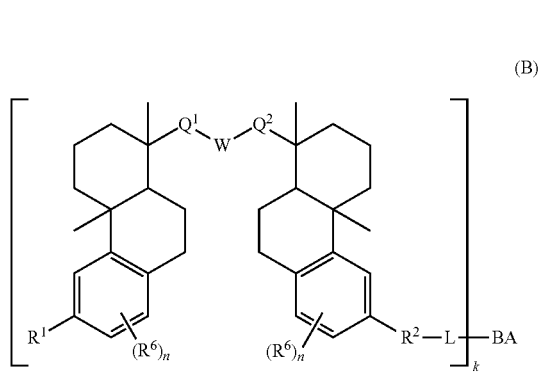

(B)

or a pharmaceutically acceptable salt, or stereoisomeric form thereof, wherein BA is a binding agent, L is a linker, $Q^1$, $Q^2$, W, $R^1$, —$R^2$—, $R^4$, $R^5$, and $R^6$ are as described above in the context of Formula I, and k is 1, 2, 3, 4, 5, 6, 7, 8, 9, or 10. In certain embodiments, compounds or payloads conjugated to -L-BA in Formula B include one or more compounds of Formulae I, II, and/or III as described above, wherein BA is a binding agent; L is a linker; and k is 1, 2, 3, 4, 5, 6, 7, 8, 9, or 10. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4. In any of the embodiments in this paragraph, each $R^4$ is, independently in each instance, hydrogen, an amino acid residue, an N-alkyl amino acid residue, a peptide residue, a biodegradable moiety, alkyl, substituted alkyl, acyl, or substituted acyl. In any of the embodiments in this paragraph, each $R^4$ is, independently in each instance, hydrogen, an amino acid residue, an N-alkyl amino acid residue, a peptide residue, a biodegradable moiety, or alkyl.

Provided herein are compounds or conjugates of Formula C:

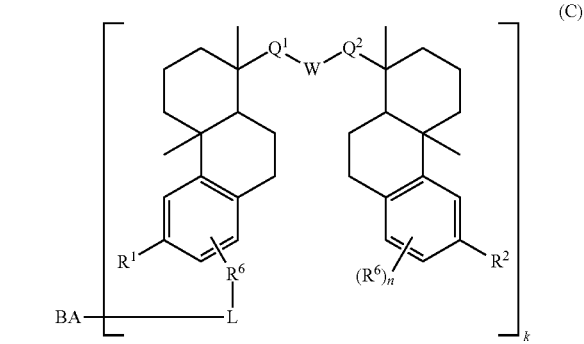

(C)

or a pharmaceutically acceptable salt, or stereoisomeric form thereof, wherein BA is a binding agent, L is a linker, $Q^1$, $Q^2$, W, $R^1$, $R^2$, $R^4$, $R^5$, and —$R^6$— are as described above in the context of Formula I, and k is 1, 2, 3, 4, 5, 6, 7, 8, 9, or 10. In certain embodiments, compounds or payloads conjugated to -L-BA in Formula C include one or more compounds of Formulae I, II, and/or III as described above, wherein BA is a binding agent; L is a linker; and k is 1, 2, 3, 4, 5, 6, 7, 8, 9, or 10. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4. In any of the embodiments in this paragraph, each $R^4$ is, independently in each instance, hydrogen, an amino acid residue, an N-alkyl amino acid residue, a peptide residue, a biodegradable moiety, alkyl, substituted alkyl, acyl, or substituted acyl. In any of the embodiments in this paragraph, each $R^4$ is, independently in each instance, hydrogen, an amino acid residue, an N-alkyl amino acid residue, a peptide residue, a biodegradable moiety, or alkyl.

Provided herein are compounds or conjugates of Formula D:

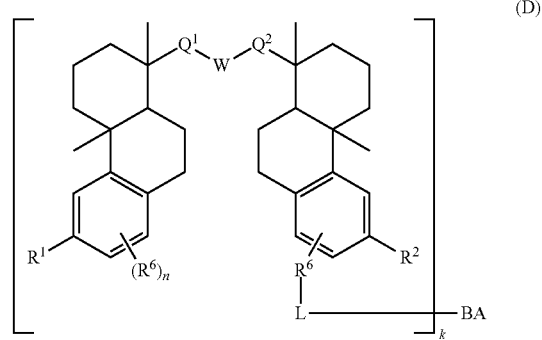

(D)

or a pharmaceutically acceptable salt, or stereoisomeric form thereof, wherein BA is a binding agent, L is a linker, $Q^1$, $Q^2$, W, $R^1$, $R^2$, $R^4$, $R^5$, and —$R^6$— are as described above in the context of Formula I, and k is 1, 2, 3, 4, 5, 6, 7, 8, 9, or 10. In certain embodiments, compounds or payloads conjugated to -L-BA in Formula D include one or more compounds of Formulae I, II, and/or III as described above, wherein BA is a binding agent; L is a linker; and k is 1, 2, 3, 4, 5, 6, 7, 8, 9, or 10. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4. In any of the embodiments in this paragraph, each $R^4$ is, independently in each instance, hydrogen, an amino acid residue, an N-alkyl amino acid residue, a peptide residue, a biodegradable moiety, alkyl, substituted alkyl, acyl, or substituted acyl. In any of the embodiments in this paragraph, each $R^4$ is, independently in each instance, hydrogen, an amino acid residue, an N-alkyl amino acid residue, a peptide residue, a biodegradable moiety, or alkyl.

In any of the embodiments of the preceding four paragraphs, L is a linker or X—Y—Z, wherein X is —NH— or —O—; Y is an enzymatically cleavable moiety, a self-immolative group, an acid-labile moiety, $PEG_{n1}$, a sugar moiety, or an enhancement group; and Z is a binding agent linker (BL) wherein Z is covalently bound to BA. Exemplary enzymatically cleavable moieties include, but are not limited to, any di- or tri-peptides (e.g., VC-PAB and VA, as described elsewhere herein). Exemplary self-immolative groups are described elsewhere herein. Exemplary acid-labile moieties include, but are not limited to, alkoxamines, ketoxamines, carbonates, or phosphonates. Exemplary enhancement groups are described elsewhere herein. Exemplary reactive moieties are described elsewhere herein. In certain embodiments, Y does not include $PEG_{n1}$, where n1 is 1, 2, 3, 4, or 5. In certain embodiments, an amino acid may be used to connect the payload, enhancement group, and antibody (each as described elsewhere herein) to one another, as described and apparent elsewhere herein. Connection of the payload, enhancement group, and antibody via the amino acid may be carried out by amide coupling reactions, thio-Michael additions, or aniline-NH-alkylations as would be appreciated by those of skill in the art. For example, the amino acid that connects the payload, enhancement group, and antibody is lysine. By way of further example, in one embodiment, the amino acid that connects the payload, enhancement group, and antibody is D-lysine. By way of further example, in one embodiment, the amino acid that connects the payload, enhancement group, and antibody is aspartic acid. By way of further example, in one embodiment, the amino acid that connects the payload, enhancement group, and antibody is glutamic acid. By way of further example, in one embodiment, the amino acid that connects the payload, enhancement group, and antibody is serine. By way of further example, in one embodiment, the amino acid that connects the payload, enhancement group, and antibody is cysteine. By way of further example, in one embodiment, the amino acid that connects the payload, enhancement group, and antibody is tyrosine.

Provided herein are compounds or conjugates having the Formula A', B', C', or D':

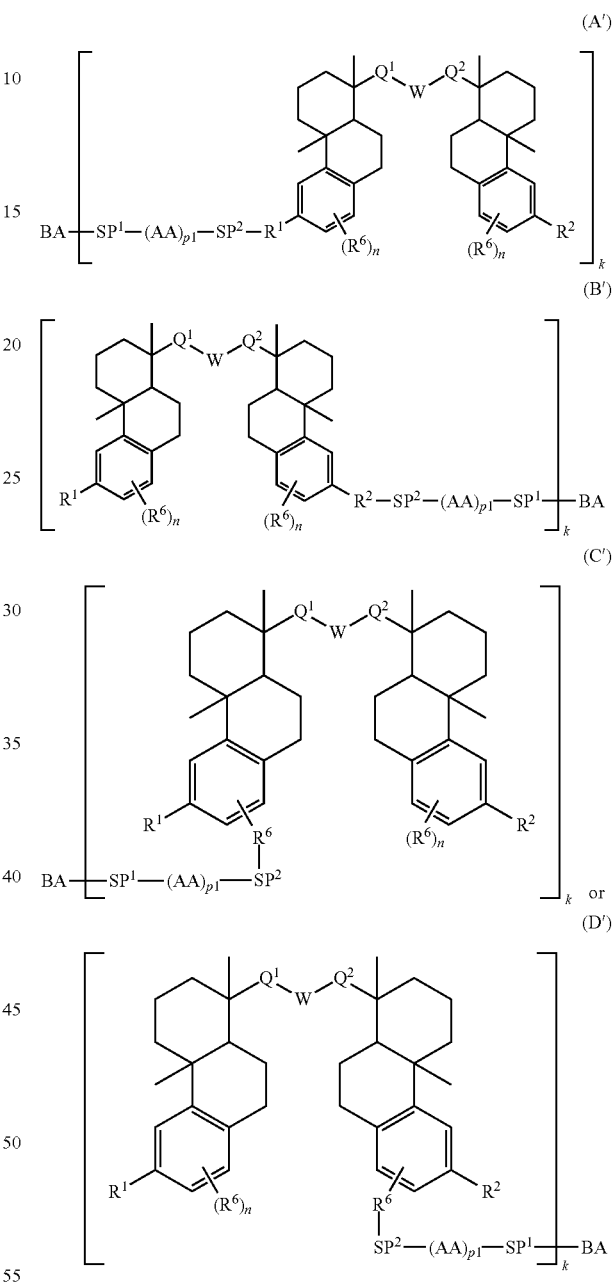

or a pharmaceutically acceptable salt, or stereoisomeric form thereof, wherein B is a binding agent, $Q^1$, $Q^2$, W, $R^1$, —$R^1$—, $R^2$, $R^2$—, $R^4$, $R^5$, and $R^6$ or —$R^6$— are as described above in the context of Formula I, $SP^1$ and $SP^2$, when present, are spacer groups, each AA is an amino acid residue, and p1 is an integer from 1 to 10. In one embodiment, the compound or conjugate is Formula A', or a pharmaceutically acceptable salt, or stereoisomeric form thereof, wherein BA is a binding agent, $Q^1$, $Q^2$, W, —$R^1$—, $R^2$, $R^4$, $R^5$, and $R^6$ are as described above in the context of Formula I, $SP^1$ and $SP^2$, when present, are spacer groups, each AA is an amino acid residue, and p1 is an integer from 1 to 10. In one embodiment, the compound or conjugate is Formula B', or a pharmaceutically acceptable salt, or stereoisomeric form thereof, wherein BA is a binding agent, $Q^1$, $Q^2$, W, $R^1$, —$R^2$—, $R^4$, $R^5$, and $R^6$ are as described above in the context of Formula I, $SP^1$ and $SP^2$, when present, are spacer groups, each AA is an amino acid residue, and p1 is an integer from 1 to 10. In one embodiment, the compound or conjugate is Formula C', or a pharmaceutically acceptable salt, or stereoisomeric form thereof, wherein BA is a binding agent, $Q^1$, $Q^2$, W, $R^1$, $R^2$, $R^4$, $R^5$, and —$R^6$— are as described above in the context of Formula I, $SP^1$ and $SP^2$, when present, are spacer groups, each AA is an amino acid residue, and p1 is an integer from 1 to 10. In one embodiment, the compound or conjugate is Formula D', or a pharmaceutically acceptable salt, or stereoisomeric form thereof, wherein BA is a binding agent, $Q^1$, $Q^2$, W, $R^1$, $R^2$, $R^4$, $R^5$, and —$R^6$— are as described above in the context of Formula I, $SP^1$ and $SP^2$, when present, are spacer groups, each AA is an amino acid residue, and p1 is an integer from 1 to 10. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any of the embodiments in this paragraph, p1 is 1, 2, 3, 4, or 5. In any of the embodiments in this paragraph, k is 1, 2, 3, 4, 5, 6, 7, 8, 9, or 10. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In some embodiments, the compound or conjugate is Formula A":

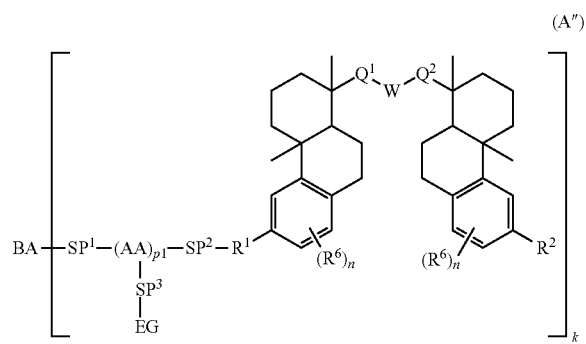

(A")

or a pharmaceutically acceptable salt, or stereoisomeric form thereof, or a regioisomer thereof, wherein:
BA is a binding agent;
each $SP^1$, $SP^2$, and $SP^3$ is a spacer group as described above, where $SP^3$ is linked to one amino acid residue AA of $(AA)_{p1}$;
p1 is an integer from 1 to 10;
EG is an enhancement agent;
k is an integer from 1 to 30;
$Q^1$, $Q^2$, W, —$R^1$—, $R^2$, $R^4$, $R^5$, and $R^6$ are as described in the context of Formula I.

As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N$((CH_2)_{1-5}C(O)NH(CH_2)_{1-5}SO_3H)_2$, —$(CH_2)_{n2}$—C(O)N$((CH_2)_{1-5}C(O)NH(CH_2)_{1-5}SO_3H)_2$, or —$(CH_2CH_2O)_{m2}$—C(O)N$((CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N$((CH_2)_{1-5}C(O)NH(CH_2)_{1-5}SO_3H)_2$, wherein m2 is 1, 2, 3, 4, or 5. In one embodiment, the $SP^1$ spacer is:

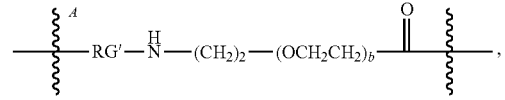

wherein RG' is a reactive group residue following reaction of a reactive group RG with a binding agent; —ξ— is a bond, direct or indirect, to the binding agent; and b is an integer from 1 to 4; the $(AA)_{p1}$-$SP^2$- is —NH-lysine-valine-alanine-, —NH-lysine-valine-citrulline-, or —NH-lysine-valine-citrulline-PABC-; the $SP^3$ spacer is:

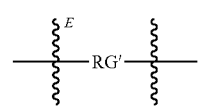

wherein RG' is a reactive group residue following reaction of a reactive group RG with an enhancement agent EG;

$-\xi^E-$ is a bond to the enhancement agent; and $-\xi^1-$ is a bond to $(AA)_{p1}$. In any embodiment in this paragraph, BA is antibody, or antigen binding fragment thereof, wherein the antibody is conjugated to a compound of Formula I, as described above. In any embodiment in this paragraph, BA is antibody, or antigen binding fragment thereof, wherein the antibody is conjugated to a compound of Formula II, as described above. In any embodiment in this paragraph, BA is antibody, or antigen binding fragment thereof, wherein the antibody is conjugated to a compound of Formula III, as described above. In any of the embodiments in this paragraph, p1 is 1, 2, 3, 4, or 5. In any of the embodiments in this paragraph, k is 1, 2, 3, 4, 5, 6, 7, 8, 9, or 10. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

In some embodiments, the compound or conjugate is:

or a pharmaceutically acceptable salt, solvate, or stereoisomeric form thereof, or a regioisomer thereof, wherein:

BA is a binding agent;

each RG' is the residue of a reactive group, as described herein;

EG is an enhancement agent;

k is an integer from 1 to 30;

$Q^1$, $Q^2$, W, $R^1$, $R^2$, $R^4$, $R^5$, and $R^6$ are as described in the context of Formula I;

each $R^9$ is —$CH_3$ or —$(CH_2)_3N(H)C(O)NH_2$; and each A is —O—, —N(H)—,

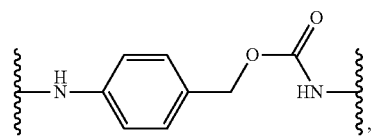

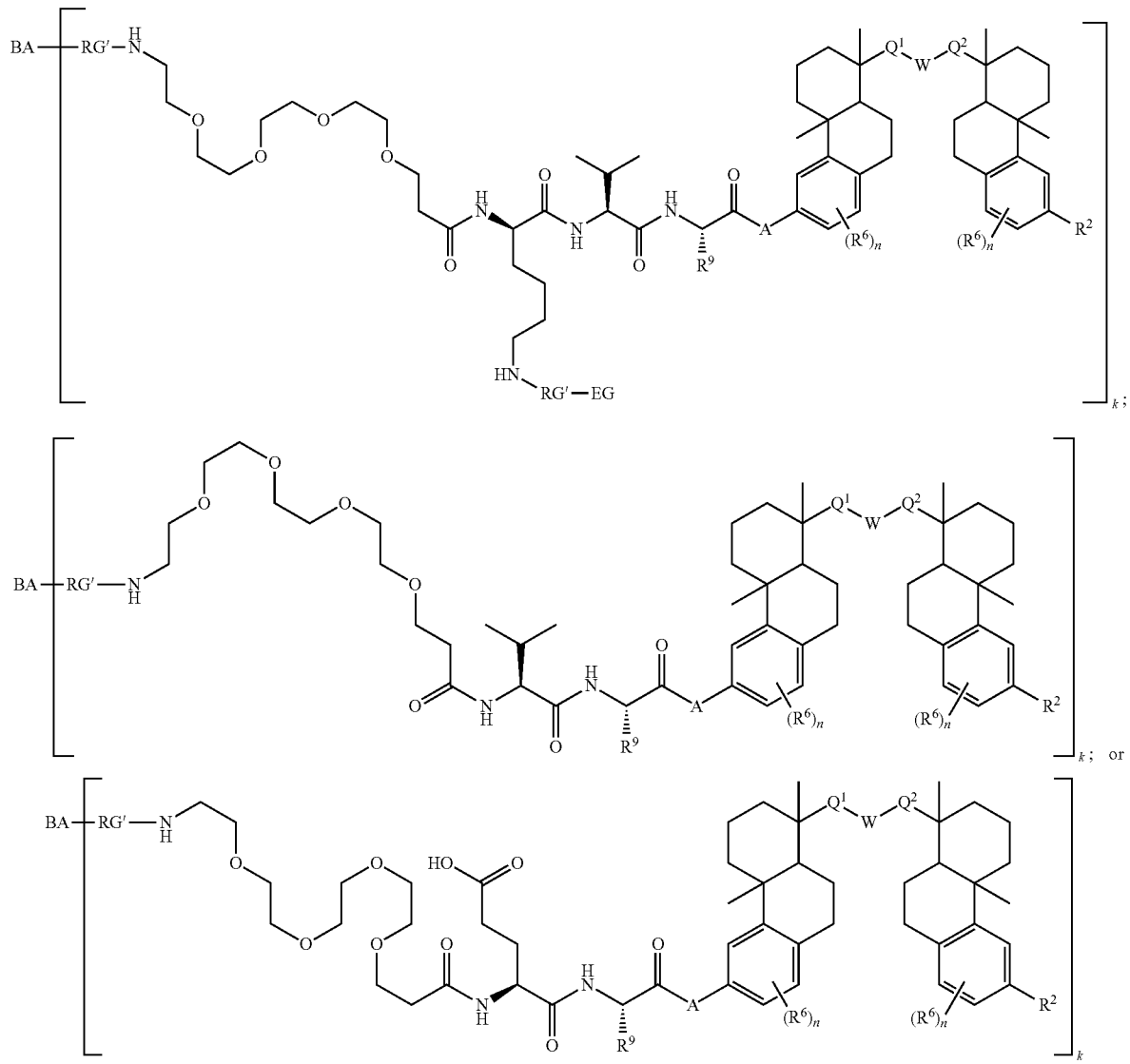

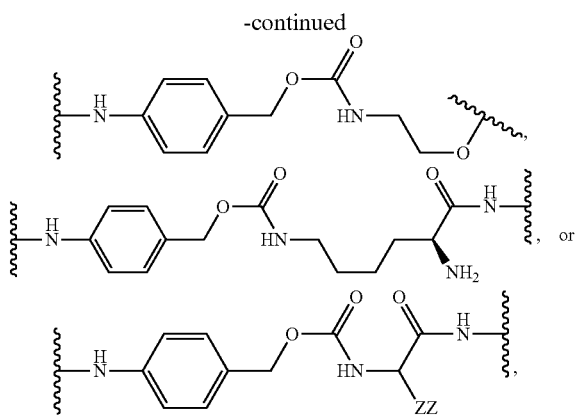

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N($(CH_2)_{1-5}C(O)NH(CH_2)_{1-5}SO_3H)_2$, —$(CH_2)_{n2}$—C(O)N($(CH_2)_{1-5}C(O)NH(CH_2)_{1-5}SO_3H)_2$, or —$(CH_2CH_2O)_{m2}$—C(O)N($(CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N($(CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N($(CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N($(CH_2)_{1-5}C(O)NH(CH_2)_{1-5}SO_3H)_2$, wherein m2 is 1, 2, 3, 4, or 5.

In some embodiments, the compound or conjugate is:

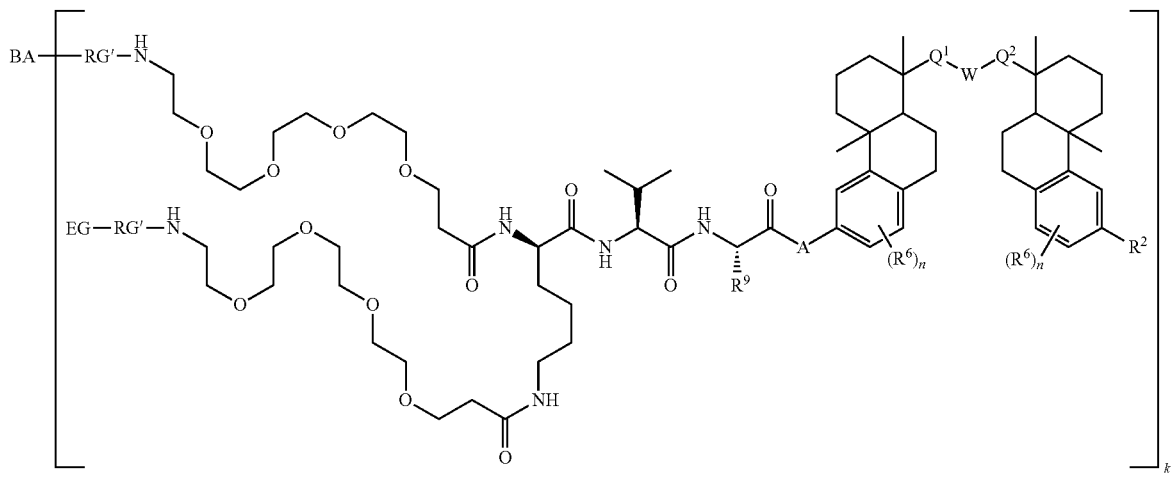

or a pharmaceutically acceptable salt, solvate, or stereoisomeric form thereof, or a regioisomer thereof, wherein:

BA is a binding agent;

each RG' is the residue of a reactive group, as described herein;

EG is an enhancement agent;

k is an integer from 1 to 30;

$Q^1$, $Q^2$, W, $R^1$, $R^2$, $R^4$, $R^5$, and $R^6$ are as described in the context of Formula I;

each $R^9$ is —$CH_3$ or —$(CH_2)_3N(H)C(O)NH_2$; and each A is —O—, —N(H)—,

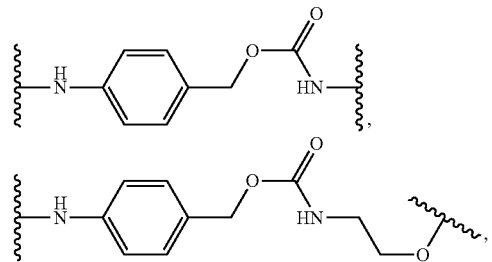

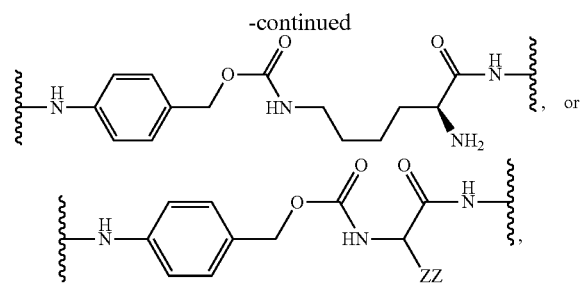

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. As discussed above, the bond to the binding agent can be direct, or via a spacer. In certain embodiments, the bond to the binding agent is via a PEG spacer to a glutamine residue of the binding agent. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N$((CH_2)_{1-5}C(O)NH(CH_2)_{1-5}SO_3H)_2$, —$(CH_2)_{n2}$—C(O)N$((CH_2)_{1-5}C(O)NH(CH_2)_{1-5}SO_3H)_2$, or —$(CH_2CH_2O)_{m2}$—C(O)N$((CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N$((CH_2)_{1-5}C(O)NH(CH_2)_{1-5}SO_3H)_2$, wherein m2 is 1, 2, 3, 4, or 5.

In some embodiments, the compound or conjugate is:

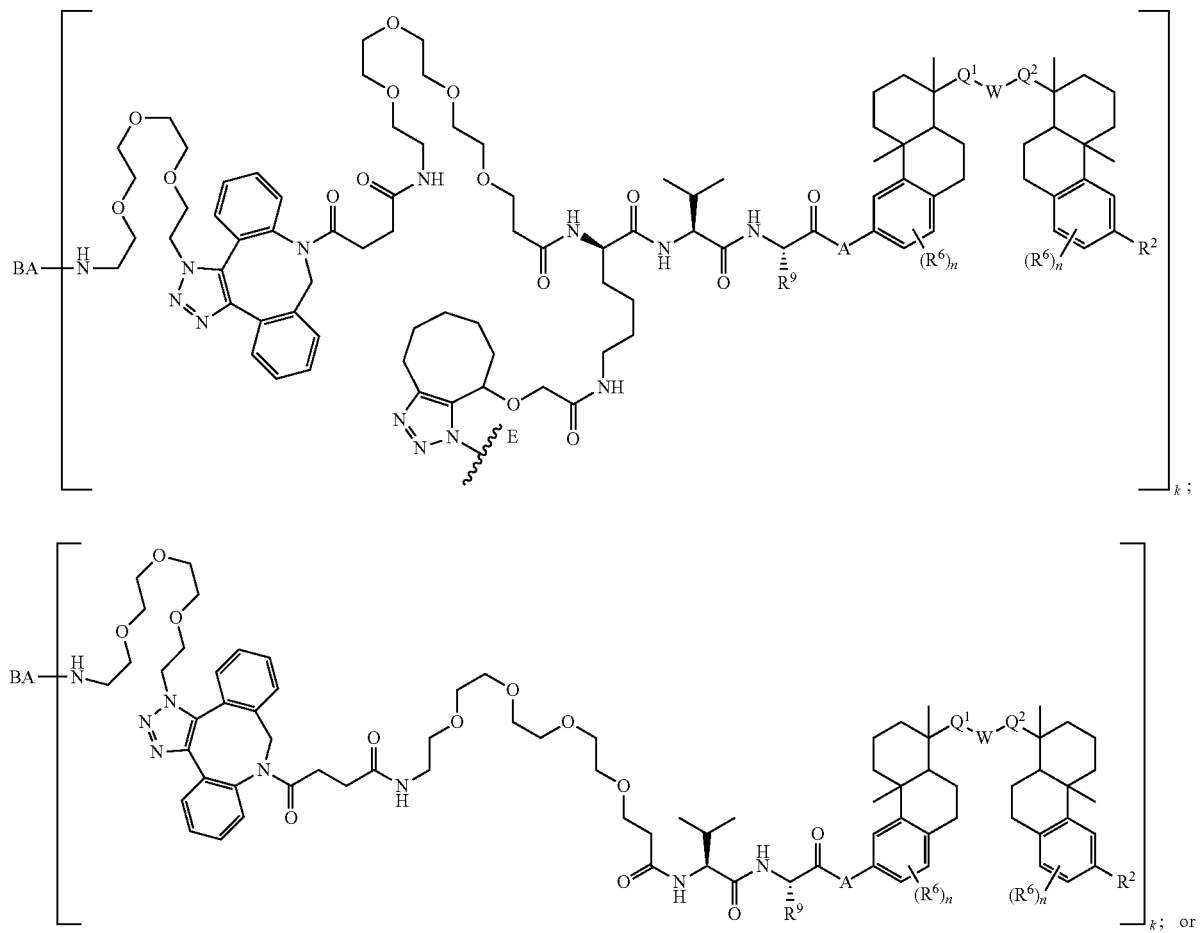

-continued

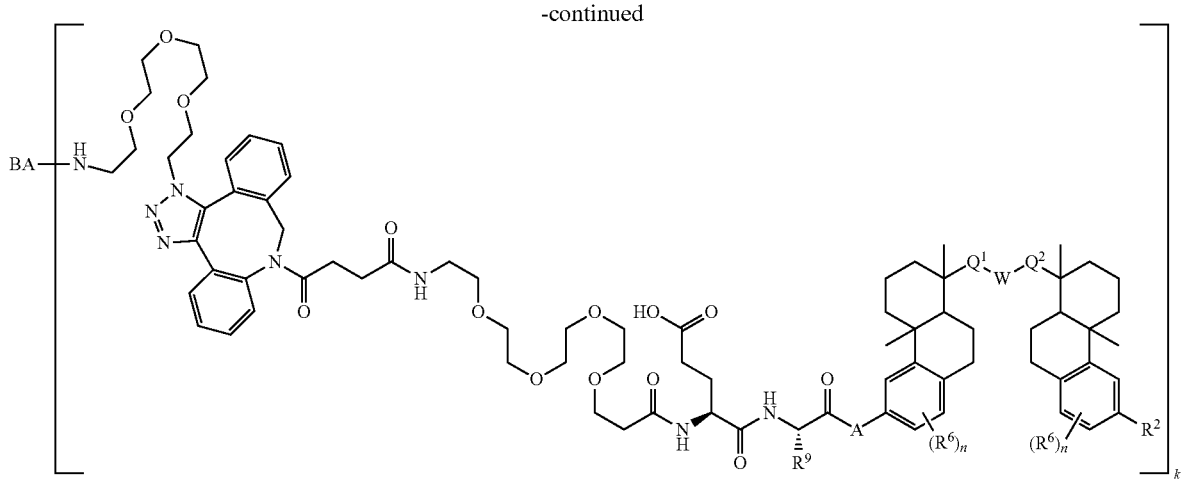

or a pharmaceutically acceptable salt, solvate, or stereoisomeric form thereof, or a regioisomer thereof, wherein:
BA is a binding agent;
k is an integer from 1 to 30;
$Q^1$, $Q^2$, W, $R^1$, $R^2$, $R^4$, $R^5$, and $R^6$ are as described in the context of Formula I;

each $-\xi-^E$ is a bond to the enhancement group;
each $R^9$ is —$CH_3$ or —$(CH_2)_3N(H)C(O)NH_2$; and
each A is —O—, —N(H)—,

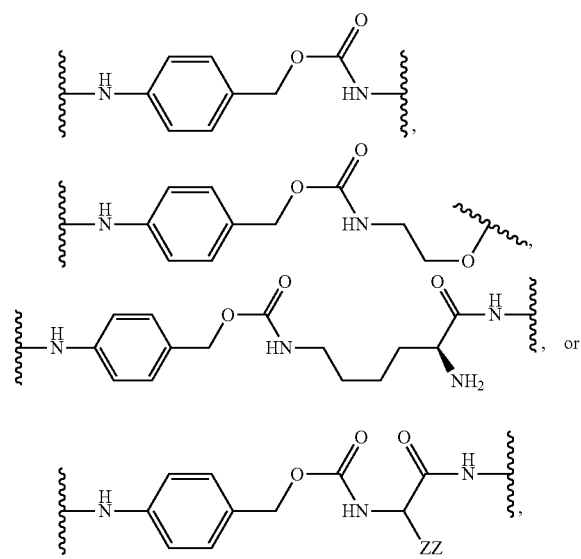

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N$((CH_2)_{1-5}C(O)NH(CH_2)_{1-5}SO_3H)_2$, —$(CH_2)_{n2}$—C(O)N$((CH_2)_{1-5}C(O)NH(CH_2)_{1-5}SO_3H)_2$, or —$(CH_2CH_2O)_{m2}$—C(O)N$((CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N$((CH_2)_{1-5}C(O)NH(CH_2)_{1-5}SO_3H)_2$, wherein m2 is 1, 2, 3, 4, or 5.

In some embodiments, the conjugate is:

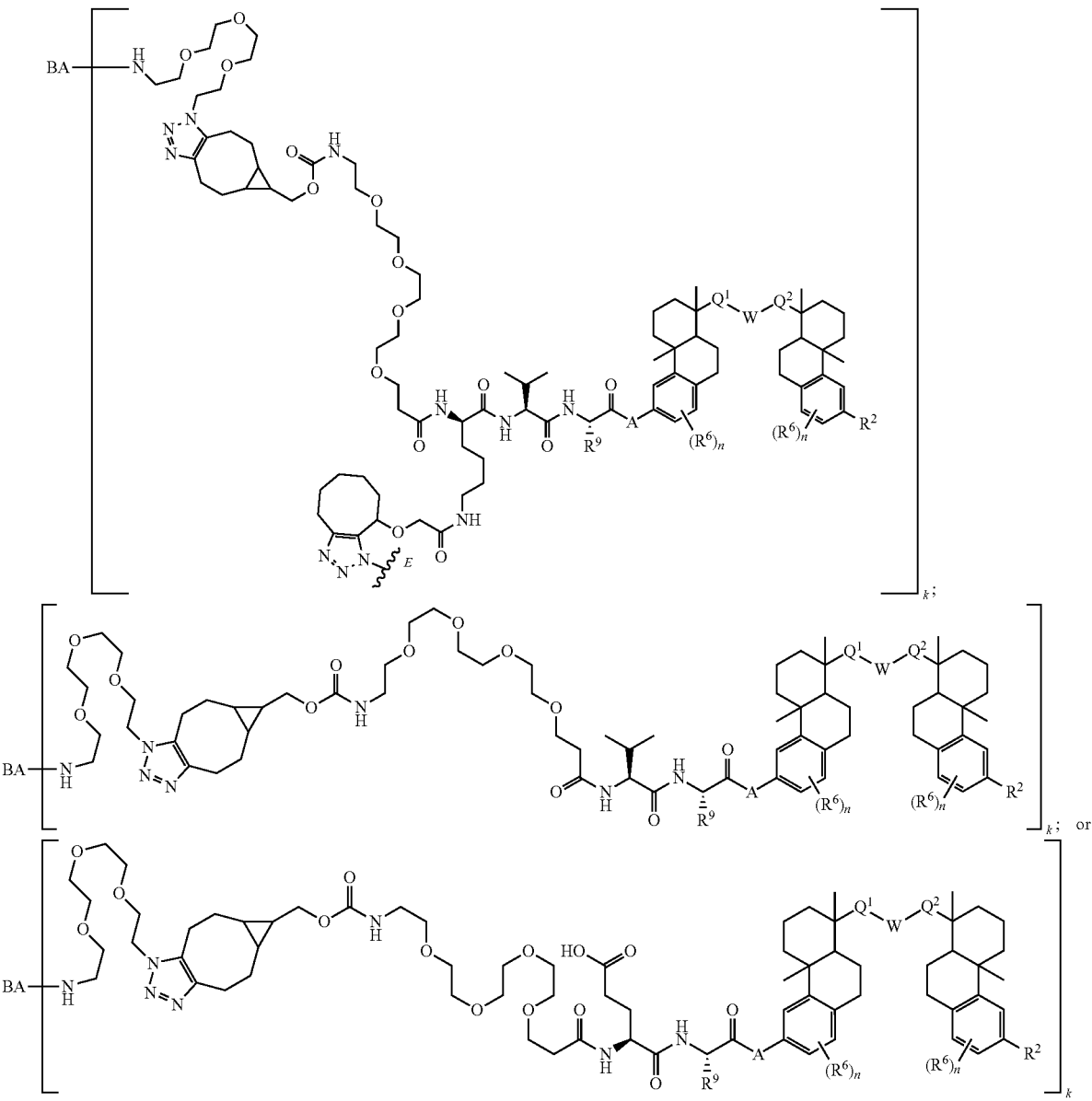

or a pharmaceutically acceptable salt, solvate, or stereoisomeric form thereof, or a regioisomer thereof, wherein:
  BA is a binding agent;
  k is an integer from 1 to 30;
  $Q^1$, $Q^2$, W, $R^1$, $R^2$, $R^4$, $R^5$, and $R^6$ are as described in the context of Formula I;
  each ⁓ξ⁓ is a bond to the enhancement group;
  each $R^9$ is —$CH_3$ or —$(CH_2)_3N(H)C(O)NH_2$; and
  each A is —O—, —N(H)—,

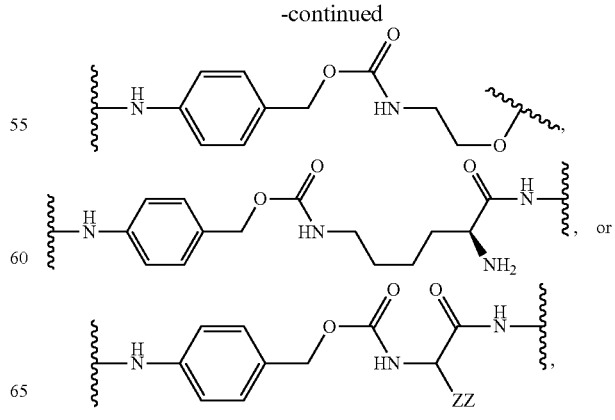

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N($(CH_2)_{1-5}C(O)NH(CH_2)_{1-5}SO_3H)_2$, —$(CH_2)_{n2}$—C(O)N($(CH_2)_{1-5}C(O)NH(CH_2)_{1-5}SO_3H)_2$, or —$(CH_2CH_2O)_{m2}$—C(O)N($(CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N($(CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N($(CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N($(CH_2)_{1-5}C(O)NH(CH_2)_{1-5}SO_3H)_2$, wherein m2 is 1, 2, 3, 4, or 5.

In some embodiments, the compound or conjugate is:

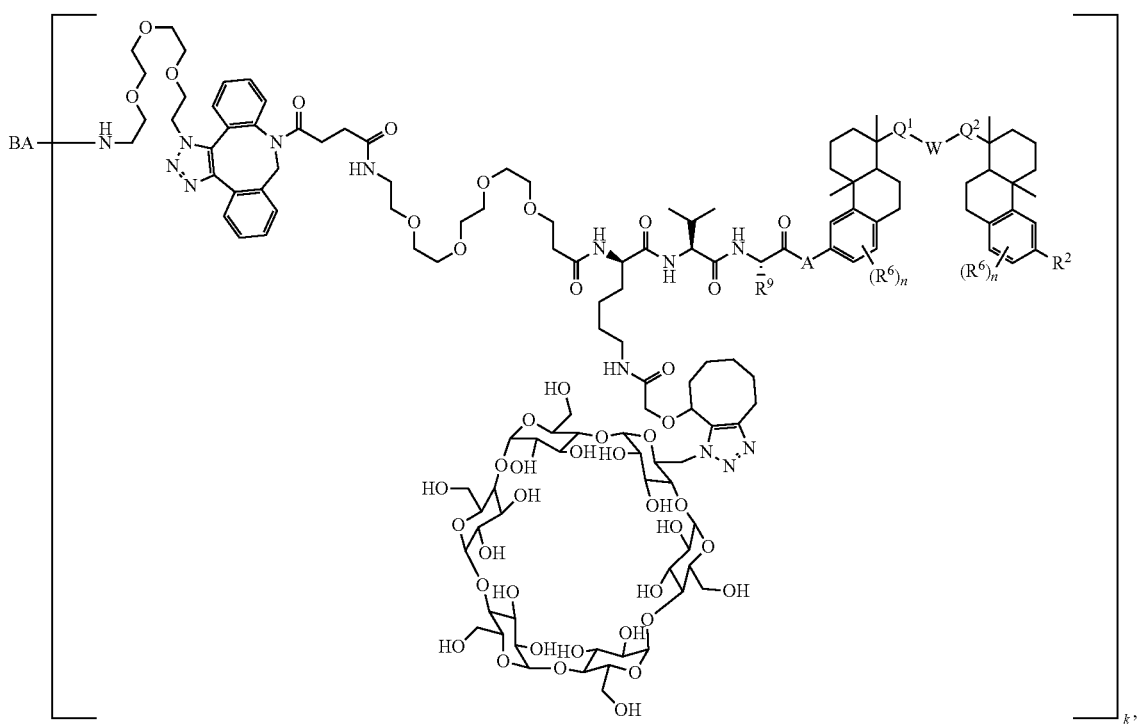

-continued
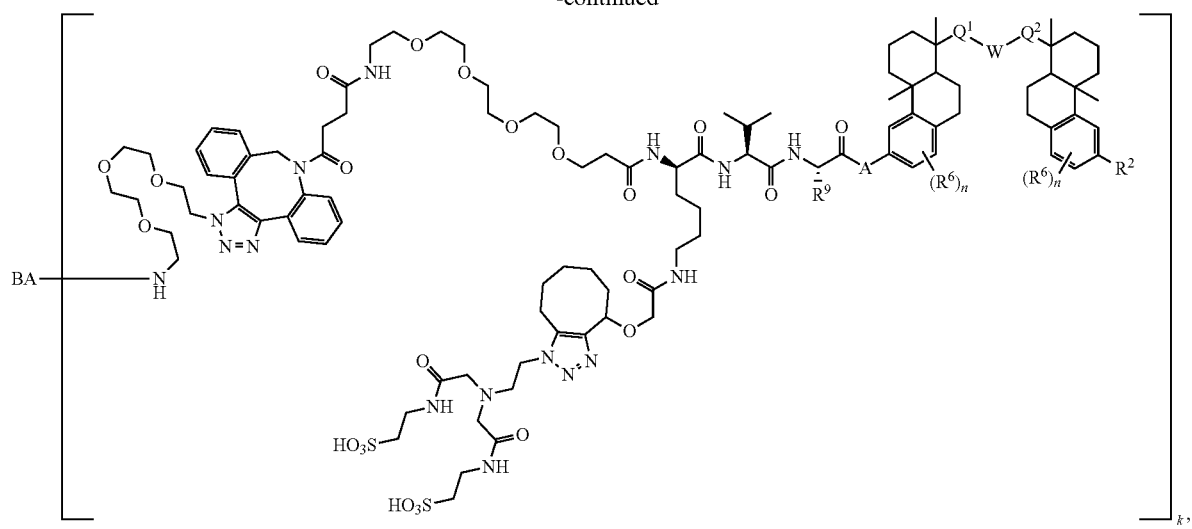
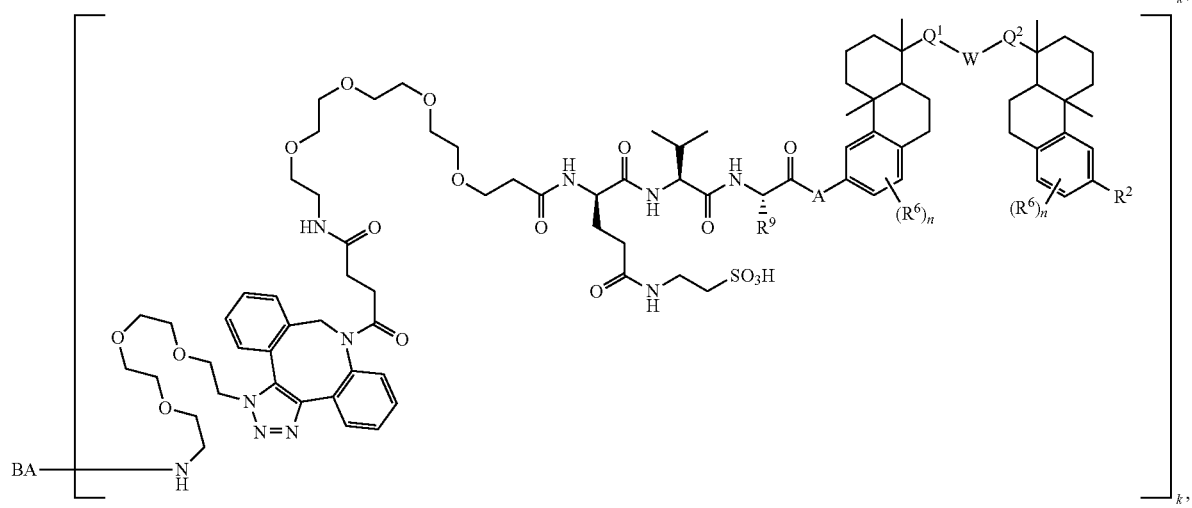
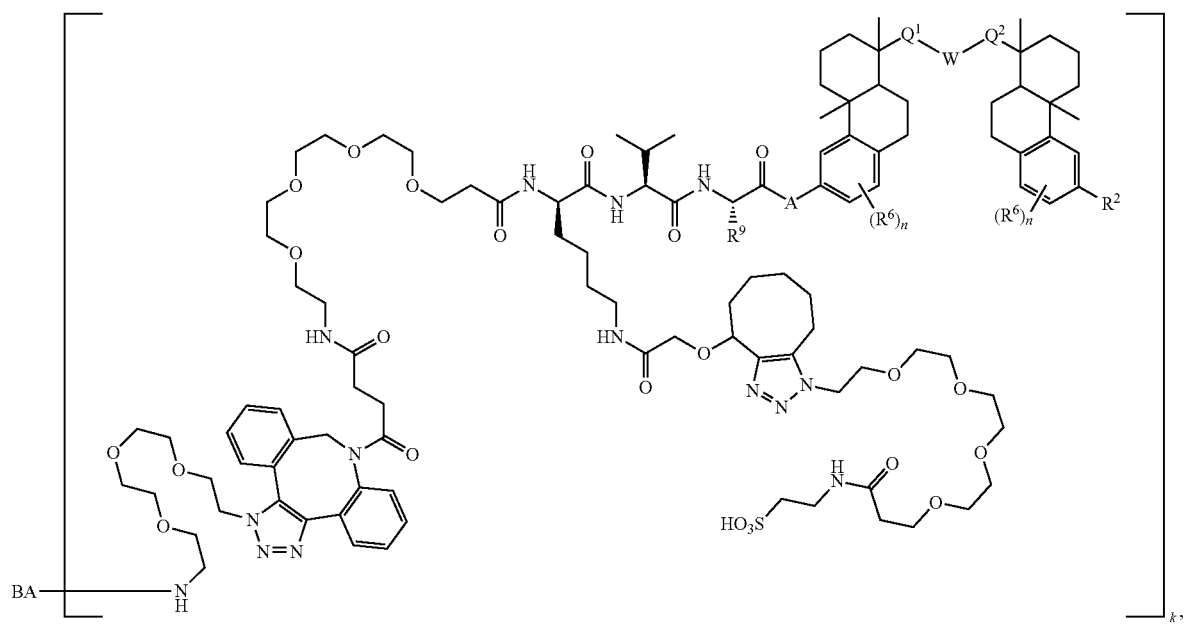

or a pharmaceutically acceptable salt, solvate, or stereoisomeric form thereof, or a regioisomer thereof, wherein:
BA is a binding agent;
k is an integer from 1 to 30;
$Q^1$, $Q^2$, W, $R^1$, $R^2$, $R^4$, $R^5$, and $R^6$ are as described in the context of Formula I;
each $R^9$ is —$CH_3$ or —$(CH_2)_3N(H)C(O)NH_2$; and
each A is —O—, —N(H)—,

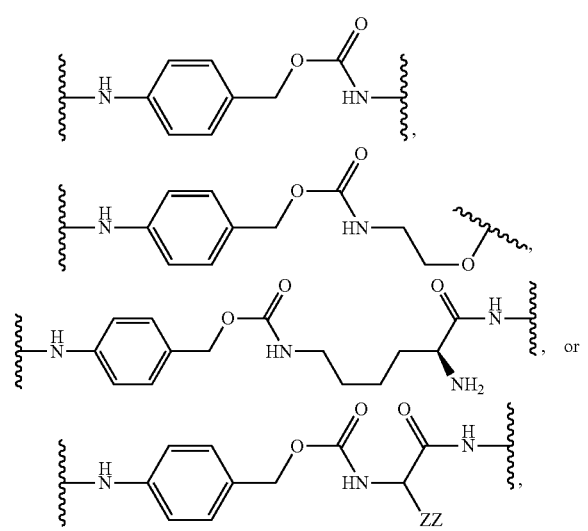

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the compound or conjugate is:

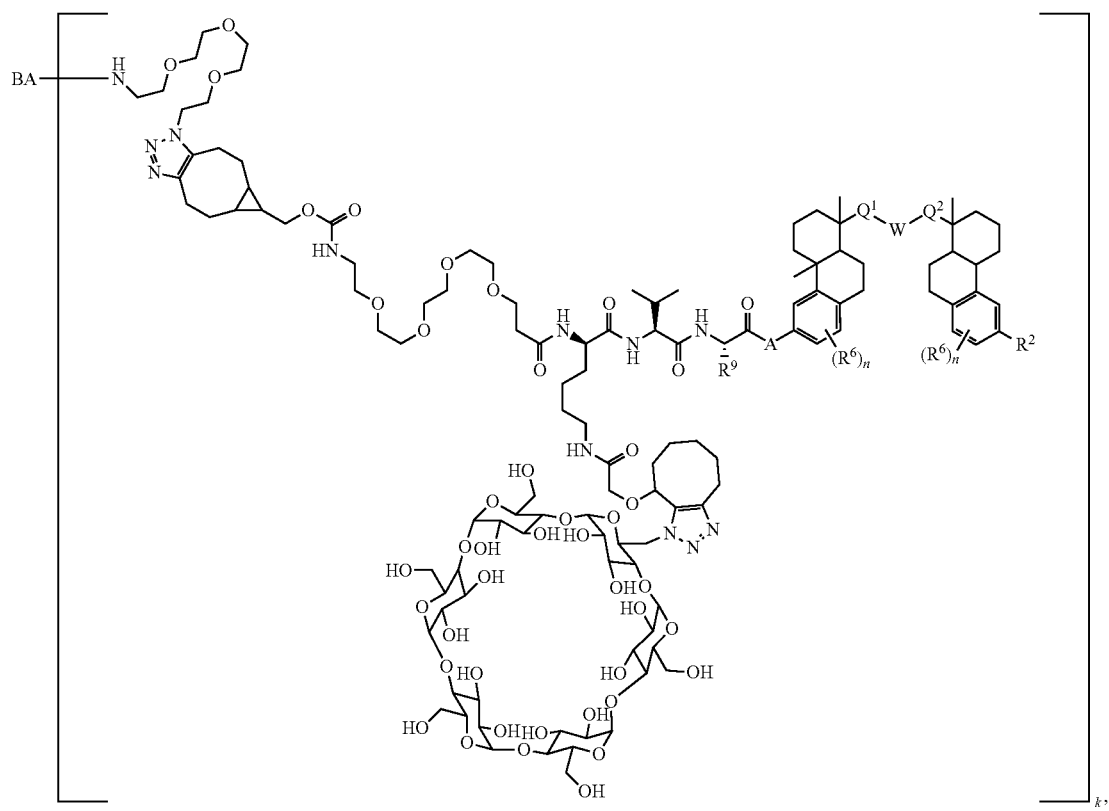

173
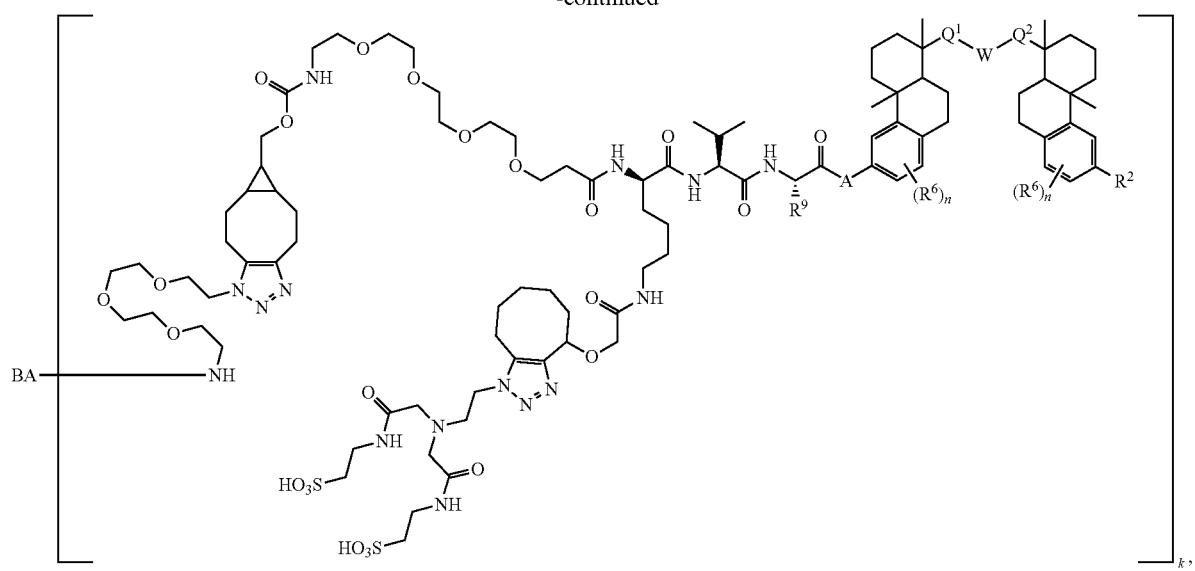
174
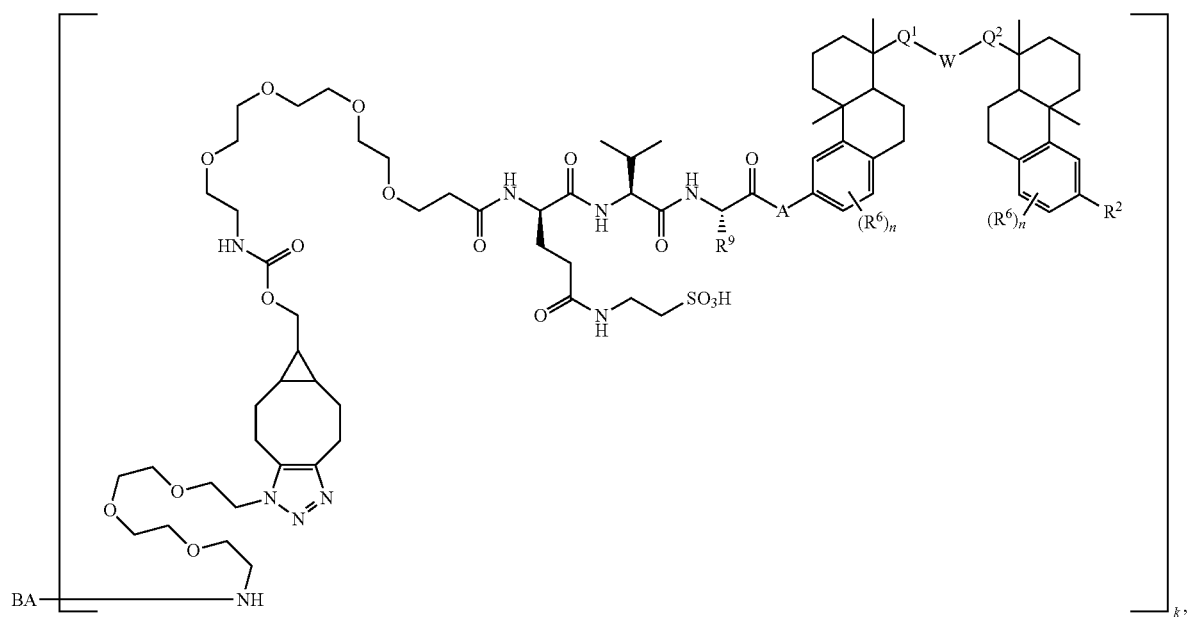

-continued

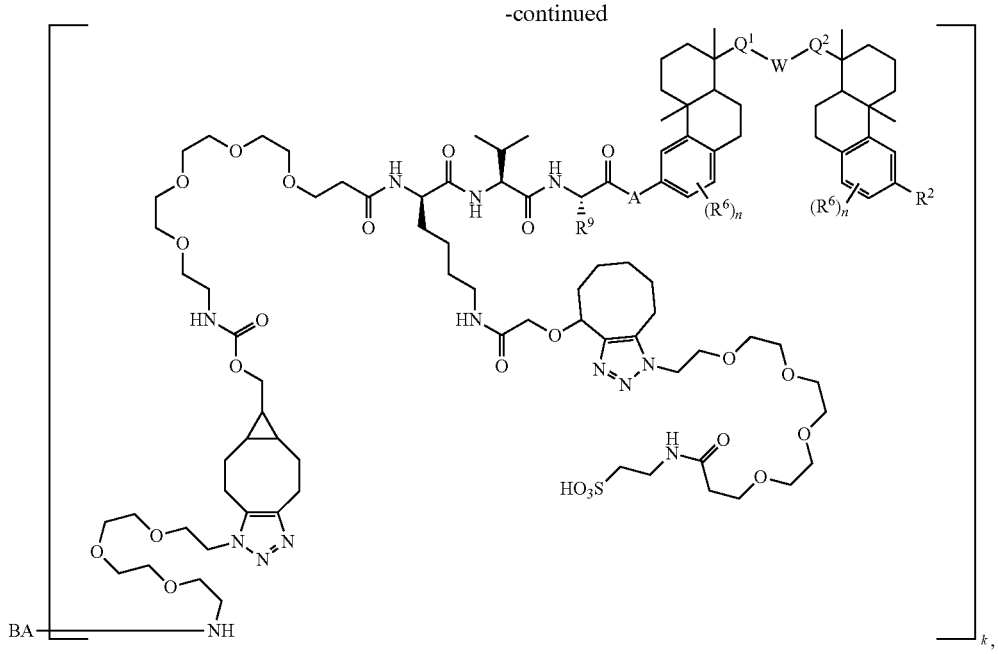

or a pharmaceutically acceptable salt, solvate, or stereoisomeric form thereof, or a regioisomer thereof, wherein:

BA is a binding agent;

k is an integer from 1 to 30;

$Q^1$, $Q^2$, W, $R^1$, $R^2$, $R^4$, $R^5$, and $R^6$ are as described in the context of Formula I;

each $R^9$ is —$CH_3$ or —$(CH_2)_3N(H)C(O)NH_2$; and each A is —O—, —N(H)—,

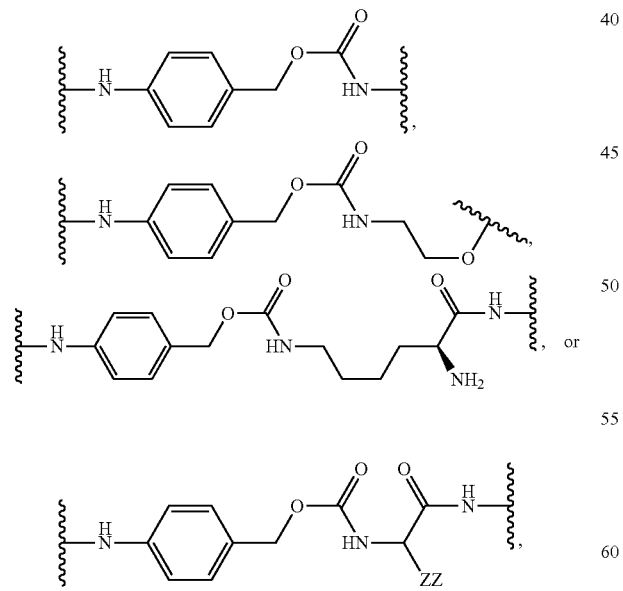

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the compound or conjugate is:

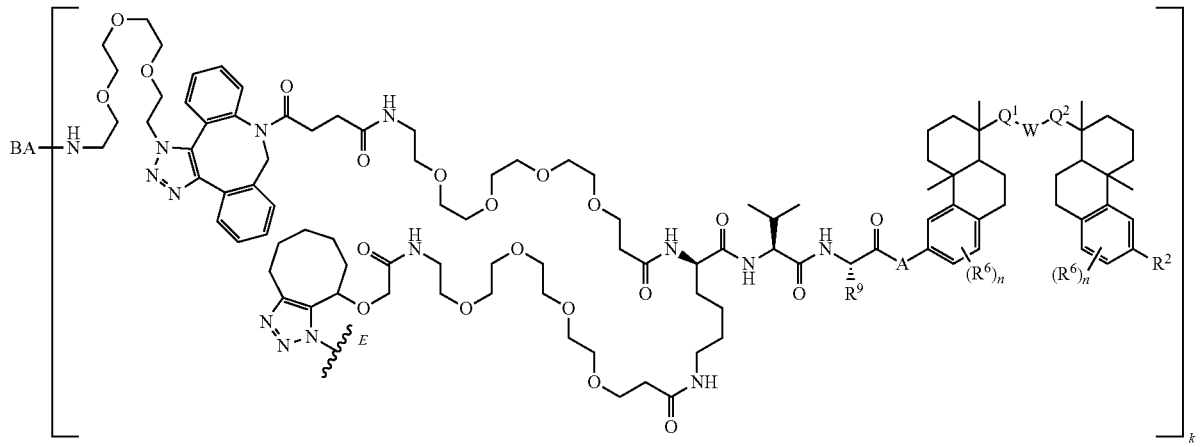

or a pharmaceutically acceptable salt, solvate, or stereoisomeric form thereof, or a regioisomer thereof, wherein:
BA is a binding agent;
k is an integer from 1 to 30;
$Q^1$, $Q^2$, W, $R^1$, $R^2$, $R^4$, $R^5$, and $R^6$ are as described in the context of Formula each $-\xi^E-$ is a bond to the enhancement group;
each $R^9$ is —$CH_3$ or —$(CH_2)_3N(H)C(O)NH_2$; and
each A is —O—, —N(H)—,

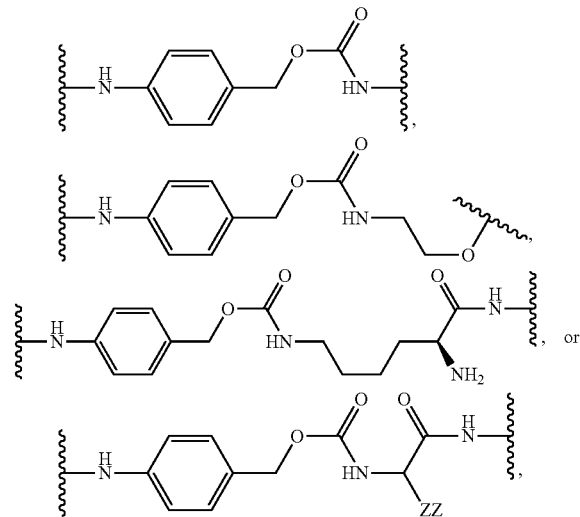

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N$((CH_2)_{1-5}C(O)NH(CH_2)_{1-5}SO_3H)_2$, —$(CH_2)_{n2}$—C(O)N$((CH_2)_{1-5}C(O)NH(CH_2)_{1-5}SO_3H)_2$, or —$(CH_2CH_2O)_{m2}$—C(O)N$((CH_2)_{1-5}C(O)NH(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N$((CH_2)_{1-5}C(O)NH(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N$((CH_2)_{1-5}C(O)NH(CH_2)_{1-5}SO_3H)_2$, wherein m2 is 1, 2, 3, 4, or 5.

In some embodiments, the compound or conjugate is:

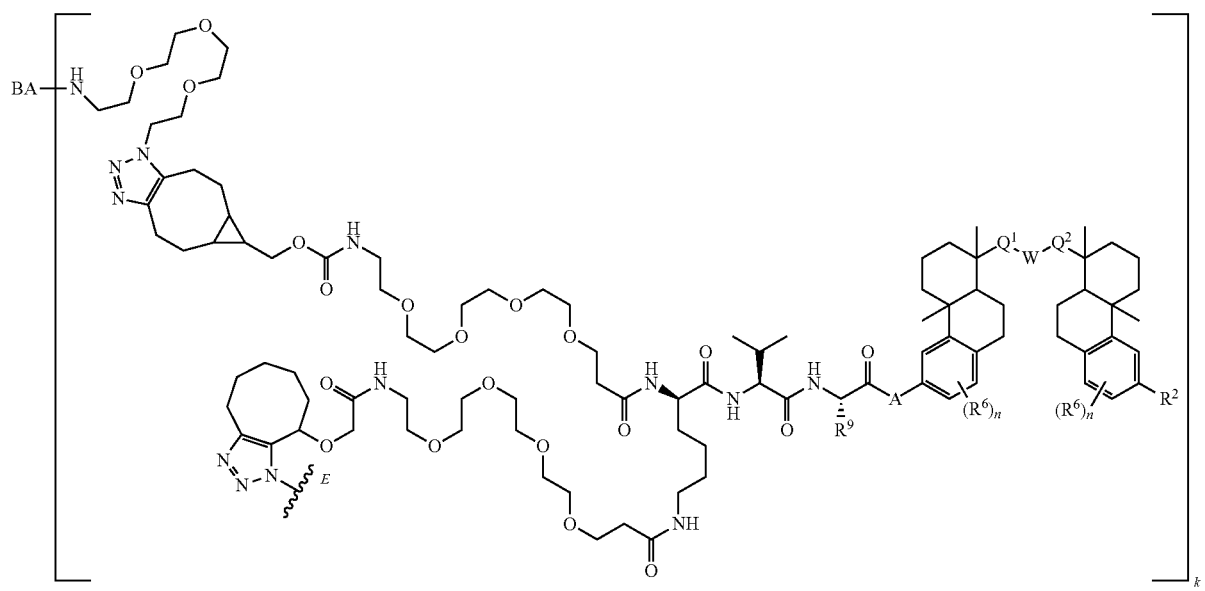

or a pharmaceutically acceptable salt, solvate, or stereoisomeric form thereof, or a regioisomer thereof, wherein:
BA is a binding agent;
k is an integer from 1 to 30;
$Q^1$, $Q^2$, W, $R^1$, $R^2$, $R^4$, $R^5$, and $R^6$ are as described in the context of Formula I; each ⁓𝑬⁓ is a bond to the enhancement group;
each $R^9$ is —$CH_3$ or —$(CH_2)_3N(H)C(O)NH_2$; and
each A is —O—, —N(H)—,

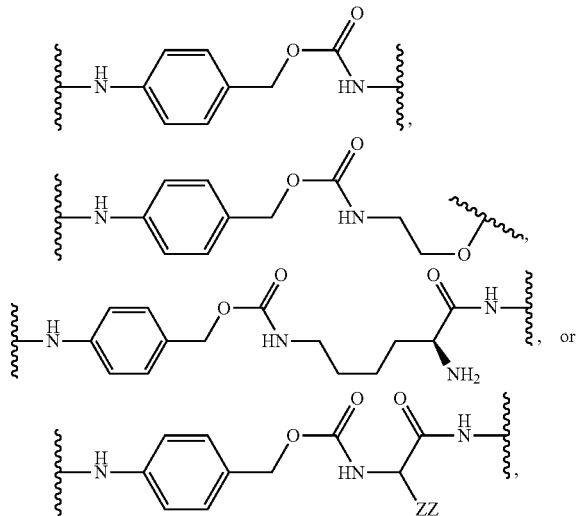

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl. In certain embodiments, the enhancement agent is a hydrophilic group. In certain embodiments, the enhancement agent is cyclodextrin. In certain embodiments, the enhancement group is an alkyl, heteroalkyl, alkylenyl, or heteroalkylenyl sulfonic acid. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the alkyl, heteroalkyl, alkylenyl, or heteroalkylenyl sulfonic acid is —$(CH_2)_{1-5}SO_3H$, —$(CH_2)_{n2}$—NH—$(CH_2)_{1-5}SO_3H$, —$(CH_2)_{n2}$—C(O)NH—$(CH_2)_{1-5}SO_3H$, —$(CH_2CH_2O)_{m2}$—C(O)NH—$(CH_2)_{1-5}SO_3H$, —$(CH_2)_{n2}$—N$((CH_2)_{1-5}$C(O)NH$(CH_2)_{1-5}SO_3H)_2$, —$(CH_2)_{n2}$—C(O)N$((CH_2)_{1-5}$C(O)NH$(CH_2)_{1-5}SO_3H)_2$, or —$(CH_2CH_2O)_{m2}$—C(O)N$((CH_2)_{1-5}$C(O)NH$(CH_2)_{1-5}SO_3H)_2$, wherein n2 is 1, 2, 3, 4, or 5, and m2 is 1, 2, 3, 4, or 5. In one embodiment, the alkyl or alkylenyl sulfonic acid is —$(CH_2)_{1-5}SO_3H$. In another embodiment, the heteroalkyl or heteroalkylenyl sulfonic acid is —$(CH_2)_{n2}$—NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)NH—$(CH_2)_{1-5}SO_3H$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)NH—$(CH_2)_{1-5}SO_3H$, wherein m2 is 1, 2, 3, 4, or 5. In another embodiment, the alkyl, heteroalkyl, alkylenyl, or heteroalkylenyl sulfonic acid is —$(CH_2)_{n2}$—N$((CH_2)_{1-5}$C(O)NH$(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2)_{n2}$—C(O)N$((CH_2)_{1-5}$C(O)NH$(CH_2)_{1-5}SO_3H)_2$, wherein n2 is 1, 2, 3, 4, or 5. In another embodiment, the alkyl, heteroalkyl, alkylenyl, or heteroalkylenyl sulfonic acid is —$(CH_2CH_2O)_{m2}$—C(O)N$((CH_2)_{1-5}$C(O)NH$(CH_2)_{1-5}SO_3H)_2$, wherein m2 is 1, 2, 3, 4, or 5.

In some embodiments, the compound or conjugate is:
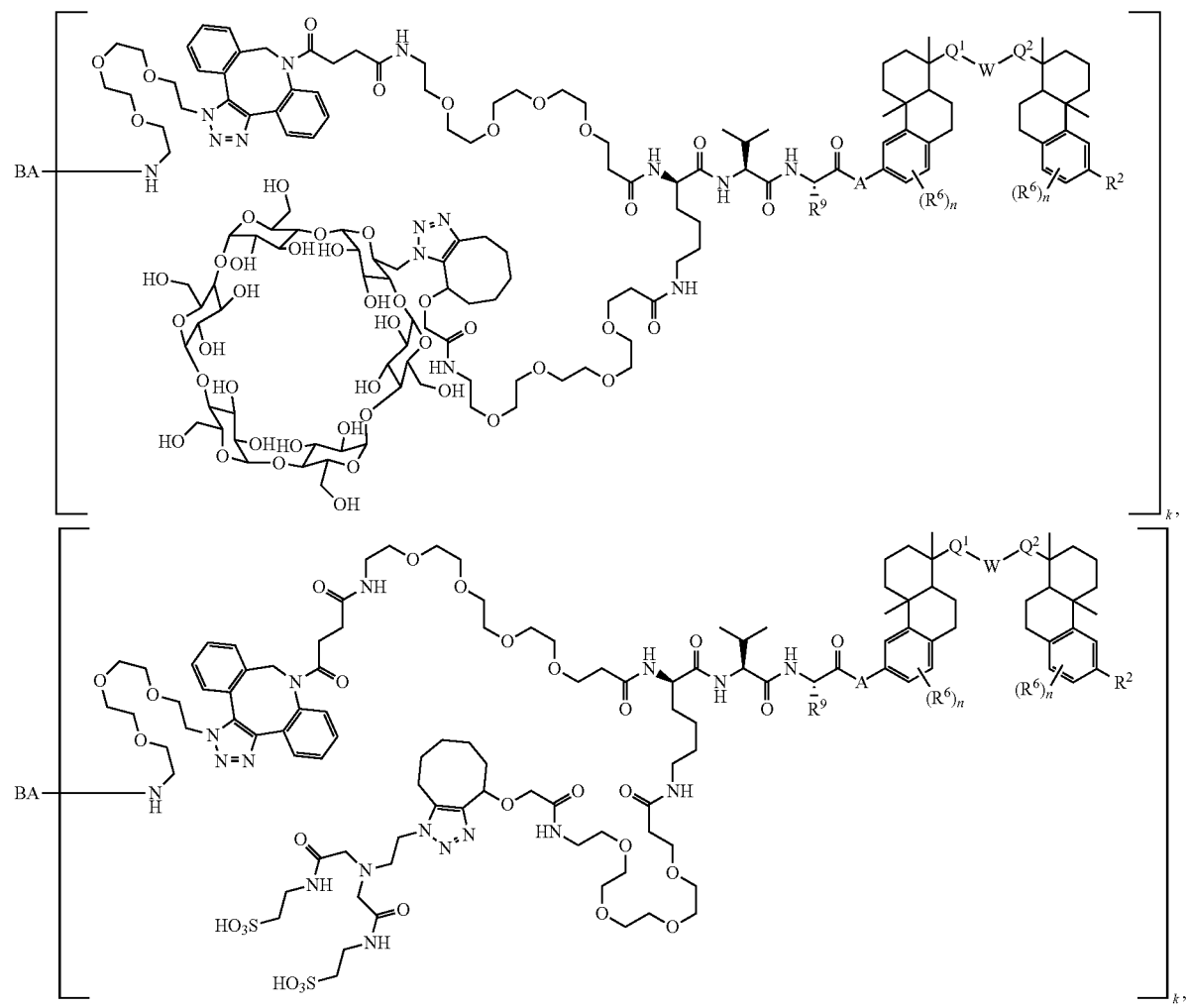
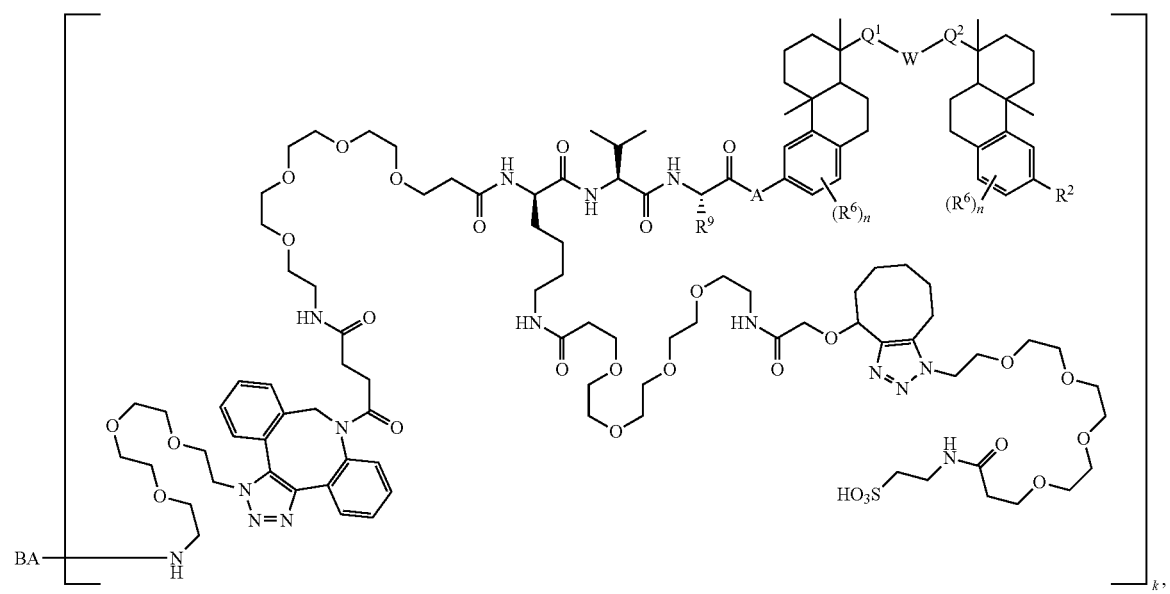

or a pharmaceutically acceptable salt, solvate, or stereoisomeric form thereof, or a regioisomer thereof, wherein:
BA is a binding agent;
k is an integer from 1 to 30;
$Q^1$, $Q^2$, W, $R^1$, $R^2$, $R^4$, $R^5$, and $R^6$ are as described in the context of Formula I;
each $R^9$ is —$CH_3$ or —$(CH_2)_3N(H)C(O)NH_2$; and
each A is —O—, —N(H)—,

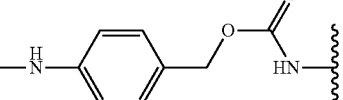

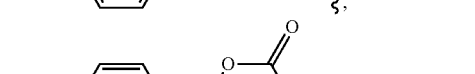

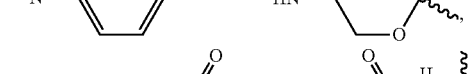

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In some embodiments, the compound or conjugate is:

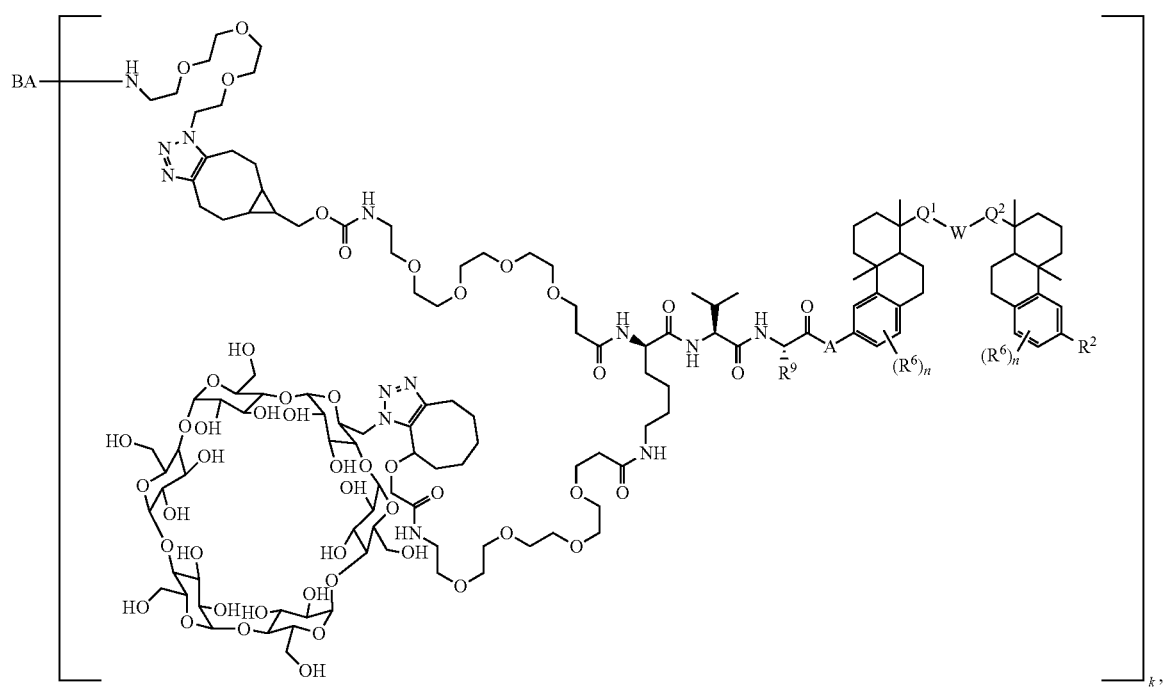

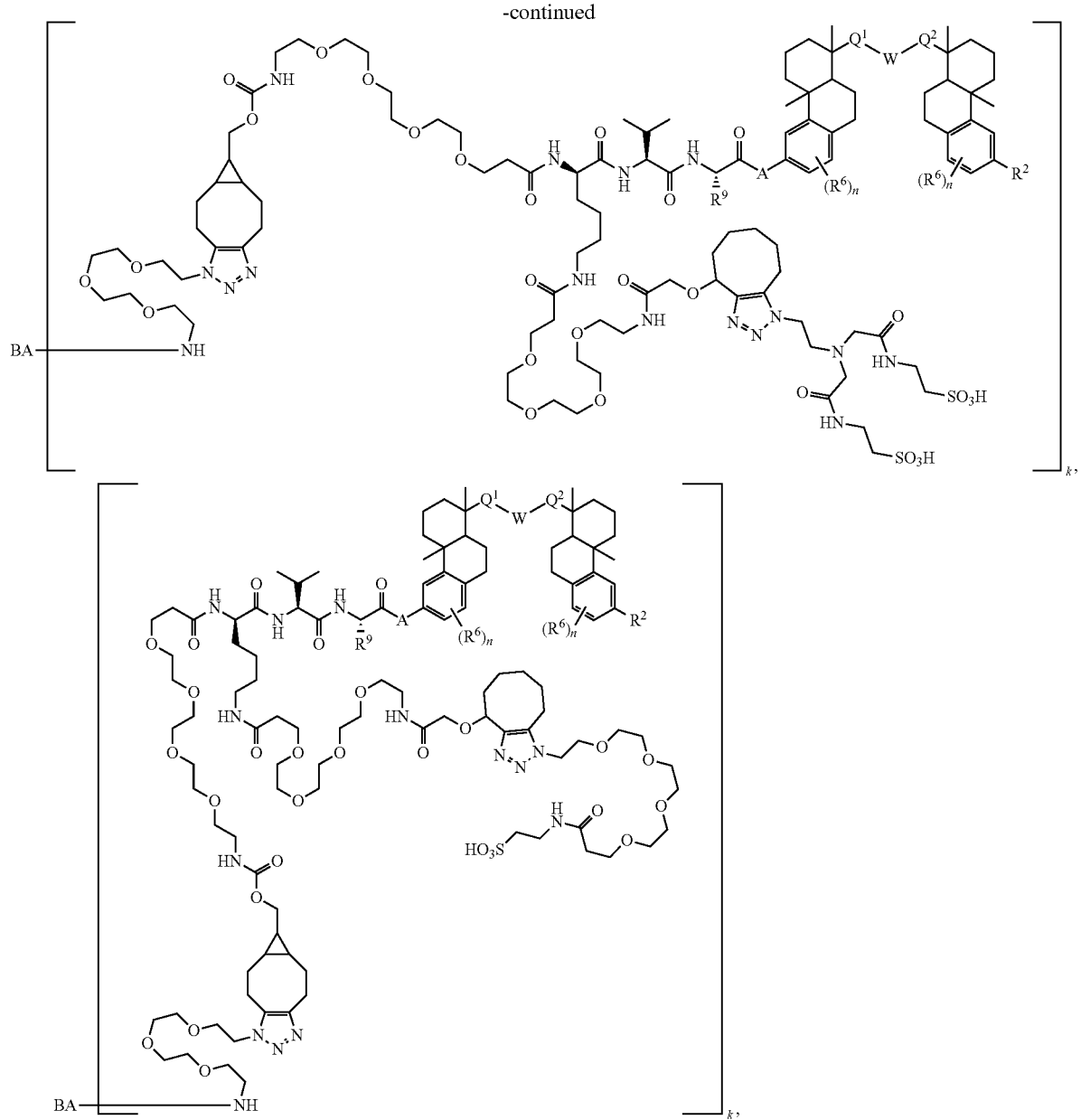
or a pharmaceutically acceptable salt, solvate, or stereoisomeric form thereof, or a regioisomer thereof, wherein:
BA is a binding agent;
k is an integer from 1 to 30;
$Q^1$, $Q^2$, W, $R^1$, $R^2$, $R^4$, $R^5$, $R^6$ are as described in the context of Formula I;
each $R^9$ is —$CH_3$ or —$(CH_2)_3N(H)C(O)NH_2$; and
each A is —O—, —N(H)—,
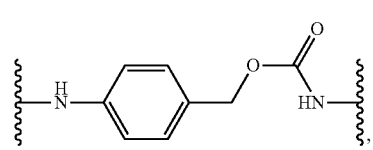
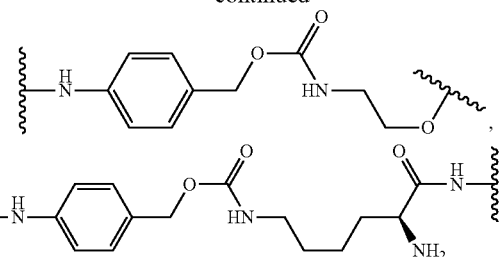

where ZZ is hydrogen, or a side chain for an amino acid as discussed elsewhere herein. For example, in one embodiment, ZZ is $C_{1-6}$ alkyl. By way of further example, in one embodiment, ZZ is $C_{1-6}$ heteroalkyl.

In each of the above embodiments, the conjugates can be prepared from binding agents functionalized with azide groups, and residues thereof, as described in the sections below. For convenience, the triazole residue in several structures above is depicted within parentheses. Those of skill will recognize that the triazole can be formed from an azide group of an azide-derivatized binding agent and an alkyne of the linker-payload LP.

In some embodiments, the compound or conjugate is selected from:

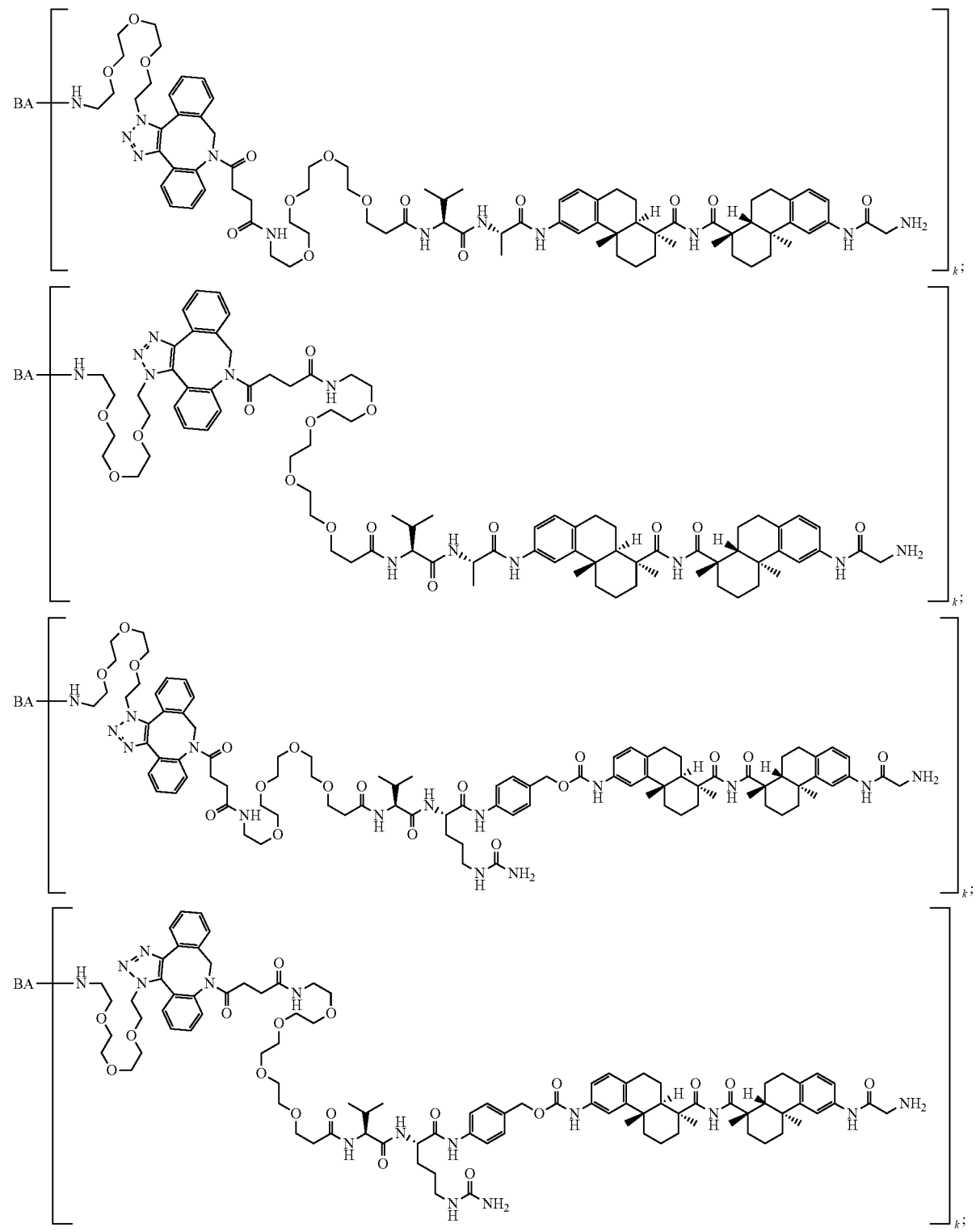

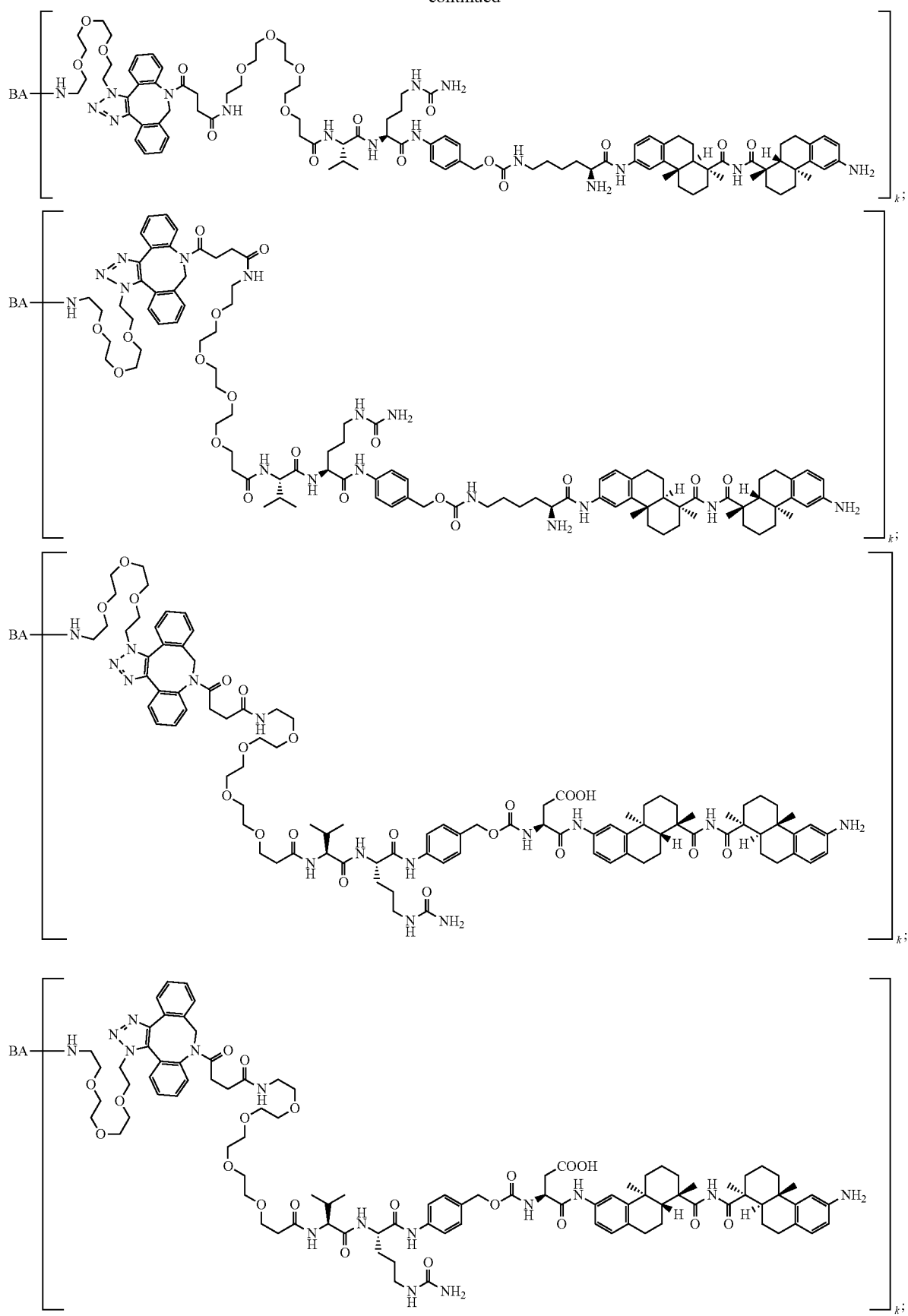

191 192
-continued
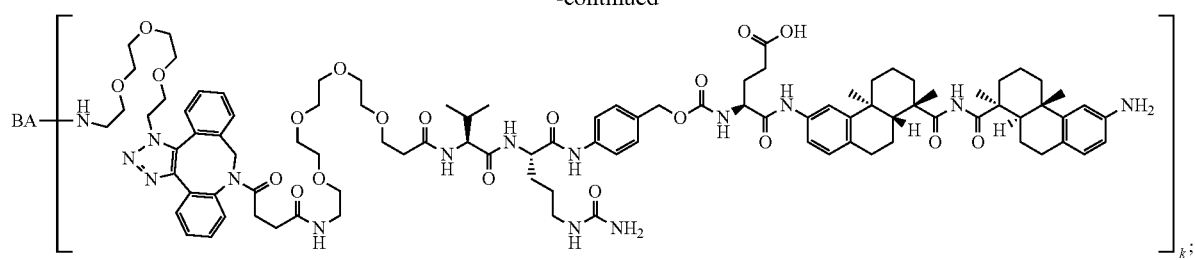
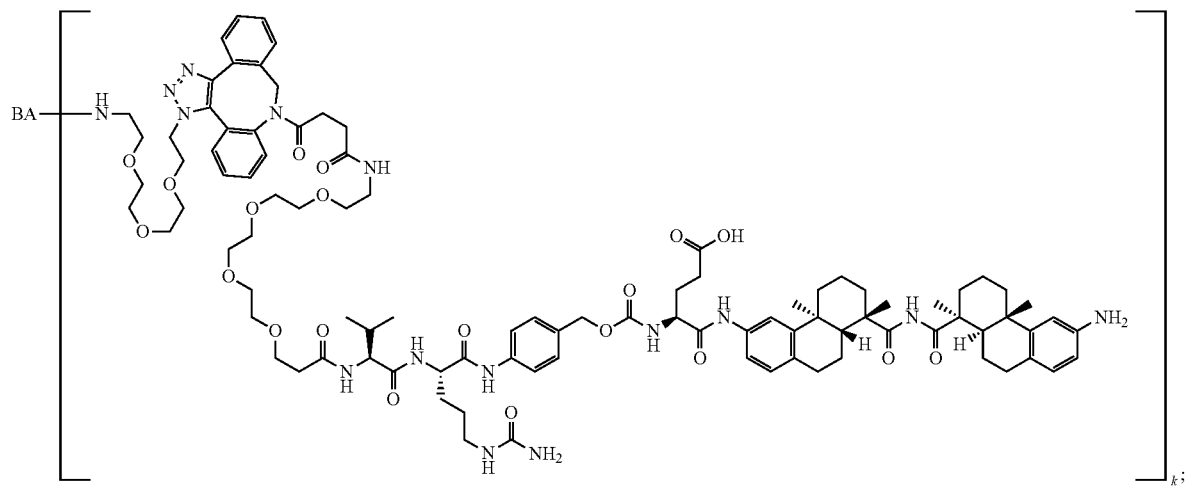
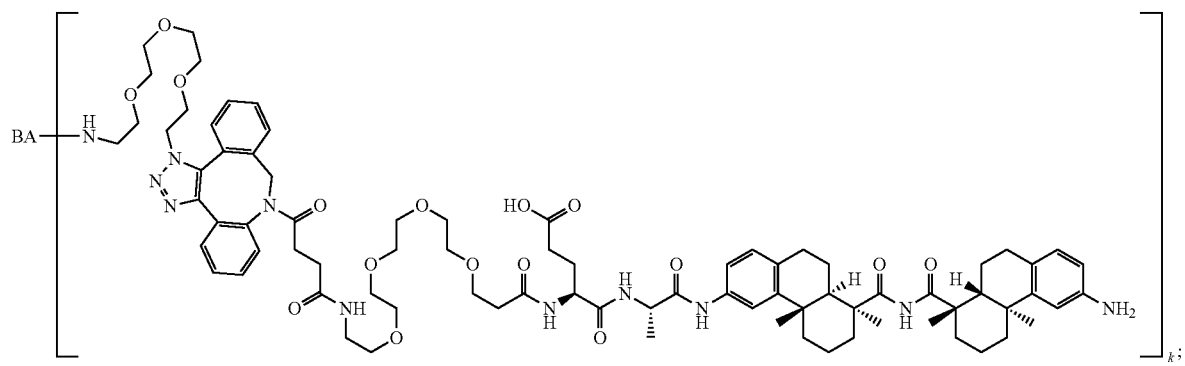
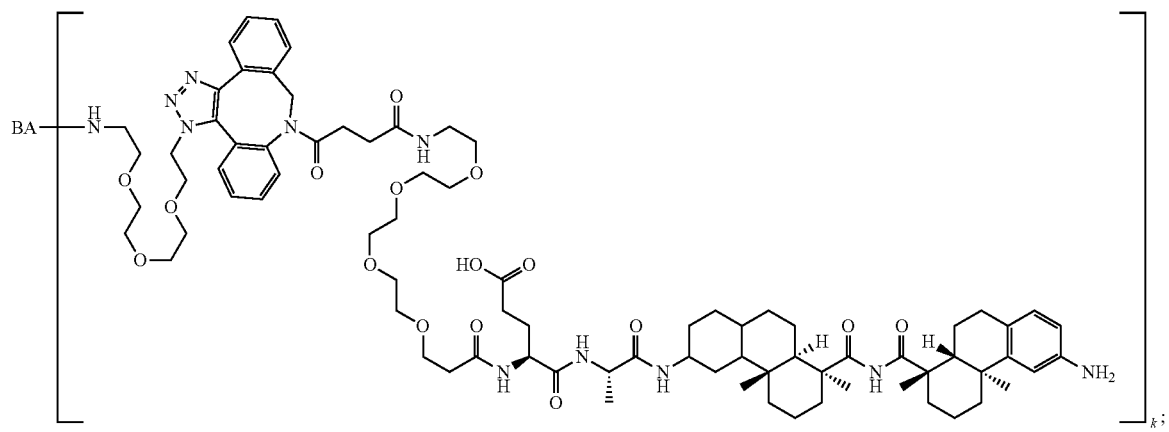

193
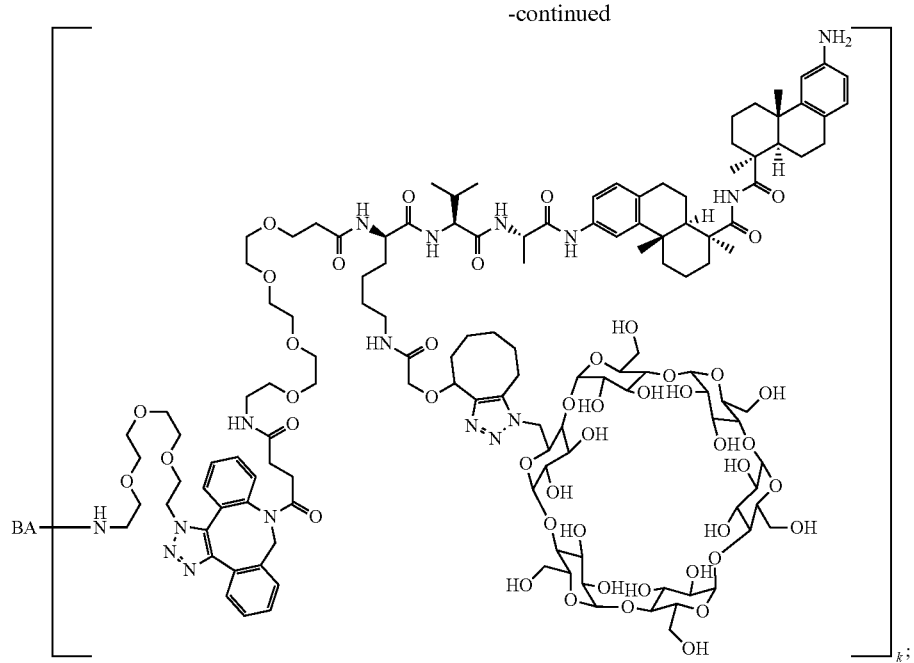
194
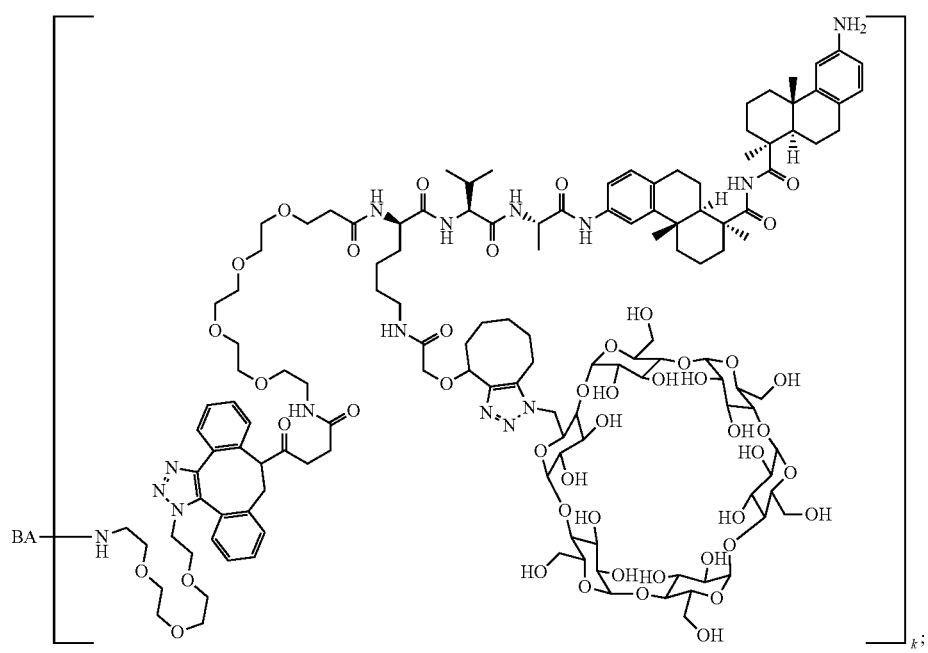

195
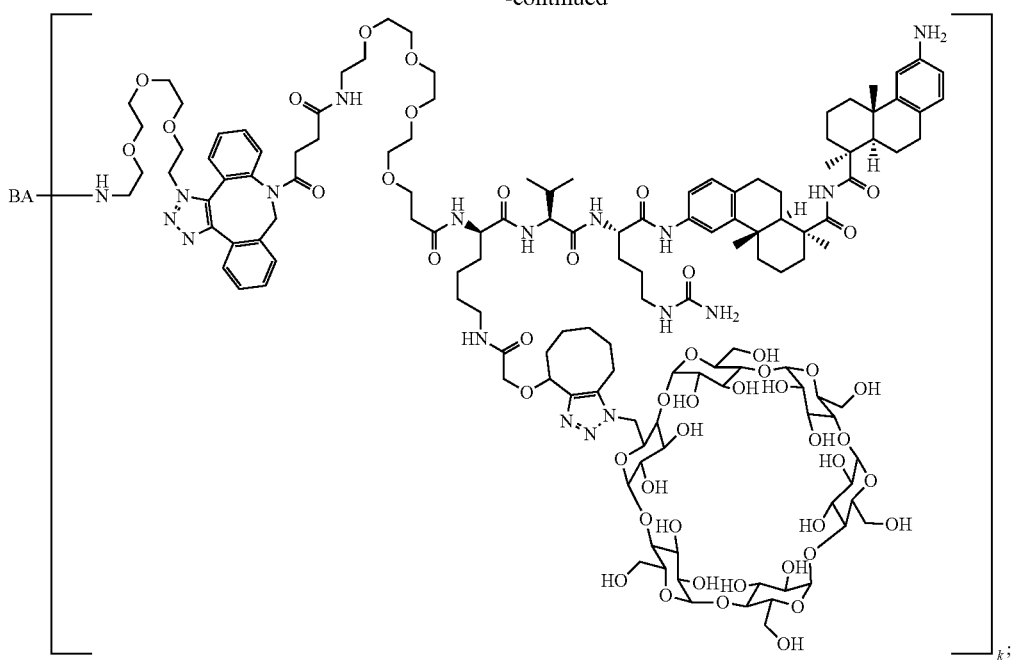
196
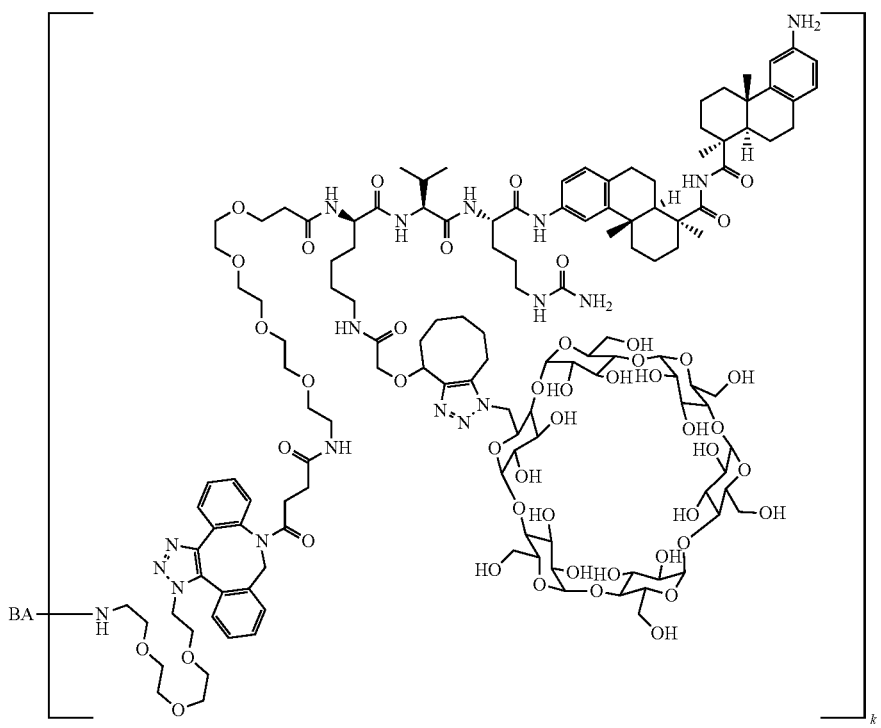

197
-continued
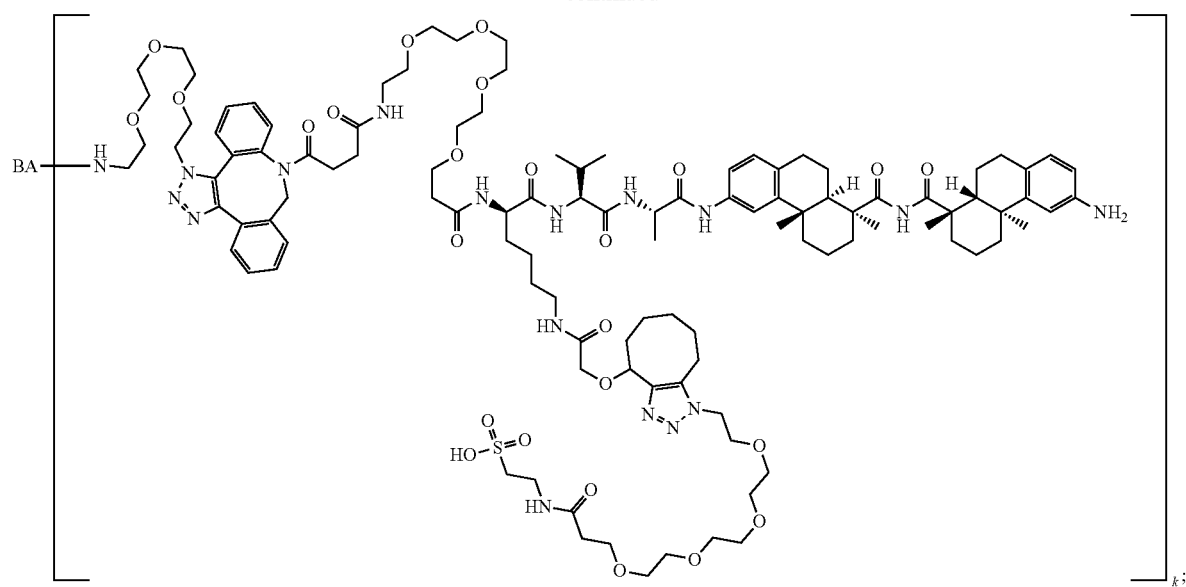
198
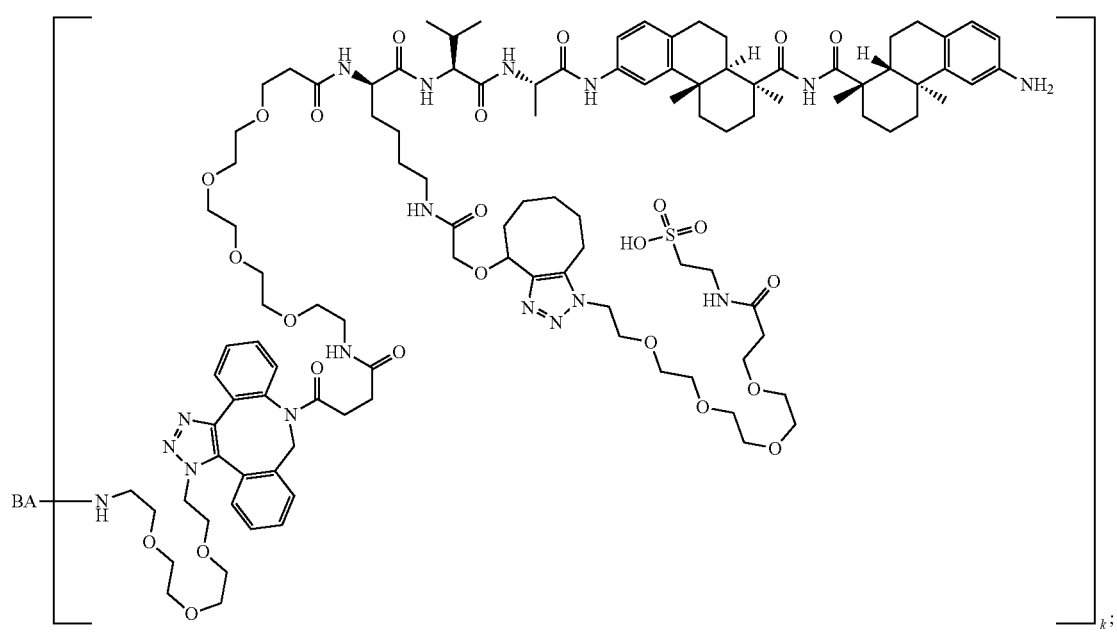

199
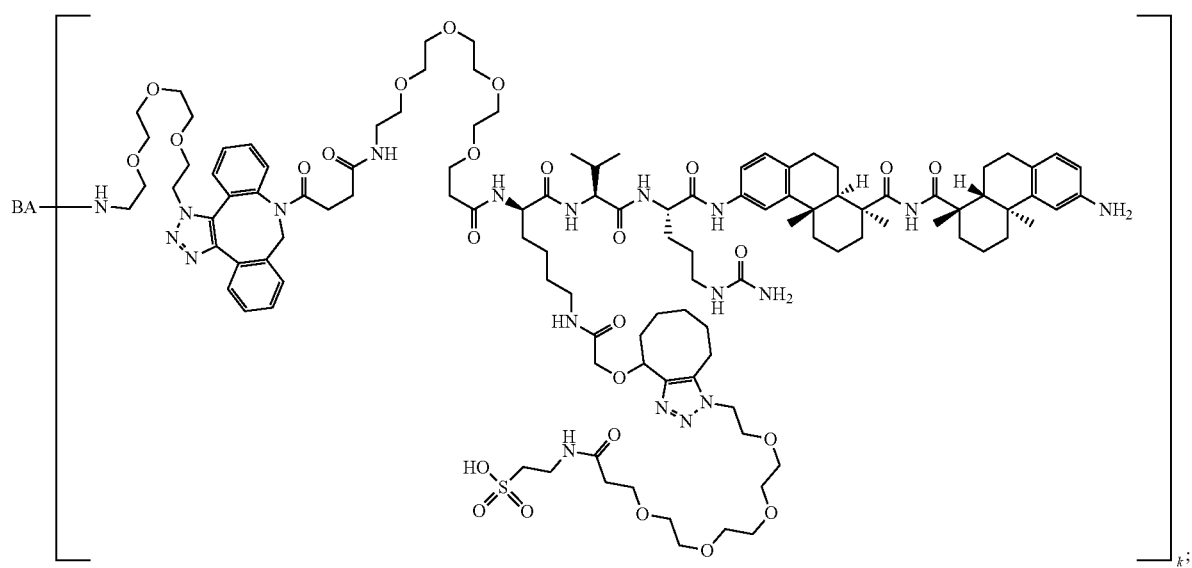
200
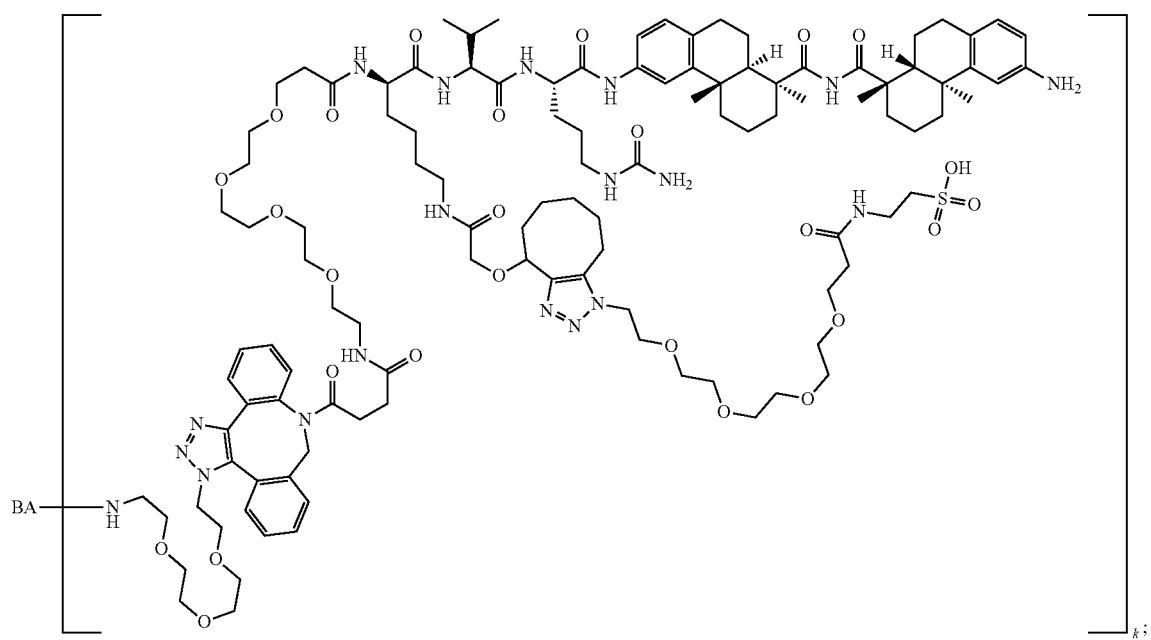

-continued
201
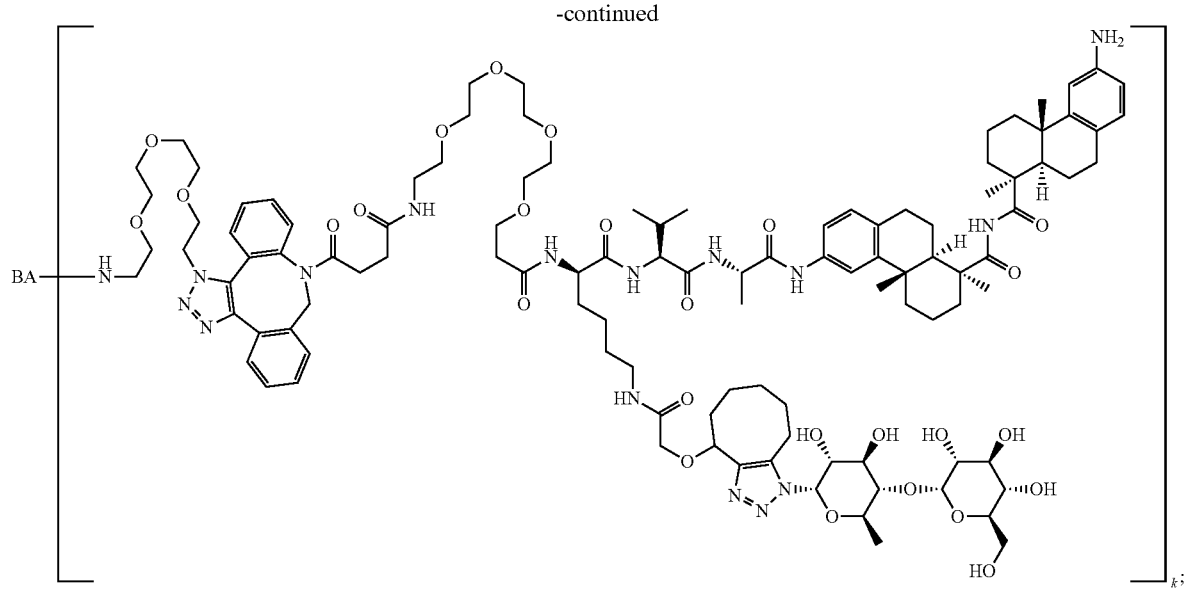
202
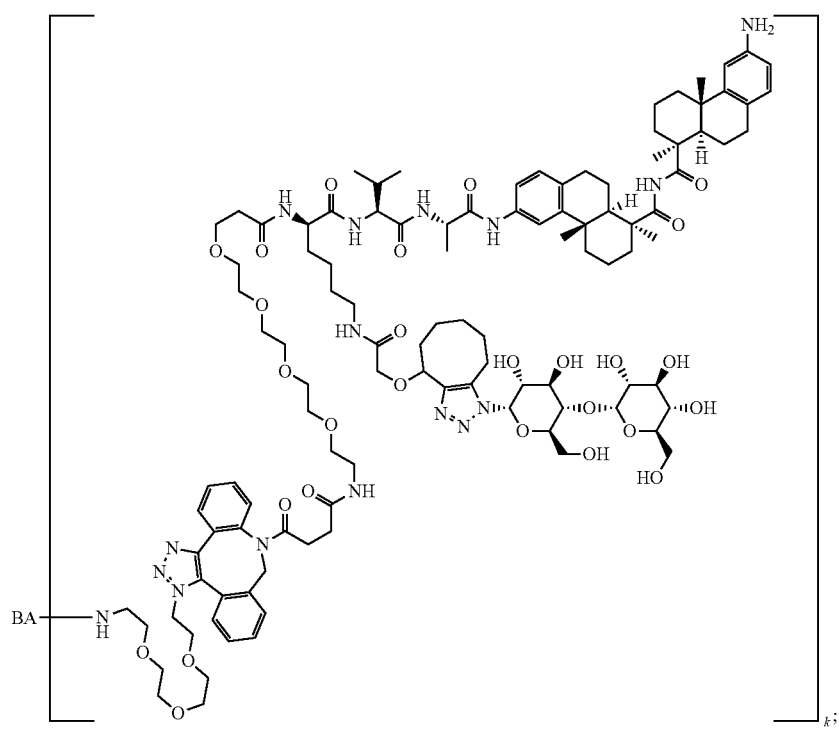

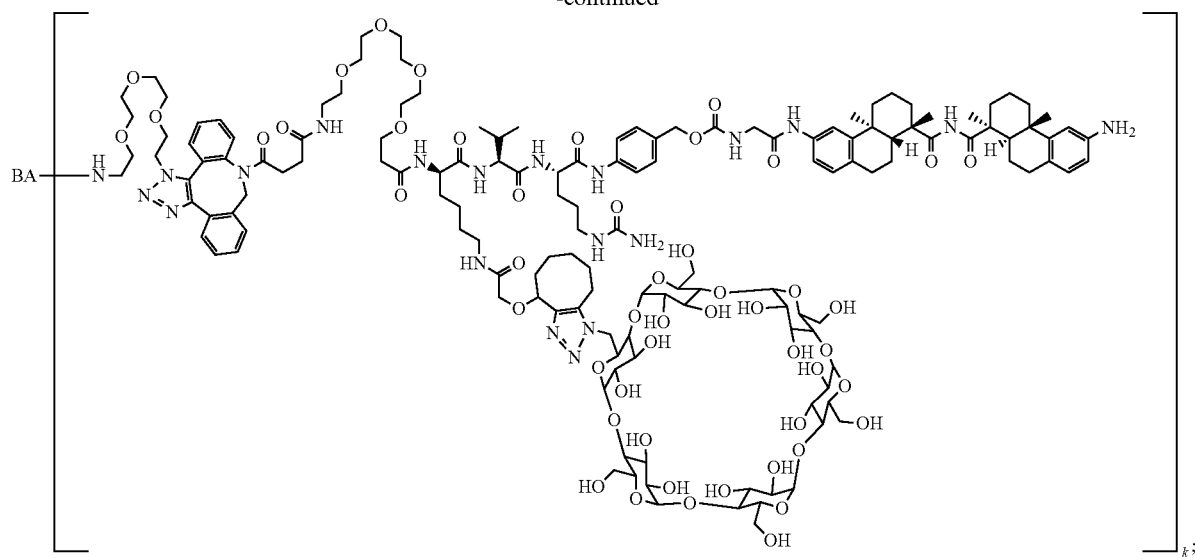
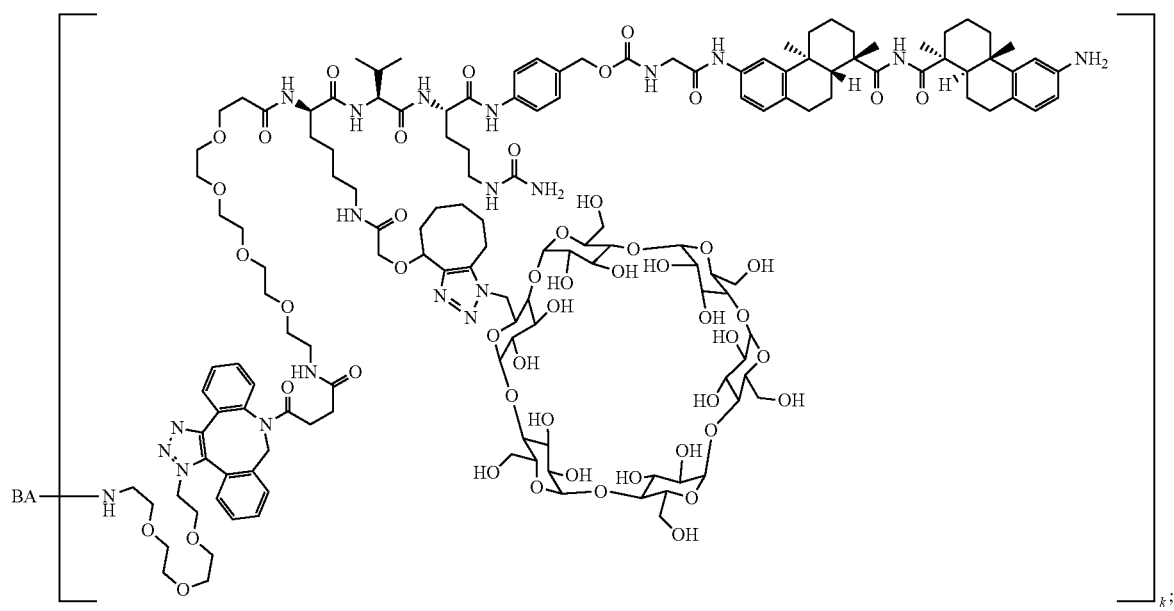
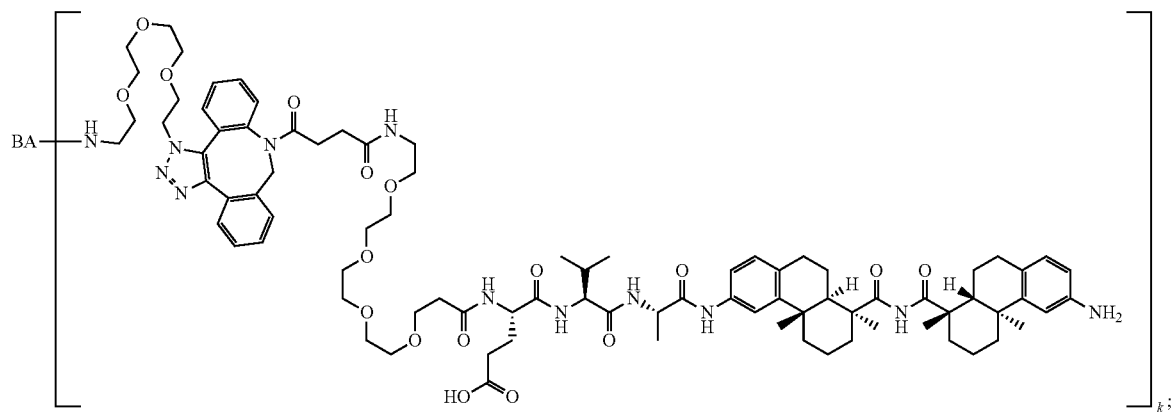

205 206
-continued
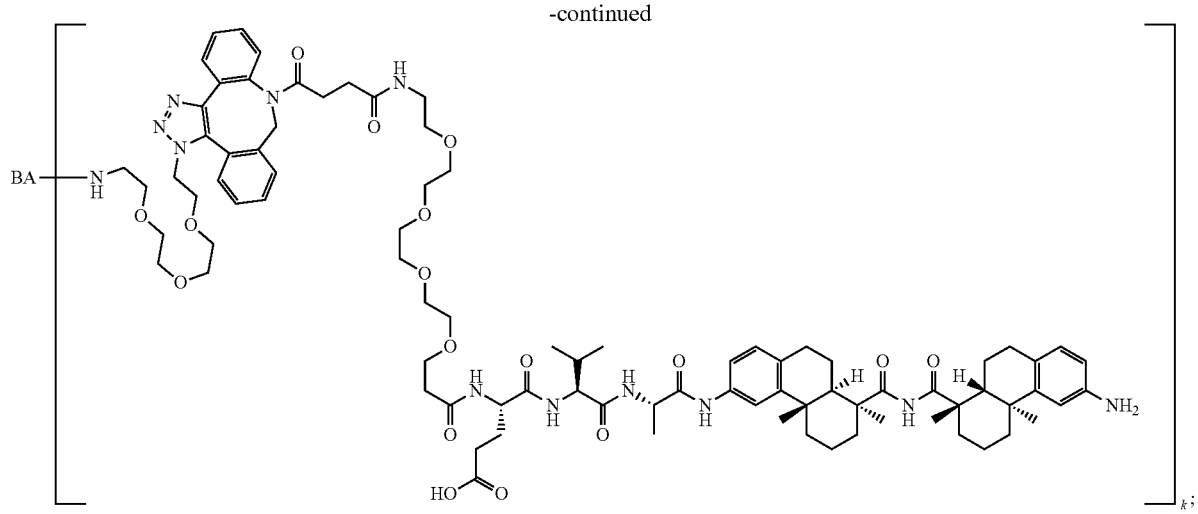
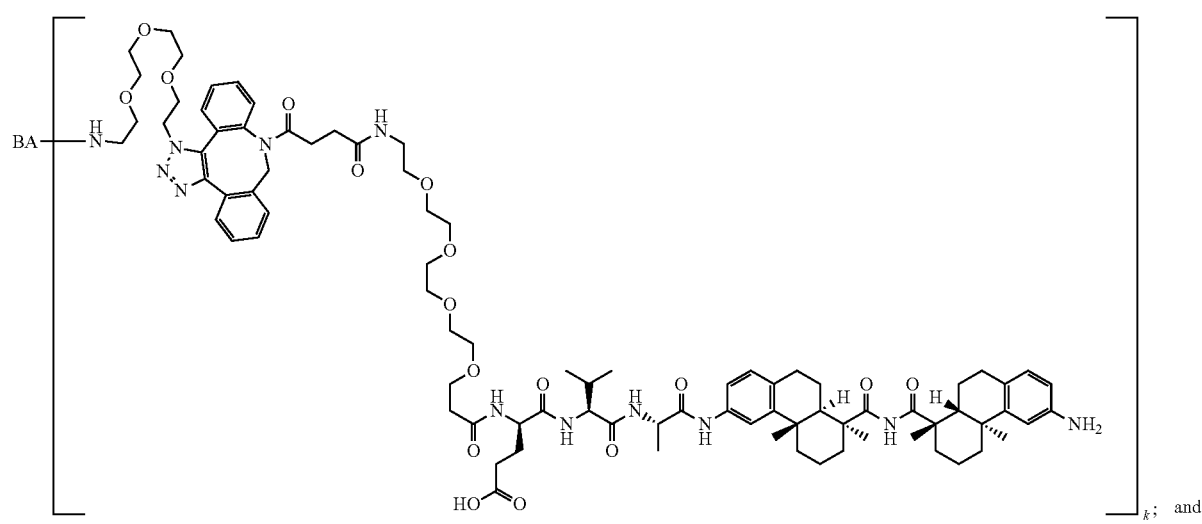
and
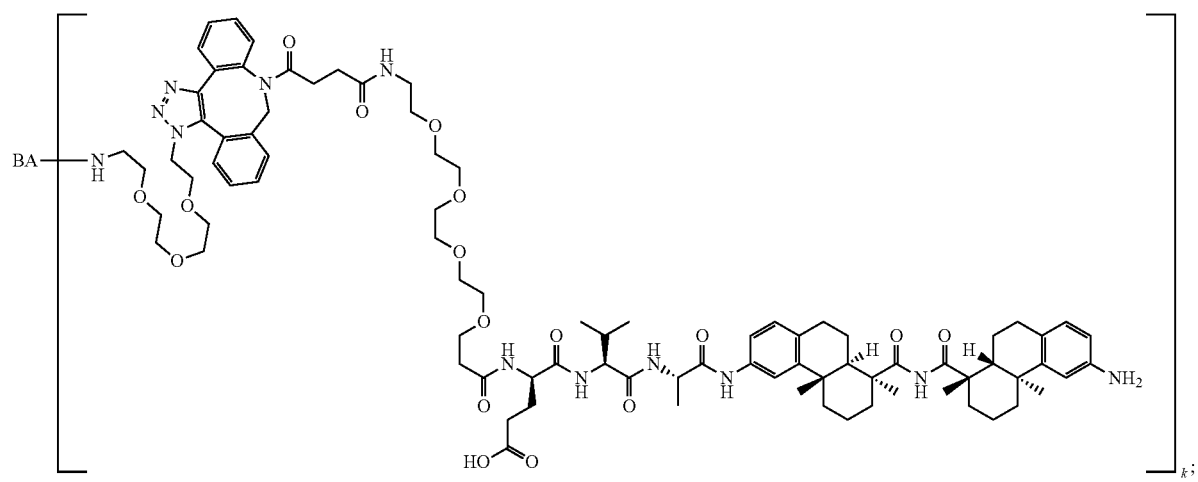

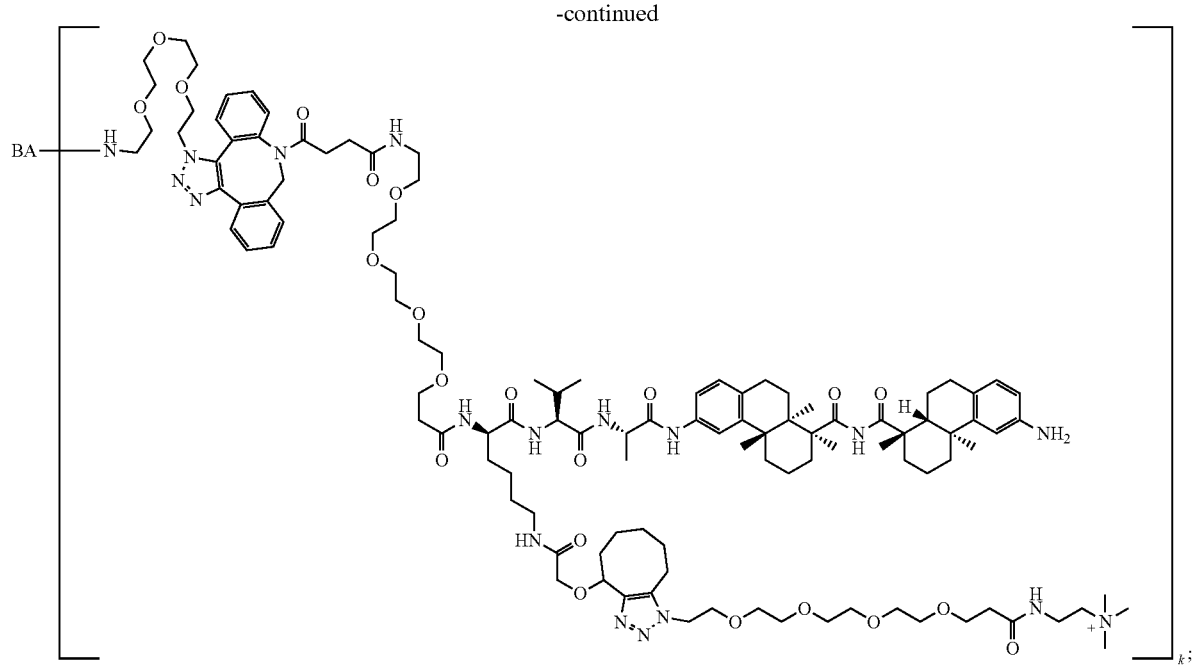

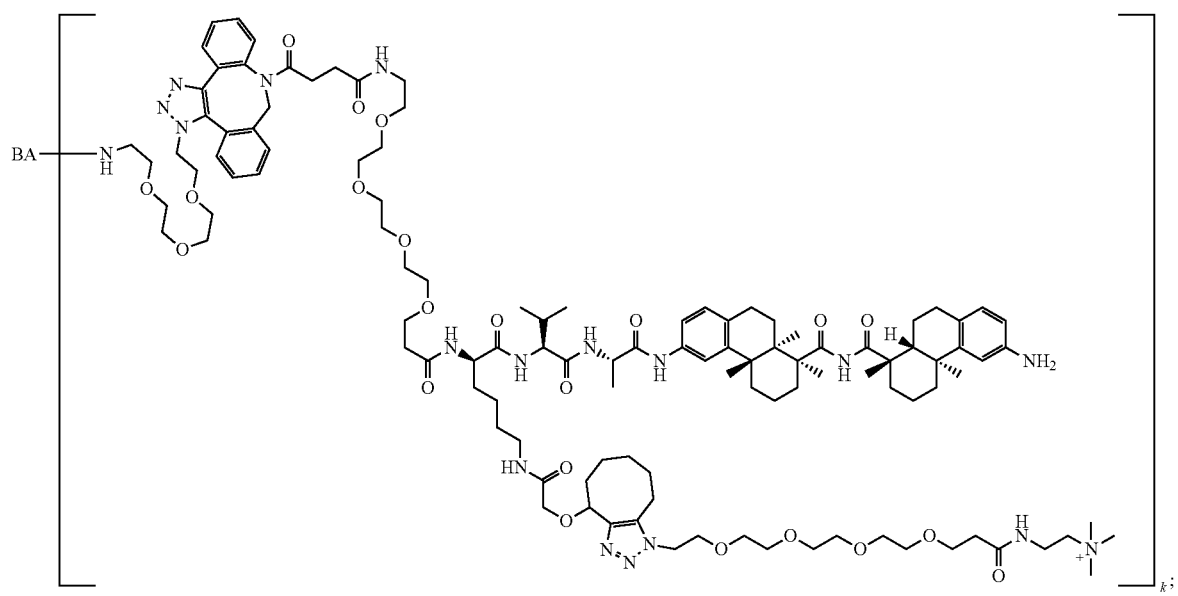

or a regioisomer, or stereoisomeric form thereof. In any embodiment in this paragraph, BA is a binding agent. In any embodiment in this paragraph, BA is antibody, or antigen binding fragment thereof. In any of the embodiments in this paragraph, k is an integer from 1 to 30. In any of the embodiments in this paragraph, k is 1, 2, 3, 4, 5, 6, 7, 8, 9, or 10. In any of the embodiments in this paragraph, k is a range from 1-2, 1-3, 2-3, 2-4, 3-4, or 1-4. In any of the embodiments in this paragraph, k is 1. In any of the embodiments in this paragraph, k is 2. In any of the embodiments in this paragraph, k is 3. In any of the embodiments in this paragraph, k is 4.

Further provided herein are ADCs selected from the group consisting of:

209 210
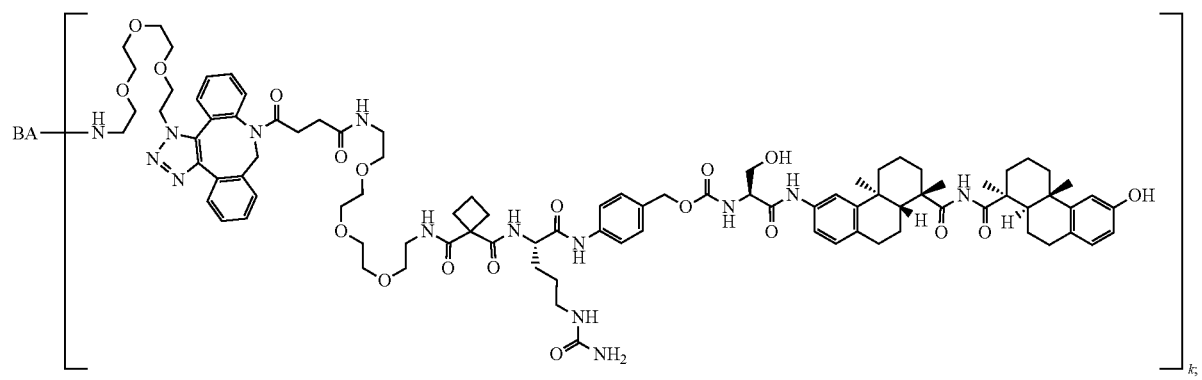
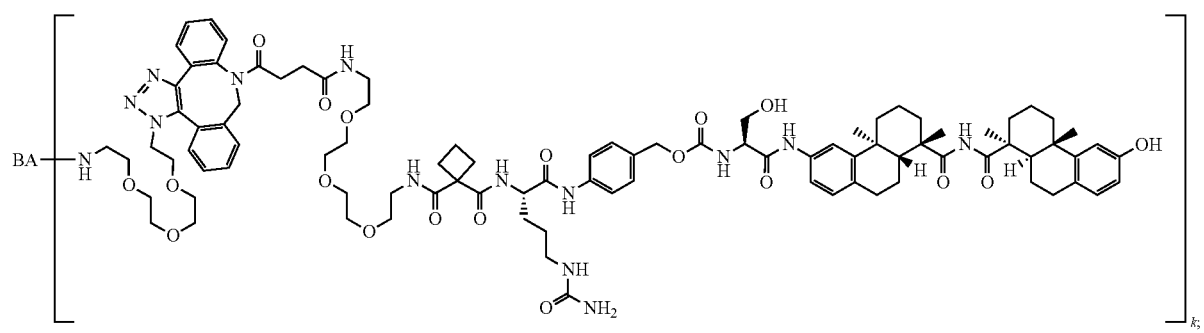
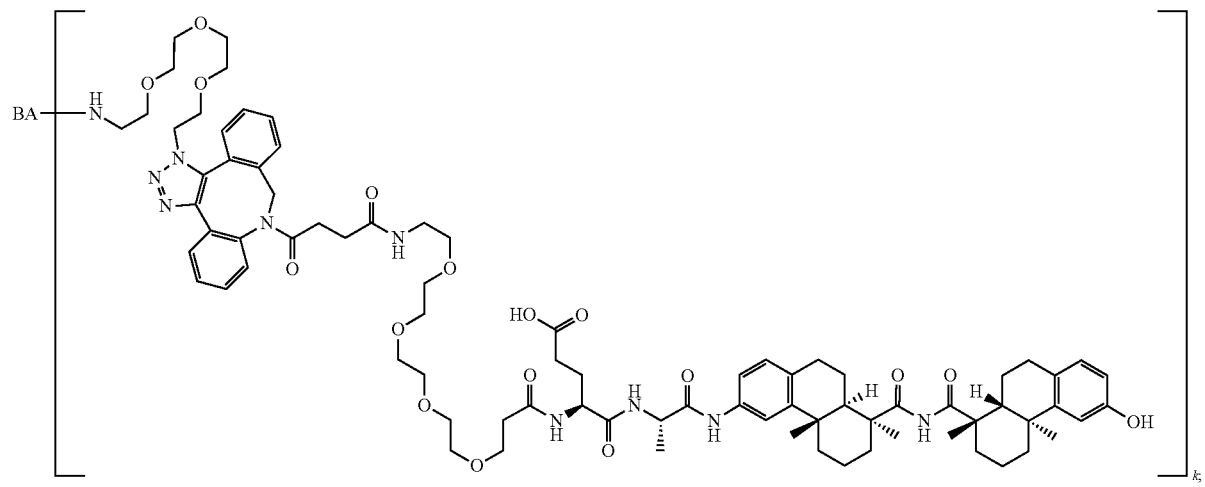
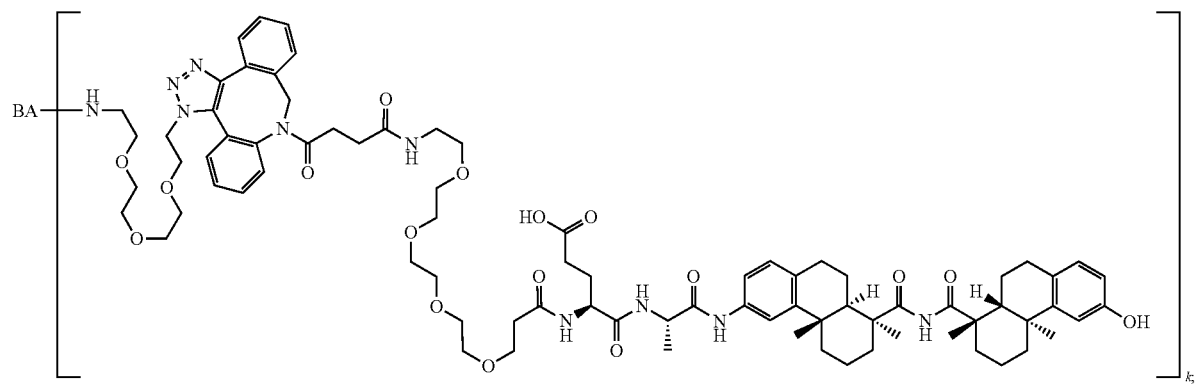

211 212
-continued
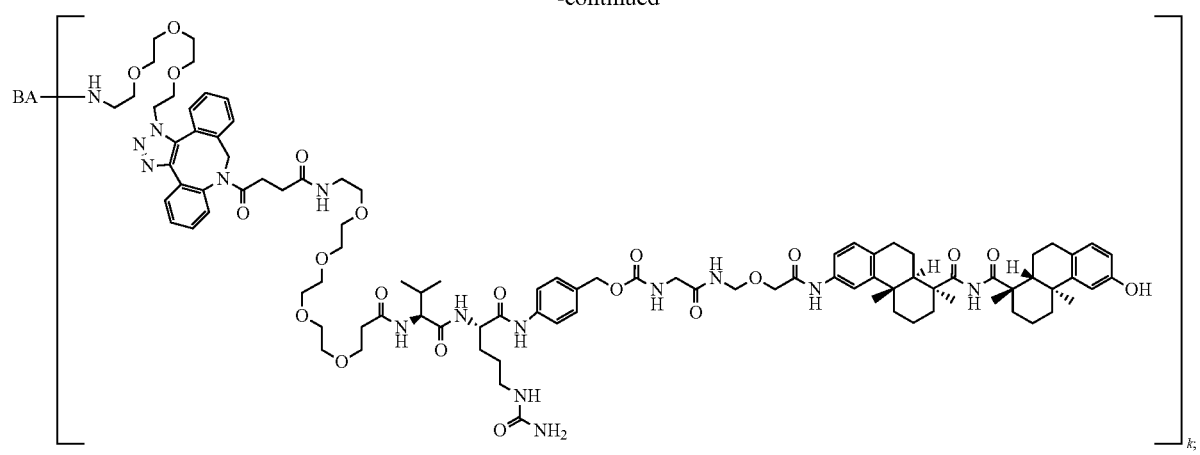
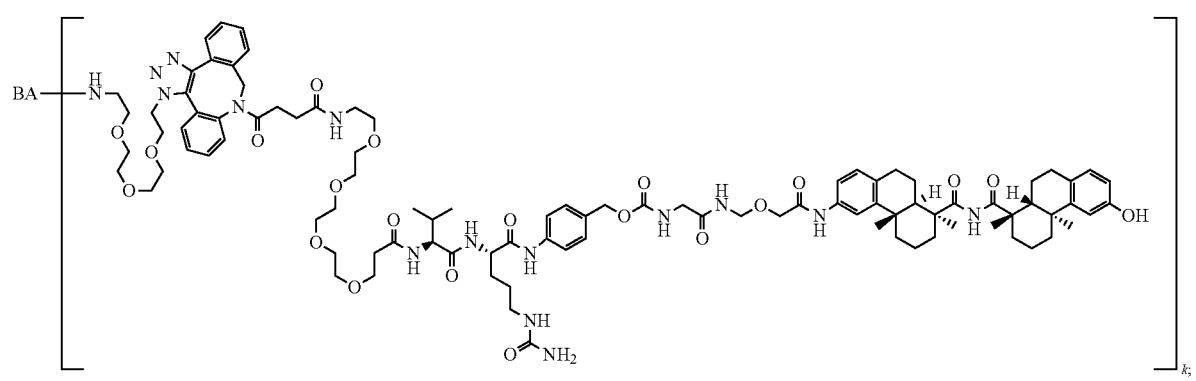
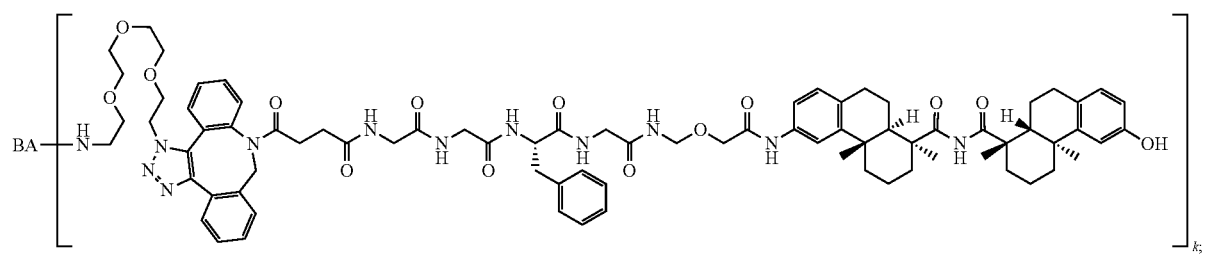
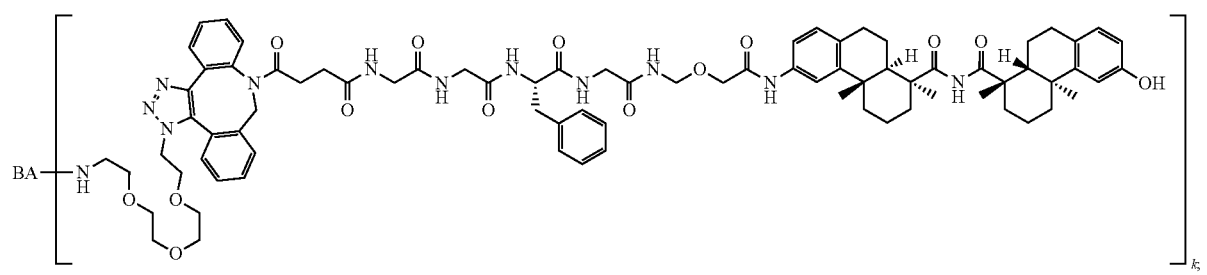

-continued

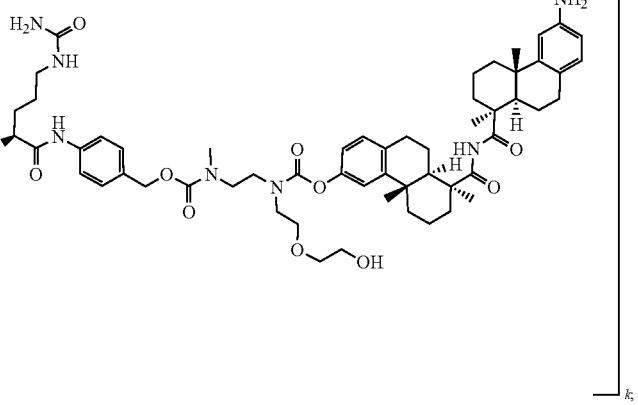
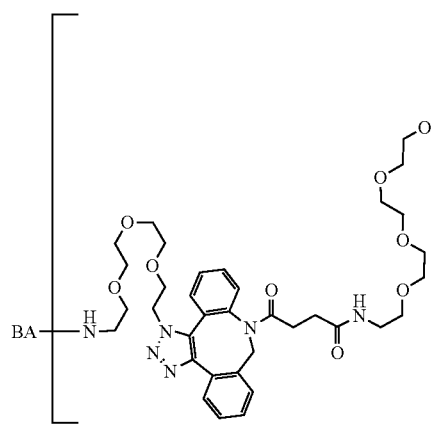

and

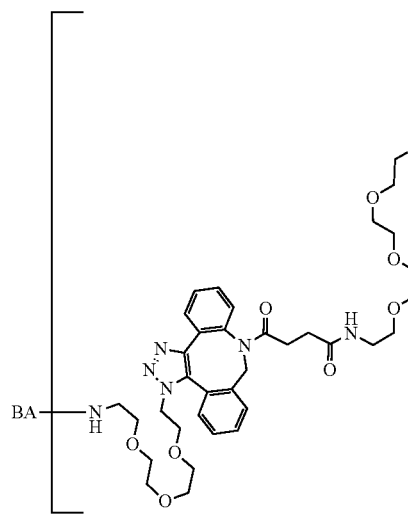

In any of the compound or conjugate embodiments provided, BA is an antibody, or antigen binding fragment thereof, that binds HER2. In any of the compound or conjugate embodiments provided, BA is an antibody, or antigen binding fragment thereof, that binds PRLR. In any of the compound or conjugate embodiments provided, BA is an antibody or antigen-binding fragment thereof, and conjugation is through at least one Q295 residue. In any of the compound or conjugate embodiments provided, BA is an antibody or antigen-binding fragment thereof, and conjugation is through two Q295 residues. In any of the compound or conjugate embodiments provided, BA is a N297Q antibody or antigen-binding fragment thereof. In any of the compound or conjugate embodiments provided, BA is a N297Q antibody or antigen-binding fragment thereof, and conjugation is through at least one Q295 and at least one Q297 residue. In any of the compound or conjugate embodiments provided, BA is a N297Q antibody or antigen-binding fragment thereof, and conjugation is through two Q295 residues and two Q297 residues. In particular embodiments, numbering is according to the EU numbering system.

In any of the embodiments above, BA is an anti-MSR1 antibody. In certain embodiments, BA is the anti-MSR1 antibody H1H21234N described in the Examples below. In certain embodiments, BA is the anti-MSR1 antibody H1H21234N N297Q described in the Examples below. In certain embodiments, BA is an anti-MSR1 antibody comprising an HCVR according to SEQ ID NO:2 and an LCVR according to SEQ ID NO:10. In certain embodiments, BA is an anti-MSR1 antibody comprising one, two, three, four, five, or six of HCDR1, HCDR2, HCDR3, LCDR1, LCDR2, and LCDR3 according to SEQ ID NOS:4, 6, 8, 12, 14, and 16, respectively. In certain embodiments, the HCVR is encoded by SEQ ID NO:1. In certain embodiments, the LCVR is encoded by SEQ ID NO:9. In certain embodiments, one, two, three, four, five, or six of HCDR1, HCDR2, HCDR3, LCDR1, LCDR2, and LCDR3 are encoded by the polynucleotide sequences SEQ ID NOS: 3, 5, 7, 11, 13, and 15, respectively. N297Q indicates that one or more residues 297 are mutated from asparagine (N) to glutamine (Q). Preferably, each residue 297 is mutated to Q. In preferred embodiments, numbering is according to the EU numbering system. In certain embodiments of this paragraph, k is from 1 to 4. In certain embodiments, k is 1, 2, 3, or 4. In certain embodiments, k is 4. In certain embodiments, BA is an anti-MSR1 antibody described in WO 2019/217591, filed May 8, 2019, the content of which are incorporated herein by reference in its entirety.

Methods of Preparing Compounds

The compounds provided herein can be prepared, isolated, or obtained by any method apparent to those of skill in the art. Exemplary methods of preparation are described Scheme A. Exemplary Preparation Scheme

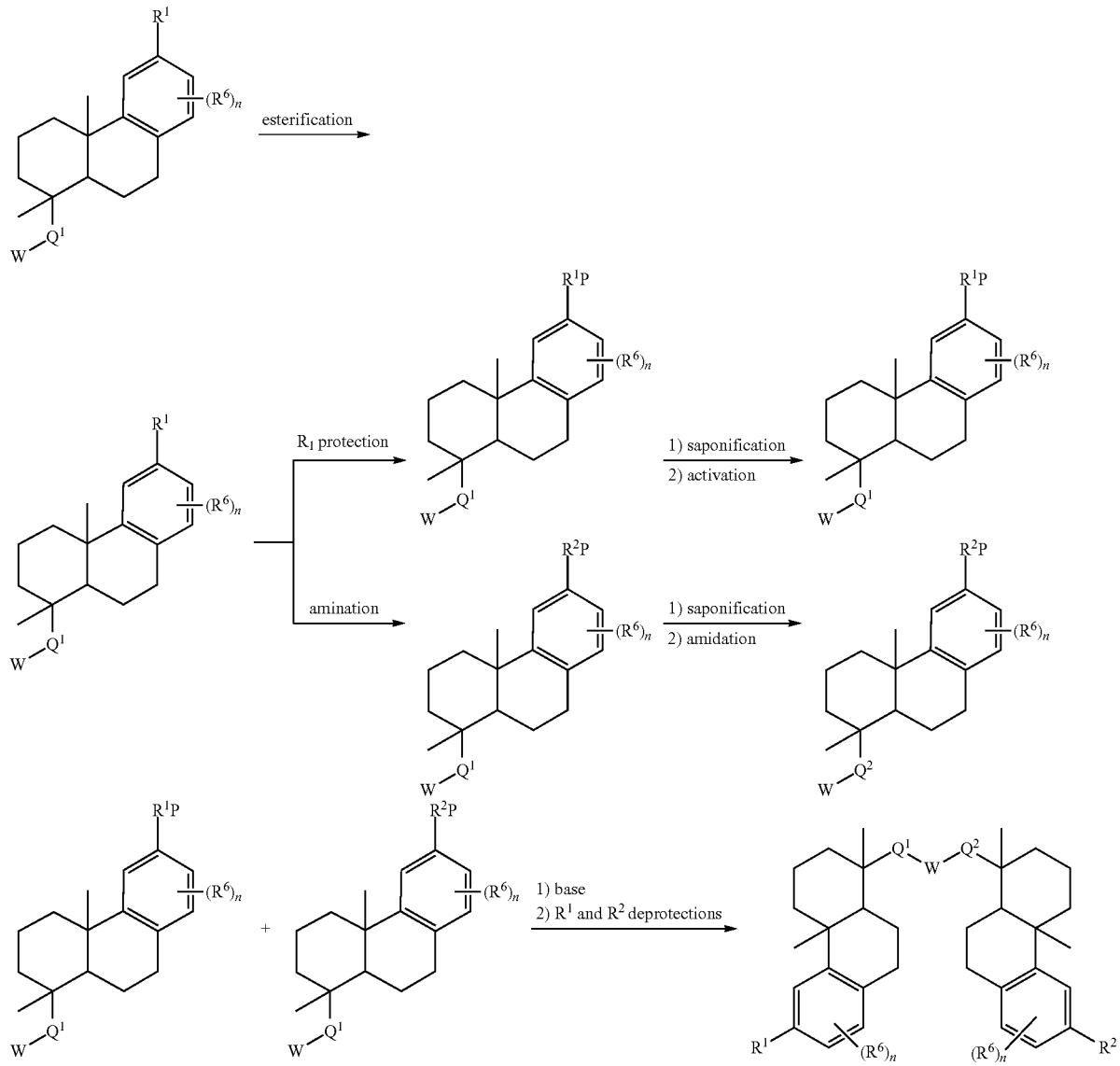

Formula I

In the Exemplary Preparation Scheme A, $Q^1$, $Q^2$, W, $R^1$, $R^2$, $R^6$, and n are defined as described in the context of Formula (I). Initial esterification is followed by either protection of $R^1$ and/or amination of $R^1$ to beget $R^2P$. Following protection of $R^1$, a saponification and activation of, for example, a carboxylic acid moiety provides a first coupling partner having $Q^1$. Following amination, saponification, and amidation of, for example, a carboxylic acid moiety, provides a second coupling partner having $Q^2$. Unification of coupling partners having $Q^1$ and $Q^2$, respectively, followed by deprotections of $R^1$ and $R^2$, respectively, provides compounds of Formula I. Exemplary methods of preparation are described in detail in the Examples below.

In certain embodiments, one or more protection or deprotection steps may be included in the methods of preparation described in Scheme A, above.

The linker-payloads described herein can be synthesized by a series of coupling steps. For instance, the payload at the right side can be linked to $SP^2$ via one or more standard coupling reactions. In advantageous embodiments, the payload compounds described herein include free amino groups available for coupling by amide synthesis conditions, described herein. The amino acids of $(AA)_{p1}$ can be added by amide synthesis conditions, for instance, peptide synthesis conditions. The spacer $SP^2$ can be linked to $(AA)_{p1}$ via one or more standard coupling reactions. In advantageous embodiments, the $SP^2$ and $(AA)_{p1}$ groups described herein include free amino or carboxyl groups available for coupling by amide synthesis conditions, described herein. When present, the spacer $SP^3$ can be linked to $(AA)_{p1}$ via one or more standard coupling reactions. In advantageous embodiments, the SP³ and (AA)$_{p1}$ groups described herein include free amino or carboxyl groups available for coupling by amide synthesis conditions, described herein.

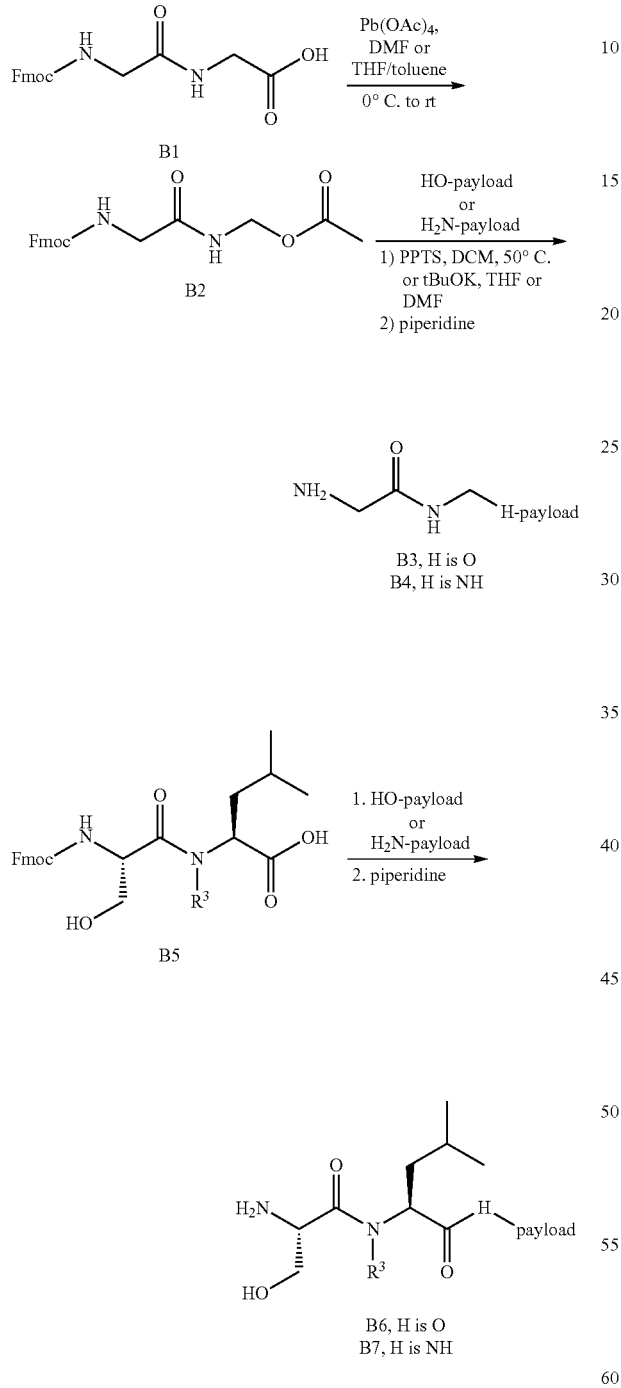

In Exemplary Preparation Scheme B1, B1 is oxidatively decarboxylated to provide B2, and then B2 is substituted with payloads (HO-payload or H₂N-payload) to give B3 or B4. Alternatively, B5 is esterified or peptide coupled with payloads (HO-payload or H₂N-payload, respectively) to give B6 or B7.

Scheme B2. Exemplary Preparation Scheme

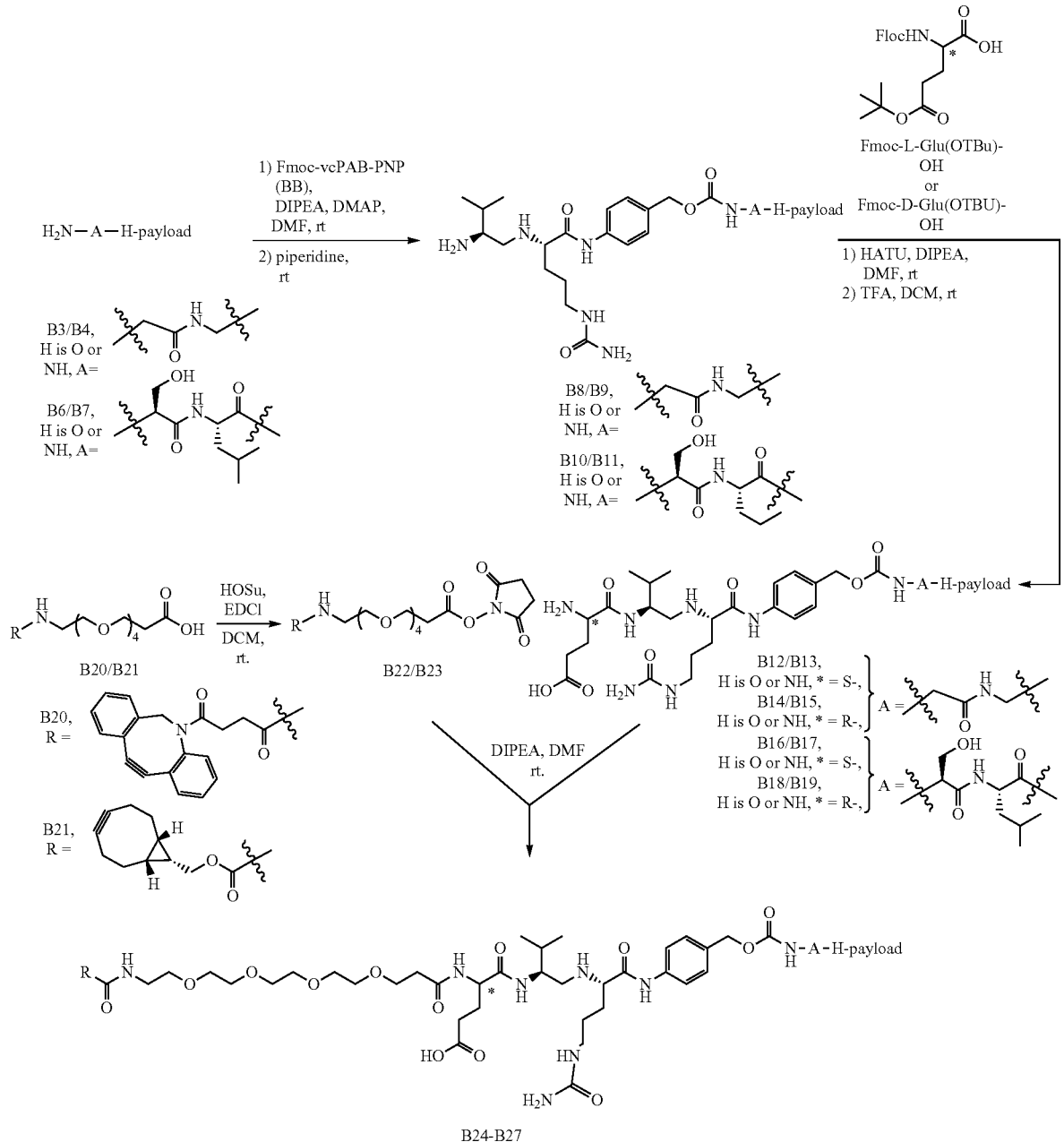

In Exemplary Preparation Scheme B2, B3, B4, B6, or B7 is peptide coupled with BB, and then deprotected to give B8, B9, B10, or B11. B8-B11 are independently peptide coupled with either antipode of protected glutamic acid to give B12-B19. B20 or B21 carboxylates are activated to provide B22 or B23, which are then independently coupled to one of B12-B19 to provide B24-B27.

The spacer $SP^3$, when present, terminates with a reactive group RG. This reactive group can be linked to the enhancement agent EG via coupling conditions deemed suitable to those of skill in the art. In certain embodiments, spacer $SP^3$ is linked to enhancement agent EG via amide synthesis conditions. In certain embodiments, spacer $SP^3$ is linked to enhancement agent EG via click chemistry. In these embodiments, spacer $SP^3$ terminates with a reactive group suitable for a click reaction, for instance, an azide or an alkyne, and enhancement agent EG comprises a complementary reactive group suitable for a click reaction, for instance an alkyne or an azide. In preferred embodiments, $SP^3$ terminates with a strained alkyne and EG comprises an azide; or $SP^3$ terminates with an carboxylic acid and EG comprises an amine. When EG is a cyclodextrin moiety, the cyclodextrin can comprise an azide. Azido cyclodextrins can be prepared synthetically or obtained from commercial sources. When EG is a sulfonic acid moiety, one end(s) of the EG terminate with a sulfonic acid group(s), and the other end terminates with a primary or secondary amine.

The conjugates described herein can be synthesized by coupling the linker-payloads described herein with a binding agent, for example, an antibody under standard conjugation conditions (see, e.g., Doronina et al. *Nature Biotechnology* 2003, 21, 7, 778, which is incorporated herein by reference in its entirety). When the binding agent is an antibody, the antibody may be coupled to a linker-payload via one or more cysteine or lysine residues of the antibody. Linker-payloads can be coupled to cysteine residues, for example, by subjecting the antibody to a reducing agent, for example, dithiotheritol, to cleave the disulfide bonds of the antibody, purifying the reduced antibody, for example, by gel filtration, and subsequently treating the antibody with a linker-payload containing a suitable reactive moiety, for example, a maleimido group. Suitable solvents include, but are not limited to water, DMA, DMF, and DMSO. Linker-payloads containing a reactive group, for example, an activated ester or acid halide group, can be coupled to lysine residues of the antibody. Suitable solvents include, but are not limited to water, DMA, DMF, and DMSO. Conjugates can be purified using known protein techniques, including, for example, size exclusion chromatography, dialysis, and ultrafiltration/diafiltration.

Binding agents, for example antibodies, can also be conjugated via click chemistry reactions. In some embodiments of said click chemistry reactions, the linker-payload includes a reactive group, for example an alkyne, that is capable of undergoing a 1,3-cycloaddition reaction with an azide. Such suitable reactive groups are described above. The antibody includes one or more azide groups. Such antibodies include antibodies functionalized with, for example, azido-polyethylene glycol groups. In certain embodiments, such functionalized antibody is derived by treating an antibody having at least one glutamine residue, for example, heavy chain Gln295 or Gln55, with a primary amine compound in the presence of the enzyme transglutaminase. In certain embodiments, such functionalized antibody is derived by treating an antibody having at least one glutamine residue, for example, heavy chain Gln297, with a primary amine compound in the presence of the enzyme transglutaminase. Such antibodies include Asn297Gln (N297Q) mutants. In certain embodiments, such functionalized antibody is derived by treating an antibody having at least two glutamine residues, for example, heavy chain Gln295 and heavy chain Gln297, with a primary amine compound in the presence of the enzyme transglutaminase. Such antibodies include Asn297Gln (N297Q) mutants. In certain embodiments, the antibody has two heavy chains as described in this paragraph for a total of two or a total of four glutamine residues.

In certain embodiments, the antibody comprises two glutamine residues, one in each heavy chain. In particular embodiments, the antibody comprises a Q295 residue in each heavy chain. In further embodiments, the antibody comprises one, two, three, four, five, six, seven, eight, or more glutamine residues. These glutamine residues can be in heavy chains, light chains, or in both heavy chains and light chains. Exemplary glutamine residues include Q55. These glutamine residues can be wild-type residues, or engineered residues. The antibodies can be prepared according to standard techniques.

Those of skill will recognize that antibodies are often glycosylated at residue N297, near residue Q295 in a heavy chain sequence. Glycosylation at residue N297 can interfere with a transglutaminase at residue Q295 (Dennler et al., supra). Accordingly, in advantageous embodiments, the antibody is not glycosylated. In certain embodiments, the antibody is deglycoslated or aglycosylated. In particular embodiments, an antibody heavy chain has an N297 mutation. Alternatively stated, the antibody is mutated to no longer have an asparagine residue at position 297. In particular embodiments, an antibody heavy chain has an N297Q mutation. Such an antibody can be prepared by site-directed mutagenesis to remove or disable a glycosylation sequence or by site-directed mutagenesis to insert a glutamine residue at a site without resulting in disabled antibody function or binding. In some embodiments, an antibody having a Q295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the antibody conjugated via transglutaminase can have a higher than expected drug:antibody ratio (DAR) value (e.g., a DAR higher than 4). Any such antibodies can be isolated from natural or artificial sources.

The antibody without interfering glycosylation is then reacted with a primary amine compound. In certain embodiments, an aglycosylated antibody is reacted with a primary amine compound to produce a glutaminyl-modified antibody. In certain embodiments, a deglycosylated antibody is reacted with a primary amine compound to produce a glutaminyl-modified antibody.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plickthun, *J. Mol. Biol.*, 2001, 309:657-70 ("AHo" numbering scheme). Unless otherwise specified, the numbering scheme used herein is the Kabat numbering scheme. However, selection of a numbering scheme is not intended to imply differences in sequences where they do not exist, and one of skill in the art can readily confirm a sequence position by examining the amino acid sequence of one or more antibodies. Unless stated otherwise, the "EU numbering scheme" is generally used when referring to a residue in an antibody heavy chain constant region (e.g., as reported in Kabat et al., supra).

The term "aglycosylated antibody" refers to an antibody that does not comprise a glycosylation sequence that might interfere with a transglutamination reaction, for instance an antibody that does not have saccharide group at N297 on one or more heavy chains. In particular embodiments, an antibody heavy chain has an N297 mutation. In other words, the antibody is mutated to no longer have an asparagine residue at position 297 according to the EU numbering system as disclosed by Kabat et al. In particular embodiments, an antibody heavy chain has an N297Q or an N297D mutation. Such an antibody can be prepared by site-directed mutagenesis to remove or disable a glycosylation sequence or by site-directed mutagenesis to insert a glutamine residue at site apart from any interfering glycosylation site or any other interfering structure. Such an antibody also can be isolated from natural or artificial sources.

The term "deglyosylated antibody" refers to an antibody in which a saccharide group at N297 was removed, thereby opening Q295 to transglutamination. In particular embodiments, provided herein are processes that encompass an additional step of deglycosylating an antibody, for instance an N297 antibody.

The primary amine can be any primary amine that is capable of forming a covalent bond with a glutamine residue in the presence of a transglutaminase. Useful primary amines are described above. The transglutaminase can be any transglutaminase deemed suitable by those of skill in the art. In certain embodiments, the transglutaminase is an enzyme that catalyzes the formation of an isopeptide bond between a free amine group on the primary amine compound and the acyl group on the side chain of a glutamine residue. Transglutaminase is also known as protein-glutamine-γ-glutamyltransferase. In particular embodiments, the transglutaminase is classified as EC 2.3.2.13. The transglutaminase can be from any source deemed suitable. In certain embodiments, the transglutaminase is microbial. Useful transglutaminases have been isolated from *Streptomyces mobaraense, Streptomyces cinnamoneum, Streptomyces griseo-carneum, Streptomyces lavendulae*, and *Bacillus subtilis*. Non-microbial transglutaminases, including mammalian transglutaminases, can also be used. In certain embodiments, the transglutaminase can be produced by any technique or obtained from any source deemed suitable by the practitioner of skill. In particular embodiments, the transglutaminase is obtained from a commercial source.

In particular embodiments, the primary amine compound comprises a reactive group capable of further reaction after transglutamination. In these embodiments, the glutaminyl-modified antibody can be reacted or treated with a reactive payload compound, linker-payload, or a reactive linker-payload compound to form an antibody-payload conjugate. In certain embodiments, the primary amine compound comprises an azide.

In certain embodiments, the glutaminyl-modified antibody is reacted or treated with a linker-payload or reactive linker-payload to form an antibody-payload conjugate. The reaction can proceed under conditions deemed suitable by those of skill in the art. In certain embodiments, the glutaminyl-modified antibody is contacted with the linker-payload or reactive linker-payload compound under conditions suitable for forming a bond between the glutaminyl-modified antibody and the linker-payload compound. Suitable reaction conditions are well known to those in the art.

Exemplary reactions are provided in the Examples below.

Pharmaceutical Compositions and Methods of Treatment

Provided herein are methods of treating and preventing diseases, conditions, or disorders comprising administering a therapeutically or prophylactically effective amount or one or more of the compounds or payloads disclosed herein, for example, one or more of the compounds of a formula provided herein. Diseases, disorders, and/or conditions include, but are not limited to, those associated with the antigens listed herein.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second glucocorticoid, an autoimmune therapeutic agent, a hormone, a biologic, or a monoclonal antibody. Suitable therapeutic agents also include, but are not limited to any pharmaceutically acceptable salts, acids, or derivatives of a compound set forth herein.

In some embodiments of the methods described herein, multiple doses of a compound described herein (or a pharmaceutical composition comprising a combination of an compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks, or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all include the same amount the compound described herein, but generally can differ from one another in terms of frequency of administration. In certain embodiments, the amount of the compound included in the initial, secondary, and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds, payloads, linker-payloads, and/or conjugates described herein, e.g., the compounds of Formula I, II, and/or III, e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to, buffers for maintenance of proper composition pH (e.g., citrate buffers, succinate buffers, acetate buffers, phosphate buffers, lactate buffers, oxalate buffers, and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

In some examples, set forth herein is a method of treating a disease, disorder or condition comprising administering to a patient having said disorder a therapeutically effective amount of a compound of Formula I, II, and/or III or a pharmaceutical composition thereof.

In some examples, set forth herein is a method of preventing a disease, disorder or condition comprising administering to a patient having said disorder a prophylactically effective amount of a compound of Formula I, II, and/or III or a pharmaceutical composition thereof.

In some examples, set forth herein are methods for treating or preventing any disease, disorder, or condition responsive to modulation of LXR signaling. In some examples, the disease or disorder is associated with LXR function, LXR polymorphisms, LXR agonist activity, or LXR antagonist activity. In some examples, set forth herein is a method of treating or preventing a disease, disorder, or condition selected from the group consisting of a proliferative disorder, a neurodegenerative disorder, an immunological disorder, an autoimmune disease, an inflammatory disorder, a dermatological disease, a metabolic disease, cardiovascular disease, and a gastrointestinal disease.

The proliferative disorder can be any proliferative disorder known to those of skill. In certain embodiments, proliferative disorders include, without limitation, oncology disorders, where the oncology disorder can be any cancer disorder known to those of skill. In certain embodiments, provided herein are methods of treating or preventing a melanoma. In certain embodiments, provided herein are methods of treating or preventing metastatic melanoma. In certain embodiments, provided herein are methods of treating or preventing lung cancer. In certain embodiments, provided herein are methods of treating or preventing EGFR-tyrosine kinase inhibitor resistant lung cancer. In certain embodiments, provided herein are methods of treating or preventing oral cancer. In certain embodiments, provided herein are methods of treating or preventing oral squamous cell carcinoma. In certain embodiments, provided herein are methods of treating or preventing prostate cancer. In certain embodiments, provided herein are methods of treating or preventing Hodgkin's lymphoma. In certain embodiments, provided herein are methods of treating or preventing breast cancer.

The neurodegenerative disorder can be any neurodegenerative disorder known to those of skill. In certain embodiments, provided herein are methods of treating or preventing Alzheimer's disease. In certain embodiments, provided herein are methods of treating or preventing Parkinson's disease. In certain embodiments, provided herein are methods of treating or preventing Huntington's disease. In certain embodiments, provided herein are methods of treating or preventing amyotrophic lateral sclerosis. In certain embodiments, provided herein are methods of treating or preventing myelin gene expression. In certain embodiments, provided herein are methods of treating or preventing myelination and remyelination conditions, diseases, or disorders.

The immunological disorder can be any immunological disorder known to those of skill. In certain embodiments, provided herein are methods of treating or preventing imflammatory bowel disease. In certain embodiments, provided herein are methods of treating or preventing ulcerative colitis. In certain embodiments, provided herein are methods of treating or preventing Crohn's disease.

The inflammatory disorder can be any inflammatory disorder known to those of skill. In certain embodiments, provided herein are methods of treating or preventing arthritis. In certain embodiments, provided herein are methods of treating or preventing rheumatoid arthritis.

The metabolic disease can be any metabolic disease known to those of skill. In certain embodiments, the metabolic disease is dyslipidemia. Dyslipidemia can be any dyslipidemia known to those of skill. In certain embodiments, dyslipidemia is selected from the group consisting of hyperlipidemia, hypercholesterolemia, hypertriglyceridemia, hyperlipoproteinemia, HDL deficiency, ApoA-I deficiency, and cardiovascular disease such as coronary artery disease (including, for example, treatment and prevention of angina, myocardial infarction, and sudden cardiac death); atherosclerosis (including, for example, treatment and prevention of atherosclerosis); and restenosis (including, for example, preventing or treating atherosclerotic plaques which develop as a consequence of medical procedures such as balloon angioplasty). In certain embodiments, provided herein are methods of treating or preventing diabetes.

The cardiovascular disease can be any cardiovascular disease known to those of skill. In certain embodiments, provided herein are methods of treating or preventing atherosclerosis. In certain embodiments, provided herein are methods of treating or preventing atherosclerosis derived from abnormal macrophage processing. In certain embodiments, provided herein are methods of treating or preventing atherosclerosis derived from the formation of oxidized low-density lipoproteins (oxLDLs), where marcrophages fail to process oxLDLs. In certain embodiments, provided herein are methods of treating or preventing ischemic heart disease. In certain embodiments, provided herein are methods of treating or preventing stroke. In certain embodiments, provided herein are methods of treating or preventing hypertensive heart disease. In certain embodiments, provided herein are methods of treating or preventing aortic aneurysm. In certain embodiments, provided herein are methods of treating or preventing endocarditis. In certain embodiments, provided herein are methods of treating or preventing peripheral artery disease. In certain embodiments, provided herein are methods of treating or preventing combinations of any of the diseases provided in this paragraph.

In some examples, set forth herein is a method for modulating the function of a nuclear receptor. By way of non-limiting example, the function may be selected from expression/secretion of inflammatory mediators (e.g. cytokines, chemokines), cholesterol regulation, cholesterol intake, cholesterol efflux, cholesterol oxidation, migration, chemotaxis, apoptosis and necrosis, an inflammatory activity, lipid regulation, apoptosis, migration, chemotaxis, gene transcription, and protein expression.

EXAMPLES

Provided herein are novel bis-octahydrophenanthrene carboxamides, protein conjugates thereof, and methods for treating diseases, disorders, and conditions including administering the bis-octahydrophenanthrene carboxamides and conjugates.

In some examples, the compound of Formula (I) is a compound identified in Table 1.

TABLE 1

| | List of Payloads | | | |
|---|---|---|---|---|
| Cpd code | Structures | MF | FW | Exact Mass |
| P1 | | $C_{34}H_{44}N_2O_3$ | 528.72 | 528.72 |
| P2 | | $C_{34}H_{45}N_3O_2$ | 527.74 | 527.74 |

TABLE 1-continued

List of Payloads

| Cpd code | Structures | MF | FW | Exact Mass |
|---|---|---|---|---|
| P3 | 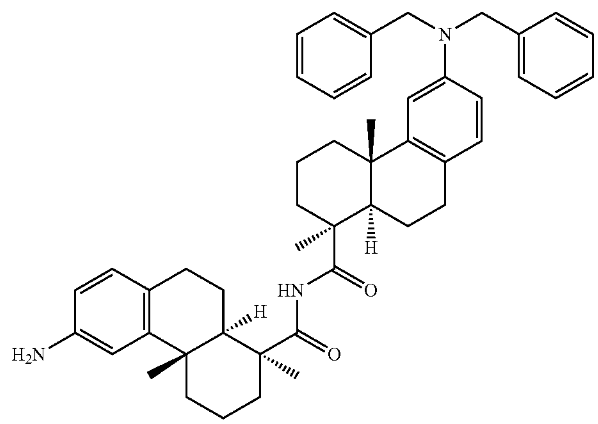 [SMILES: C[C@]1(C(=O)NC(=O)[C@@]2(C)CCC[C@]3(C)c4cc(N(Cc5ccccc5)Cc5ccccc5)ccc4CC[C@@H]23)CCC[C@]2(C)c3cc(N)ccc3CC[C@@H]12] | $C_{48}H_{57}N_3O_2$ | 707.99 | 707.45 |
| P4 | 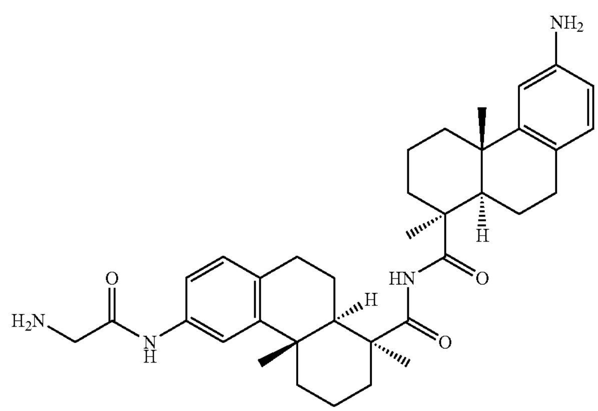 [SMILES: C[C@]1(C(=O)NC(=O)[C@@]2(C)CCC[C@]3(C)c4cc(NC(=O)CN)ccc4CC[C@@H]23)CCC[C@]2(C)c3cc(N)ccc3CC[C@@H]12] | $C_{36}H_{48}N_4O_3$ | 584.79 | 584.37 |
| P5 | 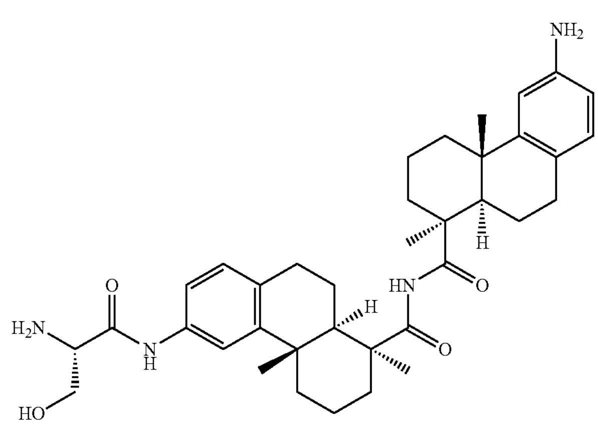 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(N)ccc3CC[C@@H]12] | $C_{37}H_{50}N_4O_4$ | 614.82 | 614.38 |

TABLE 1-continued

List of Payloads

| Cpd code | Structures | MF | FW | Exact Mass |
|---|---|---|---|---|
| P6 | 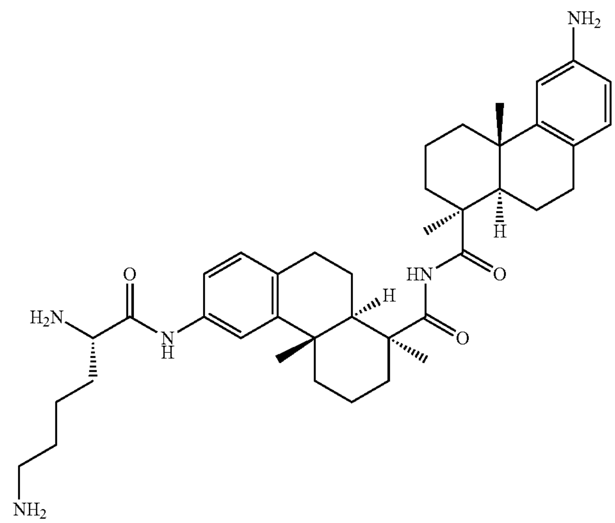 [SMILES: C[C@]1(C(=O)NC(=O)[C@@]2(C)CCC[C@]3(C)c4cc(NC(=O)[C@@H](N)CCCCN)ccc4CC[C@@H]23)CCC[C@]2(C)c3cc(N)ccc3CC[C@@H]12] | $C_{40}H_{57}N_5O_3$ | 655.91 | 655.45 |
| P7 | 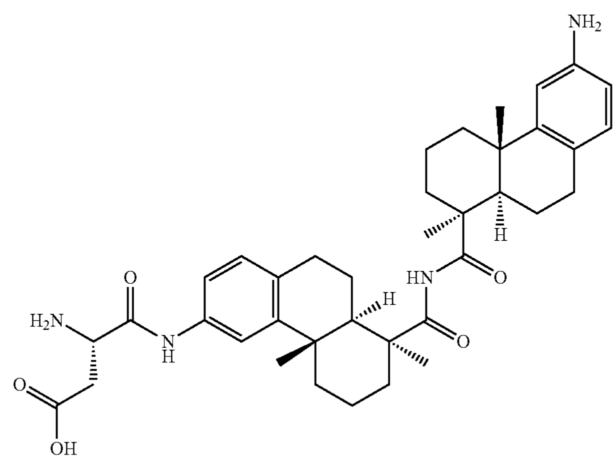 [SMILES: C[C@]1(C(=O)NC(=O)[C@@]2(C)CCC[C@]3(C)c4cc(NC(=O)[C@@H](N)CC(=O)O)ccc4CC[C@@H]23)CCC[C@]2(C)c3cc(N)ccc3CC[C@@H]12] | $C_{38}H_{50}N_4O_5$ | 642.83 | 642.38 |
| P8 | 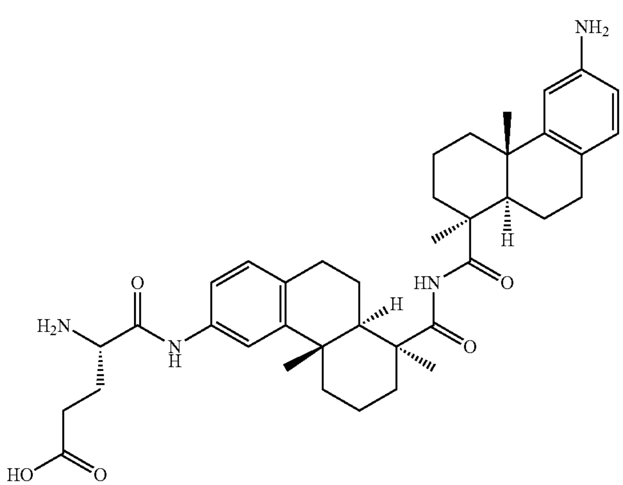 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(N)ccc3CC[C@@H]12] | $C_{39}H_{52}N_4O_5$ | 656.85 | 656.39 |

TABLE 1-continued

List of Payloads

| Cpd code | Structures | MF | FW | Exact Mass |
|---|---|---|---|---|
| P9 | 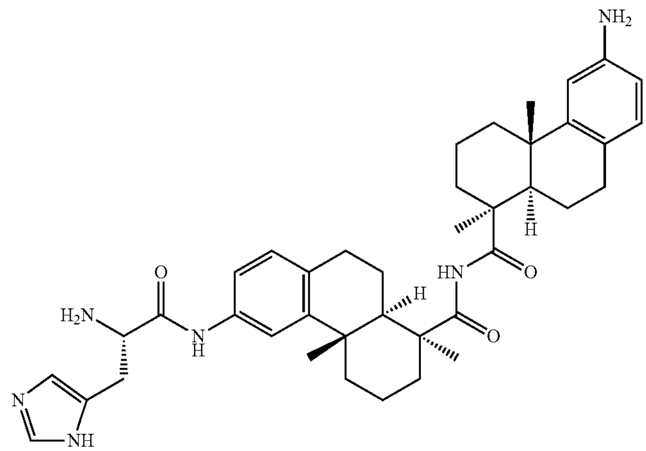 [SMILES: C[C@]1(C(=O)NC(=O)[C@@]2(C)CCC[C@]3(C)c4cc(NC(=O)[C@@H](N)Cc5cnc[nH]5)ccc4CC[C@@H]23)CCC[C@]2(C)c3cc(N)ccc3CC[C@@H]12] | $C_{40}H_{52}N_6O_3$ | 664.88 | 664.41 |
| P10 | 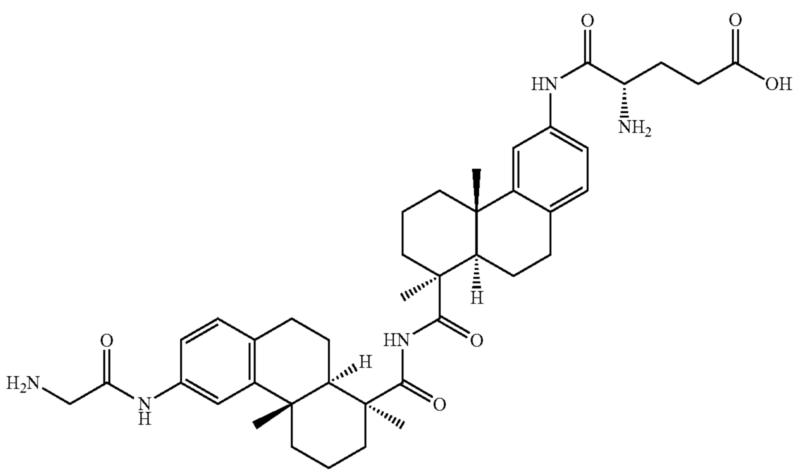 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)CN)ccc3CC[C@@H]12] | $C_{41}H_{55}N_5O_6$ | 713.91 | 713.42 |
| P11 | 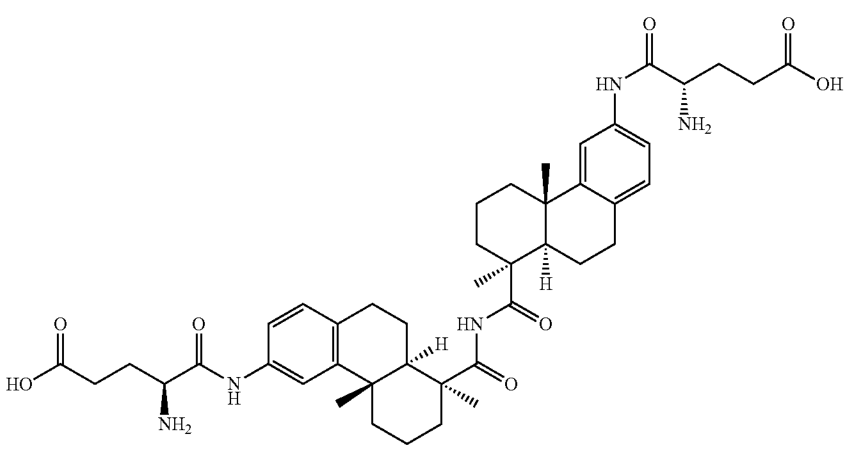 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)[C@@H](N)CCC(=O)O)ccc3CC[C@@H]12] | $C_{44}H_{59}N_5O_8$ | 785.97 | 785.44 |

TABLE 1-continued
List of Payloads
| Cpd code | Structures | MF | FW | Exact Mass |
|---|---|---|---|---|
| P12 | 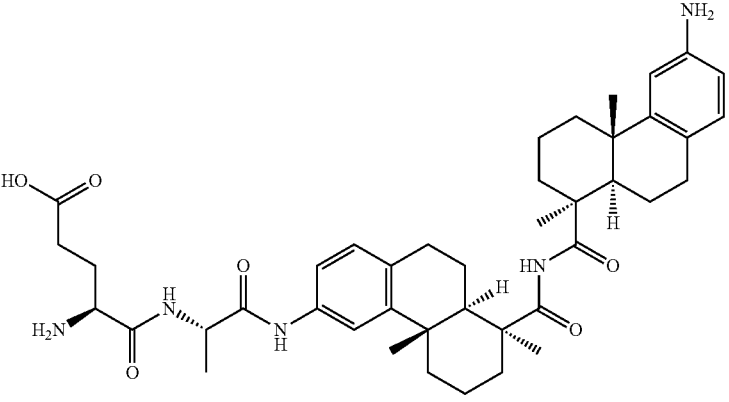 [SMILES: C[C@H](NC(=O)[C@@H](N)CCC(=O)O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] | $C_{42}H_{57}N_5O_6$ | 727.93 | 727.43 |
| P13 | 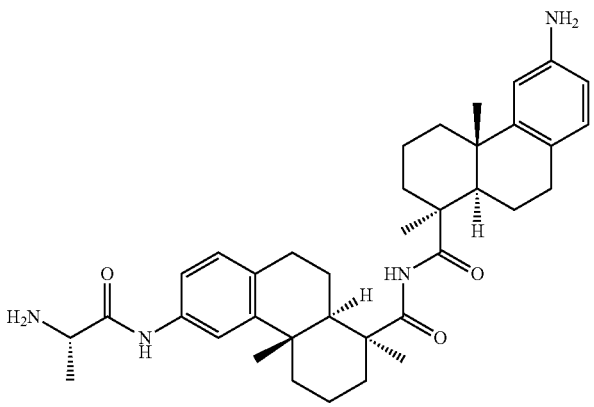 [SMILES: C[C@H](N)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] | $C_{37}H_{50}N_4O_3$ | 598.82 | 398.39 |
| P14 | 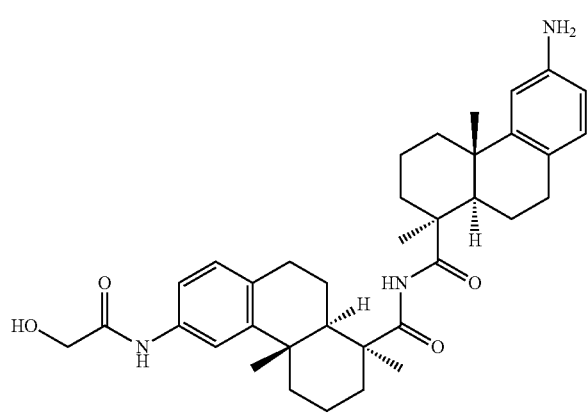 [SMILES: C[C@]1(C(=O)NC(=O)[C@@]2(C)CCC[C@]3(C)c4cc(NC(=O)CO)ccc4CC[C@@H]23)CCC[C@]2(C)c3cc(N)ccc3CC[C@@H]12] | $C_{36}H_{47}N_3O_4$ | 585.78 | 585.36 |

TABLE 1-continued

List of Payloads

| Cpd code | Structures | MF | FW | Exact Mass |
|---|---|---|---|---|
| P15 | 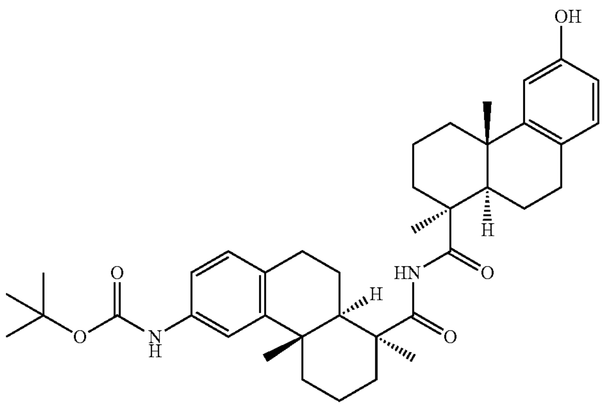 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | $C_{39}H_{52}N_2O_5$ | 628.84 | 628.39 |
| P16 | 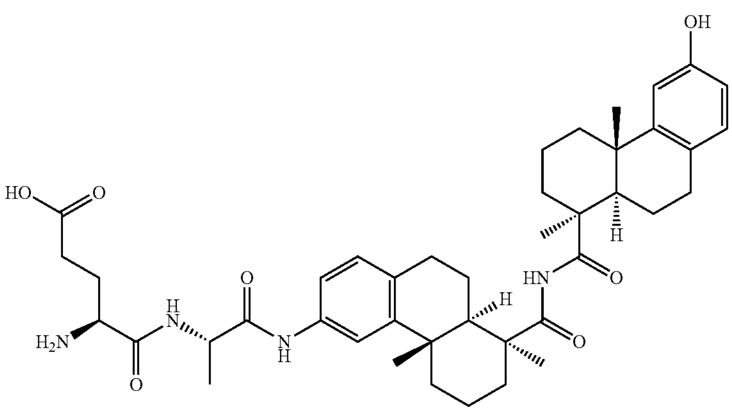 [SMILES: C[C@H](NC(=O)[C@@H](N)CCC(=O)O)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] | $C_{42}H_{56}N_4O_7$ | 728.92 | 728.41 |
| P17 | 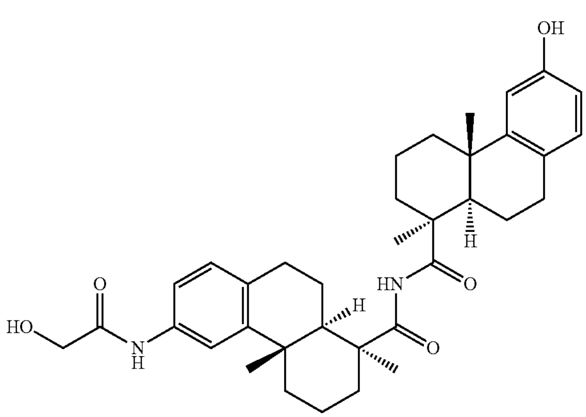 [SMILES: C[C@]1(C(=O)NC(=O)[C@@]2(C)CCC[C@]3(C)c4cc(NC(=O)CO)ccc4CC[C@@H]23)CCC[C@]2(C)c3cc(O)ccc3CC[C@@H]12] | $C_{36}H_{46}N_2O_5$ | 586.77 | 586.34 |

TABLE 1-continued

List of Payloads

| Cpd code | Structures | MF | FW | Exact Mass |
|---|---|---|---|---|
| P18 | 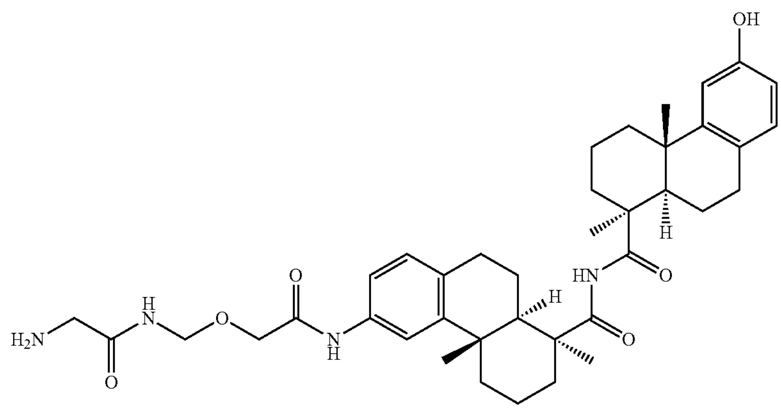 [SMILES: C[C@]1(C(=O)NC(=O)[C@@]2(C)CCC[C@]3(C)c4cc(NC(=O)COCNC(=O)CN)ccc4CC[C@@H]23)CCC[C@]2(C)c3cc(O)ccc3CC[C@@H]12] | $C_{39}H_{52}N_4O_6$ | 672.87 | 672.39 |
| P19 | 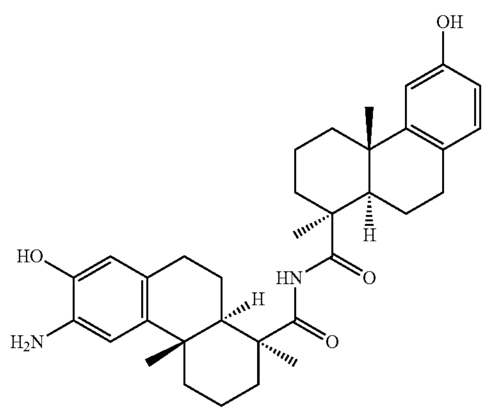 [SMILES: C[C@]1(C(=O)NC(=O)[C@@]2(C)CCC[C@]3(C)c4cc(N)c(O)cc4CC[C@@H]23)CCC[C@]2(C)c3cc(O)ccc3CC[C@@H]12] | $C_{34}H_{44}N_2O_4$ | 544.74 | 544.33 |

Examples of linker-payloads of the instant disclosure include, but are not limited to, those described in Table 2 below.

TABLE 2
List of Linker-payloads
| LP | Linker name | Structures |
|---|---|---|
| LP1 | DIBAC-suc-PEG4-dLys(COT-CD)-VA | 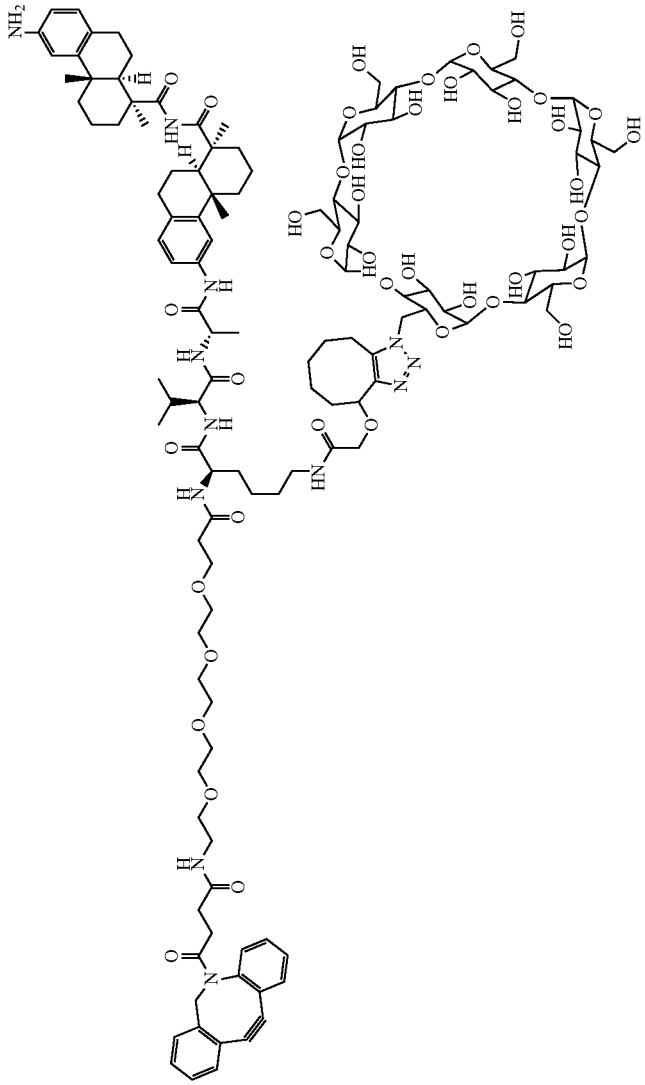 |

TABLE 2-continued
List of Linker-payloads
| LP | Linker name | Structures |
|---|---|---|
| LP2 | DIBAC-suc-PEG4-dLys(COT-CD)-vc | 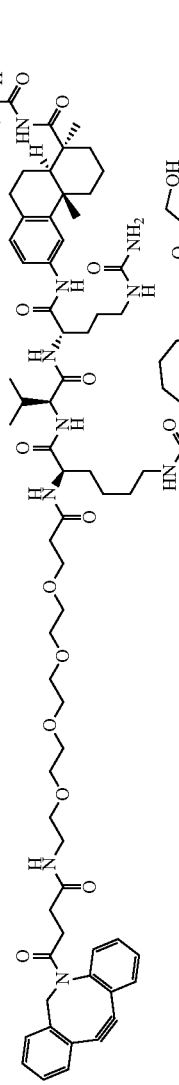 |
| LP3 | DIBAC-suc-PEG4-dLys(COT-PEG4-taurine)-VA | 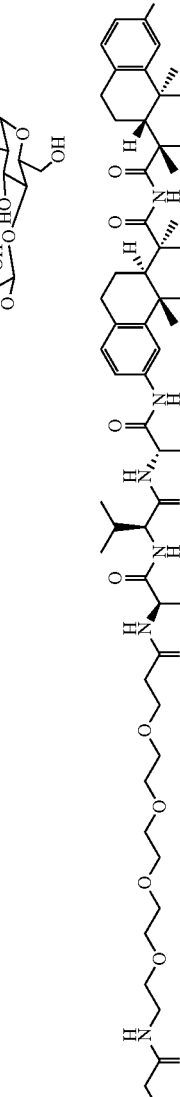 |

TABLE 2-continued

List of Linker-payloads

| LP | Linker name | Structures |
|---|---|---|
| LP4 | DIBAC-suc-PEG4-dLys(COT-PEG4-taurine)-vc | 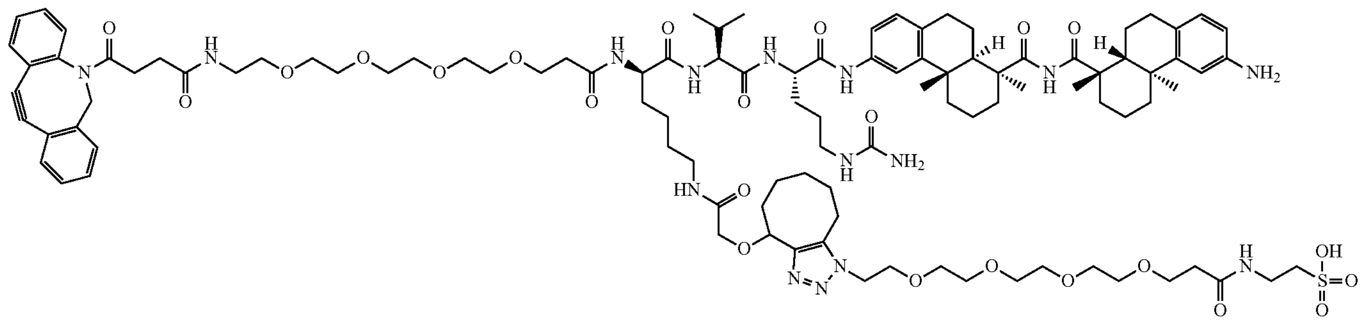 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] |
| LP5 | DIBAC-suc-PEG4-dLys(COT-PEG4-Maltose)-VA | 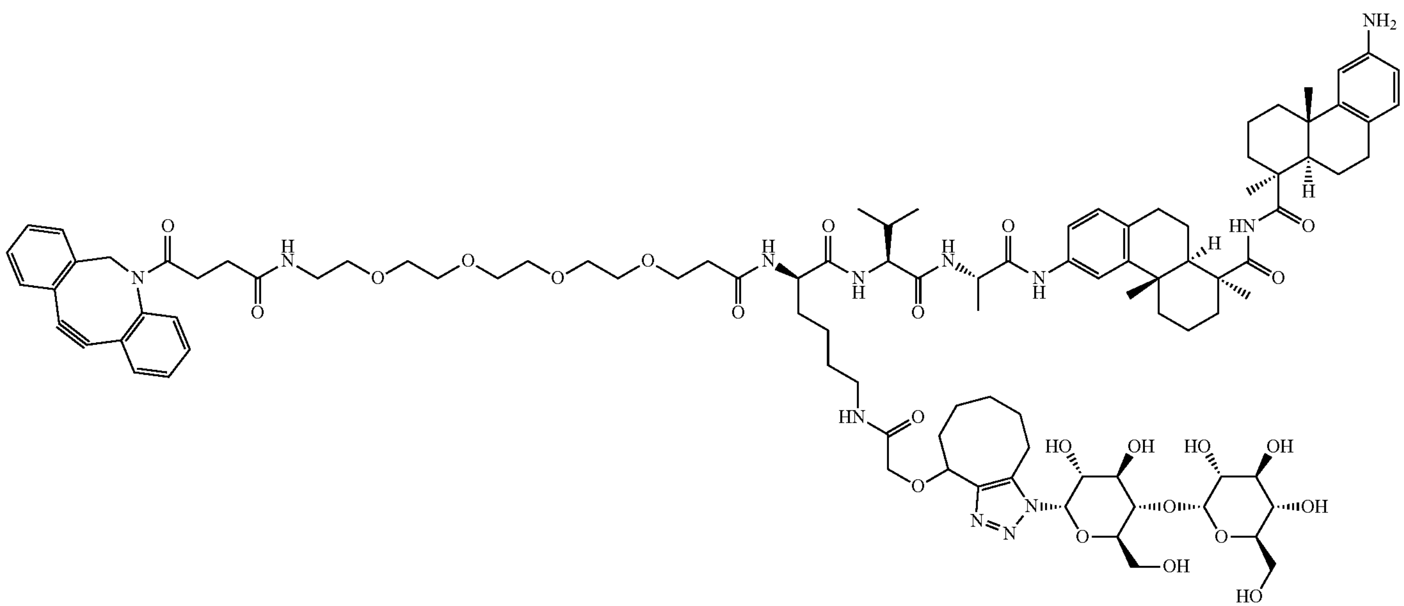 [SMILES: CC(C)[C@H](NC(=O)[C@@H](CCCCNC(=O)COC1CCCCCc2c1nnn2[C@H]1O[C@H](CO)[C@@H](O[C@H]2O[C@H](CO)[C@@H](O)[C@H](O)[C@H]2O)[C@H](O)[C@H]1O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] |

TABLE 2-continued

List of Linker-payloads

| LP | Linker name | Structures |
|---|---|---|
| LP6 | DIBAC-suc-PEG4-VA | 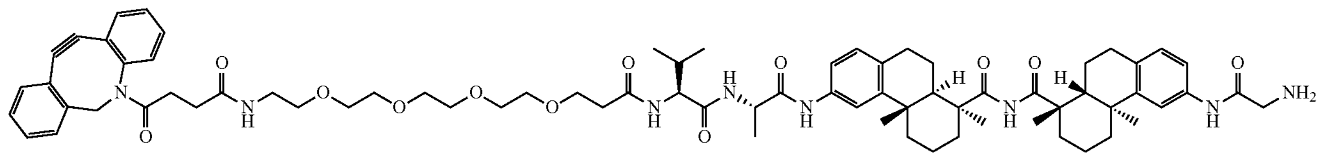 [SMILES: CC(C)[C@H](NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(NC(=O)CN)ccc5CC[C@@H]34)[C@@H]1CC2] |
| LP7 | DIBAC-suc-PEG4-vcPABC | 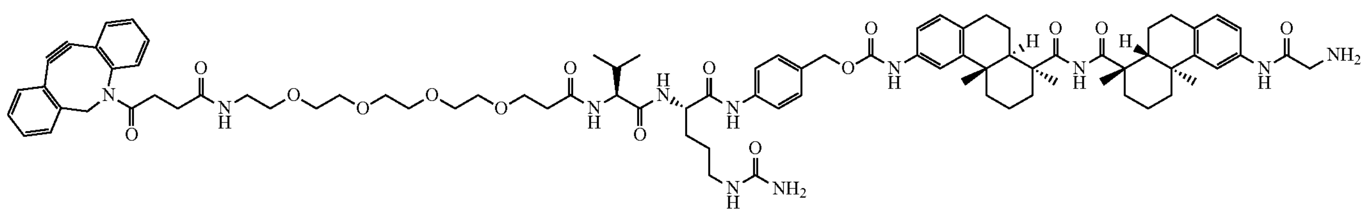 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)Nc2ccc3c(c2)[C@@]2(C)CCC[C@](C)(C(=O)NC(=O)[C@@]4(C)CCC[C@]5(C)c6cc(NC(=O)CN)ccc6CC[C@@H]45)[C@@H]2CC3)cc1] |
| LP8 | DIBAC-suc-PEG4-dLys(COT-CD)-vcPABC | 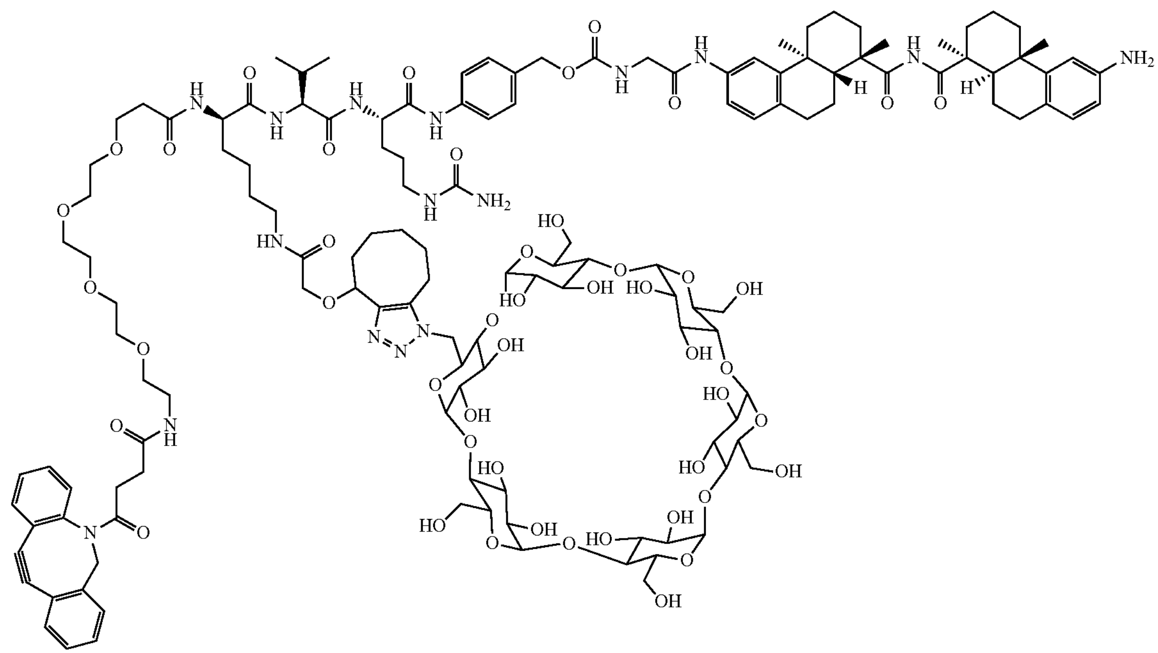 |

TABLE 2-continued

List of Linker-payloads

| LP | Linker name | Structures |
|---|---|---|
| LP9 | DIBAC-suc-PEG4-vcPABC | 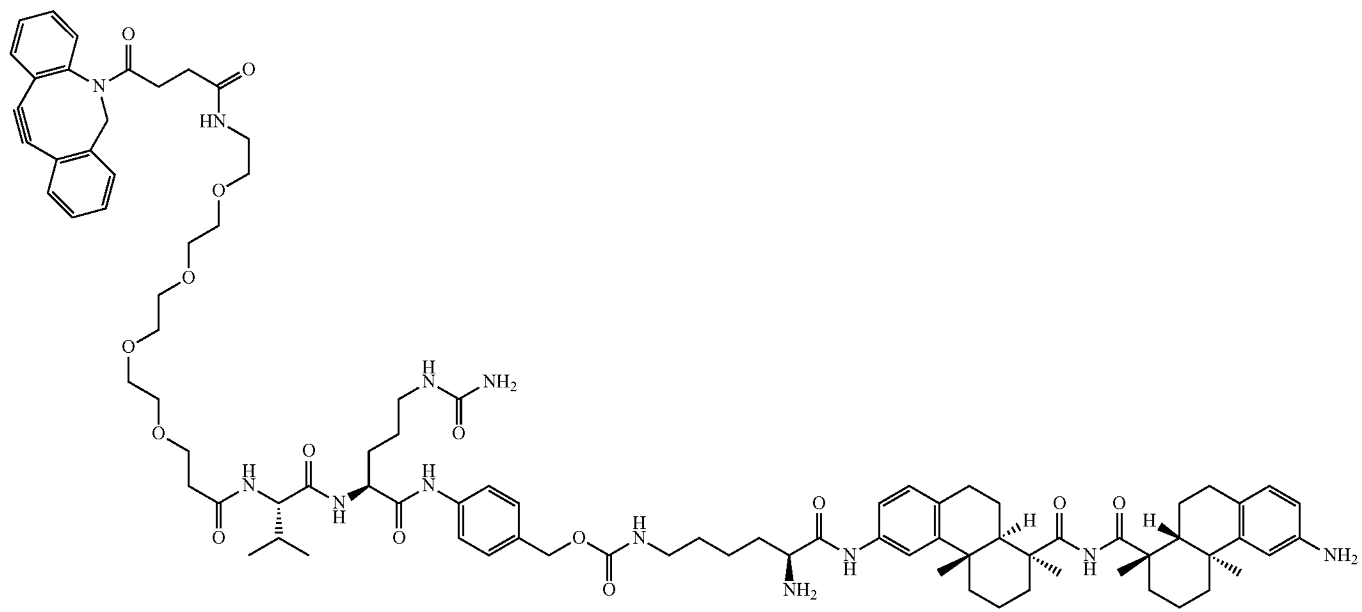 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)NCCCC[C@H](N)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1] |
| LP10 | DIBAC-suc-PEG4-vcPABC | 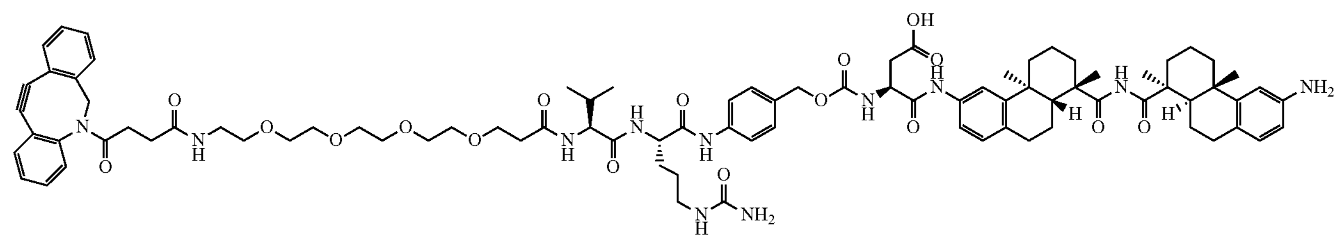 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1] |

TABLE 2-continued

List of Linker-payloads

| LP | Linker name | Structures |
|---|---|---|
| LP11 | DIBAC-suc-PEG4-vcPABC | 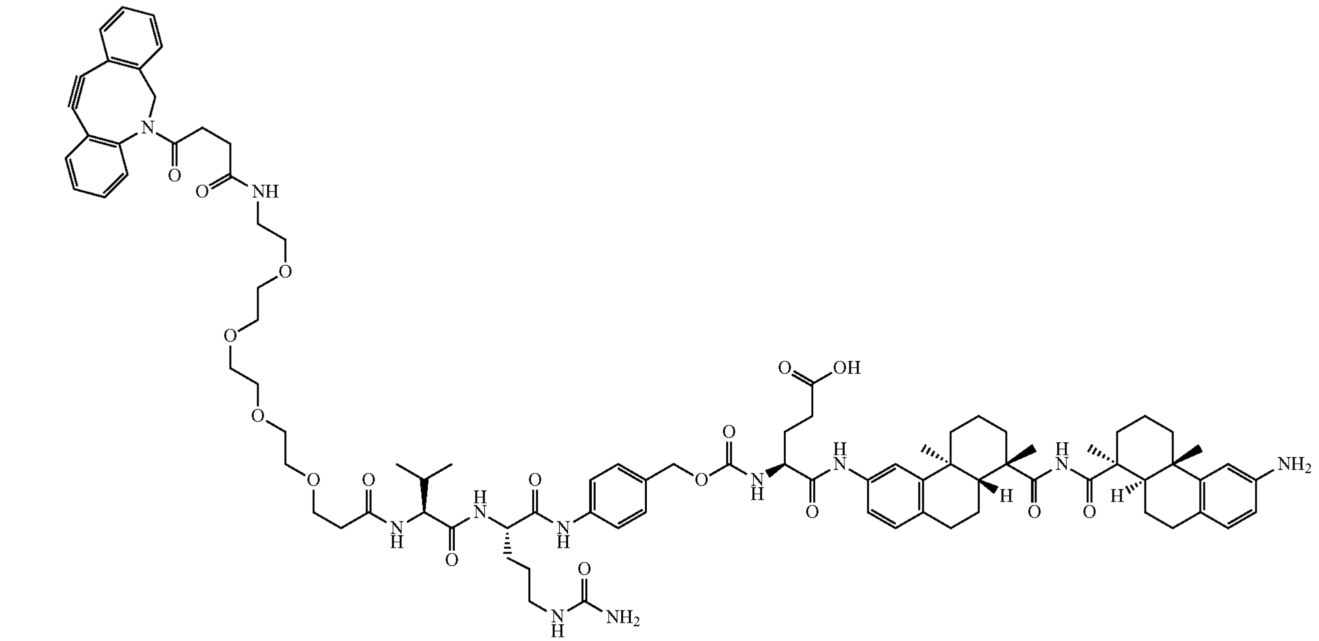 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1] |
| LP12 | DIBAC-suc-PEG4-EA | 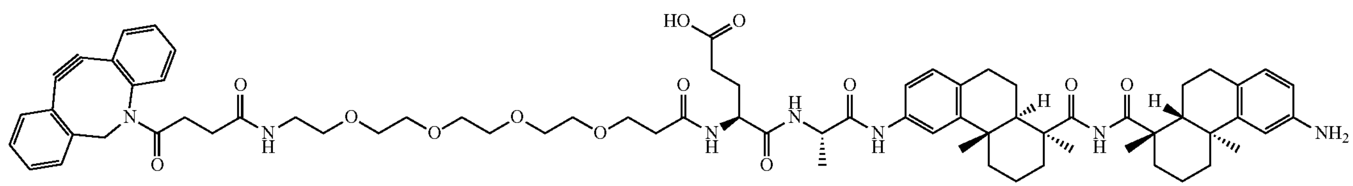 [SMILES: C[C@H](NC(=O)[C@H](CCC(=O)O)NC(=O)CCOCCOCCOCCOCCNC(=O)CCC(=O)N1Cc2ccccc2C#Cc2ccccc21)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] |
| LP13 | DIBAC-suc-PEG4-Glu-VA | 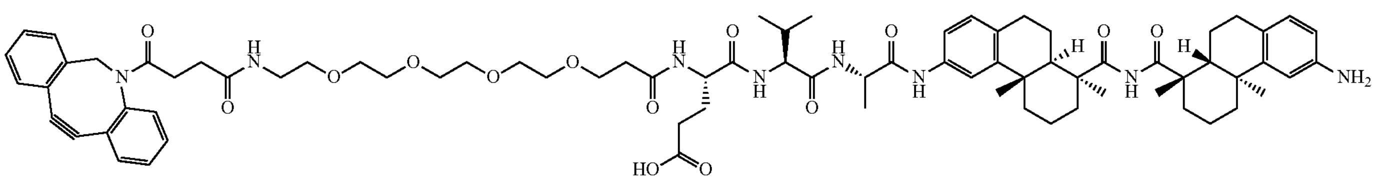 [SMILES: CC(C)[C@H](NC(=O)[C@H](CCC(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] |

TABLE 2-continued

List of Linker-payloads

| LP | Linker name | Structures |
|---|---|---|
| LP14 | DIBAC-suc-PEG4-dGlu-VA | 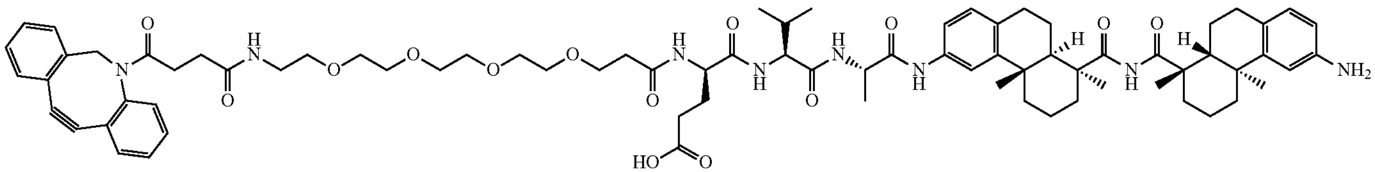 [SMILES: CC(C)[C@H](NC(=O)[C@@H](CCC(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] |
| LP15 | DIBAC-suc-PEG3-CDBCA-Cit-PAB | 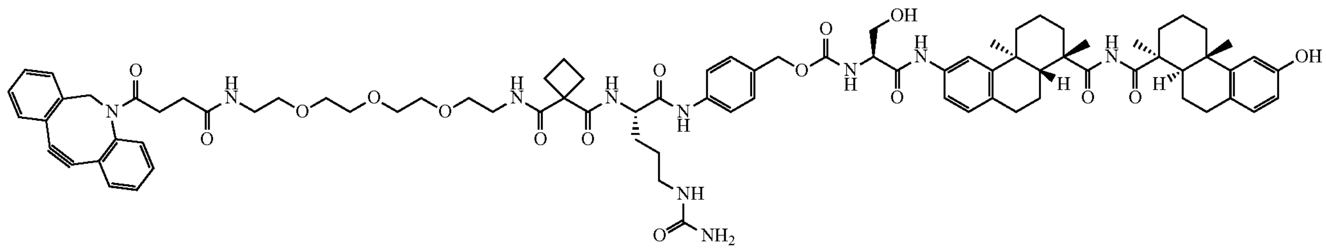 [SMILES: C[C@]1(C(=O)NC(=O)[C@@]2(C)CCC[C@]3(C)c4cc(NC(=O)[C@H](CO)NC(=O)OCc5ccc(NC(=O)[C@H](CCCNC(N)=O)NC(=O)C6(C(=O)NCCOCCOCCOCCNC(=O)CCC(=O)N7Cc8ccccc8C#Cc8ccccc87)CCC6)cc5)ccc4CC[C@@H]23)CCC[C@]2(C)c3cc(O)ccc3CC[C@@H]12] |
| LP16 | DIBAC-suc-PEG4-Glu-Ala | 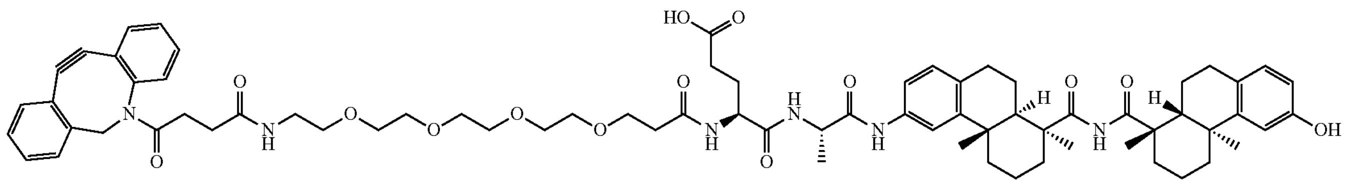 [SMILES: C[C@H](NC(=O)[C@H](CCC(=O)O)NC(=O)CCOCCOCCOCCOCCNC(=O)CCC(=O)N1Cc2ccccc2C#Cc2ccccc21)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2] |
| LP17 | DIBAC-suc-PEG4-vcPAB-Gly-NCO-GLA | 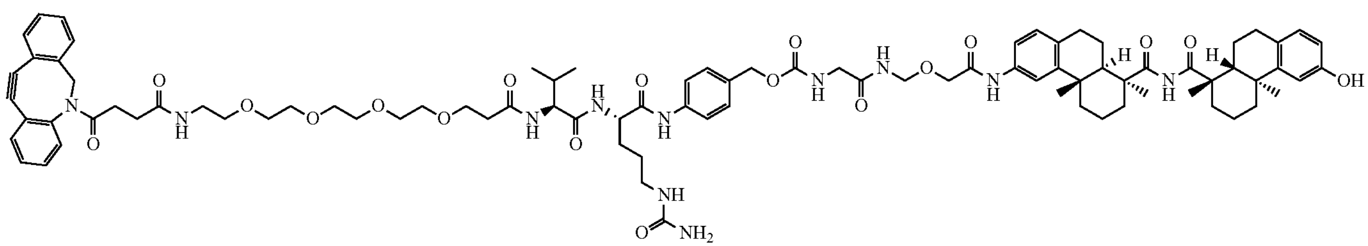 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)NCC(=O)NCOCC(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1] |

TABLE 2-continued
List of Linker-payloads
| LP | Linker name | Structures |
|---|---|---|
| LP18 | DIBAC-suc-GGFG-NCO-GLA | 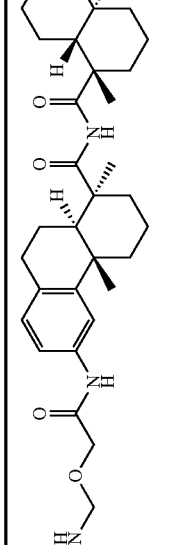 |
| LP19 | DIBAC-suc-PEG4-vcPABC-MeEDA(PEG) | 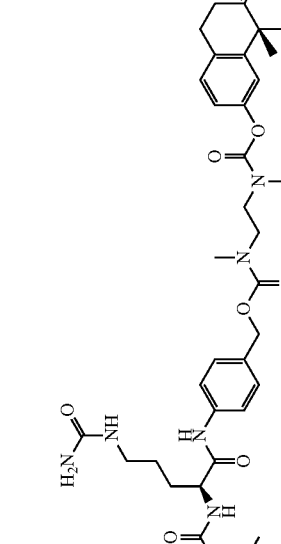 |

TABLE 2-continued
List of Linker-payloads
| LP | Linker name | Structures |
|---|---|---|
| LP20 | DIBAC-suc-PEG4-dLys(COT-PEG4-taurine)-VA | 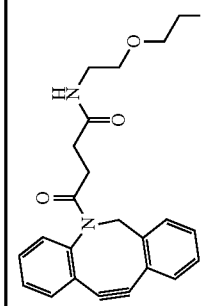 |

Certain embodiments of the invention are illustrated by the following non-limiting examples.

Reagents and solvents were obtained from commercial sources such as Sinopharm Chemical Reagent Co. (SCRC), Sigma-Aldrich, Alfa or other vendors, unless explicitly stated otherwise.

$^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethylsilane.

HPLC-MS measurement was run on Agilent 1200 HPLC/6100 SQ System using the follow conditions:

Method A for HPLC-MS measurement included, as the Mobile Phase: A: Water (0.01% TFA) and B: acetonitrile (0.01% TFA). The Gradient Phase was 5% of B increased to 95% of B over 15 minutes (min) at 1.0 mL/min. The column used was a SunFire C18, 4.6×50 mm, 3.5 μm. The column Temperature was 50° C. The detectors included an Analog to Digital Converter Evaporative Lightscattering Detector (hereinafter "ADC ELSD"), Diode array detector (DAD, 214 nm and 254 nm), and Electrospray Ionization-Atmospheric Pressure Ionization (ES-API).

Method B for HPLC-MS measurement included, as the Mobile Phase: A: Water (10 mM NH$_4$HCO$_3$) and B: acetonitrile. The Gradient Phase was 5% of B increased to 95% of B over 15 min at 1.0 mL/min. The column used was a XBridge C18, 4.6×50 mm, 3.5 μm. The column temperature was 50° C. The detectors included an ADC ELSD, DAD (214 nm and 254 nm), and a mass-selective detector (MSD ES-API).

LC-MS measurement was run on Agilent 1200 HPLC/6100 SQ System using the following conditions:

Method A for LC-MS measurement was performed on a WATERS 2767 instrument. The column was a Shimadzu Shim-Pack, PRC-ODS, 20×250 mm, 15 μm, two connected in series. The Mobile Phase was A: Water (0.01% TFA) and B: acetonitrile (0.01% TFA). The Gradient Phase was 5% of B increased to 95% of B over 3 min at 1.8-2.3 mL/min. The column used was SunFire C18, 4.6×50 mm, 3.5 μm. The column temperature was 50° C. The detectors included an ADC ELSD, DAD (214 nm and 254 nm), and a MSD ES-API.

Method B for LC-MS measurement was performed on a Gilson GX-281 instrument. The column was an Xbridge Prep C18 10 μm OBD, 19×250 mm. The Mobile Phase was A: Water (10 mM NH$_4$HCO$_3$) B: Acetonitrile. The Gradient Phase was 5% of B increased to 95% of B over 3 min at 1.8-2.3 mL/min. The column used was an XBridge C18, 4.6×50 mm, 3.5 μm. The column temperature was 50° C. The detectors included ADC ELSD, DAD (214 nm and 254 nm), and a MSD ES-API.

Preparative high pressure liquid chromatography (Prep-HPLC) was performed on a Gilson GX-281 instrument. Two solvent systems were used, one acidic and one basic. The acidic solvent system (Method A) included a Waters Sunfire 10 μm C18 column (100 Å, 250×19 mm). Solvent A for prep-HPLC was 0.05% TFA in water and solvent B was acetonitrile. The elution condition was a linear gradient that increased solvent B from 5% to 100% over 20 min at 30 mL/min. The basic solvent system (Method B) included a Waters Xbridge 10 μm C18 column (100 Å, 250×19 mm). Solvent A for prep-HPLC was 10 mM ammonium bicarbonate (NH$_4$HCO$_3$) in water and solvent B was acetonitrile. The elution condition was a linear gradient that increased solvent B from 5 to 100 over 20 min at 30 mL/min.

Flash chromatography was performed on a Biotage instrument, with Agela Flash Column silica-CS. Reversed phase flash chromatography was performed on a Biotage instrument, with Boston ODS or Agela C18, unless explicitly indicated otherwise.

As used herein, the symbols and conventions used in these processes, schemes, and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the Examples and throughout the specification:

| Abbreviation | Term |
| --- | --- |
| ADC | Antibody-drug conjugate |
| Aglycosylated antibody | Antibody does not have any glycan |
| Aq. | Aqueous |
| Boc | N-tert-butoxycarbonyl |
| BupH | Thermo Scientific Prod# 28372, containing 100 mM sodium phosphate and 150 mM sodium chloride, potassium free, pH was adjusted from 7.2 to 7.6-7.8 MQ, unless otherwise noted |
| CD | Cyclodextrin |
| COT | Cyclooctynol |
| Da | Dalton |
| DAR | Drug to antibody ratio |
| DCM | Dichloromethane or methylene chloride |
| DIBAC | Dibenz[b,f]azocine, 11,12-didehydro-5,6-dihydro- |
| DIBAC-Suc | Dibenz[b,f]azocine-5(6H)-butanoic acid, 11,12-didehydro |
| DIBACT | 3H-Benzo[c]-1,2,3-triazolo[4,5-e][1]benzazocine, 8,9-dihydro- |
| DIPEA | Diisopropylethylamine |
| DMF | N,N-dimethylformamide |
| DMSO | Dimethylsulfoxide |
| EC | Enzyme commission |
| ELSD | Evaporating light scattering detector |
| ESI | Electrospray ionization |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney cells |
| HPLC | High performance liquid chromatography |
| h, hr or hrs | Hours |
| LC | Light chain of immunoglobulin |
| LCh | Liquid chromatography |
| MALDI | Matrix-assisted laser desorption/ionization |
| MC | Maleimidocaproyl |
| mg | milligrams |
| min | minutes |
| mL | milliliters |
| mmh | myc-myc-hexahistidine tag |
| μL | microliters |
| mM | millimolar |
| μM | micromolar |
| MMAE | Monomethyl auristatin E |
| MS | Mass spectrometry |
| MsCl | Methanesulfonyl chloride |
| MSD | Mass-selective detector |
| MW | Molecular weight |
| NHS | N-hydroxy succinimide |
| nM | nanomolar |
| NMR | Nuclear magnetic resonance |
| PAB | Para-aminobezyloxycarbonyl |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| ppm | Parts per million (chemical shift) |
| RP | Reversed phase |
| RT or rt | Room temperature |

| Abbreviation | Term |
|---|---|
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra-Performance Liquid Chromatography |
| UV | Ultraviolet |
| VA | Valine-Alanine |
| VC | Valine-citrulline |

Preparation Methods

Example 1

This example demonstrates general methods for the synthesis of the podocarpic acid derivatives P1, P15, and P2 in Table 1, above. This example refers to the compounds numbered from 1 to 12a-b and P1, P15, and P2 in FIG. 1. Methyl (1S,4aS,10aR)-6-hydroxy-1,4a-dimethyl-1,2,3,4,4a,9,10,10a-octahydrophenanthrene-1-carboxylate (2)

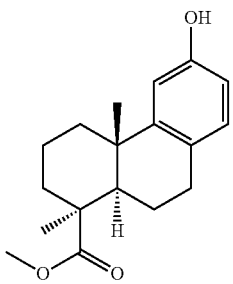 [SMILES: COC(=O)[C@@]1(C)CCC[C@]2(C)c3cc(O)ccc3CC[C@@H]12]

To a solution of podocarpic acid (1, 90 g, 0.33 mol) in methanol (200 mL) and toluene (600 mL) was added (trimethylsilyl)diazomethane (2 M in hexane, 200 mL). The reaction mixture was stirred at RT for 2 hours. The podocarpic acid was totally consumed according to LCMS. The volatiles were removed in vacuo, and the residue was triturated from petroleum ether (2 L) to give compound 2 (91 g, 96% yield) as a white solid. ESI m/z: 289 (M+H)$^+$. $^1$H NMR (400 MHz, DMSO$_{d6}$) δ 8.95 (s, 1H), 6.79 (d, J=8.2 Hz, 1H), 6.63 (d, J=2.4 Hz, 1H), 6.48 (dd, J=8.2, 2.4 Hz, 1H), 3.58 (s, 3H), 2.80-2.55 (m, 2H), 2.20-2.02 (m, 3H), 1.96-1.71 (m, 2H), 1.56-1.45 (m, 2H), 1.27 (t, J=13.5 Hz, 1H), 1.21 (s, 3H), 1.09 (td, J=13.5, 4.1 Hz, 1H), 0.91 (s, 3H) ppm.

Methyl (1S,4aS,10aR)-1,4a-dimethyl-6-(trifluoromethanesulfonyloxy)-1,2,3,4,4a,9,10,10a-octahydrophenanthrene-1-carboxylate (3)

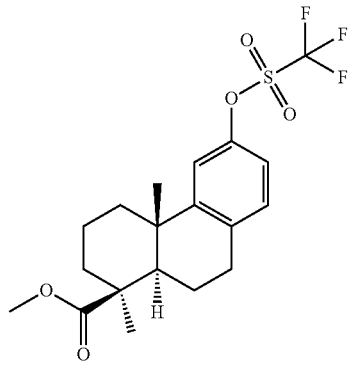 [SMILES: COC(=O)[C@@]1(C)CCC[C@]2(C)c3cc(OS(=O)(=O)C(F)(F)F)ccc3CC[C@@H]12]

To a solution of compound 2 (10 g, 35 mmol) in methylene chloride (200 mL) were added pyridine (3.3 g, 42 mmol) and DMAP (0.84 g, 6.9 mmol) under nitrogen. The mixture was cooled to −78° C. and triflic anhydride (12 g, 42 mmol) was added. The resulting mixture was allowed to warm to 25° C. and stirred at 25° C. for another 4 h. The reaction mixture was diluted with DCM (500 mL), washed with water (100 mL), aq. hydrochloride (1N, 150 mL) and brine (100 mL), dried over sodium sulfate, and concentrated in vacuo to give crude compound 3 (14 g, 97% crude yield) as viscous oil, which was pure enough for the next step. The crude compound 3 could be purified by flash chromatography (0-10% ethyl acetate in petroleum ether) to give pure 3 as a viscous oil. ESI m/z: 421.2 (M+1)$^+$. $^1$H NMR (400 MHz, CDCl$_3$) δ 7.12 (d, J=2.5 Hz, 1H), 7.10 (d, J=8.5 Hz, 1H), 6.97 (dd, J=8.5, 2.5 Hz, 1H), 3.67 (s, J=3.4 Hz, 3H), 2.93 (dd, J=17.2, 4.4 Hz, 1H), 2.85-2.71 (m, 1H), 2.29 (d, J=13.5 Hz, 1H), 2.25-2.14 (m, 2H), 2.03-1.89 (m, 2H), 1.71-1.61 (m, 1H), 1.56-1.48 (m, 1H), 1.40 (td, J=13.4, 4.2 Hz, 1H), 1.30-1.22 (m, 3H), 1.09 (td, J=13.6, 4.2 Hz, 1H), 1.02 (s, 3H) ppm.

Methyl (1S,4aS,10aR)-6-((tert-butoxycarbonyl)amino)-1,4a-dimethyl-1,2,3,4,4a,9,10,10a-octahydrophenanthrene-1-carboxylate (4)

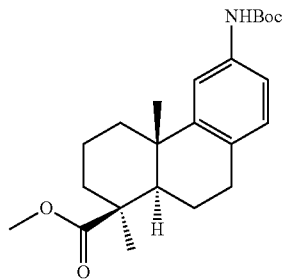 [SMILES: COC(=O)[C@@]1(C)CCC[C@]2(C)c3cc(NC(=O)OC(C)(C)C)ccc3CC[C@@H]12]

To a solution of compound 3 (14 g, 34 mmol) and tert-butyl carbamate (BocNH$_2$, 7.9 g, 68 mmol) in tert-butanol (100 mL) were added, successively, cesium carbonate (22 g, 68 mmol), tris(dibenzylideneacetone)dipalladium (0) (Pd$_2$(dba)$_3$, 1.8 g, 2.0 mmol) and X-Phos (1.8 g, 4.0 mmol) at RT. The mixture was de-gassed and purged with argon 3 times and was then stirred at 80° C. under an argon balloon overnight until compound 3 was totally consumed, as monitored by TLC. After cooling to RT, the reaction mixture was diluted with ethyl acetate and filtered through Celite. The solids were washed with ethyl acetate 3 times. The combined filtrate was concentrated in vacuo and the residue was purified by silica gel column chromatography (0-6.25% ethyl acetate in petroleum ether) to give compound 4 (11 g, 80% yield) as a white solid. ESI m/z: 410 (M+23)$^+$. $^1$H NMR (500 MHz, DMSO$_{d6}$) δ 9.07 (s, 1H), 7.39 (s, 1H), 7.13 (d, J=8.5 Hz, 1H), 6.87 (d, J=8.3 Hz, 1H), 3.59 (s, 3H), 2.76 (dd, J=16.4, 4.5 Hz, 1H), 2.70-2.61 (m, 1H), 2.16-2.05 (m, 3H), 2.00-1.75 (m, 2H), 1.65-1.50 (m, 2H), 1.45 (s, 9H), 1.31-1.25 (m, 1H), 1.21 (s, 3H), 1.10 (td, J=13.5, 4.1 Hz, 1H), 0.92 (s, 3H) ppm.

(1S,4aS,10aR)-6-{[(tert-Butoxy)carbonyl]amino}-1, 4a-dimethyl-1,2,3,4,4a,9,10,10a-octahydro-phenanthrene-1-carboxylic acid (5)

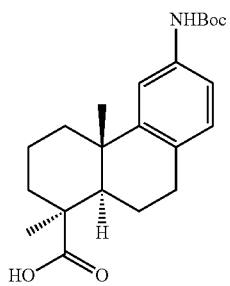 [SMILES: CC(C)(C)OC(=O)Nc1ccc2c(c1)[C@@]1(C)CCC[C@](C)(C(=O)O)[C@@H]1CC2]

To a solution of compound 4 (4.9 g, 13 mmol) in DMSO was added potassium tert-butoxide (15 g, 0.13 mol) in one portion at RT. The reaction mixture was stirred at 60° C. for 3 h under argon until the reaction was complete according to LCMS. After cooling to RT, the reaction mixture was poured into ice and acidified slowly with aq. hydrochloride (0.5 M) to pH 5, during which the temperature was not allowed to reach higher than 25° C. The precipitates were collected by filtration and washed with water several times. The crude product was further purified by silica gel column chromatography (0-20% ethyl acetate in petroleum ether) to give compound 5 (4.5 g, 93% yield) as a white solid. ESI m/z: 318 (M-55)$^+$. $^1$H NMR (500 MHz, DMSO$_{d6}$) δ 12.08 (s, 1H), 9.08 (s, 1H), 7.40 (s, 1H), 7.11 (s, 1H), 6.87 (d, J=8.3 Hz, 1H), 2.79-2.68 (m, 1H), 2.65 (d, J=12.6 Hz, 1H), 2.17-2.03 (m, 4H), 1.94-1.76 (m, 2H), 1.53 (d, J=13.7 Hz, 1H), 1.46 (d, J=7.4 Hz, 9H), 1.29-1.14 (m, 5H), 1.04 (s, 3H) ppm.

tert-Butyl N-[(4bS,8S,8aR)-8-carbamoyl-4b,8-dimethyl-4b,5,6,7,8,8a,9,10-octahydrophenanthren-3-yl] carbamate (6)

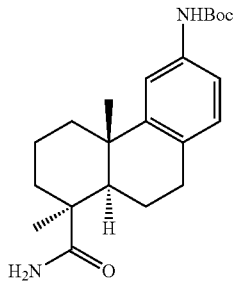 [SMILES: CC(C)(C)OC(=O)Nc1ccc2c(c1)[C@@]1(C)CCC[C@](C)(C(N)=O)[C@@H]1CC2]

To a solution of 5 (4.5 g, 12 mmol) and HATU (4.9 g, 13 mmol) in DMF (50 mL) was added diisopropylethylamine (20 mL, 0.12 mol), and the mixture was stirred at 25° C. for an hour. To the mixture was then added ammonium chloride (16 g, 0.30 mol) and the mixture was stirred at RT overnight. The resulting mixture was diluted with ethyl acetate, washed with water and brine, dried over sodium sulfate, and concentrated in vacuo. The residue was purified by flash chromatography (0-20% ethyl acetate in petroleum ether) to give compound 6 (4.2 g, 94% yield) as a white solid. ESI m/z: 373.3 (M+1)$^+$. H NMR (500 MHz, methanol$_{d4}$) δ 7.20 (s, 1H), 6.97 (d, J=7.7 Hz, 1H), 6.80 (d, J=8.3 Hz, 1H), 2.77-2.68 (m, 2H), 2.66-2.55 (m, 1H), 2.20 (d, J=12.9 Hz, 1H), 2.13 (dd, J=13.2, 5.3 Hz, 1H), 2.08 (d, J=14.0 Hz, 1H), 2.03-1.86 (m, 2H), 1.54 (d, J=11.1 Hz, 1H), 1.40 (s, 9H), 1.26 (t, J=26.7 Hz, 1H), 1.18 (s, 3H), 1.14-1.03 (m, 4H) ppm.

Methyl (1S,4aS,10aR)-6-amino-1,4a-dimethyl-1,2,3, 4,4a,9,10,10a-octahydrophenanthrene-1-carboxylate trifluoroacetic acid salt (7)

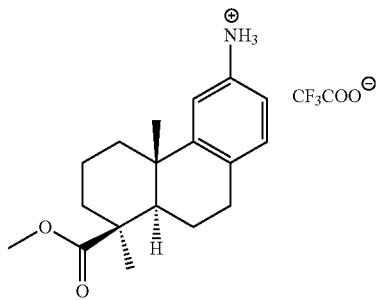

To a solution of compound 4 (6.0 g, 15 mmol) in DCM (60 mL) was added TFA (12 mL) at RT. The resulting mixture was stirred at RT for 2 h until Boc was totally removed, as monitored by TLC. The reaction mixture was concentrated in vacuo to give crude compound 7 as a TFA salt, which was used in the next step without further purification. ESI m/z: 288 (M+1)$^+$.

Methyl (1S,4aS,10aR)-6-(benzyloxy)-1,4a-dimethyl-1,2,3,4,4a,9,10,10a-octahydrophenanthrene-1-carboxylate (8a)

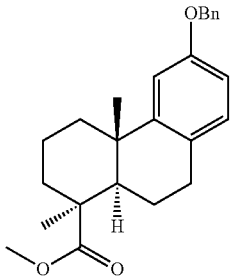 [SMILES: COC(=O)[C@@]1(C)CCC[C@]2(C)c3cc(OCc4ccccc4)ccc3CC[C@@H]12]

A mixture of compound 2 (12 g, 40 mmol) and cesium carbonate (14 g, 44 mmol) in DMF (100 mL) was stirred at 20-25° C. for 15 min. To the mixture was added benzyl bromide (7.1 mL, 60 mmol) at RT. After stirring at RT for 4 h, the resulting mixture was poured into cold water and extracted with ethyl acetate. The combined organic solution was washed with water and brine, dried over sodium sulfate, and concentrated in vacuo. The crude product was purified by flash chromatography (0-10% ethyl acetate in petroleum ether) to give the title compound 8a (13 g, 89% yield) as a white solid. ESI m/z: 379 (M+H)$^+$. $^1$H NMR (500 MHz, methanol$_{d4}$) δ 7.60-7.20 (m, 5H), 7.00-6.82 (m, 2H), 6.73 (d, J=7.1 Hz, 1H), 5.03 (s, 2H), 3.66 (s, 3H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

Methyl (1S,4aS,10aR)-6-(dibenzylamino)-1,4a-dimethyl-1,2,3,4,4a,9,10,10a-octahydrophenanthrene-1-carboxylate (8b)

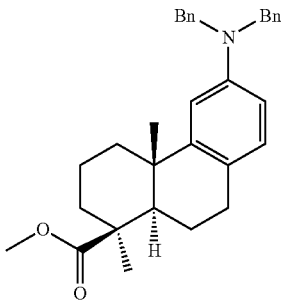 [SMILES: COC(=O)[C@@]1(C)CCC[C@]2(C)c3cc(N(Cc4ccccc4)Cc4ccccc4)ccc3CC[C@@H]12]

To a solution of the crude compound 7 obtained above (calc. 15 mmol) in DMF (60 mL) were added potassium carbonate (6.4 g, 46 mmol) and benzylbromide (5.8 g, 34 mmol) at RT. The reaction mixture was stirred at 80° C. overnight until the reaction was complete as monitored by TLC. After cooling to RT, the mixture was poured into cold water (300 mL) and extracted with ethyl acetate (×3). The combined organic solution was washed with water and brine, dried over sodium sulfate, and concentrated in vacuo to give crude product 8b, which was used in the next step without further purification. ESI m/z: 468 (M+1)$^+$.

(1S,4aS,10aR)-6-(Benzyloxy)-1,4a-dimethyl-1,2,3,4,4a,9,10,10a-octahydrophenanthrene-1-carboxylic acid (9a)

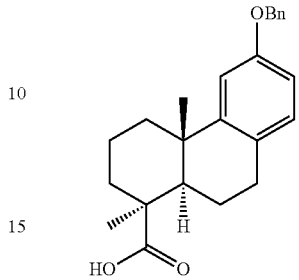

A mixture of compound 8a (11 g, 29 mmol) and potassium tert-butoxide (33 g, 0.29 mol) in DMSO (0.19 L) was stirred at 100° C. for an hour until the ester was totally consumed, as monitored by LCMS and TLC. After cooling to 25° C., the mixture was quenched with aqueous hydrochloride (1 N) and extracted with ethyl acetate. The combined organic solution was washed with brine, dried over sodium sulfate, and concentrated in vacuo. The residue was purified by silica gel column chromatography (0-24% ethyl acetate in petroleum ether) to give compound 9a (7.5 g, 71% yield) as a white solid. ESI m/z: 365 (M+H)$^+$. $^1$H NMR (500 MHz, methanol$_{d4}$) δ 7.42 (d, J=7.4 Hz, 2H), 7.36 (t, J=7.5 Hz, 2H), 7.30 (t, J=7.3 Hz, 1H), 6.92 (d, J=8.4 Hz, 1H), 6.87 (d, J=2.5 Hz, 1H), 6.72 (dd, J=8.4, 2.5 Hz, 1H), 5.02 (s, 2H), 2.82 (dd, J=16.3, 4.4 Hz, 1H), 2.77-2.65 (m, 1H), 2.24 (d, J=13.2 Hz, 2H), 2.19 (dd, J=13.8, 6.0 Hz, 1H), 2.11-1.96 (m, 2H), 1.64-1.56 (m, 1H), 1.53 (d, J=11.0 Hz, 1H), 1.35 (td, J=13.3, 3.7 Hz, 1H), 1.30 (s, 3H), 1.13 (s, 3H), 1.11-1.05 (m, 1H) ppm.

(1S,4aS,10aR)-6-(Dibenzylamino)-1,4a-dimethyl-1,2,3,4,4a,9,10,10a-octahydrophenanthrene-1-carboxylic acid (9b)

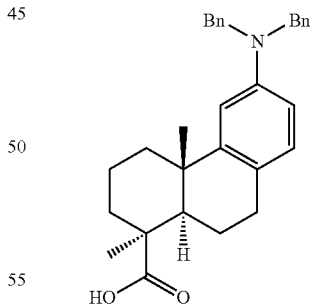

To a solution of the crude compound 8b obtained above (calc. 15 mmol) in DMSO (100 mL) was added potassium tert-butoxide (17 g, 0.15 mol) in one portion at RT. The reaction mixture was stirred at 100° C. for 2 h under argon until the reaction was complete according to LCMS. After cooling to RT, the reaction mixture was poured into ice and acidified slowly with aq. hydrochloride (4 M) to pH 5, during which the temperature was not allowed to reach higher than 25° C. The mixture was extracted with ethyl acetate and the combined organic solution was washed with water and brine, dried over sodium sulfate, and concentrated in vacuo. The crude product was purified by silica gel column chromatography (0-20% ethyl acetate in petroleum ether) to give compound 9b (6.8 g, 99% yield in 3 steps from compound 4) as a white solid. ESI m/z: 454 (M+1)⁺.

Pentafluorophenyl (1S,4aS,10aR)-6-(benzyloxy)-1,4a-dimethyl-1,2,3,4,4a,9,10,10a-octahydro-phenanthrene-1-carboxylate (10a)

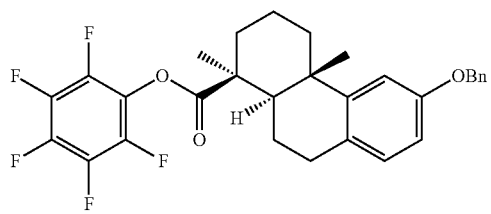 [SMILES: C[C@]1(C(=O)Oc2c(F)c(F)c(F)c(F)c2F)CCC[C@]2(C)c3cc(OCc4ccccc4)ccc3CC[C@@H]12]

To a solution of 9a (9.6 g, 26 mmol) in DMF (100 mL) was added DIPEA (14 mL, 79 mmol), and perfluorophenyl 2,2,2-trifluoroacetate (15 g, 53 mmol). This mixture was stirred at RT overnight, and monitored by LCMS. The reaction mixture was then diluted with ether (200 mL) and washed with water (300 mL) and brine (200 mL). The organic solution was dried over sodium sulfate, and concentrated in vacuo. The residue was purified by flash chromatography (0-10% ethyl acetate in petroleum ether) to give compound 10a (12 g, 88% yield) as a white solid. ESI m/z: 531 (M+H)⁺. ¹H NMR (500 MHz, DMSO$_{d6}$) δ 7.43 (d, J=7.1 Hz, 2H), 7.38 (t, J=7.4 Hz, 2H), 7.31 (t, J=7.2 Hz, 1H), 6.93 (dd, J=10.2, 5.5 Hz, 2H), 6.76 (dd, J=8.4, 2.5 Hz, 1H), 5.05 (s, 2H), 2.81 (dd, J=16.3, 4.5 Hz, 1H), 2.77-2.68 (m, 1H), 2.28-2.19 (m, 2H), 2.18 (dd, J=13.4, 5.6 Hz, 1H), 2.00-1.83 (m, 2H), 1.74 (d, J=11.8 Hz, 1H), 1.65 (d, J=14.1 Hz, 1H), 1.47 (s, 3H), 1.38-1.27 (m, 2H), 1.08 (s, 3H) ppm.

Pentafluorophenyl (1S,4aS,10aR)-6-(dibenzylamino)-1,4a-dimethyl-1,2,3,4,4a,9,10,10a-octahydrophenanthrene-1-carboxylate (10b)

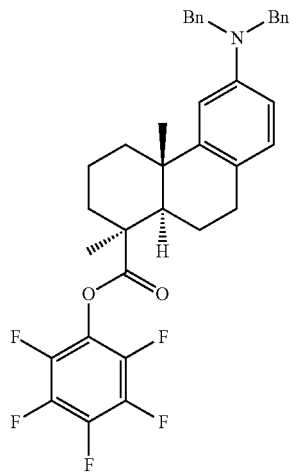 [SMILES: C[C@]1(C(=O)Oc2c(F)c(F)c(F)c(F)c2F)CCC[C@]2(C)c3cc(N(Cc4ccccc4)Cc4ccccc4)ccc3CC[C@@H]12]

To a solution of 9b (6.8 g, 15 mmol) in DMF (100 mL) was added DIPEA (10 mL, 0.61 mol), and perfluorophenyl 2,2,2-trifluoroacetate (10 mL, 58 mmol). This mixture was stirred at 25° C. overnight under nitrogen, and was then diluted with ether. The organics were washed with water and brine, dried over sodium sulfate, and concentrated in vacuo. The residue was purified by silica gel column chromatography (0-10% ethyl acetate in petroleum ether) to give compound 10b (7.5 g, 81% yield) as a white solid. ESI m/z: 620 (M+1)⁺. ¹H NMR (400 MHz, CDCl₃) δ 7.36-7.25 (m, 10H), 6.92 (d, J=8.4 Hz, 1H), 6.67 (d, J=2.8 Hz, 1H), 6.63 (dd, J=8.4, 2.6 Hz, 1H), 4.63 (m, 4H), 2.85-2.73 (m, 2H), 2.41-2.37 (m, 1H), 2.22-2.20 (m, 1H), 2.15-1.91 (m, 3H), 1.71-1.65 (m, 2H), 1.51 (s, 3H), 1.37-1.19 (m, 2H), 1.10 (s, 3H) ppm.

tert-Butyl N-[(4bS,8S,8aR)-8-({[(1S,4aS,10aR)-6-(benzyloxy)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (11a)

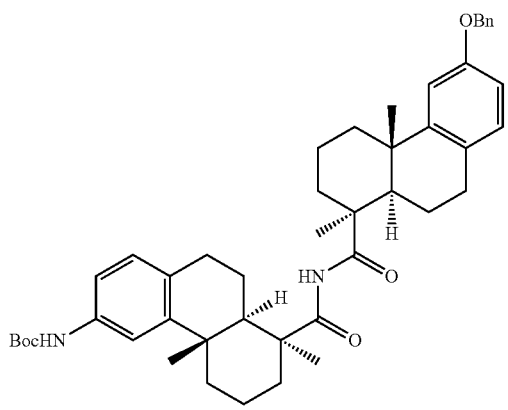 [SMILES: CC(C)(C)OC(=O)Nc1ccc2c(c1)[C@@]1(C)CCC[C@](C)(C(=O)NC(=O)[C@@]3(C)CCC[C@]4(C)c5cc(OCc6ccccc6)ccc5CC[C@@H]34)[C@@H]1CC2]

To a solution of compound 6 (2.3 g, 6.2 mmol) in THF (20 mL) was added dropwise n-BuLi (2.5 M in hexane, 5.5 mL, 14 mmol) at −78° C. The reaction was stirred at −78° C. for 1 h. To the mixture was added a solution of 10a (3.0 g, 5.6 mmol) in THF (20 mL), and the resulting mixture was then stirred at 10-20° C. overnight until compound 10a was consumed, as monitored by LCMS. The reaction was quenched with sat. aq. ammonium chloride and extracted with ethyl acetate. The combined organic solution was washed with water and brine, dried over sodium sulfate, and concentrated in vacuo. The residue was purified by flash chromatography (0-30% ethyl acetate in petroleum ether) to give compound 11a (1.59 g, 51% yield) as a white solid. ESI m/z: 719 (M+1)⁺.

(Compared with the procedure of 11b below, n-BuLi was used here instead of LiHMDS. Although 6 was not completely consumed, this procedure led to less side-product and the yield of 11a was increased from ca. 40% to 0.51%. The unreacted compound 6 was recovered (recovered yield: 10-20%).

tert-Butyl N-[(4bS,8S,8aR)-8-({[(1S,4aS,10aR)-6-(dibenzylamino)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (11b)

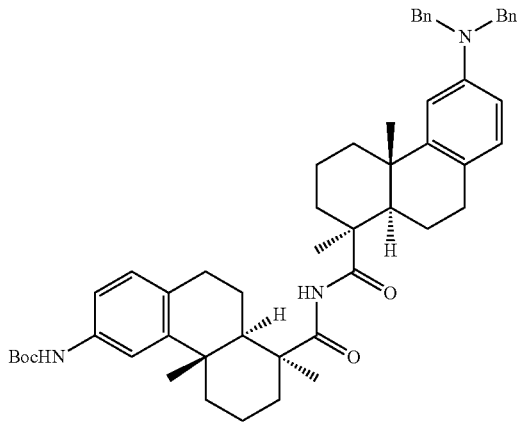 [SMILES: CC(C)(C)OC(=O)Nc1ccc2c(c1)[C@@]1(C)CCC[C@](C)(C(=O)NC(=O)[C@@]3(C)CCC[C@]4(C)c5cc(N(Cc6ccccc6)Cc6ccccc6)ccc5CC[C@@H]34)[C@@H]1CC2]

To a solution of compound 6 (1 g, 2.7 mmol) in THF (15 mL) was added dropwise lithium bis(trimethylsilyl)amide (1 M in hexane, 8.0 mL) at 0° C. The reaction was stirred at 0° C. for an hour. To the mixture was added a solution of compound 10b (2.5 g, 4.0 mmol) in THF (10 mL), and the resulting mixture was then stirred at RT overnight. The reaction was then quenched with sat. aq. ammonium chloride and extracted with ethyl acetate. The combined organic solution was washed with water and brine, dried over sodium sulfate, and concentrated in vacuo. The residue was purified by flash chromatography (0-35% ethyl acetate in petroleum ether) to give compound 11b (0.95 g, 44% yield) as a white solid; and recovered compound 6 (recovered yield 37%). ESI m/z: 808 (M+1)$^+$. $^1$H NMR (400 MHz, CDCl$_3$) δ 8.16 (s, 1H), 7.35-7.24 (m, 10H), 7.12 (d, J=8 Hz, 1H), 7.00 (d, J=8.4 Hz, 1H), 6.91 (d, J=8.4 Hz, 1H), 6.62-6.59 (m, 2H), 6.42 (s, 1H), 4.62 (s, 3H), 2.98-2.75 (m, 4H), 2.31-2.22 (m, 5H), 2.10-1.97 (m, 5H), 1.69-1.63 (m, 4H), 1.56 (s, 9H), 1.32-1.27 (m, 9H), 1.43-1.27 (m, 5H), 1.05 (s, 3H) ppm.

tert-Butyl N-[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (12a) (P15)

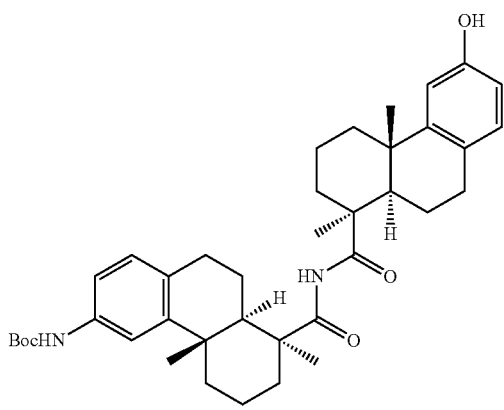 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of 11a (2.0 g, 2.78 mmol) in ethyl acetate (40 mL) was added wet palladium on carbon (10% Pd, 0.9 g) under nitrogen. The mixture was degassed, purged with hydrogen, and stirred at RT under a hydrogen balloon overnight until 11a was totally consumed, as monitored by LCMS. The mixture was filtered through Celite and the filtrate was concentrated in vacuo. The residue was purified by silica gel column chromatography (0-55% ethyl acetate in petroleum ether) to give 12a (P15; 1.06 g, 61% yield) as a white solid. ESI m/z: 629 (M+H)$^+$. $^1$H NMR (500 MHz, DMSO$_{d6}$) δ 9.10 (s, 1H), 8.98 (s, 1H), 8.11 (s, 1H), 7.40 (s, 1H), 7.15 (d, J=7.5 Hz, 1H), 6.90 (d, J=8.4 Hz, 1H), 6.81 (d, J=8.3 Hz, 1H), 6.63 (d, J=2.3 Hz, 1H), 6.50 (dd, J=8.2, 2.4 Hz, 1H), 2.84 (td, J=16.3, 3.8 Hz, 2H), 2.77-2.64 (m, 2H), 2.30-2.22 (m, 2H), 2.14 (t, J=10.9 Hz, 4H), 2.00-1.80 (m, 4H), 1.65-1.54 (m, 4H), 1.45 (s, 9H), 1.34-1.28 (m, 2H), 1.27 (d, J=2.5 Hz, 6H), 1.15-1.08 (m, 2H), 0.99 (s, 6H) ppm.

tert-Butyl N-[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (12b)

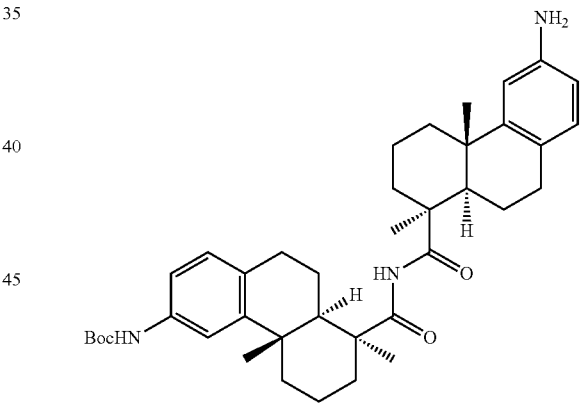

To a solution of 11b (0.45 g, 0.56 mmol) in ethyl acetate (5 mL) was added wet palladium on carbon (10% Pd, 50 mg) under nitrogen. The mixture was degassed, purged with hydrogen 3 times, and was stirred at RT under a hydrogen balloon overnight. The mixture was filtered through Celite and the filtrate was concentrated in vacuo to give compound 12b (0.33 g, 94% yield) as a white solid. ESI m/z: 628 (M+1)$^+$.

271

(1S,4aS,10aR)-N-[(1S,4aS,10aR)-6-Amino-1,4a-dimethyl-1,2,3,4,4a,9,10,10a-octahydro-phenanthrene-1-carbonyl]-6-hydroxy-1,4a-dimethyl-1,2,3,4,4a,9,10,10a-octahydrophenanthrene-1-carboxamide (P1)

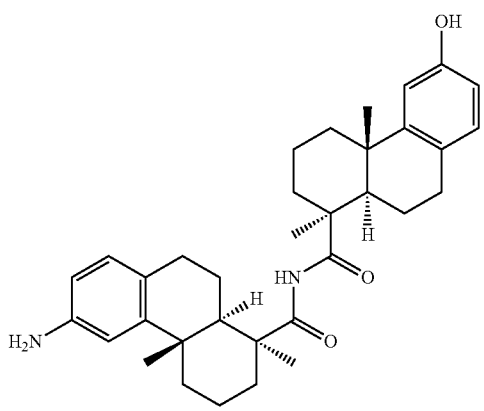 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12]

To a solution of compound 12a (0.17 g, 0.27 mmol) in DCM (10 mL) was added dropwise TFA (3 mL) at RT. The reaction mixture was stirred at RT for an hour until Boc was removed according to LCMS. The volatiles were removed in vacuo and the residue was purified by prep-HPLC (method B) to give P1 (0.10 g, 70% yield) as a white solid. ESI m/z: 529.3 (M+1)$^+$. Optical rotation (a): +2.53° (1.7 g/100 mL THF, 25° C.).

$^1$H NMR (400 MHz, CDCl$_3$) δ 8.14 (s, 1H), 6.92 (d, J=8.3 Hz, 1H), 6.86 (d, J=8.1 Hz, 1H), 6.73 (d, J=2.5 Hz, 1H), 6.65-6.57 (m, 2H), 6.50 (dd, J=8.1, 2.3 Hz, 1H), 4.75 (s, 1H), 3.49 (s, 1H), 2.99-2.85 (m, 2H), 2.79 (tt, J=11.6, 5.8 Hz, 2H), 2.34-2.14 (m, 6H), 2.15-1.95 (m, 4H), 1.74-1.51 (m, 5H), 1.46-1.34 (m, 2H), 1.30 (s, 6H), 1.21-1.06 (m, 8H) ppm.

$^1$H NMR (400 MHz, DMSO$_{d6}$) δ 8.99 (s, 1H), 8.09 (s, 1H), 6.81 (d, J=8.0 Hz, 1H), 6.68 (d, J=8.0 Hz, 1H), 6.63 (d, J=2.5 Hz, 1H), 6.50 (dd, J=8.0, 2.5 Hz, 1H), 6.48 (d, J=2.5 Hz, 1H), 6.34 (dd, J=8.0, 2.5 Hz, 1H), 4.69 (s, 2H), 2.86-2.60 (m, 4H), 2.28-2.10 (m, 6H), 1.94-1.75 (m, 4H), 1.65-1.53 (m, 4H), 1.35-1.20 (m, 8H), 1.20-1.06 (m, 2H), 0.98 (s, 6H) ppm.

$^{13}$C NMR (100 MHz, DMSO$_{d6}$) δ 174.03, 173.92, 155.34, 148.39, 147.63, 146.43, 129.56, 129.09, 124.60, 121.65, 113.23, 112.58, 111.81, 110.77, 52.32, 52.09, 45.56, 45.52, 39.20, 39.36, 38.23, 38.17, 37.18, 37.12, 31.08, 31.00, 27.65, 27.64, 23.08, 23.03, 21.43, 21.27, 19.64, 19.61 ppm.

HPLC (method B): Retention time: 8.92 min, purity: 99.4%. chiral HPLC: >99.9% (in column AD, AS, OD and OJ).

272

(1S,4aS,10aR)-6-Amino-N-((1S,4aS,10aR)-6-amino-1,4a-dimethyl-1,2,3,4,4a,9,10,10a-octahydro-phenanthrene-1-carbonyl)-1,4a-dimethyl-1,2,3,4,4a,9,10,10a-octahydrophenanthrene-1-carboxamide (P2)

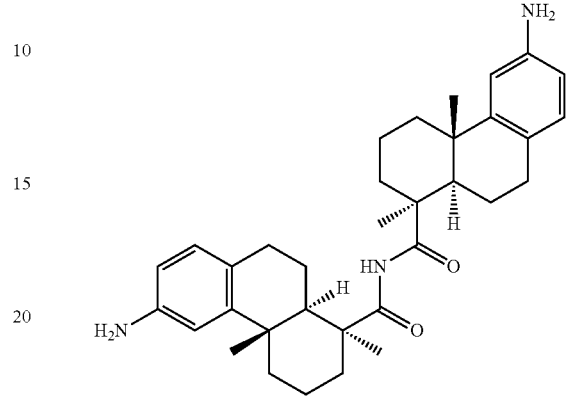

To the solution of compound 12b (0.63 g, 1.0 mmol) in DCM (10 mL) was added dropwise TFA (3 mL) at RT. The reaction mixture was stirred at RT for 4 h until Boc was removed according to LCMS. The mixture was directly purified by prep-HPLC (method B) to give P2 (0.42 g, 79% yield) as a white solid. ESI m/z: 528.2 (M+1)$^+$. $^1$H NMR (500 MHz, DMSO$_{d6}$) δ 8.28 (s, 1H), 6.67 (d, J=8.0 Hz, 2H), 6.47 (d, J=2.0 Hz, 2H), 6.33 (dd, J=8.0, 2.0 Hz, 2H), 4.69 (s, 4H), 2.80-2.75 (m, 2H), 2.70-2.60 (m, 2H), 2.26-2.20 (m, 2H), 2.19-2.05 (m, 4H), 1.95-1.75 (m, 4H), 1.62-1.50 (m, 4H), 1.33-1.20 (m, 8H), 1.12 (t, J=8.8 Hz, 2H), 0.98 (s, 6H) ppm.

Example 2

This example demonstrates general methods for the synthesis of the podocarpic acid derivative P3 in Table 1, above. This example refers to the compounds numbered from 11b and P3 in FIG. 2A.

(3S,8R,9S,10R,13S,14S)-17-imino-10,13-dimethyl-2,3,4,7,8,9,10,11,12,13,14,15,16,17-tetradecahydro-1H-cyclopenta[a]phenanthren-3-ol, trifluoroacetic acid salt (P3)

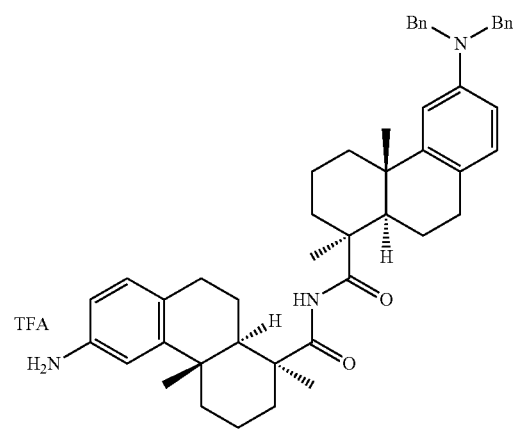 [SMILES: C[C@]1(C(=O)NC(=O)[C@@]2(C)CCC[C@]3(C)c4cc(N(Cc5ccccc5)Cc5ccccc5)ccc4CC[C@@H]23)CCC[C@]2(C)c3cc(N)ccc3CC[C@@H]12]

To a solution of compound 11b (10 mg, 12 μmol) in DCM (2 mL) was added TFA (1 mL). The reaction mixture was stirred at RT for 2 h until Boc was removed according to LCMS. The volatiles were removed in vacuo and the residue was dissolved in 5% acetonitrile in water. The solution was lyophilized to afford compound P3 (7 mg, 80% yield) as a light yellow solid. ESI m/z: 354.8 (M/2+H)$^+$. $^1$H NMR (400 MHz, DMSO$_{d6}$) δ 9.38 (br s, 2H), 8.08 (s, 1H), 7.35-7.06 (m, 12H), 6.97 (d, J=8.8 Hz, 1H), 6.73 (d, J=8.8 Hz, 1H), 6.51 (s, 1H), 6.46 (d, J=6.4 Hz, 1H), 4.68-4.55 (m, 4H), 3.00-2.50 (m, 4H), 2.40-2.00 (m, 6H), 1.94-1.73 (m, 5H), 1.70-1.50 (m, 3H), 1.50-1.00 (m, 11H), 0.98 (s, 3H), 0.83 (s, 3H) ppm. $^{19}$F NMR (376 MHz, DMSO$_{d6}$) δ −74.08 ppm.

Example 3

This example demonstates general methods for the synthesis of the podocarpic acid derivatives P4-P8 in Table 1, above. This example refers to the compounds numbered from 12b and P4-P9, P13, P14, and P17 in FIG. 2A.

Example 3a

Intermediates 13a-e

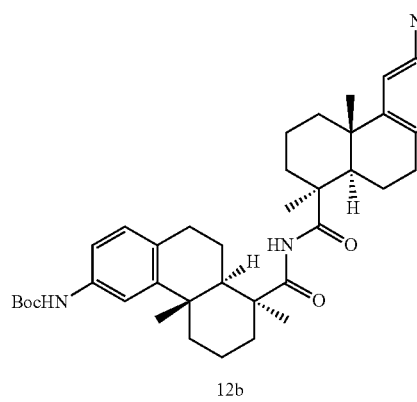

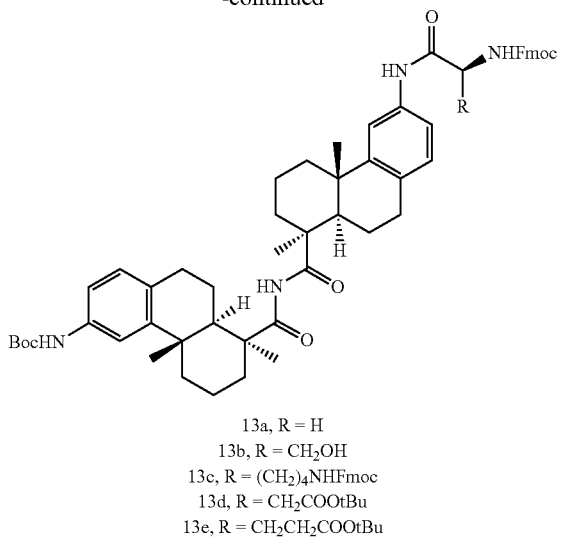

13a, R = H
13b, R = CH$_2$OH
13c, R = (CH$_2$)$_4$NHFmoc
13d, R = CH$_2$COOtBu
13e, R = CH$_2$CH$_2$COOtBu To a solution of compound 12b (1.0 equiv.) in DMF or DCM were added Fmoc-amino acid (1.1-1.2 equiv.), HATU (1.2-1.5 equiv.) and DIPEA (2.0-3.0 equiv.) successively. The reaction mixture was stirred at RT for 4 h, which was monitored by LCMS. The mixture was concentrated in vacuo (when DCM was solvent) and the residue was purified by silica gel column chromatography (0-90% ethyl acetate in petroleum ether); or the reaction mixture (when DMF was solvent) was directly purified by reverse phase flash chromatography (50-90% acetonitrile in aq. ammonium bicarbonate (10 mM)) to give compound 13 as white solids.

| 12b g (mmol) | R | Fmoc-aminoacid g (mmol) | HATU g (mmol) | DIPEA g (mmol) | Solvent (mL) | Time (h) | purification | Product # | g | Yield (%) |
|---|---|---|---|---|---|---|---|---|---|---|
| 0.13 (0.20) | H | 0.071 (0.24) | 0.11 (0.29) | 0.077 (0.60) | DMF (10) | 4 | RP-B | 13a | 0.14 | 78 |
| 0.31 (0.50) | CH$_2$OH | 0.18 (0.55) | 0.23 (0.60) | 0.19 (1.50) | DCM (20) | 4 | SGC | 13b | 0.39 | 83 |
| 0.20 (0.32) | (CH$_2$)$_4$NHFmoc | 0.21 (0.35) | 0.15 (0.38) | 0.083 (0.64) | DMF (20) | 4 | RP-B | 13c | 0.30 | 78 |
| 0.31 (0.50) | CH$_2$COOtBu | 0.22 (0.55) | 0.23 (0.60) | 0.19 (1.50) | DCM (20) | 4 | SGC | 13d | 0.43 | 85 |
| 0.31 (0.50) | (CH$_2$)$_2$COOtBu | 0.23 (0.55) | 0.23 (0.60) | 0.19 (1.50) | DCM (20) | 4 | SGC | 13e | 0.42 | 82 |

9H-Fluoren-9-ylmethyl N-({[(4bS,8S,8aR)-8-({[(1S,4aS,10aR)-6-{[(tert-butoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl)carbamate (13a)

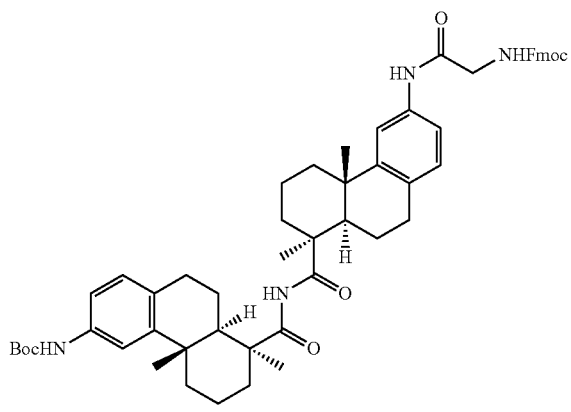

Following the general procedure for Intermediates 13a-e, compound 13a (0.14 g, 78% yield) was obtained as a white solid. ESI m/z: 907 (M+H)+.

9H-Fluoren-9-ylmethyl N-[(1S)-1-{[(4bS,8S,8aR)-8-({[(1S,4aS,10aR)-6-{[(tert-butoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (13b)

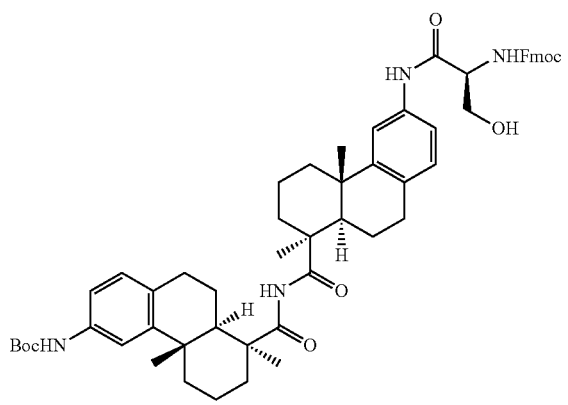

Following the general procedure for Intermediates 13a-e, compound 13b (0.39 g, 83% yield) was obtained as a white solid. ESI m/z: 938 (M+H)+.

9H-Fluoren-9-ylmethyl N-[(5S)-5-{[(4bS,8S,8aR)-8-({[(1S,4aS,10aR)-6-{[(tert-butoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-5-{[(9H-fluoren-9-ylmethoxy)carbonyl]amino}pentyl]carbamate (13c)

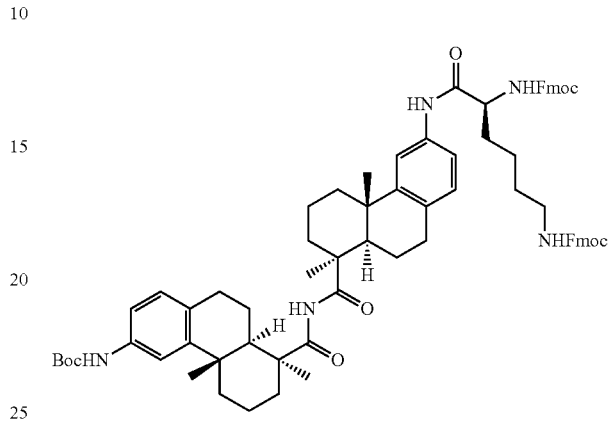

Following the general procedure for Intermediates 13a-e, compound 13c (0.30 g, 78% yield) was obtained as a white solid. ESI m/z: 1201 (M+H)+.

(S)-tert-Butyl 3-(((9H-fluoren-9-yl)methoxy)carbonylamino)-4-((4bS,8S,8aR)-8-((1S,4aS,10aR)-6-(tert-butoxycarbonylamino)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-oxobutanoate (13d)

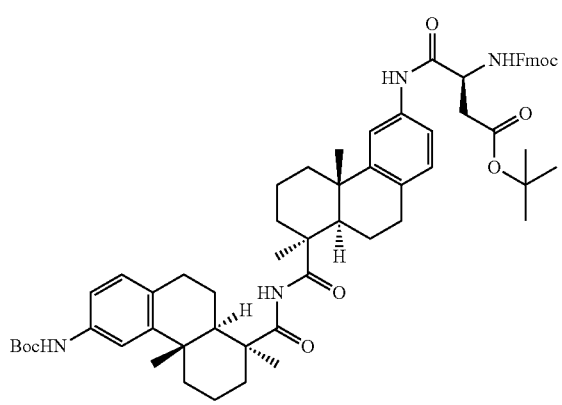

Following the general procedure for Intermediates 13a-e, compound 13d (0.43 g, 85% yield) was obtained as a white solid. ESI m/z: 1021 (M+H)+.

277

(S)-tert-Butyl 4-(((9H-fluoren-9-yl)methoxy)carbo-
nylamino)-5-((4bS,8S,8aR)-8-((1S,4aS,10aR)-6-
(tert-butoxycarbonylamino)-1,4a-dimethyl-1,2,3,4,
4a,9,10,10a-octahydrophenanthrene-1-
carbonylcarbamoyl)-4b,8-dimethyl-4b,5,6,7,8,8a,9,
10-octahydrophenanthren-3-ylamino)-5-
oxopentanoate (13e)

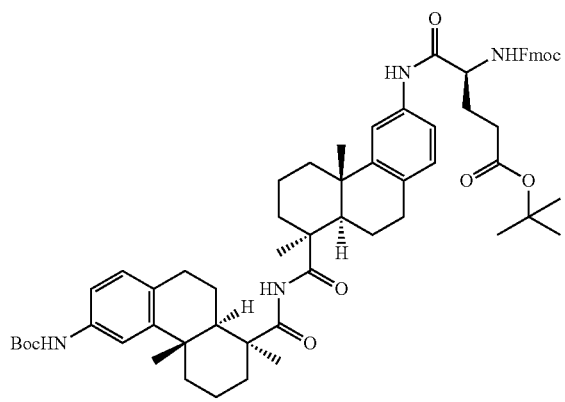

Following the general procedure for Intermediates 13a-e, compound 13e (0.42 g, 82% yield) was obtained as a white solid. ESI m/z: 1036 (M+H)⁺.

Example 3b

Intermediates 14a-e

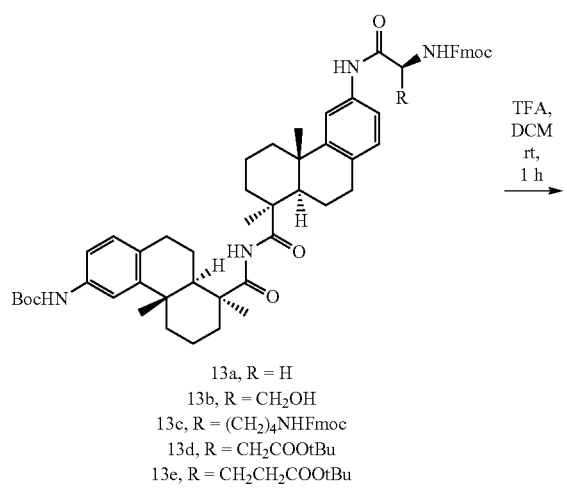

13a, R = H
13b, R = CH₂OH
13c, R = (CH₂)₄NHFmoc
13d, R = CH₂COOtBu
13e, R = CH₂CH₂COOtBu TFA, DCM rt, 1 h →

278

-continued

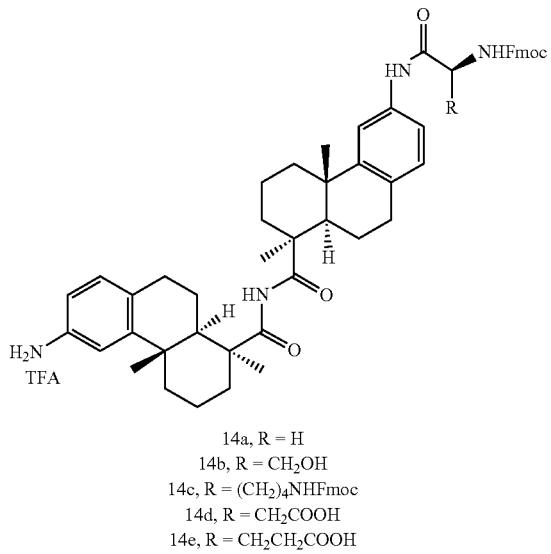

14a, R = H
14b, R = CH₂OH
14c, R = (CH₂)₄NHFmoc
14d, R = CH₂COOH
14e, R = CH₂CH₂COOH To a solution of compound 13 (1.0 equiv.) in DCM was added TFA at RT. The reaction mixture was stirred at RT for an hour and concentrated in vacuo to give crude product 14 as colorless oil, which was used for the next step without further purification.

| | 13 | | TFA | DCM | Crude Product 14 | | |
|---|---|---|---|---|---|---|---|
| # | R | g (mmol) | (mL) | (mL) | # | R | g |
| 13a | H | 0.14 (0.16) | 3 | 10 | 14a | H | 0.13 |
| 13b | CH₂OH | 0.10 (0.11) | 3 | 10 | 14b | CH₂OH | 0.09 |
| 13c | (CH₂)₄NHFmoc | 0.24 (0.20) | 3 | 10 | 14c | (CH₂)₄NHFmoc | 0.22 |
| 13d | CH₂COOtBu | 0.12 (0.12) | 3 | 10 | 14d | CH₂COOH | 0.10 |
| 13e | (CH₂)₂COOtBu | 0.10 (0.10) | 3 | 20 | 14e | (CH₂)₂COOH | 0.08 |

9H-Fluoren-9-ylmethyl N-({[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl)carbamate, trifluoroacetic acid salt (14a)

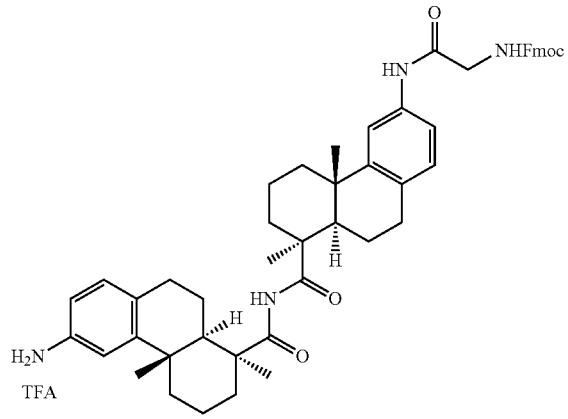

Following the general procedure for Intermediates 14a-e, crude compound 14a (0.14 g, 99% yield, TFA salt) was obtained as colorless oil. ESI m/z: 807 (M+1)$^+$.

9H-Fluoren-9-ylmethyl (S)-1-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-3-hydroxy-1-oxopropan-2-ylcarbamate, trifluoroacetic acid salt (14b)

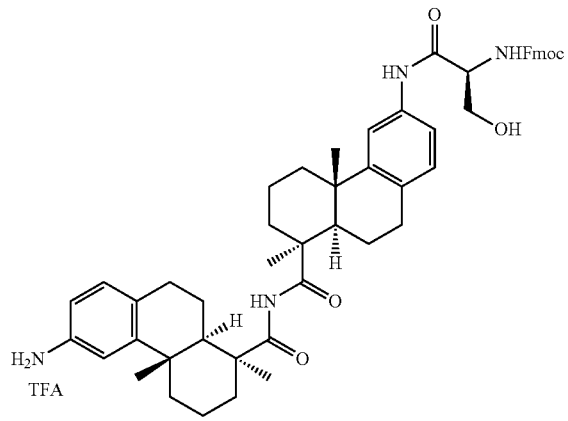

Following the general procedure for Intermediates 14a-e, crude compound 14b (0.14 g, 99% yield, TFA salt) was obtained as colorless oil. ESI m/z: 837 (M+1)$^+$.

9H-Fluoren-9-ylmethyl N-[(5S)-5-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-5-{[(9H-fluoren-9-ylmethoxy)carbonyl]amino}pentyl]carbamate, trifluoroacetic acid salt (14c)

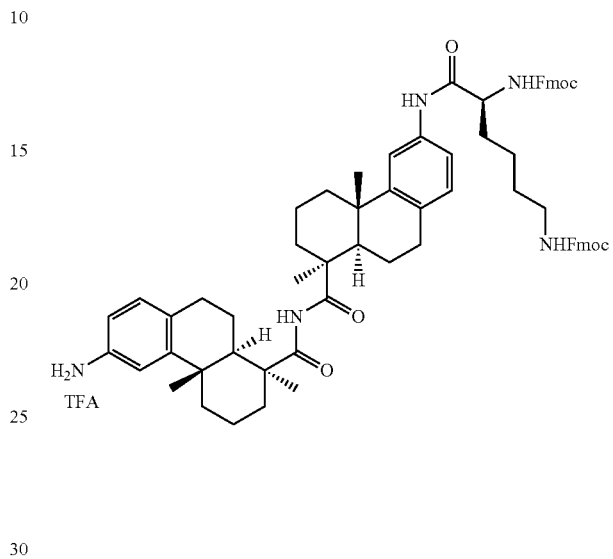

Following the general procedure for Intermediates 14a-e, crude compound 14c (0.22 g, 92% yield, TFA salt) was obtained as colorless oil. ESI m/z: 1101 (M+1)$^+$.

(S)-3-(((9H-Fluoren-9-yl)methoxy)carbonylamino)-4-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-oxobutanoic acid, trifluoroacetic acid salt (14d)

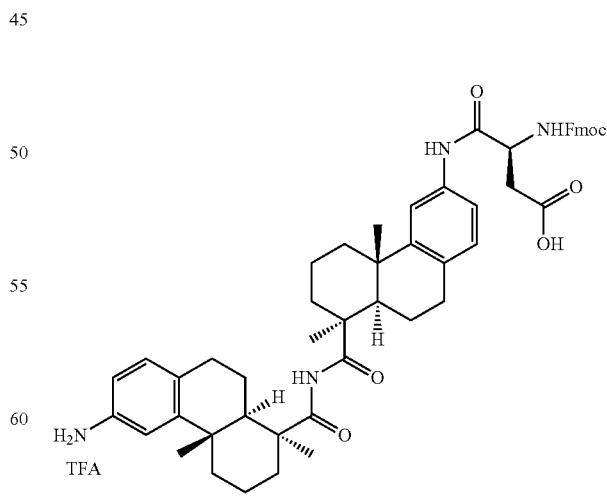

Following the general procedure for Intermediates 14a-e, crude compound 14d (0.10 g, 87% yield, TFA salt) was obtained as colorless oil. ESI m/z: 866 (M+1)$^+$.

(S)-4-(((9H-Fluoren-9-yl)methoxy)carbonylamino)-5-((4bS,8S,8aR)-8-((1S,4aS,10aR)-6-amino-1,4a-dimethyl-1,2,3,4,4a,9,10,10a-octahydro-phenanthrene-1-carbonylcarbamoyl)-4b,8-dimethyl-4b,5,6,7,8,8a,9,10-octahydrophenanthren-3-ylamino)-5-oxopentanoic acid, trifluoroacetic acid salt (14e)

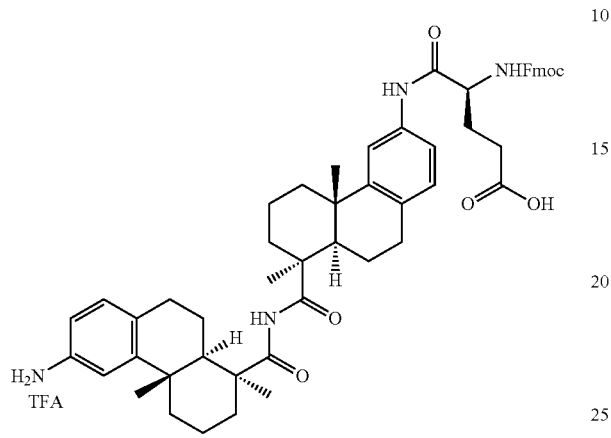

Following the general procedure for Intermediates 14a-e, crude compound 14e (84 mg, 86% yield, TFA salt) was obtained as colorless oil. ESI m/z: 880 (M+1)⁺.

Example 3c

Payloads P4-9, 13, 14, and 17

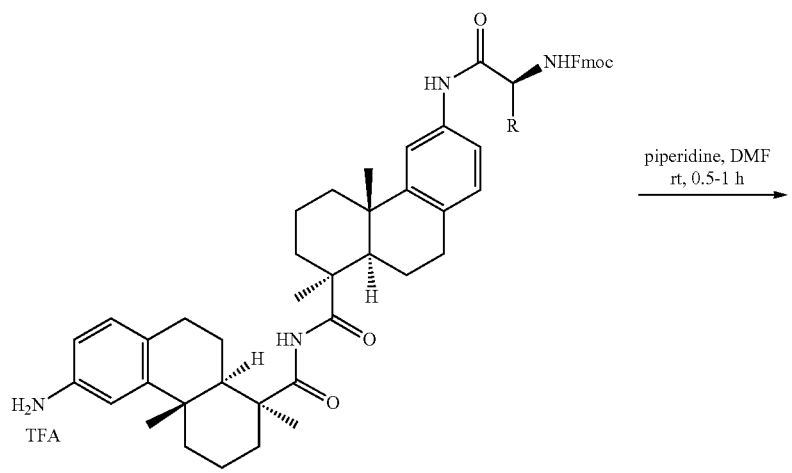

14a, R = H
14b, R = CH$_2$OH
14c, R = (CH$_2$)$_4$NHFmoc
14d, R = CH$_2$COOH
14e, R = CH$_2$CH$_2$COOH

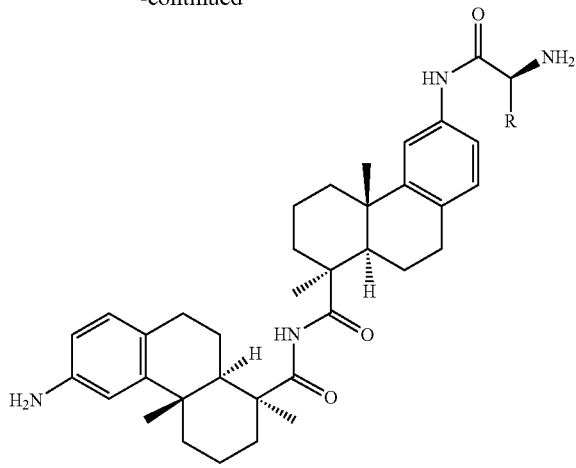

P4, R = H
P5, R = CH₂OH
P6, R = (CH₂)₄NH₂
P7, R = CH₂COOH
P8, R = CH₂CH₂COOH

To a solution of crude 14, obtained above, in DMF was added piperidine. The mixture was stirred at RT for half an hour, which was monitored by LCMS. The mixture was directly purified by prep-HPLC (method B) to give payloads P4-8 as white solids.

| | Crude 14 | | | | | | Payloads P4-8 | |
|---|---|---|---|---|---|---|---|---|
| # | R | g (mmol) | piperidine (mL) | DMF (mL) | Time (hour) | purification | # | R | mg (Yield) |
| 14a | H | 0.066 (0.073) | 0.5 | 3 | 0.5 | Prep-B | P4 | H | 12 (28%) |
| 14b | CH₂OH | 0.10 (0.11) | 0.5 | 3 | 0.5 | Prep-B | P5 | CH₂OH | 41 (67%) |
| 14c | (CH₂)₄NHFmoc | 0.050 (0.045) | 0.5 | 5 | 1 | Prep-B | P6 | (CH₂)₄NH₂ | 5 (17%) |
| 14d | CH₂COOH | 0.10 (0.12) | 0.5 | 3 | 0.5 | Prep-B | P7 | CH₂COOH | 39 (51%) |
| 14e | (CH₂)₂COOH | 0.10 (0.12) | 0.5 | 3 | 0.5 | Prep-B | P8 | (CH₂)₂COOH | 44 (58%) |

(1S,4aS,10aR)-N-[(1S,4aS,10aR)-6-(2-Aminoacetamido)-1,4a-dimethyl-1,2,3,4,4a,9,10,10a-octahydrophenanthrene-1-carbonyl]-6-amino-1,4a-dimethyl-1,2,3,4,4a,9,10,10a-octahydrophenanthrene-1-carboxamide (P4)

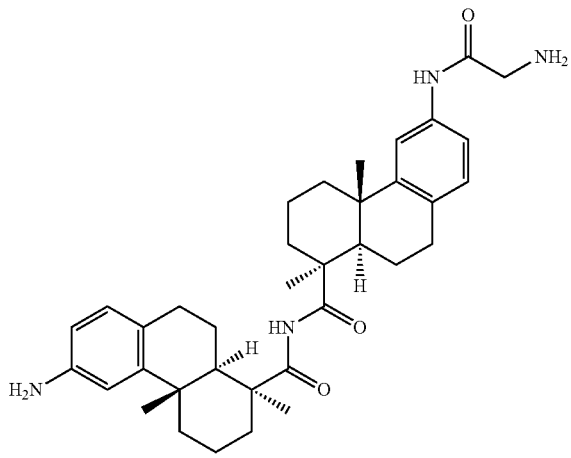 [SMILES: C[C@]1(C(=O)NC(=O)[C@@]2(C)CCC[C@]3(C)c4cc(NC(=O)CN)ccc4CC[C@@H]23)CCC[C@]2(C)c3cc(N)ccc3CC[C@@H]12]

Following the general procedure for Payloads P4-8, compound P4 (12 mg, 28% yield) was obtained as a white solid. ESI m/z: 585 (M+1)+. $^1$H NMR (500 MHz, DMSO$_{d6}$) δ 9.79 (s, 1H), 8.12 (s, 1H), 7.50 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.70 (m, 2H), 3.20 (s, 3H), 2.95-2.83 (m, 1H), 2.80-2.70 (m, 2H), 2.70-2.60 (m, 1H), 2.30-2.20 (m, 2H), 2.20-2.10 (m, 4H), 2.05-1.70 (m, 4H), 1.70-1.50 (m, 4H), 1.31-1.25 (m, 8H), 1.20-1.10 (m, 2H), 1.05 (d, J=7.5 Hz, 6H) ppm.

(1S,4aS,10aR)-6-Amino-N-((1S,4aS,10aR)-6-((S)-2-amino-3-hydroxypropanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P5)

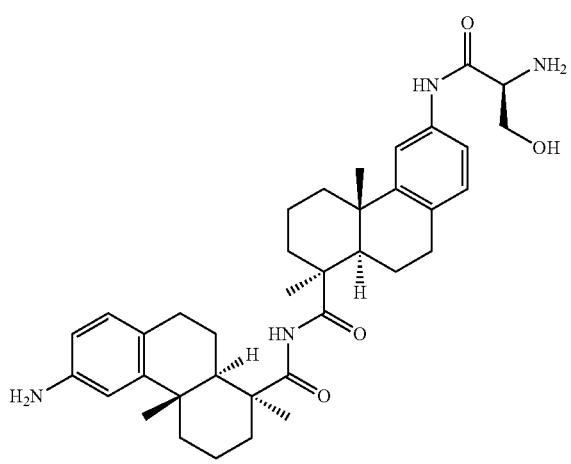 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(N)ccc3CC[C@@H]12]

Following the general procedure for Payloads P4-8, compound P5 (41 mg, 67% yield) was obtained as a white solid. ESI m/z: 615 (M+1)+. $^1$H NMR (500 MHz, DMSO$_{d6}$) δ 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.84-4.76 (m, 1H), 4.67 (s, 2H), 3.60-3.45 (m, 2H), 2.95-2.83 (m, 1H), 2.80-2.60 (m, 4H), 2.30-2.20 (m, 3H), 2.20-2.10 (m, 4H), 1.95-1.75 (m, 5H), 1.70-1.50 (m, 4H), 1.40-1.30 (m, 2H), 1.28 (s, 3H), 1.26 (s, 3H), 1.20-1.10 (m, 3H), 1.01 (s, 3H), 0.98 (s, 3H) ppm.

(1S,4aS,10aR)-6-Amino-N-((1S,4aS,10aR)-6-((S)-2,6-diaminohexanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P6)

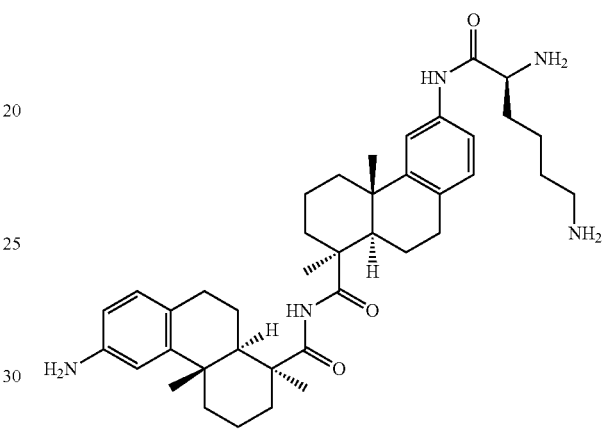

Following the general procedure for Payloads P4-8, compound P6 (5 mg, 17% yield) was obtained as a white solid. ESI m/z: 656 (M+1)+. $^1$H NMR (500 MHz, DMSO$_{d6}$) δ 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.70 (m, 2H), 3.20 (s, 2H), 2.95-2.83 (m, 2H), 2.80-2.70 (m, 2H), 2.70-2.60 (m, 2H), 2.37-2.35 (m, 1H), 2.30-2.20 (m, 3H), 2.20-2.10 (m, 5H), 2.05-1.95 (m, 2H), 1.95-1.75 (m, 5H), 1.70-1.50 (m, 6H), 1.31-1.25 (m, 8H), 1.20-1.10 (m, 3H), 1.05 (d, J=7.5 Hz, 6H), 0.85 (t, J=6.0 Hz, 1H) ppm.

(S)-3-Amino-4-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-oxobutanoic acid (P7)

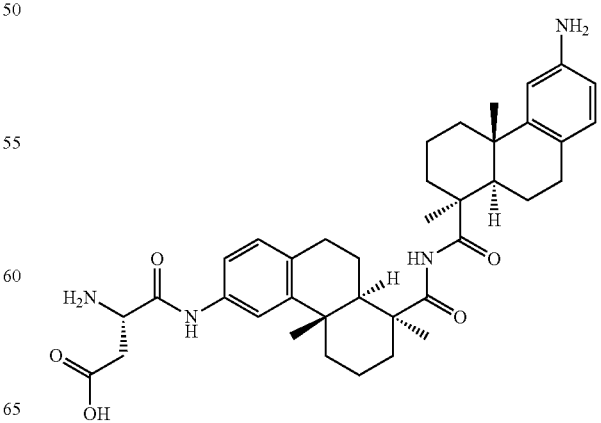

Following the general procedure for Payloads P4-8, compound P7 (39 mg, 51% yield) was obtained as a white solid. ESI m/z: 643 (M+1)⁺. ¹H NMR (500 MHz, DMSO$_{d6}$) δ 10.5-10.0 (br, 1H), 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.84-4.50 (m, 2H), 3.75-3.68 (m, 2H), 2.95-2.83 (m, 1H), 2.80-2.60 (m, 4H), 2.40-2.20 (m, 4H), 2.20-2.10 (m, 5H), 1.95-1.70 (m, 5H), 1.70-1.50 (m, 5H), 1.27 (d, J=7.5 Hz, 6H), 1.20-1.10 (m, 2H), 1.01 (s, 3H), 0.98 (s, 3H) ppm.

(S)-4-Amino-5-((4bS,8S,8aR)-8-((1S,4aS,10aR)-6-Amino-1,4a-dimethyl-1,2,3,4,4a,9,10,10a-octahydro-phenanthrene-1-carbonylcarbamoyl)-4b,8-dimethyl-4b,5,6,7,8,8a,9,10-octahydrophenanthren-3-ylamino)-5-oxopentanoic acid (P8)

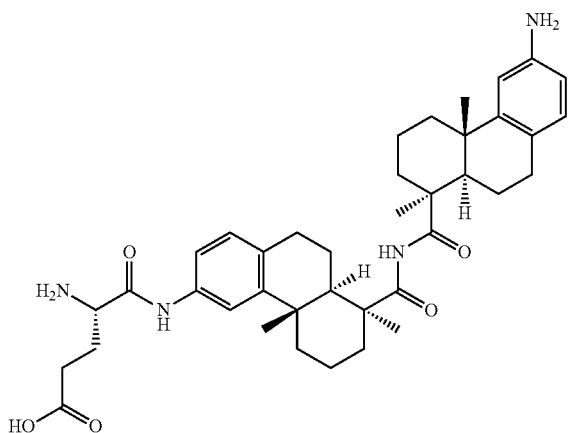 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(N)ccc3CC[C@@H]12]

Following the genera procedure or Payloads P4-8, compound P8 (44 mg, 58% yield) was obtained as a white solid. ESI m/z: 657 (M+1)⁺. ¹H NMR (500 MHz, DMSO$_{d6}$) δ 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.70 (m, 2H), 2.95-2.83 (m, 1H), 2.80-2.60 (m, 5H), 2.30-2.20 (m, 4H), 2.20-2.10 (m, 5H), 1.95-1.75 (m, 5H), 1.70-1.50 (m, 5H), 1.50-1.40 (m, 4H), 1.27 (d, J=7.5 Hz, 6H), 1.20-1.10 (m, 2H), 1.01 (s, 3H), 0.98 (s, 3H) ppm.

(1S,4aS,10aR)-6-amino-N-((1S,4aS,10aR)-6-((S)-2-amino-3-(1H-imidazol-4-yl)propanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P9)

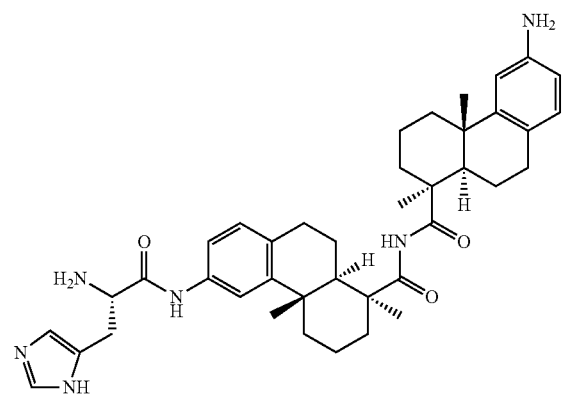 [SMILES: C[C@]1(C(=O)NC(=O)[C@@]2(C)CCC[C@]3(C)c4cc(NC(=O)[C@@H](N)Cc5cnc[nH]5)ccc4CC[C@@H]23)CCC[C@]2(C)c3cc(N)ccc3CC[C@@H]12]

To a solution of Fmoc-His-OH (0.38 g, 1.0 mmol) in DCM (5 mL) were added Fmoc-OSu (0.37 g, 1.1 mmol) and DIPEA (0.26 g, 2.0 mmol). The reaction mixture was stirred at RT overnight. The volatiles were removed in vacuo and the residue was purified by flash chromatography (5-10% methanol in DCM) to give Fmoc-His(Fmoc)-OH (0.50 g, 84% yield, ESI m/z: 600 (M+1)⁺) as a white solid.

To a solution of compound 12b (0.31 g, 0.50 mmol) in DCM (20 mL) were added the Fmoc-His(Fmoc)-OH (0.33 g, 0.55 mmol), obtained above, HATU (0.23 g, 0.60 mmol) and DIPEA (0.19 g, 1.5 mmol) successively. The resulting mixture was stirred at RT for 4 h, which was monitored by LCMS. To the reaction mixture was added piperidine (0.5 mL) and the mixture was stirred at RT for an hour until Fmoc was totally removed, as monitored by LCMS. The mixture was concentrated in vacuo and the residue was purified by reverse phase flash chromatography (50-80% acetonitrile in water) to give Boc-P9 (0.15 g) as a white solid, half of which was dissolved in DCM (20 mL). To the solution was added TFA (3 mL). The mixture was stirred at RT for an hour until Boc was removed according to LCMS. The volatiles were removed in vacuo and the residue was purified by prep-HPLC (method B) to give compound P9 (17 mg, 12% yield) as a white solid. ESI m/z: 665 (M+1)⁺. ¹H NMR (500 MHz, DMSO$_{d6}$) δ 11.82 (s, 1H), 9.75 (s, 1H), 8.09 (s, 1H), 7.52-7.50 (m, 2H), 7.41 (dd, J=8.5 Hz, 1.5 Hz, 1H), 6.96 (d, J=8.5 Hz, 1H), 6.90-6.80 (m, 1H), 6.68 (d, J=8.5 Hz, 1H), 6.48 (d, J=1.5 Hz, 1H), 6.34 (dd, J=7.5 Hz, 1.5 Hz, 1H), 4.84-4.50 (m, 2H), 3.60-3.45 (m, 2H), 2.95-2.83 (m, 2H), 2.80-2.70 (m, 2H), 2.70-2.60 (m, 2H), 2.40-2.10 (m, 8H), 1.95-1.70 (m, 5H), 1.70-1.50 (m, 4H), 1.27 (d, J=7.5 Hz, 6H), 1.20-1.10 (m, 2H), 1.01 (s, 3H), 0.98 (s, 3H) ppm.

(1S,4aS,10aR)-N-[(1S,4aS,10aR)-6-amino-1,4a-dimethyl-1,2,3,4,4a,9,10,10a-octahydro-phenanthrene-1-carbonyl]-6-[(2S)-2-aminopropanamido]-1,4a-dimethyl-1,2,3,4,4a,9,10,10a-octahydrophenanthrene-1-carboxamide (13)

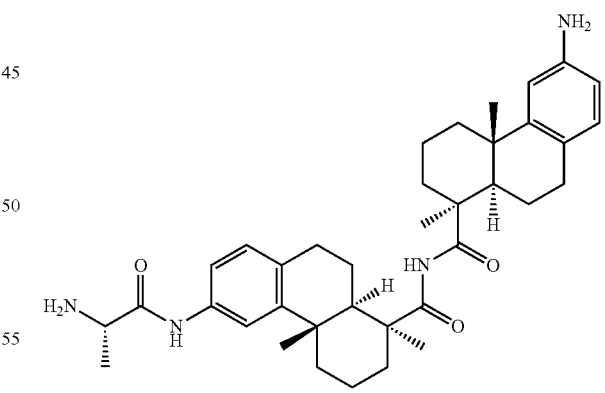

Following the similar procedure as P9, except substituting Fmoc-Ala-OH for Fmoc-His(Fmoc)-OH, payload P13 (12 mg, 59% yield) was obtained as a white solid. ¹H NMR (400 MHz, DMSO$_{d6}$) δ 9.85 (br s, 1H), 8.09 (s, 1H), 7.54-7.51 (m, 1H), 7.41-7.39 (m, 1H), 6.95 (d, J=8.4 Hz, 1H), 6.68 (d, J=8.0 Hz, 1H), 6.48 (d, J=1.6 Hz, 1H), 6.35-6.32 (m, 1H), 4.69 (s, 2H), 3.58-3.41 (m, 3H), 2.91-2.61 (m, 4H), 2.26-2.14 (m, 6H), 1.91-1.78 (m, 4H), 1.66-1.55 (m, 4H), 1.33-1.08 (m, 13H), 1.00 (s, 3H), 0.98 (s, 3H) ppm.

289

(1S,4aS,10aR)-N-[(1S,4aS,10aR)-6-(2-hydroxyacetamido)-1,4a-dimethyl-1,2,3,4,4a,9,10,10a-octahydrophenanthrene-1-carbonyl]-6-amino-1,4a-dimethyl-1,2,3,4,4a,9,10,10a-octahydrophenanthrene-1-carboxamide P14)

290

(1S,4aS,10aR)-N-[(1S,4aS,10aR)-6-(2-hydroxyacetamido)-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (P17)

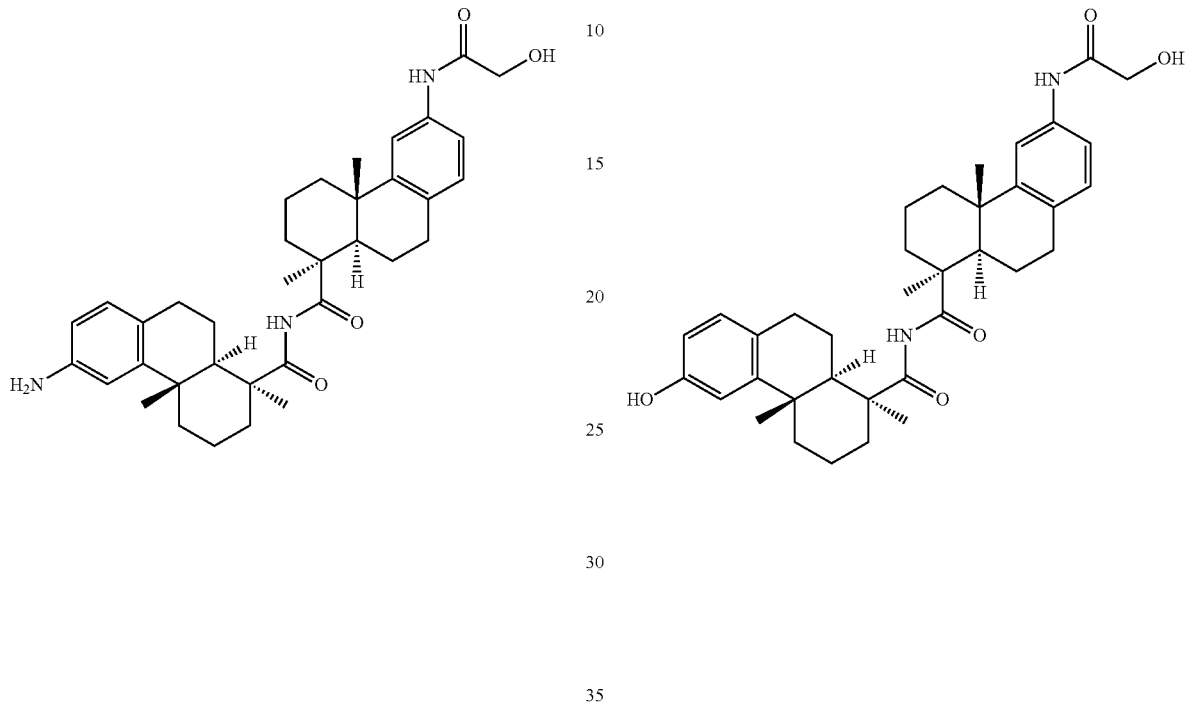

To a mixture of glycolic acid (2.2 mg, 29 µmol) and HATU (18.2 mg, 48 µmol) in DMF (2.0 mL) were added DIPEA (12 µL, 72 µmol) and compound 12b (15 mg, 24 µmol). The reaction mixture was stirred at RT for 2 hours, which was monitored by LCMS. The resulting mixture was directly purified by reversed phase flash chromatography (0-100% acetonitrile in aq. ammonium bicarbonate (10 mM)) to give Boc-P14, which was dissolved into DCM (2 mL). To the solution was added TFA (0.5 mL), and the mixture was stirred at RT for 2 hours until Boc was totally removed, which was monitored by LCMS. The resulting mixture was concentrated in vacuo and the residue was purified by prep-HPLC (method B) to give payload P14 (4.3 mg, 31% yield) as a white solid. ESI m/z: 686.5 (M+1)$^+$. $^1$H NMR (400 MHz, DMSO$_{d6}$) δ 9.46 (s, 1H), 8.10 (s, 1H), 7.59 (d, J=1.8 Hz, 1H), 7.49 (dd, J=8.3, 1.9 Hz, 1H), 6.96 (d, J=8.3 Hz, 1H), 6.68 (d, J=8.2 Hz, 1H), 6.47 (d, J=2.1 Hz, 1H), 6.33 (dd, J=8.1, 2.1 Hz, 1H), 5.65 (t, J=6.0 Hz, 1H), 4.70 (s, 2H), 3.94 (d, J=6.0 Hz, 2H), 2.93-2.85 (m, 1H), 2.80-2.72 (m, 2H), 2.71-2.63 (m, 1H), 2.34-2.08 (m, 6H), 1.94-1.76 (m, 4H), 1.68-1.52 (m, 4H), 1.35-1.23 (m, 8H), 1.19-1.10 (m, 2H), 0.99 (d, J=8.1 Hz, 6H) ppm.

To a solution of payload P1 (10 mg, 0.019 mmol) in DMF (2 mL) were added HATU (14 mg, 0.038 mmol) and DIPEA (9.8 mg, 0.076 mmol) at RT. The mixture was stirred at RT for 15 minutes before the addition of glycolic acid (1.73 mg, 0.0228 mmol). The reaction mixture was stirred at RT, which was monitored by LCMS. The resulting mixture was directly purified by prep-HPLC (method B) to give the P17 (5.7 mg, 51% yield) as a white solid. ESI m/z: 587.4 (M+1)$^+$. $^1$H NMR (400 MHz, DMSO$_{d6}$) δ 9.46 (s, 1H), 9.00 (s, 1H), 8.11 (s, 1H), 7.59 (s, 1H), 7.53-7.45 (m, 1H), 6.96 (d, J=8.3 Hz, 1H), 6.82 (d, J=8.3 Hz, 1H), 6.63 (d, J=2.3 Hz, 1H), 6.50 (dd, J=8.2, 2.4 Hz, 1H), 5.64 (t, J=6.0 Hz, 1H), 3.94 (d, J=5.9 Hz, 2H), 2.93-2.66 (m, 4H), 2.29-2.10 (m, 6H), 2.00-1.80 (m, 4H), 1.72-1.50 (m, 4H), 1.30-0.90 (m, 16H) ppm.

Example 4

This example demonstrates general methods for the synthesis of the podocarpic acid derivatives P10 and P11 in Table 1, above. This example refers to the compounds numbered from 14a, 15a-b, and P10 and P11 in FIG. 2B.

(S)-tert-Butyl 4-amino-5-((4bS,8S,8aR)-8-((1S,4aS, 10aR)-6-(2-aminoacetamido)-1,4a-dimethyl-1,2,3,4, 4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoate, di-trifluoroacetic acid salt (15a)

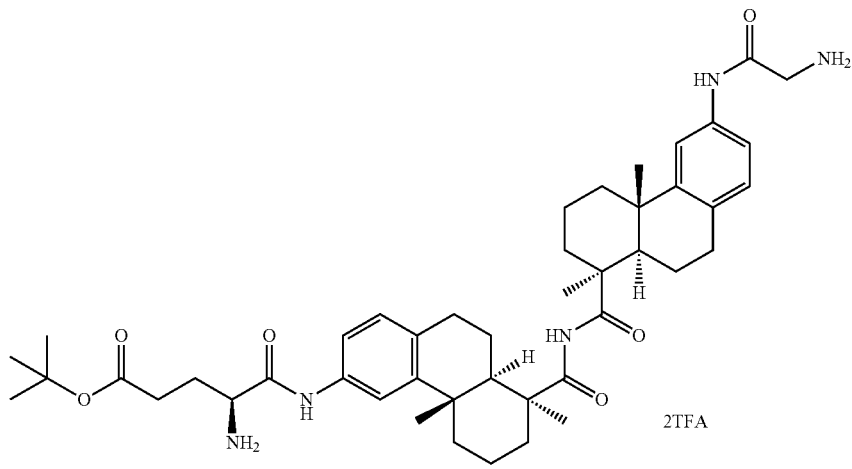 [SMILES: CC(C)(C)OC(=O)CC[C@H](N)C(=O)Nc1ccc2c(c1)[C@@]1(C)CCC[C@](C)(C(=O)NC(=O)[C@@]3(C)CCC[C@]4(C)c5cc(NC(=O)CN)ccc5CC[C@@H]34)[C@@H]1CC2]

To a solution of Fmoc-Glu(OtBu)-OH (74 mg, 0.17 mmol) and DIPEA (55 µL, 0.32 mmol) in DMF (5.0 mL) was added HATU (91 mg, 0.24 mmol). The mixture was stirred at RT for 15 min before the addition of compound 14a (0.14 g, 0.16 mmol). The reaction mixture was stirred at RT overnight, which was monitored by LCMS. To the reaction mixture was then added piperidine (1 mL) dropwise. The reaction mixture was stirred at RT for an hour until Fmoc was totally removed according to LCMS. The resulting mixture was directly separated by reverse phase flash chromatography (0-100% acetonitrile in aq. TFA (0.01%)) to give compound 15a (0.13 g, 80% yield) as a yellow solid. ESI m/z: 770.5 (M+1)$^+$.

(4S,4'S)-tert-Butyl 5,5'-(4bS,4b'S,8S,8aR,8'S,8a'R)-8,8'-(azanediylbis(oxomethylene))bis(4b,8-dimethyl-4b,5,6,7,8,8a,9,10-octahydrophenanthrene-8,3-diyl) bis(azanediyl)bis(4-amino-5-oxopentanoate) di-trifluoroacetic acid salt (15b)

To a solution of Fmoc-Glu(OtBu)-OH (0.15 g, 0.35 mmol) and DIPEA (83 µL, 0.48 mmol) in DMF (5.0 mL) was added HATU (0.15 g, 0.40 mmol). The mixture was stirred at RT for 30 min before the addition of compound P2 (0.10 g, 0.16 mmol). The reaction mixture was stirred at RT overnight, which was monitored by LCMS. To the reaction mixture was then added piperidine (1 mL) dropwise. The reaction mixture was stirred at RT for 3 h until Fmoc was totally removed according to LCMS. The resulting mixture was directly separated by reverse phase flash chromatography (0-100% acetonitrile in aq. TFA (0.01%)) to give compound 15b (0.14 g, 78% yield) as a yellow solid. ESI m/z: 899 (M+1)$^+$.

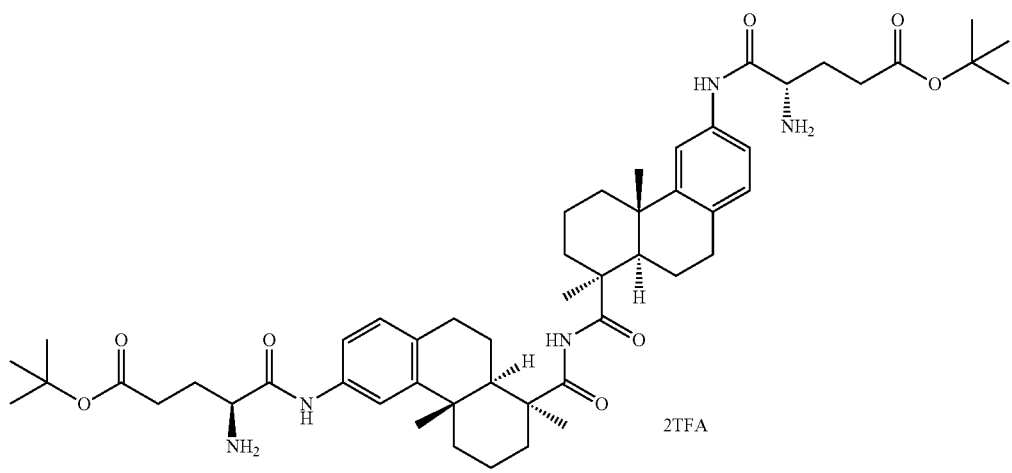 [SMILES: CC(C)(C)OC(=O)CC[C@H](N)C(=O)Nc1ccc2c(c1)[C@@]1(C)CCC[C@](C)(C(=O)NC(=O)[C@@]3(C)CCC[C@]4(C)c5cc(NC(=O)[C@@H](N)CCC(=O)OC(C)(C)C)ccc5CC[C@@H]34)[C@@H]1CC2]

(S)-4-Amino-5-((4bS,8S,8aR)-8-((1S,4aS,10aR)-6-(2-aminoacetamido)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoic acid (P10)

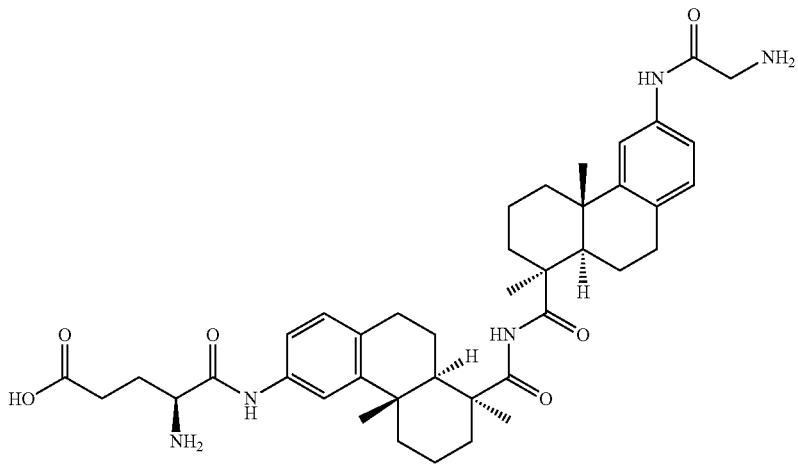 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)CN)ccc3CC[C@@H]12]

A mixture of compound 15a (0.13 g, 0.13 mmol) in neat TFA (2.0 mL) was stirred at RT for an hour, which was monitored by LCMS. The resulting mixture was diluted with DCM (20 mL) and concentrated in vacuo. The residue was purified by reversed phase flash chromatography (0-100% acetonitrile in aq. sodium bicarbonate (10 mM)) to give P10 (20 mg, 22% yield) as a white solid. ESI m/z: 358 (M/2+1)$^+$; 714.5 (M+1)$^+$. $^1$H NMR (400 MHz, DMSO$_{d6}$) δ 9.85 (br s, 1H), 8.12 (s, 1H), 7.51 (s, 2H), 7.42-7.36 (m, 2H), 6.96 (dd, J=8.0 Hz and 3.0 Hz, 2H), 3.67 (br s, 8H), 3.36-3.33 (m, 1H), 3.22 (s, 2H), 2.91-2.87 (m, 2H), 2.80-2.71 (m, 2H), 2.31-2.28 (m, 4H), 2.17-2.14 (m, 4H), 1.91-1.82 (m, 5H), 1.69-1.58 (m, 5H), 1.34-1.23 (m, 6H), 1.19-1.12 (m, 2H), 1.01 (s, 6H) ppm.

(4S,4'S)-5,5'-(4bS,4b'S,8S,8aR,8'S,8a'R)-8,8'-(Azanediylbis(oxomethylene))bis(4b,8-dimethyl-4b,5,6,7,8,8a,9,10-octahydrophenanthrene-8,3-diyl)bis(azanediyl)bis(4-amino-5-oxopentanoic acid) (P11)

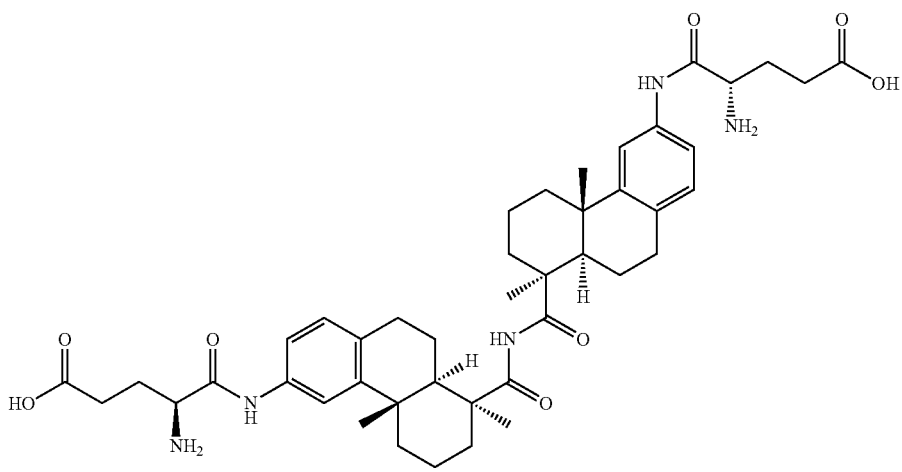 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)[C@@H](N)CCC(=O)O)ccc3CC[C@@H]12]

A mixture of compound 15b (0.14 g, 0.14 mmol) in neat 1FA-(3.0 mL) was stirred at RT for an hour, which was monitored by LCMS. The resulting mixture was diluted with DCM (30 mL) and concentrated in vacuo. The residue was purified by reverse phase flash chromatography (0-100% acetonitrile in aq. sodium bicarbonate (10 mM)) to give P11 (20 mg, 18% yield) as a white solid. ESI m/z: 394 (M/2+1)⁺. ¹H NMR (400 MHz, DMSO$_{d6}$) δ 9.85 (br s, 2H), 8.12 (s, 1H), 7.51 (s, 2H), 7.9 (dd, J=8.4 Hz and 1.6 Hz, 2H), 6.97 (d, J=8.0 Hz, 2H), 3.5 (br s, 6H), 3.40-3.37 (m, 2H), 3.16 (s, 1H), 2.91-2.88 (m, 2H), 2.79-2.66 (m, 2H), 2.33-2.29 (m, 7H), 2.18-2.15 (m, 4H), 1.91-1.84 (m, 6H), 1.71-1.59 (m, 6H), 1.35-1.23 (m, 6H), 1.18-1.12 (m, 2H), 1.01 (s, 6H) ppm.

Example 4a

This example demonstrates general methods for the synthesis of the podocarpic acid derivative P19 in Table 1, above. This example refers to the compounds in FIG. 2C.

(4bS,8S,8aR)-8-{[(1S,4aS,10aR)-6-{[(tert-butoxy)carbonyl]amino}-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl tert-butyl carbonate (16)

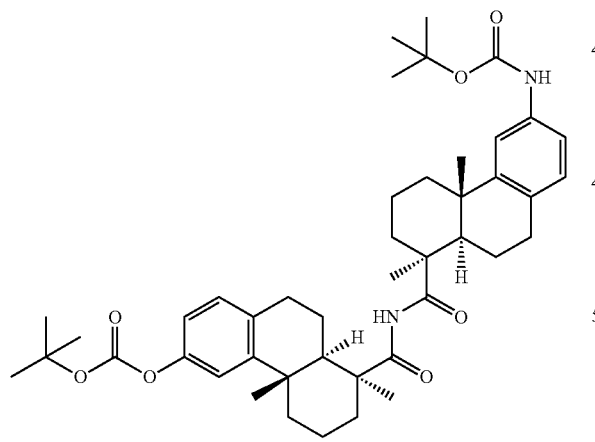

To a mixture of payload P1 (0.10 g, 0.19 mmol) in tert-butanol (2 mL) were added potassium carbonate (78 mg, 0.57 mmol) and Boc anhydride (0.12 g, 0.57 mmol) at RT, and the reaction mixture was stirred at 60° C. for 3 hours, which was monitored by LCMS. The resulting mixture was then cooled and concentrated in vacuo. The residue was dissolved into DCM (100 mL) and the solution was washed with water and brine, dried over anhydrous sodium sulfate and concentrated in vacuo to give crude product 16 (0.14 g, crude) as a white solid, which was used for the next step without further purification. ESI m/z: 729.4 (M+1)⁺.

(4bS,8S,8aR)-8-{[(1S,4aS,10aR)-7-bromo-6-{[(tert-butoxy)carbonyl]amino}-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl tert-butyl carbonate (17)

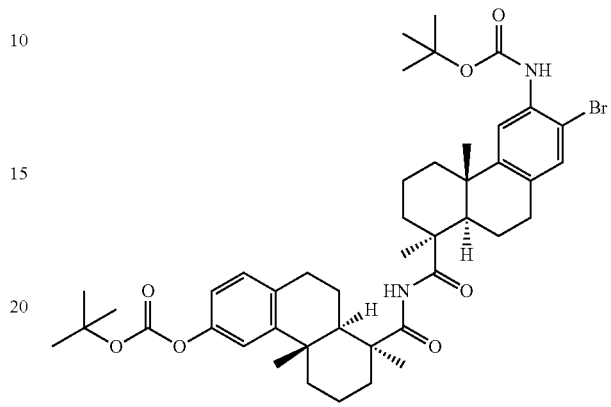

To a solution of crude compound 16 (0.14 g, obtained above) in DMF (4 mL) was added NBS (50 mg, 0.28 mmol), and the reaction mixture was stirred at RT overnight, which was monitored by LCMS. The resulting mixture was directly purified by reversed phase flash chromatography (0-100% acetonitrile in aq. TFA (0.01%)) to give compound 17 (40 mg, 26% yield in 2 steps) as a yellow solid. ESI m/z: 807.3 (M+1)⁺.

(4bS,8S,8aR)-8-{[(1S,4aS,10aR)-6-{[(tert-butoxy)carbonyl]amino}-7-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl tert-butyl carbonate (19)

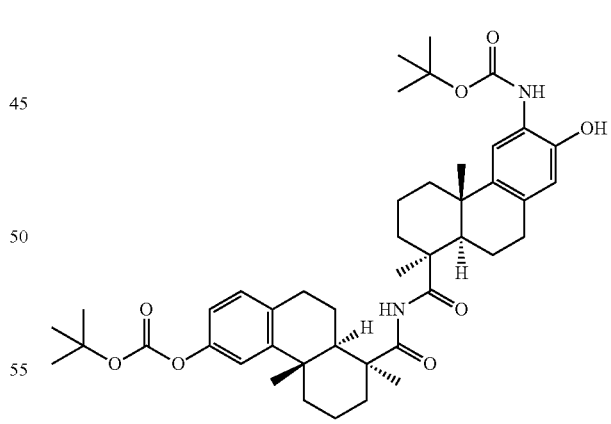

A mixture of compound 17 (40 mg, 50 μmol), potassium acetate (12 mg, 0.12 mmol) and bis(pinacolato)diboron 18 (50 mg, 0.20 mmol) in dry dioxane (5 mL) was degassed and purged with nitrogen 3 times. To the mixture was added Pd(dppf)Cl₂ (1.8 mg, 2.5 μmol) under nitrogen. The resulting suspension was stirred at 90° C. under nitrogen for half an hour, which was monitored by LCMS. The mixture was then cooled to RT and filtered through Celite. To the filtrate was added hydrogen peroxide (30% aq., 2.0 mL) dropwise over 10 minutes at 0° C. The reaction mixture was stirred at 0° C. for another half an hour, which was monitored by LCMS. The resulting mixture was then directly purified by reversed phase flash chromatography (0-100% acetonitrile in aq. TFA (0.01%)) to give crude compound 19 (35 mg, 50% purity, 95% crude yield) as a yellow solid, which was used for the next step without further purification. ESI m/z: 745.5 (M+1)$^+$.

(1S,4aS,10aR)-N-[(1S,4aS,10aR)-6-amino-7-hydroxy-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (P19)

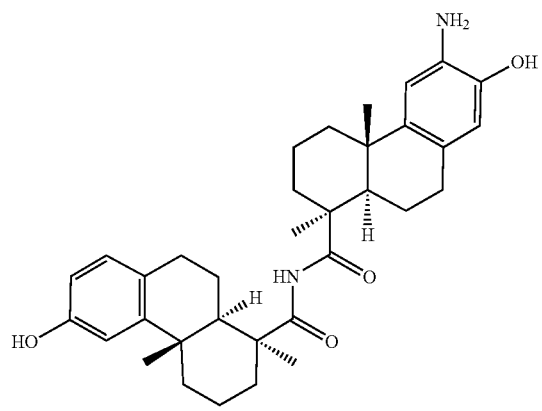 [SMILES: C[C@]1(C(=O)NC(=O)[C@@]2(C)CCC[C@]3(C)c4cc(N)c(O)cc4CC[C@@H]23)CCC[C@]2(C)c3cc(O)ccc3CC[C@@H]12]

To a solution of crude compound 19 (35 mg, obtained above) in DCM (5 mL) was added TFA (2 mL) dropwise at 0° C. over 5 minutes. The reaction mixture was stirred at RT for half an hour until Boc was totally removed, which was monitored by LCMS. The volatiles were removed in vacuo and the residue was purified by prep-HPLC (method A) to give payload P19 (6.5 mg, 24% yield from compound 17) as an off-white solid. ESI m/z: 545.3 (M+1)$^+$. $^1$H NMR (400 MHz, DMSO$_{d6}$) δ 9.03 (s, 1H), 8.76 (s, 1H), 8.08 (s, 1H), 6.81 (d, J=8.4 Hz, 1H), 6.62 (d, J=2.4 Hz, 1H), 6.49 (dd, J=8.4, 2.8 Hz, 1H), 6.47 (s, 1H), 6.27 (s, 1H), 4.21 (s, 2H), 2.84-2.80 (m, 1H), 2.73-2.57 (m, 3H), 2.25-2.19 (m, 2H), 2.15-2.08 (m, 4H), 1.89-1.77 (m, 4H), 1.62-1.54 (m, 4H), 1.30 (s, 3H), 1.28 (s, 3H), 1.31-1.20 (m, 2H), 1.14-1.10 (m, 2H), 0.98 (s, 3H), 0.94 (s, 3H) ppm.

Example 5

This example demonstrates methods for the synthesis of the linker-payloads LP1-LP5, and LP20 in Table 2, above. This example refers to the compounds numbered 12b and from 102a-b to 106a-e and linker-payloads LP1-LP5 in FIG. 3.

Example 5a

Intermediates 102a-b

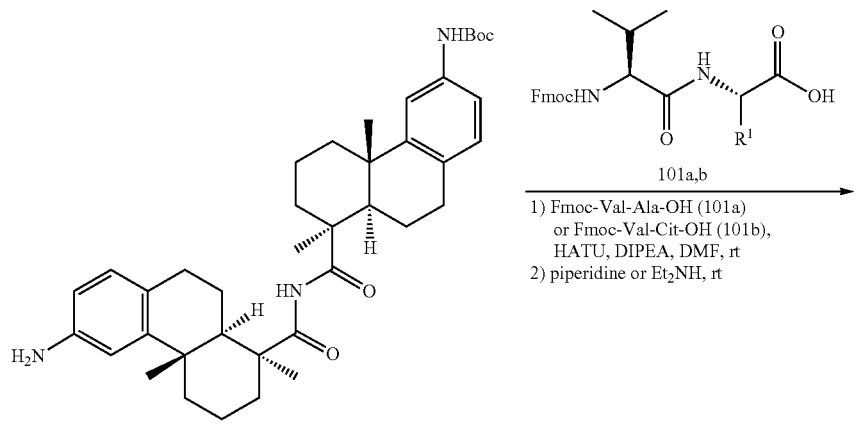

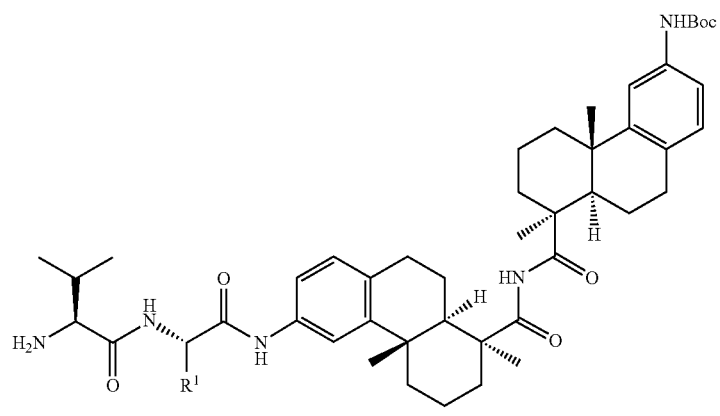

102a, R$^1$ = CH$_3$
102b, R$^1$ = (CH$_2$)$_3$NHCONH$_2$

To a solution of acid (Fmoc-Val-Ala-OH (101a, 1.2 equiv.) or Fmoc-Val-Cit-OH (101b, 1.2 equiv.) in DMF were added HATU (1.2 equiv.) and DIPEA (2.0-3.0 equiv.) at RT. After the mixture was stirred at RT for 5 min, compound 12b (1.0 equiv.) was added. The resulting mixture was stirred at RT for 4-20 h until the amine was consumed according to LCMS. To the mixture was then added piperidine (excess), and the mixture was stirred at RT for 1-6 h until Fmoc was totally removed, as monitored by LCMS. The reaction mixture was filtered through a membrane and the filtrate was directly purified by prep-HPLC (method B) or reverse phase flash chromatography to give compound 102 (38-72% yield) as a white solid.

| | | Step 1 | | | | Step 2 | | | Product | |
|---|---|---|---|---|---|---|---|---|---|---|
| Amine g (mmoL) | Acid g (mmoL) | HATU g (mmol) | DIPEA g (mmol) | DMF (mL) | Time (hr) | Piperidine (mL) | Time (hr) | Purification | # | g (yield) |
| 12b 0.31 (0.50) | 101a 0.25 (0.60) | 0.23 (0.60) | 0.19 (1.5) | 20 | 4 | 0.5 | 1 | RP | 102a | 0.29 (72%) |
| 12b 0.50 (0.80) | 101b 0.48 (0.96) | 0.36 (0.96) | 0.28 mL (1.6) | 6 | 20 | 0.5 | 6 | Prep-B | 102b | 0.27 (38%) | tert-Butyl N-[(4bS,8S,8aR)-8-({[(1S,4aS,10aR)-6-[(2S)-2-[(2S)-2-amino-3-methylbutanamido]pro-panamido]-1,4a-dimethyl-1,2,3,4,4a,9,10,10a-octa-hydrophenanthren-1-yl]carbonyl}carbamoyl)-4b,8-dimethyl-4b,5,6,7,8,8a,9,10-octahydrophenanthren-3-yl]carbamate (102a)

tert-Butyl N-[(4bS,8S,8aR)-8-({[(1S,4aS,10aR)-6-[(2S)-2-[(2S)-2-amino-3-methylbutanamido]-5-(car-bamoylamino)pentanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (102b)

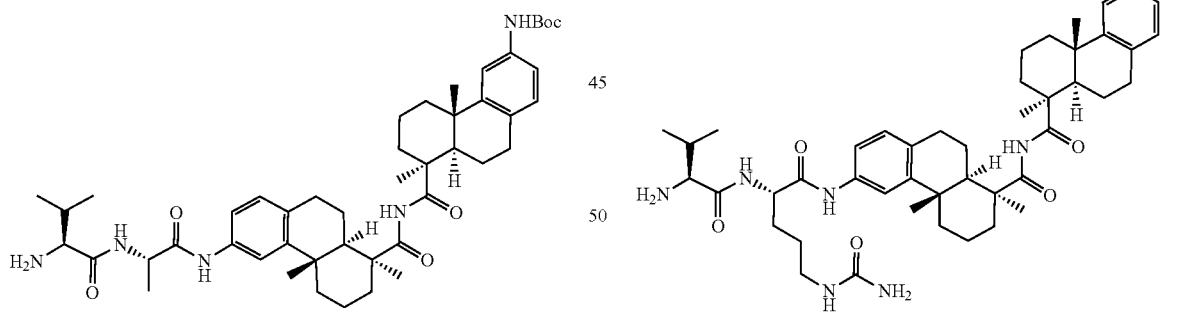

Following the general procedure for Intermediates 102a, b, compound 102a (0.29 g, 72% yield) was obtained as a white solid. ESI m/z: 799 (M+1)$^+$.

Following the general procedure for Intermediates 102a, b, compound 102b (0.27 g, 38% yield) was obtained as a white solid. ESI m/z: 885 (M+1)$^+$.

Example 5b

Intermediates 104a-b tert-Butyl N-[(4bS,8S,8aR)-8-({[(1S,4aS,10aR)-6-[(2S)-2-[(2S)-2-{2-amino-6-[2-(cyclooct-2-yn-1-yloxy)acetamido]hexanamido}-3-methylbutanamido]propanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (104a)

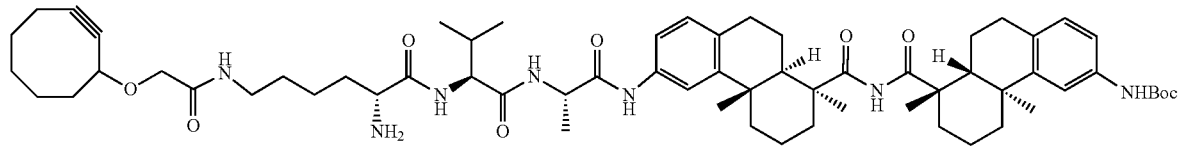 [SMILES: CC(C)[C@H](NC(=O)[C@H](N)CCCCNC(=O)COC1C#CCCCCC1)C(=O)N[C@@H](C)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

To a solution of compound 103 (70 mg, 0.13 mmol) in DMF (2 mL) were added HATU (68 mg, 0.18 mmol) and DIPEA (44 μL, 0.24 mmol) at RT. The mixture was stirred at RT for 5 min before the addition of compound 102a (95 mg, 0.12 mmol). The reaction mixture was then stirred at RT for 3 h until compound 102a was totally consumed, as monitored by LCMS. To the reaction mixture was then added piperidine (0.5 mL, excess). The mixture was stirred at RT for 2 h. The mixture was then filtered and the filtrate was concentrated. The residue was purified by reverse phase flash chromatography (0-100% acetonitrile in aq. ammonium bicarbonate (10 mM)) to give compound 104a (0.13 g, 96% yield) as a white solid. ESI m/z: 518.0 ((M-55)/2)$^+$.

tert-Butyl N-[(4bS,8S,8aR)-8-({[(1S,4aS,10aR)-6-[(2S)-2-[(2S)-2-{2-amino-6-[2-(cyclooct-2-yn-1-yloxy)acetamido]hexanamido}-3-methylbutanamido]-5-(carbamoylamino)pentanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (104b)

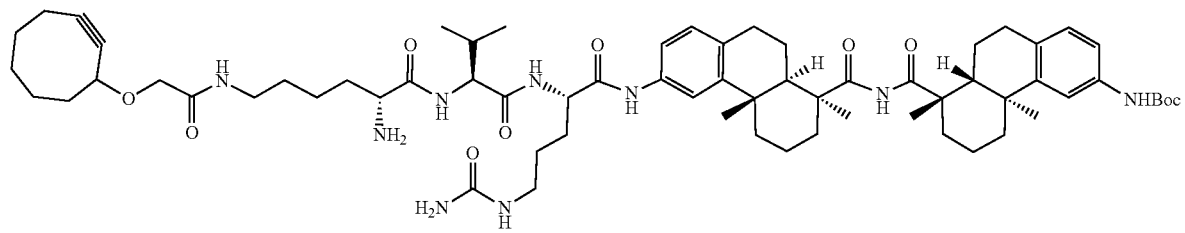 [SMILES: CC(C)[C@H](NC(=O)[C@H](N)CCCCNC(=O)COC1C#CCCCCC1)C(=O)N[C@@H](CCCNC(N)=O)C(=O)Nc1ccc2c(c1)[C@@]1(C)CCC[C@](C)(C(=O)N(C)C(=O)[C@@]3(C)CCC[C@]4(C)c5cc(NC(=O)OC(C)(C)C)ccc5CC[C@@H]34)[C@@H]1CC2]

To a solution of compound 103 (0.27 g, 0.31 mmol) and DIPEA (0.11 mL, 0.61 mmol) in DMF (6 mL) was added compound 102b (0.18 g, 0.34 mmol) followed by the addition of HATU (0.14 g, 0.37 mmol). The reaction mixture was stirred at RT for 3 h, which was monitored by LCMS. The resulting solution was directly purified by reverse phase flash chromatography to give compound Fmoc-104b (0.30 g, ESI m/z: 711 ((M+Na)/2+1)$^+$) as a pale yellow solid, which was dissolved in DCM (6.0 mL). To the solution was added piperidine (0.5 mL) and the reaction mixture was stirred at RT for 2 h until Fmoc was totally removed according to LCMS. The volatiles were removed in vacuo and the residue was triturated with petroleum ether to give compound 104b (0.26 g, 65% yield) as a light yellow solid. ESI m/z: 1177.6 ((M+H)$^+$.

Example 5c

Intermediates 105a-c

Azido intermediate α-CD-N$_3$ (105a) was synthesized according to *J. Am. Chem. Soc.*, 2012, 134(46), 19108-19117 (FIG. 10).

Azido-15-oxo-3,6,9,12-tetraoxa-16-azaoctadecane-18-sulfonic acid (105b) (FIG. 11)

To a solution of 2,5-dioxopyrrolidin-1-yl 1-azido-3,6,9,12-tetraoxapentadecan-15-oate (N$_3$—PEG$_4$-OSu, 0.10 g, 0.26 mmol) and taurine 105b-A (39 mg, 0.31 mmol) in anhydrous DMF (4 mL) was added DIPEA (15 mg, 0.52 mmol). The mixture was stirred at RT overnight. The reaction mixture was filtered and the solution was purified by prep-HPLC (method A) to give intermediate 105b (0.80 g, yield 78%) as colorless oil. ESI m/z: 399.1 (M+H)$^+$. $^1$H NMR (500 MHz, D$_2$O) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

[2-(1-Azido-3,6,9,12-tetraoxapentadecan-15-amido)ethyl]trimethylazanium chloride (105d)

Following a similar procedure for 105b above, except substituting 105d-A for 105b-A, trimethylammonium chloride 105d (0.13 g, 64% yield) was obtained as colorless oil. ESI m/z: 376 (M+H)$^+$. $^1$H NMR (500 MHz, DMSO$_{d6}$) δ 3.65-3.58 (m, 4H), 3.58-3.45 (m, 16H), 3.45-3.30 (m, 12H), 2.35 (t, J=6.5 Hz, 2H) ppm.

Azido intermediate maltose-N$_3$ (105c) was synthesized according to *Tetrahedron Letters*, 2001, 42 (7), 1325-1328 (FIG. 12).

Example 5d

Intermediates 106a-f

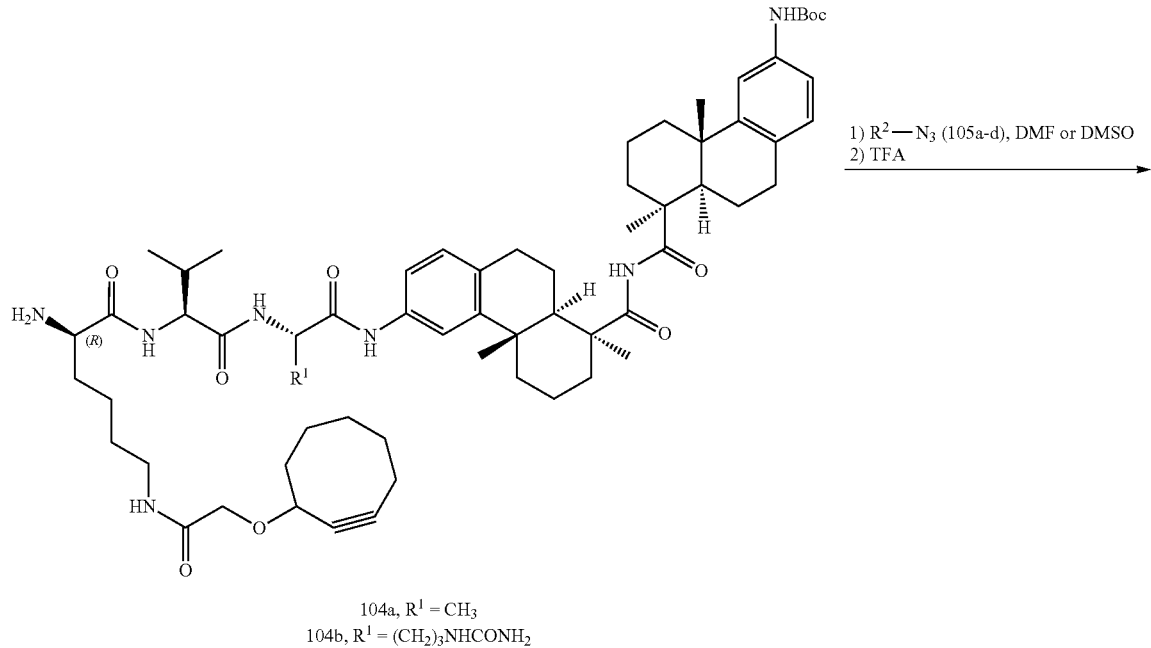

104a, R¹ = CH₃
104b, R¹ = (CH₂)₃NHCONH₂

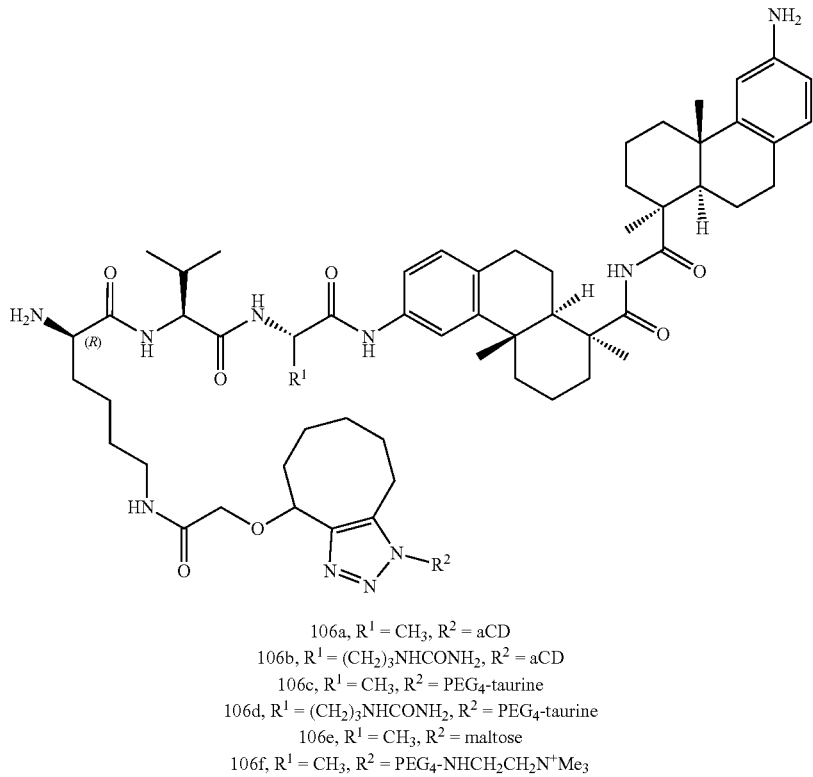

106a, R¹ = CH₃, R² = aCD
106b, R¹ = (CH₂)₃NHCONH₂, R² = aCD
106c, R¹ = CH₃, R² = PEG₄-taurine
106d, R¹ = (CH₂)₃NHCONH₂, R² = PEG₄-taurine
106e, R¹ = CH₃, R² = maltose
106f, R¹ = CH₃, R² = PEG₄-NHCH₂CH₂N⁺Me₃

To a solution of compound 104 in DMF were added azido intermediate 105 at RT. The reaction was stirred at RT for 3-48 h until LCMS showed complete reaction. The reaction mixture was directly purified by prep-HPLC to give compound Boc-106 as a white solid, which was dissolved in TFA solution (or neat TFA). The solution was stirred at RT for 0.5-20 h until Boc was removed according to LCMS. The solution was concentrated to give 106 (as the TFA salt).

| | Step 1 | | | | | | | Step 2 | | | Product | |
|---|---|---|---|---|---|---|---|---|---|---|---|---|
| Alkyne g (mmoL) | | Azide g (mmoL) | | DMF (mL) | T (° C.) | Time (hr) | Purification | TFA (mL) | solvent (mL) | Time (hr) | # | g (yield) |
| 104a | 0.050 (0.045) | 105a | 0.11 (0.12) | 4 | RT | 48 | RP-A | 1 | DCM (3 mL) | 1 | 106a | 0.019* (69%) |
| 104b | 0.050 (0.042) | 105a | 0.085 (0.085) | 4 | RT | 20 | RP | 2 | / | 0.5 | 106b | 0.076 (87%) |
| 104a | 0.17 (0.16) | 105b | 0.12 (0.31) | 6 | RT | 20 | RP-A | 2 | / | 1 | 106c | 0.090 (39%) |
| 104b | 0.050 (0.1042) | 105b | 0.034 (0.084) | 2 | RT | 3 | RP | 1 | MeOH (2 mL) | 20 | 106d | 0.022 (36%) |
| 104a | 0.035 (0.032) | 105c | 0.024 (0.064) | DMSO 5 mL | RT | 4 | RP | 3 | / | 2 | 106e | 0.034 (77%) |
| 104a | 0.035 (0.032) | 105d | 0.026 (0.064) | 4 | RT | 20 | RP | 1 | DCM (9 mL) | 2 | 106f | 0.020 (42%) |

*not all Boc-106a was used for de-Boc.

(1S,4aS,10aR)-N-[(1S,4aS,10aR)-6-Amino-1,4a-dimethyl-2,3,4,9,10,10a-hexahydrophenanthrene-1-carbonyl]-6-[(2S)-2-[(2S)-2-[(2R)-2-amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-4H,5H,6H,7H,8H,9H-cycloocta[d][1,2,3]triazol-4-yl)oxy]acetamido}hexanamido]-3-methylbutanamido]propanamido]-1,4a-dimethyl-2,3,4,9,10,10a-hexahydrophenanthrene-1-carboxamide trifluoroacetic acid salt (106a)

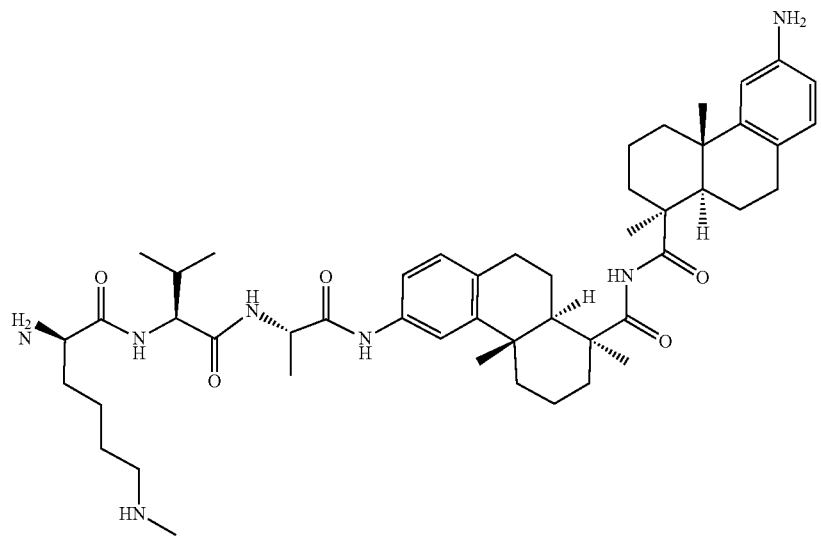

-continued

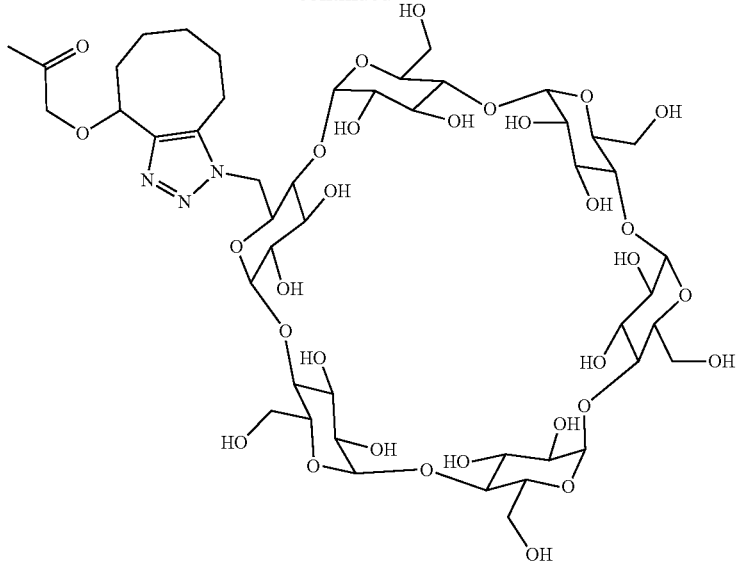

Following the general procedure for Intermediates 106a-e, compound Boc-106a (72 mg, 76% yield, as a mixture of triazole regioisomers) was obtained as a white solid (ESI m/z: 1045 (M/2+1)$^+$). A small amount of the pure major isomer (7 mg) could be obtained after further purification by reverse phase flash chromatography (0-60% acetonitrile in aq. TFA (0.01%)), which was determined by $^1$H NMR (500 MHz, DMSO$_{d6}$) ((with regioisomers) δ 9.92 (s, 0.5H), 9.82 (s, 0.5H), 9.10 (s, 1H), 8.58-8.53 (m, 1H), 8.50-8.35 (m, 1H), 8.12 (s, 1H), 8.04 (s, 3H), 7.88-7.82 (m, 1H), 7.55 (s, 0.5H), 7.46 (s, 0.5H), 7.41 (s, 1H), 7.40-7.26 (m, 1H), 7.14 (d, J=7.0 Hz, 1H), 6.97 (d, J=8.0 Hz, 1H), 6.90 (d, J=8.5 Hz, 1H), 5.51 (br, 12H), 4.83-4.70 (m, 8H), 4.57-4.51 (m, 3H), 4.44-4.36 (m, 4H), 4.00-3.98 (m, 1H), 3.88-3.55 (m, 27H), 3.26-3.09 (m, 6H), 2.91-2.85 (m, 4H), 2.76-2.63 (m, 3H), 2.29-2.25 (m, 2H), 2.17-1.99 (m, 4H), 1.96-1.93 (m, 6H), 1.88-1.63 (m, 9H), 1.56-1.54 (m, 15H), 1.33-1.28 (m, 15H), 1.18-1.13 (m, 3H), 1.01-0.99 (m, 6H), 0.89-0.83 (m, 7H) ppm). To a mixture of Boc-106a (as a mixture of regioisomers) (20 mg, 9.6 μmol) in DCM (3 mL) was added TFA (1 mL). The resulting mixture was stirred at RT for an hour until Boc was removed, as monitored by LCMS. The volatiles were removed in vacuo to give compound 106a (19 mg, 69% yield from 104a) as a pale-yellow solid, which was used for the next step without further purification. ESI m/z: 995 (M/2+1)$^+$.

(1S,4aS,10aR)-N-{[(1S,4aS,10aR)-6-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]-1,4a-dimethyl-1,2,3,4,4a,9,10,10a-octahydrophenanthren-1-yl]carbonyl}-6-amino-1,4a-dimethyl-1,2,3,4,4a,9,10,10a-octahydrophenanthrene-1-carboxamide trifluoroacetic acid salt (106b)

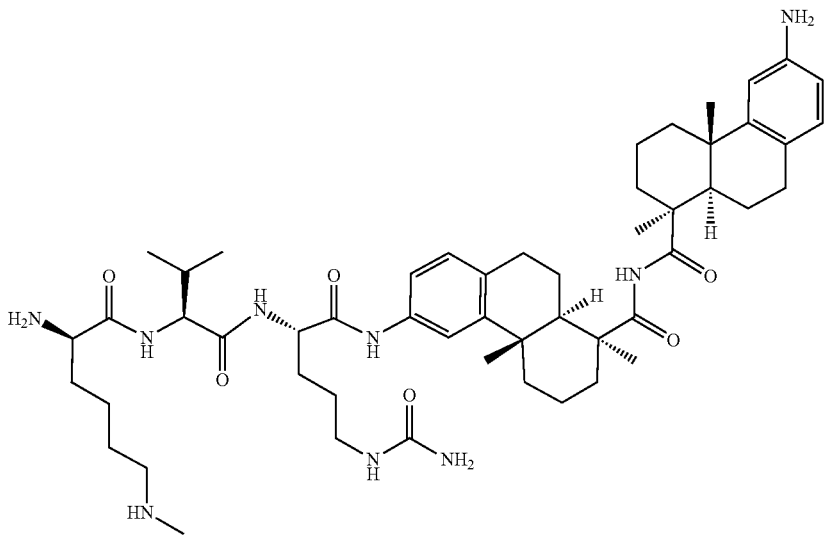

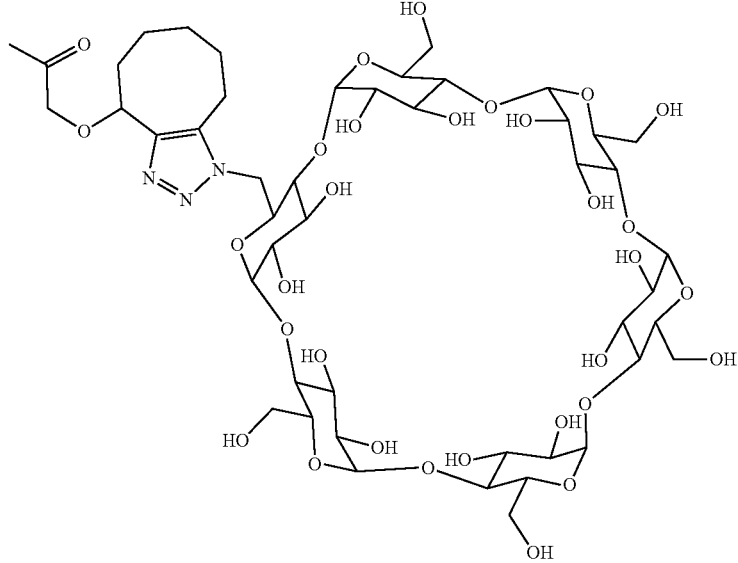

Following the general procedure for Intermediates 106a-e, compound 106b (76 mg, 87% yield from 104b) was obtained as a yellow solid. ESI m/z: 692 (M/3+1)+.

1-(4-(2-(((R)-5-Amino-6-(((S)-1-(((S)-1-(((4bS,8S,8aR)-8-(((1S,4aS,10aR)-6-amino-1,4a-dimethyl-1,2,3,4,4a,9,10,10a-octahydrophenanthrene-1-carbonyl)carbamoyl)-4b,8-dimethyl-4b,5,6,7,8,8a,9,10-octahydrophenanthren-3-yl)amino)-1-oxopropan-2-yl)amino)-3-methyl-1-oxobutan-2-yl)amino)-6-oxohexyl)amino)-2-oxoethoxy)-4,5,6,7,8,9-hexahydro-1H-cycloocta[d][1,2,3]triazol-1-yl)-15-oxo-3,6,9,12-tetraoxa-16-azaoctadecane-18-sulfonic acid (106c)

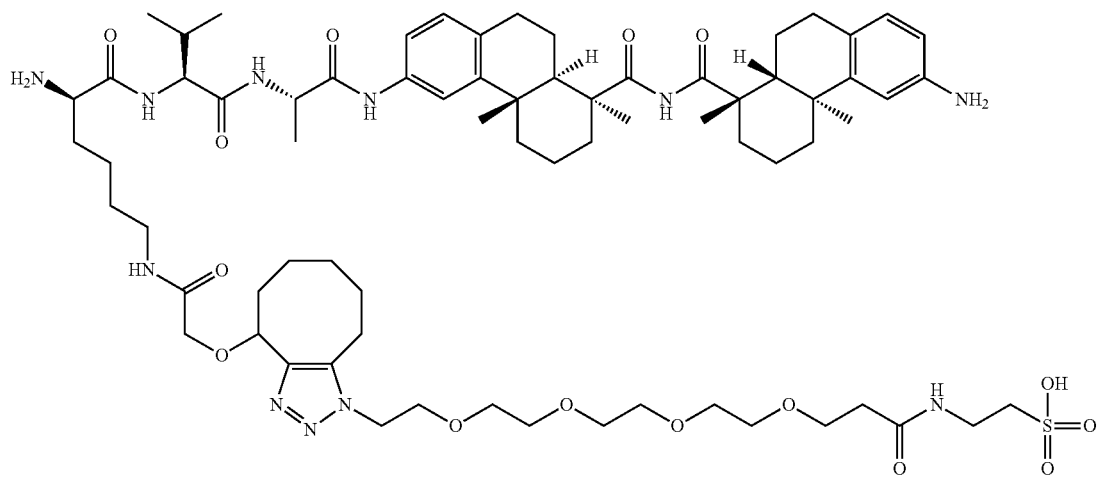 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Intermediates 106a-e, compound 106c (90 mg, 39% yield from 104c) was obtained as a yellow solid. ESI m/z: 463.8 (M/3+1).

1-(4-((((6S,9S,12R)-1,12-Diamino-6-((((4bS,8S,8aR)-8-(((1S,4aS,10aR)-6-amino-1,4a-dimethyl-1,2,3,4,4a,9,10,10a-octahydrophenanthrene-1-carbonyl)carbamoyl)-4b,8-dimethyl-4b,5,6,7,8,8a,9,10-octahydrophenanthren-3-yl)carbamoyl)-9-isopropyl-1,8,11,18-tetraoxo-2,7,10,17-tetraazanonadecan-19-yl)oxy)-4,5,6,7,8,9-hexahydro-1H-cycloocta[d][1,2,3]triazol-1-yl)-15-oxo-3,6,9,12-tetraoxa-16-azaoctadecane-18-sulfonic acid (106d)

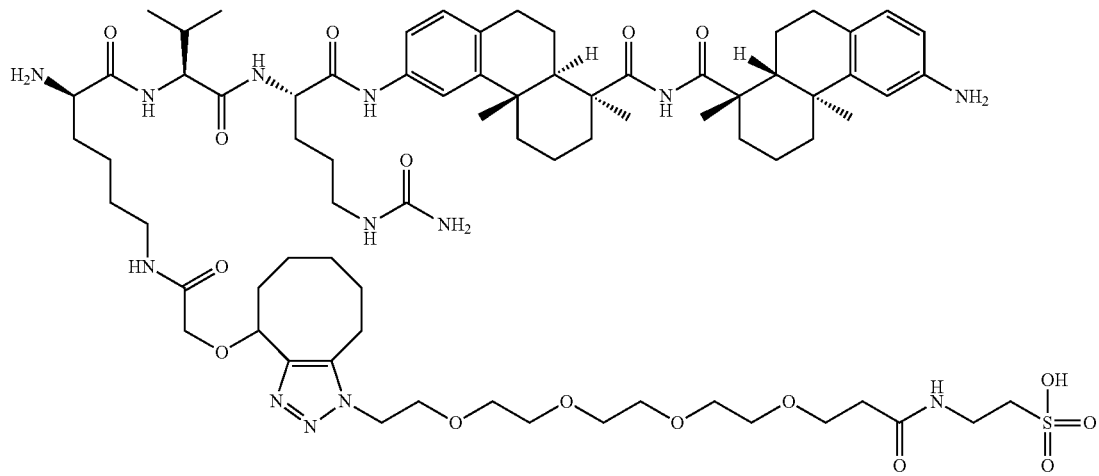 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Intermediates 106a-e, compound 106d as its TFA salt (22 mg, 36% yield) was obtained as a white solid after purification by reverse phase flash chromatography (0-80% acetonitrile in water during 25 minutes). ESI m/z: 788 (M/2+H)$^+$.

(1S,4aS,10aR)-6-Amino-N-((1S,4aS,10aR)-6-((2S)-2-((2S)-2-((2R)-2-amino-6-(2-((1-((2S,3R,4R,5S,6R)-3,4-dihydroxy-6-(hydroxymethyl)-5-(((2R,3R,4S,5S,6R)-3,4,5-trihydroxy-6-(hydroxymethyl)tetrahydro-2H-pyran-2-yl)oxy)tetrahydro-2H-pyran-2-yl)-3a,4,5,6,7,8,9,9a-octahydro-1H-cycloocta[d][1,2,3]triazol-4-yl)oxy)acetamido)hexanamido)-3-methylbutanamido)propanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (106e)

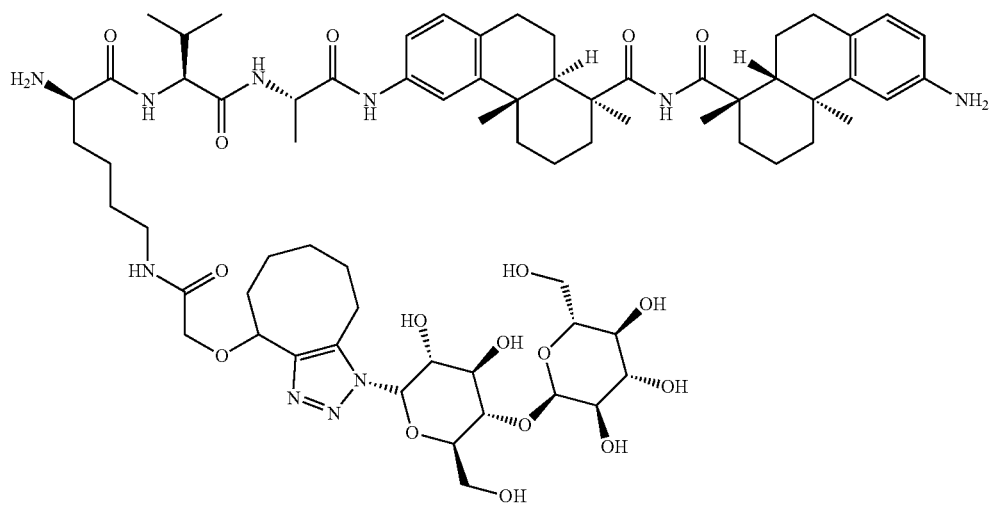

Following the general procedure for Intermediates 106a-e, compound 106e as its TFA salt (34 mg, 77% yield) was obtained as colorless oil. ESI m/z: 1358 (M+H)⁺.

(2-{1-[4-({[(5R)-5-Amino-5-{[(1S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethyl)trimethylazanium trifluoroacetate (106f)

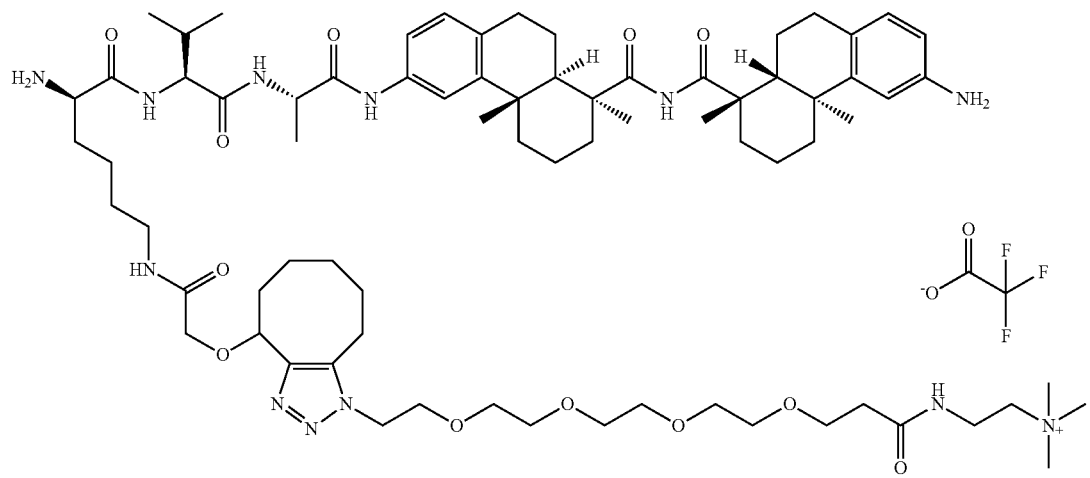

Following the general procedure, compound 106f (20 mg, 42% yield from 104a) was obtained as a white solid. ESI m/z: 455.8 (M/3)⁺.

Example 5e

Linker-Payloads LP1-LP5 and LP20

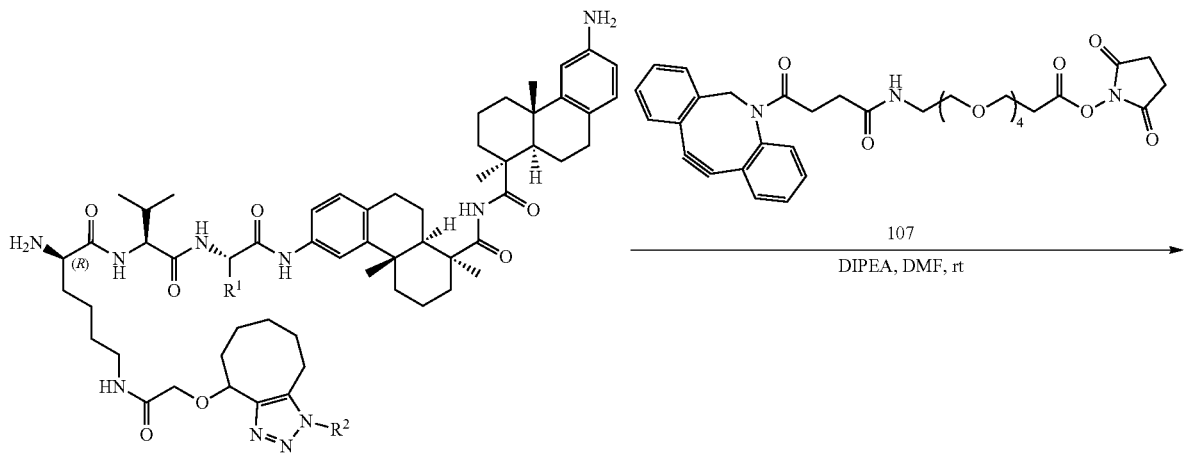

106a, R¹ = CH₃, R² = aCD
106b, R¹ = (CH₂)₃NHCONH₂, R² = aCD
106c, R¹ = CH₃, R² = PEG₄-taurine
106d, R¹ = (CH₂)₃NHCONH₂, R² = PEG₄-taurine
106e, R¹ = CH₃, R² = maltose
106f, R¹ = CH₃, R² = PEG₄-NHCH₂CH₂N⁺Me₃

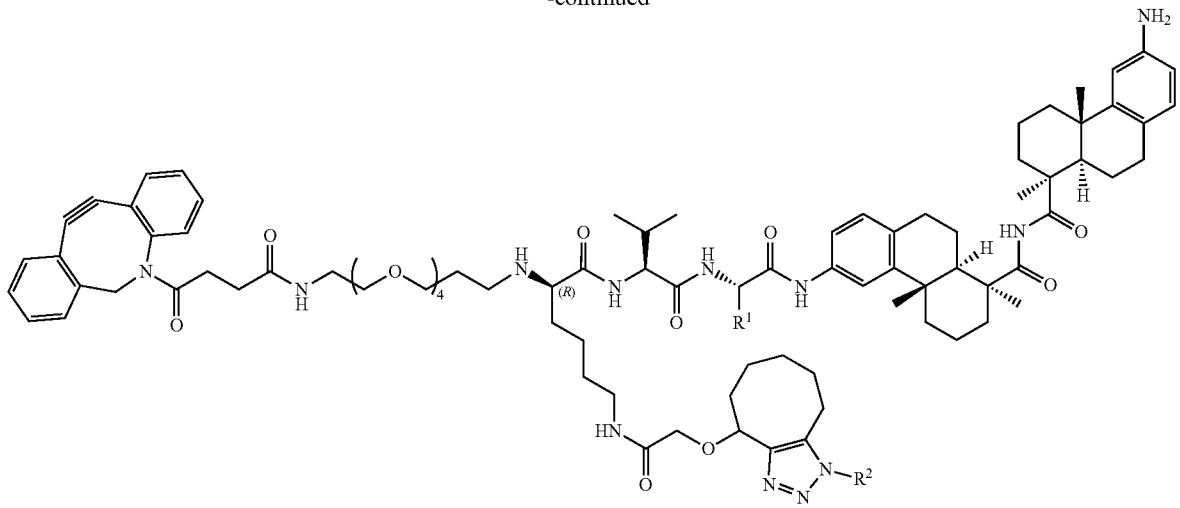

LP1-5, LP20

To a solution of compound 106 in DMF were added compound DIBAC-PEG$_4$-NHS 107 and DIPEA at RT. The reaction mixture was stirred at RT for 3 h. The reaction mixture was directly purified by prep-HPLC (method B) or reverse phase flash chromatography (method B) to give compound LP1-5 and LP20.

| # | Amine 106 mg (μmol) | NHS ester 107 mg (μmol) | DIPEA (mmol) | DMF (mL) | Time (hr) | Purification | Product LP # | mg (yield) |
|---|---|---|---|---|---|---|---|---|
| 106a | 19 (8.7) | 7.0 (11) | 4.0 mg (0.031) | 1.5 | 1.5 | RP-B (twice) | LP1 | 8 (36%)* |
| 106b | 76 (37) | 24 (37) | 12 μL (0.073) | 5 | 1.5 | Prep-B (twice) | LP2 | 20 (21%) |
| 106c | 90 (65) | 39 (60) | 0.02 mL (0.12) | 5 | 1.5 | Prep-B | LP3 | 60 (52%) |
| 106d | 22 (15) | 9.7 (15) | 5 μL (0.030) | 2 | 1.5 | Prep-B | LP4 | 6 (20%) |
| 106e | 40 (29) | 23 (35) | 7.6 mg (59) | 5 | 4 | Prep-B | LP5 | 15 (27%) |
| 106f | 22 (15) | 9.7 (15) | 5 μL (0.030) | 2 | 1.5 | RP | LP20 | 7 (24%) |

*7 mg of compound 106a as free base was recycled.

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-{[(1S,4aS,10aR)-6-amino-1,4a-dimethyl-2,3,4,9,10,10a-hexahydrophenanthrene-1-carbonyl]carbamoyl}-4b,8-dimethyl-5,6,7,8a,9,10-hexahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-4H,5H,6H,7H,8H,9H-cycloocta[d][1,2,3]triazol-4-yl)oxy]acetamido}pentyl]-3,6,9,12-tetraoxapentadecan-15-amide (LP1)

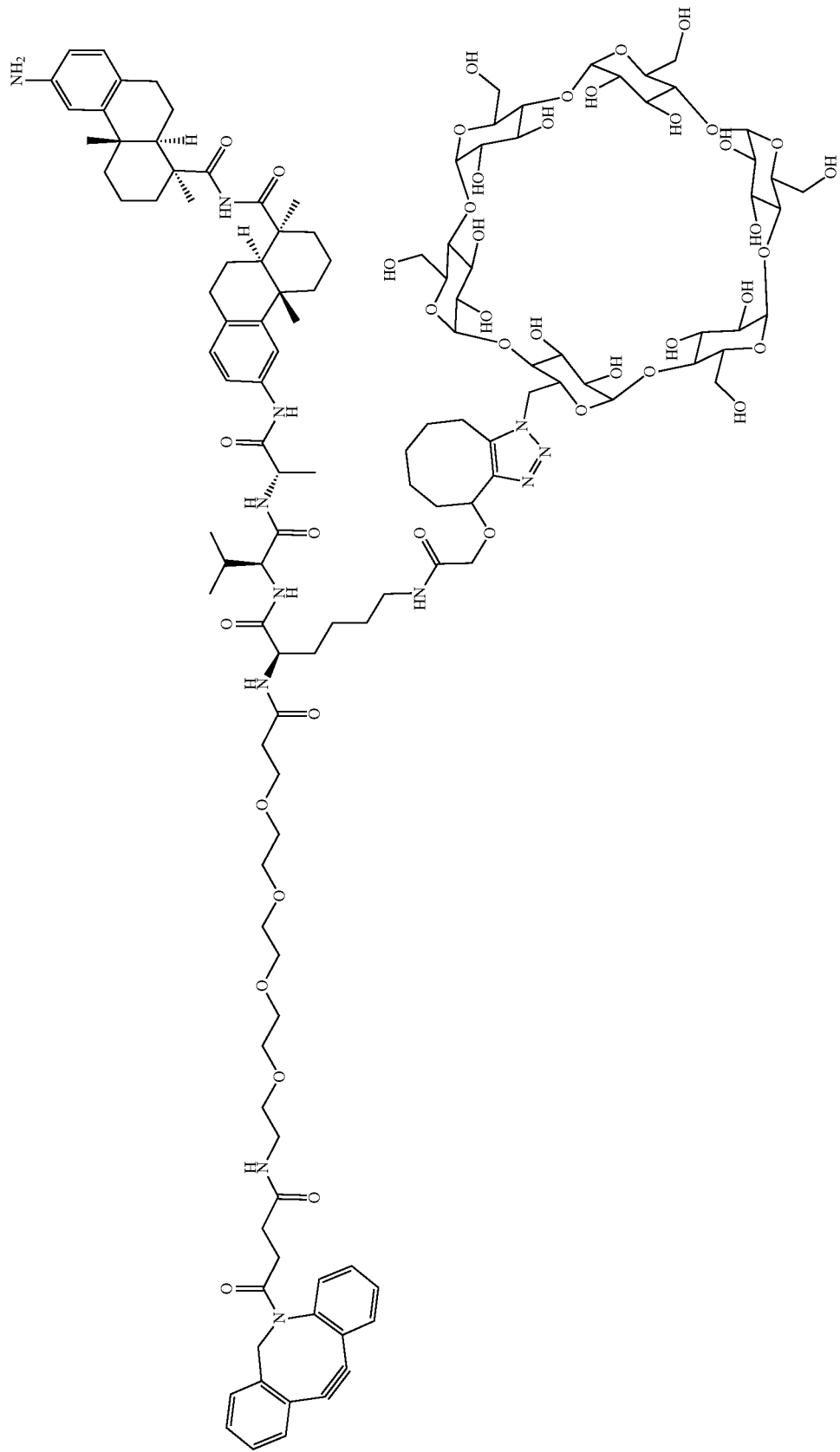

Following the general procedure for Linker-payloads LP1-5, linker-payload LP1 (8 mg, 36% yield) was obtained as a white solid. ESI m/z: 842 (M/3+1)$^+$; 1262 (M/2+1)$^+$. $^1$H NMR (400 MHz, DMSO$_{d6}$) δ 9.69 (s, 0.5H), 9.28 (s, 0.5H), 8.20-8.00 (m, 5H), 7.81-7.75 (m, 2H), 7.66 (d, J=7.6 Hz, 1H), 7.60 (d, J=7.6 Hz, 1H), 7.53-7.27 (m, 9H), 6.96-6.92 (m, 1H), 6.67 (d, J=8.0 Hz, 1H), 6.47 (s, 1H), 6.32 (d, J=8.4 Hz, 1H), 5.57-5.47 (m, 14H), 5.13-4.99 (m, 2H), 4.81-4.68 (m, 11H), 4.59-4.52 (m, 5H), 4.36-4.29 (m, 3H), 4.16-4.08 (m, 1H), 3.99-3.98 (m, 1H), 3.84-3.53 (m, 30H), 3.45-3.38 (m, 12H), 3.13-3.03 (m, 4H), 2.90-2.66 (m, 5H), 2.36-2.32 (m, 1H), 2.26-2.20 (m, 3H), 2.15-2.12 (m, 4H), 2.00-1.99 (m, 2H), 1.88-1.72 (m, 6H), 1.64-1.40 (m, 14H), 1.33-1.24 (m, 17H), 1.14-1.09 (m, 3H), 1.00-0.97 (m, 7H), 0.89-0.81 (m, 8H) ppm.

Anal. HPLC: 95%, Retention time: 7.93 min (method B).

1-(4-{2-Azatricyclo[10.4.0.0$^{4,9}$]hexadeca-1(12),4(9), 5,7,13,15-hexaen-10-yn-2-yl}-4-oxobutanamido)-N-[(1R)-1-{1[(1S)-1-{[(1S)-1-{[(4bS,8S,8aR)-8-({ [(1S,4aS,10aR)-6-amino-1,4a-dimethyl-1,2,3,4,4a,9, 10,10a-octahydrophenanthren-1-yl] formamido}carbonyl)-4b,8-dimethyl-4b,5,6,7,8,8a,9, 10-octahydrophenanthren-3-yl]carbamoyl}-4-(carbamoylamino)butyl]carbamoyl}-2-methylpropyl]carbamoyl}-5-{2-[(1-{[31,32,33,34, 35,36,37,38,39,40,41,42-dodecahydroxy-10,15,20, 25,30-pentakis(hydroxymethyl)-2,4,7,9,12,14,17,19, 22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (LP2)

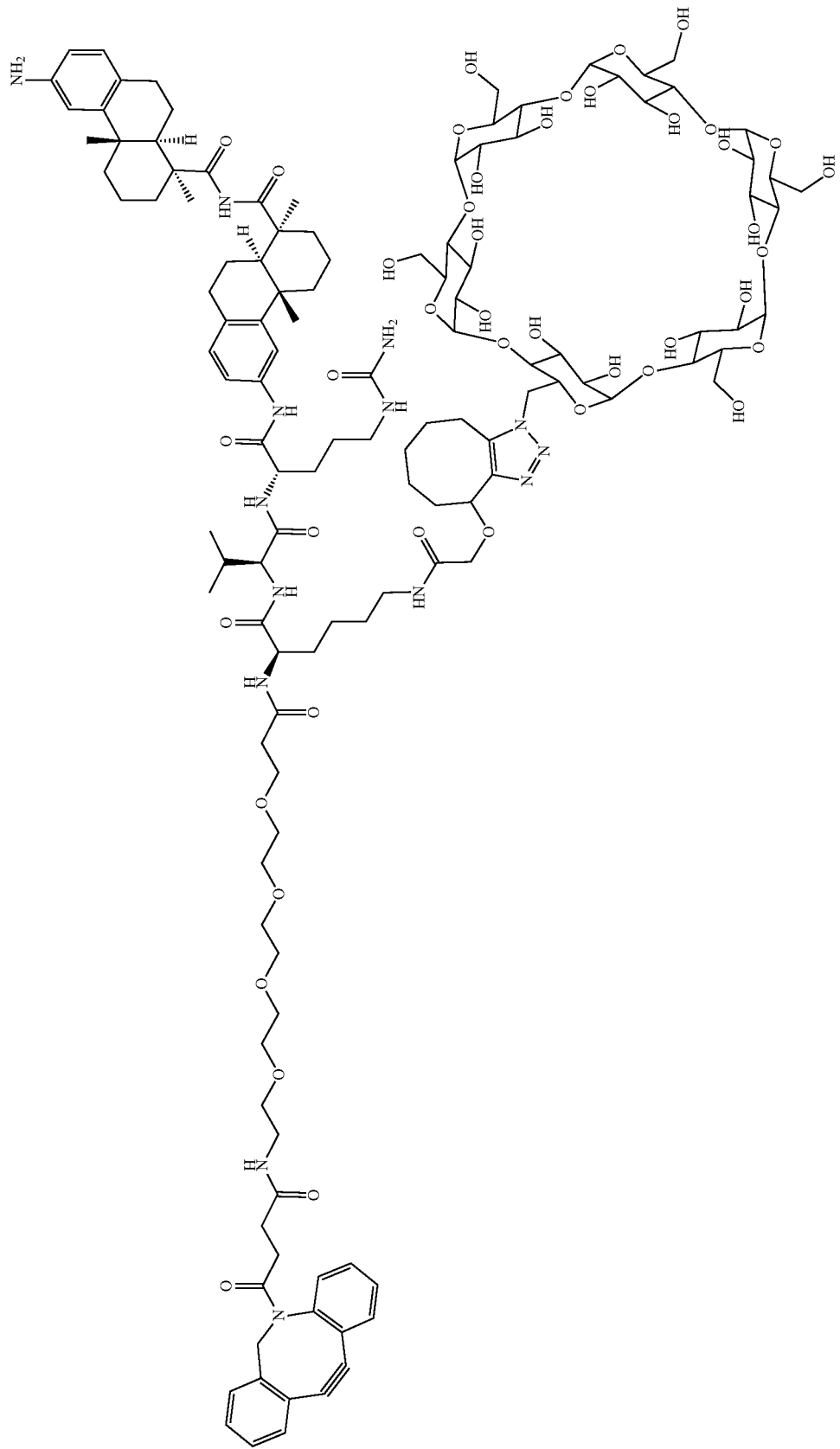

Following the general procedure for Linker-payloads LP1-5, linker-payload LP2 (20 mg, 21% yield) was obtained as a white solid. ESI m/z: 870 (M/3+H)+. ¹H NMR (400 MHz, DMSO$_{d6}$) δ 9.76 (s, 1H), 9.31 (s, 1H), 8.26-8.16 (m, 1H), 8.11-8.07 (m, 1H), 8.03-7.98 (m, 1H), 7.78-7.75 (m, 1H), 7.68-7.66 (m, 1H), 7.62-7.60 (d, J=7.2 Hz, 1H), 7.55-7.52 (m, 1H), 7.48-7.44 (m, 4H), 7.39-7.30 (m, 4H), 6.96-6.93 (m, 1H), 6.68-6.77 (d, J=8.4 Hz, 1H), 6.47 (m, 1H), 6.34-6.32 (dd, J=8.0 Hz, 1.6 Hz, 1H), 5.96 (br s, 1H), 5.59-5.56 (m, 5H), 5.52-5.45 (m, 7H), 5.38 (s, 2H), 5.13 (br s, 1H), 5.04-5.00 (d, J=14.0 Hz, 1H), 4.81-4.69 (m, 10H), 4.60-4.51 (m, 5H), 4.36-4.11 (m, 5H), 3.98 (br s, 2H), 3.85-3.77 (m, 11H), 3.70-3.58 (m, 10H), 3.45-3.40 (m, 20H), 3.30-3.27 (m, 4H), 3.12-3.04 (m, 5H), 2.98-2.86 (m, 4H), 2.77-2.67 (m, 4H), 2.27-2.19 (m, 4H), 2.16-2.10 (m, 4H), 2.02-1.96 (m, 2H), 1.89-1.73 (m, 8H), 1.64-1.57 (m, 11H), 1.50-1.43 (m, 7H), 1.26-1.20 (m, 12H), 1.15-1.10 (m, 4H), 1.01-0.97 (m, 6H), 0.89-0.82 (m, 6H) ppm. Anal. HPLC: 100%, Retention time: 7.35 min (method B). Solubility: <0.1 mg/mL water.

2-{1-[4-({[(5R)-5-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-5-{[(1S)-1-{[(1S)-1-{1[(4bS,8S,8aR)-8-({[(1S,4aS,10aR)-6-amino-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamoyl}ethyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP3)

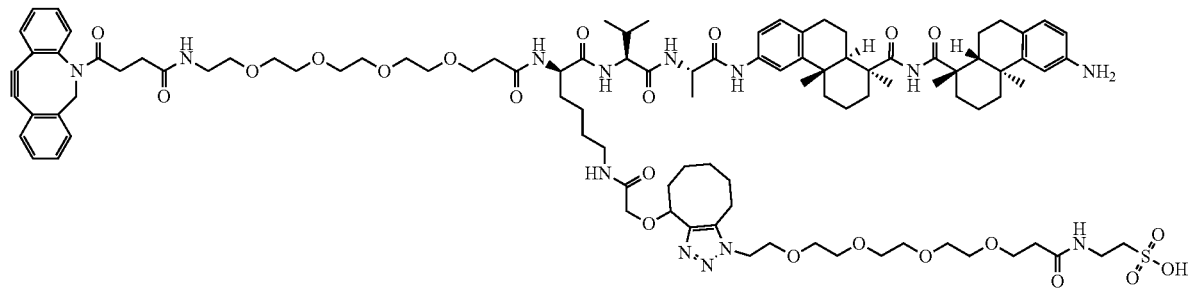 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Linker-payloads LP1-5, linker-payload LP3(60 mg, 52% yield) was obtained as a white solid. ESI m/z: 642 (M/3+H)+. ¹H NMR (500 MHz, CDCl₃) δ 9.68 (s, 0.6H), 9.25 (s, 0.4H), 8.22-8.07 (m, 3H), 8.02-7.86 (m, 2H), 7.77-7.72 (m, 2H), 7.68-7.60 (m, 2H), 7.54-7.52 (m, 1H), 7.50-7.42 (m, 4H), 7.39-7.27 (m, 4H), 7.22 (s, 1H), 7.08 (s, 1H), 6.97-6.94 (m, 2H), 6.74 (d, J=10.5 Hz, 1H), 6.58 (s, 1H), 6.43 (dd, J=10.0 Hz, 2.0 Hz, 1H), 5.62 (br s, 1H), 5.04-5.00 (m, 1H), 4.93-4.90 (m, 0.4H), 4.76-4.72 (m, 0.6H), 4.52-4.26 (m, 4H), 4.16-4.08 (m, 1H), 3.81-3.75 (m, 4H), 3.61-3.55 (m, 4H), 3.46-3.44 (m, 24H), 3.30-3.27 (m, 5H), 3.08-3.06 (m, 5H), 2.97-2.89 (m, 2H), 2.80-2.74 (m, 4H), 2.54-2.52 (m, 2H), 2.40-2.31 (m, 2H), 2.27-2.22 (m, 4H), 2.16-2.13 (m, 4H), 2.02-1.71 (m, 8H), 1.69-1.45 (m, 10H), 1.40-1.21 (m, 14H), 1.17-1.08 (m, 4H), 1.01-0.98 (m, 6H), 0.89-0.82 (m, 6H) ppm.

2-{1-[4-({[(5R)-5-[1-(4-{2-Azatricyclo[10.4.0.0⁴,⁹]
hexadeca-1(12),4(9),5,7,13,15-hexaen-10-yn-2-yl}-
4-oxobutanamido)-3,6,9,12-tetraoxapentadecan-15-
amido]-5-{[(1S)-1-{[(1S)-1-{[(4bS,8S,8aR)-8-
({[(1S,4aS,10aR)-6-amino-1,4a-dimethyl-1,2,3,4,4a,
9,10,10a-octahydrophenanthren-1-yl]
carbonyl}carbamoyl)-4b,8-dimethyl-4b,5,6,7,8,8a,9,
10-octahydrophenanthren-3-yl]carbamoyl}-4-
(carbamoylamino)butyl]carbamoyl}-2-
methylpropyl]carbamoyl}pentyl]
carbamoyl}methoxy)-1H,4H,5H,6H,7H,8H,9H-
cycloocta[d][1,2,3]triazol-1-yl]-3,6,9,12-
tetraoxapentadecan-15-amido}ethane-1-sulfonic
acid (LP4)

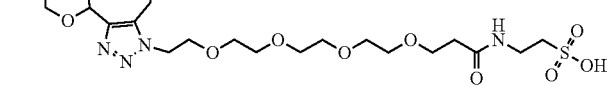

Following the general procedure for Linker-payloads LP1-5, compound LP4 (6.0 mg, 20% yield) was obtained as a white solid. ESI m/z: 671 (M/3+H)⁺. ¹H NMR (500 MHz, CDCl₃) δ 9.37 (s, 1H), 9.29 (s, 1H), 8.24-8.22 (m, 1H), 8.18-8.17 (m, 2H), 8.09 (s, 2H), 8.01-7.99 (m, 1H), 7.97-7.94 (m, 2H), 7.89-7.84 (m, 1H), 7.76 (m, 5H), 7.68 (d, J=7.5 Hz, 2H), 7.62 (d, J=7.5 Hz, 2H), 7.55 (m, 2H), 7.51-7.43 (m, 7H), 7.39-7.28 (m, 7H), 7.08 (m, 4H), 6.96-6.93 (t, J=7.0 Hz, 2H), 6.68 (d, J=8.5 Hz, 2H), 6.48 (s, 2H), 6.35-6.33 (m, 2H), 5.97-5.95 (m, 2H), 5.37 (s, 4H), 5.04-5.01 (m, 2H), 4.74-4.69 (m, 5H), 4.52 (m, 1H), 4.42 (t, J=5.5 Hz, 2H), 4.34-4.27 (m, 4H), 4.18 (m, 1H), 4.13-4.11 (m, 1H), 3.82-3.77 (m, 5H), 3.58-3.55 (m, 6H), 3.49-3.44 (m, 14H), 3.10-3.05 (m, 4H), 2.98-2.93 (m, 4H), 2.77-2.75 (m, 4H), 2.28-2.25 (m, 4H), 2.03-1.99 (m, 2H), 1.64-1.51 (m, 6H), 1.27-1.24 (m, 11H), 1.01-0.98 (m, 11H), 0.89-0.82 (m, 8H) ppm.

1-(4-{2-Azatricyclo[10.4.0.0⁴,⁹]hexadeca-1(12),4(9),
5,7,13,15-hexaen-10-yn-2-yl}-4-oxobutanamido)-N-
[(1R)-1-{[(1S)-1-{[(1S)-1-{[(4bS,8S,8aR)-8-{[(1S,
4aS,10aR)-6-amino-1,4a-dimethyl-1,2,3,4,4a,9,10,
10a-octahydrophenanthrene-1-carbonyl]carbamoyl}-
4b,8-dimethyl-4b,5,6,7,8,8a,9,10-
octahydrophenanthren-3-yl]carbamoyl}ethyl]
carbamoyl}-2-methylpropyl]carbamoyl}-5-[2-({1-
[(2S,3R,4R,5S,6R)-3,4-dihydroxy-6-
(hydroxymethyl)-5-{[(2R,3R,4S,5S,6R)-3,4,5-
trihydroxy-6-(hydroxymethyl)oxan-2-yl]oxy}oxan-
2-yl]-1H,4H,5H,6H,7H,8H,9H-cycloocta[d][1,2,3]
triazol-4-yl}oxy)acetamido]pentyl]-3,6,9,12-
tetraoxapentadecan-15-amide (LP5)

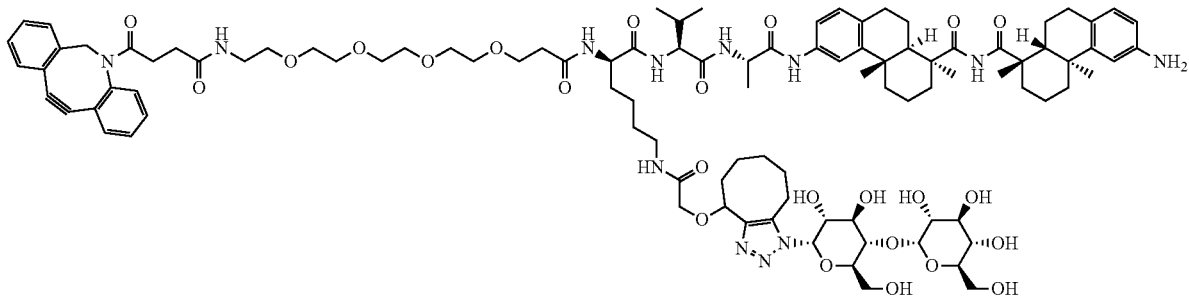 [SMILES: CC(C)[C@H](NC(=O)[C@@H](CCCCNC(=O)COC1CCCCCc2c1nnn2[C@H]1O[C@H](CO)[C@@H](O[C@H]2O[C@H](CO)[C@@H](O)[C@H](O)[C@H]2O)[C@H](O)[C@H]1O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Linker-payloads LP1-5, compound LP5 (15 mg, 27% yield) was obtained as a white solid. ESI m/z: 947 (M/2+H)$^+$. $^1$H NMR (400 MHz, DMSO$_{d6}$) δ 9.69 (s, 0.55H), 9.27 (s, 0.45H), 8.25-8.15 (m, 2H), 8.15-8.05 (m, 2H), 8.05-7.90 (m, 1H), 7.90-7.80 (m, 1H), 7.76 (t, J=6.4 Hz, 1H), 7.66 (d, J=8.0 Hz, 1H), 7.60 (d, J=6.8 Hz, 1H), 7.55-7.40 (m, 4H), 7.40-7.25 (m, 3H), 7.00-6.90 (m, 1H), 6.67 (d, J=8.4 Hz, 1H), 6.47 (s, 1H), 6.32 (d, J=8.0 Hz, 1H), 5.75-5.70 (m, 1H), 5.56 (d, J=6.0 Hz, 1H), 5.50-5.40 (m, 2H), 5.20-4.92 (m, 4H), 4.80-4.70 (m, 1H), 4.70-4.65 (m, 2H), 4.65-4.55 (m, 2H), 4.40-4.25 (m, 2H), 4.20-3.95 (m, 2H), 3.80-3.75 (m, 2H), 3.75-3.45 (m, 23H), 3.30-3.20 (m, 3H), 3.20-2.90 (m, 5H), 2.90-2.65 (m, 3H), 2.60-2.55 (m, 1H), 2.40-1.95 (m, 12H), 1.90-1.70 (m, 5H), 1.70-1.35 (m, 14H), 1.35-1.20 (m, 15H), 1.15-1.05 (m, 3H), 1.00-0.90 (m, 7H), 0.90-0.80 (m, 7H) ppm.

(2-{1-[4-({[(5R)-5-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-5-{1[(1S)-1-{[(1S)-1-{1[(4bS,8S,8aR)-8-({[(1S,4aS,10aR)-6-amino-1,4a-dimethyl-1,2,3,4,4a,9,10,10a-octahydrophenanthren-1-yl] formamido}carbonyl)-4b,8-dimethyl-4b,5,6,7,8,8a,9,10-octahydrophenanthren-3-yl]carbamoyl}ethyl] carbamoyl}-2-methylpropyl]carbamoyl}pentyl] carbamoyl}methoxy)-1H,4H,5H,6H,7H,8H,9H-cycloocta[d][1,2,3]triazol-1-yl]-3,6,9,12-tetraoxapentadecan-15-amido}ethyl) trimethylazanium trifluoroacetate (LP20)

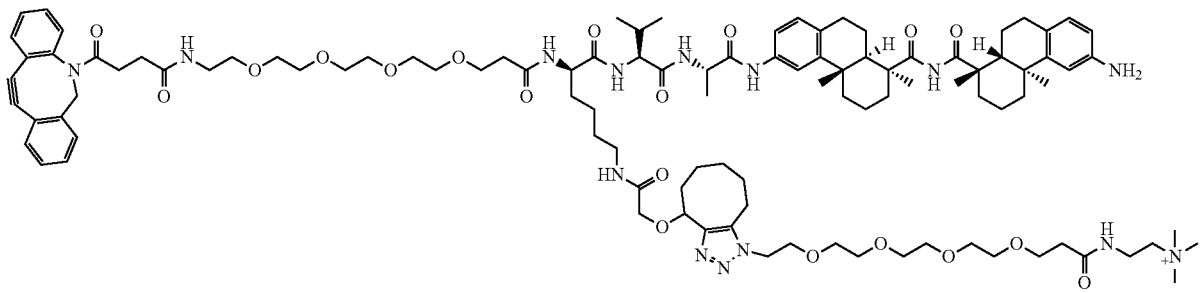 [SMILES: CC(C)[C@H](NC(=O)[C@@H](CCCCNC(=O)COC1CCCCCc2c1nnn2CCOCCOCCOCCOCCC(=O)NCC[N+](C)(C)C)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Linker-payloads LP1-5, compound LP20 (7 mg, 24% yield) was obtained as a white solid. ESI m/z: 950.8 (M/2)$^+$.

Example 6

Linker-Payload LP6

This example demonstrates methods for the synthesis of the linker-payload LP6 in Table 2, above. This example refers to the compounds numbered from 109 to 113 and linker-payload LP6 in FIG. 4.

1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-4-(carbamoylamino)-1-{[4-(hydroxymethyl)phenyl]carbamoyl}butyl]carbamoyl}-2-methylpropyl]-3,6,9,12-tetraoxapentadecan-15-amide (110)

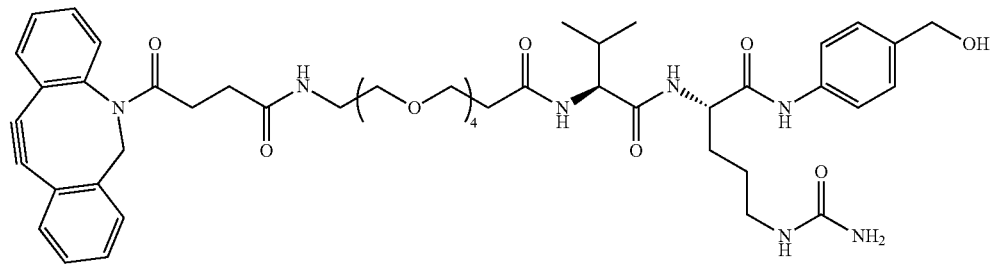

To a solution of compound 108 (0.30 g, 0.54 mmol) in DMF (10 mL) were added HATU (0.31 g, 0.81 mmol) and DIPEA (0.14 g, 1.1 mmol) successively at RT. The mixture was stirred at RT for 15 min. To the reaction solution was then added VC-PAB-OH 109 (CAS: 159857-79-1, 0.21 g, 0.54 mmol) at RT, and the resulting mixture was stirred at RT for 3 h until 108 or 109 were consumed, as monitored by LCMS. The reaction mixture was then filtered through a filtering membrane and the filtrate was concentrated and directly purified by reverse phase flash chromatography (0-100% acetonitrile in water (with 10 mmol/L ammonium bicarbonate)) to give compound 110 (0.30 g, 60% yield) as a white solid. ESI m/z: 617 (M+H)$^+$.

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl 4-nitrophenyl carbonate (112)

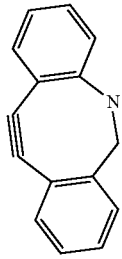
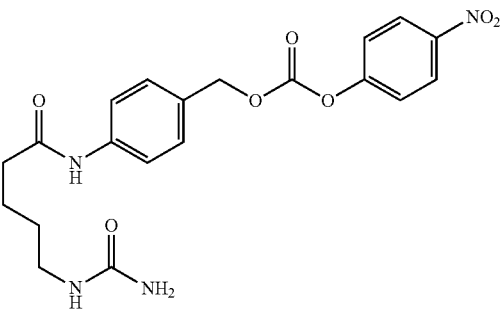

To a solution of compound 110 (0.15 g, 0.16 mmol) in DMF (10 mL) were added bis(4-nitrophenyl) carbonate 111 (0.15 g, 0.49 mmol) and DIPEA (63 mg, 0.49 mmol) successively at 0° C. The mixture was then stirred at RT for 3 h until 110 was consumed, as monitored by LCMS. The reaction mixture was filtered through a filtering membrane and the filtrate was concentrated and directly purified by reverse phase flash chromatography (0-100% acetonitrile in water (with 10 mmol/L ammonium bicarbonate)) to give compound 112 (50 mg, 28% yield) as a white solid. ESI m/z: 1079 (M+H)$^+$.

9H-Fluoren-9-ylmethyl N-({[(4bS,8S,8aR)-8-({[(1S, 4aS,10aR)-6-{[({4-[(2S)-2-[(2S)-2-[1-(4-{2-azatri-cyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methoxy)carbonyl]amino}-1, 4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl) carbamate (113)

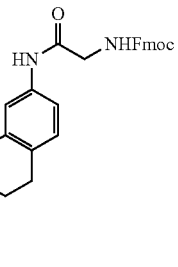
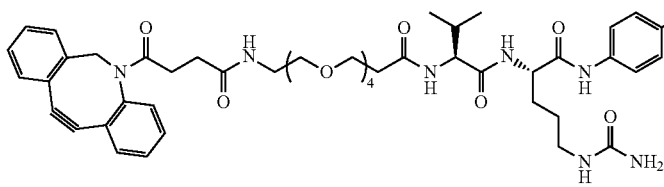

To a mixture of compound 14a (0.10 g, 0.12 mmol) and compound 112 (0.15 g, 0.14 mmol) in DMF (5 mL) were added HOBt (20 mg, 0.15 mmol) and DIPEA (48 mg, 0.37 mmol), and the mixture was stirred at RT for 4 h, which was monitored by LCMS. The reaction mixture was purified by prep-HPLC (method B) to give compound 113 (0.16 g, 72% yield) as a light yellow solid. ESI m/z: 874 (M/2+1)$^+$.

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N-[(4bS,8S,8aR)-8-{[(1S,4aS,10aR)-6-(2-aminoacetamido)-1,4a-dimethyl-1,2,3,4,4a,9,10,10a-octahydrophenanthrene-1-carbonyl]carbamoyl}-4b,8-dimethyl-4b,5,6,7,8,8a,9, 10-octahydrophenanthren-3-yl]carbamate (LP6)

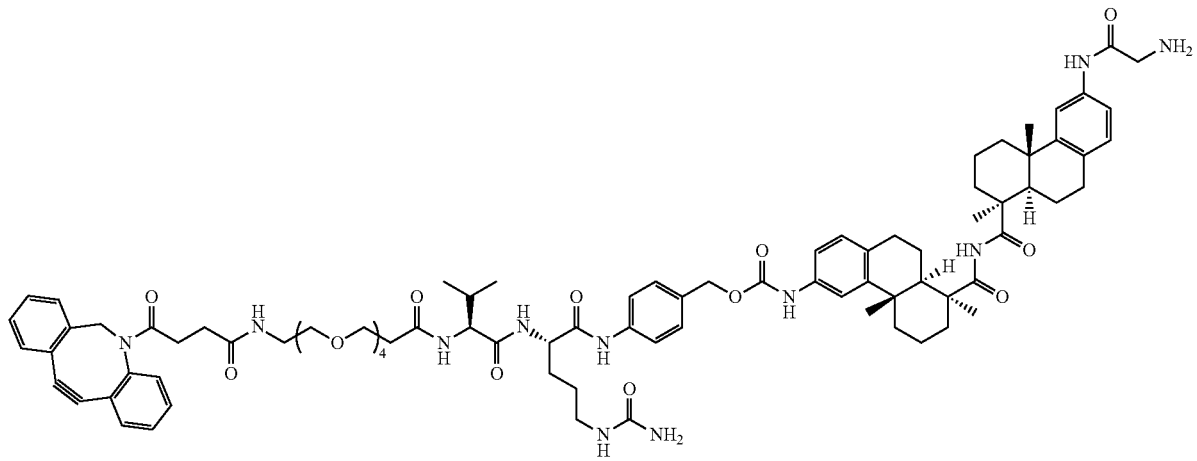

To a solution of compound 113 (0.10 g, 0.057 mmol) in DMF (5 mL) was added piperidine (1 mL) and the mixture was stirred at RT for half an hour until Fmoc was totally removed according to LCMS. The reaction mixture was directly purified by Prep-HPLC (method B) to give compound LP6 (35 mg, 23% yield) as a white solid. ESI m/z: 763 (M/2+1)$^+$. $^1$H NMR (500 MHz, DMSO$_{d6}$) δ 10.0 (s, 1H), 9.51 (s, 1H), 8.15-8.08 (m, 2H), 7.87 (d, J=8.5 Hz, 1H), 7.76 (t, J=5.0 Hz, 1H), 7.70-7.65 (m, 1H), 7.61 (t, J=8.5 Hz, 3H), 7.51-7.42 (m, 4H), 7.41-7.30 (m, 8H), 7.20-7.10 (m, 1H), 7.00-6.90 (m, 2H), 6.00-5.95 (m, 1H), 5.40 (s, 2H), 5.35-5.30 (m, 1H), 5.10-5.00 (m, 3H), 4.40-4.35 (m, 1H), 4.25-4.20 (m, 1H), 3.65-3.55 (m, 3H), 3.50-3.40 (m, 14H), 3.25 (s, 3H), 3.10-3.00 (m, 4H), 3.00-2.85 (m, 4H), 2.80-2.70 (m, 2H), 2.63-2.61 (m, 1H), 2.60-2.55 (m, 1H), 2.45-2.35 (m, 3H), 2.31-2.20 (m, 3H), 2.20-2.10 (m, 4H), 2.10-1.92 (m, 5H), 1.90-1.82 (m, 4H), 1.68-1.53 (m, 6H), 1.50-1.40 (m, 2H), 1.20-1.10 (m, 2H), 1.02-0.96 (m, 6H), 0.90-0.80 (m, 8H) ppm.

Example 7

Linker-Payload LP7

This example demonstrates methods for the synthesis of the linker-payload LP7 in Table 2, above. This example refers to the compounds numbered 14a, 107, 114 and 115 and linker-payload LP7 in FIG. 5.

9H-Fluoren-9-ylmethyl N-({[(4bS,8S,8aR)-8-({[(1S,4aS,10aR)-6-[(2S)-2-[(2S)-2-{[(tert-butoxy)carbonyl]amino}-3-methylbutanamido]propanamido]-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl) carbamate (114)

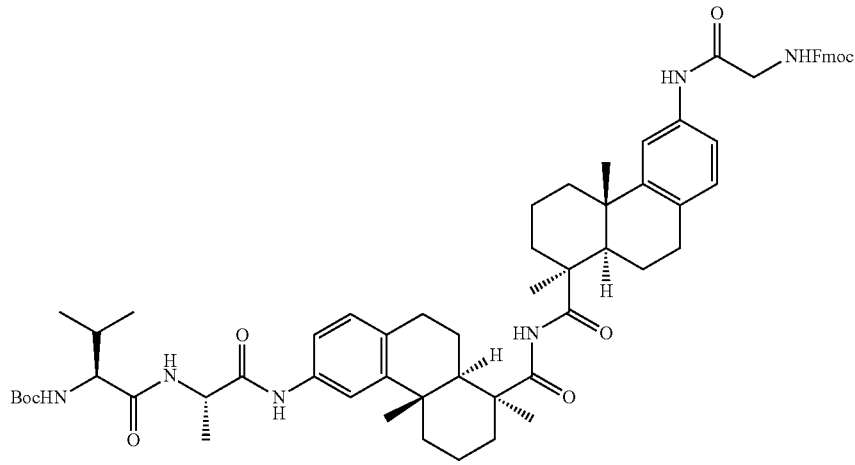

To a solution of compound 14a (66 mg, 0.082 mmol) in DMF (10 mL) were added Boc-Val-Ala-OH 101c (28 mg, 0.098 mmol), DIPEA (32 mg, 0.25 mmol) and HATU (47 mg, 0.12 mmol). The reaction mixture was stirred at RT for 4 h, and monitored by LCMS. The mixture was directly purified by reverse phase flash chromatography (50-90% acetonitrile in aq. ammonium bicarbonate (10 mM)) to give compound 114 (74 mg, 84% yield) as a white solid. ESI m/z: 978 (M-Boc+1)$^+$.

9H-Fluoren-9-ylmethyl N-({[(4bS,8S,8aR)-8-({[(1S,4aS,10aR)-6-[(2S)-2-[(2S)-2-amino-3-methylbutanamido]propanamido]-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl) carbamate trifluoroacetic acid salt (115)

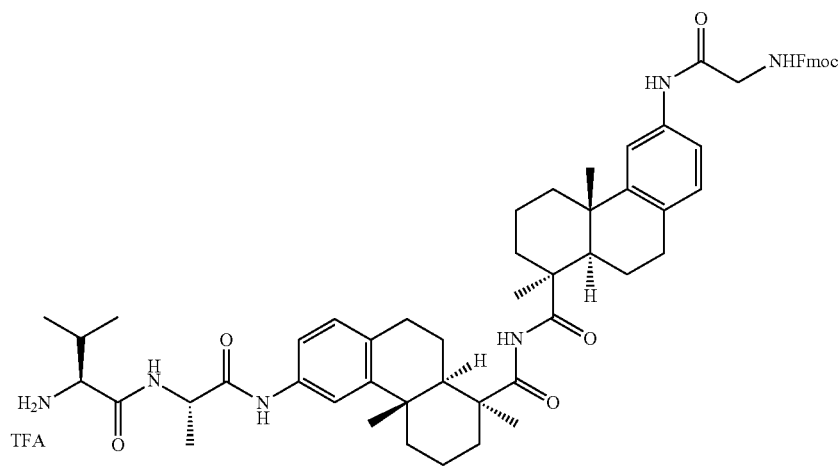

To a solution of compound 114 (74 mg, 0.069 mmol) in DCM (3 mL) was added TFA (1 mL). The reaction mixture was stirred at RT for an hour until Boc was totally removed according to LCMS. The volatiles were removed in vacuo to give crude product 115 (66 mg, 97% yield as TFA salt) as colorless oil. ESI m/z: 978 (M+1)$^+$.

1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-{[(4bS,8S,8aR)-8-{[(1S,4aS,10aR)-6-(2-aminoacetamido)-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]-3,6,9,12-tetraoxapentadecan-15-amide (LP7)

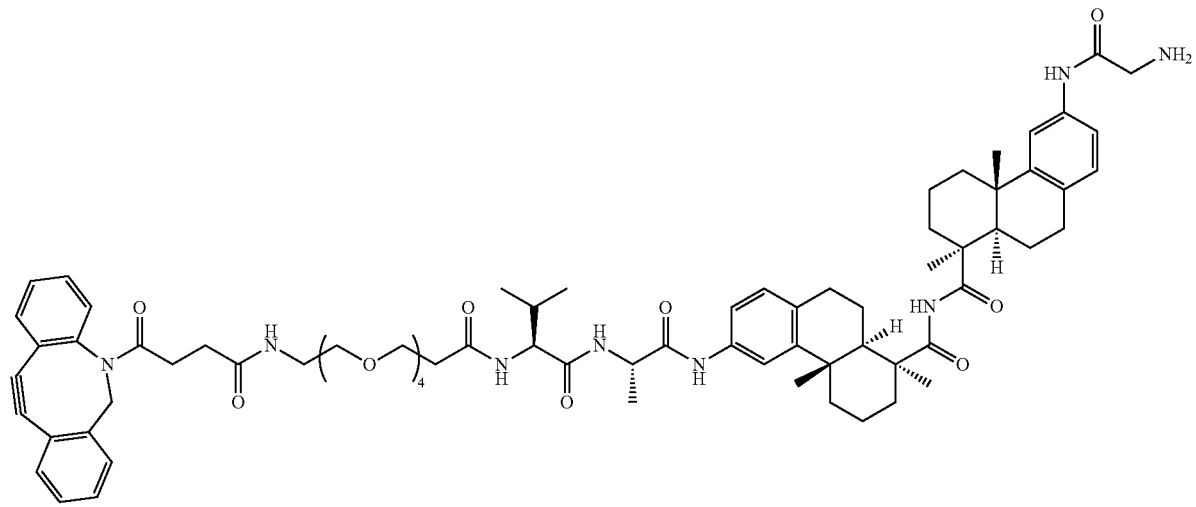

To a solution of compound 115 (60 mg, 61 μmol) in DMF (5 mL) was added DIBAC-suc-PEG4-OSu 107 (48 mg, 74 μmol) and DIPEA (24 mg, 0.18 mmol). The reaction mixture was stirred at RT for 4 h, and monitored by LCMS. To the reaction was then added piperidine (0.2 mL, excess). The reaction mixture was stirred at RT for 30 min until Fmoc was totally removed according to LCMS. The reaction mixture was directly purified by Prep-HPLC (method B) to give LP7 (22 mg, 28% yield) as a white solid. ESI m/z: 1292 (M+H)$^+$.
$^1$H NMR (500 MHz, DMSO$_{d6}$) (with regioisomers) δ 9.66 (s, 0.5H), 9.51 (s, 0.5H), 8.43 (d, J=7.5 Hz, 0.5H), 8.15-8.10 (m, 1.5H), 8.05 (d, J=7.5 Hz, 0.5H), 7.90 (d, J=7.5 Hz, 0.5H), 7.77 (t, J=5.5 Hz, 1H), 7.70-7.65 (m, 1H), 7.65-7.60 (m, 1H), 7.55-7.25 (m, 11H), 6.97 (d, J=8.5 Hz, 2H), 5.02 (d, J=14.5 Hz, 1H), 4.40-4.35 (m, 1H), 4.18 (t, J=7.5 Hz, 0.5H), 4.04 (t, J=7.5 Hz, 0.5H), 3.65-3.50 (m, 3H), 3.50-3.40 (m, 14H), 3.23 (s, 3H), 3.15-3.05 (m, 3H), 2.95-2.85 (m, 3H), 2.80-2.70 (m, 3H), 2.60-2.55 (m, 1H), 2.40-2.10 (m, 12H), 2.00-1.80 (m, 5H), 1.80-1.70 (m, 1H), 1.70-1.55 (m, 5H), 1.24 (s, 1H), 1.20-1.10 (m, 3H), 1.10-0.90 (m, 8H), 0.90-0.80 (m, 8H) ppm.

Example 8

Linker-Payload LP8

This example demonstrates methods for the synthesis of the linker-payload LP8 in Table 2, above. This example refers to the compounds numbered P4, 117-120 and linker-payload LP8 in FIG. 6.

{4-[(2S)-2-[(2S)-2-Amino-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (117)

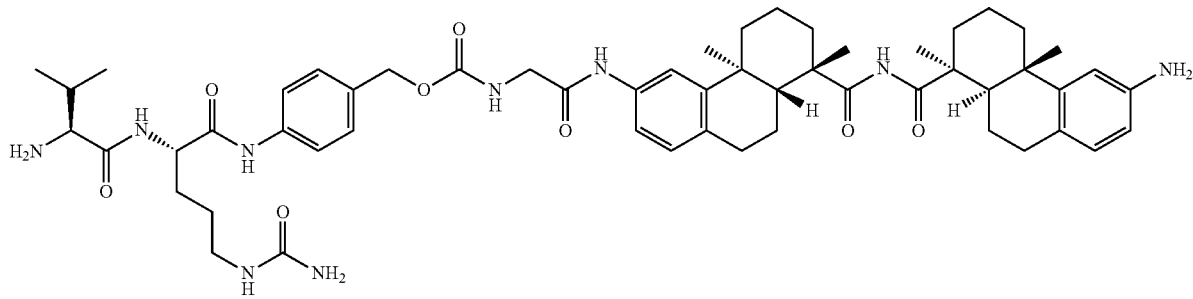 [SMILES: CC(C)[C@H](N)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of Fmoc-vc-PAB-PNP 116 (0.14 g, 0.18 mmol) and payload P4 (0.11 g, 0.18 mmol) in DMF (2 mL) were added HOBt (24 mg, 0.18 mmol) and DIPEA (70 mg, 0.54 mmol) at RT by syringe. The mixture was stirred at RT for 2 h and compound P4 was consumed according to LCMS. To the resulting mixture was added piperidine (42 mg, 0.50 mmol) and the reaction was stirred at RT for 2 h until Fmoc was totally removed, as monitored by LCMS. After filtering through a membrane, the filtrate was concentrated and directly purified by prep-HPLC (method B) to give a compound 117 (45 mg, 27% yield) as a white solid. ESI m/z: 991 (M+1)$^+$. $^1$H NMR (400 MHz, DMSO$_{d6}$) δ 10.11 (s, 1H), 9.80 (s, 1H), 8.20-8.04 (m, 2H), 7.60 (d, J=8.4 Hz, 2H), 7.52-7.44 (m, 2H), 7.36-7.20 (m, 3H), 6.96 (d, J=8.4 Hz, 1H), 6.68 (d, J=8.2 Hz, 1H), 6.48 (d, J=1.7 Hz, 1H), 6.36-6.29 (m, 1H), 5.98 (t, J=5.6 Hz, 1H), 5.41 (s, 2H), 4.97 (s, 2H), 4.70 (s, 2H), 4.52-4.42 (m, 1H), 3.75 (d, J=6.0 Hz, 2H), 3.07-2.85 (m, 4H), 2.82-2.61 (m, 3H), 2.31-2.06 (m, 6H), 2.00-1.78 (m, 6H), 1.72-1.52 (m, 6H), 1.44-1.09 (m, 13H), 0.99 (d, J=8.5 Hz, 6H), 0.87 (d, J=8.1 Hz, 3H), 0.78 (d, J=6.8 Hz, 3H) ppm.

2,5-Dioxopyrrolidin-1-yl (2R)-6-[2-(cyclooct-2-yn-1-yloxy)acetamido]-2-{[(9H-fluoren-9-ylmethoxy)carbonyl]amino}hexanoate (118)

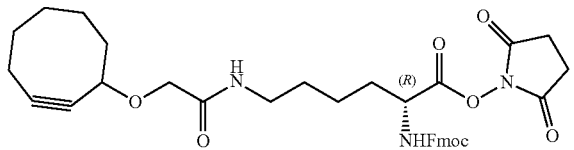

A mixture of compound 103 (0.10 g, 0.19 mmol), EDCI (72 mg, 0.38 mmol) and HOSu (43 mg, 0.38 mmol) in DCM (3 mL) was stirred at RT for 3 h. The reaction mixture was concentrated and the residue was purified by silica gel column chromatography (70% of ethyl acetate in petroleum ether) to give intermediate 118 (55 mg, 47% yield) as a white solid, which was used in the next step without purification. ESI m/z: 630 (M+1)$^+$.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (119)

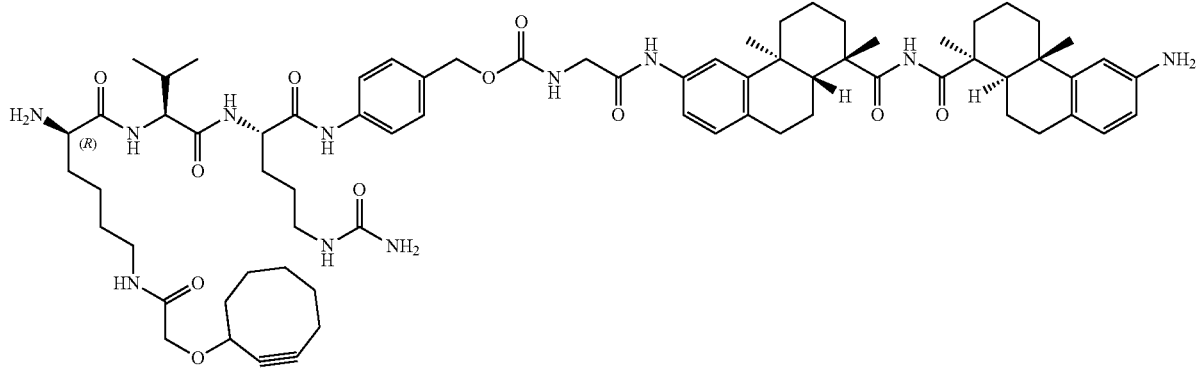

To a solution of compound 117 (55 mg, 56 µmol) and DIPEA (24 mg, 0.19 mmol) in DMF (1.5 mL) was added the crude intermediate 118 (40 mg, 63 µmol). The reaction mixture was stirred at RT for 2 h until 118 was consumed according to LCMS. The reaction mixture was directly purified by reverse phase flash chromatography (0-100% acetonitrile in water) to give Fmoc-119 (60 mg, ESI m/z: 753 (M/2+1)$^+$) as a white solid, which was dissolved in DMF (1.5 mL). To the solution was added diethylamine (24 mg, 0.33 mmol) and the solution was stirred at RT for 2 h until Fmoc was totally removed according to LCMS. The reaction mixture was directly purified by reverse phase flash chromatography (0-100% acetonitrile in aq. ammonium bicarbonate) to give compound 119 (35 mg, 50% yield from compound 117) as a white solid. ESI m/z: 1282 (M+H)$^+$.

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (120)

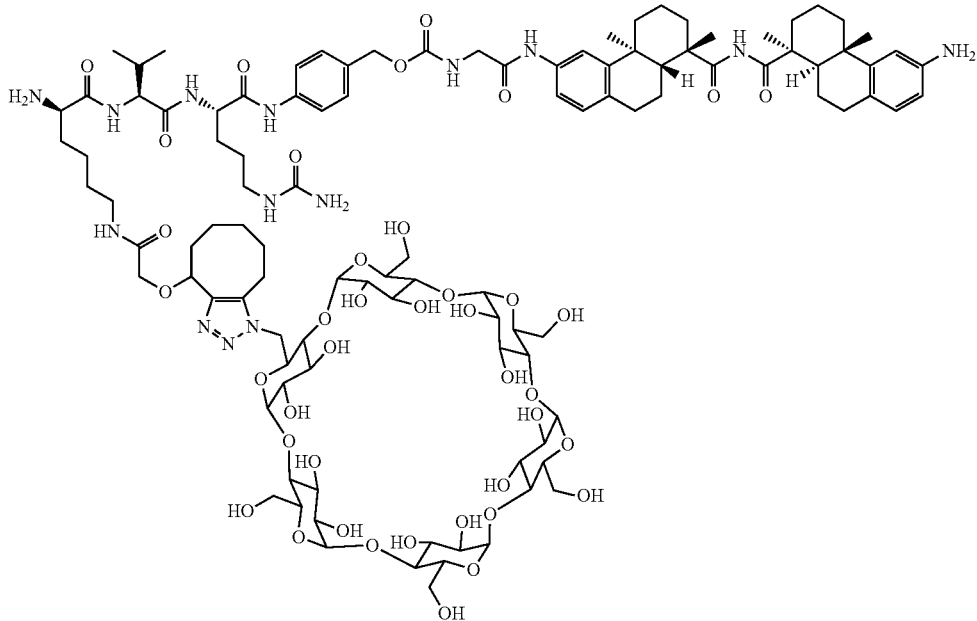 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of compound 119 (70 mg, 54 µmol) in DMF (3 mL) was added ax-CD-N$_3$ 105a (0.16 g, 0.16 mmol). The reaction mixture was stirred at 50° C. for 3 days, which was monitored by LCMS. The resulting mixture was then directly purified by reverse phase flash chromatography (0-100% acetonitrile in aq. ammonium bicarbonate (10 mM) to give compound 120 (20 mg, 16% yield) as a white solid. ESI m/z: 1141 (M/2+1)$^+$.

{4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (LP8)

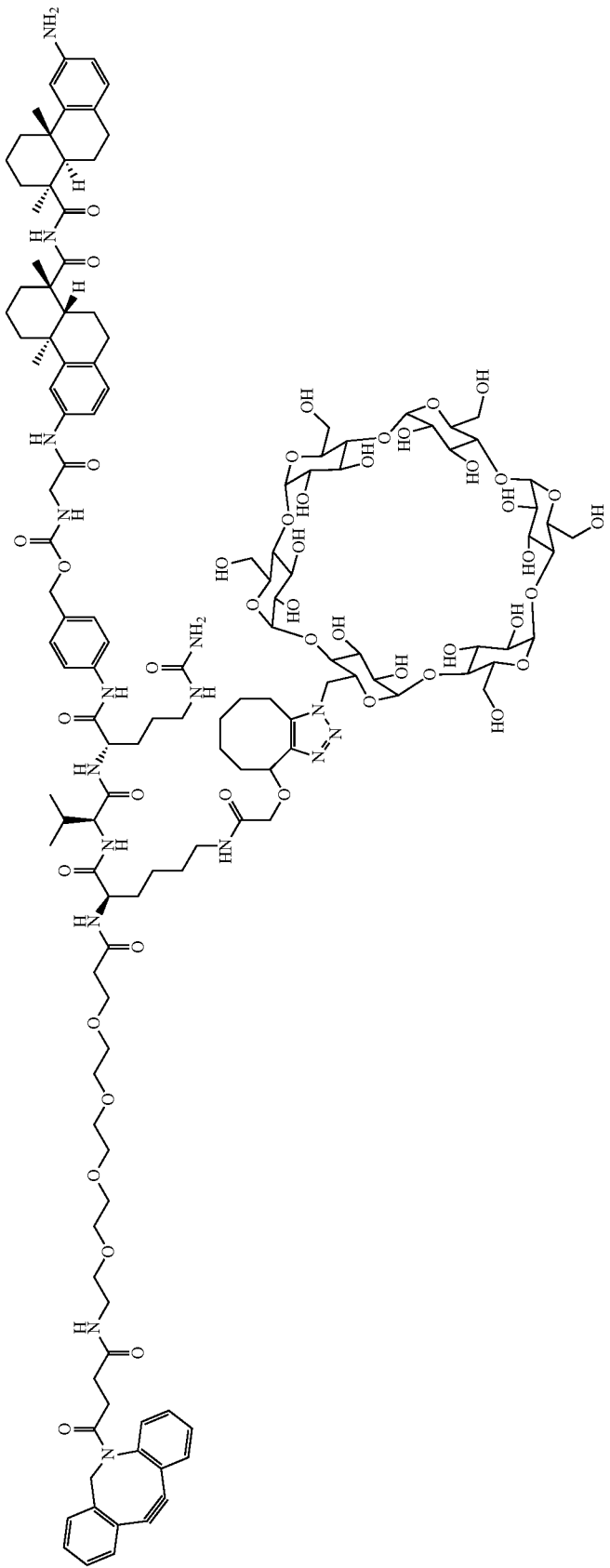

To a solution of compound 120 (10 mg, 4.4 μmol) and intermediate 107 (5 mg, 7.7 μmol) in DMF (2 mL) was added DIPEA (16 mg, 0.12 mmol) and the mixture was stirred at room temperature for 16 h. The reaction mixture was directly purified by prep-HPLC (method B) twice to give LP8 (1.5 mg, 12% yield) as a white solid. ESI m/z: 939 (M/3+H)$^+$. $^1$H NMR (500 MHz, DMSO$_{d6}$) δ 9.87-9.66 (m, 1H), 8.22-8.08 (m, 4H), 7.91-7.76 (m, 2H), 7.71-7.61 (m, 4H), 7.56-7.45 (m, 4H), 7.40-7.28 (m, 5H), 6.96 (d, J=8.5 Hz, 1H), 6.68 (d, J=8.1 Hz, 1H), 6.48 (s, 1H), 6.34 (d, J=8.2 Hz, 1H), 6.03-5.96 (m, 1H), 5.67-5.31 (m, 12H), 5.06-4.95 (m, 3H), 4.87-4.66 (m, 7H), 4.63-4.50 (m, 3H), 4.38-4.29 (m, 3H), 4.22-4.13 (m, 1H), 4.06-3.93 (m, 1H), 3.86-3.40 (m, 54H), 3.30-3.19 (m, 4H), 3.17-2.85 (m, 4H), 2.81-2.62 (m, 2H), 2.60-2.54 (m, 3H), 2.41-1.95 (m, 11H), 1.92-1.71 (m, 5H), 1.68-1.40 (m, 13H), 1.33-1.09 (m, 22H), 1.02-0.93 (m, 10H), 0.89-0.78 (m, 9H) ppm. Anal. HPLC (as a mixture of triazole regioisomers): 63%, Retention time: 6.03 min; 36%, Retention time: 6.13 min (method B).

Example 9

Linker-Payload LP9

This example demonstrates methods for the synthesis of the linker-payload LP9 in Table 2, above. This example refers to the compounds numbered 12b, 15, 112, 121, and 122 and linker-payload LP9 in FIG. 7.

9H-Fluoren-9-ylmethyl N-[(4bS,8S,8aR)-8-({[(1S, 4aS,10aR)-6-amino-1,4a-dimethyl-1,2,3,4,4a,9,10, 10a-octahydrophenanthren-1-yl] formamido}carbonyl)-4b,8-dimethyl-4b,5,6,7,8,8a,9, 10-octahydrophenanthren-3-yl]carbamate, trifluoroacetic acid salt (15)

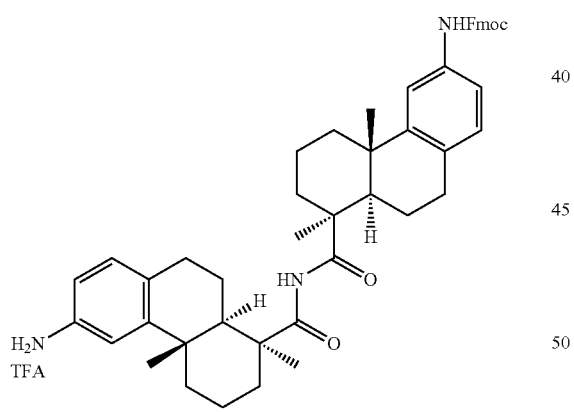

To a solution of compound 12b (0.63 g, 1.0 mmol) in DCM (50 mL) were added Fmoc-OSu (0.40 g, 1.2 mmol) and DIPEA (0.26 g, 2.0 mmol). The mixture was stirred at RT for 16 h, which was monitored by LCMS. The mixture was concentrated in vacuo and the residue was purified by silica gel column chromatography (50-80% ethyl acetate in petroleum ether) to give Boc-15 (0.71 g) as a white solid, which was dissolved in DCM (10 mL). To the solution was added TFA (3 mL) at RT. The reaction mixture was stirred at RT for 4 h until Boc was totally removed according to LCMS. The volatiles were removed in vacuo to give compound 15 as a TFA salt (0.62 g, 74% yield) and colorless oil. ESI m/z: 751 (M+H)$^+$.

9H-Fluoren-9-ylmethyl N-[(4bS,8S,8aR)-8-({[(1S, 4aS,10aR)-6-[(2S)-6-amino-2-{[(9H-fluoren-9-yl-methoxy)carbonyl]amino}hexanamido]-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate, trifluoroacetic acid salt (122)

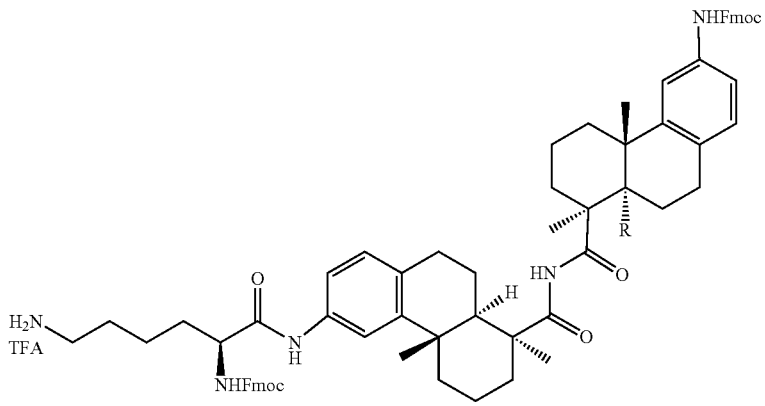

To the solution of compound 15 (0.30 g, 0.40 mmol) in DMF (20 mL) were added Fmoc-Lys(Boc)-OH 121 (0.23 g, 0.48 mmol), HATU (228 mg, 0.60 mmol) and DIPEA (0.16 g, 1.2 mmol) successively at RT. The reaction mixture was stirred at RT for 4 h, and monitored by LCMS. The resulting mixture was directly purified by reverse phase flash chromatography (50-90% acetonitrile in aq. ammonium bicarbonate (10 mM)) to give Boc-122 (0.41 g) as a white solid, 0.24 g of which was dissolved in DCM (20 mL). To the solution was added TFA (3 mL) and the reaction mixture was stirred at RT for an hour until Boc was totally removed according to LCMS. The volatiles were removed in vacuo to give compound 122 as a TFA salt (0.22 g, 79% yield) and colorless oil. ESI m/z: 1101 (M+H)$^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(5S)-5-amino-5-{[(4bS,8S,8aR)-8-{[(1S,4aS,10aR)-6-amino-1,4a-dimethyl-1,2,3,4,4a,9,10,10a-octahydro-phenanthrene-1-carbonyl]carbamoyl}-4b,8-dimethyl-4b,5,6,7,8,8a,9,10-octahydrophenanthren-3-yl]carbamoyl}pentyl]carbamate (LP9)

To a mixture of compound 122 (14 mg, 12 μmol) and compound 112 (15 mg, 14 μmol) in DMF (5 mL) were added HOBt (2 mg, 15 μmol) and DIPEA (5 mg, 37 μmol), and the mixture was stirred at RT for 4 h, which was monitored by LCMS. To the reaction mixture was then added piperidine (0.5 mL) and the mixture was stirred at RT for 0.5 h until Fmoc was totally removed according to LCMS. The reaction mixture was then filtered through a membrane and the filtrate was concentrated and directly purified by prep-HPLC (method B) to give LP9 (6 mg, 31% yield) as a white solid. ESI m/z: 798 (M/2+H)$^+$. $^1$H NMR (500 MHz, DMSO$_{d6}$) δ 10.0 (s, 1H), 8.15-8.08 (m, 2H), 7.87 (d, J=8.5 Hz, 1H), 7.76 (t, J=5.0 Hz, 1H), 7.67 (d, J=7.0 Hz, 1H), 7.61 (d, J=7.0 Hz, 1H), 7.60-7.56 (m, 2H), 7.51-7.42 (m, 4H), 7.41-7.24 (m, 6H), 7.20-7.16 (m, 1H), 6.95 (d, J=8.5 Hz, 1H), 6.68 (d, J=8.0 Hz, 1H), 6.50-6.46 (m, 1H), 6.36-6.32 (m, 1H), 6.00-5.96 (m, 1H), 5.40 (s, 2H), 5.02 (d, J=9.0 Hz, 1H), 4.91 (s, 2H), 4.69 (s, 2H), 4.40-4.35 (m, 1H), 4.25-4.20 (m, 1H), 3.65-3.55 (m, 3H), 3.50-3.40 (m, 14H), 3.24-3.20 (m, 2H), 3.10-3.05 (m, 2H), 3.00-2.92 (m, 3H), 2.92-2.85 (m, 1H), 2.80-2.70 (m, 2H), 2.65-2.55 (m, 2H), 2.45-2.35 (m, 2H), 2.31-2.20 (m, 4H), 2.20-2.10 (m, 4H), 2.10-1.92 (m, 3H), 1.90-1.70 (m, 6H), 1.68-1.53 (m, 6H), 1.50-1.30 (m, 8H), 1.25-1.20 (m, 7H), 1.20-1.10 (m, 3H), 1.02-0.96 (m, 6H), 0.90-0.80 (m, 6H) ppm.

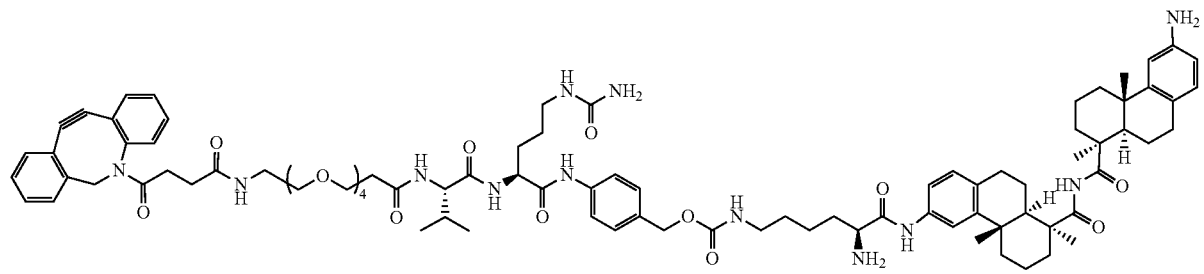

Example 10

Linker-Payloads LP10 and LP11

This example demonstrates methods for the synthesis of the linker-payloads LP10-LP11 in Table 2, above. This example refers to the compounds numbered P7, P8, 116, 123a-b, linker-payloads LP10 and LP11 in FIG. 8.

(S)-4-((4bS,8S,8aR)-8-((1S,4aS,10aR)-6-Amino-1,
4a-dimethyl-1,2,3,4,4a,9,10,10a-octahydro-
phenanthrene-1-carbonylcarbamoyl)-4b,8-dimethyl-
4b,5,6,7,8,8a,9,10-octahydrophenanthren-3-
ylamino)-3-((4-((S)-2-((S)-2-amino-3-
methylbutanamido)-5-ureidopentanamido)
benzyloxy)carbonylamino)-4-oxobutanoic acid
(123a)

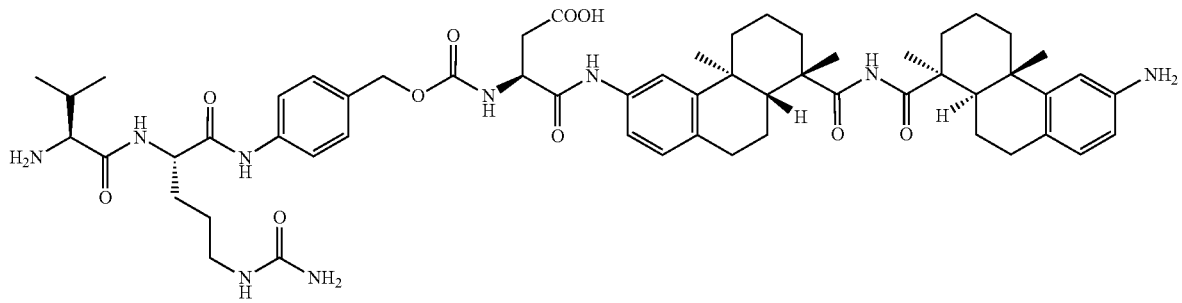 [SMILES: CC(C)[C@H](N)C(=O)N[C@@H](CCCNC(N)=O)C(=O)Nc1ccc(COC(=O)N[C@@H](CC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of payload P7 (64 mg, 0.10 mmol) in DMF (5 mL) were added intermediate 116 (92 mg, 0.12 mmol) and DIPEA (26 mg, 0.20 mmol) successively at RT. The reaction mixture was stirred at RT for 4 h, and monitored by LCMS. To the mixture was then added piperidine (0.5 mL), and the reaction mixture was stirred at RT for 10 min until Fmoc was totally removed according to LCMS. The mixture was directly purified by reverse phase flash chromatography (40-70% acetonitrile in aq. ammonium bicarbonate (10 mM)) to give compound 123a (41 mg, 39% yield) as a white solid. ESI m/z: 1049 (M+H)$^+$.

(S)-5-((4bS,8S,8aR)-8-((1S,4aS,10aR)-6-Amino-1,
4a-dimethyl-1,2,3,4,4a,9,10,10a-octahydro-
phenanthrene-1-carbonylcarbamoyl)-4b,8-dimethyl-
4b,5,6,7,8,8a,9,10-octahydrophenanthren-3-
ylamino)-4-((4-((S)-2-((S)-2-amino-3-
methylbutanamido)-5-ureidopentanamido)
benzyloxy)carbonylamino)-5-oxopentanoic acid
(123b)

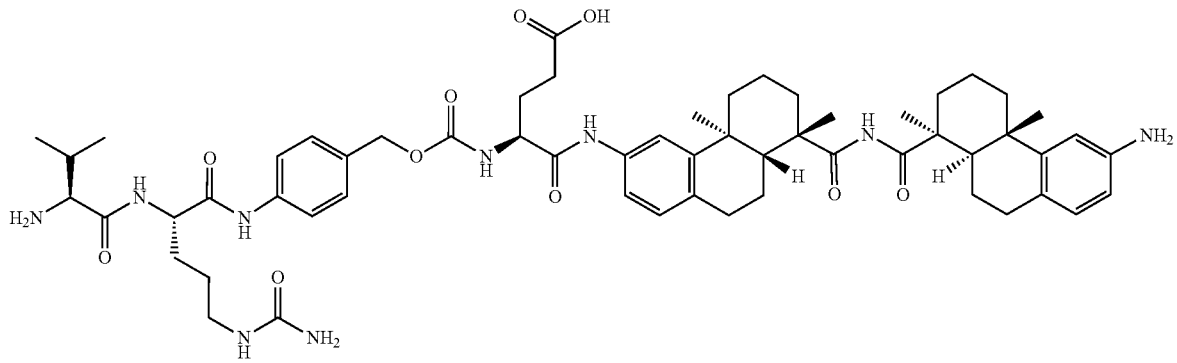 [SMILES: CC(C)[C@H](N)C(=O)N[C@@H](CCCNC(N)=O)C(=O)Nc1ccc(COC(=O)N[C@@H](CCC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

Following a similar procedure for 123a except substituting P8 (0.53 g, 0.81 mmol) for P7, provides compound 123b (0.61 g, 71% yield) as a white solid. ESI m/z: 1063 (M+H)+.

(3S)-3-{[({4-[(2S)-2-[(2S)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]amino}-3-{[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}propanoic acid (LP10)

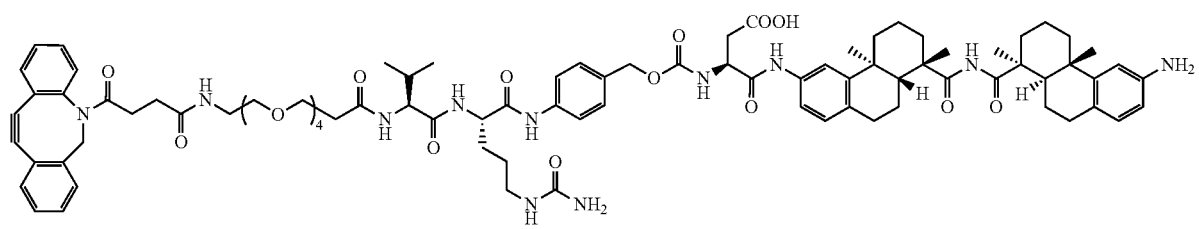

To a solution of compound 123 (21 mg, 20 µmol) in DMF (2 mL) was added intermediate 107 (16 mg, 24 µmol) and DIPEA (5 mg, 40 µmol) successively at RT. The reaction mixture was stirred at RT for 4 h, and monitored by LCMS. The resulting mixture was directly purified by Prep-HPLC (method B) to give compound LP10 (12 mg, 38% yield) as a white solid. ESI m/z: 792 (M/2+H)+. ¹H NMR (400 MHz, DMSO$_{d6}$) δ 10.0 (s, 1H), 8.14 (d, J=7.2 Hz, 1H), 8.09 (s, 1H), 7.90 (d, J=8.8 Hz, 1H), 7.85-7.75 (m, 1H), 7.68 (d, J=8.0 Hz, 1H), 7.65-7.55 (m, 3H), 7.55-7.40 (m, 4H), 7.40-7.25 (m, 5H), 6.95 (d, J=8.8 Hz, 1H), 6.67 (d, J=8.0 Hz, 1H), 6.47 (s, 1H), 6.32 (d, J=8.0 Hz, 1H), 6.05-5.95 (m, 1H), 5.43 (s, 2H), 5.05-4.90 (m, 3H), 4.80-4.60 (m, 1H), 4.40-4.35 (m, 2H), 4.25-4.20 (m, 1H), 3.65-3.55 (m, 3H), 3.50-3.40 (m, 25H), 3.20-2.85 (m, 4H), 2.80-2.55 (m, 3H), 2.40-2.30 (m, 3H), 2.30-2.20 (m, 3H), 2.20-2.05 (m, 4H), 2.0-1.50 (m, 12H), 1.50-1.30 (m, 3H), 1.30-1.20 (m, 6H), 1.20-1.05 (m, 2H), 1.05-0.90 (m, 5H), 0.90-0.80 (in, 6H) ppm.

(4S)-4-{[({4-[(2S)-2-[(2S)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]amino}-4-{[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}butanoic acid (LP11)

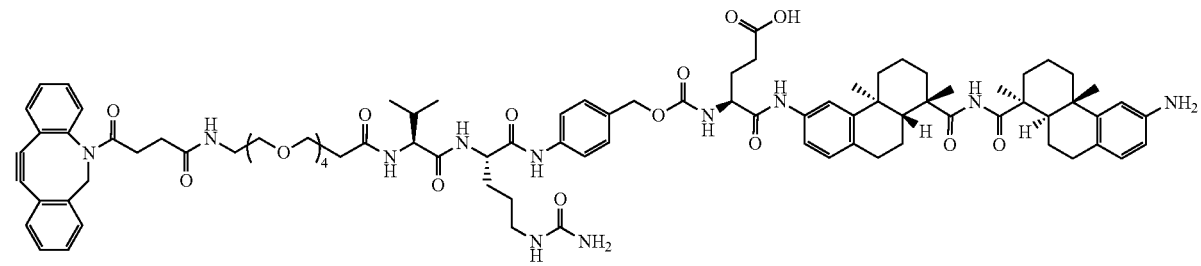

Following a similar procedure for LP10 except substituting 123b (0.10 g, 94 µmol) for 123a, provides compound LP11 (50 mg, 33% yield) as a white solid. ESI m/z: 799 (M/2+H)⁺. ¹H NMR (400 MHz, DMSO$_{d6}$) δ 10.0 (s, 1H), 9.91 (s, 1H), 8.14 (d, J=7.2 Hz, 1H), 8.09 (s, 1H), 7.90 (d, J=8.8 Hz, 1H), 7.85-7.75 (m, 1H), 7.68 (d, J=8.0 Hz, 1H), 7.65-7.55 (m, 3H), 7.55-7.40 (m, 4H), 7.40-7.25 (m, 6H), 6.95 (d, J=8.8 Hz, 1H), 6.67 (d, J=8.0 Hz, 1H), 6.47 (s, 1H), 6.32 (d, J=8.0 Hz, 1H), 6.05-5.95 (m, 1H), 5.43 (s, 2H), 5.05-4.90 (m, 3H), 4.40-4.35 (m, 2H), 4.25-4.20 (m, 1H), 3.65-3.55 (m, 4H), 3.50-3.40 (m, 25H), 3.20-2.85 (m, 4H), 2.80-2.55 (m, 3H), 2.40-2.30 (m, 3H), 2.30-2.20 (m, 3H), 2.20-2.05 (m, 4H), 2.00-1.50 (m, 12H), 1.50-1.30 (m, 3H), 1.30-1.20 (m, 6H), 1.20-1.05 (m, 2H), 1.05-0.90 (m, 5H), 0.90-0.80 (m, 6H) ppm.

Example 11

Payload P12 and P16; and Linker-Payload LP12 and LP16

This example demonstrates methods for the synthesis of the payload P12 and P16 in Table 1, above, and the linker-payload LP12 and LP16 in Table 2, above. This example refers to the compounds numbered 12b, 107, 124, 125, and 126; and payload P12 and P16; and linker-payload LP12 and LP16 in FIG. 9

((S)-2-((((9H-Fluoren-9-yl)methoxy)carbonyl)amino)-5-(tert-butoxy)-5-oxopentanoyl)-L-alanine
(125)

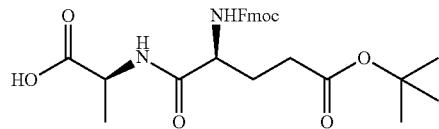

To a solution of Fmoc-Glu(OtBu)-OH (6.0 g, 14 mmol) in DCM (300 mL) were added HOSu (3.2 g, 28 mmol) and EDCI (5.4 g, 28 mmol). The reaction mixture was stirred at RT overnight, and monitored by LCMS. The resulting mixture was diluted with DCM (200 mL) and washed with water (100 mL×2) and brine (100 mL). The organic solution was dried over anhydrous sodium sulfate, filtered, and concentrated in vacuo to give crude compound 124 (8.5 g, ESI m/z: 545 (M+23)⁺), which was dissolved into DMF (10 mL). To the solution were added alanine (4.2 g, 48 mmol) and DIPEA (6.2 g, 48 mmol). The reaction mixture was stirred at RT overnight, and monitored by LCMS. The resulting mixture was poured into water (100 mL) and acidified with acetic acid to pH 5-6. The mixture was extracted with ethyl acetate and the combined organic solution was concentrated in vacuo. The crude product was purified by reverse phase flash chromatography (0-60% acetonitrile in aq. TFA (0.01%)) to give compound 125 (1 g, 15% yield) as a white solid. ESI m/z: 497 (M+H)⁺.

(S)-tert-Butyl 4-amino-5-((S)-1-((4bS,8S,8aR)-8-((1S,4aS,10aR)-6-(tert-butoxycarbonylamino)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-1-oxopropan-2-ylamino)-5-oxopentanoate
(126a)

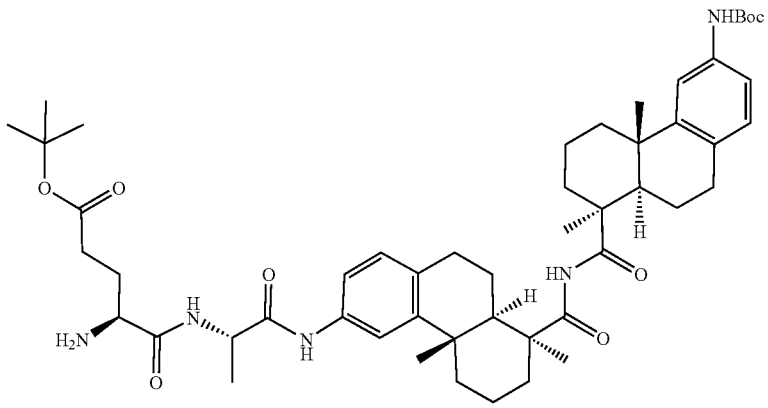 [SMILES: C[C@H](NC(=O)[C@@H](N)CCC(=O)OC(C)(C)C)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

To a solution of compound 125 (42 mg, 84 µmol) and DIPEA (28 µl, 0.16 mmol) in DMF (3.0 mL) was added HATU (36 mg, 95 µmol). The reaction mixture was stirred at RT for 10 min before the addition of compound 12b (50 mg, 80 µmol), and the mixture was stirred at RT overnight, which was monitored by LCMS. To the reaction mixture was then added piperidine (1.0 mL) and the mixture was stirred at RT for 3 h until Fmoc was totally removed according to LCMS. The resulting mixture was directly purified by reverse phase flash chromatography (0-100% acetonitrile in aq. TFA (0.01%)) to give compound 126a (20 mg, 28% yield) as a yellow solid. ESI m/z: 885 (M+H)⁺.

tert-Butyl (4S)-4-amino-4-{[(1S)-1-{[(4bS,8S,8aR)-
8-({[(1S,4aS,10aR)-6-hydroxy-1,4a-dimethyl-1,2,3,
4,4a,9,10,10a-octahydrophenanthren-1-yl]
formamido}carbonyl)-4b,8-dimethyl-4b,5,6,7,8,8a,9,
10-octahydrophenanthren-3-yl]carbamoyl}ethyl]
carbamoyl}butanoate (126b)

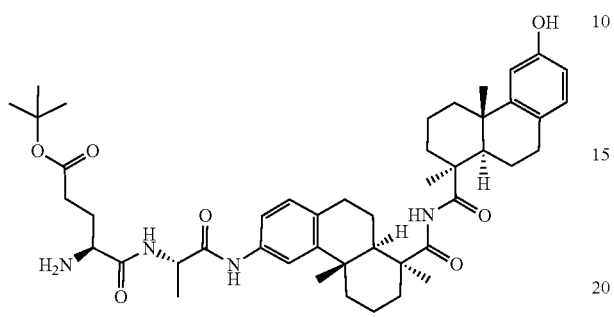

Following a similar procedure for 126a, except substituting P1 for 12b, compound 126b (37 mg, 47% yield) was obtained as a white solid. ESI m/z: 393.4 (M/2+1)⁺.

(S)-4-Amino-5-((S)-1-((4bS,8S,8aR)-8-((1S,4aS,
10aR)-6-amino-1,4a-dimethyl-1,2,3,4,4a,9,10,10a-
octahydrophenanthrene-1-carbonylcarbamoyl)-4b,8-
dimethyl-4b,5,6,7,8,8a,9,10-octahydrophenanthren-
3-ylamino)-1-oxopropan-2-ylamino)-5-oxopentanoic
acid (P12)

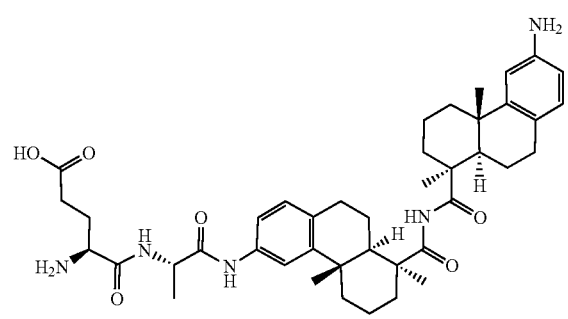 [SMILES: C[C@H](NC(=O)[C@@H](N)CCC(=O)O)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

A mixture of compound 126a (57 mg, 64 μmol) in neat TFA (2.0 mL) was stirred at RT for an hour, and monitored by LCMS. The resulting mixture was diluted with DCM (20 mL) and concentrated in vacuo. The residue was purified by reverse phase flash chromatography (0-100% acetonitrile in aq. sodium bicarbonate (10 mM)) to give P12 (20 mg, 43% yield) as a white solid. ESI m/z: 365 (M/2+H)⁺. ¹H NMR (400 MHz, DMSO$_{d6}$) δ 9.90 (s, 1H), 8.30 (br s, 1H), 8.09 (s, 1H), 7.50 (s, 1H), 7.33 (d, J=8.4 Hz, 1H), 6.96 (d, J=8.4 Hz, 1H), 6.67 (d, J=8.0 Hz, 1H), 6.46 (s, 1H), 6.33 (dd, J=7.6 Hz and 2.0 Hz, 1H), 4.70 (br s, 1H), 4.41-4.36 (m, 1H), 3.42-3.30 (m, 6H), 2.91-2.85 (m, 1H), 2.78-2.75 (m, 2H), 2.67-2.61 (m, 1H), 2.32-2.27 (m, 4H), 2.16-2.13 (m, 4H), 1.88-1.77 (m, 4H), 1.65-1.58 (m, 4H), 1.29-1.23 (m, 12H), 1.14-1.11 (m, 2H), 1.01 (d, J=7.6 Hz, 6H) ppm.

(4S)-4-Amino-4-{[(1S)-1-{[(4bS,8S,8aR)-8-({[(1S,
4aS,10aR)-6-hydroxy-1,4a-dimethyl-1,2,3,4,4a,9,10,
10a-octahydrophenanthren-1-yl]
formamido}carbonyl)-4b,8-dimethyl-4b,5,6,7,8,8a,9,
10-octahydrophenanthren-3-yl]carbamoyl}ethyl]
carbamoyl}butanoic acid (P16)

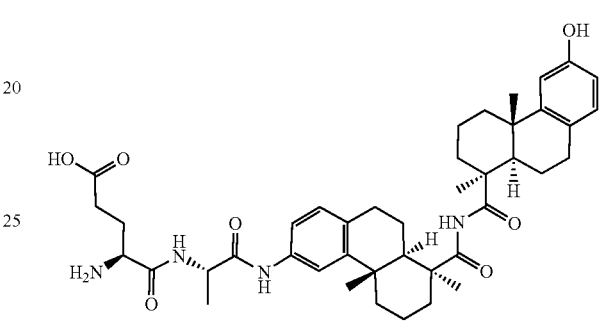

Following a similar procedure for P12, except substituting 126b for 126a, payload P16 (18 mg, 53% yield) was obtained as a yellow solid. ESI m/z: 729.5 (M+1)⁺. ¹H NMR (400 MHz, DMSO$_{d6}$) δ 9.95-9.90 (d, J=18.8 Hz, 1H), 8.30 (br s, 1H), 8.11 (s, 1H), 7.52 (s, 1H), 7.37-7.33 (m, 1H), 6.96 (d, J=8.0 Hz, 1H), 6.81 (d, J=8.0 Hz, 1H), 6.63 (d, J=2.8 Hz, 1H), 6.50 (dd, J=8.0, 2.0 Hz, 1H), 4.39 (br s, 1H), 3.32-3.16 (m, 4H), 2.90-2.66 (m, 5H), 2.27-2.13 (m, 8H), 1.88-1.80 (m, 4H), 1.66-1.59 (m, 4H), 1.47 (br s, 1H), 1.31-1.23 (m, 11H), 1.17-1.10 (m, 2H), 1.00-0.98 (m, 6H) ppm.

(4S)-4-[1-(4-{2-Azatricyclo[10.4.0.0⁴,⁹]hexadeca-1
(12),4(9),5,7,13,15-hexaen-10-yn-2-yl}-4-oxobu-
tanamido)-3,6,9,12-tetraoxapentadecan-15-amido]-
4-{[(1S)-1-{[(4bS,8S,8aR)-8-({[(1S,4aS,10aR)-6-
amino-1,4a-dimethyl-1,2,3,4,4a,9,10,10a-
octahydrophenanthren-1-yl]formamido}carbonyl)-
4b,8-dimethyl-4b,5,6,7,8,8a,9,10-
octahydrophenanthren-3-yl]carbamoyl}ethyl]
carbamoyl}butanoic acid (LP12)

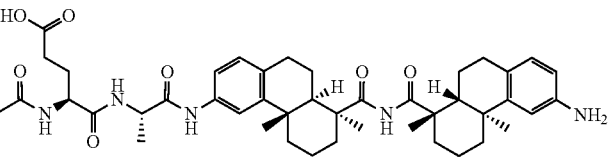

To a solution of compound P12 (10 mg, 14 μmol) in DMF (2.0 ml) were added DIPEA (6 μl, 21 μmol) and compound 107 (11 mg, 16 μmol). The reaction mixture was stirred at RT for 3 h, and monitored by LCMS. The resulting mixture was directly purified by Prep-HPLC (method B) to give compound LP12 (3.5 mg, 20% yield) as a white solid. ESI m/z: 632 (M/2+H)$^+$. $^1$H NMR (400 MHz, DMSO$_{d6}$) δ 9.64 (s, 1H), 9.49 (s, 1H), 8.41-8.39 (m, 1H), 8.12-8.09 (m, 1H), 7.79 (br s, 1H), 7.67 (d, J=7.2 Hz, 1H), 7.61 (d, J=7.2 Hz, 1H), 7.60 (br s, 1H), 7.52-7.27 (m, 8H), 6.95 (d, J=8.4 Hz, 1H), 6.67 (d, J=8.4 Hz, 1H), 6.47 (s, 1H), 6.33 (dd, J=8.4 Hz and 1.6 Hz, 1H), 5.02 (d, J=14.0 Hz, 1H), 4.70-4.67 (br s, 1H), 4.36-4.30 (m, 1H), 4.21-4.14 (m, 1H), 3.61-3.58 (m, 3H), 3.46-3.45 (m, 15H), 3.08-3.06 (m, 2H), 2.90-2.55 (m, 5H), 2.42-2.09 (m, 12H), 1.98-1.73 (m, 7H), 1.65-1.54 (m, 3H), 1.29-1.25 (m, 12H), 1.17-1.11 (m, 2H), 0.99-0.97 (m, 6H) ppm.

(4S)-4-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-4-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}butanoic acid (LP16)

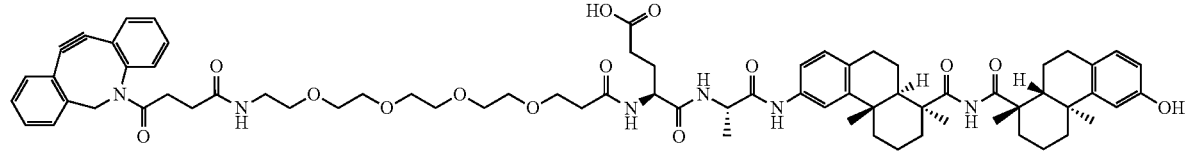 [SMILES: C[C@H](NC(=O)[C@H](CCC(=O)O)NC(=O)CCOCCOCCOCCOCCNC(=O)CCC(=O)N1Cc2ccccc2C#Cc2ccccc21)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Following a similar procedure for LP12, except substituting P16 for P12, linker-payload LP16 (12 mg, 69% yield) was obtained as a white solid. ESI m/z: 632.5 (M/2+1)$^+$. $^1$H NMR (400 MHz, DMSO$_{d6}$) δ 9.63 (s, 1H), 9.49 (s, 1H), 8.97 (s, 1H), 8.38 (d, J=5.6 Hz, 1H), 8.11 (s, 1H), 7.78 (br s, 1H), 7.67 (d, J=7.6 Hz, 1H), 7.61 (d, J=6.4 Hz, 1H), 7.56-7.27 (m, 8H), 6.95 (d, J=8.0 Hz, 1H), 6.81 (d, J=8.4 Hz, 1H), 6.63 (d, J=8.4 Hz, 1H), 6.51-6.48 (m, 1H), 5.02 (d, J=13.6 Hz, 1H), 4.36-4.30 (m, 1H), 4.20-4.15 (m, 1H), 3.61-3.54 (m, 3H), 3.46-3.43 (m, 14H), 3.10-3.06 (m, 2H), 2.89-2.66 (m, 5H), 2.44-2.11 (m, 12H), 2.02-1.73 (m, 7H), 1.65-1.56 (m, 3H), 1.31-1.22 (m, 12H), 1.17-1.09 (m, 2H), 1.00-0.98 (m, 6H) ppm.

Example 12

Linker-Payload LP13 and LP14

This example demonstrates methods for the synthesis of the linker-payloads LP13 and LP14 in Table 2, above. This example refers to the compounds numbered 102a, 127a/b, 128a/b, 107, and linker-payloads LP13 and LP14 in FIG. 9A.

(4S)-4-Amino-4-{[(1S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}butanoic acid (128a)

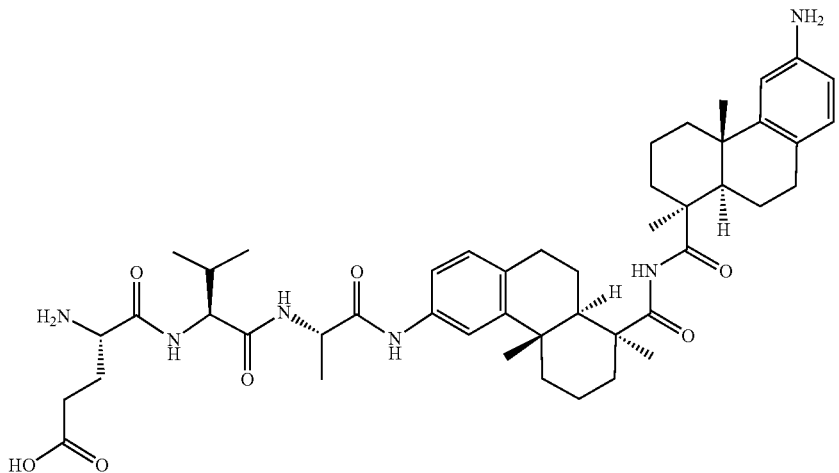 [SMILES: CC(C)[C@H](NC(=O)[C@@H](N)CCC(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

A solution of compound 127a (6.4 mg, 21 µmol) and HATU (8.0 mg, 21 µmol) in DMF (2.0 mL) was stirred at RT for 15 min before the addition of compound 102a (14 mg, 17.5 µmol) and DIPEA (6.8 mg, 52.5 µmol) were added. The reaction mixture was stirred at RT for an hour, which was monitored by LCMS. The mixture was directly purified by reversed phase flash chromatography (0-100% acetonitrile in water) to give protected 128a (12 mg) as a white solid, which was dissolved into DCM (4 mL). To the stirred solution was added TFA (0.5 mL), and the mixture was stirred at RT for an hour, which was monitored by LCMS. The resulting mixture was directly purified by reversed phase flash chromatography (0-100% acetonitrile in aq. ammonium bicarbonate (10 mM)) to give compound 128a (7.1 mg, 49% yield) as a white solid. ESI m/z: 827.5 (M+1)+.

(4R)-4-amino-4-{[(1S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}butanoic acid (128b)

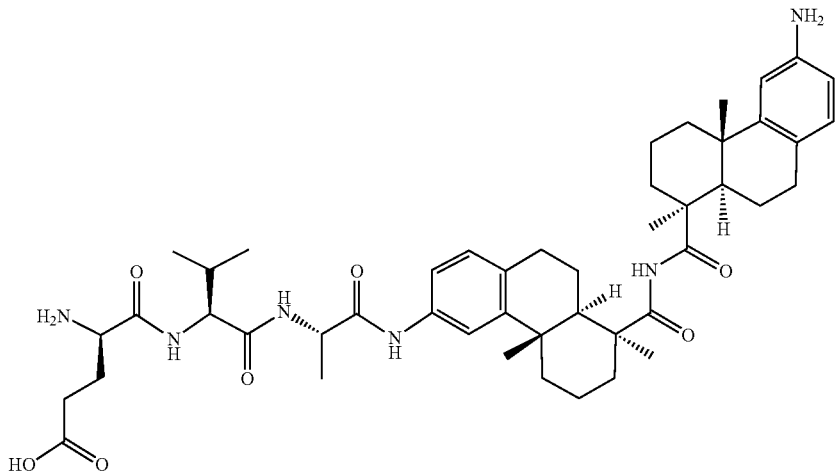 [SMILES: CC(C)[C@H](NC(=O)[C@H](N)CCC(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following a similar procedure for 128a, except substituting compound 127b for 127a, compound 128b (16 mg, 56% yield) was obtained as a white solid. ESI m/z: 827.5 (M+1)+.

(4S)-4-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-4-{[(1S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}butanoic acid (LP13)

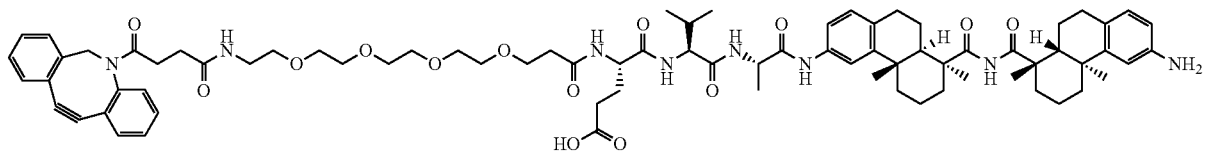 [SMILES: CC(C)[C@H](NC(=O)[C@H](CCC(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

To a mixture of compound 128a (7.1 mg, 8.6 µmol) in DMF (2.0 mL) were added compound 107 (5.6 mg, 8.6 µmol) and DIPEA (3.3 mg, 26 µmol), and the reaction mixture was stirred at RT for an hour, which was monitored by LCMS. The resulting mixture was directly purified by reversed phase flash chromatography (0-100% acetonitrile in aq. ammonium bicarbonate (10 mM)) to give linker-payload LP13 (5.5 mg, 47% yield) as a white solid. ESI m/z: 681.6 (M/2+1)$^+$. H NMR (400 MHz, DMSO$_{d6}$) δ 9.75 (dd, J=12, 0.6 Hz, 1H), 8.31 (dd, J=12, 3.5 Hz, 1H), 8.19 (dd, J=7.5, 2.1 Hz, 1H), 8.16-8.08 (m, 2H), 7.82-7.70 (m, 2H), 7.68 (dd, J=7.5, 1.1 Hz, 1H), 7.64-7.59 (m, 1H), 7.56-7.44 (m, 4H), 7.41-7.27 (m, 4H), 6.96 (dd, J=8.8, 3.2 Hz, 1H), 6.68 (d, J=8.2 Hz, 1H), 6.47 (d, J=1.8 Hz, 1H), 6.33 (dd, J=8.1, 2.1 Hz, 1H), 5.02 (d, J=14.0 Hz, 1H), 4.43-4.26 (m, 3H), 4.22-4.08 (m, 2H), 3.62-3.55 (m, 3H), 3.51-3.42 (m, 12H), 3.30-3.20 (m, 2H), 3.12-2.84 (m, 3H), 2.80-2.55 (m, 4H), 2.47-2.10 (m, 12H), 2.04-1.52 (m, 13H), 1.37-1.23 (m, 10H), 1.17-1.08 (m, 2H), 0.99 (d, J=7.7 Hz, 6H), 0.88-0.78 (m, 6H) ppm.

(4R)-4-[1-(4-{2-Azatricyclo[10.4.0.04,9]hexadeca-1 (12),4(9),5,7,13,15-hexaen-10-yn-2-yl}-4-oxobutanamido)-3,6,9,12-tetraoxapentadecan-15-amido]-4-{[(1S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl] carbamoyl}-2-methylpropyl]carbamoyl}butanoic acid (LP14)

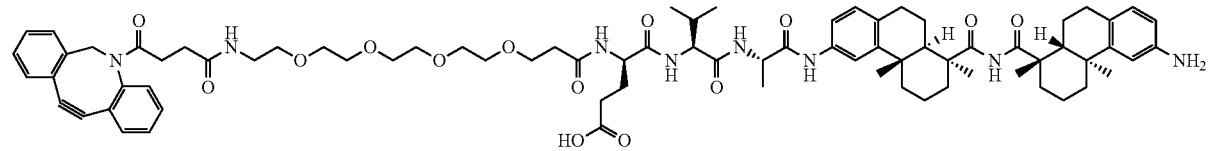 [SMILES: CC(C)[C@H](NC(=O)[C@@H](CCC(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following a similar procedure for LP13, except substituting 128b for 128a, linker-payload LP14 (10 mg, 76% yield) was obtained as a white solid. ESI m/z: 681.5 (M/2+1)$^+$. $^1$H NMR (400 MHz, DMSO$_{d6}$) δ 9.79 (br, 1H), 9.35 (s, 1H), 8.28-8.23 (m, 1H), 8.21 (d, J=6.6 Hz, 1H), 8.17-8.13 (m, 1H), 8.12-8.03 (m, 2H), 8.02-7.95 (m, 1H), 7.76 (t, J=5.8 Hz, 1H), 7.67 (dd, J=7.3, 1.1 Hz, 1H), 7.64-7.60 (m, 1H), 7.51 (dd, J=5.0, 1.9 Hz, 1H), 7.49-7.42 (m, 3H), 7.40-7.31 (m, 3H), 7.29 (dd, J=7.4, 1.5 Hz, 1H), 6.95 (dd, J=8.2, 4.7 Hz, 1H), 6.68 (d, J=8.2 Hz, 1H), 6.48 (d, J=2.1 Hz, 1H), 6.33 (dd, J=7.9, 2.1 Hz, 1H), 5.02 (d, J=14.0 Hz, 1H), 4.40-4.30 (m, 2H), 4.20-4.12 (m, 1H), 3.62-3.49 (m, 4H), 3.45-3.33 (m, 12H), 3.33-3.28 (m, 2H), 3.12-3.05 (m, 2H), 2.92-2.85 (m, 1H), 2.81-2.73 (m, 2H), 2.69-2.63 (m, 1H), 2.61-2.54 (m, 1H), 2.43-2.20 (m, 7H), 2.20-1.95 (m, 6H), 1.91-1.70 (m, 6H), 1.68-1.50 (m, 5H), 1.34-1.22 (m, 10H), 1.18-1.08 (m, 2H), 1.03-0.96 (m, 6H), 0.90 (d, J=6.8 Hz, 2H), 0.86-0.80 (m, 4H) ppm.

Example 12A

Linker-Payload LP15

This example demonstrates methods for the synthesis of the linker-payload LP15 in Table 2, above. This example refers to the compounds numbered 129, 130, 131, 132, 133, Ser-P1, and linker-payload LP15 in FIG. 9B. Compound 129 was synthesized according to WO 2015/095124 A1.

1-N-(2-{2-[2-(2-Azidoethoxy)ethoxy]ethoxy}ethyl)-1-N'-[(1S)-4-(carbamoylamino)-1-{[4-(hydroxymethyl)phenyl]carbamoyl}butyl]cyclobutane-1,1-dicarboxamide (130)

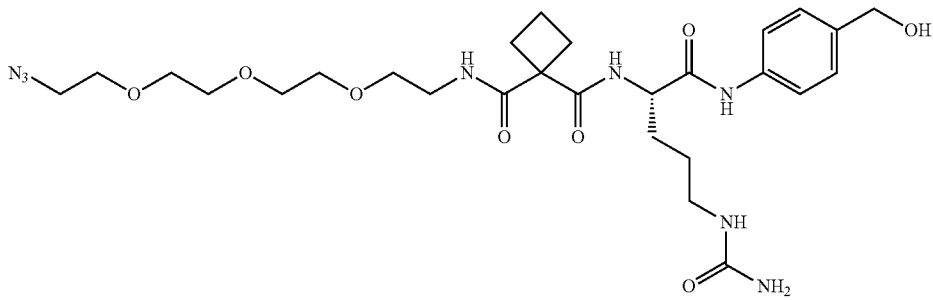 [SMILES: [N-]=[N+]=NCCOCCOCCOCCNC(=O)C1(C(=O)N[C@@H](CCCNC(N)=O)C(=O)Nc2ccc(CO)cc2)CCC1]

To a solution of compound 129 (0.18 g, 0.44 mmol) in dry DMF (6 mL) were added amino-PEG3-azide (0.10 g, 0.46 mmol) and EDCI (0.13 g, 0.65 mmol), and the mixture was stirred at RT for 20 hours. The resulting mixture was directly purified by reversed phase flash chromatography (0-100% acetonitrile in water) to give compound 130 (0.19 g, 70% yield) as an off-white solid. ESI m/z: 607.3 (M+1)$^+$.

1-N-(2-{2-[2-(2-Aminoethoxy)ethoxy]ethoxy}ethyl)-1-N'-[(1S)-4-(carbamoylamino)-1-{[4-(hydroxymethyl)phenyl]carbamoyl}butyl]cyclobutane-1,1-dicarboxamide (131)

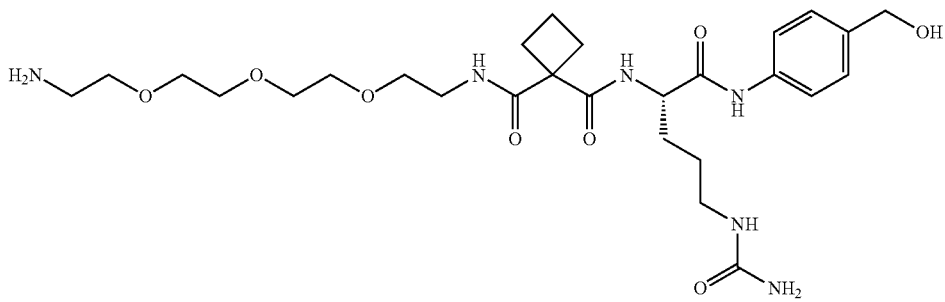 [SMILES: NCCOCCOCCOCCNC(=O)C1(C(=O)N[C@@H](CCCNC(N)=O)C(=O)Nc2ccc(CO)cc2)CCC1]

To a solution of compound 130 (0.18 g, 0.30 mmol) in methanol (10 mL) was added 10% palladium on carbon (20 mg) under nitrogen. The mixture was degassed and purged with hydrogen 3 times, and was then stirred at RT under hydrogen for 20 hours. The resulting mixture was filtered through Celite and the filtrate was concentrated in vacuo to give crude compound 131 (0.16 g, 92% yield) as a white solid. ESI m/z: 581.4 (M+1)$^+$.

(2S)-2-[(1-{[2-(2-{2-[2-(4-{2-azatricyclo[10.4.0.0⁴,⁹]hexadeca-1(12),4(9),5,7,13,15-hexaen-10-yn-2-yl}-4-oxobutanamido)ethoxy]ethoxy}ethoxy)ethyl]carbamoyl}cyclobutyl)formamido]-5-(carbamoylamino)-N-[4-(hydroxymethyl)phenyl]pentanamide (133)

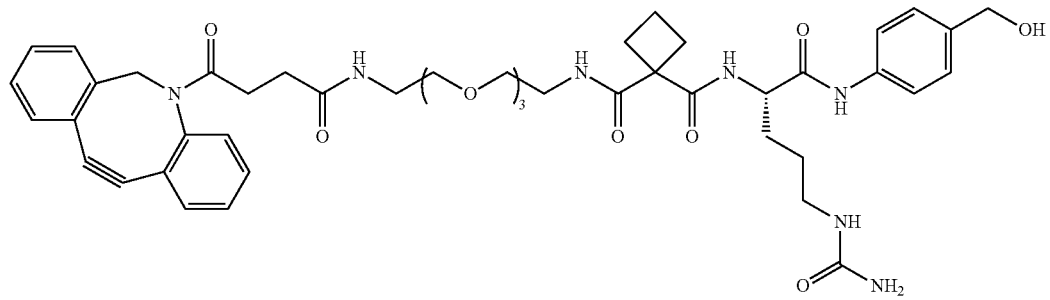

To a solution of crude compound 131 (0.16 g, 0.28 mmol) in DMF (4 mL) were added DIBAC-suc-OSu 132 (0.12 g, 0.30 mmol) and DIPEA (0.2 mL, 0.83 mmol), and the reaction mixture was stirred at RT for 2 hours, which was monitored by LCMS. The resulting mixture was directly purified by reversed phase flash chromatography (0-100% acetonitriled in aq. ammonium bicarbonate (10 mM)) to give compound 133 (50 mg, 21% yield) as a yellow solid. ESI m/z: 434.8 (M/2+1)⁺.

{4-[(2S)-2-[(1-{[2-(2-{2-[2-(4-{2-Azatricyclo[10.4.0.0⁴,⁹]hexadeca-1(12),4(9),5,7,13,15-hexaen-10-yn-2-yl}-4-oxobutanamido)ethoxy]ethoxy}ethoxy)ethyl]carbamoyl}cyclobutyl)formamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP15)

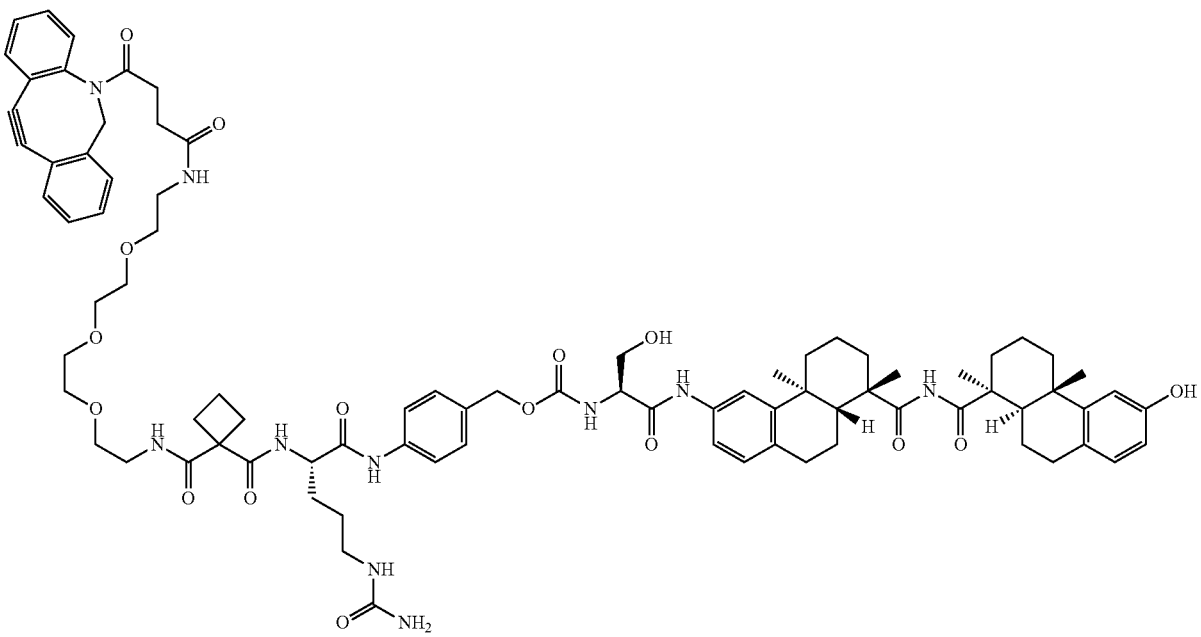 [SMILES: C[C@]1(C(=O)NC(=O)[C@@]2(C)CCC[C@]3(C)c4cc(NC(=O)[C@H](CO)NC(=O)OCc5ccc(NC(=O)[C@H](CCCNC(N)=O)NC(=O)C6(C(=O)NCCOCCOCCOCCNC(=O)CCC(=O)N7Cc8ccccc8C#Cc8ccccc87)CCC6)cc5)ccc4CC[C@@H]23)CCC[C@]2(C)c3cc(O)ccc3CC[C@@H]12]

To a solution of compound 133 (50 mg, 58 μmol) in dry DMF (3 mL) were added bis(4-nitrophenyl) carbonate (PNPC) (35 mg, 0.12 mmol) and DIPEA (45 μL, 0.17 mmol) successively, and the reaction mixture was stirred at RT overnight. The mixture was purified by reversed phase flash chromatography (0-100% acetonitrile in water). The solution was lyophilized to give a yellow solid, 16 mg of which (16 μmol) was dissolved in DMF (5 mL). To the solution were added Px2 (Ser-P1, which was reported in WO 2018/213082 A1, incorporated herein by reference) (10 mg, 16 μmol) and DIPEA (10 μL, 64 μmol). The resulting mixture was stirred at RT overnight, which was monitored by LCMS. The mixture was directly purified by prep-HPLC (method B) to give linker-payload LP15 (4.0 mg, 16% yield from Px2) as an orange solid. ESI m/z: 755.5 (M/2+1)$^+$. $^1$H NMR (400 MHz, DMSO$_{d6}$) δ δ 10.0 (s, 1H), 9.84 (s, 1H), 8.11 (s, 1H), 7.89-7.84 (m, 2H), 7.78-7.75 (tm, 1H), 7.68-7.65 (m, 1H), 7.62-7.60 (m, 3H), 7.54 (s, 1H), 7.50-7.44 (m, 3H), 7.39-7.22 (m, 10H), 6.96 (d, J=8.4 Hz, 1H), 6.81 (d, J=8.4 Hz, 1H), 6.67 (br s, 1H), 6.63 (d, J=2.0 Hz, 1H), 6.50 (dd, J=2.0 Hz, 8.0 Hz, 1H), 6.04-6.02 (m, 1H), 5.43 (s, 2H), 5.32 (t, J=4.8 Hz, 2H), 5.04-4.95 (m, 3H), 4.44-4.37 (m, 1H), 4.20-4.15 (m, 1H), 3.71-3.62 (m, 2H), 3.53-3.48 (m, 12H), 3.34-3.25 (m, 2H), 2.47-2.37 (m, 3H), 2.16-2.13 (m, 4H), 2.03-1.95 (m, 8H), 1.79-1.71 (m, 4H), 1.66-1.54 (m, 6H), 1.49-1.42 (m, 4H), 1.27-1.26 (m, 8H), 1.00 (s, 3H), 0.98 (s, 3H), 0.87-0.83 (m, 6H) ppm.

Example 12B

Payload P18; and Linker-Payloads LP17 and LP18

This example demonstrates methods for the synthesis of payload P18 in Table 1, above, and the linker-payloads LP17 and LP18 in Table 2, above. This example refers to the compounds numbered 134, P1, P18, 112, 135, and linker-payloads LP17 and LP18 in FIG. 9C. Compound 134 was synthesized according to WO 2015/155998 A1.

(1S,4aS,10aR)-N-[(1S,4aS,10aR)-6-{2-[(2-aminoacetamido)methoxy]acetamido}-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (P18)

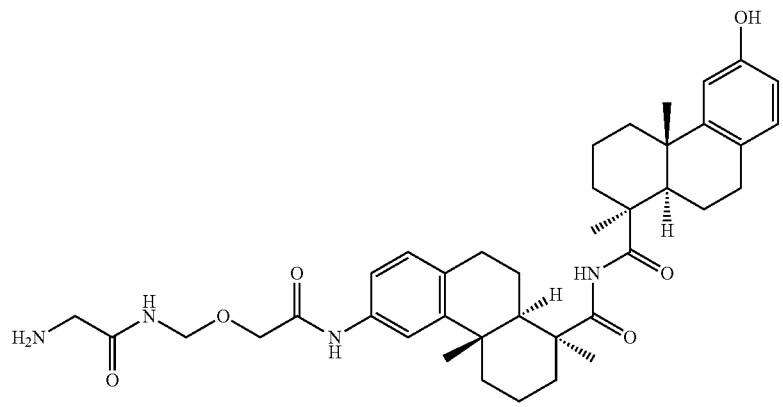 [SMILES: C[C@]1(C(=O)NC(=O)[C@@]2(C)CCC[C@]3(C)c4cc(NC(=O)COCNC(=O)CN)ccc4CC[C@@H]23)CCC[C@]2(C)c3cc(O)ccc3CC[C@@H]12]

To a solution of compound 134 (42 mg, 0.11 mmol) in DMF (5 mL) were added HATU (79 mg, 0.21 mmol) and DIPEA (54 mg, 0.44 mmol), and the mixture was stirred at RT for 15 minutes before the addition of payload P1 (63 mg, 0.12 mmol). The reaction mixture was stirred at RT for 2 hours, which was monitored by LCMS. The resulting mixture was directly purified by prep-HPLC (method B) to give Fmoc-P18 (47 mg, ESI m/z: 895.4 (M+1)$^+$), which was dissolved in DMF (5 mL). To the solution was added piperidine (13 mg, 0.15 mmol), and the mixture was stirred at RT for an hour until Fmoc was totally removed, which was monitored by LCMS. The resulting mixture was directly purified by prep-HPLC (method B) to give compound P18 (34 mg, 47% yield) as a white solid. ESI m/z: 673.5 (M+1)$^+$. $^1$H NMR (400 MHz, DMSO$_{d6}$) δ 9.54 (s, 1H), 8.99 (s, 1H), 8.85 (br s, 1H), 8.11 (s, 1H), 7.59 (d, J=1.5 Hz, 1H), 7.45 (dd, J=8.4, 1.5 Hz, 1H), 6.97 (d, J=8.4 Hz, 1H), 6.82 (d, J=8.4 Hz, 1H), 6.63 (d, J=2.2 Hz, 1H), 6.50 (dd, J=8.4, 2.2 Hz, 1H), 4.66 (d, J=1.6 Hz, 2H), 4.00 (s, 2H), 3.14 (s, 2H), 2.94-2.64 (m, 4H), 2.35-2.32 (m, 1H), 2.32-2.22 (m, 2H), 2.22-2.09 (m, 4H), 1.95-1.78 (m, 4H), 1.68-1.52 (m, 4H), 1.36-1.28 (m, 2H), 1.28 (s, 3H), 1.27 (s, 3H), 1.20-1.09 (m, 2H), 1.01 (s, 3H), 0.99 (s, 3H) ppm.

{4-[(2S)-2-[(2S)-2-[1-(4-{2-Azatricyclo[10.4.0.0⁴,⁹]
hexadeca-1(12),4(9),5,7,13,15-hexaen-10-yn-2-yl}-
4-oxobutanamido)-3,6,9,12-tetraoxapentadecan-15-
amido]-3-methylbutanamido]-5-(carbamoylamino)
pentanamido]phenyl}methyl N-({[({[(4bS,8S,8aR)-
8-{[(1S,4aS,10aR)-6-hydroxy-1,4a-dimethyl-1,2,3,4,
4a,9,10,10a-octahydrophenanthrene-1-carbonyl]
carbamoyl}-4b,8-dimethyl-4b,5,6,7,8,8a,9,10-
octahydrophenanthren-3-yl]carbamoyl}methoxy)
methyl]carbamoyl}methyl)carbamate (LP17)

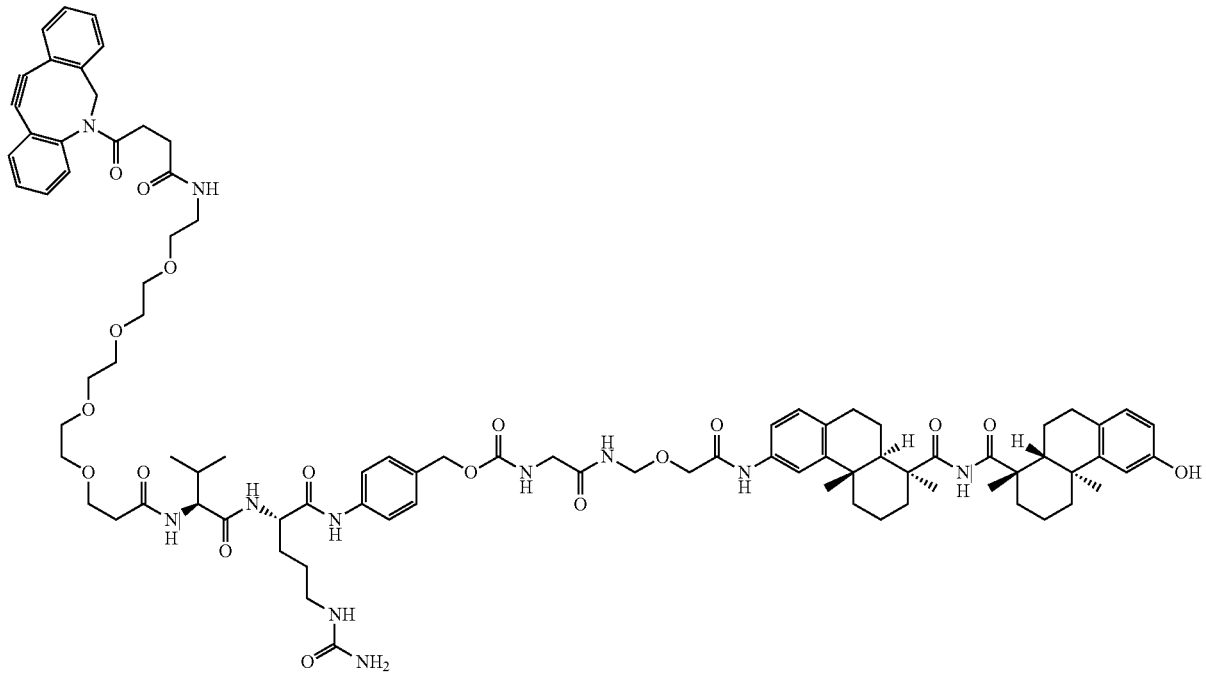

To a solution of compound P18 (16 mg, 24 µmol) in DMF (5 mL) were added compound 112 (26 mg, 24 µmol) and DIPEA (6.2 mg, 0.048 mmol) at 25° C. The mixture was stirred at 25° C. overnight, which was monitored by LCMS. The resulting mixture was directly purified by prep-HPLC (method B) to give linker-payload LP17 (20 mg, 53% yield) as a white solid. ESI m/z: 807 (M/2+1)⁺. H NMR (400 MHz, DMSO$_{d6}$) δ 10.00 (s, 1H), 9.53 (s, 1H), 8.99 (s, 1H), 8.92-8.83 (m, 1H), 8.19-8.07 (m, 2H), 7.88 (d, J=8.1 Hz, 1H), 7.77 (t, J=5.6 Hz, 1H), 7.68 (d, J=6.0 Hz, 1H), 7.64-7.56 (m, 4H), 7.53-7.25 (m, 9H), 6.96 (d, J=8.5 Hz, 1H), 6.81 (d, J=8.3 Hz, 1H), 6.63 (s, 1H), 6.50 (d, J=7.9 Hz, 1H), 6.02-5.94 (m, 1H), 5.42 (s, 2H), 5.02 (d, J=14 Hz, 1H), 4.95 (s, 2H), 4.65 (d, J=6.5 Hz, 2H), 4.43-4.32 (m, 1H), 4.26-4.19 (m, 1H), 4.00 (s, 2H), 3.70-3.54 (m, 5H), 3.50-3.41 (m, 12H), 3.31-3.26 (m, 1H), 3.13-2.54 (m, 8H), 2.41-2.08 (m, 11H), 2.06-1.52 (m, 14H), 1.47-1.08 (m, 12H), 1.00 (s, 3H), 0.98 (s, 3H), 0.86 (d, J=6.8 Hz, 3H), 0.82 (d, J=6.8 Hz, 3H) ppm.

(2S)-2-{2-[2-(4-{2-Azatricyclo[10.4.0.0⁴,⁹]hexa-
deca-1(12),4(9),5,7,13,15-hexaen-10-yn-2-yl}-4-
oxobutanamido)acetamido]acetamido}-3-phenylpro-
panoic acid (135)

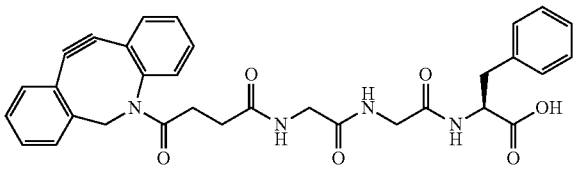 [SMILES: O=C(CCC(=O)N1Cc2ccccc2C#Cc2ccccc21)NCC(=O)NCC(=O)N[C@@H](Cc1ccccc1)C(=O)O]

To a solution of peptide Gly-Gly-Phe (65 mg, 0.16 mmol) in DMF (5 mL) were added compound 132 (56 mg, 0.16 mmol) and DIPEA (63 mg, 0.49 mmol), and the reaction mixture was stirred at RT for 2 hours, which was monitored by LCMS. The mixture was directly purified by prep-HPLC (method B) to give compound 135 (58 mg, 64% yield) as a white solid. ESI m/z: 567 (M+1)⁺.

(1S,4aS,10aR)-N-[(1S,4aS,10aR)-6-[2-({2-[(2S)-2-{2-[2-(4-{2-Azatricyclo[10.4.0.0^{4,9}]hexadeca-1(12),4(9),5,7,13,15-hexaen-10-yn-2-yl}-4-oxobutanamido)acetamido]acetamido}-3-phenylpropanamido]acetamido}methoxy)acetamido]-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (LP18)

tert-Butyl methyl(2-oxoethyl)carbamate (138)

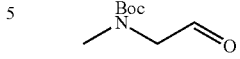

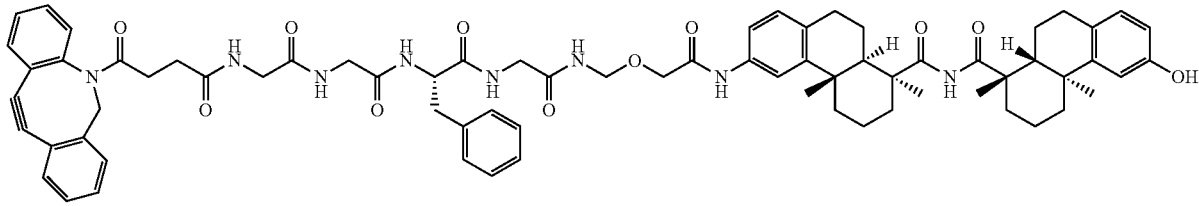 [SMILES: C[C@]1(C(=O)NC(=O)[C@@]2(C)CCC[C@]3(C)c4cc(NC(=O)COCNC(=O)CNC(=O)[C@H](Cc5ccccc5)NC(=O)CNC(=O)CNC(=O)CCC(=O)N5Cc6ccccc6C#Cc6ccccc65)ccc4CC[C@@H]23)CCC[C@]2(C)c3cc(O)ccc3CC[C@@H]12]

To a solution of compound 135 (8.5 mg, 15 µmol) in DMF (5 mL) were added HATU (11 mg, 30 µmol) and DIPEA (7.7 mg, 60 µmol), and the mixture was stirred at RT for 15 minutes before the addition of compound P18 (10 mg, 15 µmol). The reaction mixture was stirred at RT for 2 hours, which was monitored by LCMS. The resulting mixture was directly purified by prep-HPLC (method B) to give linker-payload LP18 (8.4 mg, 46% yield) as a white solid. ESI m/z: 635 (M-MP17)$^+$. $^1$H NMR (400 MHz, DMSO$_{d6}$) δ 9.53 (s, 1H), 8.99 (s, 1H), 8.70 (d, J=5.2 Hz, 1H), 8.36 (d, J=5.0 Hz, 1H), 8.20-7.96 (m, 4H), 7.69-7.62 (m, 1H), 7.61-7.56 (m, 2H), 7.51-7.39 (m, 4H), 7.38-7.32 (m, 2H), 7.31-7.20 (m, 5H), 7.19-7.13 (m, 1H), 6.95 (d, J=8.7 Hz, 1H), 6.82 (d, J=8.2 Hz, 1H), 6.63 (d, J=2.2 Hz, 1H), 6.50 (dd, J=8.2 and 2.2 Hz, 1H), 4.99 (dd, J=13.9 and 1.9 Hz, 1H), 4.64 (d, J=6.6 Hz, 2H), 4.51-4.43 (m, 1H), 4.00 (s, 2H), 3.80-3.66 (m, 3H), 3.62-3.56 (m, 3H), 3.08-2.99 (m, 1H), 2.91-2.59 (m, 7H), 2.34-2.23 (m, 3H), 2.20-2.10 (m, 4H), 2.08-2.00 (m, 1H), 1.95-1.72 (m, 5H), 1.67-1.51 (m, 4H), 1.27 (s, 3H), 1.27 (s, 3H), 1.25-1.22 (m, 2H), 1.17-1.08 (m, 2H), 0.99 (s, 3H), 0.98 (s, 3H) ppm.

Example 12C

Linker-Payload LP19

This example demonstrates methods for the synthesis of linker-payload LP19 in Table 2, above. This example refers to the compounds numbered 136-138, 140, P15, 141-143, 106, 116, and linker-payloads LP19 in FIG. 9D.

tert-Butyl 2-hydroxyethyl(methyl)carbamate (137)

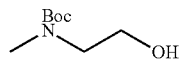

To a mixture of compound 136 (3.8 g, 50 mmol) in DCM (90 mL) was added dropwise a solution of Boc$_2$O (11 g, 52 mmol) in DCM (10 mL) at 0° C. The mixture was stirred at room temperature overnight. The mixture was washed with brine twice and the organic solution was concentrated in vacuo to give compound 137 (8.5 g, 97% yield) as colorless oil. ESI m/z: 198 (M+Na)$^+$.

To a solution of compound 137 (4.4 g, 25 mmol) in dry DCM (50 mL) was added portionwise Dess-Martin peroxide (12 g, 25 mmol) at 0° C. The reaction mixture was stirred at room temperature overnight and was quenched with sat. aq. sodium bicarbonate and sat. aq. sodium thiosulfate. The quenched mixture was stirred at room temperature for 0.5 hours. The organic solution was collected and washed with sat. aq. sodium bicarbonate, dried over magnesium sulfate and concentrated in vacuo to give crude 138, which was purified by flash chromatography (12-18% acetate in petroleum ether, detected by TLC using PMA) to give compound 138 (2.6 g, 60% yield) as light yellow oil. $^1$H NMR (400 MHz, DMSO$_{d6}$) δ 9.48 (d, J=8.4 Hz, 1H), 4.03 (br, 2H), 2.85 (s, 3H), 1.41 (s, 9H) ppm.

tert-Butyl 2-(2-(2-hydroxyethoxy)ethylamino)ethyl(methyl)carbamate (140)

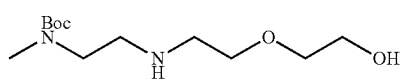 [SMILES: CN(CCNCCOCCO)C(=O)OC(C)(C)C]

A mixture of compound 138 (2.6 g, 15 mmol) and compound 139 (1.7 g, 16 mmol) in dry methanol (20 mL) was stirred at room temperature for 4 hours before sodium borohydride (1.1 g, 30 mmol) was added portionwise into the mixture at 0° C. The mixture was slowly warmed to room temperature and stirred at room temperature overnight. The mixture was quenched with cold water and concentrated in vacuo. The residue was purified by flash chromatography (0-100% methanol in DCM) to give compound 140 (2.4 g, 61% yield) as yellow oil. ESI m/z: 263.1 (M+H)$^+$. $^1$H NMR (400 MHz, DMSO$_{d6}$) δ 3.50-3.43 (m, 4H), 3.41-3.38 (m, 2H), 3.21 (t, J=6.4 Hz, 2H), 2.78 (s, 3H), 2.69-2.63 (m, 4H), 2.08 (s, 1H), 1.39 (s, 9H) ppm.

tert-Butyl N-[(4bS,8S,8aR)-8-({[(1S,4aS,10aR)-6-{
[(2-{[(tert-butoxy)carbonyl](methyl)amino}ethyl)[2-
(2-hydroxyethoxy)ethyl]carbamoyl]oxy}-1,4a-dim-
ethyl-1,2,3,4,4a,9,10,10a-octahydrophenanthren-1-
yl]formamido}carbonyl)-4b,8-dimethyl-4b,5,6,7,8,
8a,9,10-octahydrophenanthren-3-yl]carbamate (141)

(4bS,8S,8aR)-8-((1S,4aS,10aR)-6-Amino-1,4a-dim-
ethyl-1,2,3,4,4a,9,10,10a-octahydrophenanthrene-1-
carbonylcarbamoyl)-4b,8-dimethyl-4b,5,6,7,8,8a,9,
10-octahydrophenanthren-3-yl 2-(2-hydroxyethoxy)
ethyl(2-(methylamino)ethyl)carbamate (142)

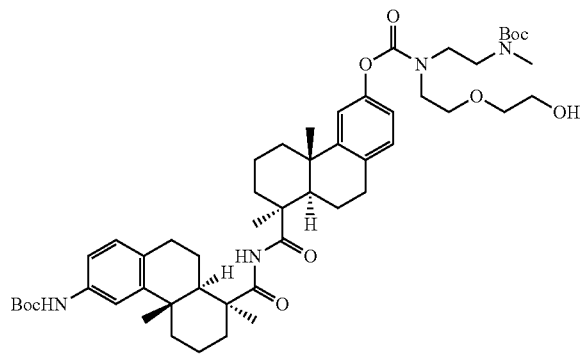 [SMILES: CN(CCN(CCOCCO)C(=O)Oc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2)C(=O)OC(C)(C)C]

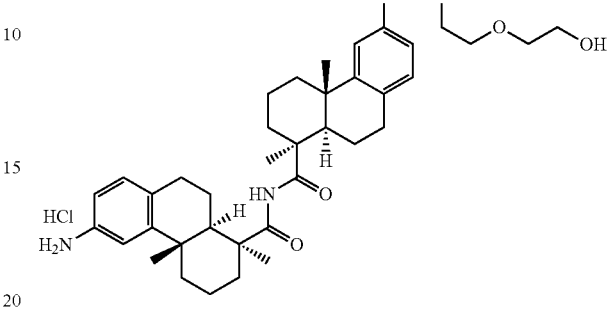

To a solution of payload P15 (0.44 g, 0.70 mmol) in dry DCM (15 mL) were added triethylamine (0.21 g, 2.1 mmol) and a solution of 4-nitrophenyl chloroformate (0.15 g, 0.74 mmol) in dry DCM (5 mL). The reaction mixture was stirred at room temperature for 1.5 hours, which was monitored by LCMS. The mixture was concentrated in vacuo to give crude PNP ester (0.58 g), which was dissolved in DCM (15 mL). To the solution were added HOBt (19 mg, 0.14 mmol) and a solution of compound 140 (0.32 g, 1.2 mmol) in DCM (5 mL). The reaction mixture was stirred at room temperature for 18 hours until the reaction was completed according to LCMS. The reaction mixture was diluted with DCM and washed with water and brine, dried over sodium sulfate and concentrated in vacuo. The residue was purified by reversed phase flash chromatography (0-100% acetonitrile in aq. TFA (0.01%)) to give compound 141 (0.50 g, 78% yield) as a white solid. ESI m/z: 940.5 (M+Na)⁺.

To a solution compound 141 (0.30 g, 0.33 mmol) in acetonitrile (5 mL) was added a solution of HCl in dioxane (4 N, 3 mL). The reaction mixture was stirred at room temperature for 3 hours until Boc was totally removed according to LCMS. The volatiles were removed, and the residue was purified by reversed phase flash chromatography (0-100% acetonitrile in water) to give compound 142 as HCl salt (0.19 g, 73% yield), as a white solid, which was not stable, even under basic buffer (pH>7). ESI m/z: 717.2 (M+H)⁺.

(4bS,8S,8aR)-8-(((1S,4aS,10aR)-6-Amino-1,4a-
dimethyl-1,2,3,4,4a,9,10,10a-octahydro-
phenanthrene-1-carbonyl)carbamoyl)-4b,8-dimethyl-
4b,5,6,7,8,8a,9,10-octahydrophenanthren-3-yl (2-
((((4-((S)-2-((S)-2-amino-3-methylbutanamido)-5-
ureidopentanamido)benzyl)oxy)carbonyl)(methyl)
amino)ethyl)(2-(2-hydroxyethoxy)ethyl)carbamate
(143)

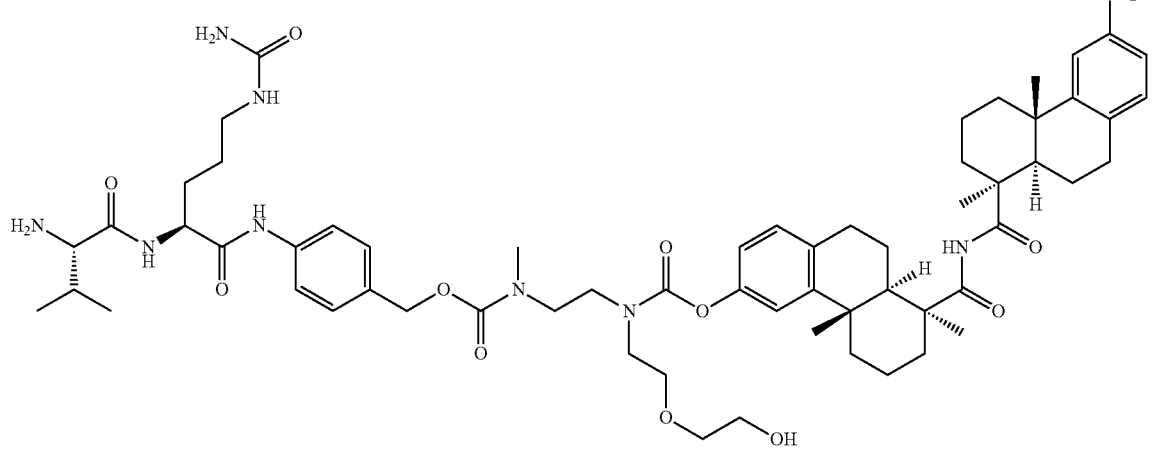

To a mixture of freshly synthesized compound 142 (35 mg, 49 µmol) in dry DMF were added triethylamine (15 mg, 0.15 mmol), HOBt (7.0 mg, 49 µmol) and a solution of Fmoc-vcPAB-PNP (116, 35 mg, 45 µmol) in dry DMF (5 mL) successively at RT. The mixture was stirred at RT overnight. To the reaction mixture was added piperidine (13 mg, 0.15 mmol). The mixture was stirred at RT for 3 hours until Fmoc was totally removed according to LCMS. The reaction mixture was directly purified by reversed phase flash chromatography (5-95% acetonitrile in aq. ammonium bicarbonate (10 mM)) to give compound 143 (62 mg, 58% yield) as a white solid. ESI m/z: 1145.6 (M+Na)$^+$.

(4bS,8S,8aR)-8-{[(1S,4aS,10aR)-6-Amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl N-(2-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](methyl)amino}ethyl)-N-[2-(2-hydroxyethoxy)ethyl]carbamate (LP19)

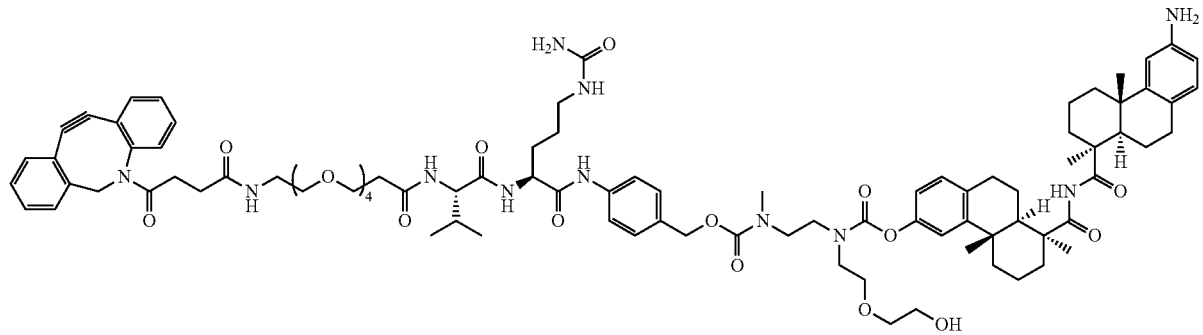

To a solution of compound 143 (30 mg, 27 μmol) in dry DMF (5 mL) were added DIBAC-suc-PEG$_4$-OSu (107, 21 mg, 30 μmol) and DIPEA (10 mg, 78 μmol) successively at RT. The reaction mixture was stirred at RT overnight. The reaction mixture was directly purified by prep-HPLC (method B) to give compound LP19 (15 mg, 34% yield) as a white solid. ESI m/z: 829.0 (M/2+H)$^+$. $^1$H NMR (400 MHz, DMSO$_{d6}$) δ 10.00 (br, 1H), 8.13-8.10 (m, 2H), 7.88-7.86 (m, 1H), 7.78-7.74 (m, 1H), 7.69-7.66 (m, 1H), 7.62-7.44 (m, 6H), 7.39-7.28 (m, 4H), 7.22-7.20 (m, 1H), 6.99-6.97 (m, 2H), 6.75-6.74 (m, 1H), 6.69-6.66 (m, 1H), 6.47 (s, 1H), 6.35-6.32 (m, 1H), 5.97-5.96 (m, 1H), 5.41 (s, 2H), 5.04-4.92 (m, 3H), 4.69 (s, 2H), 4.60-4.58 (m, 1H), 4.39-4.35 (m, 1H), 4.30-4.20 (m, 1H), 3.62-2.53 (m, 39H), 2.40-1.36 (m, 25H), 1.27-1.25 (m, 8H), 1.14-1.11 (m, 2H), 0.99-0.97 (m, 6H), 0.87-0.81 (m, 7H) ppm.

ANALYTICAL EXAMPLES

Example 13

The structures, calculated Log P values, MS and HPLC results for the above payload compounds are summarized in Table 3.

TABLE 3

Chemical-Physical Properties of Payloads

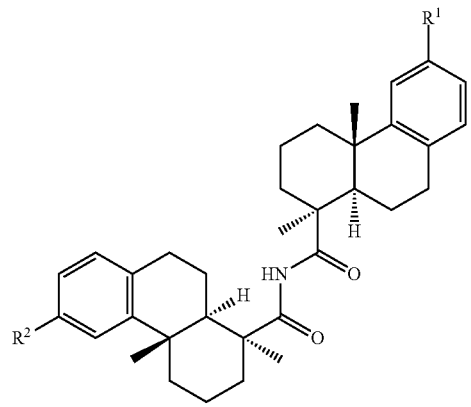

| Cpd | R1 | R2 | cLogP | MS (M + H) | HPLC Purity (%) | HPLC RT (min) |
|---|---|---|---|---|---|---|
| P1 | OH | $NH_2$ | +++ | 529.3 | 95 | 8.66 |
| P2 | $NH_2$ | $NH_2$ | +++ | 528.2 | 95 | 9.11 |
| P3 | $NH_2$ | $NBn_2$ | +++ | 354.8 (M/2 + H) | 95 | 8.87 |
| P4 | $NH_2$ | $NHC(O)CH_2NH_2$ (Gly) | ++ | 585.4 | 98 | 8.20 |
| P5 | $NH_2$ | $NHC(O)(S)$—$CH(CH_2OH)NH_2$ (Ser) | ++ | 615.4 | 100 | 7.86 |
| P6 | $NH_2$ | $NHC(O)CH((CH_2)_4NH_2)NH_2$ (Lys) | +++ | 656.5 | 100 | 8.89 |
| P7 | $NH_2$ | $NHC(O)CH(CH_2CO_2H)NH_2$ (Asp) | + | 643.4 | 100 | 6.64 |
| P8 | $NH_2$ | $NHC(O)CH(CH_2CH_2COOH)NH_2$ (Glu) | + | 657.4 | 97 | 6.69 |
| P9 | $NH_2$ | $NHC(O)CH(CH_2\text{-imidazole})NH_2$ (His) | ++ | 665.3 | 97 | 5.94 |
| P10 | $NHC(O)CH_2NH_2$ (Gly) | $NHC(O)CH(CH_2CH_2COOH)NH_2$ (Glu) | + | 714.5 | 100 | 6.12 |
| P11 | $NHC(O)CH(CH_2CH_2COOH)NH_2$ (Glu) | $NHC(O)CH(CH_2CH_2COOH)NH_2$ (Glu) | + | 393.8 (M/2 + H) | 100 | 5.45 |
| P12 | $NH_2$ | $NHC(O)CH(CH_3)NHC(O)CH(CH_2CH_2COOH)NH_2$ (AlaGlu) | + | 728.5 | 100 | 6.61, 6.67 |
| P13 | $NH_2$ | $NHC(O)CH(CH_3)NH_2$ (Ala) | +++ | 599.5 | 100 | 5.21 |
| P14 | $NH_2$ | $NHC(O)CH_2OH$ | ++ | 586.3 | 100 | 8.26 |
| P15 | OH | $NHC(O)O^tBu$ (Boc) | +++ | 629.4 | 100 | 9.78 |
| P16 | OH | $NHC(O)CH(CH_3)NHC(O)CH(CH_2CH_2COOH)NH_2$ (AlaGlu) | + | 729.5 | 98 | 6.62 |
| P17 | OH | $NHC(O)CH_2OH$ | +++ | 587.3 | 97 | 8.17 |
| P18 | OH | $NHC(O)CH_2OCH_2NHC(O)CH_2NH_2$ | ++ | 673.3 | 98 | 7.83 |
| P19 | OH | $NH_2$ | +++ | 545.3 | 99 | 6.54 |

6 < +++ < 12; 4 < ++ ≤ 6; 0 < + < 4

Example 14

The molecular formulae, molecular weights, calculated Log P values, MS, and HPLC results for the above linker-payload compounds are summarized in Table 4.

TABLE 4

Chemical-Physical Properties of Payloads

| Cpd | MF | MW | cLogP | Purity (%) | MS m/z (100%) | highest MS m/z | HPLC RT (min) |
|---|---|---|---|---|---|---|---|
| LP1 | $C_{124}H_{176}N_{12}O_{43}$ | 2522.81 | + | 95 | 841.7 [M/3 + H] | 1262.0 [M/2 + H] | 7.93 (B) |
| LP2 | $C_{127}H_{182}N_{14}O_{44}$ | 2608.87 | + | 100 | 870.3 [M/3 + H] | 870.3 [M/3 + H] | 7.35 (B) |
| LP3 | $C_{101}H_{143}N_{13}O_{22}S$ | 1923.36 | +++ | 100 | 641.8 [M/3 + H] | 962.5 [M/2 + H] | 6.20 (B) |
| LP4 | $C_{104}H_{149}N_{15}O_{23}S$ | 2009.45 | ++ | 99 | 670.5 [M/3 + H] | 1004.9 [M/2 + H] | 5.94 (B) |
| LP5 | $C_{100}H_{138}N_{12}O_{24}$ | 1892.23 | ++ | 95 | 631.5 [M/3 + H] | 946.6 [M/2 + H] | 6.94 (B) |

TABLE 4-continued

Chemical-Physical Properties of Payloads

| Cpd | MF | MW | cLogP | Purity (%) | MS m/z (100%) | highest MS m/z | HPLC RT (min) |
|-----|-----|-----|-------|-----------|---------------|----------------|---------------|
| LP6 | $C_{85}H_{109}N_{11}O_{15}$ | 1524.84 | +++ | 96 | 763.0 [M/2 + H] | 763.0 [M/2 + H] | 8.63 (B) |
| LP7 | $C_{74}H_{96}N_8O_{12}$ | 1289.60 | +++ | 97 | 645.4 [M/2 + H] | 1290.7 [M + H] (23%) | 8.67 (B) |
| LP8 | $C_{137}H_{192}N_{16}O_{47}$ | 2815.07 | + | 99 | 939.2 [M/2 + H] | 939.2 [M/2 + H] | 7.60 (B) |
| LP9 | $C_{89}H_{118}N_{12}O_{15}$ | 1595.96 | +++ | 100 | 798.3 [M/2 + H] | 798.3 [M/2 + H] | 8.58 (B) |
| LP10 | $C_{87}H_{111}N_{11}O_{17}$ | 1582.88 | +++ | 97 | 528.4 [M/3 + H] | 792.0 [M/2 + H] | 7.11 (B) |
| LP11 | $C_{88}H_{113}N_{11}O_{17}$ | 1596.90 | +++ | 96 | 799.2 [M/2 + H] | 799.2 [M/2 + H] | 7.10 (B) |
| LP12 | $C_{72}H_{91}N_7O_{13}$ | 1262.53 | +++ | 100 | 631.8 [M/2 + H] | 631.8 [M/2 + H] | 7.51 (B) |
| LP13 | $C_{77}H_{100}N_8O_{14}$ | 1361.69 | +++ | 100 | 681.6 [M/2 + H] | 681.6 [M/2 + H] | 7.12 (B) |
| LP14 | $C_{77}H_{100}N_8O_{14}$ | 1361.69 | +++ | 100 | 681.5 [M/2 + H] | 681.5 [M/2 + H] | 7.66 (B) |
| LP15 | $C_{84}H_{104}N_{10}O_{16}$ | 1509.81 | +++ | 96 | 755.5 [M/2 + H] | 755.5 [M/2 + H] | 8.26 (B) |
| LP16 | $C_{72}H_{90}N_6O_{14}$ | 1263.54 | +++ | 100 | 632.5 [M/2 + H] | 632.5 [M/2 + H] | 7.45 (B) |
| LP17 | $C_{88}H_{113}N_{11}O_{18}$ | 1612.90 | +++ | 97 | 807.0 [M/2 + H] | 807.0 [M/2 + H] | 8.29 (B) |
| LP18 | $C_{71}H_{80}N_8O_{11}$ | 1221.44 | +++ | 100 | 635.2 [M-payload] | 635.2 [M-payload] | 8.88 (B) |
| LP19 | $C_{91}H_{121}N_{11}O_{18}$ | 1657.00 | +++ | 100 | 829.3 [M/2 + H] | 829.3 [M/2 + H] | 8.66 (B) |
| LP20 | $C_{106}H_{151}F_3N_{14}O_{21}$ | 2014.45 | + | >95 | 950.8 [M/2] | 950.8 [M/2] | 6.54 (A) |

$6 < +++ < 12$;
$4 < ++ < 6$;
$-2 < + \leq 4$

Example 15

The activity of certain LXR agonist payloads described herein were assessed in a cell based LXR responsive luciferase reporter assay. To generate the assay cell line, an LXR regulated luciferase reporter gene (Cignal Lenti LXR Reporter (luc) kit (Qiagen, Cat #CLS-001L)) was transduced into THP1 cells and the cells were selected for two weeks in puromycin. The lentivirus expresses the firefly luciferase gene under the control of a minimal CMV promoter and tandem repeats of the LXR transcriptional response element. The resulting cell line is referred to as THP1/LXR-Luc cells. For the assay, THP1/LXR-Luc cells were seeded onto 96 well plates at 40,000 cells/well in media containing RPMI supplemented with 10% FBS and penicillin/streptomycin and were then differentiated with 200 nM Phorbol Myristate Acetate (PMA) for 3 days. The media was subsequently removed and replaced with 80 uL of fresh media without PMA. Three-fold serial dilutions of free payloads were prepared in 100% DMSO, transferred to fresh media, and 20 uL were added to the cells at a final constant DMSO concentration of 0.2% and free payloads at final concentrations ranging from 100 nM to 0.015 nM. The last well in the plate served as blank control containing only the media and 0.2% DMSO (untreated well) and was plotted as a continuation of the 3-fold serial dilution. Forty-eight hours later, luciferase activity was determined after the addition of One-Glo™ reagent (Promega, Cat #E6130) to each well. Relative light units (RLUs) were measured on a Victor luminometer (PerkinElmer) and $EC_{50}$ values were determined using a four-parameter logistic equation over a 10-point dose response curve (GraphPad Prism). The $EC_{50}$ value of each molecule tested is shown in the Table 1. The signal to noise (S/N) was determined by taking the ratio of the highest RLU on the dose response curve to the RLU in the untreated wells. As shown in Table 5, all of the tested payload compounds increased LXR-dependent luciferase activity in THP1/LXR-Luc cells with $EC_{50}$ values ranging from 112 pM to 3.51 nM and S/N values ranging from 10.4 to 13.8.

TABLE 5

LXR-Reporter Activity by Payload Compounds in Differentiated THP-1/LXR-Luc cells

| Payload Compound | $EC_{50}$ (M) | S/N |
|------------------|---------------|-----|
| P1 | 1.14E−09 | 11.4 |
| P2 | 2.92E−10 | 11.3 |
| P4 | 1.25E−10 | 10.4 |
| P6 | 3.34E−09 | 10.9 |
| P5 | 1.74E−10 | 13.8 |
| P7 | 2.53E−10 | 12.5 |
| P9 | 2.34E−10 | 12.8 |
| P8 | 3.51E−09 | 10.8 |
| P10 | 2.22E−10 | 11.1 |
| P12 | 2.96E−10 | 11.4 |
| P11 | 1.12E−10 | 10.7 |

Example 16

Conjugation through antibody cysteines is performed in two steps using methods similar to those described in Mol.

Pharm. 2015, 12(6), 1863-71. In an exemplary procedure, a monoclonal antibody (mAb) is reduced with dithiothreitol or TCEP. After gel filtration, the appropriate linker-payload in DMSO solution is added to the reduced antibody, and the mixture is adjusted to appropriate pH. The reaction is allowed to stir. The resulting conjugate is purified by SEC. The DAR (UV) values are determined using the measured absorbances of the ADC and the extinction coefficients of the antibody linker-payload.

Site-specific antibody conjugation can be performed, e.g., in two steps: (1) microbial transglutaminase e.g., (MTG EC 2.3.2.13, Zedira, Darmstadt, Germany)-based enzymatic attachment of an azido-PEG-amine to a site-specifically mutated antibody and (2) attachment of an appropriate linker-payload to the azido-PEG-amine functionalized antibody via a [2+3]cycloaddition, e.g., 1,3-dipolar cycloaddition between the azido moiety of the functionalized antibody and appropriate cyclooctyne moiety of the linker-payload, e.g., copper-free click chemistry. See, Baskin, J. M.; Prescher, J. A.; Laughlin, S. T.; Agard, N. J.; Chang, P. V.; Miller, I. A.; Lo, A.; Codelli, J. A.; Bertozzi, C. R. *PNAS* 2007, 104 (43), 16793-7. For example, aglycosylated human antibody IgG (IgG1, IgG4, etc.) or a human IgG1 isotype in BupH™ (pH 6.5-8.0) is mixed with ≥200 molar equivalents of azido-dPEG$_3$-amine (MW=218.26 g/mol). The resulting solution is mixed with transglutaminase (25 U/mL; 5 U MTG per mg of antibody, from Zedira, Darmstadt, Germany, or Ajinomoto, Japan) resulting in a final concentration of the antibody at 0.5-5 mg/mL, and the solution is kept at pH 6.5-8.0 and then incubated at 37° C. for 4-24 h while gently shaking. The reaction is monitored by ESI-MS. Upon reaction completion, excess amine and MTG is removed by SEC or protein A column eluting with acidic buffer and then neutralizing with Tris buffer (pH 8) to generate the azido-functionalized antibody. This product is analyzed by SDS-PAGE and ESI. The azido-dPEG$_3$-amine adds to two sites— Q295 and Q297- of the antibody resulting in an 804 Da increase for the 4DAR aglycosylated antibody-PEG$_3$-azide conjugate. The conjugation sites are identified and confirmed at EEQ$^{Linker}$YQ$^{Linker}$STYR for the 4DAR azido-functionalized antibody via peptide sequence mapping of trypsin digested heavy chains.

In another example, site-specific aglycosylated antibody drug conjugates with a human IgG (IgG1, IgG4, etc.) containing an N297Q mutation (EU numbering) are prepared by a [2+3] click reaction between azido-functionalized antibodies with an alkyne containing linker-payload. Specifically, an azido-functionalized aglycosylated human IgG1 antibody (mAb-PEG$_3$-N$_3$) is conjugated to an appropriate linker payload by incubating mAb-PEG$_3$-N$_3$ (1-3 mg/mL) in an aqueous medium (e.g., PBS, PBS containing 5% glycerol, HBS) with ≥6 molar equivalents of a linker payload dissolved in a suitable organic solvent, such as DMSO, DMF or DMA (i.e., the reaction mixture contains 5-20% organic solvent, v/v) at 24° C. to 37° C. for over 6 h. The progress of the reaction is monitored by ESI-MS and the absence of mAb-PEG$_3$-N$_3$ indicated the completion of the conjugation. The excess amount of the linker payload and organic solvent are removed by SEC via elution with PBS, or via protein A column eluting with acidic buffer followed by neutralization with Tris (pH 8). The purified conjugates are analyzed by SEC, SDS-PAGE, and ESI-MS.

The antibody and antibody-drug conjugates can be characterized by SDS-PAGE, SEC, and MS (ESI). In one method, SDS-PAGE conditions including non-reduced and reduced samples (2-4 µg) along with BenchMark Pre-Stained Protein Ladder (Invitrogen, cat #10748-010; L #1671922) are loaded per lane in (1.0 mm×10 well) Novex 4-20% Tris-Glycine Gel and are ran at 180 V, 300 mA, for 80 min. An analytic sample is prepared using Novex Tris-Glycine SDS buffer (2×) (Invitrogen, Cat #LC2676) and the reducing sample is prepared with SDS sample buffer (2×) containing 10% 2-mecaptoethanol.

Example 16a

Cell-Based LXR Luciferase Reporter Assay

LXR agonists described herein were evaluated in a cell-based LXR responsive luciferase reporter assay. To generate the assay cell line, an LXR regulated luciferase reporter gene [Cignal Lenti LXR Reporter (luc) kit (Qiagen, Cat #CLS-001L)] was transduced into THP1 cells and the cells were selected for two weeks in puromycin. The lentivirus expresses the firefly luciferase gene under the control of a basal promoter and tandem repeats of the LXR transcriptional response element. The resulting cell line is referred to as THP1/LXR-Luc cells. For the assay, THP1/LXR-Luc cells were seeded onto 96-well plates at 40,000 cells/well in media containing RPMI supplemented with 10% FBS and penicillin/streptomycin and were then differentiated with 200 nM Phorbol Myristate Acetate (PMA) for 3 days. The media was subsequently removed and replaced with 80 µL of fresh media without PMA. Three-fold serial dilutions of free payloads were prepared in 100% DMSO, transferred to fresh growth media, and 20 µL were added to the cells at a final constant DMSO concentration of 0.2% and free payloads at final concentrations ranging from 100 nM to 0.015 nM. The last well in the plate served as blank control containing only the media and 0.2% DMSO (untreated well) and was plotted as a continuation of the 3-fold serial dilution. Forty-eight hours later, luciferase activity was determined after the addition of One-Glo™ reagent (Promega, Cat #E6130) to each well. Relative light units (RLUs) were measured on an Envision luminometer (PerkinElmer) and EC$_{50}$ values were determined using a four-parameter logistic equation over a 10-point dose response curve (GraphPad Prism). The EC$_{50}$ value of each molecule tested is shown in Table 5a. The signal to noise (S/N) was determined by taking the ratio of the highest RLU on the dose response curve to the RLU in the untreated wells. As shown in Table 5a, the LXR agonists increased LXR-dependent luciferase activity in THP1/LXR-Luc cells with EC$_{50}$ values ranging from 78.8 pM to 72.9 nM and S/N values ranging from 8.8 to 13.1.

TABLE 5a

| LXR-Reporter Activity by LXR Agonists in Differentiated THP-1/LXR-Luc cells | | |
|---|---|---|
| LXR Agonist Payload | EC$_{50}$ (M) | S/N |
| P14 | 1.52E−10 | 10.8 |
| P18 | 2.78E−09 | 11.5 |
| P1 | 1.91E−10 | 11.9 |
| P2 | 4.50E−10 | 13.1 |
| P15 | 7.29E−08 | 8.8 |
| P13 | 7.88E−11 | 11.9 |
| P16 | 5.08E−10 | 11.5 |
| P17 | 1.03E−09 | 12.5 |
| P19 | 5.64E−10 | 11.4 |

Example 17

Several linker-payloads (LPs) were derived from the payload compounds in Table 1 and conjugated to an anti- MSR1 antibody (H1H21234N-N297Q) or a non-binding control using the techniques described in the previous example. The resulting anti-MSR1 LXR agonist antibody drug conjugates (ADCs) were tested for activity in the THP1/LXRLuc reporter assay as described above for the payload compounds. As shown in Table 6, all of the tested anti-MSR1 LXR agonist ADCs demonstrated stimulation of the THP1/LXR-Luc cells with $EC_{50}$ values ranging from 414 pM to 2.11 nM and S/N values ranging from 9.4 to 13.7. The unconjugated anti-MSR1 had no impact on LXR-Luc activity and a nonbinding control antibody conjugated to LP1 (Control ADC-LP1) had $EC_{50}$ values of >100 nM and maximum S/N values <5.0.

Anti-MSR1 antibody H1H21234N has the HCVR according to SEQ ID NO:2 and the LCVR according to SEQ ID NO:10. It comprises HCDR1, HCDR2, HCDR3, LCDR1, LCDR2, and LCDR3 according to SEQ ID NOS:4, 6, 8, 12, 14, and 16, respectively. The polypeptide sequences can be encoded by the polynucleotide sequences SEQ ID NOS: 1, 3, 5, 7, 9, 11, 13, and 15. N297Q indicates that residue 297 is mutated from asparagine (N) to glutamine (Q). All numbering is according to the EU numbering system.

TABLE 6

Anti-MSR1-LXR Agonist Conjugate Activity in Differentiated THP-1/LXR-Luc cells

| Anti-MSR1-LXR agonist ADC | LXR agonist LP | LXR Agonist Payload | $EC_{50}$ (M) | S/N |
|---|---|---|---|---|
| H1H21234N-N297Q-LP1 | LP1 | P2 | 7.38E−10 | 11.8 |
| H1H21234N-N297Q-LP4 | LP4 | P2 | 9.23E−10 | 11.9 |
| H1H21234N-N297Q-LP5 | LP5 | P2 | 1.20E−09 | 11.0 |
| H1H21234N-N297Q-LP2 | LP2 | P2 | 8.68E−10 | 13.7 |
| H1H21234N-N297Q-LP12 | LP12 | P2 | 1.30E−09 | 11.6 |
| H1H21234N-N297Q-LP6 | LP6 | P4 | 6.85E−10 | 12.5 |
| H1H21234N-N297Q-LP7 | LP7 | P4 | 5.60E−10 | 11.6 |
| H1H21234N-N297Q-LP8 | LP8 | P4 | 6.19E−10 | 12.5 |
| H1H21234N-N297Q-LP9 | LP9 | P6 | 4.14E−10 | 11.2 |
| H1H21234N-N297Q-LP10 | LP10 | P6 | 9.60E−10 | 12.5 |
| H1H21234N-N297Q-LP11 | LP11 | P8 | 9.78E−10 | 12.4 |
| Unconjugated anti-MSR1 | NA | NA | >1.00E−07 | 0.8 |
| Control ADC-LP1 | LP1 | P2 | >1.00E−07 | 4.4 |

Example 18

Characterization of ADCs by LC-ESI-MS

Measurement of intact mass for the ADC samples by LC-ESI-MS was performed to determine the drug-payload distribution profile and to calculate the average DAR. Each testing sample (20-50 ng, 5 µL) was loaded onto an Acquity UPLC Protein BEH C4 column (10K psi, 300 Å, 1.7 m, 75 m×100 mm; Cat No. 186003810). After 3 min. desalting, the protein was eluted and mass spectra were acquired by a Waters Synapt G2-Si mass spectrometer. As summarized in Table 7, most site-specific ADCs have 3.9 DAR for the site specific conjugates.

TABLE 7

ADC Properties

| LP # | LXR (LP) | MW (LP) | MW (ESI-MS) | DAR (ESI-MS) |
|---|---|---|---|---|
| LP1 | DIBAC-Suc-PEG$_4$-D-Lys(COT-α-CyD)-VA-P2 | 2522.84 | 156687 | 3.6 |
| LP2 | DIBAC-Suc-PEG$_4$-D-Lys(COT-αCyD)-VC-P2 | 2608.93 | 157020 | 3.9 |
| LP3 | DIBAC-Suc-PEG$_4$-D-Lys(COT-PEG$_4$-AES)-VA-P2 | 1923.38 | 154277 | 3.9 |
| LP4 | DIBAC-Suc-PEG$_4$-D-Lys(COT-PEG$_4$-AES)-VC-P2 | 2009.50 | 154622 | 3.9 |
| LP5 | DIBAC-Suc-PEG$_4$-D-Lys(COT-Glucose-Glucose)-VA-P2 | 1892.26 | 154152 | 3.9 |
| LP6 | DIBAC-Suc-PEG$_4$-VA-P4 | 1285.64 | 151742 | 3.9 |
| LP7 | DIBAC-Suc-PEG$_4$-VC-PABC-P4 | 1524.88 | 152680 | 3.9 |
| LP8 | DIBAC-Suc-PEG$_4$-D-Lys(COT-αCyD)-VC-PABC-P4 | 2815.10 | 157859 | 3.8 |
| LP9 | DIBAC-Suc-PEG$_4$-VC-PABC-Lys-P2 | 1596.0 | 152979 | 3.9 |
| LP10 | DIBAC-Suc-PEG$_4$-VC-PABC-P7 | 1582.92 | 152915 | 3.8 |
| LP11 | DIBAC-Suc-PEG$_4$-VC-PABC-P8 | 1596.95 | 152977 | 3.9 |
| LP12 | DIBAC-Suc-PEG$_4$-EA-P2 | 1262.57 | 151642 | 3.9 |
| LP16 | DIBAC-Suc-PEG$_4$-EA-P1 | 1263.55 | 151645 | 3.9 |
| LP19 | DIBAC-Suc-PEG$_4$-VC-PABC-N-CH$_3$-N-PEG$_2$-EDC-P1 | 1657.04 | 153210 | 3.8 |

Example 19

Activation of Cholesterol Efflux in Differentiated THP1 Macrophages by LXR Agonist Antibody-Drug Conjugates The ability of anti-MSR1-LXR agonist ADCs to activate cholesterol efflux in a human macrophage cell line (THP-1; ATTC Catalog #TIB-202) were assessed using a fluorescent cholesterol analog. For the assay, THP-1 cells were seeded onto 96-well poly-lysine coated plates (Corning, Catalog #354640) at 100,000 cells/well in RPMI 1640 media (Irvine Scientific, Catalog #9160) containing 10% FBS (Gibco, Catalog #1043010), 10 ag/mL penicillin-streptomycin (Gibco, Catalog #15140122) in 5% $CO_2$ at 37° C. Cells were differentiated into macrophages by treatment with 100 nM Phorbol-12 myristate 13-acetate (Sigma, Catalog #P8139), which was added to the media (described above), for 96 hours. Differentiated macrophages were then incubated in phenol red free RPMI 1640 media (Gibco, Catalog #32404-014) containing 25 µM BODIPY-cholesterol (Avanti Polar Lipids, Catalog #810255P), 0.2% bovine serum albumin (BSA; Sigma Catalog #A7211) and 10 µg/mL penicillin-streptomycin for 24 hours, followed by a 24-hour treatment with serial dilutions ranging from $1\times10^{-7}$ M to $5\times10^{-17}$ M of either free payloads (P1 or P2), anti-MSR1 Ab-LXR agonists ncADC (H1H21234N-N297Q-29d1 and H1H21234N-N297Q-LP1), or isotype control-LXR agonist ncADC (Isotype control-N297Q-LP1) in phenol red free RPMI 1640 media containing 0.2% BSA. Cells were washed with phenol red free RPMI 1640 media and incubated with 100 μL of acceptor media containing 50 μg/mL high density lipoprotein (Millipore Catalog #437641), 10 μg/mL apolipoprotein A1 (Millipore, Catalog #ALP10) in phenol red free RPMI 1640 media for 5 hours, after which, the acceptor media was collected and cells were lysed in 100 μL of RIPA buffer (Millipore, Catalog #20-188) for 2 hours with gentle agitation at room temperature. Fluorescence was measured in these fractions at excitation 482 nm, emission 515 nm in SpectraMax i3 plate reader (Molecular Devices). Percentage of BODIPY-cholesterol efflux was calculated using the following formula: [fluorescence in acceptor media/(fluorescence in acceptor media+fluorescence in cell lysate)]× 100.

As shown in Table 8 and FIG. 13, after 24 hours, the free payloads P1 and P2 demonstrated similar amount of cholesterol efflux $EC_{50}$ values of 20 pM and 14 pM, respectively. H1H21234N-N297Q-29d1 ncADC demonstrated an $EC_{50}$ value of 12 pM and H1H21234N-N297Q-LP1 ncADC displayed an $EC_{50}$ value of 98 pM. The isotype control-N297Q-LP1 ncADC demonstrated minimal cholesterol efflux with $EC_{50}$ value of 13 nM.

TABLE 8

Activation of Cholesterol Efflux by LXR Agonists and LXR Agonists Antibody-Drug Conjugates

| Molecule tested | Cholesterol Efflux activation $EC_{50}$ (M) |
| --- | --- |
| P1 | 2.0E−11 |
| P2 | 1.4E−11 |
| H1H21234N-N297Q-29d1 | 1.2E−11 |
| H1H21234N-N297Q-LP1 | 9.8E−11 |
| Isotype control-N297Q-LP1 | 1.3E−8 |

What is claimed is:

1. A compound of Formula I

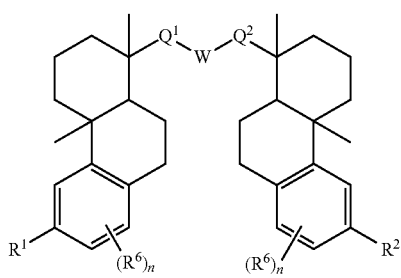

(I)

or a pharmaceutically acceptable salt, solvate, or stereoisomeric form thereof, wherein each of $Q^1$ and $Q^2$ is independently —$CH_2$—, —C(O)—, —C(H)(OH)—, —C(OH)$_2$—, —SO$_2$—, —SO—, —PO(OR$_3$)—, —PO(NR$^3$NR$^4$)—, —NR$^3$—, or —N=;

W is —CH$_2$—, —N(H)—, or —O—;

$R^1$ is —N(H)R$^4$ or —N(R$^5$)$_2$;

$R^2$ is —N(H)R$^4$;

each $R^4$ is, independently in each instance, hydrogen, an amino acid residue, an N-alkyl amino acid residue, a peptide residue, a biodegradable moiety comprising aliphatic polyesters, alkyl, substituted alkyl, acyl, or substituted acyl;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —CH$_2$OH, or at least one primary or secondary nitrogen;

each $R^6$ is independently halo, $C_{1-6}$ alkyl, $C_{1-6}$ alkoxy, —CN, O-glucose, O-amino acid residue, or O-PEG$_{n1}$, wherein each n is an integer from zero to fourteen, and each n1 is an integer from one to twelve; and each R$^3$ is independently hydrogen, alkyl, or aryl.

2. The compound of claim 1 according to Formula I

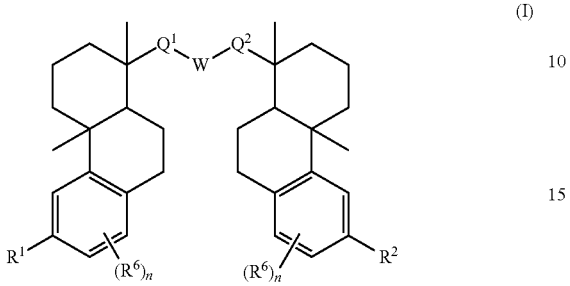

(I)

or a pharmaceutically acceptable salt, solvate, or stereoisomeric form thereof, wherein each of Q$^1$ and Q$^2$ is independently —CH$_2$—, —C(O)—, —C(H)(OH)—, —C(OH)$_2$—, —SO$_2$—, —SO—, —PO(OR$^3$)—, —PO(NR$^3$NR$^4$)—, —NR$^3$—, or —N=;

W is —CH$_2$—, —N(H)—, or —O—;

R$^1$ is —N(H)R$^4$ or —N(R$^5$)$_2$;

R$^2$ is —N(H)R$^4$;

each R$^4$ is, independently in each instance, hydrogen, an amino acid residue, an N-alkyl amino acid residue, a peptide residue, a biodegradable moiety comprising aliphatic polyesters, or alkyl;

R$^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —CH$_2$OH, or at least one primary or secondary nitrogen;

each R$^6$ is independently halo, C$_{1-6}$ alkyl, C$_{1-6}$ alkoxy, —CN, O-glucose, O-amino acid residue, or O-PEG$_{n1}$, wherein each n is an integer from zero to fourteen, and each n1 is an integer from one to twelve; and each R$^3$ is independently hydrogen, alkyl, or aryl.

3. The compound of claim 1 according to Formula I

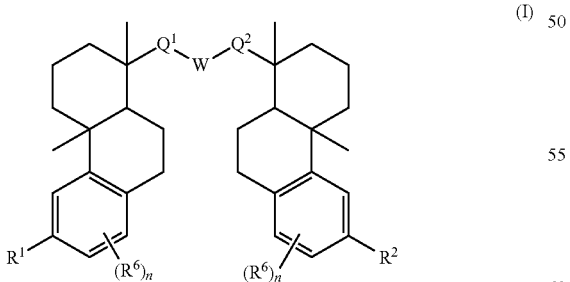

(I)

or a pharmaceutically acceptable salt, solvate, or stereoisomeric form thereof, wherein each of Q$^1$ and Q$^2$ is independently —CH$_2$—, —C(O)—, —C(H)(OH)—, or —C(OH)$_2$—;

W is —CH$_2$, —N(H)—, or —O—;

R$^1$ is —N(H)R$^4$ or —N(R$^5$)$_2$;

R$^2$ is —N(H)R$^4$;

each R$^4$ is, independently in each instance, hydrogen, an amino acid residue, an N-alkyl amino acid residue, a peptide residue, a biodegradable moiety comprising aliphatic polyesters, or alkyl;

R$^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —CH$_2$OH, or at least one primary or secondary nitrogen; and each R$^6$ is independently halo, C$_{1-6}$ alkyl, C$_{1-6}$ alkoxy, —CN, O-glucose, O-amino acid residue, or O-PEG$_{n1}$, wherein each n is an integer from zero to fourteen, and each n1 is an integer from one to twelve.

4. The compound of claim 3 according to Formula II

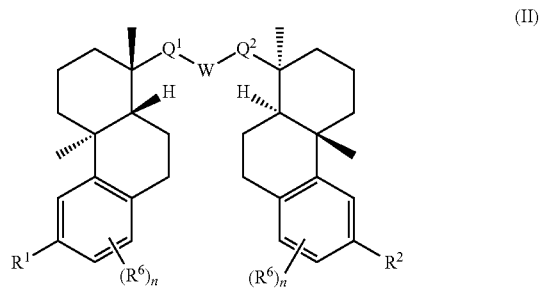

(II)

or a pharmaceutically acceptable salt, solvate, or stereoisomeric form thereof.

5. The compound of claim 1 wherein Q$^1$ is —CH$_2$— and Q$^2$ is —C(O)—.

6. The compound of claim 1 wherein Q$^1$ is —C(H)(OH)— and Q$^2$ is —C(O)—.

7. The compound of claim 1 wherein Q$^1$ is —C(O)— and Q$^2$ is —C(O)—.

8. The compound of claim 1 wherein Q$^1$ is —C(O)— and Q$^2$ is —CH$_2$—.

9. The compound of claim 1 wherein Q$^1$ is —C(O)— and Q$^2$ is —C(H)(OH)—.

10. The compound of claim 1 wherein W is —CH$_2$—.

11. The compound of claim 1 wherein W is —O—.

12. The compound of claim 1 wherein W is —NH—.

13. The compound of claim 1 according to Formula III

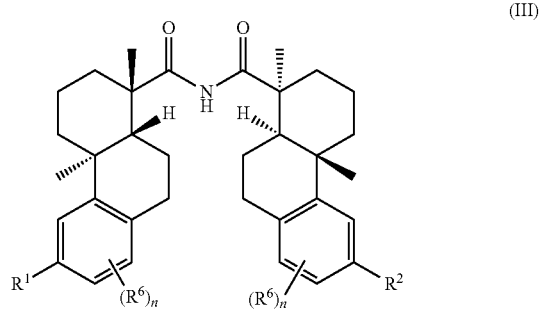

(III)

or a pharmaceutically acceptable salt, solvate, or stereoisomeric form thereof.

14. The compound of claim 1 wherein $R^1$ is —N(H)$R^4$.

15. The compound of claim 1 wherein $R^1$ is —N($R^5$)$_2$.

16. The compound of claim 14, wherein $R^1$ is —NH$_2$; and each $R^4$ is, independently in each instance, an amino acid residue, an N-alkyl amino acid residue, a peptide residue, a biodegradable moiety comprising aliphatic polyesters, or alkyl.

17. The compound of claim 16, wherein each $R^4$ is, independently in each instance, an amino acid residue; and the amino acid residue is selected from the group consisting of alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid.

18. The compound of claim 17 selected from the group consisting of

P4

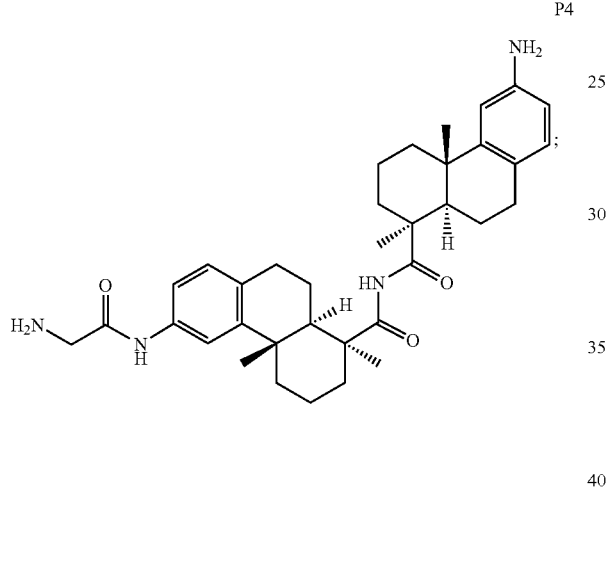

P5

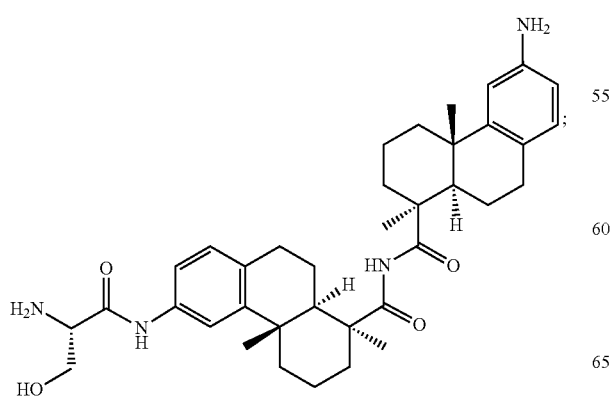

-continued

P6

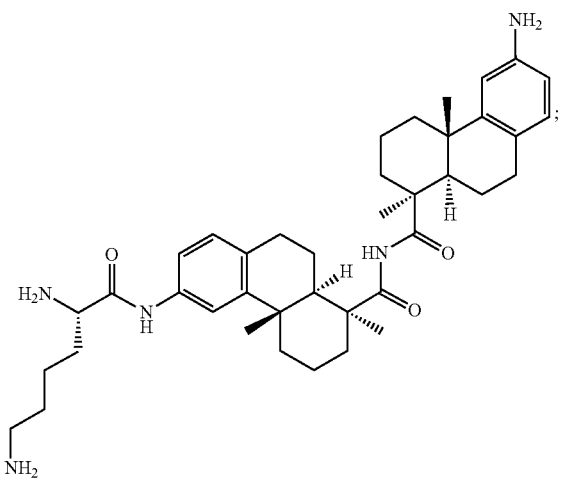

P7

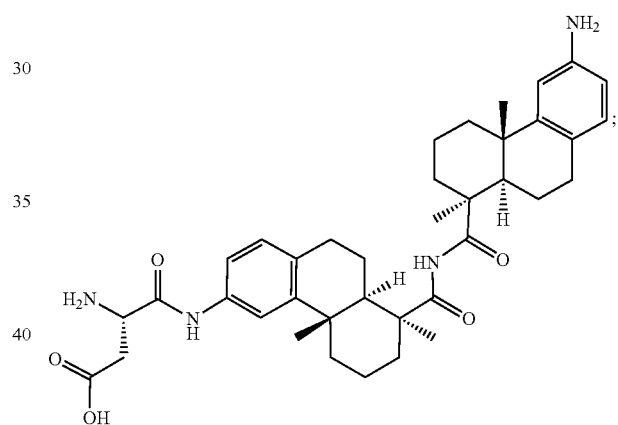

P8

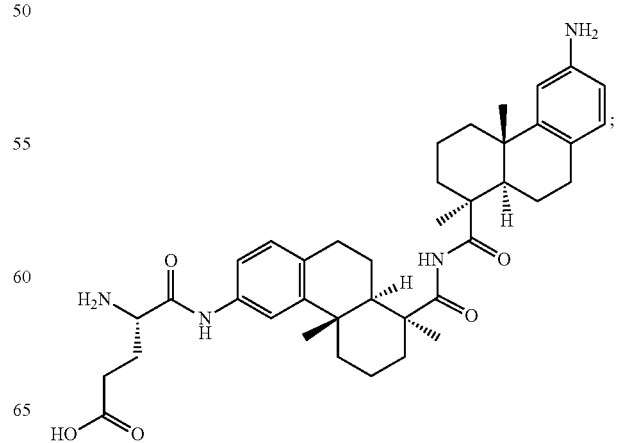

-continued

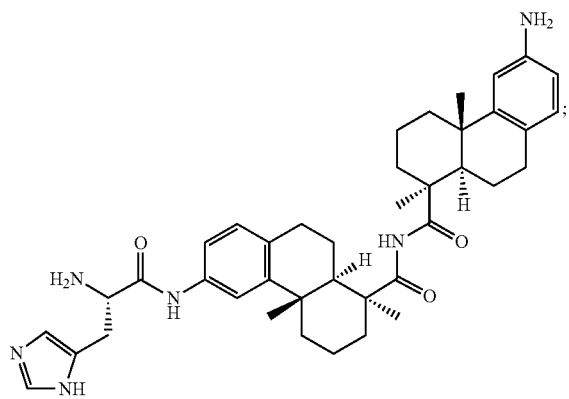

and

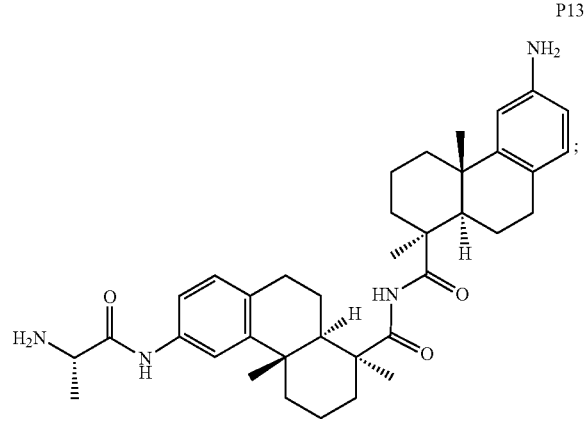 [SMILES: C[C@]1(C(=O)NC(=O)[C@@]2(C)CCC[C@]3(C)c4cc(NC(=O)CO)ccc4CC[C@@H]23)CCC[C@]2(C)c3cc(N)ccc3CC[C@@H]12]

a pharmaceutically acceptable salt or solvate thereof.

19. The compound of claim 16, wherein each $R^4$ is, independently in each instance, a peptide residue, wherein the peptide residue comprises an amino acid selected from the group consisting of alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid, and the residues thereof.

20. The compound of claim 19 wherein the compound is

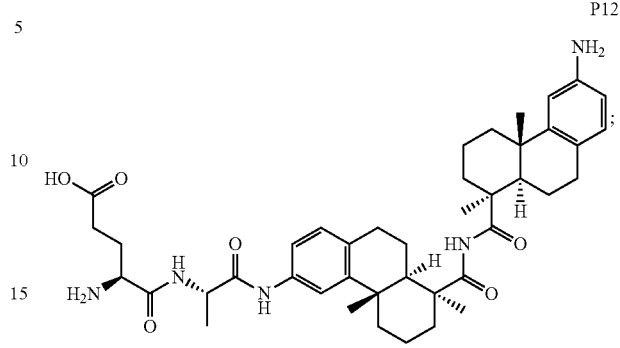

or a pharmaceutically acceptable salt or solvate thereof.

21. The compound of claim 14, wherein the compound is

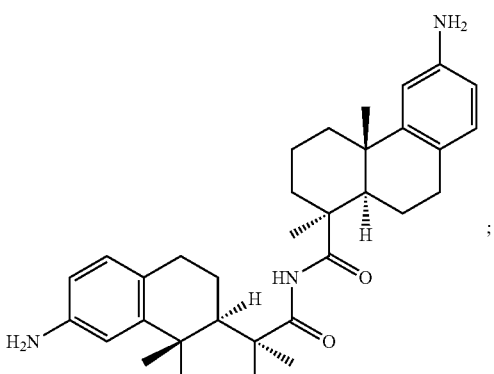

or a pharmaceutically acceptable salt or solvate thereof.

22. The compound of claim 1, wherein $R^1$ and $R^2$ are —N(H)$R^4$.

23. The compound of claim 22, wherein each $R^4$ is, independently in each instance, an amino acid residue; wherein
the amino acid is selected from the group consisting of alanine, isoleucine, leucine, methionine, phenylalanine, tryptophan, tyrosine, valine, serine, threonine, asparagine, glutamine, cysteine, selenocysteine, glycine, proline, arginine, histidine, lysine, aspartic acid, and glutamic acid, and the residues thereof.

24. The compound of claim 23, where the compound is selected from the group consisting of

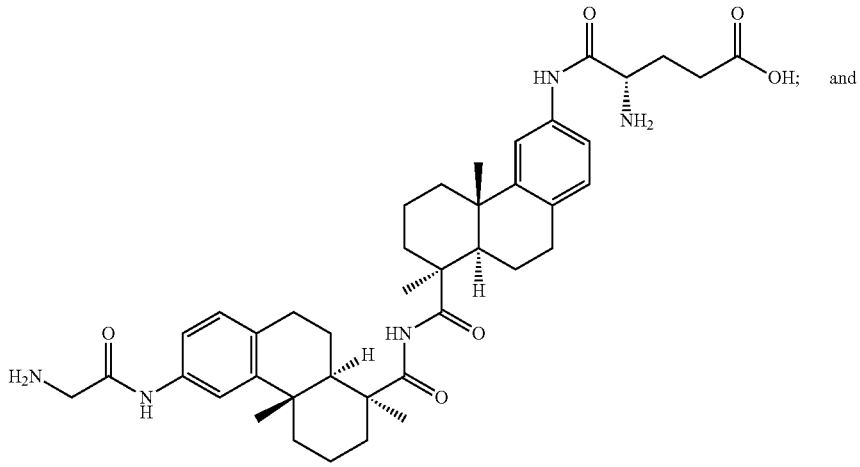

P10

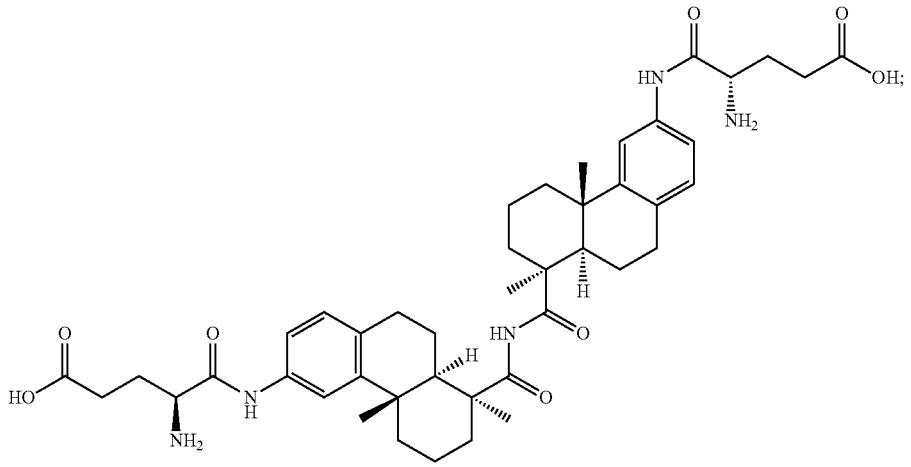

P11 or a pharmaceutically acceptable salts or solvates thereof.

25. The compound of claim 15, wherein the compound is

26. The compound of claim 22, wherein the compound is

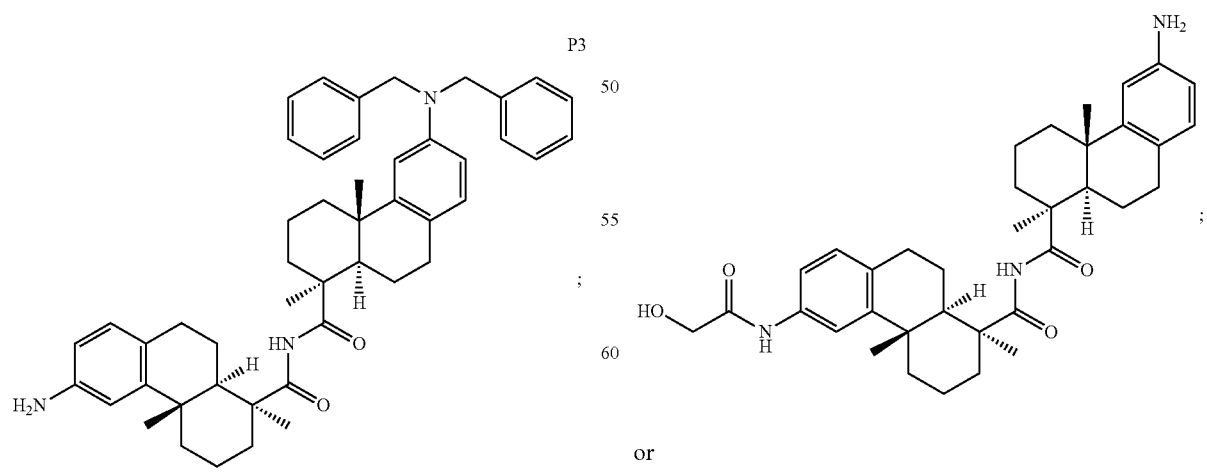

or a pharmaceutically acceptable salt or solvate thereof.

27. A linker-payload comprising the compound of claim 1 bonded to a linker.

28. The linker-payload of claim 27 having a Formulae LPa, LPb, LPc, or LPd

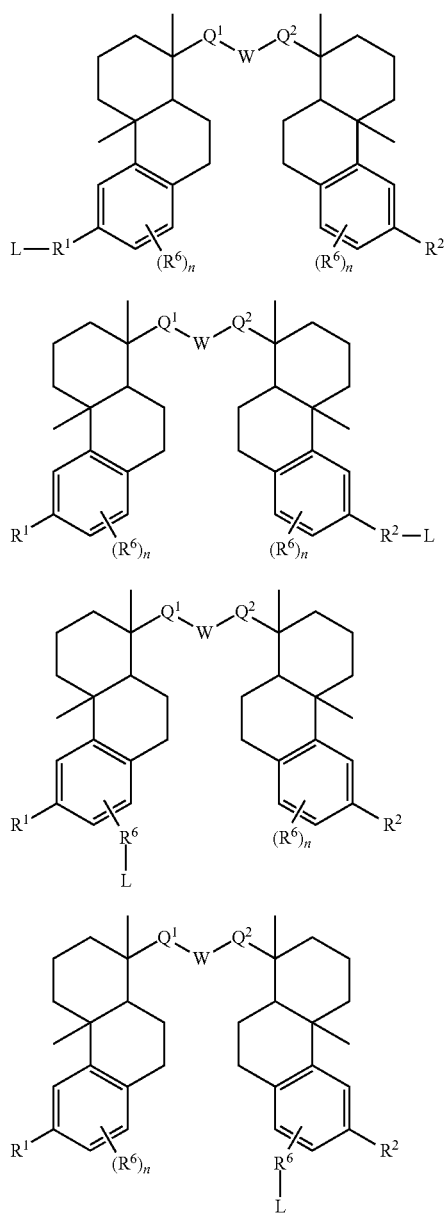

or a pharmaceutically acceptable salt, solvate, or stereoisomeric form thereof, wherein
L is a linker;
each of $Q^1$ and $Q^2$ is independently —$CH_2$—, C (O)—, —C(H)(OH)—, —C(OH)$_2$—, —$SO_2$—, —SO—, —PO(OR$^3$)—, —PO(NR$^3$NR$^4$)—, —NR$^3$—, or —N═;
W is —$CH_2$—, —N(H)—, or —O—;
$R^1$ is —N(H)R$^4$, —N(H)R$^4$—, —N(H)—, —N(R$^5$)$_2$, or —N(R$^5$)$_2$—;
$R^2$ is —N(H)R$^4$, —N(H)R$^4$—, or —N(H)—;
each $R^4$ is, independently in each instance, hydrogen, an amino acid residue, an N-alkyl amino acid residue, a peptide residue, a biodegradable moiety comprising aliphatic polyesters, alkyl, substituted alkyl, acyl, substituted acyl, or -alkylene-;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one-OH and —$CH_2OH$, or at least one primary or secondary nitrogen;
each $R^6$ is independently halo, $C_{1-6}$ alkyl, $C_{1-6}$ alkylene, $C_{1-6}$ alkoxy, —CN, O-glucose, O-amino acid residue, or O-PEG$_{n1}$, wherein each n is an integer from zero to fourteen, and each n1 is an integer from one to twelve; and
each $R^3$ is independently hydrogen, alkyl, or aryl.

29. An antibody-drug-conjugate comprising the compound of claim 1 bonded to an antibody, or an antigen binding fragment thereof.

30. A compound of Formula A, B, C, or D

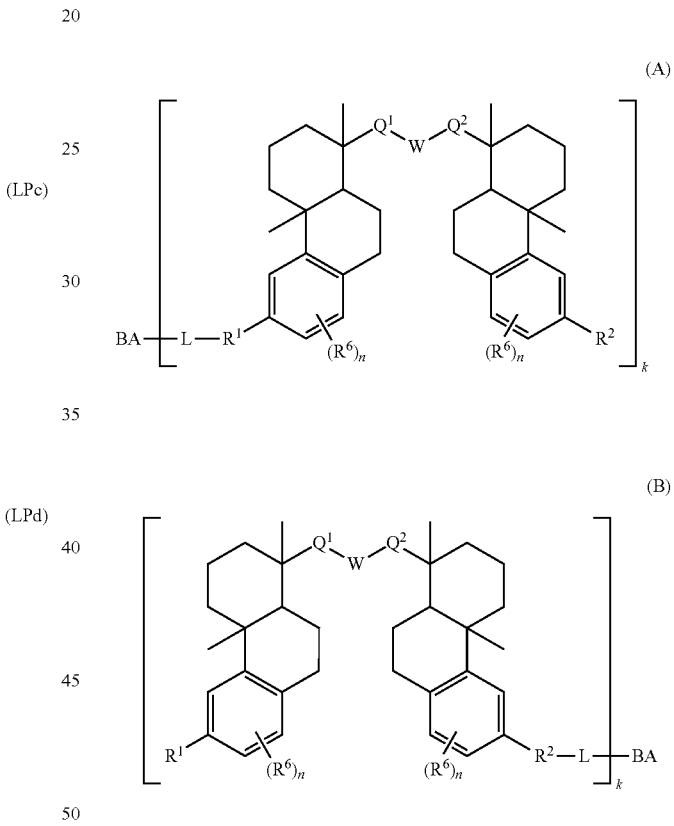

-continued (D)

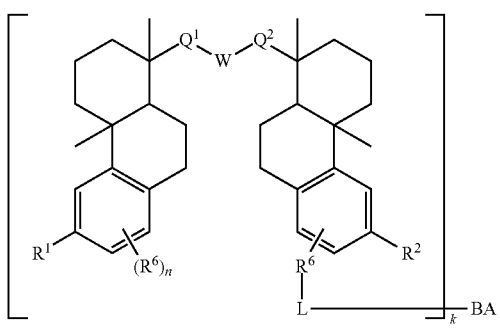

or a pharmaceutically acceptable salt, or stereoisomeric form thereof, wherein

L is a linker;

BA is an antibody or antigen binding fragment thereof;

k ranges from about one to about thirty;

each of $Q^1$ and $Q^2$ is independently —CH$_2$—, —C(O)—, —C(H)(OH)—, C (OH)$_2$—, —SO$_2$—, —SO—, —PO(OR$^3$)—, —PO(NR$^3$NR$^4$)—, —NR$^3$—, or —N=;

W is —CH$_2$—, —N(H)—, or —O—;

$R^1$ is —N(H)R$^4$, —N(H)R$^4$—, —N(H)—, —N(R$^5$)$_2$, or —N(R$^5$)$_2$—;

$R^2$ is —N(H)R$^4$, —N(H)R$^4$—, or —N(H);

each $R^4$ is, independently in each instance, hydrogen, an amino acid residue, an N-alkyl amino acid residue, a peptide residue, a biodegradable moiety comprising aliphatic polyesters, alkyl, substituted alkyl, acyl, substituted acyl, or —alkylene-;

$R^5$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —CH$_2$OH, or at least one primary or secondary nitrogen;

each $R^6$ is independently halo, $C_{1-6}$ alkyl, $C_{1-6}$ alkylene, $C_{1-6}$ alkoxy, —CN, O-glucose, O-amino acid residue, or O-PEG$_{n1}$, wherein each n is an integer from zero to fourteen, and each n1 is an integer from one to twelve; and each $R^3$ is independently hydrogen, alkyl, or aryl.

31. The compound of claim 30, wherein each $R^4$ is, independently in each instance, hydrogen, an amino acid residue, an N-alkyl amino acid residue, a peptide residue, a biodegradable moiety comprising aliphatic polyesters, alkyl, or —alkylene-.

32. The compound of claim 30, having the Formulae A', B', C', or D'

(A')

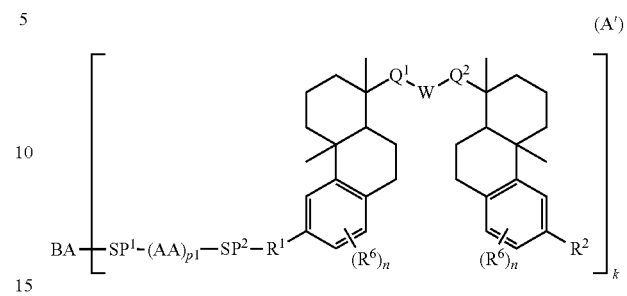

(B')

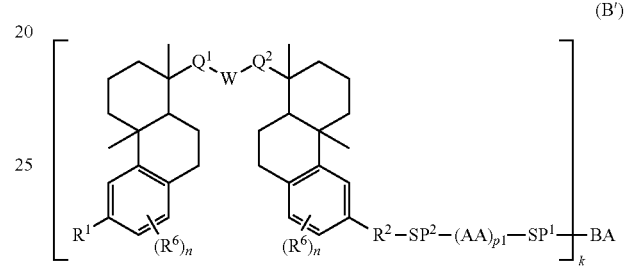

(C')

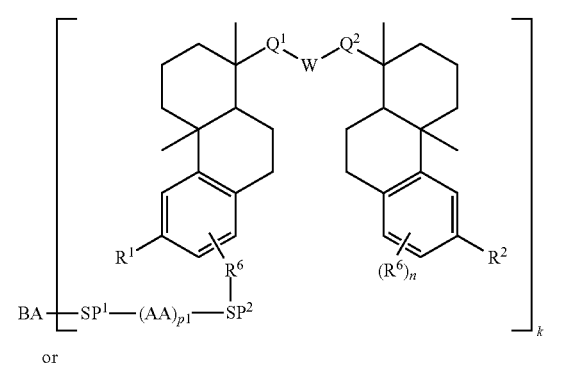

or (D')

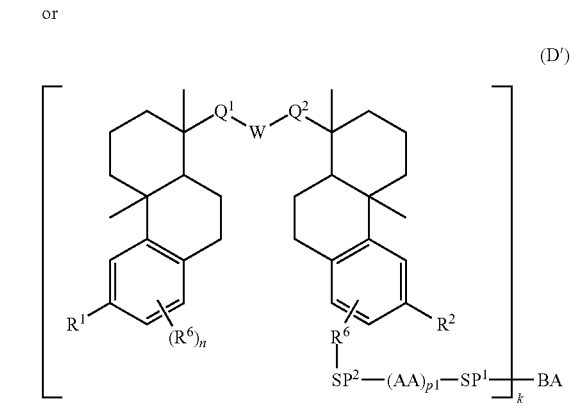

wherein SP$^1$ and SP$^2$, when present, are spacer groups;

each AA is an amino acid residue; and p1 is an integer from one to ten.

33. The compound of claim 32, wherein the compound is selected from the group consisting of
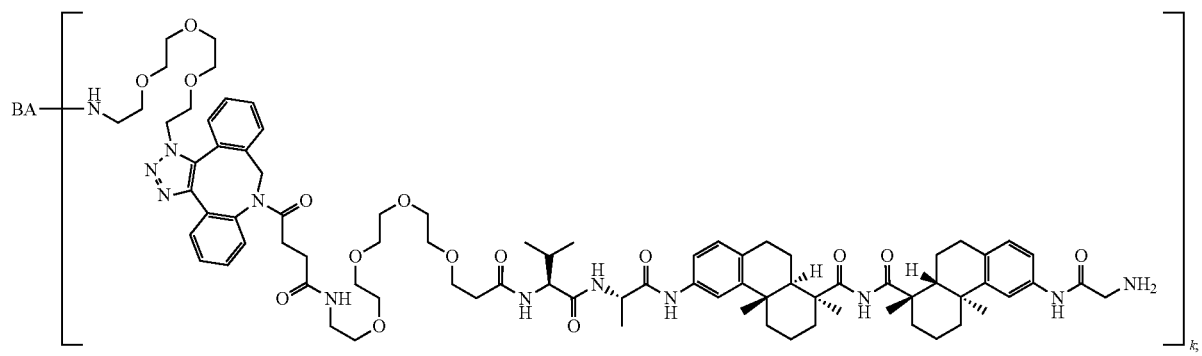
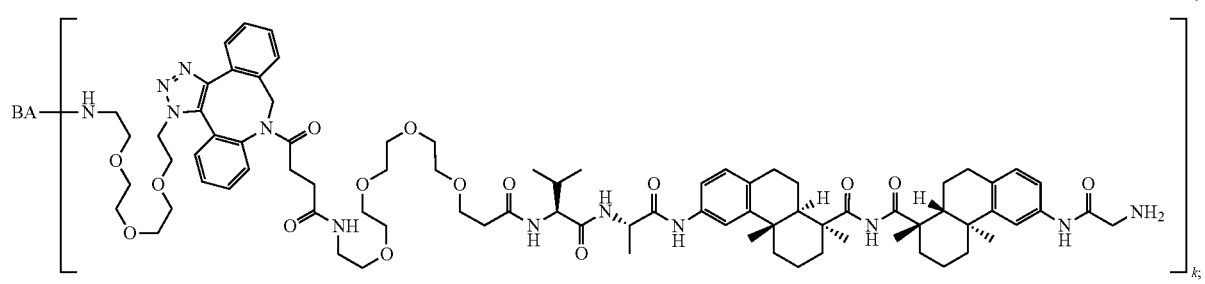
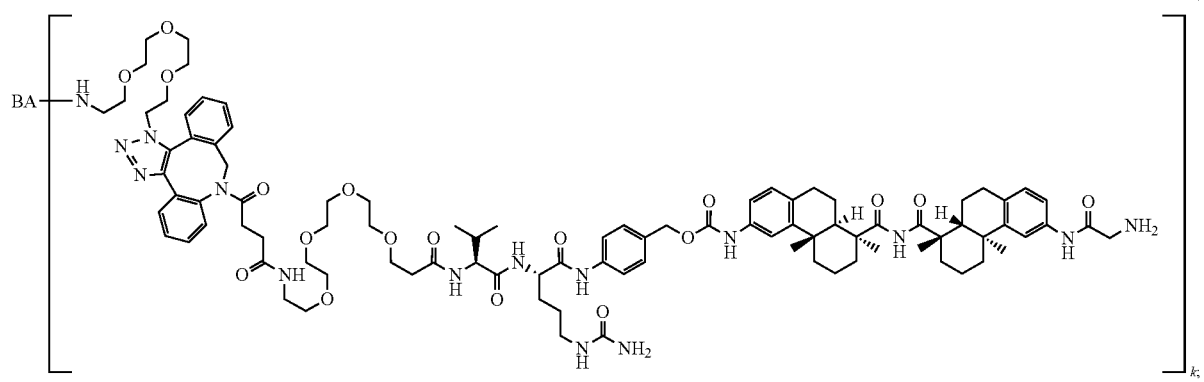
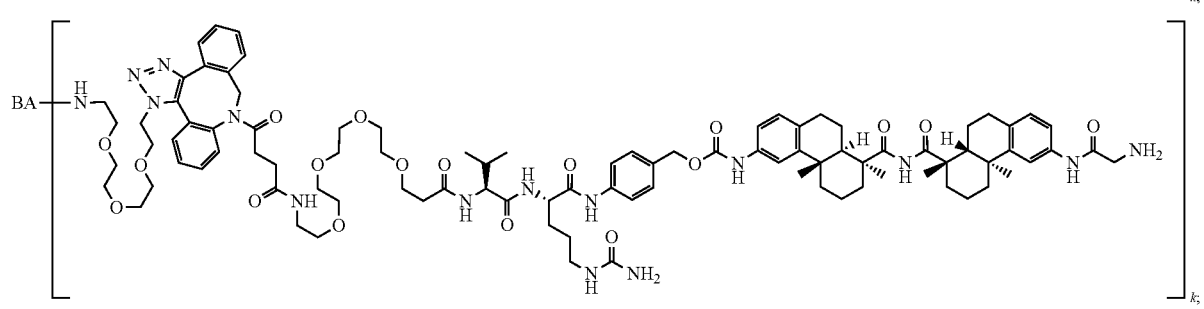
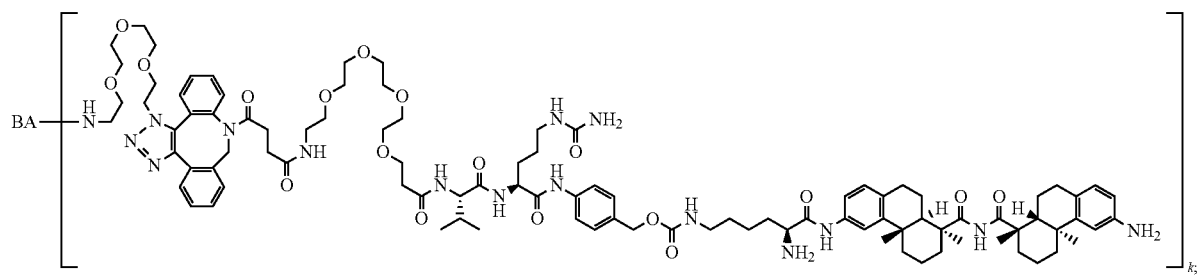

-continued
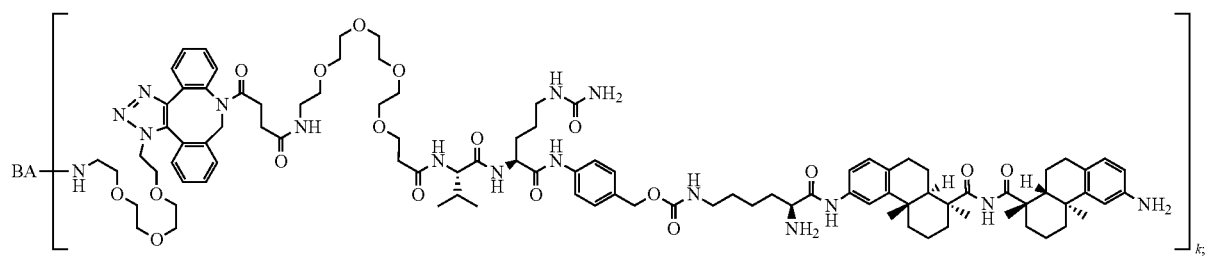
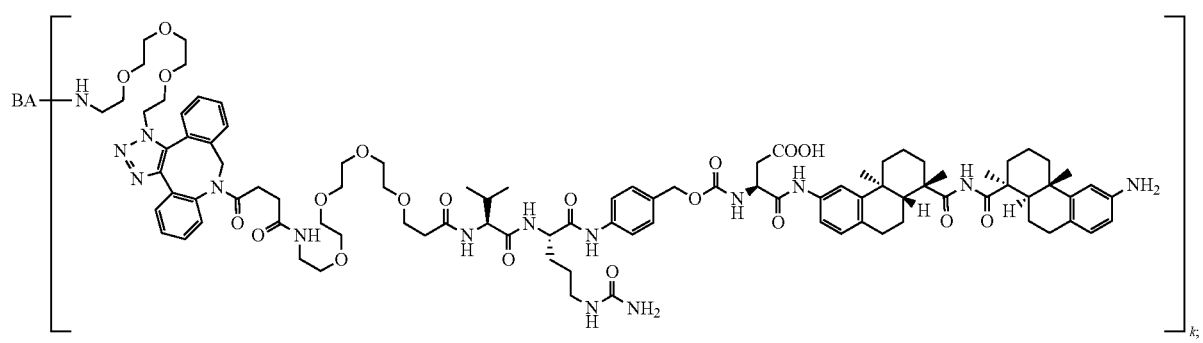
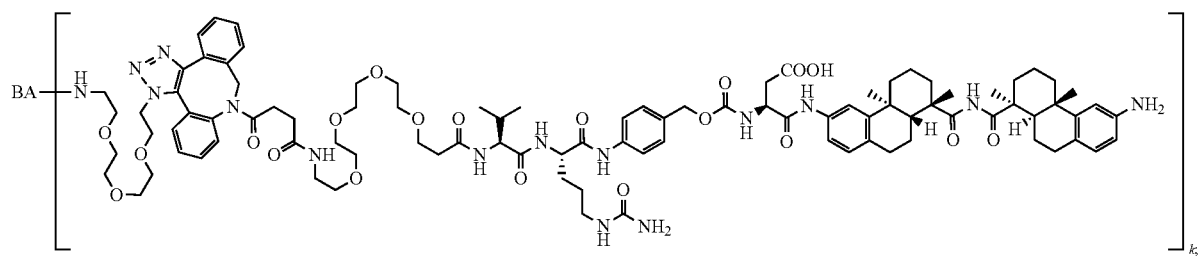
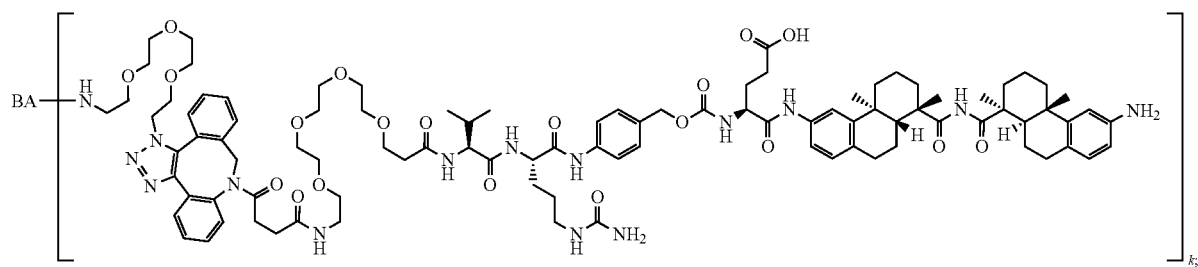
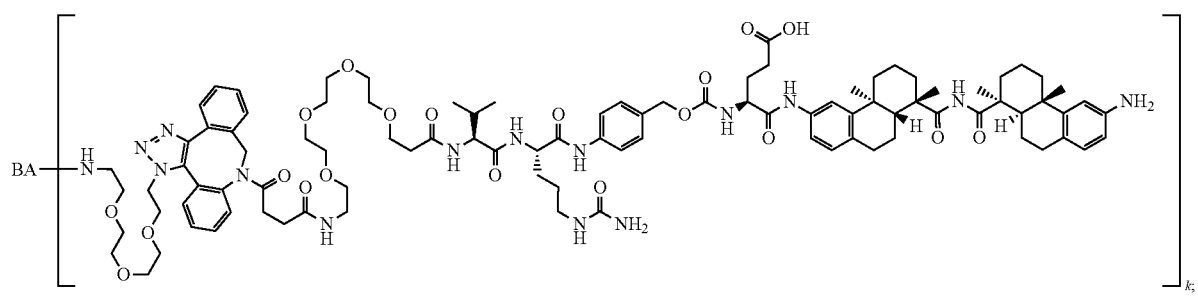

407
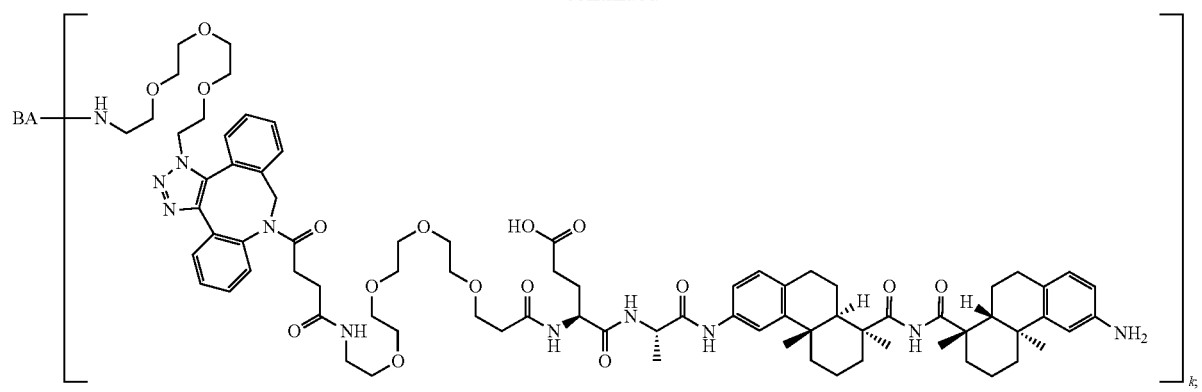
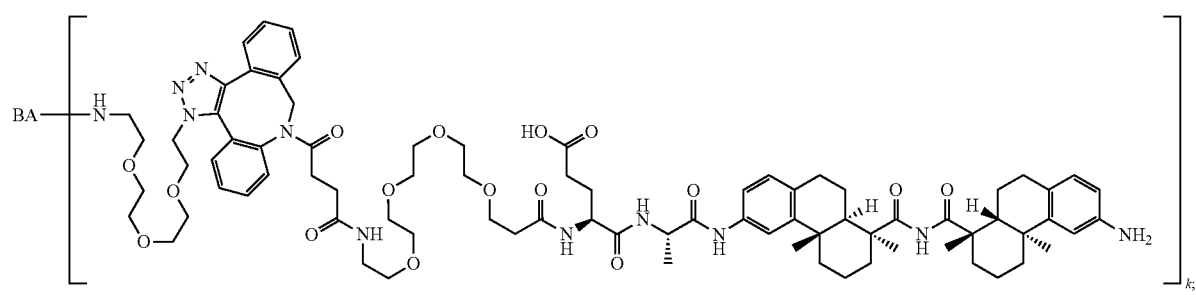
408
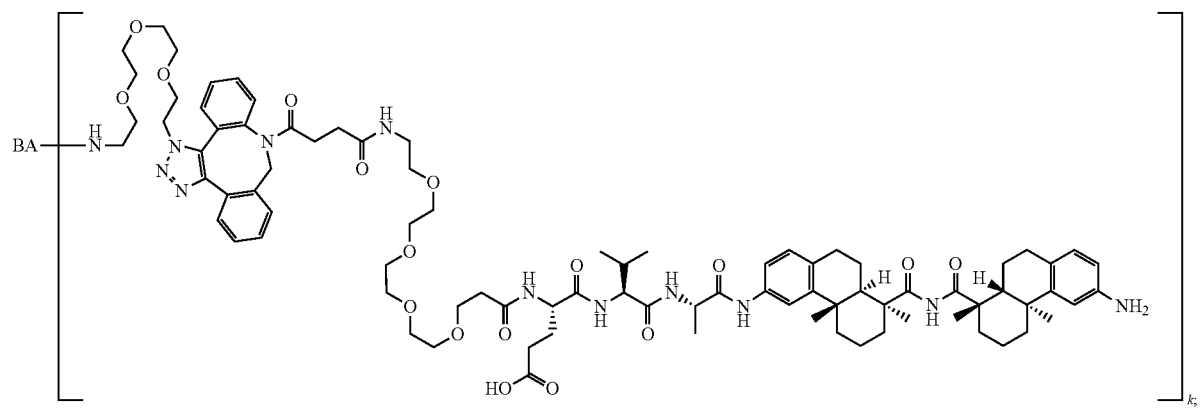
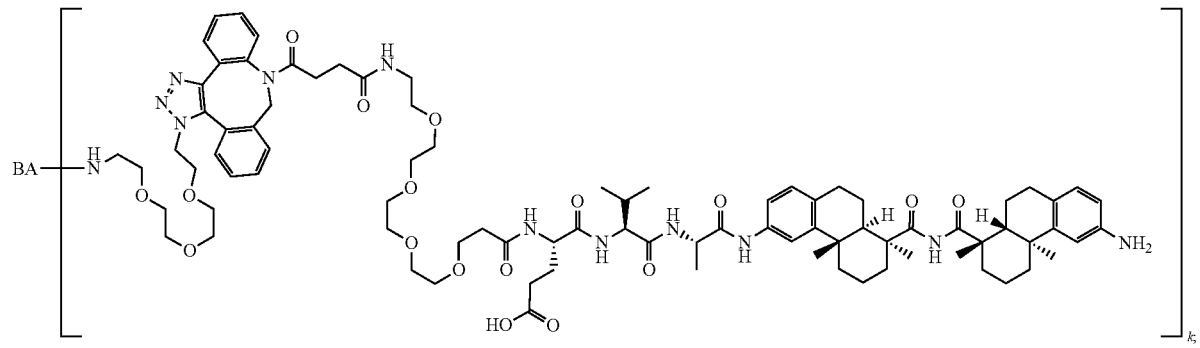

-continued

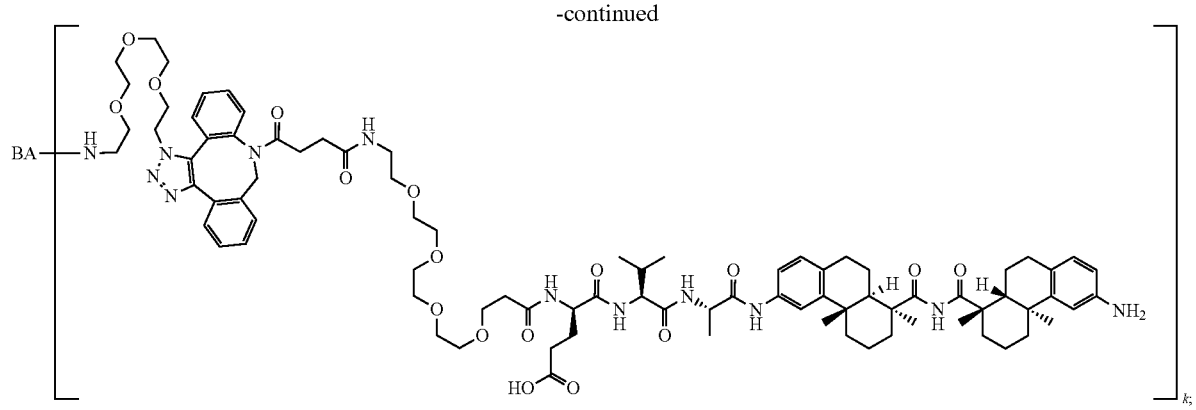

and

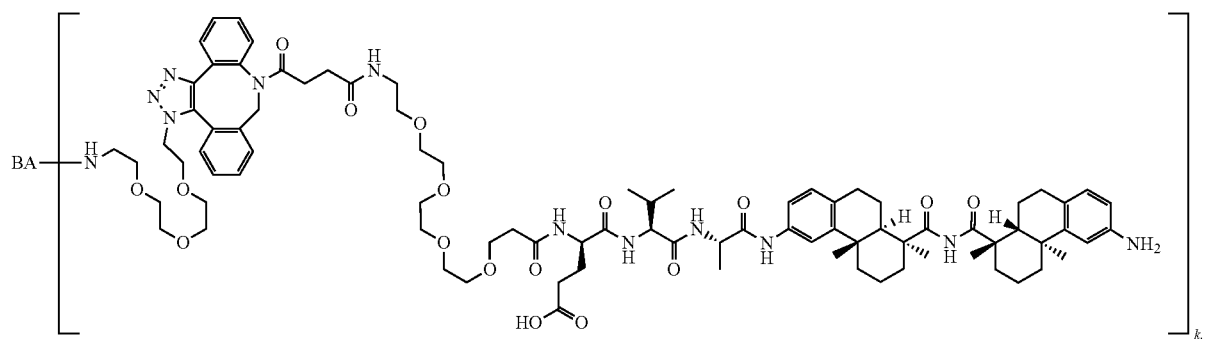

34. The compound of claim 30, of the Formula (A″)

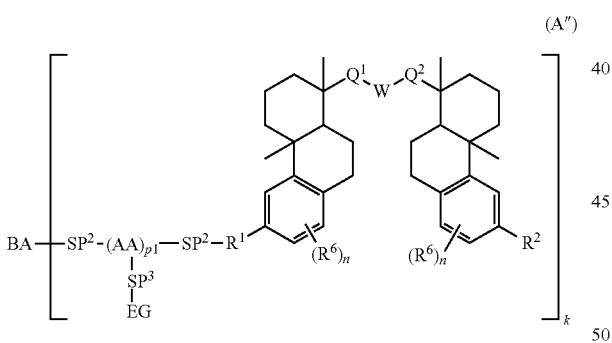

(A″)

or a pharmaceutically acceptable salt, or stereoisomeric form thereof, or a regioisomer thereof, wherein
each $SP^1$, $SP^2$, and $SP^3$ is a spacer group, where $SP^3$ is linked to one AA of $(AA)_{p1}$;
each AA is an amino acid residue;
p1 is an integer from one to ten; and
EG is an enhancement agent.

35. The compound of claim 34, wherein the $SP^1$ spacer is

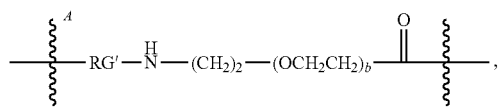

wherein
RG' is a reactive group residue following reaction of a reactive group RG with a binding agent;

$-\xi^A-$ is a bond, direct or indirect, to the binding agent; and b is an integer from one to four;
the $(AA)_{p1}$-$SP^2$— is —NH-lysine-valine-alanine-, —NH-lysine-valine-citrulline-, or —NH-lysine-valine-citrulline-PABC-;
the $SP^3$ spacer is

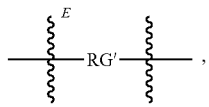

wherein
RG' is a reactive group residue following reaction of a reactive group RG with an enhancement agent EG;

$-\xi^E-$ is a bond to the enhancement agent; and $-\xi-$ is a bond to $(AA)_{p1}$.

36. The compound of claim 34, wherein the compound is selected from the group consisting of 411
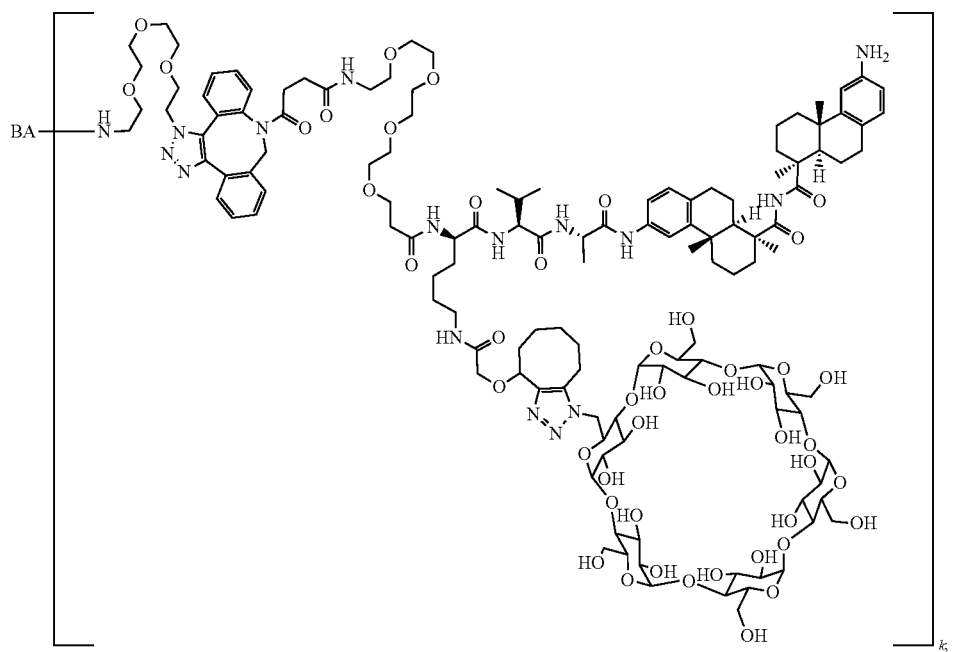
412
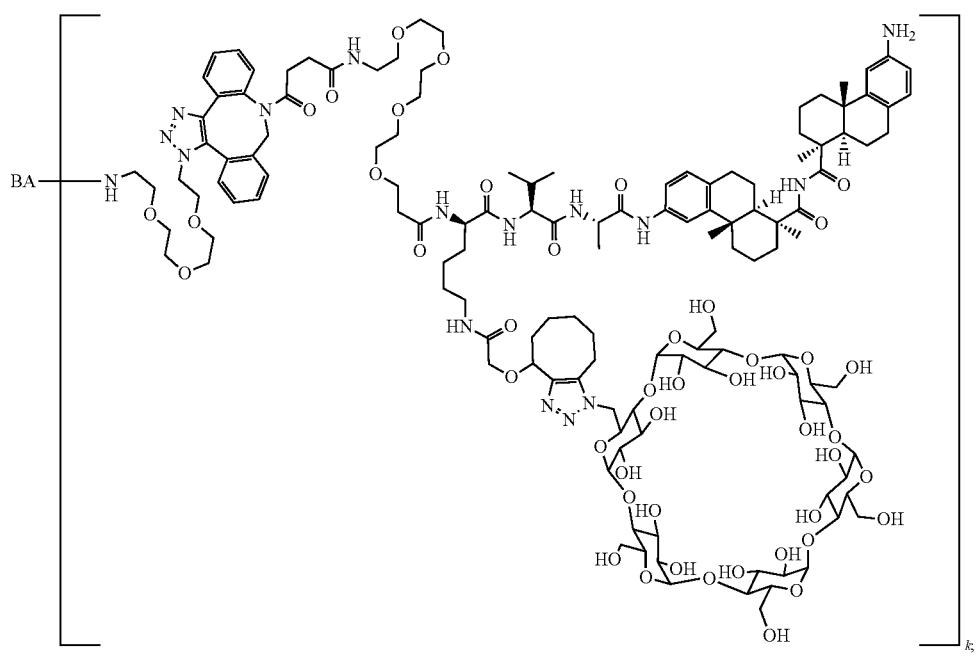

413
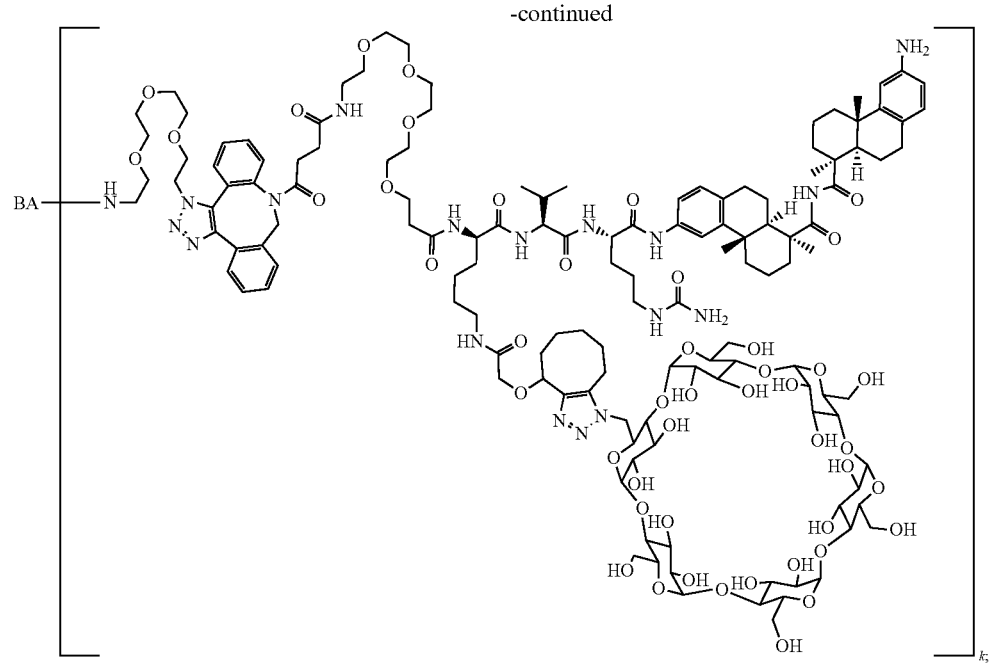
414
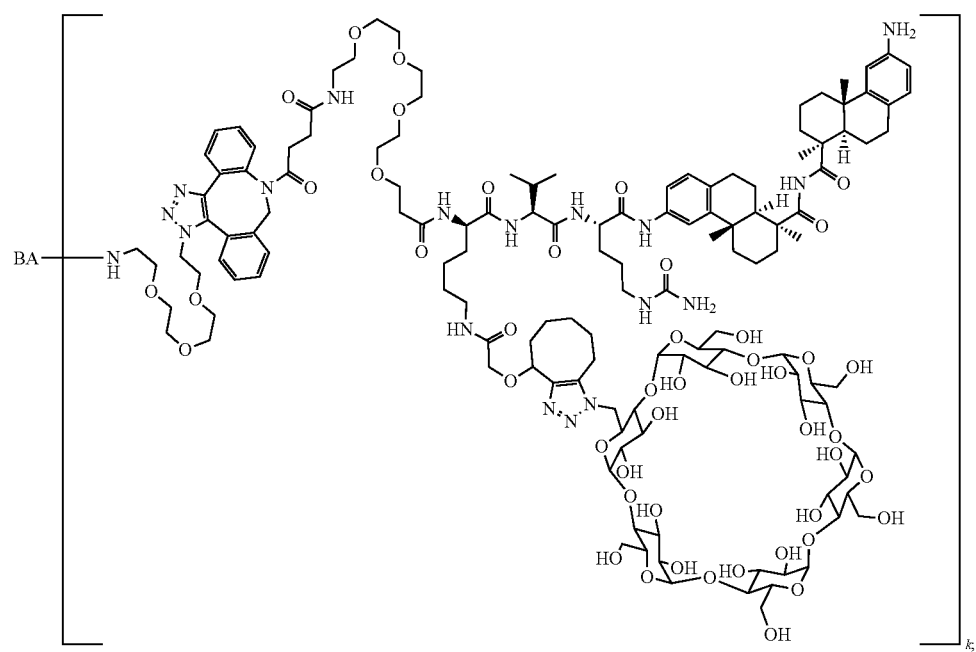

415
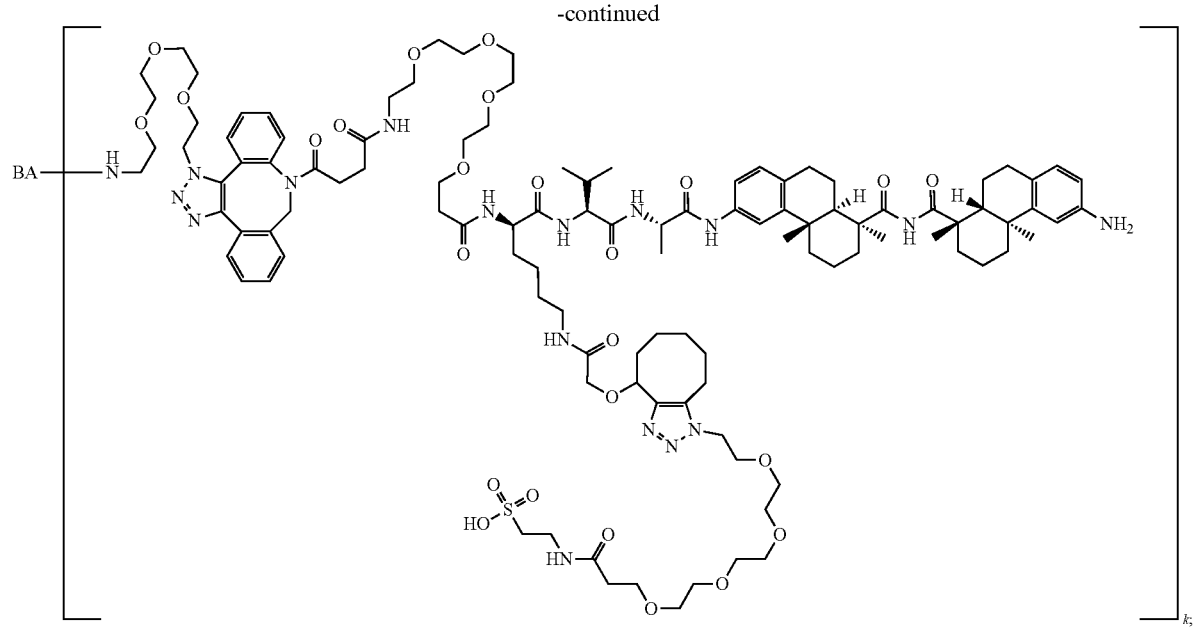
416
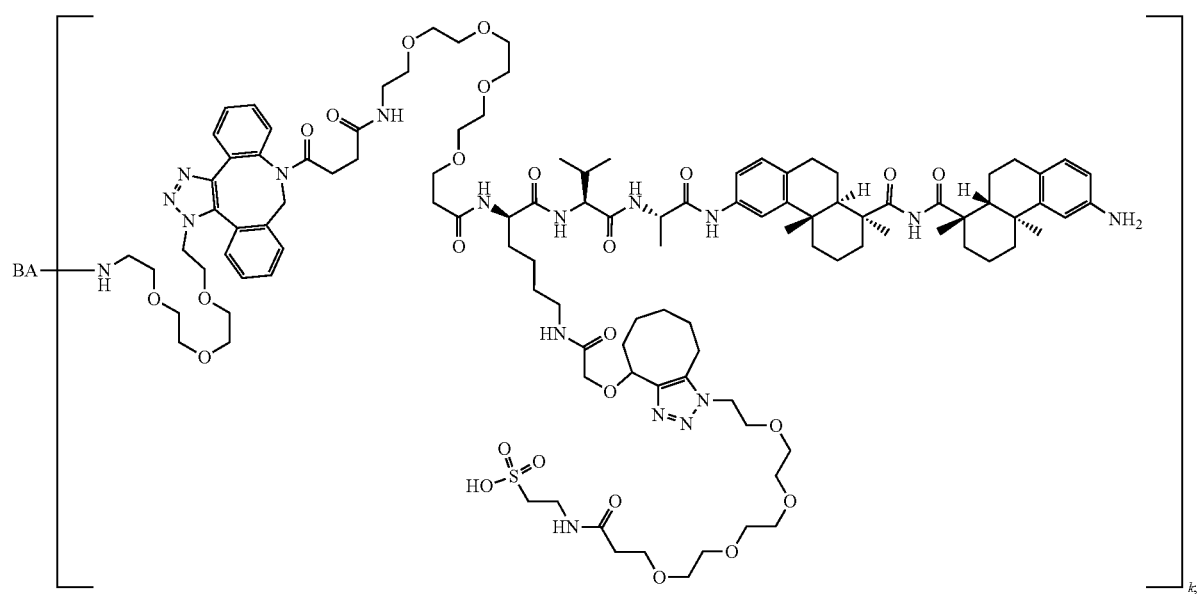

417 418
-continued
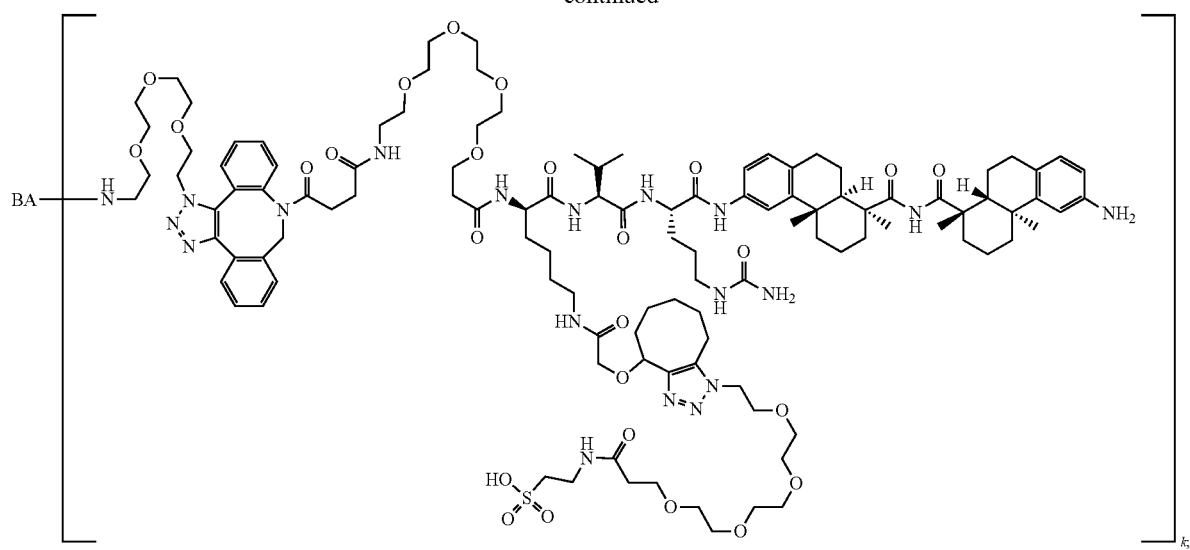
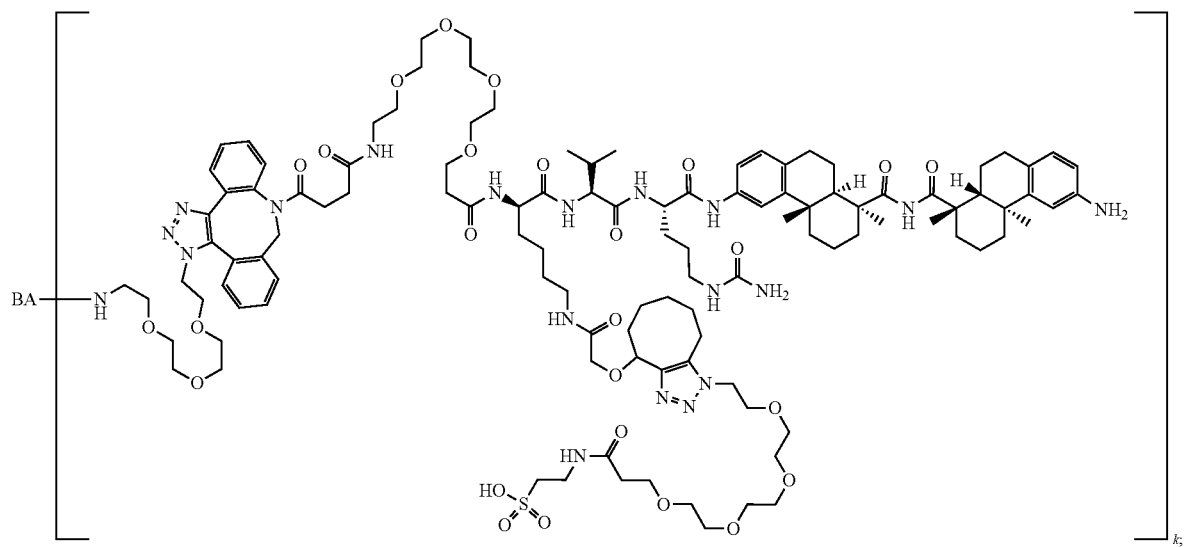
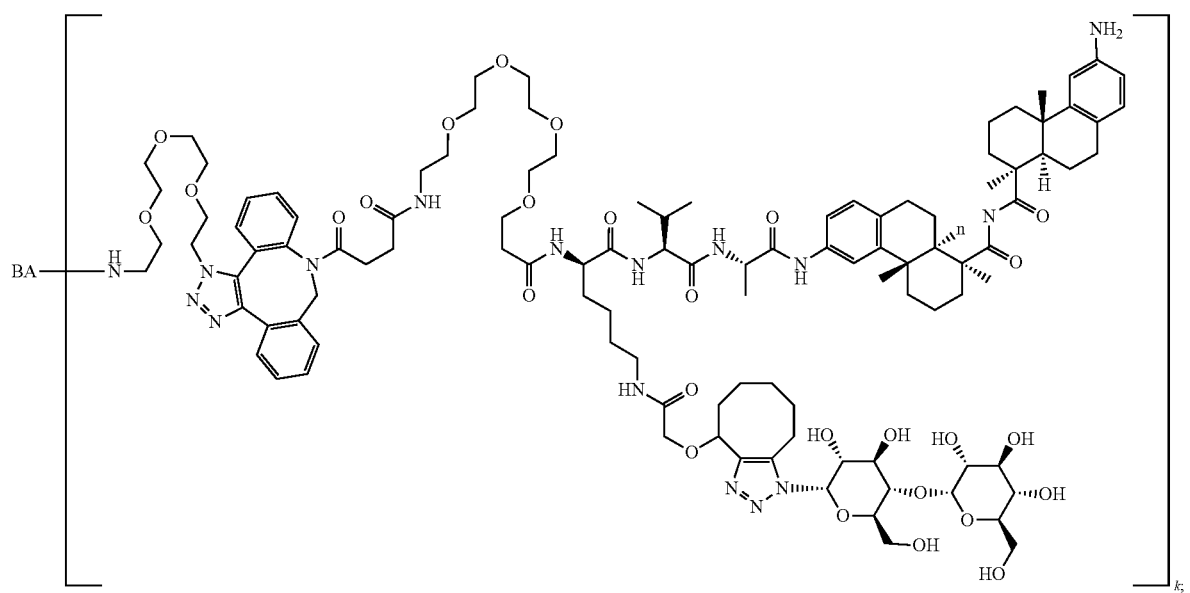

419
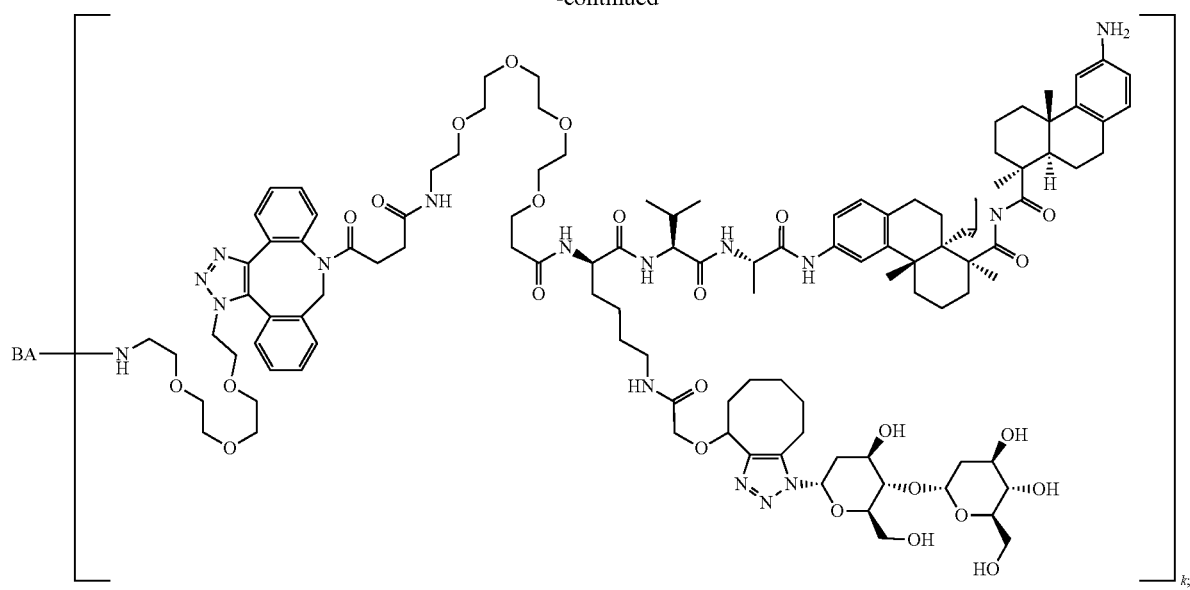
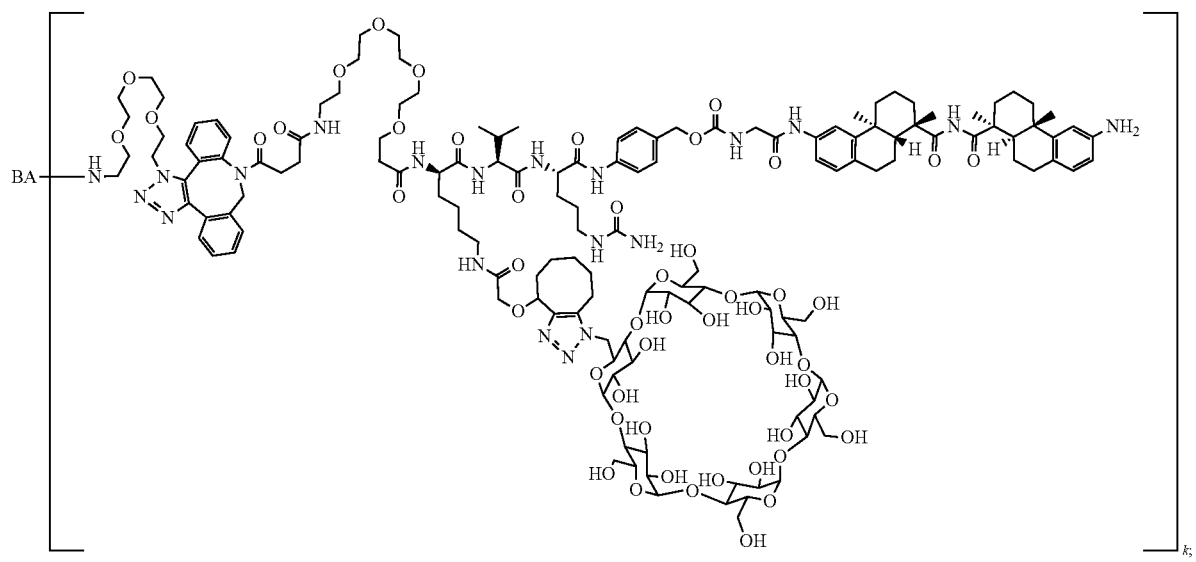
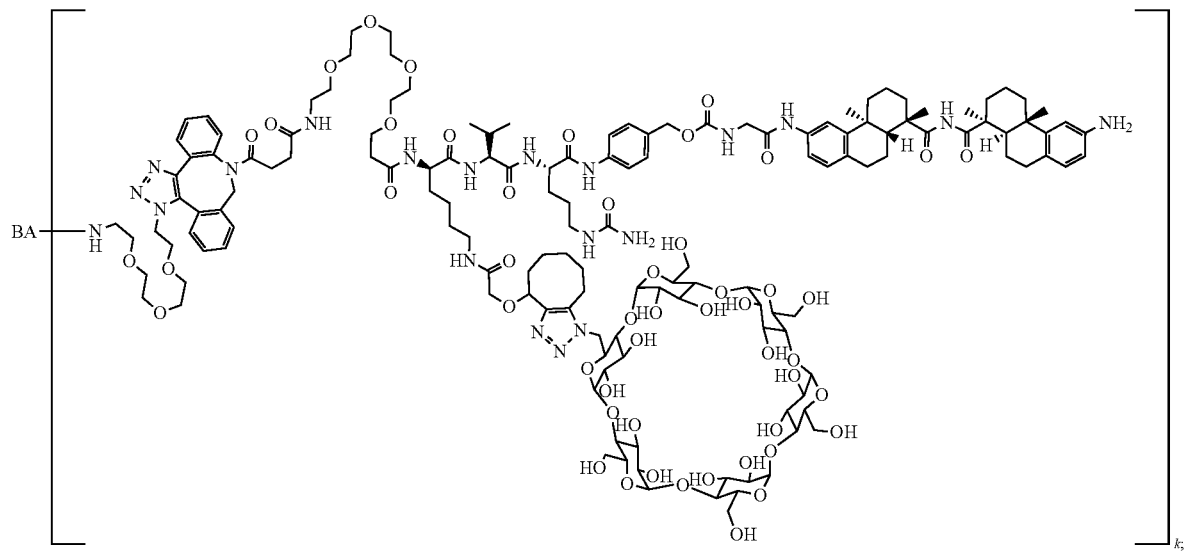

-continued

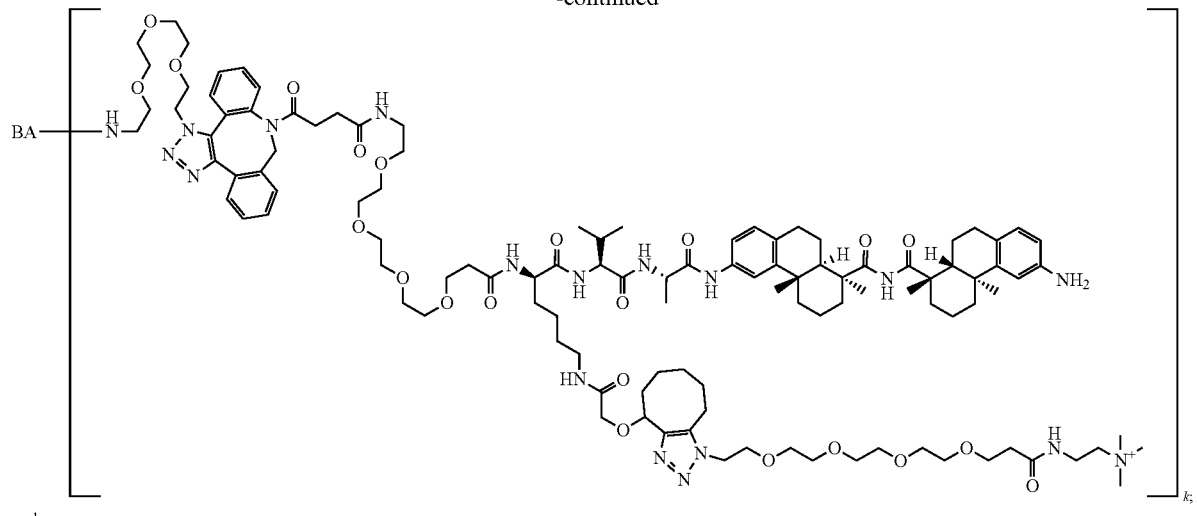

and

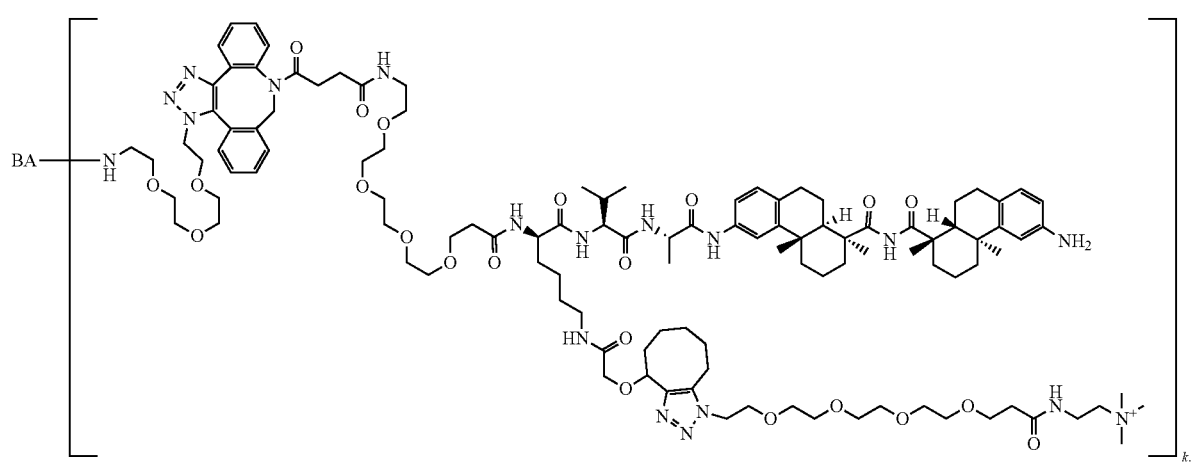

37. The compound of claim 30, wherein k ranges from about 0.5 to about five.

38. The compound of claim 30, wherein BA is an antibody, or antigen binding fragment thereof, that binds HER2, PRLR, or MSR1.

39. The compound of claim 30, wherein BA is an antibody or antigen-binding fragment thereof, and conjugation is through at least one Q295 residue.

40. The compound of claim 30, wherein BA is an antibody or antigen-binding fragment thereof, and conjugation is through two Q295 residues.

41. The compound of claim 30, wherein BA is a N297Q antibody or antigen-binding fragment thereof.

42. The compound of claim 30, wherein BA is a N297Q antibody or antigen-binding fragment thereof, and conjugation is through at least one Q295 and at least one Q297 residue.

43. The compound of claim 30, wherein BA is a N297Q antibody or antigen-binding fragment thereof, and conjugation is through two Q295 residues and two Q297 residues.

44. A pharmaceutical composition comprising the compound of claim 30 and a pharmaceutically acceptable excipient, carrier, or diluent.

45. A method for the treatment of dyslipidemia, a metabolic disease, inflammation, or a neurodegenerative disease in a subject comprising the administration to the subject of an effective treatment amount of the compound of claim 30.

* * * * *

SEQUENCE LISTING

<160> NUMBER OF SEQ ID NOS: 16

<210> SEQ ID NO 1
<211> LENGTH: 357
<212> TYPE: DNA
<213> ORGANISM: Artificial Sequence
<220> FEATURE:
<223> OTHER INFORMATION: Synthetic

<400> SEQUENCE: 1

```
caggtgcagc tgcaggagtc gggcccagga ctggtgaagc cttcggagac cctgtccctc      60
acctgcactg tcactggtgg ctccatcagt aggaactact ggagttggat ccggcagccc     120
ccagggaagg gactggaatg gattggatat atctattaca gtgggagtat cgactacaat     180
ccctccctca agagtcgagt caccatatca gtagacacgt ccaagaacca gttctccctg     240
aagctgagtt ctatgaccgc tgcggacacg gccgtatact actgtgcgag agatcggtgg     300
aactggaaat acggtatgga cgtctggggc caagggacca cggtcatcgt ctcgtca       357
```

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Gln Glu Ser Gly Pro Gly Leu Val Lys Pro Ser Glu
1               5                   10                  15

Thr Leu Ser Leu Thr Cys Thr Val Thr Gly Gly Ser Ile Ser Arg Asn
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Ile Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95
```

```
Arg Asp Arg Trp Asn Trp Lys Tyr Gly Met Asp Val Trp Gly Gln Gly
            100                 105                 110

Thr Thr Val Ile Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggtggctcca tcagtaggaa ctac                                              24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Gly Ser Ile Ser Arg Asn Tyr
1               5

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
atctattaca gtgggagtat c                                                 21

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Tyr Tyr Ser Gly Ser Ile
1               5

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gcgagagatc ggtggaactg gaaatacggt atggacgtc                              39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8
```

Ala Arg Asp Arg Trp Asn Trp Lys Tyr Gly Met Asp Val
1               5                   10

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9

```
gaaattgtgt tgacgcagtc tccaggcacc ctgtctttgt ctccagggga aagagccacc      60
ctctcctgca gggccagtca gactgttaga acaactact tagcctggta ccaccagaaa      120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttacagtgta ttactgtcac cagtatggta actcaccttg gacgttcggc    300
caagggacca aatggaaat caaacga                                          327
```

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Arg Asn Asn
            20                  25                  30

Tyr Leu Ala Trp Tyr His Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Thr Val Tyr Tyr Cys His Gln Tyr Gly Asn Ser Pro
                85                  90                  95

Trp Thr Phe Gly Gln Gly Thr Lys Met Glu Ile Lys Arg
            100                 105

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagactgtta gaaacaacta c                                               21

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gln Thr Val Arg Asn Asn Tyr

```
<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgcatcc                                                                9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caccagtatg gtaactcacc ttggacg                                           27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

His Gln Tyr Gly Asn Ser Pro Trp Thr
1               5
```